United States Patent [19]
Bastian et al.

[11] Patent Number: 6,025,382
[45] Date of Patent: Feb. 15, 2000

[54] ANTITHROMBOTIC DIAMINES

[75] Inventors: Jolie Anne Bastian, Beech Grove; Nickolay Yuri Chirgadze, Carmel; Michael Lyle Denney, Franklin; Matthew Joseph Fisher, Carmel, all of Ind.; Robert James Foglesong, Durham, N.C.; Richard Waltz Harper, Indianapolis, Ind.; Mary George Johnson, Durham, N.C.; Valentine Joseph Klimkowski, Carmel, Ind.; Todd Jonathan Kohn, Fishers, Ind.; Ho-Shen Lin, Indianapolis, Ind.; Michael Patrick Lynch, Raleigh, N.C.; Jefferson Ray McCowan, Indianapolis, Ind.; Alan David Palkowitz, Carmel, Ind.; Michael Enrico Richett, Indianapolis, Ind.; Daniel Jon Sall, Greenwood, Ind.; Gerald Floyd Smith; Kumiko Takeuchi, both of Indianapolis, Ind.; Jennifer Marie Tinsley, Martinsville, Ind.; Minsheng Zhang, Nutley, N.J.

[73] Assignee: Eli Lilly and Company, Indianapolis, Ind.

[21] Appl. No.: 08/846,647

[22] Filed: Apr. 30, 1997

Related U.S. Application Data

[63] Continuation-in-part of application No. 08/836,680, filed as application No. PCT/US96/17995, Oct. 30, 1996, abandoned
[60] Provisional application No. 60/007,120, Oct. 31, 1995, and provisional application No. 60/028,252, Oct. 9, 1996.
[51] Int. Cl.$^7$ .......................... A61K 31/40; A61K 31/38; C07D 409/14; C07D 409/12
[52] U.S. Cl. .................. 514/422; 514/212; 514/233.5; 514/318; 514/326; 514/380; 514/443; 540/602; 544/141; 546/194; 546/202; 548/518; 548/523; 548/525; 548/243; 549/58
[58] Field of Search ..................... 548/518, 523, 548/525, 243; 549/58; 546/194, 202; 544/141; 540/602; 514/212, 233.5, 318, 326, 380, 422, 443

[56] References Cited

U.S. PATENT DOCUMENTS

| | | | |
|---|---|---|---|
| 3,274,213 | 9/1966 | Lednicer | 260/326.5 |
| 3,293,263 | 12/1966 | Lednicer | 260/326.5 |
| 4,001,426 | 1/1977 | Brenner et al. | 424/285 |
| 4,007,204 | 2/1977 | Desamps et al. | 260/330.5 |
| 4,133,814 | 1/1979 | Jones et al. | 260/326.55 |
| 5,371,091 | 12/1994 | Misra et al. | 514/314 |
| 5,441,965 | 8/1995 | Sall et al. | 514/324 |
| 5,472,962 | 12/1995 | Koizumi | 514/233.5 |
| 5,523,309 | 6/1996 | Bryant | 514/320 |

FOREIGN PATENT DOCUMENTS

WO 95/10513  4/1995  WIPO .

OTHER PUBLICATIONS

Jones, C., et al., "Synthesis and Antiestrogenic Activity of [3,4–Dihydro–2–(4–methoxyphenyl) –1–napthalenyl] [4–[2–(1–pyrrolidinyl) ethoxy] phenyl] methanone, Methanesulfonic Acid Salt", *J. Med. Chem.*, 22(8), 962–966, 1979.
Jones, C., et al., "Antiestrogens. 2. Structure–Activity Studies in a Series of 3–Aroyl–2–arylbenzo [b] thiophene Derivatives Leading to [6–Hydroxy–2–(4–hydroxyphenyl) benzo [b] thien–3–yl] [4–[2–(1–piperidinyl) ethoxy] phenyl] methanone Hydrochloride (LY156758), a Remarkably Effective Estrogen Antagonist with Only Minimal Intrinsic Estrogencity," *J. Med. Chem.*, 27 (8), 1057–1066, 1984.

*Primary Examiner*—Evelyn Mei Huang
*Attorney, Agent, or Firm*—Thomas E. Jackson

[57] ABSTRACT

This application relates to the use as thrombin inhibitors, coagulation inhibitors and thromboembolic disorder agents of diamines of formula I as defined herein. It also provides novel compounds of formula I, processes and intermediates for their preparation, and pharmaceutical formulations comprising the novel compounds of formula I.

21 Claims, No Drawings

ANTITHROMBOTIC DIAMINES

This application is a continuation-in-part of U.S. national application Ser. No. 08/836,680, filed on Apr. 30, 1996, now abandoned the national stage application of international application PCT/US96/17995, filed Oct. 30, 1996, which international application claims priority from U.S. provisional application Ser. No. 60/007,120, filed Oct. 31, 1995, and U.S. provisional application Ser. No. 60/028,252, filed Oct. 9, 1996.

This invention relates to thrombin inhibitors which are useful anticoagulants in mammals. In particular it relates to diamine derivatives having high anticoagulant activity, and antithrombotic activity. Thus, this invention relates to new inhibitors of thrombin, pharmaceutical compositions containing the compounds as active ingredients, and the use of the compounds as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the diamine derivatives are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin. See, for example Robert M. Scarborough, *Annual Reports in Medicinal Chemistry*, (1995), 30, 71–80.

Although the heparins and coumarins are effective anticoagulants, no commercial drug has yet emerged from the small synthetic molecules; and despite the continuing promise for this class of compounds, there still exists a need for anticoagulants which act selectively on thrombin, and which, independent of antithrombin III, exert inhibitory action shortly after administration, preferably by an oral route, and do not interfere with lysis of blood clots, as required to maintain hemostasis.

The present invention is directed to the discovery that the compounds of the present invention, as defined below, are potent thrombin inhibitors that may have high bioavailability following oral administration.

According to the invention there is provided a method of inhibiting thrombin comprising using an effective amount of a thrombin inhibiting compound of formula I (or a pharmaceutically acceptable salt thereof)

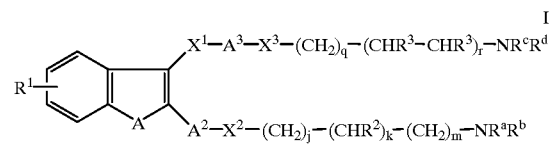

wherein

A is O, S, —CH=CH— or —CH$_2$—CH$_2$—;

A$^2$ is an aromatic or heteroaromatic divalent radical selected from para-phenylene, a 6-membered ring heteroaromatic divalent radical containing 1 or 2 ring nitrogens in which the valences are in the 1,4- or 2,5- or 3,6- relationship, and a 5-membered ring heteroaromatic divalent radical containing one oxygen or sulfur ring atom and 0, 1 or 2 ring nitrogens in which the valences are in the 2,5- (or 3,5-) relationship and which divalent radical may bear a hydroxymethyl, benzyloxymethyl, (1–3C)alkyl, (1–2C)alkoxy, hydroxy or halo substituent;

A$^3$ is an aromatic or heteroaromatic divalent radical selected from para-phenylene, a 6-membered ring heteroaromatic divalent radical containing 1 or 2 ring nitrogens in which the valences are in the 1,4- or 2,5- or 3,6- relationship, and a 5-membered ring heteroaromatic divalent radical containing one oxygen or sulfur ring atom and 0, 1 or 2 ring nitrogens in which the valences are in the 2,5- (or 3,5-) relationship and which divalent radical may bear one or two substituents independently selected from dimethylamino, (1–4C) alkyl, halo, trifluoromethyl, (1–2C)alkoxy, hydroxy, cyano, aminomethyl, nitro, —NHCH$_2$R$^f$, NHC(O)R$^f$ or —NHS(O)$_2$R$^g$ in which R$^f$ is hydrogen or (1–2C)alkyl and R$^g$ is (1–2C)alkyl or phenyl;

R$^1$ denotes 0, 1 or 2 substituents on the benz-ring independently selected from halo, methyl, ethyl, hydroxy, ethoxy, carbamoyl, aminomethyl and hydroxymethyl;

X$^1$ is O, S, methylene, carbonyl or ethene-1,1-diyl;

(a) X$^2$ is imino, a direct bond, methylene, O or S; j is 0; k is 0; m is 5, 1, 2, 3 or 4; provided that when m is 1, then X$^2$ is a direct bond; and R$^a$ and R$^b$ are independently hydrogen or (1–3C)alkyl or the group NR$^a$R$^b$ is 1-imidazolyl, 1-pyrazolyl, N-(1,2,4-triazolyl), neopentylamino, (cyclohexylmethyl)amino, benzylamino, (3-pyridylmethyl)amino, (2,3-dihydroxypropyl)amino, (1-iminoethyl)amino, 2-(hydroxymethyl)-1-pyrrolidinyl, 2-(methoxymethyl)-1-pyrrolidinyl, pyrrolidino, piperidino, 2-methyl-1-piperidinyl, morpholino or hexamethyleneimino; or (b) X$^2$ is imino, O or S; j is 1; k is 1; m is 1; R$^2$ is hydroxy; and R$^a$ and R$^b$ are independently hydrogen or (1–3C) alkyl or the group NR$^a$R$^b$ is pyrrolidino, piperidino, morpholino or hexamethyleneimino; or (c) X$^2$ is imino, O or S; j is 1; k is 1; m is 0; R$^2$ is methyl, carboxy, hydroxymethyl or methoxycarbonyl; and R$^a$ and R$^b$ are independently hydrogen or (1–3C)alkyl; or (d) X$^2$ is imino, O or S; j is 0, 1, 2 or 3; k is 1; m is 0 or 1; provided that j and m are not both 0; R$^2$ and R$^a$ together form a diradical —(CH$_2$)$_n$— in which n is 2, 3 or 4 and the sum of m and n is 3 or 4; and R$^b$ is hydrogen or (1–3C)alkyl; or (e) X$^2$ is —NH—C(O)—; j is 0; k is 0; m is 1; and R$^a$ and R$^b$ are independently hydrogen or (1–3C)alkyl or the group NR$^a$R$^b$ is 1,1-dioxothiomorpholin-4-yl, pyrrolidino, piperidino, morpholino or hexamethyleneimino; and (1) X$^3$ is a direct bond, methylene, imino, O or S; q is 0, 1 or 2; and r is 0 or 1; provided that q and r are not both zero, and provided that when q is 1 and r is 0, then X$^3$ is a direct bond; each R$^3$ is hydrogen or the two R$^3$ groups together form a divalent radical —(CH$_2$)$_s$— in which s is 3 or 4; or q and r are each 1 and the group —(CHR$^3$—CHR$^3$)— is propane-2,2-diyl; and R$^c$ and R$^d$ are independently hydrogen or (1–4C)alkyl or the group NR$^c$R$^d$ is 1-pyrazolyl, 2-(hydroxymethyl)-1-pyrrolidinyl, 2-(methoxymethyl)-1-pyrrolidinyl, pyrrolidino, piperidino, morpholino, hexamethyleneimino, 1-imidazolyl or 4,5-dihydro-1-imidazolyl; or (2) X$^3$ is imino, O or S; q is 0; r is 1; one R$^3$ group is (1–5C)alkyl and the other R$^3$ group is independently hydrogen or (1–5C)alkyl; and R$^c$ and R$^d$ are independently hydrogen or (1–3C)alkyl or the group NR$^c$R$^d$ is pyrrolidino, piperidino, morpholino or hexamethyleneimino; or (3) X$^3$ is imino, O or S; q is 0, 1 or 2; r is 1; one R$^3$ group is hydrogen and the other R$^3$ group together with the group R$^c$ forms a divalent radical —(CH$_2$)$_t$— in which t is 2, 3 or 4 such that the resulting ring is a pyrrolidine or piperidine; and R$^d$ is hydrogen or (1–3C)alkyl; or (4) X$^3$ is —N(R$^h$)—; q is 0; r is 1; the R$^3$ group on the carbon bonded to X$^3$ and the group R$^h$ together form a diradical —(CH$_2$)$_3$—; the other R$^3$ group is hydrogen; and R$^c$ and R$^d$ are independently (1–3C)alkyl or the group NR$^c$R$^d$ is pyrrolidino, piperidino, morpholino or hexamethyleneimino; or (5) X$^3$ is ethene-1,2-diyl or ethyne-1,2-diyl; q is 1; r is 0; and R$^c$ and R$^d$ are independently (1–3C)alkyl or the group NR$^c$R$^d$ is pyrrolidino, piperidino, morpholino or hexamethyleneimino.

One particular method of inhibiting thrombin comprises using an effective amount of a thrombin inhibiting compound of formula I, or a pharmaceutically acceptable salt thereof, wherein A is S, —CH=CH— or —CH$_2$—CH$_2$—;

A$^2$ is an aromatic or heteroaromatic divalent radical selected from para-phenylene, a 6-membered ring heteroaromatic divalent radical containing 1 or 2 ring nitrogens and a 5-membered ring heteroaromatic divalent radical containing one oxygen or sulfur ring atom and 0, 1 or 2 ring nitrogens in which heteroaromatic divalent radical the valences are in the 1,4- or 2,5- or 3,6- relationship and which divalent radical may bear a methyl, hydroxy or methoxy substituent (and more particularly, which divalent radical does not bear a substituent);

A$^3$ is an aromatic or heteroaromatic divalent radical selected from para-phenylene, a 6-membered ring heteroaromatic divalent radical containing 1 or 2 ring nitrogens and a 5-membered ring heteroaromatic divalent radical containing one oxygen or sulfur ring atom and 0, 1 or 2 ring nitrogens in which heteroaromatic divalent radical the valences are in the 1,4- or 2,5- or 3,6- relationship and which divalent radical may bear a (1–3C)alkyl, (1–2C)alkoxy or halo substituent (and more particularly, which divalent radical may bear a (1–3C)alkyl or halo substituent);

R$^1$ denotes 0, 1 or 2 substituents on the benz-ring independently selected from halo, methyl, ethyl, hydroxy, methoxy, carbamoyl, aminomethyl and hydroxymethyl;

X$^1$ is O, S, methylene, carbonyl or ethene-1,1-diyl;

X$^2$ is a direct bond, methylene, O or S; j and k are both 0; m is 1, 2, 3 or 4; provided that when m is 1, then X$^2$ is a direct bond; and R$^a$ and R$^b$ are independently hydrogen or (1–3C)alkyl or the group NR$^a$R$^b$ is pyrrolidino, piperidino, morpholino or hexamethyleneimino;

X$^3$ is a direct bond, methylene, imino, O or S; q is 0, 1 or 2; and r is 0 or 1; provided that q and r are not both zero, and provided that when q is 1 and r is 0, then X$^3$ is a direct bond; each R$^3$ is hydrogen or the two R$^3$ groups together form a divalent radical —(CH$_2$)$_s$— in which s is 3 or 4; and R$^c$ and R$^d$ are independently (1–3C)alkyl or the group NR$^c$R$^d$ is pyrrolidino, piperidino, morpholino, hexamethyleneimino or 1-imidazolyl.

A compound of formula I in which j and k are both 0 may be denoted as a compound of formula I'.

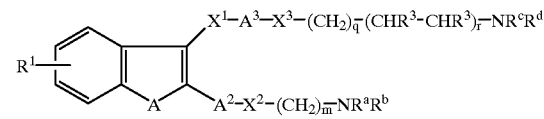

I'

A particular aspect of the above method is one wherein said compound is a compound of formula I in which A is S, —CH=CH— or —CH$_2$—CH$_2$—;

A$^2$ is para-phenylene which may bear a substituent R$^j$ ortho to the group X$^2$ and R$^j$ is methyl, hydroxy or methoxy or A$^2$ is pyridine-2,5-diyl in which the 2-position is joined to X$^2$ (and more particularly, which divalent radical does not bear a substituent);

A$^3$ is para-phenylene which may bear a substituent R$^e$ ortho to the group X$^3$ and R$^e$ is (1–3)alkyl, (1–2C)alkoxy or halo or A$^3$ is pyridine-2,5-diyl in which the 2-position is joined to X$^3$ (and more particularly, R$^e$ is (1–3)alkyl or halo);

R$^1$ denotes 0, 1 or 2 substituents on the benz-ring independently selected from halo, methyl, ethyl, hydroxy, methoxy, carbamoyl, aminomethyl and hydroxymethyl;

X$^1$ is O, S, methylene, carbonyl or ethene-1,1-diyl;

X$^2$ is a direct bond, methylene, O or S; j and k are both 0; m is 1, 2, 3 or 4; provided that when m is 1, then X$^2$ is a direct bond; and R$^a$ and R$^b$ are independently hydrogen or (1–3C)alkyl or the group NR$^a$R$^b$ is pyrrolidino, piperidino or morpholino;

X$^3$ is a direct bond, methylene, imino, O or S; q is 0, 1 or 2; and r is 0 or 1; provided that q and r are not both zero, and provided that when q is 1 and r is 0, then X$^3$ is a direct bond; each R$^3$ is hydrogen or the two R$^3$ groups together form a divalent radical —(CH$_2$)$_s$— in which s is 3 or 4; and R$^c$ and R$^d$ are independently (1–3C)alkyl or the group NR$^c$R$^d$ is pyrrolidino, piperidino, morpholino, hexamethyleneimino or 1-imidazolyl.

A more particular aspect of any of the above methods is one wherein said compound is a compound of formula Ia

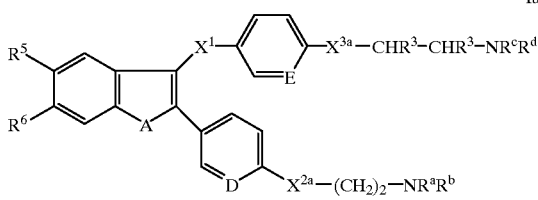

wherein

A is S, —CH=CH— or —CH₂—CH₂—;

D is CH, CR$^j$ or N in which R$^j$ is methyl, hydroxy or methoxy (and more particularly D is CH or N);

E is CH, CR$^e$ or N in which R$^e$ is (1–3C)alkyl, (1–2C) alkoxy or halo (and more particularly E is CH, CR$^e$ or N in which R$^e$ is (1–3C)alkyl or halo);

R$^5$ is hydrogen, halo, methyl, hydroxy or methoxy;

R$^6$ is hydrogen, hydroxy or methoxy;

X$^1$ is O, S, methylene, carbonyl or ethene-1,1-diyl;

X$^{2a}$ is methylene or O; and R$^a$ and R$^b$ are independently hydrogen or (1–3C)alkyl or the group NR$^a$R$^b$ is pyrrolidino or piperidino;

X$^{3a}$ is methylene, imino, O or S; and each R$^3$ is hydrogen or the two R$^3$ groups together form a divalent radical —(CH₂)$_s$— in which s is 3 or 4; and R$^c$ and R$^d$ are independently (1–3C)alkyl or the group NR$^c$R$^d$ is pyrrolidino, piperidino, morpholino, hexamethyleneimino or 1-imidazolyl.

A particular method in which said compound is one of formula Ia is wherein A is S; D is CH; E is CR$^e$ in which R$^e$ is methoxy; R$^5$ is hydrogen; R$^6$ is hydroxy; X$^1$ is methylene; X$^{2a}$ is O; and the group NR$^a$R$^b$ is pyrrolidino; X$^{3a}$ is O; and the two R$^3$ groups together form a divalent radical —(CH₂)$_s$— in which s is 4 and which forms a trans-1,2-cyclohexanediyl group; and R$^c$ and R$^d$ are each methyl or the group NR$^c$R$^d$ is pyrrolidino.

It will be clear that a compound of formula Ia also may be expressed as a compound of formula I or as a compound of formula I'.

An additional particular aspect of the above method is one wherein said compound of formula I is one which may be denoted as a compound of formula Ib

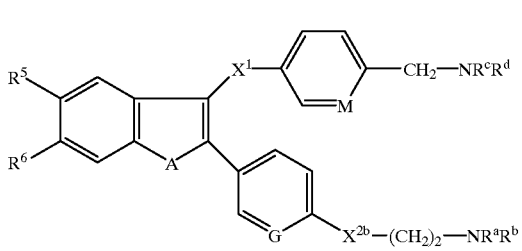

wherein

A is S, —CH=CH— or —CH₂—CH₂—;

G is CH, CR$^k$ or N in which R$^k$ is methyl, hydroxy or methoxy;

M is CH, CR$^m$ or N in which R$^m$ is (1–3C)alkyl, (1–2C) alkoxy or halo;

R$^5$ is hydrogen, halo, methyl, hydroxy or methoxy;

R$^6$ is hydrogen, hydroxy or methoxy;

X$^1$ is O, S, methylene, carbonyl or ethene-1,1-diyl;

X$^{2b}$ is a direct bond or O; and R$^a$ and R$^b$ are independently hydrogen or (1–3C)alkyl or the group NR$^a$R$^b$ is pyrrolidino or piperidino; and R$^c$ and R$^d$ are independently (1–3C)alkyl or the group NR$^c$R$^d$ is 2-(hydroxymethyl)-1-pyrrolidinyl, 2-(methoxymethyl)-1-pyrrolidinyl, pyrrolidino, piperidino or morpholino.

A more particular method in which said compound is one of formula Ib is wherein A is S; G is CH or N; M is CH, CR$^m$ or N in which R$^m$ is methyl, methoxy, chloro or bromo; R$^5$ is hydrogen; R$^6$ is hydroxy; X$^1$ is methylene; X$^{2b}$ is a direct bond or O; the group NR$^a$R$^b$ is pyrrolidino; and R$^c$ and R$^d$ are each methyl or the group NR$^c$R$^d$ is 2-(hydroxymethyl)-1-pyrrolidinyl, 2-(methoxymethyl)-1-pyrrolidinyl, pyrrolidino or morpholino.

A further particular aspect of any of the above methods is one wherein said compound is one in which X$^1$ is methylene.

A further particular aspect of any of the above methods (in which the radical —(CH₂)$_s$— is present) is one wherein said compound is one in which s is 4.

Another particular aspect of any of the above methods is one wherein said compound is one in which A is S.

A further particular aspect of any of the above methods is one wherein said compound is a compound of formula I in which R$^1$ denotes a hydroxy substituent at the position corresponding to the 6-position of a benzo[b]thiophene or a compound of formula Ia or of formula Ib in which R$^5$ is hydrogen and R$^6$ is hydroxy.

A selected aspect of the above methods is one in which said compound is a compound of formula Ia in which A is S, D is CH or N, E is CH or N, R$^5$ is hydrogen, R$^6$ is hydroxy, the group —X$^{2a}$—(CH₂)₂—NR$^a$R$^b$ is 2-(1-pyrrolidinyl)ethoxy, and the group —X$^{3a}$—CHR$^3$—CHR$^3$—NR$^c$R$^d$ is 3-(1-pyrrolidinyl)propyl 2-(1-pyrrolidinyl)ethoxy, trans-2-(1-pyrrolidinyl)cyclohexyloxy or trans-2-(1-piperidyl)cyclohexyloxy.

A preferred method of the invention includes one wherein said compound of formula I is one of those described herein at Examples 123, 124 and 164.

The present invention also provides a method of inhibiting coagulation in a mammal comprising administering to a mammal in need of treatment, a coagulation inhibiting dose of a thrombin inhibiting compound of formula I having any of the above definitions.

The present invention further provides a method of inhibiting thrombin comprising administering to a mammal in need of treatment, a thrombin inhibiting dose of a thrombin inhibiting compound of formula I having any of the above definitions.

Further, the present invention provides a method of treating a thromboembolic disorder comprising administering to a mammal in need of treatment, an effective dose of a thrombin inhibiting compound of formula I having any of the above definitions.

In addition, there is provided the use of a thrombin inhibiting compound of formula I having any of the above definitions for the manufacture of a medicament for treatment of a thromboembolic disorders.

As a further aspect of the invention, there is provided a prodrug (or a pharmaceutically acceptable salt thereof) of any of the above described thrombin inhibiting compounds of formula I which will form a prodrug. A compound of formula I (or formula Ia or formula Ib) which will form a prodrug includes one in which R$^1$ (or R$^5$ or R$^6$) or a substituent on A$^2$ or A$^3$ is hydroxy, carbamoyl, aminomethyl or hydroxymethyl, or one in which one or both of R$^a$ and R$^b$ is hydrogen or the group $NR^aR^b$ includes a hydroxymethyl group, or one in which $R^2$ is hydroxy, or one in which one or both of $R^c$ and $R^d$ is hydrogen or the group $NR^cR^d$ includes a hydroxymethyl group. Particular compounds of formula I (or formula Ia) which will form a prodrug include those in which $R^1$ (or $R^5$ or $R^6$) is hydroxy, carbamoyl, aminomethyl or hydroxymethyl or in which one or both of $R^a$ and $R^b$ is hydrogen. (It will be recognized that a thrombin inhibiting compound of formula I also may serve as a prodrug for a different thrombin inhibiting compound of formula I).

As an additional feature of the invention there is provided a pharmaceutical formulation comprising in association with a pharmaceutically acceptable carrier, diluent or excipient, a prodrug of a thrombin inhibiting compound of formula I (or of a pharmaceutically acceptable salt thereof) as provided in any of the above descriptions.

Certain diamine compounds corresponding to formula I are included in the generic disclosure of U.S. Pat. No. 4,133,814; issued to Jones et al., as antifertility agents. Weak antifertility activity is described therein for the compound 2-[4-(2-pyrrolidinoethoxy)phenyl]-3-[4-(2-pyrrolidinoethoxy)benzoyl]-benzo[b]thiophene (isolated as its dicitrate salt). The remaining thrombin inhibiting compounds of formula I are believed to be novel and, thus, to constitute an additional aspect of the invention. Thus, according to the invention there is provided a novel compound of formula I (or a pharmaceutically acceptable salt thereof)

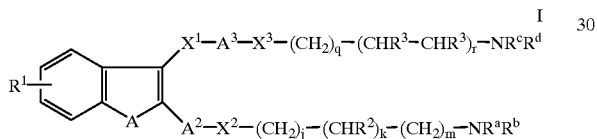

I wherein

A is O, S, —CH=CH— or —CH$_2$—CH$_2$—;

$A^2$ is an aromatic or heteroaromatic divalent radical selected from para-phenylene, a 6-membered ring heteroaromatic divalent radical containing 1 or 2 ring nitrogens in which the valences are in the 1,4- or 2,5- or 3,6- relationship, and a 5-membered ring heteroaromatic divalent radical containing one oxygen or sulfur ring atom and 0, 1 or 2 ring nitrogens in which the valences are in the 2,5- (or 3,5-) relationship and which divalent radical may bear a hydroxymethyl, benzyloxymethyl, (1–3C)alkyl, (1–2C)alkoxy, hydroxy or halo substituent;

$A^3$ is an aromatic or heteroaromatic divalent radical selected from para-phenylene, a 6-membered ring heteroaromatic divalent radical containing 1 or 2 ring nitrogens in which the valences are in the 1,4- or 2,5- or 3,6- relationship, and a 5-membered ring heteroaromatic divalent radical containing one oxygen or sulfur ring atom and 0, 1 or 2 ring nitrogens in which the valences are in the 2,5- (or 3,5-) relationship and which divalent radical may bear one or two substituents independently selected from dimethylamino, (1–4C) alkyl, halo, trifluoromethyl, (1–2C)alkoxy, hydroxy, cyano, aminomethyl, nitro, —NHCH$_2$R$^f$, —NHC(O)R$^f$ or —NHS(O)$_2$R$^g$ in which R$^f$ is hydrogen or (1–2C) alkyl and R$^g$ is (1–2C)alkyl or phenyl;

$R^1$ denotes 0, 1 or 2 substituents on the benz-ring independently selected from halo, methyl, ethyl, hydroxy, methoxy, carbamoyl, aminomethyl and hydroxymethyl;

$X^1$ is O, S, methylene, carbonyl or ethene-1,1-diyl;

(a) $X^2$ is imino, a direct bond, methylene, O or S; j is 0; k is 0; m is 5, 1, 2, 3 or 4; provided that when m is 1, then $X^2$ is a direct bond; and $R^a$ and $R^b$ are independently hydrogen or (1–3C)alkyl or the group $NR^aR^b$ is 1-imidazolyl, 1-pyrazolyl, N-(1,2,4-triazolyl), neopentylamino, (cyclohexylmethyl)amino, benzylamino, (3-pyridylmethyl)amino, (2,3-dihydroxypropyl) amino, (1-iminoethyl) amino, 2-(hydroxymethyl)-1-pyrrolidinyl, 2-(methoxymethyl)-1-pyrrolidinyl, pyrrolidino, piperidino, 2-methyl-1-piperidinyl, morpholino or hexamethyleneimino; or (b) $X^2$ is imino, O or S; j is 1; k is 1; m is 1; $R^2$ is hydroxy; and $R^a$ and $R^b$ are independently hydrogen or (1–3C) alkyl or the group $NR^aR^b$ is pyrrolidino, piperidino, morpholino or hexamethyleneimino; or (c) $X^2$ is imino, O or S; j is 1; k is 1; m is 0; $R^2$ is methyl, carboxy, hydroxymethyl or methoxycarbonyl; and $R^a$ and $R^b$ are independently hydrogen or (1–3C)alkyl; or (d) $X^2$ is imino, O or S; j is 0, 1, 2 or 3; k is 1; m is 0 or 1; provided that j and m are not both 0; $R^2$ and $R^a$ together form a diradical —(CH$_2$)$_n$— in which n is 2, 3 or 4 and the sum of m and n is 3 or 4; and $R^b$ is hydrogen or (1–3C)alkyl; or (e) $X^2$ is —NH—C(O)—; j is 0; k is 0; m is 1; and $R^a$ and $R^b$ are independently hydrogen or (1–3C)alkyl or the group $NR^aR^b$ is 1,1-dioxothiomorpholin-4-yl, pyrrolidino, piperidino, morpholino or hexamethyleneimino; and (1) $X^3$ is a direct bond, methylene, imino, O or S; q is 0, 1 or 2; and r is 0 or 1; provided that q and r are not both zero, and provided that when q is 1 and r is 0, then $X^3$ is a direct bond; each $R^3$ is hydrogen or the two $R^3$ groups together form a divalent radical —(CH$_2$)$_s$— in which s is 3 or 4; or q and r are each 1 and the group —(CHR$^3$—CHR$^3$)— is propane-2,2-diyl; and R$^c$ and $R^d$ are independently hydrogen or (1–4C)alkyl or the group $NR^cR^d$ is 1-pyrazolyl, 2-(hydroxymethyl)-1-pyrrolidinyl, 2-(methoxymethyl)-1-pyrrolidinyl, pyrrolidino, piperidino, morpholino, hexamethyleneimino, 1-imidazolyl or 4,5-dihydro-1-imidazolyl; or (2) $X^3$ is imino, O or S; q is 0; r is 1; one $R^3$ group is (1–5C)alkyl and the other $R^3$ group is independently hydrogen or (1–5C)alkyl; and R$^c$ and R$^d$ are independently hydrogen or (1–3C)alkyl or the group $NR^cR^d$ is pyrrolidino, piperidino, morpholino or hexamethyleneimino; or (3) $X^3$ is imino, O or S; q is 0, 1 or 2; r is 1; one $R^3$ group is hydrogen and the other $R^3$ group together with the group R$^c$ forms a divalent radical —(CH$_2$)$_t$— in which t is 2, 3 or 4 such that the resulting ring is a pyrrolidine or piperidine; and R$^d$ is hydrogen or (1–3C)alkyl; or (4) $X^3$ is —N(Rh)—; q is 0; r is 1; the $R^3$ group on the carbon bonded to $X^3$ and the group R$^h$ together form a diradical —(CH$_2$)$_3$—; the other $R^3$ group is hydrogen; and R$^c$ and R$^d$ are independently (1–3C)alkyl or the group $NR^cR^d$ is pyrrolidino, piperidino, morpholino or hexamethyleneimino; or (5) $X^3$ is ethene-1,2-diyl or ethyne-1,2-diyl; q is 1; r is 0; and R$^c$ and R$^d$ are independently (1–3C)alkyl or the group $NR^cR^d$ is pyrrolidino, piperidino, morpholino or hexamethyleneimino;

provided that the compound is not one in which A is S; $A^2$ is para-phenylene; $A^3$ is para-phenylene; $R^1$ denotes zero substituents on the benz-ring or $R^1$ denotes a hydroxy or methoxy substituent at the 6-position of the benzo[b]thiophene ring; $X^1$ is carbonyl; $X^2$ is O; j and k are both 0, the group —$(CH_2)_m$— is ethylene; $R^a$ and $R^b$ are independently (1–3C)alkyl or the group $NR^aR^b$ is pyrrolidino, piperidino, morpholino or hexamethyleneimino; $X^3$ is O; the group —$(CH_2)_q$—$(CHR^3$—$CHR^3)_r$— is ethylene; and $R^c$ and $R^d$ are independently (1–3C)alkyl or the group $NR^cR^d$ is pyrrolidino, piperidino, morpholino or hexamethyleneimino.

One particular novel compound of formula I, or a pharmaceutically acceptable salt thereof, is one wherein A is S, —CH=CH— or —$CH_2$—$CH_2$—;

$A^2$ is an aromatic or heteroaromatic divalent radical selected from para-phenylene, a 6-membered ring heteroaromatic divalent radical containing 1 or 2 ring nitrogens and a 5-membered ring heteroaromatic divalent radical containing one oxygen or sulfur ring atom and 0, 1 or 2 ring nitrogens in which heteroaromatic divalent radical the valences are in the 1,4- or 2,5- or 3,6- relationship and which divalent radical may bear a methyl, hydroxy or methoxy substituent (and more particularly, which divalent radical does not bear a substituent);

$A^3$ is an aromatic or heteroaromatic divalent radical selected from para-phenylene, a 6-membered ring heteroaromatic divalent radical containing 1 or 2 ring nitrogens and a 5-membered ring heteroaromatic divalent radical containing one oxygen or sulfur ring atom and 0, 1 or 2 ring nitrogens in which heteroaromatic divalent radical the valences are in the 1,4- or 2,5- or 3,6- relationship and which divalent radical may bear a (1–3C)alkyl, (1–2C)alkoxy or halo substituent (and more particularly, which divalent radical may bear a (1–3C)alkyl or halo substituent);

$R^1$ denotes 0, 1 or 2 substituents on the benz-ring independently selected from halo, methyl, ethyl, hydroxy, methoxy, carbamoyl, aminomethyl and hydroxymethyl;

$X^1$ is O, S, methylene, carbonyl or ethene-1,1-diyl;

$X^2$ is a direct bond, methylene, O or S; j and k are both 0; m is 1, 2, 3 or 4; provided that when m is 1, then $X^2$ is a direct bond; and $R^a$ and $R^b$ are independently hydrogen or (1–3C)alkyl or the group $NR^aR^b$ is pyrrolidino, piperidino, morpholino or hexamethyleneimino;

$X^3$ is a direct bond, methylene, imino, O or S; q is 0, 1 or 2; and r is 0 or 1; provided that q and r are not both zero, and provided that when q is 1 and r is 0, then $X^3$ is a direct bond; each $R^3$ is hydrogen or the two $R^3$ groups together form a divalent radical —$(CH_2)_s$— in which s is 3 or 4; and $R^c$ and $R^d$ are independently (1–3C)alkyl or the group $NR^cR^d$ is pyrrolidino, piperidino, morpholino, hexamethyleneimino or 1-imidazolyl.

A particular novel compound of formula I as described above is one in which

A is S, —CH=CH— or —$CH_2$—$CH_2$—;

$A^2$ is para-phenylene which may bear a substituent $R^j$ ortho to the group $X^2$ and $R^j$ is methyl, hydroxy or methoxy or $A^2$ is pyridine-2,5-diyl in which the 2-position is joined to $X^2$ (and more particularly, which divalent radical does not bear a substituent);

$A^3$ is para-phenylene which may bear a substituent $R^e$ ortho to the group $X^3$ and $R^e$ is (1–3C)alkyl, (1–2C) alkoxy or halo or $A^3$ is pyridine-2,5-diyl in which the 2-position is joined to $X^3$ (and more particularly, $R^e$ is (1–3C)alkyl or halo);

$R^1$ denotes 0, 1 or 2 substituents on the benz-ring independently selected from halo, methyl, ethyl, hydroxy, methoxy, carbamoyl, aminomethyl and hydroxymethyl;

$X^1$ is O, S, methylene, carbonyl or ethene-1,1-diyl;

$X^2$ is a direct bond, methylene, O or S; j and k are both 0; m is 1, 2, 3 or 4; provided that when m is 1, then $X^2$ is a direct bond; and $R^a$ and $R^b$ are independently hydrogen or (1–3C)alkyl or the group $NR^aR^b$ is pyrrolidino, piperidino or morpholino;

$X^3$ is a direct bond, methylene, imino, O or S; q is 0, 1 or 2; and r is 0 or 1; provided that q and r are not both zero, and provided that when q is 1 and r is 0, then $X^3$ is a direct bond; each $R^3$ is hydrogen or the two $R^3$ groups together form a divalent radical —$(CH_2)_s$— in which s is 3 or 4; and $R^c$ and $R^d$ are independently (1–3C)alkyl or the group $NR^cR^d$ is pyrrolidino, piperidino, morpholino, hexamethyleneimino or 1-imidazolyl.

A more particular novel compound of the invention is a compound of formula Ia

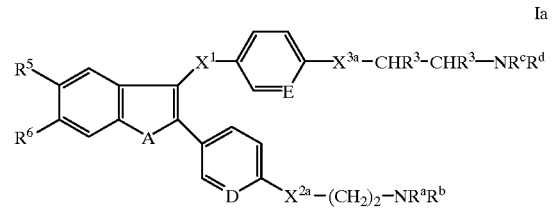

Ia wherein

A is S, —CH=CH— or —$CH_2$—$CH_2$—;

D is CH, $CR^j$ or N in which $R^j$ is methyl, hydroxy or methoxy (and more particularly D is CH or N);

E is CH, $CR^e$ or N in which $R^e$ is (1–3C)alkyl, (1–2C) alkoxy or halo (and more particularly E is CH, $CR^e$ or N in which $R^e$ is (1–3C)alkyl or halo);

$R^5$ is hydrogen, halo, methyl, hydroxy or methoxy;

$R^6$ is hydrogen, hydroxy or methoxy;

$X^1$ is O, S, methylene, carbonyl or ethene-1,1-diyl;

$X^{2a}$ is methylene or O; and $R^a$ and $R^b$ are independently hydrogen or (1–3C)alkyl or the group $NR^aR^b$ is pyrrolidino or piperidino;

$X^{3a}$ is methylene, imino, O or S; and each $R^3$ is hydrogen or the two $R^3$ groups together form a divalent radical —$(CH_2)_s$— in which s is 3 or 4; and $R^c$ and $R^d$ are independently (1–3C)alkyl or the group $NR^cR^d$ is pyrrolidino, piperidino, morpholino, hexamethyleneimino or 1-imidazolyl;

provided that the compound is not one in which A is S; D is CH; E is CH; $R^5$ is hydrogen, $R^6$ is hydrogen, hydroxy or methoxy; $X^1$ is carbonyl; $X^{2a}$ is O; $R^a$ and $R^b$ are independently (1–3C)alkyl or the group $NR^aR^b$ is pyrrolidino or piperidino; $X^{3a}$ is O; each $R^3$ is hydrogen; and $R^c$ and $R^d$ are independently (1–3C) alkyl or the group $NR^cR^d$ is pyrrolidino, piperidino, morpholino or hexamethylenemino.

A particular novel compound of formula Ia is one wherein A is S; D is CH; E is $CR^e$ in which $R^e$ is methoxy; $R^5$ is hydrogen; $R^6$ is hydroxy; $X^1$ is methylene; $X^{2a}$ is O; and the group $NR^aR^b$ is pyrrolidino; $X^{3a}$ is O; and the two $R^3$ groups together form a divalent radical —$(CH_2)_s$— in which s is 4 and which forms a trans-1,2-cyclohexanediyl group; and $R^c$ and $R^d$ are each methyl or the group $NR^cR^d$ is pyrrolidino.

An additional particular novel compound of formula I is one which may be denoted as a compound of formula Ib

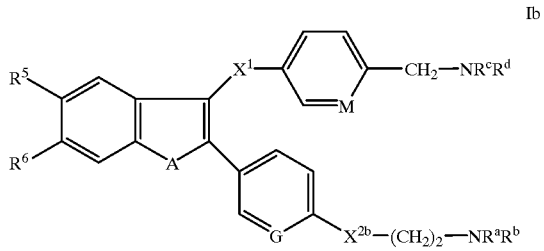

wherein

A is S, —CH=CH— or —CH$_2$—CH$_2$—;

G is CH, $CR^k$ or N in which $R^k$ is methyl, hydroxy or methoxy;

M is CH, $CR^m$ or N in which $R^m$ is (1–3C)alkyl, (1–2C) alkoxy or halo;

$R^5$ is hydrogen, halo, methyl, hydroxy or methoxy;

$R^6$ is hydrogen, hydroxy or methoxy;

$X^1$ is O, S, methylene, carbonyl or ethene-1,1-diyl;

$X^{2b}$ is a direct bond or O; and $R^a$ and $R^b$ are independently hydrogen or (1–3C)alkyl or the group $NR^aR^b$ is pyrrolidino or piperidino; and $R^c$ and $R^d$ are independently (1–3C)alkyl or the group $NR^cR^d$ is 2-(hydroxymethyl)-1-pyrrolidinyl, 2-(methoxymethyl)-1-pyrrolidinyl, pyrrolidino, piperidino or morpholino.

A more particular novel compound is one of formula Ib is wherein A is S; G is CH or N; M is CH, $CR^m$ or N in which $R^m$ is methyl, methoxy, chloro or bromo; $R^5$ is hydrogen; $R^6$ is hydroxy; $X^1$ is methylene; $X^{2b}$ is a direct bond or O; the group $NR^aR^b$ is pyrrolidino; and $R^c$ and $R^d$ are each methyl or the group $NR^cR^d$ is 2-(hydroxymethyl)-1-pyrrolidinyl, 2-(methoxymethyl)-1-pyrrolidinyl, pyrrolidino or morpholino.

A further particular novel compound of the invention is any of the above novel compounds wherein $X^1$ is methylene.

A further particular novel compound of the invention is any of the above novel compounds wherein s is 4.

Another particular novel compound of the invention is any of the above novel compounds wherein A is S.

A further particular novel compound of the invention is any of the above novel compounds wherein said compound is a compound of formula I in which $R^1$ denotes a hydroxy substituent at the position corresponding to the 6-position of a benzo[b]thiophene or a compound of formula Ia or of formula Ib in which $R^5$ is hydrogen and $R^6$ is hydroxy.

A selected novel compound of the above novel compounds is a compound of formula Ia in which A is S, D is CH or N, E is CH or N, $R^5$ is hydrogen, $R^6$ is hydroxy, the group —$X^{2a}$—(CH$_2$)$_2$—$NR^aR^b$ is 2-(1-pyrrolidinyl)ethoxy, and the group —$X^{3a}$—CHR$^3$—CHR$^3$—$NR^cR^d$ is 3-(1-pyrrolidinyl)propyl, 2-(1-pyrrolidinyl)ethoxy, trans-2-(1-pyrrolidinyl)cyclohexyloxy or trans-2-(1-piperidyl) cyclohexyloxy.

A preferred novel compound of the invention includes one wherein said compound of formula I is one of those described herein at Examples 123, 124 and 164.

A pharmaceutically acceptable salt of an antithrombotic diamine of the instant invention includes one which is an acid-addition salt made with an acid which provides a pharmaceutically acceptable anion. Thus, an acid additon salt of a novel compound of formula I as provided above made with an acid which affords a pharmaceutically acceptable anion provides a particular aspect of the invention. Examples of such acids are provided hereinbelow.

As an additional aspect of the invention there is provided a pharmaceutical formulation comprising in association with a pharmaceutically acceptable carrier, diluent or excipient, a novel compound of formula I (or a pharmaceutically acceptable salt thereof) as provided in any of the above descriptions.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted.

It will be appreciated that certain compounds of formula I (or salts or prodrugs, etc.) (such as when $R^3$ is not hydrogen) may exist in, and be isolated in, isomeric forms, including cis- or trans-isomers, as well as optically active, racemic, or diastereomeric forms. It is to be understood that the present invention encompasses a compound of formula I as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against thrombin, it being well known in the art how to prepare or isolate particular forms and how to determine inhibitory properties against thrombin by standard tests including those described below.

In addition, a compound of formula I (or salt or prodrug, etc.) may exhibit polymorphism or may form a solvate with water or an organic solvent. The present invention also encompasses any such polymorphic form, any solvate or any mixture thereof.

Particular values are listed below for radicals, substituents, and ranges, for illustration only, and they do not exclude other defined values or other values within defined ranges for the radicals and substituents.

A particular value for a (1–2C)alkyl group is methyl or ethyl; for a (1–3C)alkyl group is methyl, ethyl, propyl or isopropyl; for a (1–4C)alkyl group is methyl, ethyl, propyl, isopropyl or butyl; for a (1–5C)alkyl group is methyl, ethyl, propyl, isopropyl, butyl or pentyl; and for a (1–2C)alkoxy group is methoxy or ethoxy.

A particular value for $A^2$ or $A^3$ when it is a 6-membered ring heteroaromatic divalent radical is pyridin-2,5-diyl, pyridazin-3,6-diyl, pyrazin-2,5-diyl, or pyrimidin- 2,5-diyl (and more particularly, pyridin-2,5-diyl or pyrazin-2,5-diyl; especially pyridin-2,5-diyl). A particular value for $A^2$ or $A^3$ when it is a 5-membered ring heteroaromatic divalent radical is furan-2,5-diyl, thiophen-2,5-diyl, oxazol-2,5-diyl, thiazol-2,5-diyl, isoxazol-3,5-diyl, isothiazol-3,5-diyl, 1,3, 4-oxadiazol-2,5-diyl or 1,3,4-thiadiazol-2,5-diyl (and more particularly, isoxazol-3,5-diyl).

A compound of formula I may be made by processes which include processes known in the chemical art for the production of known compounds of formula I or of structurally analogous compounds or by a novel process described herein. A process for a novel compound of formula I (or a pharmaceutically acceptable salt thereof), novel processes for a compound of formula I and novel intermediates for the manufacture of a compound of formula I as defined above provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

Thus, there is provided a process for preparing a novel compound of formula I (or a pharmaceutically acceptable salt thereof) as provided in any of the above descriptions which is selected from:

(A) For a compound of formula I in which $X^1$ is ethene-1,1-diyl, methylenation of a corresponding compound of formula I in which $X^1$ is carbonyl. The methylenation conveniently is carried out using methylidenetriphenylphosphorane generated in situ from methylidenetriphenylphosphonium bromide and a strong base such as potassium tert-butoxide in an inert solvent such as tetrahydrofuran in a manner similar to that described in Example 12, Part A, for the preparation of an intermediate compound.

(B) For a compound of formula I (or formula Ia or formula Ib) in which $X^1$ is methylene, reductive removal of the hydroxy group of a corresponding alcohol of formula II (or formula IIa or formula IIb).

(C) For a compound of formula I in which A is O or S and $X^1$ is carbonyl, acylation of a corresponding compound of formula III

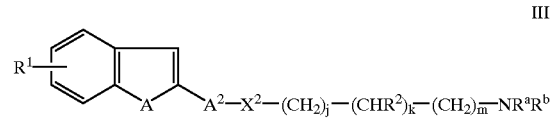

III with an activated derivative of a corresponding acid of formula IV.

Conveniently, the acylation is carried out using the hydrochloride salt of the acid chloride of the acid formula IV and a catalyst such as aluminium chloride in a manner similar to that described in Example 1, Part C or titanium tetrachloride in a manner similar to that described in Example 2, Part C.

(D) For a compound of formula I in which A is —CH═CH—, selective dehydrogenation of a corresponding compound in which A is —CH$_2$—CH$_2$—, for example using 2,3-dichloro-5,6-dicyano-1,4-benzoquinone (DDQ) at 50° C. to 100° C. in an inert solvent such as dioxane.

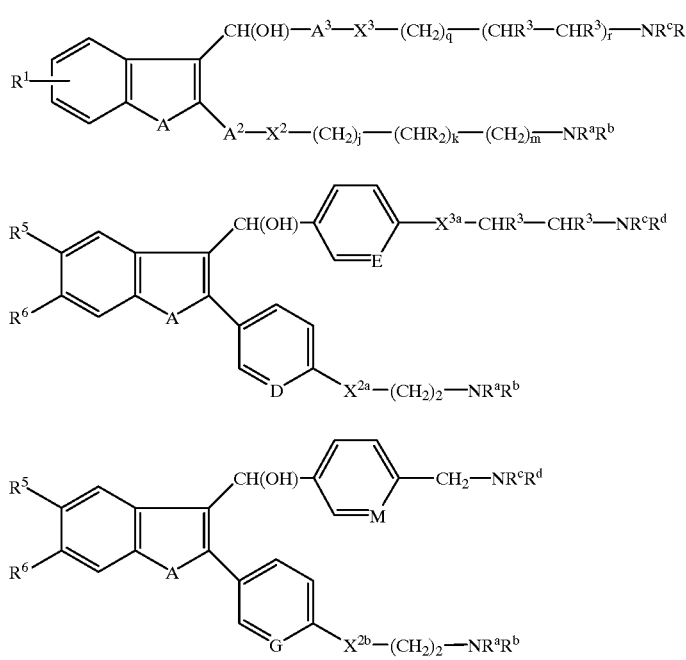

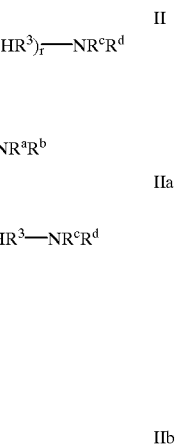

The reductive removal conveniently is carried out using sodium borohydride in trifluoroacetic acid in a manner similar to that described in Example 2, Part D, or using triethylsilane in trifluroracetic acid in a manner similar to that described in Example 3, Part E. An intermediate alcohol of formula II (or formula IIa or formula IIb) provides an additional feature of the invention; it may be obtained by reducing the carbonyl group of a corresponding ketone of formula I (or formula Ia or formula Ib) in which $X^1$ is carbonyl, for example by using lithium aluminium hydride in tetrahydrofuran in a manner similar to that described in Example 2, Part D, or Example 3, Part E or by using diisobutylaluminium hydride in tetrahydrofuran in a manner similar to that described in Example 32, Part A.

(E) For a compound of formula I in which A is —CH$_2$—CH$_2$— and $X^2$ is carbonyl, condensation of a corresponding compound of formula V

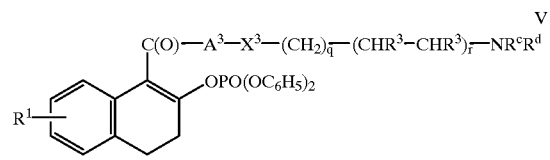

with a corresponding reagent of formula VI;

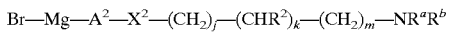

for example, in an inert solvent such as tetrahydrofuran at about 0° C.

(F) For a compound of formula I in which $X^1$ is O, cross coupling a corresponding compound of formula VII

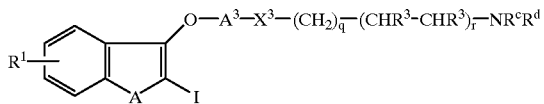

with a corresponding boronic acid of formula VIII;

for example, using a similar procedure to that described in Example 11, Part D for the preparation of an intermediate compound in which A is S.

(G) For a compound of formula I in which $X^1$ is O or S, treatment of a corresponding organolithium compound of formula IX

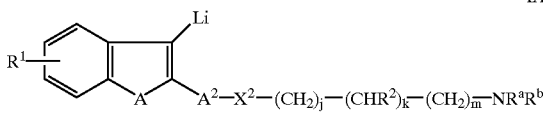

with a corresponding disulfide of formula X;

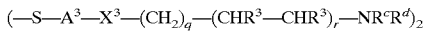

for example, using a similar procedure to that described in Example 10, Part B for the preparation of an intermediate compound in which A is S.

(H) For a compound of formula I in which $R^1$ or a substituent on $A^2$ or $A^3$ is hydroxy, removal of the O-methyl group of a corresponding compound of formula I in which $R^1$ or a substituent on $A^2$ or $A^3$ is methoxy. The removal may be carried out by any conventional manner consistent with the structure of the compound of formula I, for example, using aluminium chloride and ethanethiol in an inert solvent as described in Example 1, Part D.

(I) For a compound of formula I in which $X^2$ is O or S, alkylation at $X^2$ of a corresponding compound of formula XI

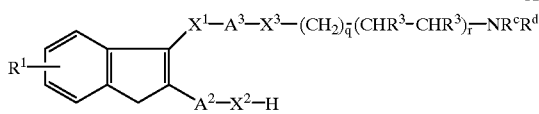

in which $X^2$ is O or S with a corresponding compound of formula XII

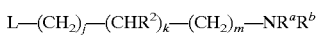

in which L denotes a leaving group. It may be preferred to generate the leaving group of the compound of formula XII in situ from the corresponding hydroxy compound and perform the alkylation under Mitsunobu conditions using triphenylphosphine and diethyl azodicarboxylate in an inert solvent, for example, as described in Example 4, Part B for the preparation of an intermediate compound. Alternatively, a compound of formula XII in which L is chloro, bromo, iodo or a sulfonate, such as methanesulfonate or p-toluenesulfonate, may be used, preferably in conjunction with a base such as cesium carbonate, using a similar procedure to that described in Example 3, Part D, for example as described in Example 5, Part C.

(J) For a compound of formula I in which $X^3$ is O or S, alkylation at $X^3$ of a corresponding compound of formula XIII

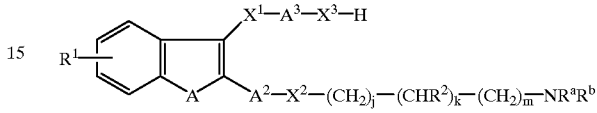

in which $X^3$ is O or S with a corresponding compound of formula XIV

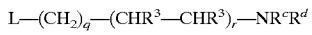

in which L denotes a leaving group as defined above. It may be preferred to generate the leaving group of the compound of formula XIV from the corresponding hydroxy compound and to perform the alkylation under Mitsunobu conditions as described above. Alternatively, L may have any of the values described above for L, and the alkylation may be carried out using a similar procedure to that described in Example 3, Part D.

(K) For a compound of formula I in which $X^2$ and $X^3$ are O or S and in which $-(CH_2)_j-(CHR^2)_k-(CH_2)_m-NR^aR^b$ is the same as $-(CH_2)_q-(CHR^3-CHR^3)_r-NR^cR^b$, dialkylation of a compound of formula XV

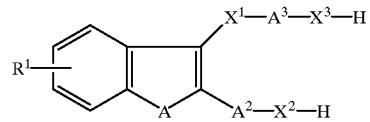

with a compound of formula XII. The dialkylation may be carried out as described above for the alkylation of a compound of formula XI or formula XIII, for example as described in Example 8, Part D or Example 10, Part D.

(L) For a compound of formula I in which $R^1$ is carbamoyl, aminolysis of a corresponding intermediate compound of formula I in which $R^1$ is a lower alkoxy-carbonyl group, such as a methoxy-carbonyl group. The aminolysis is conveniently carried out using anhydrous ammonia in a lower alcohol under pressure, for example, as described in Example 30, Part E.

(M) For a compound of formula I in which $R^1$ or a substituent on $A^3$ or the value of $-X^3-(CH_2)_q-(CHR^3-CHR^3)_r-NR^cR^b$ is aminomethyl, reduction of an intermediate compound corresponding to a compound of formula I but in which $R^1$ is cyano or of a corresponding compound of formula I in which a substituent on $A^3$ is cyano or of an intermediate compound corresponding to a compound of formula I but in which $-X^3-(CH_2)_q-(CHR^3-CHR^3)_r-NR^cR^b$ is cyano. The reduction conveniently is carried out using lithium aluminium hydride in tetrahydrofuran, for example as described in Example 31, Part D for the preparation of an intermediate alcohol of formula II in which $R^1$ is aminomethyl or as described in Example 162.

(N) For a compound of formula I in which $R^1$ or $R^2$ is hydroxymethyl, reduction of a corresponding intermediate compound of formula I in which $R^1$ or $R^2$ is a lower alkoxycarbonyl group, such as a methoxy-carbonyl group. The reduction is conveniently carried out using diisobutylaluminium hydride in toluene and tetrahydrofuran, for example, as described in Example 32, Part A for the preparation of an intermediate alcohol of formula II in which $R^1$ is hydroxymethyl or as described in Example 168.

(O) For a compound of formula I in which $A^3$ is pyridine-2,5-diyl in which the 2-position is joined to $X^3$ and $X^3$ is O, displacement of the leaving group L of a corresponding compound of formula XVI,

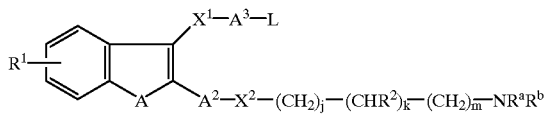

XVI in which L is defined as above, with an alkali metal alkoxide of an alcohol of formula XVII,

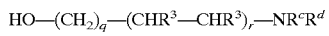

XVII for example with the sodium alkoxide. The reaction is conveniently carried out with a compound of formula XVI in which L is chloro and the sodium alkoxide derived from an alcohol of formula XVII using conditions described in Example 9, Part B and further illustrated in Example 33, Part B.

(P) For a compound of formula I in which $A^3$ bears a (1–4C)alkyl substituent, substitution of the bromo group of a corresponding compound of formula I in which $A^3$ bears a bromo substituent. The substitution is conveniently carried out using a tetralkyltin reagent and a palladium(0) catalyst in an inert solvent, for example as described in Example 8, Part B for the preparation of an intermediate compound.

(Q) For a compound of formula I in which $X^1$ is carbonyl, condensation of a corresponding organolithium compound of formula IX with a derivative of a corresponding acid of formula IV which will provide a ketone upon condensation. Derivatives of an acid of formula IV which will provide a ketone upon condensation include the lithium salt of the acid, corresponding amides such as the N-methoxy-N-methyl amide, and the corresponding nitrile. The condensation is typically carried out in an inert, aprotic solvent, for example tetrahydrofuran, at or below ambient temperature.

(R) For a compound of formula I in which $X^1$ is carbonyl, condensation of a corresponding organolithium compound of formula XVIII

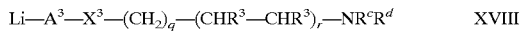

XVIII with a derivative of a corresponding acid of formula XIX

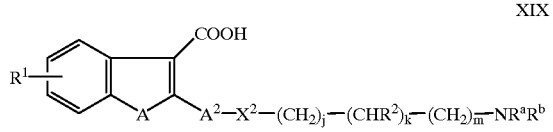

XIX which will provide a ketone upon condensation. Derivatives of an acid of formula XIX which will provide a ketone upon condensation include the lithium salt of the acid, corresponding amides such as the N-methoxy-N-methyl amide, and the corresponding nitrile. The reaction is typically carried out as described above in procedure (Q).

(S) For a compound of formula I in which A is —CH=CH— and $X^1$ is methylene, elimination of water from a corresponding compound of formula II in which A is —CH$_2$—CH$_2$—. The elimination conveniently is effected using an acid catalyst, for example by heating the compound of formula II in a solution of anhydrous ethanolic HCl.

(T) For a compound of formula I in which A is S and $X^1$ is carbonyl, condensation of a compound of formula XXV

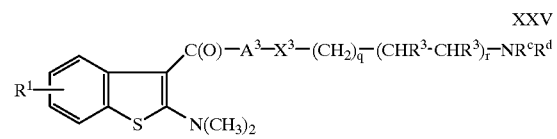

XXV with a corresponding reagent of formula VI. The condensation conveniently is carried out in an inert solvent such as tetrahydrofuran at about 0° C., for example as described in Example 34, Part B.

(U) Alkylation of an amine of formula HNR$^a$R$^b$ with a compound of formula XXVI

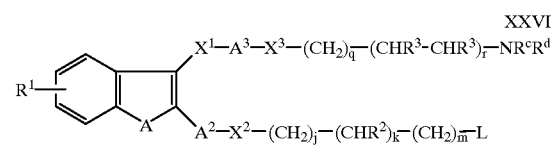

XXVI wherein L is a leaving group as defined above, or for a compound of formula I in which $R^2$ is OH, wherein L and $R^2$ form an epoxide. Conveniently, the alkylation is carried out by heating the reagents in a polar solvent, for example as described in Example 43, Part C or in Example 116, Part B.

(V) Alkylation of an amine of formula HNR$^c$R$^d$ with a compound of formula XXVII

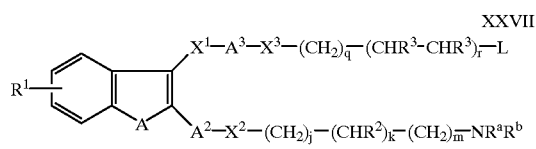

XXVII wherein L is a leaving group as defined above. Conveniently, the alkylation is carried out by mixing the reagents in a polar solvent, for example as described in Example 129, Part C.

(W) For a compound of formula I in which $X^1$ is carbonyl (particularly wherein $A^3$ is unsubstituted or substituted paraphenylene) and $X^3$ is imino, O, S or —N(R$^h$)—, substitution of the group Z wherein Z is fluoro or nitro (particularly wherein Z is fluoro) of a ketone of formula XXVIII

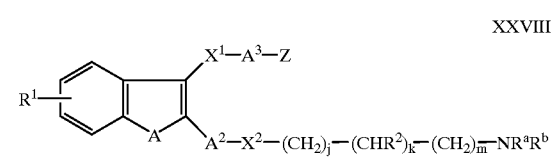

XXVIII using a compound of formula XXIX,

XXIX or a metal salt thereof, preferably an alkali metal salt. Conveniently, the substitution reaction is carried out by heating the reagents XXVIII and XXIX in dimethylformamide or tetrahydrofuran using sodium hydride or potassium carbonate, for example as illustrated in Example 59, Part B; in Example 121, Part B; in Example 145, Part C; in Example 147 or in Example 117, Part D for the preparation of an intermediate of formula XXV.

(X) For a compound of formula I in which a substituent on $A^3$ is amino, reduction of a corresponding compound of formula I in which a substituent on $A^3$ is nitro.

The reduction may be carried out using a conventional method, for example by catalytic hydrogenation as described in Example 97.

(Y) For a compound of formula I in which a substituent on $A^3$ is —NHC(O)$R^f$ or —NHS(O)$_2R^g$, substitution of the amino group of a corresponding compound of formula I in which a substituent on $A^3$ is amino using an activated derivative of an acid of formula HOC(O)$R^f$ or HOS(O)$_2R^g$. Conveniently, the activated derivative is the acid anhydride or the acid chloride, and the substitution is carried out in a polar solvent, for example as in Example 111 or Example 113.

(Z) For a compound of formula I in which a substituent on $A^3$ is —NHCH$_2R^f$ or a compound of formula I in which —(CH$_2$)$_j$—(CHR$^2$)$_k$—(CH$_2$)$_m$—NR$^aR^b$ terminates in —CH$_2$—NR$^aR^b$, reduction of the amide of a corresponding compound of formula I in which a substituent on $A^3$ is —NHC(O)$R^f$ or of an intermediate compound corresponding to a compound of formula I but in which —(CH$_2$)$_j$—(CHR$^2$)$_k$—(CH$_2$)$_m$—NR$^aR^b$ terminates in —C(O)NR$^aR^b$. The reduction conveniently is carried out using lithium aluminum hydride in tetrahydrofuran, for example as described in Example 112 or Example 166, Part E.

(AA) For a compound of formula I in which $X^3$ is ethene-1,2-diyl, reduction of the triple bond of a corresponding compound of formula I in which $X^3$ is ethyne-1,2-diyl. For a compound of formula I in which the double bond is trans-, the reduction conveniently is effected using diisobutylaluminum hydride as described in Example 130; for a compound of formula I in which the double bond is cis-, the reduction conveniently is effected using hydrogenation over a Lindlar catalyst as described in Example 131.

(AB) For a compound of formula I in which a substituent on $A^3$ is cyano, substitution of the halo group of a corresponding compound of formula I in which a substituent on $A^3$ is bromo or iodo. The substitution conveniently is effected by heating the compound with cuprous cyanide in a polar solvent such as 1-methyl-2-pyrrolidinone as described in Example 161, Part A.

Whereafter, for any of the above procedures, when a functional group is protected using a protecting group, removing the protecting group.

Whereafter, for any of the above procedures, when a pharmaceutically acceptable salt of a compound of formula I is required, it may be obtained by reacting the basic form of such a compound of formula I with an acid affording a physiologically acceptable counterion or by any other conventional procedure.

A particular process of the invention is one selected from procedures (A)–(R) above for a novel compound of formula I wherein A is S, —CH=CH— or —CH$_2$—CH$_2$—;

$A^2$ is an aromatic or heteroaromatic divalent radical selected from para-phenylene, a 6-membered ring heteroaromatic divalent radical containing 1 or 2 ring nitrogens and a 5-membered ring heteroaromatic divalent radical containing one oxygen or sulfur ring atom and 0, 1 or 2 ring nitrogens in which heteroaromatic divalent radical the valences are in the 1,4- or 2,5- or 3,6- relationship;

$A^3$ is an aromatic or heteroaromatic divalent radical selected from para-phenylene, a 6-membered ring heteroaromatic divalent radical containing 1 or 2 ring nitrogens and a 5-membered ring heteroaromatic divalent radical containing one oxygen or sulfur ring atom and 0, 1 or 2 ring nitrogens in which heteroaromatic divalent radical the valences are in the 1,4- or 2,5- or 3,6- relationship and which divalent radical may bear a (1–3C)alkyl or halo substituent;

$R^1$ denotes 0, 1 or 2 substituents on the benz-ring independently selected from halo, methyl, ethyl, hydroxy, methoxy, carbamoyl, aminomethyl and hydroxymethyl;

$X^1$ is O, S, methylene, carbonyl or ethene-1,1-diyl;

$X^2$ is a direct bond, methylene, O or S; j and k are both 0; m is 1, 2, 3 or 4; provided that when m is 1, then $X^2$ is a direct bond; and $R^a$ and $R^b$ are independently hydrogen or (1–3C)alkyl or the group NR$^aR^b$ is pyrrolidino, piperidino, morpholino or hexamethyleneimino;

$X^3$ is a direct bond, methylene, imino, O or S; q is 0, 1 or 2; and r is 0 or 1; provided that q and r are not both zero, and provided that when q is 1 and r is 0, then $X^3$ is a direct bond; each $R^3$ is hydrogen or the two $R^3$ groups together form a divalent radical —(CH$_2$)$_s$— in which s is 3 or 4; and $R^c$ and $R^d$ are independently (1–3C)alkyl or the group NR$^cR^d$ is pyrrolidino, piperidino, morpholino, hexamethyleneimino or 1-imidazolyl;

provided that the compound is not one in which A is S; $A^2$ is para-phenylene; $A^3$ is para-phenylene; $R^1$ denotes zero substituents on the benz-ring or $R^1$ denotes a hydroxy or methoxy substituent at the 6-position of the benzo[b]thiophene ring; $X^1$ is carbonyl; $X^2$ is O; the group —(CH$_2$)$_m$— is ethylene; $R^a$ and $R^b$ are independently (1–3C)alkyl or the group NR$^aR^b$ is pyrrolidino, piperidino, morpholino or hexamethyleneimino; $X^3$ is O; the group —(CH$_2$)$_q$—(CHR$^3$—CHR$^3$)$_r$— is ethylene; and $R^c$ and $R^d$ are independently (1–3C)alkyl or the group NR$^cR^d$ is pyrrolidino, piperidino, morpholino or hexamethyleneimino whereafter, for any of the procedures (A)–(R), when a pharmaceutically acceptable salt of a compound of formula I is required, it is obtained by reacting the basic form of such a compound of formula I with an acid affording a physiologically acceptable counterion or by any other conventional procedure.

As mentioned above, a compound corresponding to a compound of formula I but in which a functional group is protected may serve as an intermediate for a compound of formula I. Accordingly, such protected intermediates for a novel compound of formula I provide further aspects of the invention. Thus, as one particular aspect of the invention, there is provided a compound corresponding to a novel compound of formula I as defined above and bearing at least one substiutent $R^1$ which is hydroxy, but in which the corresponding substituent is —OR$^p$ in place of hydroxy, wherein R$^p$ is a phenol protecting group other than methyl. Phenol protecting groups are well known in the art, for example as described in T. W. Greene and P. G. M. Wuts, "Protecting Groups in Organic Synthesis" (1991). Particular values of R$^p$ include, for example, benzyl (for example as described in Example 41 or Example 81) and allyl (for example as described in Example 88). Further, $R^p$ may denote a functionalized resin, for example as disclosed in H. V. Meyers, et al., *Molecular Diversity*, (1995), 1, 13–20.

As mentioned above, the invention includes pharmaceutically acceptable salts of the thrombin inhibiting compounds defined by the above formula I. A particular diamine of this invention possesses one or more sufficiently basic functional groups to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluene sulfonic, methanesulfonic acid, oxalic acid, p-bromo phenyl sulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

If not commercially available, the necessary starting materials for the preparation of a compound of formula I may be prepared by procedures which are selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. Starting materials which are novel provide another aspect of the invention.

As noted above in procedure (B), an intermediate alcohol of formula II may be obtained by reduction of a corresponding ketone of formula I. In addition, an alcohol of formula II may be obtained by condensation of an organolithium compound of formula IX with a corresponding aldehyde of formula XX

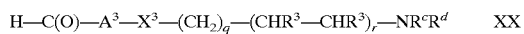

using a procedure similar to that described in procedure (Q) or by condensing an organolithium compound of formula XVIII with a corresponding aldehyde of formula XXI

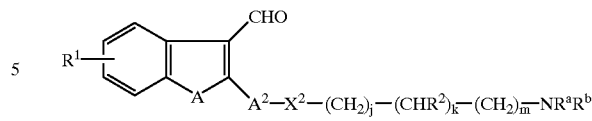

using a procedure similar to that described in procedure (R), particularly when j and k are both 0.

An intermediate of formula III may be prepared by any of a number of known procedures. A preferred method for a compound of formula III in which A is S, particularly when j and k are both 0, is the cross coupling of a boronic acid of formula XXII

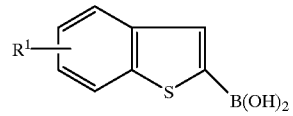

with a reagent of formula XXIII

in which X is, for example, bromo, iodo or trifluoromethanesulfonate, for example as described in Examples 1, 2, 4 and 16. For preparation of a compound of formula III in which A is O, a preferred method is a copper mediated cross coupling of a compound of formula XXIII and a 2-metalated benzofuran, such as described in Example 119, Part A. It may be preferred to cross couple a species in which the side chain is not fully elaborated, then to complete the elaboration, for example as described in Example 14 and in Example 119.

Starting material acids of formula IV may be prepared by a number of standard procedures, a number of which are described in the Examples.

Starting material enol phosphates of formula V may be prepared and used by methods similar to those described in Jones et al., *J. Med. Chem.* (1992), 35(5), 931–938; and the corresponding reagents of formula VI may be obtained by conventional methods from bromides of formula XXIII in which X is bromo.

A starting material iodide of formula VII in which A is S may be prepared in a manner similar to that described in Example 11, parts A and B, and the boronic acid of formula VIII may be obtained from a compound of formula XXIII using a procedure similar to that of Example 11, part C.

An organolithium compound of formula IX may be prepared by transmetallation of the corresponding bromide, which itself may be obtained by bromination of the compound corresponding to formula IX, but with hydrogen in the place of lithium. For a compound in which A is S, the procedure may be carried out in a manner similar to that described in Example 10, parts A and B.

A starting material of formula XI in which $X^2$ is O or S may be obtained by deprotection of $X^2$ of a corresponding compound in which $X^2$ bears a protecting group. When $X^2$ is O, it may be protected as a silyl ether, as described in Example 29, or as a methyl ether as described in several of the examples and cleaved by a variety of methods including by using pyridine hydrochloride (Example 5), aluminum chloride and ethanethiol (Examples 9, 13, 15, 17, 18, 24, 26 and 28, part C), or boron tribromide (see below).

A starting material of formula XIII in which $X^3$ is O or S may be obtained by deprotection of $X^3$ of a corresponding compound in which $X^3$ bears a protecting group. For example, when $X^3$ is O, it may be protected as a methyl ether and liberated by treatment with sodium thioethoxide (Example 28, part A), aluminum chloride and ethanethiol, or pyridine hydrochloride, depending upon the groups present in other parts of the molecule.

A starting material of formula XV in which $X^2$ and $X^3$ are O or S may be obtained by deprotection of $X^2$ and $X^3$ of a corresponding compound in which $X^2$ and $X^3$ bear protecting groups. For example, when $X^2$ and $X^3$ are both O, they may both be protected as methyl ethers and simultaneously deprotected by treatment with aluminum chloride and ethanethiol (Example 3) with boron tribromide (Examples 8 and 10) or with pyridine hydrochloride (Examples 11 and 12).

A starting material compound of formula XXV typically is prepared by acylation of a compound of formula XXIV

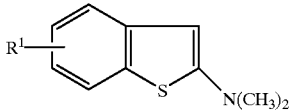

XXIV with an activated derivative of an acid of formula VI, conveniently the acid chloride, for example as described in Example 39, Part B.

Selective methods of protection and deprotection are well known in the art for preparation of compounds such as those of formula XI, XIII and XV discussed above. Selective methods for cleavage of methyl ethers, as described in the examples, are discussed in Jones, et al., *J. Med. Chem.*, (1984), 27, 1057–1066. For example, the diether 3-(4-methoxybenzoyl)-2-(4-methoxyphenyl)benzo[b]thiophene described at Example 3, part B, may be treated with boron tribromide in dichloromethane at −10° C. (1 hour) to afford the monoether 2-(4-hydroxyphenyl)-3-(4-methoxybenzoyl)benzo[b]thiophene, whereas treatment with sodium thioethoxide (Example 28, part A) affords the isomeric monoether 3-(4-hydroxybenzoyl)-2-(4-methoxyphenyl)benzo[b]thiophene. Treatment with boron tribromide under less mild conditions (0°, 6 hours, see Example 8, part C) or with aluminum chloride and ethanethiol cleaves both ethers (Example 3, part C).

The compounds of the invention are isolated best in the form of acid addition salts. Salts of the compounds of formula I formed with acids such as those mentioned above are useful as pharmaceutically acceptable salts for administration of the antithrombotic agents and for preparation of formulations of these agents. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions,* John Wiley & Sons, 1981.

The compounds of the invention are believed to selectively inhibit thrombin over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting thrombin in mammals comprising administering to a mammal in need of treatment an effective (thrombin inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in mammals comprising administering to a mammal in need of treatment an effective (coagulation inhibiting) dose of a compound of formula I.

The thrombin inhibition, coagulation inhibition and thromboembolic disorder treatment contemplated by the present method includes both medical therapeutic and/or prophylactic treatment as appropriate.

In a further embodiment the invention relates to treatment, in a human or animal, of conditions where inhibition of thrombin is required. The compounds of the invention are expected to be useful in animals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally or parenterally, e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides pharmaceutical formulations for use in the above described therapeutic method. Pharmaceutical formulations of the invention comprise an effective thrombin inhibiting amount of a compound of formula I in association with a pharmaceutically acceptable carrier, excipient or diluent. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 ml sterile glass ampoule. Another example of a unit dosage formulation comprises about 10 mg of a compound of the present invention as a pharmaceutically acceptable salt in 20 ml of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration. Another embodiment of the present invention is a pharmaceutical formulation comprising an effective amount of a novel compound of formula I or a pharmaceutically acceptable salt or solvate thereof in association with a pharmaceutically acceptable carrier, diluent or excipient therefor.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to Formula I or a pharmaceutically acceptable salt or solvate thereof.

Formulation 1: Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2: A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3: An aerosol solution is prepared containing the following components:

|  | Weight |
| --- | --- |
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C.

and transferred to a filling device. The required amount is then fed to a stainless steel container and diluted with the remainder of the propellant. The valve units are then fitted to the container.

Formulation 4: Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5: Capsules, each containing 80 mg of active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6: Suppositories, each containing 225 mg of active ingredient, are made as follows:

| Active ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7: Suspensions, each containing 50 mg of active ingredient per 5 ml dose, are made as follows:

| Active ingredient | 50 mg |
| --- | --- |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8: An intravenous formulation may be prepared as follows:

| Active ingredient | 100 mg |
| --- | --- |
| Isotonic saline | 1,000 ml |

The solution of the above ingredients generally is administered intravenously to a subject at a rate of 1 ml per minute.

The ability of the compounds of the present invention to be an effective and orally active thrombin inhibitor are evaluated in one or more of the following assays.

The compounds provided by the invention (formula I) selectively inhibit the action of thrombin in mammals. The inhibition of thrombin is demonstrated by in vitro inhibition of the amidase activity of thrombin as measured in an assay in which thrombin hydrolyzes the chromogenic substrate, N-benzoyl-L-phenylalanyl-L-valyl-L-arginyl-p-nitroanilide, N-benzoyl-L-Phe-L-Val-L-Arg-p-nitroanilide.

The assay is carried out by mixing 50 $\mu$l buffer (0.03M Tris, 0.15M NaCl, pH 7.4) with 25 $\mu$l of human thrombin solution (purified human thrombin, Enzyme Research Laboratories, South Bend, Ind., at 8 NIH units/ml) and 25 $\mu$l of test compound in a solvent (50% aqueous methanol (v:v)). Then 150 $\mu$l of an aqueous solution of the chromogenic substate (at 0.25 mg/ml) are added and the rates of hydrolysis of the substrate are measured by monitoring the reactions at 405 nm for the release of p-nitroaniline. Standard curves are constructed by plotting free thrombin concentration against hydrolysis rate. The hydrolysis rates observed with test compounds are then converted to "free thrombin" values in the respective assays by use of the standard curves. The bound thrombin (bound to test compound) is calculated by subtracting the amount of free thrombin observed in each assay from the known initial amount of thrombin used in the assay. The amount of free inhibitor in each assay is calculated by subtracting the number of moles of bound thrombin from the number of moles of added inhibitor (test compound).

The Kass value is the hypothetical equilibrium constant for the reaction between thrombin and the test compound (I).

$$\text{Thrombin} + \text{I} \rightleftharpoons \text{Thrombin} - \text{I}$$

$$\text{Kass} = \frac{[\text{Thrombin} - \text{I}]}{[(\text{Thrombin}) \times (\text{I})]}$$

Kass is calculated for a range of concentrations of test compounds and the mean value reported in units of liter per mole. In general, a thrombin inhibiting compound of formula I of the instant invention exhibits a Kass of $0.03 \times 10^6$ L/mole or much greater. For example, the compound of Example 3 was found to have a Kass of $5.0 \times 10^6$ L/mole, and the compound of Example 164 was found to have a Kass of $526 \times 10^6$ L/mole.

By substantially following the procedures described above for human thrombin, and using other human blood coagulation system serine proteases and using fibrinolytic system serine proteases, with the appropriate chromogenic substrates, identified below, the selectivity of the compounds of the present invention with respect to the coagulation factor serine proteases and to the fibronolytic serine proteases are evaluated as well as their substantial lack of interference with human plasma clot fibrinolysis.

Human factors X, Xa, IXa, XIa, and XIIa are purchased from Enzyme Research Laboratories, South Bend, Indiana; human urokinase from Leo Pharmaceuticals, Denmark; and recombinant activated Protein C (aPC) is prepared at Eli Lilly and Co. substantially according to U.S. Pat. No. 4,981,952. Chromogenic substrates: N-Benzoyl-Ile-Glu-Gly-Arg-p-nitroanilide (for factor Xa); N-Cbz-D-Arg-Gly-Arg-p-nitroanilide (for factor IXa assay as the factor Xa substrate); Pyroglutamyl-Pro-Arg-p-nitroanilide (for Factor XIa and for aPC); H-D-Pro-Phe-Arg-p-nitroanilide (for factor XIIa); and Pyroglutamyl-Gly-Arg-p-nitroanilide (for urokinase); are purchased from Kabi Vitrum, Stockholm, Sweden, or from Midwest Biotech, Fishers, Indiana. Bovine trypsin is purchased from Worthington Biochemicals, Freehold, N.J., and human plasma kallikrein from Kabi Vitrum, Stockholm, Sweden. Chromogenic substrate H-D-Pro-Phe-Arg-p-nitroanilide for plasma kallikrein is purchased from Kabi Vitrum, Stockholm, Sweden. N-Benzoyl-Phe-Val-Arg-p-nitroanilide, the substrate for human thrombin and for trypsin; is synthesized according to procedures described above for the compounds of the present invention, using known methods of peptide coupling from commercially available reactants, or purchased from Midwest Biotech, Fishers, Ind.

Human plasmin is purchased from Boehringer Mannheim, Indianapolis, Ind.; nt-PA is purchased as single chain activity reference from American Diagnostica, Greenwich, Conn.; modified-t-PA6 (mt-PA6) is prepared at Eli Lilly and Company by procedure known in the art (See, Burck, et al., *J. Biol. Chem.*, 265, 5120–5177 (1990). Plasmin chromogenic substrate H-D-Val-Leu-Lys-p-nitroanilide and tissue plasminogen activator (t-PA) substrate H-D-Ile-Pro-Arg-p-nitroanilide are purchased from Kabi Vitrum, Stockholm, Sweden.

In the chromogenic substrates described above the three-letter symbols Ile, Glu, Gly, Pro, Arg, Phe, Val, Leu and Lys are used to indicate the corresponding amino acid group isoleucine, glutamic acid, glycine, proline, arginine, phenylalanine, valine, leucine and lysine, respectively.

Thrombin inhibitors preferably should spare fibrinolysis induced by urokinase, tissue plasminogen activator (t-PA) and steptokinase. This would be important to the therapeutic use of such agents as an adjunct to streptokinase, t-PA or urokinase thrombolytic therapy and to the use of such agents as an endogenous fibrinolysis-sparing (with respect to t-PA and urokinase) antithrombotic agents. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Hazelton-LRE, Kalamazoo, Mich., U.S.A.) by venipuncture into 3.8 percent citrate. Fibrinogen is prepared from fresh dog plasma and human fibrinogen is prepared from in-date ACD human blood at the fraction I-2 according to previous procedures and specifications. Smith, *Biochem. J.*, 185, 1–11 (1980); and Smith, et al., *Biochemistry*, 11, 2958–2967, (1972). Human fibrinogen (98 percent pure/plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 µL thrombin (73 NIH unit/mL) to 100 µL human plasma which contains 0.0229 µCi 125-iodine labeled fibrinogen. Clot lysis is studied by overlaying the clots with 50 µL of urokinase or streptokinase (50, 100, or 1000 unit/mL) and incubating for 20 hours at room temperature. After incubation the tubes are centrifuged in a Beckman Microfuge. 25 µL of supernate is added into 1.0 mL volume of 0.03 M tris/0.15 M NaCl buffer for gamma counting. Counting controls 100 percent lysis are obtained by omitting thrombin (and substituting buffer). The thrombin inhibitors are evaluated for possible interference with fibrinolysis by including the compounds in the overlay solutions at 1, 5, and 10 µg/mL concentrations. Rough approximations of $IC_{50}$ values are estimated by linear extrapolations from data points to a value which would represent 50 percent of lysis for that particular concentration of fibrinolytic agent.

Anticoagulant Activity

Materials

Dog plasma and rat plasma are obtained from conscious mixed-breed hounds (either sex, hazelton-LRE, Kalamazoo, Mich., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay. For preferred compounds of the instant invention, a concentration of 30 ng/mL or less typically is sufficient to double the TT.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, Br J Pharmacol, 77:29, 1982). In this model preferred compounds of the instant invention reduce the net clot weight to approximately 25–30% of control, or even lower, at an i.v. dose of 33.176 μmol/kg/h.

FeCl$_3$ Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. FeCl$_3$ hexahydrate is dissolved in water and the concentration (20 percent) is expressed in terms of the actual weight of FeCl$_3$ only. To injure the artery and induce thrombosis, 2.85 μL is pipetted into the cuff to bathe the artery above the thermocouple probe. Arterial occlusion is indicated by a rapid drop in temperature. The time to occlusion is reported in minutes and represents the elapsed time between application of FeCl$_3$ and the rapid drop in vessel temperature (see K. D. Kurz, Thromb. Res., 60:269, 1990).

Spontaneous Thrombolysis Model

In vitro data suggests that thrombin inhibitors inhibit thrombin and, at higher concentrations, may inhibit other serine proteases, such as plasmin and tissue plasminogen activator. To assess if the compounds inhibit fibrinolysis in vivo, the rate of spontaneous thrombolysis is determined by implanting a labeled whole blood clot into the pulmonary circulation. Rat blood (1 mL) is mixed rapidly with bovine thrombin (4 IU, Parke Davis) and $^{125}$I human Fibrogen (5 μCi, ICN), immediately drawn into silastic tubing and incubated at 37° C. for 1 hour. The aged thrombus is expelled from the tubing, cut into 1 cm segments, washed 3× in normal saline and each segment is counted in a gamma counter. A segment with known counts is aspirated into a catheter that is subsequently implanted into the jugular vein. The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{\text{(injected cpm} - \text{lung cpm)}}{\text{injected cpm}} \times 100$$

The fibrinolytic dissolution of the implanted clot occurs time-dependently (see J. P. Clozel, Cardiovas. Pharmacol., 12:520, 1988).

Coagulation Parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with saline (0.1 mL) and bovine thrombin (0.1 mL, 30 U/mL in TRIS buffer; Parke Davis) at 37° C. For APTT, plasma (0.1 mL) and APTT solution (0.1 mL, Organon Teknika) are incubated for 5 minutes (37° C.) and CaCl$_2$ (0.1 mL, 0.025 M) is added to start coagulation. Assays are done in duplicate and averaged.

Index of Bioavailability

For a measure of bioactivity, plasma thrombin time (TT) serves as a substitute for the assay of parent compound on the assumption that observed increments in TT resulted from thrombin inhibition by parent only. The time course of the effect of the thrombin inhibitor upon TT is determined after i.v bolus administration to anesthetized rats and after oral treatment of fasted conscious rats. Due to limitations of blood volume and the number of points required to determine the time course from time of treatment to the time when the response returns to pretreatment values, two populations of rats are used. Each sample population represents alternating sequential time points. The average TT over the time course is used to calculate area under the curve (AUC). The index of bioavailability is calculated by the formula shown below and is expressed as percent relative activity.

The area under the curve (AUC) of the plasma TT time course is determined and adjusted for the dose. This index of bioavailability is termed "% Relative Activity" and is calculated as $$\% \text{ Relative Activity} = \frac{\text{AUCpo}}{\text{AUCiv}} \times \frac{\text{Dose iv}}{\text{Dose po}} \times 100$$

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the FeCl$_3$ model of arterial injury and in the spontaneous thrombolysis model. Bolus injection volume is 1 mL/kg for i.v., and 5 mL/kg for p.o., and infusion volume is 3 mL/hr.

Statistics

Results are expressed as means +/− SEM. One-way analysis of variance is used to detect statistically significant differences and then Dunnett's test is applied to determine which means are different. Significance level for rejection of the null hypothesis of equal means is $P<0.05$.

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66–74° F.; 45–50 percent relative humidity; and lighted from 0600–1800 hours.

Pharmacokinetic Model

Test compound is formulated immediately prior to dosing by dissolving in sterile 0.9 percent saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Surgical preparation and instrumentation of the dogs are as described in Jackson, et al., Circulation, 82, 930–940 (1990). Mixed-breed hounds (aged 6–7 months, either sex, Hazelton-LRE, Kalamazoo, Mich., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound. A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-$\mu$A direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC). Reperfusion is followed for 3 hour after administration of test compound. Reocclusion of coronary arteries after successful thrombolysis is defined as zero CBF which persisted for $\geq$30 minutes.

Hematology and Template Bleeding Time Determinations

Whole blood cell counts, hemoglobin, and hematocrit values are determined on a 40-$\mu$l sample of citrated (3.8 percent) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p<0.05$. All values are mean ±SEM. All studies are conducted in accordance with the guiding principles of the American Physiological Society. Further details regarding the procedures are described in Jackson, et al., *J. Cardiovasc. Pharmacol.*, (1993), 21, 587–599.

The following Examples are provided to further describe the invention and are not to be construed as limitations thereof.

The abbreviations, symbols and terms used in the examples have the following meanings.

Ac=acetyl
AIBN=azobisisobutyronitrile
Anal.=elemental analysis
Bn or Bzl=benzyl
Bu=butyl
n-BuLi=butyllithium
calcd=calculated
DCC=dicyclohexylcarbodiimide
DIBAL-H=diisobutyl aluminum hydride
DMF=dimethylformamide
DMSO=dimethylsulfoxide
Et=ethyl
EtOAc=ethyl acetate
$Et_3N$=triethylamine
$Et_2O$=diethyl ether
EtOH=ethanol
EtSH=ethanethiol
FAB=Fast Atom Bombardment (Mass Spectrascopy)
FDMS=field desorption mass spectrum
Hex=hexanes
HOAt=1-hydroxy-7-azabenzotriazole
HPLC=High Performance Liquid Chromatography
HRMS=high resolution mass spectrum
i-PrOH=isopropanol
IR=Infrared Spectrum
LAH=lithium aluminum hydride
Me=methyl
MeI=methyl iodide
MeOH=methanol
MPLC=Medium Pressure Liquid Chromatography
NBS=N-bromosuccinimide
NMR=Nuclear Magnetic Resonance
Ph=phenyl
PPA=polyphosphoric acid
i-Pr=isopropyl
Rochelle's Salt=potassium sodium tartrate
RPHPLC=Reversed Phase High Performance Liquid Chromatography
$SiO_2$=silica gel
SM=starting material
TBS=tert-butyldimethylsilyl
TEA=triethylamine
Temp.=temperature
TFA=trifluoroacetic acid
THF=tetrahydrofuran
TIPS=triisopropylsilyl
TLC=thin layer chromatography
triflic acid=trifluoromethanesulfonic acid Unless otherwise stated, pH adjustments and work up are with aqueous acid or base solutions. PrepLC indicates preparative liquid chromatography using "Prep Pak (TM)"

EXAMPLE 1

Preparation of 6-Hydroxy-2-[4-[2-(1-pyrrolidinyl) ethoxy]phenyl]benzo[b]thiophen-3-yl 4-[2-(1-Pyrrolidinyl)ethoxy]phenyl Ketone Dioxalate

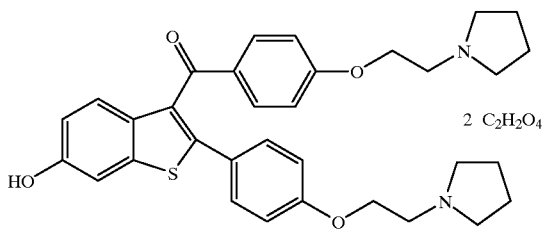

Part A. 6-Methoxybenzo[b]thiophene-2-boronic Acid

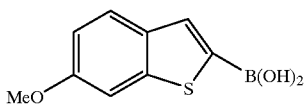

To a solution of 6-methoxybenzo[b]thiophene (Graham, S. L., et al. *J. Med. Chem.* 1989, 32, 2548–2554)(18.13 g, 0.111 mol) in 150 mL of anhydrous THF at −60° C. was added n-BuLi (76.2 mL, 0.122 mol, 1.6 M solution in hexanes), dropwise via syringe. After stirring for 30 min, triisopropyl borate (28.2 mL, 0.122 mol) was introduced via syringe. The resulting mixture was allowed to gradually warm to 0° C. and then partitioned between 1.0 N HCl and EtOAc (300 mL each). The layers were separated, and the organic phase was dried over $Na_2SO_4$. Concentration in vacuo produced a white solid that was triturated from $Et_2O$/hexanes. Filtration provided 16.4 g (71%) of 6-methoxybenzo[b]thiophene-2-boronic acid as a white solid.

mp 200° C. (dec); FDMS 208 ($M^+$; 100); $^1H$ NMR (DMSO-$d_6$) δ 8.36 (br s), 7.86–7.75 (m, 2H), 7.53 (dd, J=8.1 and 2.0 Hz, 1H), 6.98 (m, 1H), 3.82 (s, 3H).

Part B. 6-Methoxy-2-[4-[2-(1-pyrrolidinyl)ethoxy]phenyl] benzo[b]thiophene

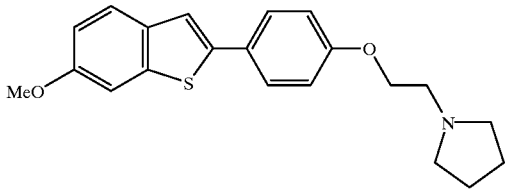

To a slurry of 6-methoxybenzo[b]thiophene-2-boronic acid (Example 1, Part A) (6.43 g, 30.9 mmol) in 310 mL of benzene was added 1-(2-(4-bromophenoxy)ethyl) pyrrolidine (5.80 mL, 28.1 mmol). Upon addition the reaction mixture turned to a yellow homogeneous solution. The reaction flask was then covered with aluminum foil to keep out light. To this was added 1.07 g (0.92 mmol) of tetrakis (triphenylphosphine)palladium(0), followed by 30 mL of 2.0 N sodium carbonate solution. The biphasic mixture was heated at 85° C. for 3 h with vigorous stirring. The mixture was cooled to 0° C. and 175 mL of brine solution was added. The layers were separated and the aqueous layer was extracted with 1.0 L of EtOAc. The combined organic layers were dried over $MgSO_4$ and concentrated under reduced pressure. The residue was purified by PrepLC (53:35:2 THF-hexanes-TEA) to afford 5.42 g (15.3 mmol, 55%) of an off-white solid.

mp 151–154° C.; $^1H$ NMR (CDCl$_3$) δ 7.61 (d, J=8.8 Hz, 1H), 7.58 (d, J=8.8 Hz, 2H), 7.33 (s, 1H), 7.29 (d, J=2.3 Hz, 1H), 6.95 (d, J=8.7 Hz, 3H), 4.18 (t, J=5.9 Hz, 2H), 3.88 (s, 3H), 2.97 (t, J=5.9 Hz, 2H), 2.71 (br t, 4H), 1.85 (m, 4H); FDMS: 353 ($M^+$); Anal. Calcd for $C_{21}H_{23}NO_2S$: C, 71.36; H, 6.56; N, 3.96. Found: C, 71.58; H, 6.35; N, 3.91.

Part C. 6-Methoxy-2-[4-[2-(1-pyrrolidinyl)ethoxy]phenyl] benzo[b]thiophen-3-yl 4-[2-(1-Pyrrolidinyl)ethoxy]phenyl Ketone Dioxalate

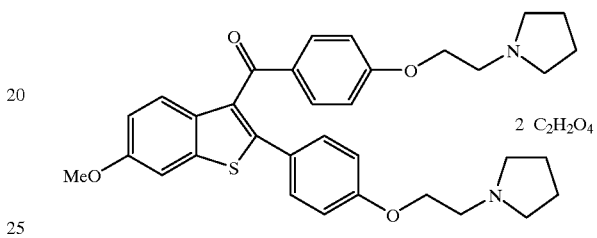

A slurry of 600 mg (2.20 mmol) of 4-[2-(1-pyrrolidinyl) ethoxy]benzoic acid hydrochloride in 20 mL of 1,2-dichloroethane and 2 drops of DMF was treated with 0.8 mL (11.0 mmol) of $SOCl_2$ and the mixture was heated to mild reflux for 2 h. The clear solution was evaporated in vacuo, the residue was re-suspended in 20 mL of 1,2-dichloroethane, and the mixture was re-concentrated. The solid was suspended in 20 mL of 1,2-dichloroethane and the mixture cooled to 0° C. 1-[2-[4-(6-Methoxybenzo[b] thiophen-2-yl)phenoxy]ethyl]pyrrolidine (part B; 650 mg, 1.97 mmol) was added to the acid chloride solution, followed by 2.10 g (15.7 mmol) of $AlCl_3$ in two portions. The mixture was stirred at 0° C. for 5 h at which time it was carefully poured into 200 mL of a 0° C. solution of saturated aq $NaHCO_3$. The mixture was extracted with EtOAc (4×100 mL). The combined organic extracts were dried over $K_2CO_3$ and evaporated in vacuo to give 735 mg of an oil. Purification by radial chromatography (SiO$_2$; 10% MeOH in $CH_2Cl_2$) afforded 330 mg (0.58 mmol; 26%) of the title compound as a viscous oil. A sample of the pure product (70 mg; 0.12 mmol) in 5 mL of EtOAc was treated with a solution of 25 mg (0.28 mmol; 2.3 eq) of oxalic acid in 3.0 mL EtOAc. The resulting solid was filtered, dried and characterized.

FDMS 571 (M+1); Anal. Calcd for $C_{34}H_{38}N_2O_4S.2C_2H_2O_4.H_2O$: C, 59.37; H, 5.77; N, 3.64. Found: C, 59.67; H, 5.56; N, 3.73.

Part D. 6-Hydroxy-2-[4-[2-(1-pyrrolidinyl)ethoxy]phenyl] benzo[b]thiophen-3-yl 4-[2-(1-Pyrrolidinyl)ethoxy]phenyl Ketone Dioxalate A 0° C. solution of 250 mg (0.45 mmol) of 6-methoxy-2-[4-[2-(1-pyrrolidinyl)ethoxy]phenyl]benzo[b]thiophen-3-yl 4-[2-(1-pyrrolidinyl)ethoxy]phenyl ketone (Part C) in 10 mL of 1,2-dichloroethane was treated with 360 mg (2.7 mmol) of $AlCl_3$, followed by 0.28 mL (3.8 mmol) of ethanethiol. The cold bath was removed and the reaction was stirred at room temperature for 10 h. The reaction mixture was poured into 200 mL of a 1:1 mixture of EtOAc and saturated aq $NaHCO_3$ with 10 mL MeOH rinse. The two layers were separated and the aqueous phase was extracted with EtOAc (3×50 mL). The combined EtOAc layers were dried over Na$_2$SO$_4$ and evaporated to give 325 mg of an oil. Purification by radial chromatography (SiO$_2$; gradient of 10% MeOH in CH$_2$Cl$_2$ to 20% MeOH and 1% TEA in CH$_2$Cl$_2$) afforded 130 mg (0.23 mmol, 52%) of an amorphous solid. The solid was converted to the dioxalate salt according to the conditions outlined in Example 1, Part C.

$^1$H NMR (DMSO-d$_6$) δ 9.77 (s, 1H), 7.63 (dd, J=8.8, 1.7 Hz, 2H), 7.31 (d, J=2.1 Hz, 1H), 7.24 (d, J=8.7 Hz, 2H), 7.19 (s, 1H), 6.95–6.79 (m, 5H) 4.05 (t, J=6.0 Hz, 2H), 3.98 (t, J=5.6 Hz, 2H), 2.78–2.63 (m, 4H), 2.53–2.37 (m, 8H) 1.66–1.57 (m, 8H); FDMS 557 (M+1; 100); Anal. Calcd for: C, 60.32; H, 5.47; N, 3.80. Found: C, 60.21; H, 5.63; N, 3.69.

EXAMPLE 2

Preparation of 1-[2-[4-[[5-Methyl-2-[4-[2-(1-pyrrolidinyl)ethoxy]phenyl]benzo[b]thiophen-3-yl]methyl]phenoxy]ethyl]pyrrolidine Dioxalate

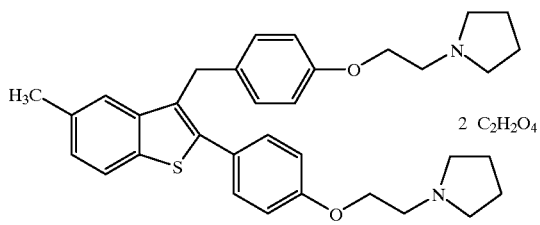

Part A. 5-Methylbenzo[b]thiophene-2-boronic Acid

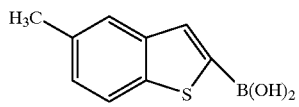

The title compound was prepared from 5-methylbenzo[b]thiophene as a white solid in 51% yield by essentially following the procedure described in Example 1, Part A.

mp>250° C.; FDMS: 192 (M$^+$).

Part B. 5-Methyl-2-[4-[2-(1-pyrrolidinyl)ethoxy]phenyl]benzo[b]thiophene

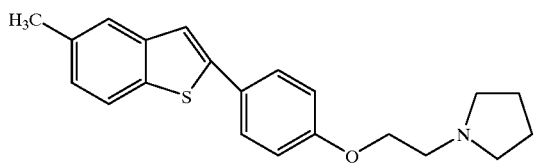

The title compound was prepared from 5-methylbenzo[b]thiophene-2-boronic acid as a light yellow solid in a 44% yield by essentially following the procedure described in Example 1, Part B.

mp 149.5–151.0° C.; FDMS 337 (M$^+$; 100); Anal. Calcd for C$_{21}$H$_{23}$NOS: C, 74.74; H, 6.87; N, 4.15. Found: C, 74.94; H, 6.82; N, 4.31.

Part C. 5-Methyl-2-[4-[2-(1-pyrrolidinyl)ethoxy]phenyl]benzo[b]thiophen-3-yl [4-[2-(1-Pyrrolidinyl)ethoxy]phenyl Ketone Dioxalate

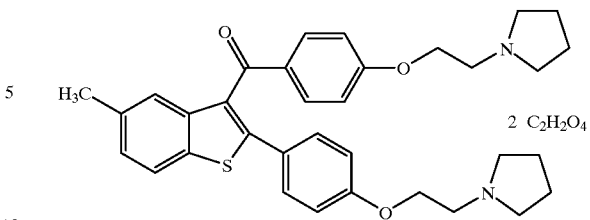

A slurry of 665 mg (2.45 mmol) of 4-[2-(1-pyrrolidinyl)ethoxy]benzoic acid hydrochloride in 20 mL of 1,2-dichloroethane and 2 drops of DMF was treated with 0.90 mL (12.3 mmol) of SOCl$_2$ and the mixture was heated to gentle reflux for 2.5 h. The resulting solution was evaporated in vacuo, the residue was re-suspended in 20 mL of 1,2-dichloroethane, and the mixture was re-concentrated. The solid was suspended in 20 mL of 1,2-dichloroethane and to this was added at 0° C. 5-methyl-2-[4-[2-(1-pyrrolidinyl)ethoxy)phenyl]benzo[b]thiophene (part B; 750 mg, 2.22 mmol). The reaction was protected from light and 1.2 mL (10.9 mmol) TiCl$_4$ was added dropwise. The reaction was stirred at 0° C. for 3 h at which time it was quenched by the careful addition of 25 mL of saturated aq NaHCO$_3$. The mixture was filtered through diatomaceous earth, and the two layers were separated. The aqueous layer was extracted with EtOAc (3×100 mL). The combined organic layers were dried over K$_2$CO$_3$ and evaporated in vacuo to give 1.34 g of crude product which was purified by radial chromatography (SiO$_2$; 10% MeOH in CH$_2$Cl$_2$) to afford 980 mg (1.77 mmol; 80%) of the title compound as a viscous oil. A 210 mg sample of this material was converted to the dioxalate salt according to the methods described in Example 1, Part C.

$^1$H NMR (DMSO-d$_6$) δ 7.98 (d, J=8.2 Hz, 1H), 7.75 (d, J=8.6 Hz, 2H), 7.40 (d, J=8.5 Hz, 2H). 7.34–7.24 (m, 2H), 7.06–6.94 (m, 4H), 4.38–4.21 (m, 4H), 3.59–3.46 (m, 4H), 3.36–3.22 (m, 8H), 2.36 (s, 3H), 1.98–1.84 (m, 8H); FDMS 555 (M+1); 645 (M+91; 100); Anal. Calcd for C$_{34}$H$_{38}$N$_2$O$_3$S.2C$_2$H$_2$O$_4$.0.5H$_2$O: C, 61.36; H, 5.83; N, 3.77. Found: C, 61.35; H, 6.04; N, 3.97.

Part D. 1-[2-[4-[[5-Methyl-2-[4-[2-(1-pyrrolidinyl)ethoxy]phenyl]benzo[b]thiophen-3-yl]methyl]phenoxy]ethyl] pyrrolidine Dioxalate A slurry of 160 mg (4.20 mmol) of LiAlH$_4$ in 20 mL THF at 0° C. was treated with a solution of 750 mg (1.35 mmol) of 5-methyl-2-[4-[2-(1-pyrrolidinyl)ethoxy]phenyl]benzo[b]thiophen-3-yl [4-[2-(1-pyrrolidinyl)ethoxy]phenyl ketone (Example 2, Part C) in 10 mL THF. The reaction was stirred at 0° C. for 2.5 h and was quenched by the sequential addition of 6 mL of H$_2$O, 6 mL of 2.0N aq NaOH, and 6 mL of H$_2$O. The mixture was filtered, the THF was evaporated in vacuo, and the resulting aqueous phase was extracted with EtOAc (2×30 mL). The combined organic layers were dried over K$_2$CO$_3$ and concentrated in vacuo. The residue was taken up in 5 mL of trifluoroacetic acid (TFA) and the mixture was cooled to 0° C. Sodium borohydride (100 mg; 2.91 mmol) was carefully added and the reaction stirred for 2 h. The mixture was evaporated in vacuo, the residue was taken up in 100 mL EtOAc, and the mixture was washed with saturated aq NaHCO$_3$ (3×50 mL). The organic layer was dried over K$_2$CO$_3$ and evaporated in vacuo to give 675 mg of an oil. Purification by radial chromatography (SiO$_2$; 10% MeOH/0.1% TEA in CH$_2$Cl$_2$) afforded 550 mg of the title compound as a light yellow oil which was converted to the dioxalate salt according the methods described in Example 1, Part C.

$^1$H NMR (DMSO-d$_6$) δ 7.85 (d, J=8.2 Hz, 1H), 7.48–7.36 (m, 3H), 7.19 (d, J=8.2 Hz, 1H). 7.10–6.96 (m, 3H), 6.91–6.80 (m, 3H), 4.17 (s, 2H), 4.11 (t, J=5.8 Hz, 2H), 3.98 (t, J=5.8 Hz, 2H), 2.81 (t, J=5.8 Hz, 2H), 2.75 (t, J=5.8 Hz, 2H), 2.36 (s, 3H), 2.58–2.44 (m, 8H), 1.78–1.60 (m, 8H); FDMS 541 (M+1; 100); Anal. Calcd for C$_{34}$H$_{40}$N$_2$O$_2$S.2C$_2$H$_2$O$_4$.0.5H$_2$O: C, 62.54; H, 6.21; N, 3.84. Found: C, 62.27; H, 6.16; N, 3.93.

EXAMPLE 3

Preparation of 1-[2-[4-[[2-[4-[2-(1-Pyrrolidinyl) ethoxy]phenyl]benzo[b]thiophen-3-yl]methyl] phenoxy]ethyl]pyrrolidine Dioxalate

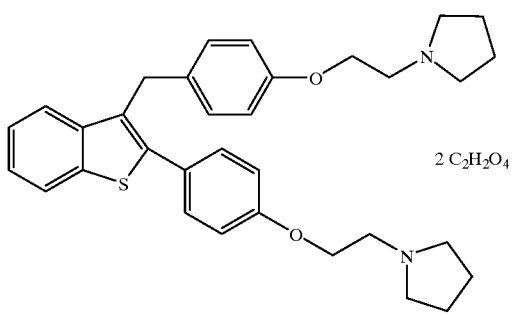

Part A. 2-(4-Methoxyphenyl)benzo[b]thiophene

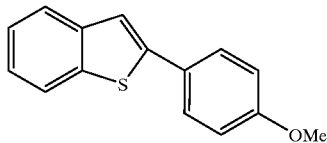

The title compound was prepared in 91% yield from benzo[b]thiophene-2-boronic acid and 4-bromoanisole by essentially following the procedure detailed Example 1, Part B.

mp 188–191° C.; $^1$H NMR (DMSO-d$_6$) δ 7.94 (d, J=8.0 Hz, 1H), 7.81 (d, J=7.0 Hz, 1H), 7.73 (m, 2H). 7.71 (s, 1H), 7.35 (m, 2H), 7.05 (d, J=8.0 Hz, 2H), 3.82 (s, 3H); FDMS 240 (M$^+$; 100); Anal. Calcd for C$_{21}$H$_{23}$NO$_2$S: C, 71.36; H, 6.56; N, 3.86. Found: C, 71.46; H, 6.60; N, 3.86.

Part B. 2-(4-Methoxyphenyl)benzo[b]thiophen-3-yl 4-Methoxyphenyl Ketone

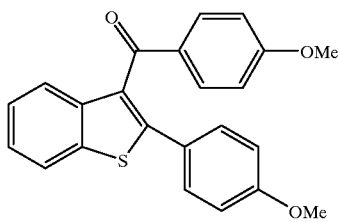

The title compound was prepared from 4-anisoyl chloride and 2-(4-methoxyphenyl)benzo[b]thiophene (Part A) as a tan solid in 90% yield following recrystallization from THF-hexanes.

FDMS 375 (M+1; 100).

Part C. 2-(4-Hydroxyphenyl)benzo[b]thiophen-3-yl 4-Hydroxyphenyl Ketone

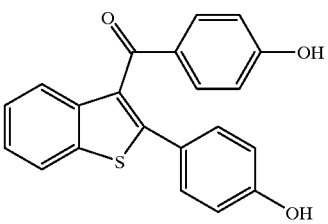

By essentially following the procedure outlined in Example 1, Part D, the title compound was prepared from 2-(4-methoxyphenyl)benzo[b]thiophen-3-yl 4-methoxyphenyl ketone (Part B) as a yellow solid in 93% yield following radial chromatography (SiO$_2$; gradient of 20–40% EtOAc in hexanes).

FDMS 347 (M+1; 100); Anal. Calcd for C$_{21}$H$_{14}$O$_3$S: C, 72.81; H, 4.07. Found: C, 72.57; H, 4.17.

Part D. 2-[4-[2-(1-Pyrrolidinyl)ethoxy]phenyl]benzo[b] thiophen-3-yl 4-[2-(1-Pyrrolidinyl)ethoxy]phenyl Ketone Dioxalate

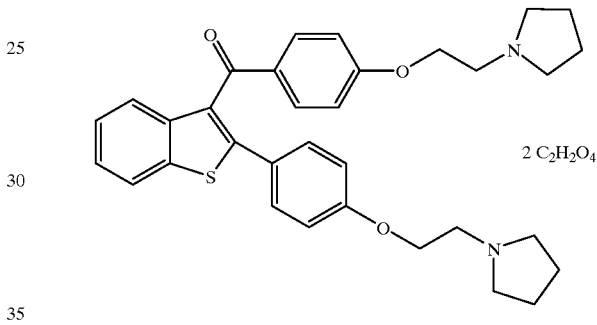

A solution of 300 mg (0.87 mmol) of 2-(4-hydroxyphenyl)benzo[b]thiophen-3-yl 4-hydroxyphenyl ketone (Part C) in 20 mL of DMF was treated with 880 mg (5.2 mmol) of 1-(2-chloroethyl)pyrrolidine hydrochloride followed by 2.26 g (6.94 mmol) of Cs$_2$CO$_3$. The mixture was heated to 80° C. for 6 h at which time it was cooled and filtered. The mother liquor was concentrated in vacuo and the residue was partitioned between H$_2$O (25 mL) and EtOAc (25 mL). The two layers were separated and the aqueous layer was extracted with EtOAc (2×25 mL). The combined organic layers were dried over K$_2$CO$_3$ and evaporated to give 516 mg of an oil which was purified by radial chromatography (SiO$_2$; 60:35:5 hexanes-THF-TEA) to afford 371 mg (0.69 mmol; 79%) of an oil. The oil was converted to the dioxalate salt according to the procedure detailed in Example 1, Part C.

FDMS 541 (M+1), 631 (M+91; 100); Anal. Calcd for C$_{33}$H$_{36}$N$_2$O$_3$S.2C$_2$H$_2$O$_4$.0.1H$_2$O: C, 61.50; H, 5.60; N, 3.88. Found: C, 61.21; H, 5.60; N, 3.91.

Part E. 1-[2-[4-[[2-[4-[2-(1-Pyrrolidinyl)ethoxy]phenyl] benzo[b]thiophen-3-yl3methyl]phenoxy]ethyl]pyrrolidine Dioxalate A slurry of 45 mg of LiAlH$_4$ in 10 mL of THF was cooled to 0° C. and was treated with a solution of 200 mg (0.37 mmol) of 2-[4-[2-(1-pyrrolidinyl)ethoxy]phenyl]benzo[b] thiophen-3-yl 4-[2-(1-pyrrolidinyl)ethoxy]phenyl ketone (Part D) in 5 mL of THF. The reaction was stirred at 0° C. for 2 h and was quenched by the sequential addition of 1 mL of H$_2$O, 1 mL of 2 N aq NaOH, and 1 mL of H$_2$O. The two layers were separated and the aqueous layer was extracted with EtOAc (3×10 mL). The combined organic layers were washed with 25 mL of brine, dried over $K_2CO_3$, and evaporated in vacuo. The residue was taken up in 10 mL of $CH_2Cl_2$, cooled to 0° C., and treated with 0.47 mL (2.94 mmol) of triethylsilane. After stirring at 0° C. for 6 h, the reaction was treated with 0.3 mL (3.9 mmol) of TFA, followed by an additional 16 h of stirring at 0° C. The reaction mixture was poured into 10 mL saturated aq $NaHCO_3$ and the two layers were separated. The aqueous layer was extracted with $CH_2Cl_2$ (2×10 mL). The combined organic layers were dried over $K_2CO_3$ and evaporated in vacuo to give 233 mg of an oil which was purified by radial chromatography ($SiO_2$; gradient 2–10% MeOH in $CH_2Cl_2$) to afford 158 mg (0.30 mmol; 81%) of the title compound as the free base. Conversion to the dioxalate salt was effected by the procedure detailed in Example 1, Part C.

$^1$H NMR (DMSO-$d_6$) δ 7.99 (d, J=7.8 Hz, 1H), 7.59 (d, J=8.5 Hz, 1H), 7.50 (d, J=8.2 Hz, 2H), 7.43–7.30 (m, 2H), 7.14 (d, J=8.1 Hz, 2H). 7.06 (d, J=8.3 Hz, 2H), 6.89 (d, J=8.1 Hz, 2H), 4.17 (s, 2H), 4.11 (t, J=5.8 Hz, 2H), 3.98 (t, J=5.8 Hz, 2H), 2.81 (t, J=5.8 Hz, 2H), 2.75 (t, J=5.8 Hz, 2H), 2.36 (s, 3H), 2.58–2.44 (m, 8H), 1.78–1.60 (m, 8H); FDMS 527 (M+1, 100).

EXAMPLE 4

Preparation of 2-[4-[2-(1-Pyrrolidinyl)ethoxy] phenyl]benzo[b]thiophen-3-yl 4-[3-(1-Pyrrolidinyl) propoxy]phenyl Ketone Dioxalate

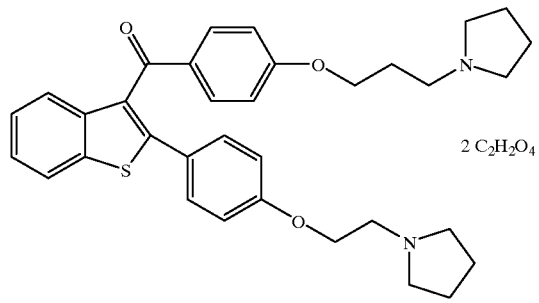

Part A. 1-[2-[4-(Benzo[b]thiophen-2-yl)phenoxy]ethyl] pyrrolidine

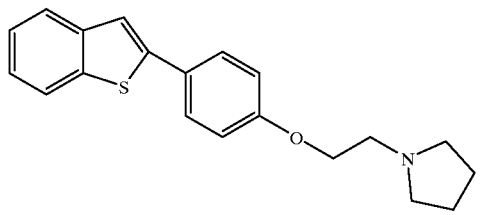

By essentially following the procedure detailed in Example 1, Part B, the title compound was prepared from benzo[b]thiophene-2-boronic acid and 1-[2-(4-bromophenoxy)ethyl]pyrrolidine in 76% yield as a white solid following flash chromatography ($SiO_2$; 36:4:60 THF-TEA-hexanes).

FDMS 324 (M+1; 100).

Part B. Methyl 4-[3-(1-Pyrrolidinyl)propoxy]benzoate

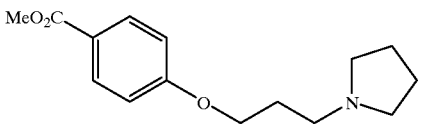

A solution of 6.25 g (23.8 mmol) of triphenylphosphine, 3.30 g (21.7 mmol) of methyl 4-hydroxybenzoate, and 2.80 g (21.7 mmol) of 1-(3-hydroxypropyl)pyrrolidine in 100 mL of $CH_2Cl_2$ was treated with 3.80 mL (24.1 mmol) of diethyl azodicarboxylate in a dropwise manner. The reaction was stirred at ambient temperature for 16 h and was quenched by the addition of 20 mL of brine. The two layers were separated, and the organic layer was dried over $K_2CO_3$ and concentrated to give 6.10 g of an oily solid which was purified by flash chromatography ($SiO_2$; 0–5% MeOH in $CH_2Cl_2$) to afford 2.46 g (9.34 mmol; 43%) of the desired product.

FDMS 263 (M$^+$; 100); HRMS Calcd for $C_{15}H_{21}NO_3$: 264.1600. Found: 264.1609.

Part C. 4-[3-(1-Pyrrolidinyl)propoxy]benzoic Acid Hydrochloride

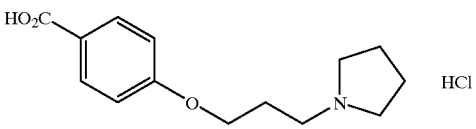

A solution of 2.0 g (7.6 mmol) of the methyl 4-[3-(1-pyrrolidinyl)propoxy]benzoate (Part B) in 90 mL of THF was treated with 90 mL of 0.1N aq LiOH for 48 h. The THF was evaporated in vacuo. The aqueous phase was adjusted to pH 11 with 1.0N aq HCl and was applied to column of Biorad AG1-X8 Resin (100–200 mesh; acetate form) which had been prewashed with 2 L of 2.0N aq NaOH. The column was sequentially eluted with 1 L of $H_2O$, 1 L of 50% THF in $H_2O$, 1 L of $H_2O$ and 2 L of 3.0N aq AcOH. The acidic fraction was evaporated in vacuo, the residue was reconstituted in 20 mL of 1.0N aq HCl and the mixture was frozen. Lyophilization afforded 1.50 g (3.9 mmol; 51%) of the desired product as a white powder.

FDMS 249 (M$^+$; 100); Anal. Calcd for $C_{14}H_{19}NO_3 \cdot HCl$: C, 58.84; H, 7.05; N, 4.90. Found: C, 58.58; H, 6.85; N, 5.13.

Part D. 2-[4-[2-(1-Pyrrolidinyl)ethoxy]phenyl]benzo[b] thiophen-3-yl 4-[3-(1-Pyrrolidinyl)propoxy]phenyl Ketone Dioxalate The title compound was prepared from 4-[3-(1-pyrrolidinyl)propoxy]benzoic acid hydrochloride (Part C) and 1-[2-[4-(benzo[b]thiophen-2-yl)phenoxy]ethyl] pyrrolidine (Part A) in 55% yield by essentially following the procedure outlined in Example 2, Part C.

$^1$H NMR (DMSO-$d_6$) δ 8.11 (d, J=7.5 Hz, 1H), 7.74 (d, J=8.7 Hz, 2H), 7.48–7.33 (m, 5H), 7.01 (d, J=8.8 Hz, 2H), 6.98 (d, J=8.8 Hz, 2H), 4.30 (t, J=3.8 Hz, 2H), 4.11 (t, J=5.2 Hz, 2H), 3.54 (t, J=4.2 Hz, 2H), 3.43–3.15 (m, 8H), 2.18–2.05 (m, 2H), 2.02–1.85 (m, 10H); FDMS 555 (M+1; 100); Anal. Calcd for $C_{34}H_{38}N_2O_3S \cdot 2C_2H_2O_4$: C, 62.11; H, 5.76; N, 3.81. Found: C, 62.08; H, 5.76; N, 3.84.

EXAMPLE 5

Preparation of 2-[4-[2-(1-Pyrrolidinyl)ethoxy]phenyl]benzo[b]-thiophen-3-yl 4-[3-(1-Pyrrolidinyl)propyl]phenyl Ketone Dioxalate

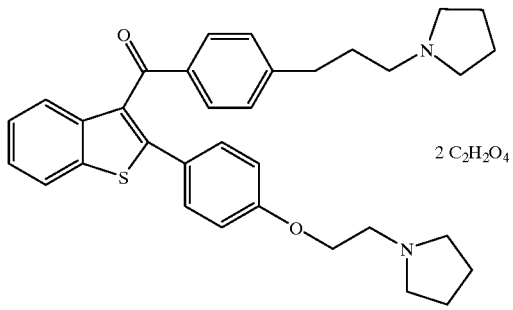

Part A. 2-(4-Methoxyphenyl)benzo[b]thiophen-3-yl 4-[3-(1-Pyrrolidinyl)propyl]phenyl Ketone

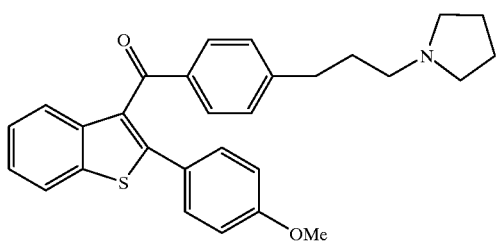

By essentially following the procedure outlined in Example 2, Part C, the title compound was prepared from 2-(4-methoxyphenyl)benzo[b]thiophene (Example 3; Part A) and 4-[3-(1-pyrrolidinyl)propyl]benzoic acid hydrochloride in 33% yield as a viscous oil.

FDMS 456 (M+1; 100); Anal. Calcd for $C_{29}H_{29}NO_2S$: C, 76.45; H, 6.42; N, 3.07. Found: C, 76.21; H, 6.39; N, 3.14.

Part B. 2-(4-Hydroxyphenyl)benzo[b]thiophen-3-yl 4-[3-(1-Pyrrolidinyl)propyl]phenyl Ketone

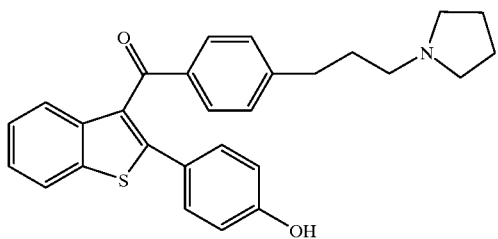

A 100 mL round bottom flask containing 300 mg (0.66 mmol) of 2-(4-methoxyphenyl)benzo[b]thiophen-3-yl 4-[3-(1-pyrrolidinyl)propyl]phenyl ketone (Part A) was filled with 20 g of pyridine hydrochloride. The flask was heated to 160° C. to melt the solid. After 16 h, the reaction was cooled to warm temperature, diluted with 50 mL of $H_2O$, and transferred to separatory funnel containing 50 mL $H_2O$ and 50 mL of EtOAc. The two layers were separated and the aqueous layer was extracted with EtOAc (2×50 mL). The combined EtOAc layers were dried over $Na_2SO_4$ and concentrated in vacuo to give 325 mg of a yellow oil. Purification by radial chromatography ($SiO_2$; gradient of 2–10% MeOH in $CH_2Cl_2$) afforded 200 mg (0.45 mmol; 69%) of the title compound as a viscous yellow oil.

FDMS 441 (M+; 100); Anal. Calcd for $C_{28}H_{27}NO_2S$: C, 76.16; H, 6.16; N, 3.17. Found: C, 76.59; H, 6.27; N, 3.07.

Part C. 2-[4-[2-(1-Pyrrolidinyl)ethoxy]phenyl]benzo[b]thiophen-3-yl 4-[3-(1-Pyrrolidinyl)propyl]phenyl Ketone Dioxalate By essentially following the procedure outlined in Example 3, Part D, the free base of the title compound was prepared from 2-(4-hydroxyphenyl)benzo[b]thiophen-3-yl 4-[3-(1-pyrrolidinyl)propyl]phenyl ketone (Part B) and 1-(2-chloroethyl)pyrrolidine hydrochloride in 36% yield as a viscous oil following radial chromatography ($SiO_2$; gradient of 5–15% MeOH in $CH_2Cl_2$). The free base was converted to the dioxalate salt according to the conditions described in Example 1, Part C.

$^1$H NMR (DMSO-$d_6$) δ 8.12 (d, J=7.8 Hz, 1H), 7.69 (d, J=7.9 Hz, 2H), 7.45–7.34 (m, 7H), 7.30 (d, J=8.0 Hz, 2H), 6.99 (d, J=8.4 Hz, 2H), 4.32–4.21 (m, 2H), 3.57–3.43 (m, 2H), 3.35–3.12 (m, 8H), 3.07 (t, J=6.2 Hz, 2H), 2.66 (t, J=6.5 Hz, 2H), 2.04–1.80 (m, 10H); FDMS 539 (M+1; 66); Anal. Calcd for $C_{34}H_{38}N_2O_2S.2C_2H_2O_4$: C, 63.50; H, 5.89; N, 3.90. Found: C, 63.75; H, 6.12; N, 3.85.

EXAMPLE 6

2-[4-[2-(1-Pyrrolidinyl)ethoxy]phenyl]benzo[b]thiophen-3-yl 4-[(1-Pyrrolidinyl)methyl]phenyl Ketone Dioxalate

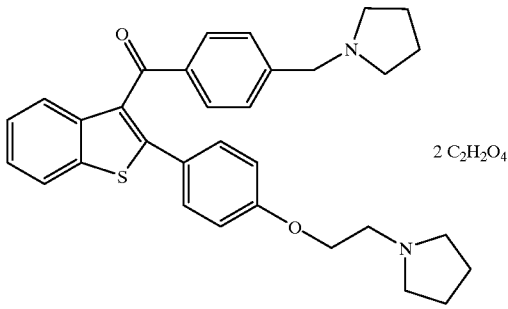

Part A. Methyl 4-[(1-Pyrrolidinyl)methyl]benzoate

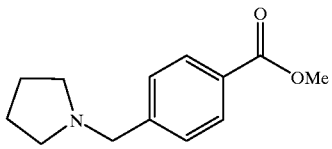

A solution of 6.20 mL (44.5 mmol) of TEA and 4.70 g (21.8 mmol) of 4-carboxybenzyl bromide in 50 mL of DMF was treated with 2.10 mL (25.2 mmol) of pyrrolidine at 50° C. for 3 h. The reaction mixture was cooled, evaporated in vacuo, and the residue was taken up in 50 mL of MeOH. The solution was treated with a rapid stream of HCl (g) for 15 min, the reaction vessel was sealed and the reaction stirred at ambient temperature for 16 h. Evaporation of the solvent afforded 2.56 g of an oil which was purified by radial chromatography ($SiO_2$; 80:18:2 hexanes-THF-TEA) to afford 2.30 g (10.5 mmol; 48%) of the title compound as an oil.

FDMS 219 (M+; 100)

Part B. 4-[(1-Pyrrolidinyl)methyl]benzoic Acid Hydrochloride

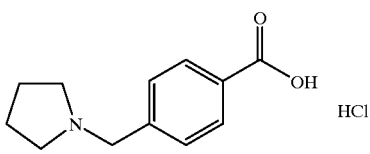

By essentially following the procedure outlined in Example 4, Part C, the title compound was prepared from methyl 4-[(1-pyrrolidinyl)methyl]benzoate in 22% yield as a white solid following ion exchange chromatography.

FDMS 206 (M+1; 100); Anal. Calcd for $C_{12}H_{15}NO_2 \cdot HCl \cdot 0.2 H_2O$: C, 58.75; H, 6.74; N, 5.71. Found: C, 58.95; H, 6.56; N, 5.54.

Part C. 2-[4-[2-(1-Pyrrolidinyl)ethoxy]phenyl]benzo[b]thiophen-3-yl 4-[(1-Pyrrolidinyl)methyl]phenyl Ketone Dioxalate By essentially following the procedure outlined in Example 2, Part C, the free base of the title compound was prepared from 4-[(1-pyrrolidinyl)methyl]benzoic acid hydrochloride (Part B) and 1-[2-[4-(benzo[b]thiophen-2-yl)phenoxy]ethyl]pyrrolidine (Example 4, Part A) in 44% yield. The free base was converted to the dioxalate salt according to the conditions described in Example 1, Part C.

$^1$H NMR (DMSO-d$_6$) δ 8.10 (dd, J=6 5, 1.8 Hz, 1H), 7.68 (d, J=8.2 Hz, 2H), 7.63 (d, J=8.5 Hz, 1H), 7.52–7.36 (m, 4H), 7.32 (d, J=8.7 Hz, 2H), 6.90 (d, J=8.7 Hz, 2H), 4.27–4.15 (m, 4H), 3.53–3.43 (m, 2H), 3.34–3.20 (m, 4H), 3.20–2.94 (m, 4H), 1.96–1.80 (m, 8H); FDMS 510 (M$^+$; 100); Anal. Calcd for $C_{32}H_{34}N_2O_2S \cdot 2C_2H_2O_4$: C, 62.60; H, 5.54; N, 4.06. Found: C, 62.79; H, 5.56; N, 4.00.

EXAMPLE 7

Preparation of 2-[4-[2-(1-Pyrrolidinyl)ethoxy]phenyl]benzo[b]thiophen-3-yl 4-[2-(1-Pyrrolidinyl)ethyl]phenyl Ketone Dioxalate

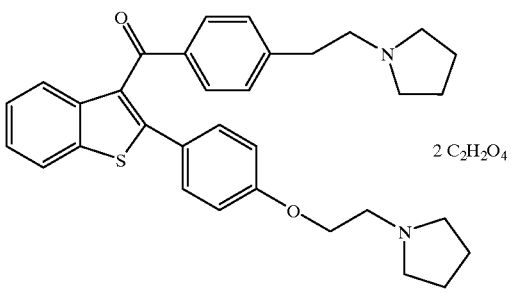

Part A. Methyl 4-[2-(1-Pyrrolidinyl)ethyl]benzoate

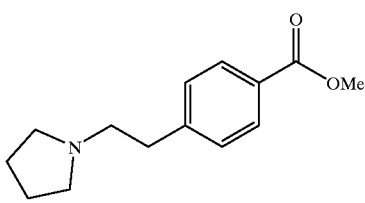

By essentially following the procedure detailed in Example 6, Part A, the title compound was prepared from 4-[2-bromoethyl)benzoic acid and pyrrolidine in 39% yield as an oil following radial chromatography (SiO$_2$; 89:9:2 hexanes-THF-TEA).

FDMS 234 (M+1; 100)

Part B. 4-[2-(1-Pyrrolidinyl)ethyl]benzoic Acid Hydrochloride

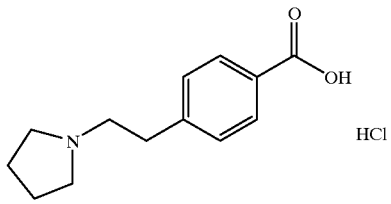

By essentially following the procedure outlined in Example 4, Part C, the title compound was prepared from methyl 4-[2-(1-pyrrolidinyl)ethyl]benzoate (Part A) in 24% yield as a white solid following ion exchange chromatography.

FDMS 220 (M+1; 100); Anal. Calcd for $C_{13}H_{17}NO_2 \cdot HCl \cdot 0.1H_2O$: C, 60.63; H, 7.12; N, 5.44. Found: C, 60.48; H, 7.08; N, 5.32.

Part C. 2-[4-[2-(1-Pyrrolidinyl)ethoxy]phenyl]benzo[b]thiophen-3-yl 4-[2-(1-Pyrrolidinyl)ethyl]phenyl Ketone Dioxalate By essentially following the procedure outlined in Example 2, Part C, the free base of the title compound was prepared from 4-[2-(1-pyrrolidinyl)ethyl]benzoic acid hydrochloride (Part B) and 1-[2-[4-(benzo[b]thiophen-2-yl)phenoxy]ethyl]pyrrolidine (Example 4, Part A) in 45% yield. The free base was converted to the dioxalate salt according to the conditions described in Example 1, Part C.

$^1$H NMR (DMSO-d$_6$) δ 8.10 (dd, J=6.4, 2.0 Hz, 1H), 7.72–7.61 (m, 3H), 7.45–7.39 (m, 4H), 7.31 (d, J=8.5 Hz, 2H), 6.89 (d, J=8.6 Hz, 2H), 4.27–4.04 (m, 4H), 3.53–3.40 (m, 2H), 3.31–3.17 (m, 4H), 3.10–2.92 (m, 2H), 2.87–2.64 (m, 2H), 1.99–1.72 (m, 8H), 1.55–1.40 (m, 2H); FDMS 524 (M$^+$; 100); Anal. Calcd for $C_{33}H_{36}N_2O_2S \cdot 2C_2H_2O_4$: C, 63.06; H, 5.72; N, 3.97. Found: C, 63.33; H, 5.67; N, 3.90.

EXAMPLE 8

Preparation of 1-[2-[2-Methyl-4-[2-[4-[2-(1-pyrrolidinyl)ethoxy]phenyl]benzo[b]thiophen-3-ylmethyl]phenoxy]ethyl]pyrrolidine Dioxalate

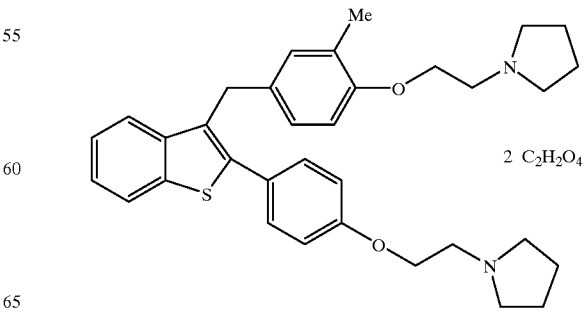

Part A. 2-(4-Methoxyphenyl)benzo[b]thiophen-3-yl 3-Bromo-4-methoxyphenyl Ketone

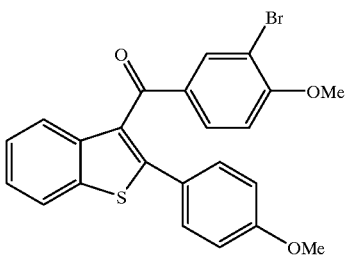

The title compound was prepared in 76% yield from 2-(4-methoxyphenyl)]benzo[b]thiophene (Example 3, Part A) and 3-bromo-4-methoxybenzoic acid by essentially following the procedures detailed in Example 2, Part C.

$^1$H NMR (DMSO-$d_6$) δ 8.12 (d, J=7.3 Hz, 1H), 7.91 (s, 1H), 7.69 (dd, J=8.7, 1.8 Hz, 1H), 7.56 (d, J=8.2 Hz, 1H), 7.52–7.41 (m, 2H), 7.37 (d, J=8.6 Hz, 2H), 7.05 (d, J=8.7 Hz, 1H), 6.94 (d, J=8.6 Hz, 2H), 3.89 (s, 3H), 3.75 (s, 3H); FDMS 452 (M−1), 454 (M+1).

Part B. 2-(4-Methoxyphenyl)benzo[b]thiophen-3-yl 3-Methyl-4-methoxyphenyl Ketone

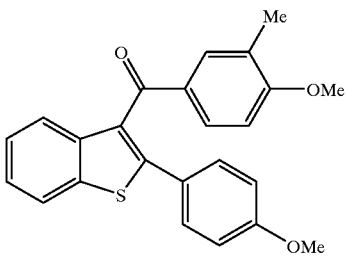

A slurry of 750 mg (1.65 mmol) of 2-(4-methoxyphenyl)benzo[b]thiophen-3-yl 3-bromo-4-methoxyphenyl ketone (Part A) in 15 mL of toluene was treated with 75 mg (0.07 mmol) of tetrakis(triphenylphosphine)palladium(0) and 0.54 mL (3.9 mmol) of tetrabutyltin. The tube was sealed and the contents were heated at 130° C. for 15 h. The reaction was cooled, evaporated in vacuo, and the residue was taken up in 75 mL of Et$_2$O. Saturated aq KF (75 mL) was added and the mixture was stirred vigorously for 6 h. The two layers were separated and the organic layer was washed with H$_2$O (3×75 mL). The organic phase was dried over Na$_2$SO$_4$ and evaporated in vacuo to give 934 mg of an oil which was purified by radial chromatography (SiO$_2$; 25% EtOAc in hexanes) to afford 602 mg (1.55 mmol; 94%) of the title compound as a white solid.

FDMS 388 (M$^+$), 389 (M+1); HRMS calcd for C$_{24}$H$_{21}$O$_3$S, 389.1211. Found 389.1180.

Part C. 2-(4-Hydroxyphenyl)benzo[b]thiophen-3-yl 3-Methyl-4-hydroxyphenyl Ketone

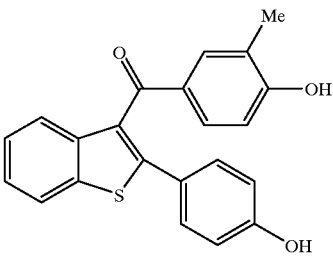

A 0° C. solution of 700 mg (1.80 mmol) of 2-(4-methoxyphenyl)benzo[b]thiophen-3-yl 3-methyl-4-methoxyphenyl ketone (Part B) in 25 mL of CH$_2$Cl$_2$ was treated with 7.2 mL of BBr$_3$ (1.0 M in CH$_2$Cl$_2$). The reaction was stirred at 0° C. for 6 h, then cooled to −78° C., and was treated carefully with 50 mL of MeOH. The mixture was allowed to warm to room temperature over 1.5 h, and the volatiles were evaporated in vacuo. The dark red residue (monomethyl ether) was taken up in 75 mL dichloroethane and was treated with AlCl$_3$ and ethanethiol according to the conditions of Example 1, Part D to afford 675 mg of an oil. Purification by radial chromatography (SiO$_2$; gradient of 20–30% EtOAc in hexanes) afforded 410 mg (1.14 mmol; 63%) of the title compound as an orange solid.

FDMS 360 (M$^+$); Anal. Calcd for C$_{22}$H$_{16}$O$_3$S: C, 73.31; H, 4.47. Found: C, 73.57; H, 4.66.

Part D. 2-[4-[2-(1-Pyrrolidinyl)ethoxy]phenyl]benzo[b]thiophen-3-yl 3-Methyl-4-[2-(1-pyrrolidinyl)ethoxy]phenyl Ketone Dioxalate

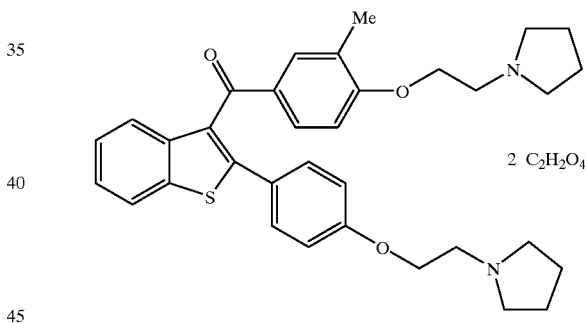

By essentially following the procedure detailed in Example 3, Part D, the free base of the title compound was prepared from 2-(4-hydroxyphenyl)benzo[b]thiophen-3-yl 3-methyl-4-hydroxyphenyl ketone (Part C) and 1-(2-chloroethyl)pyrrolidine hydrochloride in 83% yield as an oil following radial chromatography (SiO$_2$; 10% MeOH and 0.5% TEA in CH$_2$Cl$_2$). The free base was converted to the dioxalate salt according to the conditions described in Example 1, Part C.

$^1$H NMR (DMSO-$d_6$) δ 8.10 (d, J=7.8 Hz, 1H), 7.64 (s, 1H), 7.56–7.34 (m, 6H), 7.00–6.92 (m, 3H). 4.13 (t, J=5.4 Hz, 2H), 4.08 (t, J=5.7 Hz 2H), 2.95–2.78 (m, 4H) 2.68–2.56 (m, 8H), 2.12 (s, 3H), 1.78–1.64 (m, 8H); FDMS 555 (M$^+$; 100); HRMS C$_{34}$H$_{39}$N$_2$O$_3$S: 555.2681. Found: 555.2706.

Part E. 1-[2-[2-Methyl-4-[2-[4-[2-(1-pyrrolidinyl)ethoxy]phenyl]benzo[b]thiophen-3-ylmethyl]phenoxy]ethyl] pyrrolidine Dioxalate By essentially following the conditions detailed in Example 2; Part D, the free base of the title compound was prepared from 2-[4-[2-(1-pyrrolidinyl)ethoxy]phenyl]benzo[b]thiophen-3-yl 3-methyl-4-[2-(1-pyrrolidinyl)ethoxy]phenyl ketone (Part D) in 88% yield as an oil following radial chromatography (SiO$_2$; 10% MeOH and 0.5% TEA in CH$_2$Cl$_2$). The free base was converted to the dioxalate salt according to the conditions described in Example 1, Part C.

$^1$H NMR (DMSO-d$_6$) δ 8.04–7.95 (m, 1H), 7.64–7.56 (m, 1H), 7.51 (d, J=8.1 Hz, 2H), 7.42–7.32 (m, 2H). 7.14 (d, J=8.2 Hz, 2H), 6.97 (s, 1H), 6.92–6.80 (m, 2H), 4.36 (t, J=4.8 Hz, 2H), 4.22 (t, J=5.0 Hz 2H), 4.18 (s, 2H), 2.95–2.78 (m, 4H) 2.68–2.56 (m, 8H), 2.12 (s, 3H), 1.78–1.64 (m, 8H); FDMS 541 (M$^+$; 100), 631 (M$^+$+C$_2$H$_2$O$_4$); Anal. Calcd for C$_{34}$H$_{40}$N$_2$O$_2$S.2C$_2$H$_2$O$_4$.1.9H$_2$O: C, 63.78; H, 6.20; N, 3.93. Found: C, 63.81; H, 6.47; N, 3.82.

EXAMPLE 9

Preparation of 2-[4-[2-(1-Pyrrolidinyl)ethoxy]phenyl]benzo[b]thiophen-3-yl 6-[2-(1-Pyrrolidinyl)ethoxy]pyrid-3-yl Ketone Dioxalate

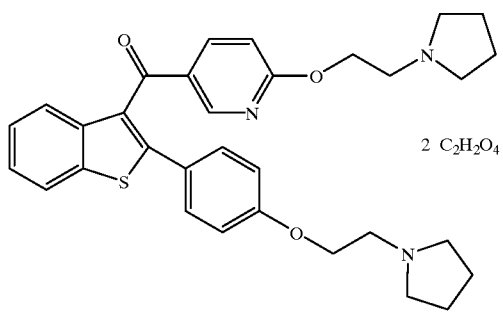

2 C$_2$H$_2$O$_4$

Part A. 2-(4-Methoxyphenyl)benzo[b]thiophen-3-yl 6-Chloro-pyrid-3-yl Ketone

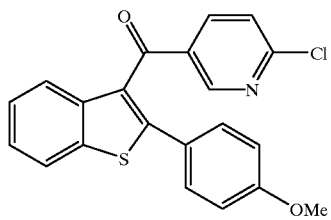

By essentially following the procedure detailed in Example 1, Part C, the title compound was prepared from 6-chloronicotinic acid and 2-(4-methoxyphenyl)benzo[b]thiophene (Example 3, Part A) in 31% yield as a yellow solid following flash chromatography (SiO$_2$; CH$_2$Cl$_2$).

FDMS 379 (M$^+$, 100), 381; Anal. Calcd for C$_{21}$H$_{14}$ClNO$_2$S: C, 66.40; H, 3.71; N, 3.69. Found: C, 66.20; H, 3.71; N, 3.79.

Part B. 2-(4-Methoxyphenyl)benzo[b]thiophen-3-yl 6-[2-(1-Pyrrolidinyl)ethoxy]pyrid-3-yl Ketone

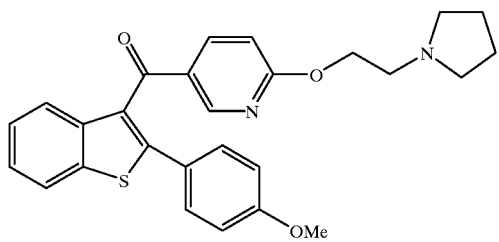

A solution of 0.50 mL (4.30 mmol) of 1-(2-hydroxyethyl)pyrrolidine in 10 mL of xylenes was treated with 50 mg (2.20 mmol) of Na. The mixture was heated to 50° C. until all the Na had disappeared, cooled to room temperature, and then treated with a solution of 420 mg (1.10 mmol) of 2-(4-methoxyphenyl)benzo[b]thiophen-3-yl 6-chloropyrid-3-yl ketone (Part A) in 5 mL of xylenes. The reaction was heated to 50° C. for 2 h and was evaporated in vacuo. The residue was partitioned between H$_2$O (50 mL) and EtOAc (50 mL). The organic layer was separated and the aqueous layer was extracted with EtOAc (2×50 mL). The combined organic layers were dried over K$_2$CO$_3$ and evaporated in vacuo to give 810 mg of a yellow solid. Purification by radial chromatography (SiO$_2$; gradient of 1–5% MeOH in CH$_2$Cl$_2$) gave 525 mg (1.09 mmol; 99%) of the title compound as an amber oil.

FDMS 459 (M$^+$; 100); Anal. Calcd for C$_{27}$H$_{26}$N$_2$O$_3$S: C, 70.72; H, 5.71; N, 6.11. Found: C, 70.43; H, 5.60; N, 6.02.

Part C. 2-(4-Hydroxyphenyl)benzo[b]thiophen-3-yl 6-[2-(1-Pyrrolidinyl)ethoxy)pyrid-3-yl Ketone

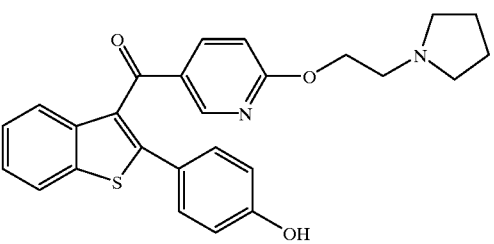

By essentially following the procedures outlined in Example 1, Part D, the title compound was prepared from 2-(4-methoxyphenyl)benzo[b]thiophen-3-yl 6-[2-(1-pyrrolidinyl)ethoxy]pyrid-3-yl ketone (Part B) in 89% yield as a yellow solid following radial chromatography (SiO$_2$, 5% MeOH in CH$_2$Cl$_2$).

FDMS 445 (M+1; 100); HRMS calcd for C$_{26}$H$_{25}$N$_2$O$_3$S: 445.1586. Found: 445.1569.

Part D. 2-[4-[2-(1-Pyrrolidinyl)ethoxy]phenyl]benzo[b]thiophen-3-yl 6-[2-(1-Pyrrolidinyl)ethoxy]pyrid-3-yl Ketone Dioxalate By essentially following the procedure detailed in Example 3, Part D, the free base of the title compound was prepared from 2-(4-hydroxyphenyl)benzo[b]thiophen-3-yl 6-[2-(1-pyrrolidinyl)ethoxy)pyrid-3-yl ketone (Part C) and 1-(2-chloroethyl)pyrrolidine hydrochloride in 84% yield as an oil following radial chromatography (SiO$_2$; gradient of 5–20% MeOH in THF). The free base was converted to the dioxalate salt according to the conditions described in Example 1, Part C.

FDMS 542 (M+1); Anal. Calcd for C$_{32}$H$_{35}$N$_3$O$_3$S.2C$_2$H$_2$O$_4$.1.5H$_2$O: C, 57.74; H, 5.65; N, 5.61. Found: C, 57.68; H, 5.42; N, 5.49.

EXAMPLE 10

Preparation of 1-[2-[4-[[2-[4-[2-(1-Pyrrolidinyl)ethoxy]phenyl]benzo[b]thiophen-3-yl]thio]phenoxy]ethyl]pyrrolidine Dioxalate

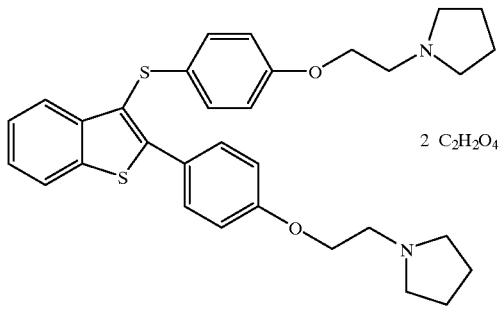

Part A. 3-Bromo-2-(4-methoxyphenyl)benzo[b]thiophene

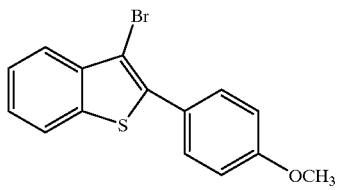

A slurry of 5.0 g (20.8 mmol) of 2-(4-methoxyphenyl)benzo[b]thiophene (Example 3, Part A) in 400 mL of $CHCl_3$ at 0° C. was treated slowly with 1.6 mL of $Br_2$, resulting in a yellow solution. The reaction was stirred at 0° C. for 1 h and then washed sequentially with 200 mL of 1.0N aq $Na_2S_2O_3$, 200 mL of 1.0N aq $NaHCO_3$, and 200 mL of $H_2O$. After drying over $Na_2SO_4$, evaporation of the solvent in vacuo gave 6.24 g (19.5 mmol; 94%) of an off-white solid which was clean by thin layer chromatography.

mp 84.5–86.5° C.; $^1$H NMR ($CDCl_3$) δ 7.86 (d, J=7.9 Hz, 1H), 7.80 (d, J=7.9 Hz, 1H), 7.72 (d, J=8.7 Hz, 2H), 7.50–7.37 (m, 2H), 7.02 (d, J=8.7 Hz, 2H), 3.88 (s, 3H); FDMS 318 (100), 320 (M+1); Anal. Calcd For $C_{15}H_{11}BrOS$: C, 56.44; H, 3.47. Found: C, 56.25; H, 3.38.

Part B. Methyl 4-[[2-(4-Methoxyphenyl)benzo[b]thiophen-3-yl]thio]phenyl Ether

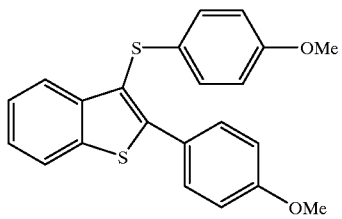

To a solution of 1.0 g (3.1 mmol) of 3-bromo-2-(4-methoxyphenyl)benzo[b]thiophene (Part A) in 20 mL of THF was added dropwise 2.9 mL of 1.6 M n-BuLi in hexanes (4.7 mmol) at −70° C. The mixture was stirred at −70° C. for 10 min and then treated with 0.87 g (3.13 mmol) of solid bis(4-methoxyphenyl)disulfide. Stirring was continued at −70° C. for 0.5 h and then the reaction was allowed to warm slowly to room temperature. The reaction was quenched with 1 mL of saturated aq $NH_4Cl$ and 1 mL of MeOH and was concentrated in vacuo. The residue was partitioned between 100 mL of EtOAc and 100 mL of $H_2O$. The organic layer was separated, dried over $MgSO_4$, and concentrated in vacuo to afford an oily solid which was subjected to flash chromatography ($SiO_2$; gradient of 1–5% EtOAc in hexanes) to afford 0.82 g of the title compound as an oil.

FDMS 378 (M+1; 100).

Part C. 4-[[2-(4-Hydroxyphenyl)benzo[b]thiophen-3-yl]thio]phenol

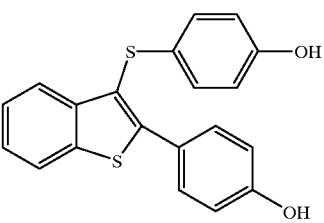

A solution of 0.82 g (2.2 mmol) of methyl 4-[[2-(4-methoxyphenyl)benzo[b]thiophen-3-yl]thio]phenyl ether (Part B) in 50 mL of dichloroethane was treated with 1.2 mL (3.3 g; 13 mmol) of $BBr_3$ at 0° C. for 5 h. The reaction was quenched by the careful addition of 15 mL of MeOH. Evaporation of the solvent in vacuo gave a residue which was subjected to flash chromatography ($SiO_2$; 1% MeOH in $CDCl_3$) to afford 0.47 g of the desired product as a solid.

FDMS 350 (M$^+$; 100); Anal. Calcd For $C_{20}H_{14}O_2S_2$ 0.5MeOH: C, 67.19; H, 4.40. Found: C, 67.04; H, 4.25.

Part D. 1-[2-[4-[[2-[4-[2-(1-Pyrrolidinyl)ethoxy]phenyl]benzo[b]thiophen-3-yl]thio]phenoxy]ethyl]pyrrolidine Dioxalate By essentially following the procedure detailed in Example 4, Part B, except using 1-(2-hydroxyethyl)pyrrolidine, the free base of the title compound was prepared from 4-[[2-(4-hydroxyphenyl)benzo[b]thiophen-3-yl]thio]phenol (Part C) and 1-(2-hydroxyethyl)pyrrolidine in 43% yield as an oil following radial chromatography ($SiO_2$; 3% TEA and 37% THF in hexanes). The free base was converted to the dioxalate salt according to the conditions described in Example 1, Part C.

$^1$H NMR (DMSO-d$_6$) δ 8.12–8.00 (m, 1H), 7.76–7.65 (m, 3H), 7.47–7.38 (m, 2H), 7.13 (d, J=8.8 Hz, 2H), 7.00 (d, J=8.8 Hz, 2H), 6.87 (d, J=8.9 Hz, 2H), 4.36 (t, J=5.0 Hz, 2H), 4.19 (d, J=5.1 Hz, 2H), 3.56 (t, J=4.8 Hz, 2H), 3.47 (t, J=4.9 Hz, 2H), 3.42–3.18 (m, 8H), 2.03–1.82 (m, 8H); FDMS 545 (M+1), 636 (M+91, 100); Anal. Calcd For $C_{32}H_{36}N_2O_2S_2$·$2C_2H_2O_4$·$0.4H_2O$: C, 59.07; H, 5.62; N, 3.83. Found: C, 59.02; H, 5.49; N, 4.22.

EXAMPLE 11

Preparation of 1-[2-[4-[3-[4-[2-(1-Pyrrolidinyl)ethoxy]phenoxy]benzo[b]thiophen-2-yl]phenoxy]ethyl]pyrrolidine Dioxalate

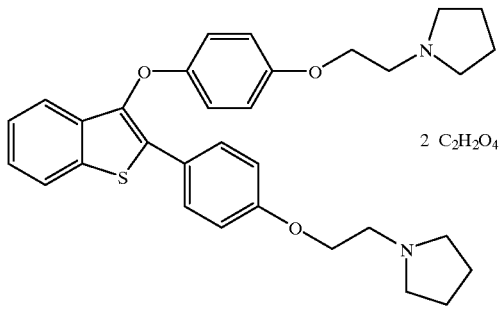

Part A. Benzo[b]thiophen-3-yl 4-Methoxyphenyl Ether

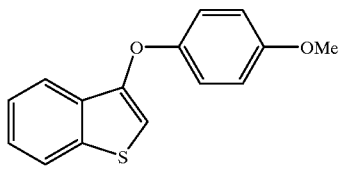

A mixture of 4.00 g (19.7 mmol) of 3-bromobenzo[b]thiophene, 4.96 g (40 mmol) of 4-methoxyphenol, 5.52 g (40 mmol) of $K_2CO_3$, and 0.20 g (1.0 mmol) of CuI was heated to 140° C. and sonicated at this temperature for 2 h. The reaction was allowed to cool, taken up in $CH_2Cl_2$, and the mixture was washed several times with 0.5N NaOH. The organic layer was dried over $Na_2SO_4$ and concentrated in vacuo to an oil that was subjected to chromatography ($SiO_2$; gradient of 0–5% EtOAc in hexanes). The fractions containing the desired product were combined, evaporated in vacuo, and the residue was recrystallized from hexanes to afford 500 mg (1.95 mmol; 10%) of the title compound as a white solid.

Anal. Calcd For $C_{15}H_{21}O_2S$: C, 70.29; H, 4.72. Found: C, 70.56; H, 4.88.

Part B. 2-Iodobenzo[b]thiophen-3-yl 4-Methoxyphenyl Ether

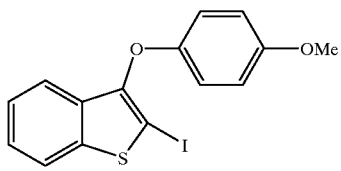

A solution of 133 mg (0.52 mmol) of 3-(4-methoxyphenoxy)benzo[b]thiophene (Part A) in 3 mL of THF was treated with 0.33 mL of 1.6 M n-BuLi in hexanes (0.54 mmol) at −78° C. for 15 min and then treated with 138 mg (0.54 mmol) of $I_2$ in 3 mL of THF. The reaction was allowed to gradually warm to room temperature and then partitioned between brine and EtOAc/hexanes. The two phases were separated, the organic phase was washed with $H_2O$, dried over $Na_2SO_4$, and concentrated in vacuo. The residue was crystallized from hexanes to afford 143 mg (0.37 mmol; 72%) of the title compound as a solid.

Anal. Calcd For $C_{15}H_{20}IO_2S$: C, 47.14; H, 2.90. Found: C, 47.21; H, 2.98.

Part C. (4-Methoxyphenyl)boronic Acid

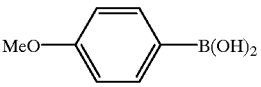

By essentially following the procedure detailed in Example 1, Part A, the title compound was prepared from 4-iodoanisole.

Part D. 2-(4-Methoxyphenyl)benzo[b]thiophen-3-yl 4-Methoxyphenyl Ether

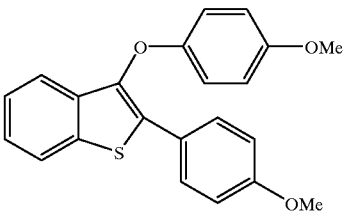

By essentially following the procedure detailed in Example 1, Part B, the title compound was prepared from 2-iodo-3-(4-methoxyphenoxy)benzo[b]thiophene (Part B) and (4-methoxyphenyl)boronic acid (Part C) in 70% yield following chromatography ($SiO_2$; 5% EtOAc in hexanes).

Anal. Calcd For $C_{22}H_{18}O_3S$: C, 72.90; H, 5.01. Found: C, 72.82; H, 5.12.

Part E. 4-[[2-(4-Hydroxyphenyl)benzo[b]thiophen-3-yl]oxy]phenol

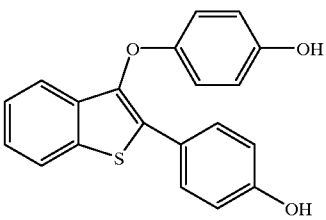

By essentially following the procedure detailed in Example 5, Part B, the title compound was prepared from 2-(4-methoxyphenyl)-3-(4-methoxyphenoxy)benzo[b]thiophene (Part D) in 87% yield following radial chromatography ($SiO_2$; 25% EtOAc in hexanes).

FDMS 334 (M+, 100); Anal. Calcd For $C_{20}H_{14}O_3S$: C, 71.84; H, 4.22. Found: C, 71.94; H, 4.35.

Part F. 1-[2-[4-[3-[4-[2-(1-Pyrrolidinyl)ethoxy]phenoxy]benzo[b]thiophen-2-yl]phenoxy]ethyl]pyrrolidine Dioxalate By essentially following the procedure detailed in Example 3, Part D the free base of the title compound was prepared from 4-[[2-(4-hydroxyphenyl)benzo[b]thiophen-3-yl]oxy]phenol (Part E) and 1-(2-chloroethyl)pyrrolidine hydrochloride in 52% yield following radial chromatography ($SiO_2$; gradient of 2–10% MeOH in $CH_2Cl_2$). The free base was converted to the dioxalate salt according to the conditions described in Example 1, Part C.

$^1$H NMR (DMSO-$d_6$) δ 7.96 (d, J=8.0 Hz, 1H), 7.68 (d, J=8.5 Hz, 2H), 7.40–7.23 (m, 3H), 7.04 (d, J=8.5 Hz, 2H), 6.91–6.80 (m, 4H), 4.38–4.13 (m, 4H), 3.55–3.41 (m, 4H), 3.36–3.14 (m, 8H), 1.97–1.78 (m, 8H); FDMS 529 (M+1; 100); Anal. Calcd For $C_{32}H_{36}N_2O_3S\cdot 2C_2H_2O_4$: C, 61.00; H, 5.69; N, 3.95. Found: C, 61.06; H, 5.86; N, 4.17.

EXAMPLE 12

Preparation of 1-[2-[4-[1-[2-[4-[2-(1-Pyrrolidinyl)ethoxy]phenyl]benzo[b]thiophen-3-yl]ethenyl]phenoxy]ethyl]pyrrolidine Dioxalate

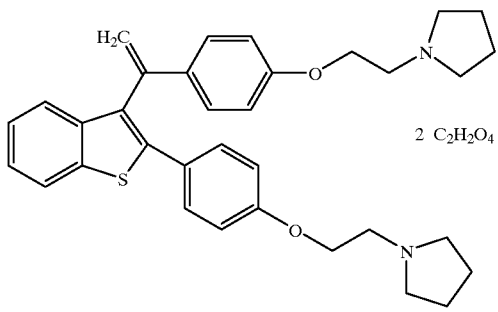

Part A. Methyl 4-[1-[2-(4-Methoxyphenyl)benzo[b]thiophen-3-yl]ethenyl]phenyl Ether

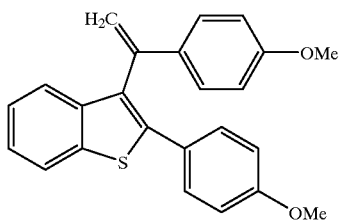

A solution of 1.20 g (3.36 mmol) of methyltriphenylphosphonium bromide in 50 mL of THF was treated with 0.45 g (4.01 mmol) of potassium tert-butoxide and the mixture stirred at room temperature for 0.5 h. To this was added dropwise 0.80 g (2.14 mmol) of 2-(4-methoxyphenyl)benzo[b]thiophen-3-yl 4-methoxyphenyl ketone (Example 3, Part B) in 10 mL of THF and the reaction was stirred at room temperature for 18 h and then heated at gentle reflux for 48 h. The reaction was quenched by 100 mL of brine. The two layers were separated and the organic layer was dried over $Na_2SO_4$. Concentration in vacuo gave 1.36 g of an oil which was purified by radial chromatography ($SiO_2$; 10% EtOAc in hexanes) to afford 0.610 g (1.64 mmol; 77%) of the desired product as an oil.

FDMS 372 ($M^+$; 100).

Part B. 4-[1-[2-(4-Hydroxyphenyl)benzo[b]thiophen-3-yl]ethenyl]phenol

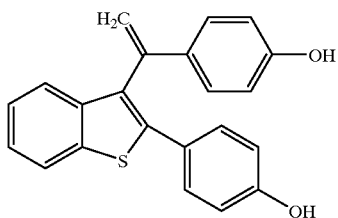

By essentially following the procedure detailed in Example 5, Part B, the title compound was prepared from methyl 4-[1-[2-(4-methoxyphenyl)benzo[b]thiophen-3-yl]ethenyl]phenyl ether (Part A) in 67% yield as a yellow solid following radial chromatography ($SiO_2$; gradient of 20–40% EtOAc in hexanes).

FDMS 344 ($M^+$; 100).

Part C. 1-[2-[4-[1-[2-[4-[2-(1-Pyrrolidinyl)ethoxy]phenyl]benzo[b]thiophen-3-yl]ethenyl]phenoxy]ethyl]pyrrolidine Dioxalate By essentially following the procedure detailed in Example 3, Part D, the free base of the title compound was prepared from 4-[1-[2-(4-hydroxyphenyl)benzo[b]thiophen-3-yl]ethenyl]phenol (Part B) and 1-(2-chloroethyl)pyrrolidine hydrochloride in 67% yield as an oil following radial chromatography ($SiO_2$; gradient of 2–10% MeOH in $CH_2Cl_2$). The free base was converted to the dioxalate salt according to the conditions described in Example 1, Part C.

$^1$H NMR (DMSO-$d_6$) δ 7.95 (d, J=7.5 Hz, 1H), 7.49 (d, J=8.0 Hz, 2H), 7.38–7.16 (m, 5H), 6.95 (d, J=8.1 Hz, 2H), 6.87 (d, J=8.2 Hz, 2H), 5.99 (s, 1H), 5.14 (s, 1H), 4.32–4.10 (m, 4H), 3.54–3.36 (m, 4H), 3.29–3.12 (m, 8H), 1.98–1.72 (m, 8H); FDMS 539 (M+1; 100); Anal. Calcd For $C_{34}H_{38}N_2O_2S.2C_2H_2O_4$: C, 63.49; H, 5.89: N, 3.90. Found: C, 63.78; H, 6.14; N, 4.10.

EXAMPLE 13

Preparation of 4-[2-(Hexahydro-1H-azepin-1-yl)ethoxy]phenyl 2-[4-[2-(1-Pyrrolidinyl)ethoxy]phenyl]benzo[b]thiophen-3-yl Ketone Dioxalate

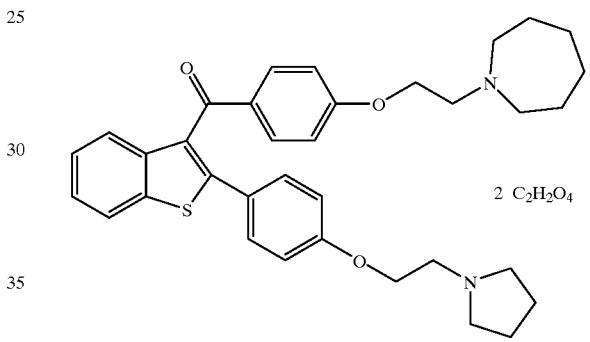

Part A. 4-[2-(Hexahydro-1H-azepin-1-yl)ethoxy]phenyl 2-(4-Methoxyphenyl)benzo[b]thiophen-3-yl Ketone

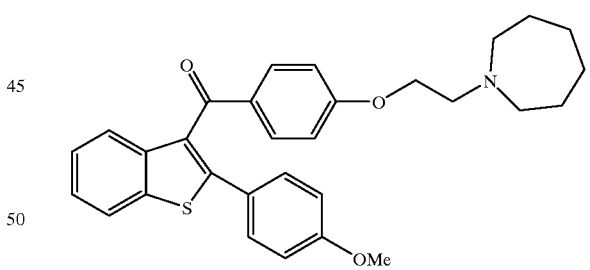

By essentially following the procedure detailed in Example 1, Part C, the title compound was prepared from 2-(4-methoxyphenyl)benzo[b]thiophene (Example 3; Part A) and 4-[2-(hexahydro-1H-azepin-1-yl)ethoxy]benzoic acid hydrochloride in 35% yield as an oil following radial chromatography ($SiO_2$; gradient of 1–10% isopropanol in $CH_2Cl_2$).

FDMS 485 ($M^+$; 100).

Part B. 4-[2-(Hexahydro-1H-azepin-1-yl)ethoxy]phenyl 2-[4-[2-(1-Pyrrolidinyl)ethoxy]phenyl]benzo[b]thiophen-3-yl Ketone Dioxalate Deprotection of the 4-[2-(hexahydro-1H-azepin-1-yl)ethoxy]phenyl] 2-(4-methoxyphenyl)benzo[b]thiophen-3-yl ketone (Part A) was effected according to the conditions described in Example 1, Part D. The resulting phenol was alkylated with 1-(2-chloroethyl)pyrrolidine hydrochloride according to the procedure detailed in Example 3, Part D to afford the free base of title compound which was converted to the dioxalate salt according to the methods described in Example 1, Part C.

FDMS 569 (M$^+$; 100); Anal. Calcd For $C_{35}H_{38}N_2O_3S \cdot 2C_2H_2O_4 \cdot H_2O$: C, 60.37; H, 6.10; N, 3.61. Found: C, 60.05; H, 5.71; N, 3.84; HRMS Calcd for $C_{35}H_{40}N_2O_3S$: 568.2838. Found: 568.2869.

EXAMPLE 14

Preparation of 4-[2-(1-Pyrrolidinyl)ethoxy]phenyl 2-[4-[3-(1-Pyrrolidinyl)propyl]phenyl]benzo[b]thiophen-3-yl Ketone Dioxalate

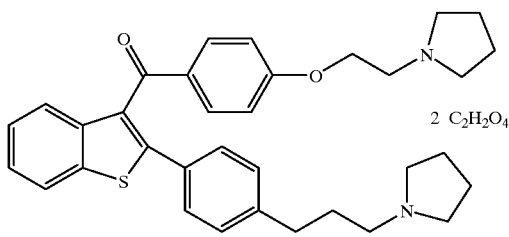

Part A. 1-(trans-4-Bromocinnamoyl)pyrrolidine

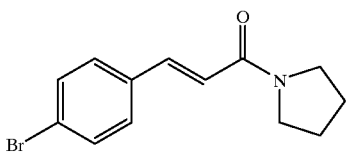

A mixture of 5.0 g (22.0 mmol) of 4-bromocinnamic acid, 6 mL of oxalyl chloride and 3 drops of DMF in 40 mL of $CH_2Cl_2$ was heated to gentle reflux until gas evolution ceased. The volatiles were removed in vacuo and the residue was taken up in 50 mL of $CH_2Cl_2$. Pyrrolidine (10 mL; 120 mmol) was added and the mixture was stirred overnight at room temperature. The reaction mixture was evaporated in vacuo and chromatographed to afford 5.36 g (19.1 mmol; 87%) of the title compound.

FDMS 279 (M−1), 281 (M+1); Anal. Calcd For $C_{13}H_{14}BrNO$: C, 55.73; H, 5.04; N, 5.00. Found: C, 56.00; H, 5.06; N, 5.04.

Part B. 1-[trans-4-(Benzo [b]thiophen-2-yl)cinnamoyl] pyrrolidine

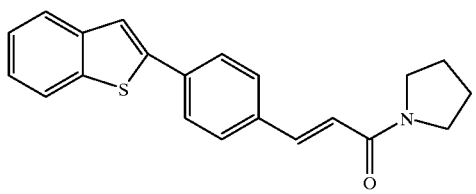

By essentially following the procedure detailed in Example 1, Part B, the title compound was prepared from benzo[b]thiophene-2-boronic acid and 1-(trans-4-bromocinnamoyl)pyrrolidine (Part A) in 43% yield following chromatography.

FDMS 333 (M$^+$), 334 (M+1).

Part C. 1-[3-[4-(Benzo[b]thiophen-2-yl)phenyl]propyl] pyrrolidine

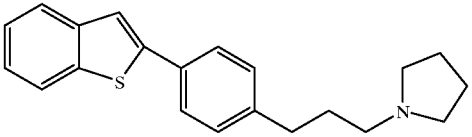

A solution of 1.2 g (3.6 mmol) of 1-[trans-4-(benzo[b]thiophen-2-yl)cinnamoyl]pyrrolidine (Part B) in 15 mL of THF was treated with 75 mg (2.0 mmol) of LiAlH$_4$ at −15° C. After complete consumption of starting material, the reaction was cautiously quenched with H$_2$O. The mixture was extracted with EtOAc and the combined organic layers were evaporated in vacuo. Chromatography afforded 600 mg (1.9 mmol; 52% yield) of the desired product.

FDMS 320 (M−1).

Part D. 4-[2-(1-Pyrrolidinyl)ethoxy]phenyl 2-[4-[3-(1-Pyrrolidinyl)propyl]phenyl]benzo[b]thiophen-3-yl Ketone Dioxalate By essentially following the procedure outlined in Example 1, Part C, the free base of the title compound was prepared from 1-[3-[4-(benzo[b]thiophen-2-yl)phenyl]propyl]pyrrolidine (Part C) and 4-[2-(1-pyrrolidinyl)ethoxy]benzoic acid hydrochloride in 11% yield. Conversion to the dioxalate salt followed from the procedure described in Example 1, Part C.

mp 105–112° C.; FDMS 536 (M+1; 100); Anal. Calcd For $C_{32}H_{38}N_2O_2S \cdot 3C_2H_2O_4$: C, 58.16; H, 5.65; N, 3.57. Found: C, 58.06; H, 5.15; N, 3.93.

EXAMPLE 15

Preparation of 4-[2-(1-Pyrrolidinyl)ethoxy]phenyl 2-[4-[3-(1-Pyrrolidinyl)propoxy]phenyl]benzo[b]thiophen-3-yl Ketone Dioxalate

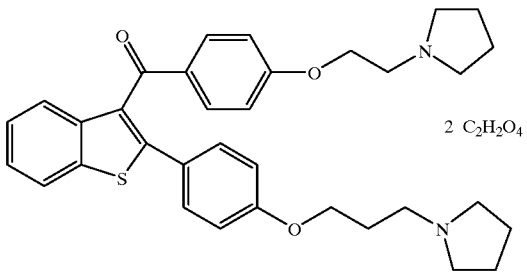

Part A. 2-(4-Methoxyphenyl)benzo[b]thiophen-3-yl 4-[2-(1-Pyrrolidinyl)ethoxy]phenyl Ketone

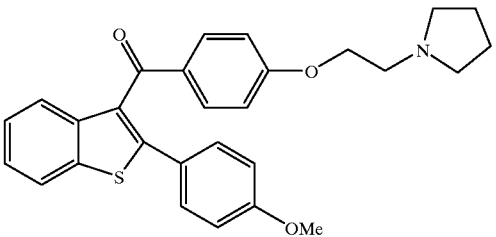

By essentially following the procedure detailed in Example 1, Part C, the title compound was prepared from 2-(4-methoxyphenyl)benzo[b]thiophene (Example 3, Part A) and 4-[2-(1-pyrrolidinyl)ethoxy]benzoic acid hydrochloride in 59% yield as an oil following radial chromatography (SiO$_2$; gradient of 2–5% MeOH in CH$_2$Cl$_2$).

Part B. 2-(4-Hydroxyphenyl)benzo[b]thiophen-3-yl 4-[2-(1-Pyrrolidinyl)ethoxy]phenyl Ketone Part A. 5-Bromopyrid-2-yl 2-(1-Pyrrolidinyl)ethyl Ether

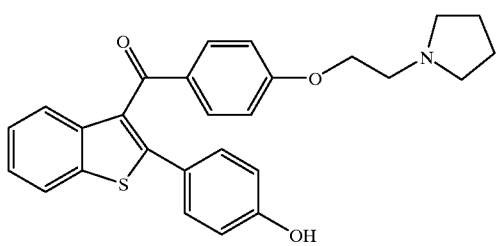

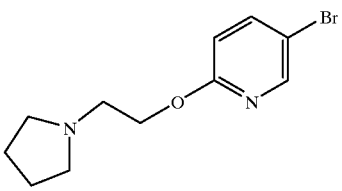

By essentially following the procedure detailed in Example 1, Part D, the title compound was prepared from 2-(4-methoxyphenyl)benzo[b]thiophen-3-yl 4-[2-(1-pyrrolidinyl)ethoxy]phenyl ketone (Part A) in 33% yield as an oil following radial chromatography (SiO$_2$; gradient of 2–10% MeOH in CH$_2$Cl$_2$).

FDMS 443 (M$^+$; 100); Anal. Calcd For C$_{27}$H$_{25}$NO$_3$S: C, 73.11; H, 5.68; N, 3.16. Found: C, 73.11; H, 5.89; N, 3.20.

Part C. 4-[2-(1-Pyrrolidinyl)ethoxy]phenyl 2-[4-[3-(1-Pyrrolidinyl)propoxy]phenyl]benzo[b]thiophen-3-yl Ketone Dioxalate By essentially following the procedure detailed in Example 3, Part D, the free base of the title compound was prepared from 2-(4-hydroxyphenyl)benzo[b]thiophen-3-yl 4-[2-(1-pyrrolidinyl)ethoxy]phenyl ketone (Part B) and 1-(2-chloroethyl)pyrrolidine hydrochloride in 69% yield following radial chromatography (SiO$_2$; gradient of 5–10% MeOH in CH$_2$Cl$_2$). The product was converted to the dioxalate salt according to the conditions of Example 1, Part C.

$^1$H NMR (DMSO-d$_6$) δ 8.04 (d, J=8.8 Hz, 1H), 7.68 (d, J=8.7 Hz, 2H), 7.42–7.29 (m, 5H), 6.95 (d, J=8.7 Hz, 2H), 6.89 (d, J=8.6 Hz, 2H), 4.35–4.23 (m, 2H), 3.98 (t, J=5.5 Hz, 2H), 3.58–3.42 (m, 2H), 3.34–3.09 (m, 10H), 2.13–1.99 (m, 2H), 1.95–1.76 (m, 8H); FDMS 555 (M+1; 100); Anal. Calcd For C$_{34}$H$_{38}$N$_2$O$_3$S.2C$_2$H$_2$O$_4$.1.5H$_2$O: C, 59.91; H, 5.95; N, 3.68. Found: C, 59.72; H, 5.70; N, 3.48.

EXAMPLE 16

Preparation of 4-[2-(1-Pyrrolidinyl)ethoxy]phenyl 2-[6-[2-(1-Pyrrolidinyl)ethoxy]pyrid-3-yl]benzo[b]thiophen-3-yl Ketone Dioxalate

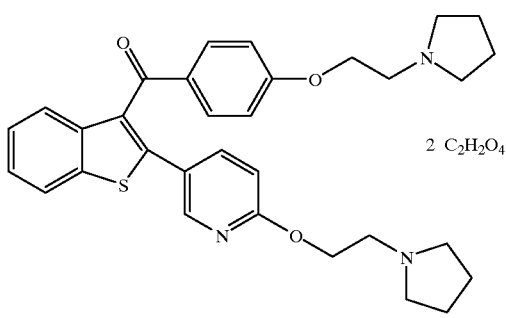

A solution of 8.00 g (69.6 mmol) of N-(2-hydroxyethyl)pyrrolidine in 150 mL of xylenes was treated with 534 mg (23.2 mmol) of Na and the mixture was heated to 80° C. until all the Na had disappeared. The reaction was cooled to 23° C. and 5.50 g (23.2 mmol) of 2,5-dibromopyridine was added. The mixture was stirred at room temperature for 2.25 h and was concentrated in vacuo. Purification by flash chromatography (SiO$_2$; gradient of 50–70% EtOAc in hexanes) afforded 3.53 g (13.0 mmol; 56%) of the title compound.

Part B. 5-(Benzo[b]thiophen-2-yl)pyrid-2-yl 2-(1-Pyrrolidinyl)ethyl Ether

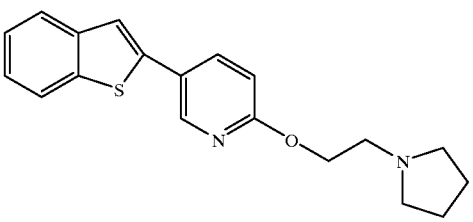

By essentially following the procedure detailed in Example 1, Part B, the title compound was prepared from benzo[b]thiophene-2-boronic acid and 5-bromopyrid-2-yl 2-(1-pyrrolidinyl)ethyl ether (Part A) in 68% yield as an oil following flash chromatography (SiO$_2$; gradient of 0–4% MeOH in CDCl$_3$).

FDMS 324 (M$^+$; 100).

Part C. 4-[2-(1-Pyrrolidinyl)ethoxy]phenyl 2-[6-[2-(1-Pyrrolidinyl)ethoxy]pyrid-3-yl]benzo[b]thiophen-3-yl Ketone Dioxalate By essentially following the procedure detailed in Example 1, Part C, the title compound was prepared from 5-(benzo[b]thiophen-2-yl)pyrid-2-yl 2-(1-pyrrolidinyl)ethyl ether (Part B) and 4-[2-(1-pyrrolidinyl)-ethoxy]benzoic acid hydrochloride in 30% yield as a solid following flash chromatography (SiO$_2$; 5% MeOH in CDCl$_3$). The free base was converted to the dioxalate salt according to the conditions outlined in Example 1, Part C.

FDMS 543 (M+2; 100); Anal. Calcd For C$_{32}$H$_{35}$N$_3$O$_3$S.2C$_2$H$_2$O$_4$: C, 59.91; H, 5.45; N, 5.82. Found: C, 59.80; H, 5.67; N, 5.61.

EXAMPLE 17

Preparation of 4-[2-(4-Morpholinyl)ethoxy]phenyl 2-[4-[2-(1-Pyrrolidinyl)ethoxy]phenyl]benzo[b]thiophen-3-yl Ketone Dioxalate

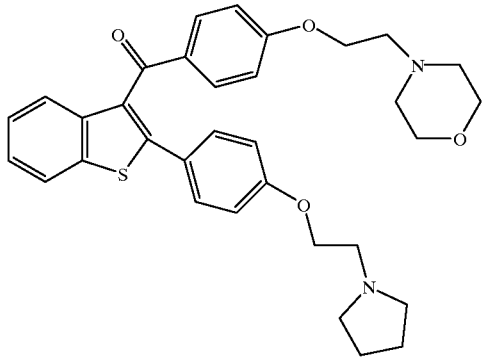

Part A. 2-(4-Methoxyphenyl)benzo [b] thiophen-3-yl 4-[2-(4-Morpholinyl)ethoxy]phenyl Ketone

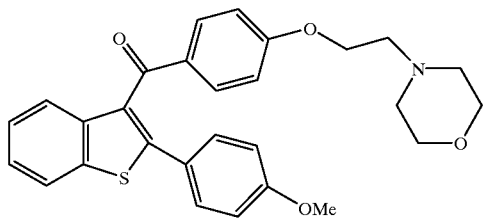

By essentially following the procedure outlined in Example 3, part D, the title compound was prepared in 96% yield from 4-hydroxyphenyl 2-(4-methoxyphenyl)benzo[b]thiophen-3-yl ketone (Example 28, Part A) to yield an off-white foam following column chromatography (SiO$_2$; gradient 0–5% MeOH in EtOAc).

$^1$H NMR (CDCl$_3$) δ 7.86–7.83 (m, 1H), 7.77 (d, J=8.8 Hz, 2H), 7.65–7.62 (m, 1H), 7.39–7.32 (m, 4H), 6.76 (d, J=8.8 Hz, 4H), 4.08 (t, J=5.6 Hz, 2H), 3.75 (s, 3H), 3.71 (t, J=4.7 Hz, 4H), 2.77 (t, J=5.6 Hz, 2H), 2.54 (t, J=4.5 Hz, 4H).

Part B. 2-(4-Hydroxyphenyl)benzo[b]thiophen-3-yl 4-[2-(4-Morpholinyl)ethoxy]phenyl Ketone

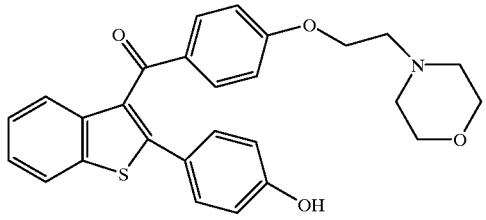

Following the procedure outlined in Example 1, part D, the title compound was prepared in 91% yield from 2-(4-methoxyphenyl)benzo[b]thiophen-3-yl 4-[2-(4-morpholinyl)ethoxy]phenyl ketone (Part A). The desired compound was isolated as a white solid after flash chromatography (SiO$_2$; gradient 0–10% MeOH in EtOAc) and recrystallization from THF-hexanes.

mp 188–189° C.; IR (KBr) 1598 cm$^{-1}$; FDMS 459 (M$^+$); Anal. Calcd for C$_{27}$H$_{25}$NO$_4$S: C, 70.57; H, 5.48; N, 3.05. Found C, 70.58; H, 5.57; N, 3.35.

Part C. 4-[2-(4-Morpholinyl)ethoxy]phenyl 2-[4-[2-(1-Pyrrolidinyl)ethoxy]phenyl]benzo[b]thiophen-3-yl Ketone Dioxalate Following Example 3, part D, the title compound was prepared from 2-(4-hydroxyphenyl)benzo[b]thiophen-3-yl 4-[2-(4-morpholinyl)ethoxy]phenyl ketone (Part B) in 78% yield as a light oil after flash chromatography [SiO$_2$; gradient 0–12% (1:2 TEA-i-PrOH) in THF]. Conversion to the dioxalate salt was carried out as detailed in Example 1, part C.

mp 73° C.; IR (KBr) 1598 cm$^{-1}$; $^1$H NMR (CD$_3$OD) δ 7.93 (d, J=7.1 Hz, 1H), 7.71 (d, J=8.8 Hz, 2H:), 7.56 (d, J=7.1 Hz, 1H), 7.36 (d, J=8.7 Hz, 4H), 6.88 (d, J=8.9 Hz, 2H), 6.87 (d, J=8.7 Hz, 2H), 4.36 (distorted t, 2H), 4.25 (distorted t, J=4.8 Hz, 2H), 3.90 (br t, J=4.6 Hz, 4H), 3.61–3.28 (m, 12H), 2.06 (m, 4H); FDMS 557 (M+1); Anal. Calcd for C$_{35}$H$_{38}$N$_2$O$_8$S.2C$_2$H$_2$O$_4$.2H$_2$O: C, 57.50; H, 5.74; N, 3.62. Found: C, 57.39; H, 5.56; N, 3.70.

EXAMPLE 18

Preparation of 4-[2-(Diethylamino)ethoxy]phenyl 2-[4-[2-(1-Pyrrolidinyl)ethoxy]phenyl]benzo[b]thiophen-3-yl Ketone Dioxalate

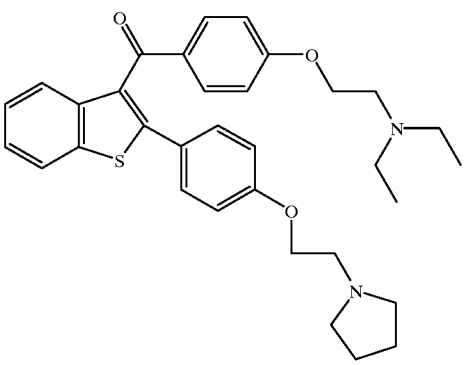

Part A. 4-[2-(Diethylamino)ethoxy]phenyl 2-(4-Methoxyphenyl)benzo[b]thiophen-3-yl Ketone

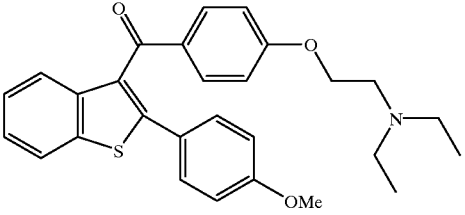

By essentially following the procedure outlined in Example 3, part D, the title compound was prepared from 4-hydroxyphenyl 2-(4-methoxyphenyl)benzo[b]thiophen-3-yl ketone (Example 28, Part A) and 2-diethylaminoethyl chloride in 86% yield. Flash chromatography [SiO$_2$; gradient 1–4% of (1:1 TEA-MeOH) in EtOAc] gave the desired compound as a light oil.

IR (CHCl$_3$) 1598 cm$^{-1}$; $^1$H NMR (CDCl$_3$) δ 7.86–7.84 (m, 1H), 7.83–7.75 (m, 2H), 7.65–7.62 (m, 1H), 7.39–7.25 (m, 4H), 6.76 (d, J=8.5 Hz, 4H), 4.03 (t, J=6.0 Hz, 2H), 3.75 (s, 3H), 2.84 (t, J=6.0 Hz, 2H), 2.66–2.59 (m, 4H), 1.05 (t, J=7.1 Hz, 6H); FDMS 459 (M$^+$); Anal. Calcd for C$_{28}$H$_{29}$NO$_3$S: C, 73.17; H, 6.36; N, 3.05. Found: C, 73.11; H, 6.49; N, 3.17.

Part B. 4-[2-(Diethylamino)ethoxy]phenyl 2-(4-Hydroxyphenyl)benzo[b]thiophen-3-yl Ketone

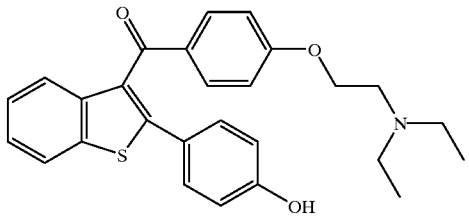

By essentially following the procedure outlined in Example 1, part D, the title compound was prepared in 71% yield from 4-[2-(diethylamino)ethoxy]phenyl 2-(4-methoxyphenyl)benzo[b]thiophen-3-yl ketone (Part A) as an orange foam following flash chromatography (SiO$_2$; 5% TEA in THF).

$^1$H NMR (CDCl$_3$) δ 7.89–7.86 (m, 1H), 7.76 (d, J=8.7 Hz, 2H), 7.72–7.69 (m, 1H), 7.39–7.36 (m, 2H), 7.25 (d, J=8.4 Hz, 2H), 6.95 (br s, 1H), 6.72 (d, J=8.7 Hz, 2H), 6.64 (d, J=8.4 Hz, 2H), 4.07 (t, J=5.8 Hz, 2H), 2.91 (t, J=5.9 Hz, 2H), 2.70 (q, J=7.1 Hz, 4H), 1.09 (t. J=7.1 Hz, 6H).

Part C. 4-[2-(Diethylamino)ethoxy]phenyl 2-[4-[2-(1-pyrrolidinyl)ethoxy]phenyl]benzo[b]thiophen-3-yl Ketone Dioxalate By essentially following the procedure outlined in Example 3, part D, the title compound was prepared from 4-[2-(diethylamino)ethoxy]phenyl 2-(4-hydroxyphenyl) benzo[b]thiophen-3-yl ketone (Part B) in 95% yield following flash chromatography (SiO$_2$; gradient 60% THF containing 3% TEA to 80% THF in hexanes) as a tan solid. Conversion to the dioxalate salt was carried out in 94% yield as detailed in Example 1, part C.

mp 176–179° C.; $^1$H NMR (CD$_3$OD) δ 7.92 (dd, J=7.0, 1.5 Hz, 1H), 7.74 (d, J=8.9 Hz, 2H), 7.54 (dd, J=7,2, 1.7 Hz, 1H), 7.41–7.34 (m, 4H), 6.92 (d, J=8.5 Hz, 2H), 6.90 (d, J=8.6 Hz, 2H), 4.36 (distorted t, 2H), 4.27 (distorted t, 2H), 3.59 (m 4H), 3.28 (m, 8H), 2.08 (br s, 4H), 1.31 (t, J=7.2 Hz, 6H); FDMS 543 (M+1), 634 (M+2+C$_2$H$_2$O$_4$).

EXAMPLE 19

Preparation of 1-[2-[4-[3-[4-[2-(Diethylamino) ethoxy]benzyl]benzo[b]thiophen-2-yl]phenoxy] ethyl]pyrrolidine Dioxalate

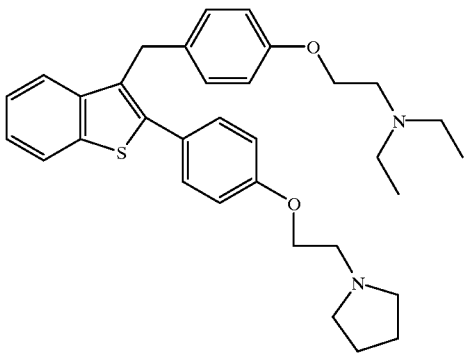

By essentially following the procedure outlined in Example 2, part D, the title compound was prepared in 91% yield from 4-[2-(diethylamino)ethoxy]phenyl 2-[4-[2-(1-pyrrolidinyl)ethoxy]phenyl]benzo[b]thiophen-3-yl ketone (Part C). Flash chromatography [SiO$_2$; 80% THF in hexanes with 3% TEA (v/v)] gave a white gummy solid which was converted to the dioxalate salt following the method described in Example 1, part C.

$^1$H NMR (DMSO-d$_6$) δ 7.99 (m, 1H), 7.59 ( br d, J=6.3 Hz, 1H), 7.50 (d, J=8.3 Hz, 2H), 7.36 (m, 2H), 7.13 (d, J=8.3 Hz, 2H), 7.07 (d, J=8.2 Hz, 2H), 6.89 (d, J=8.3 Hz, 2H), 4.38 (br s, 2H), 4.27 (br. s, 2H), 4.22 (br s, 2H), 3.57 (br s, 2H), 3.44 (br s, 2H), 3.35 (br. s, 4H), 3.16 (dt, J=7.1, 6.7 Hz, 4H), 1.96 (br s, 4H), 1.21 (t, J=6.9 Hz, 6H); FDMS 529 (M+1; Anal. Calcd for C$_{33}$H$_{40}$N$_2$O$_2$S.2C$_2$H$_2$O$_4$.H$_2$O: C, 61.14; H, 6.38; N, 3.85. Found: C, 61.04; H, 6.32; N, 3.61.

EXAMPLE 20

Preparation of (±)-6-Hydroxy-2-[4-[2-(1-pyrrolidinyl)ethoxy]phenyl]benzo[b]thiophen-3-yl 4-[[trans-2-(1-Piperidyl)cyclohexyl]oxy]phenyl Ketone Dioxalate

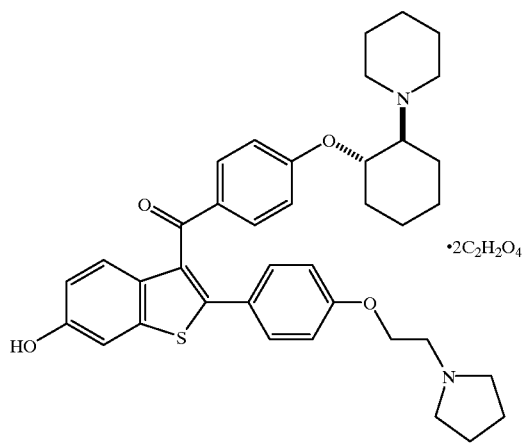

Part A. (+)-trans-(1-Piperidyl)cyclohexan-2-ol

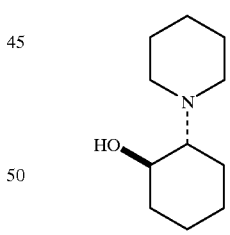

To a solution of 41.63 g (0.30 mol) of K$_2$CO$_3$ in ca. 200 mL of H$_2$O was added 12.16 g (0.10 mol) of piperidine hydrochloride at 0° C., followed by 10.1 mL (0.10 mol) of cyclohexene oxide. After 5 min at 0° C., the ice bath was removed and the cloudy solution was stirred at room temperature overnight (18 h). The mixture was then extracted with EtOAc (3×500 mL) which was washed with 200 mL of H$_2$O and 200 mL of brine. The combined extracts were dried over MgSO$_4$, concentrated, and dried under vacuum to afford 3.64 g (20%) of the crude amine which was used without further purification for the following reaction.

IR (KBr) 3435 cm$^{-1}$; FDMS 184 (M+1), 229 (100).

Part B. Methyl (±)-4-[[trans-2-(1-piperidyl)cyclohexyl]oxy]benzoate

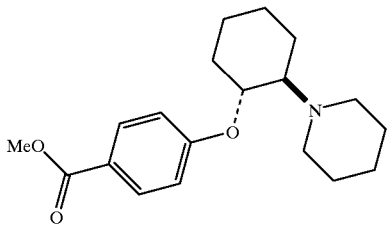

To a solution of methyl 4-hydroxybenzoate (1.476 g, 9.70 mmol) in 175 mL of anhydrous THF was added 3.557 g (19.4 mmol) of trans-(1-piperidyl)cyclohexan-2-ol, (Part A), 5.090 g (19.4 mmol) of triphenylphosphine and 3.10 mL (19.4 mmol) of diethyl azodicarboxylate at room temperature. The reaction mixture was stirred for 3 days and then concentrated under reduced pressure. The residue was purified by PrepLC (2.5 to 4% of (10% concd $NH_4OH$ in MeOH) in $CH_2Cl_2$) to afford 2.232 g (7.03 mmol, 73%) of an orange solid.

mp 88–91° C.; $^1H$ NMR (CDCl$_3$) δ 7.97 (d, J=8.8 Hz, 2H), 6.92 (d J=8.9 Hz, 2H), 4.32 (td, J=9.8, 4.2 Hz, 1H), 3.88 (s, 3H), 2.80–2.47 (m, 5H), 2.23–2.15 (m, 1H), 2.07–1.92 (m, 1H), 1.76 (m, 2H), 1.57–1.20 (m, 10H); FDMS 317 (M$^+$).

Part C. (±)-4-[[trans-2-(1-Piperidyl)cyclohexyl]oxy]benzoic Acid

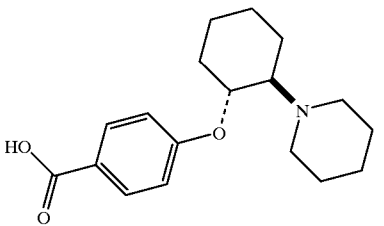

A solution of methyl 4-[[trans-2-(1-piperidyl)cyclohexyl]oxy]benzoate (Part B) (2.232 g, 7.03 mmol) and 10.6 mL (10.6 mmol) of 1.0N NaOH in 60 mL of 1:1 mixture of MeOH/THF was stirred at 80° C. for 20 h. The mixture was then cooled to room temperature, stirred for additional 7 h, and concentrated under reduced pressure. The residue was dissolved in 50 mL of 1.0N HCl. This solution was extracted with 200 mL of EtOAc. The organic layer was washed with 200 mL of water. The combined aqueous layers were cooled to 0° C. and neutralized with 15 mL of 2.0N NaOH. They were then concentrated under reduced pressure and the residue was taken up in 10% MeOH in $CH_2Cl_2$ and then filtered. The filtrate was concentrated and the residue was dried over $P_2O_5$ in a vacuum oven at 55° C.

mp 264–266° C. (dec); $^1H$ NMR (DMSO-d$_6$) δ 7.79 (d, J=7.7 Hz, 2H), 6.87 (d, J=8.1 Hz, 2H), 4.40 (m, 1H), 2.65–2.55 (m, 4H), 2.07 (m, 1H), 1.77–1.58 (m, 3H), 1.40–1.15 (m, 11H); FDMS 304 (M+1), 482 (base); Anal. Calcd for $C_{18}H_{25}NO_3$·0.73NaCl: C, 62.47, H, 7.28, N, 4.05. Found: C, 62.92, H, 7.47, N, 4.15.

Part D. (±)-6-Methoxy-2-[4-[2-(1-pyrrolidinyl)ethoxy]phenyl]benzo[b]thiophen-3-yl 4-[[trans-2-(1-Piperidyl)cyclohexyl]oxy]phenyl Ketone

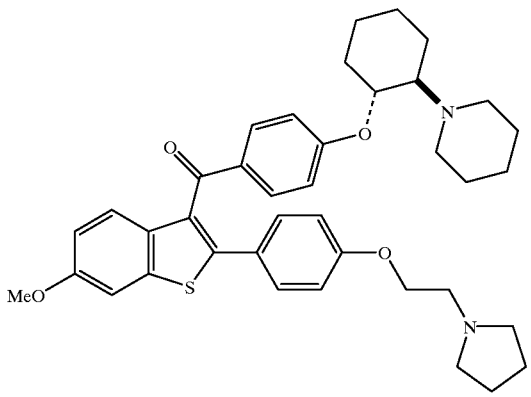

1.698 g (5.60 mmol) of 4-[[trans-2-(1-piperidyl)cyclohexyl]oxy]benzoic acid (Part C) was dissolved in 30 mL of thionyl chloride at room temperature. To this was added 434 μL (5.60 mmol) of DMF as a catalyst. The mixture was stirred for 3 days at room temperature. The thionyl chloride was removed under reduced pressure and the residue was treated with dry benzene to remove azeotropically the residual thionyl chloride and then placed under high vacuum. The crude acid chloride was suspended in 50 mL of anhydrous dichloroethane, and to this was added 1.799 g (5.09 mmol) of 6-methoxy-2-[4-[2-(1-pyrrolidinyl)ethoxy]phenyl]benzo[b]-thiophene (Example 1, Part B). After cooling the slurry to 0° C., aluminum bromide (6.79 g, 25.4 mmol) was added, producing a dark red mixture. The ice bath was removed and the reaction mixture was stirred at room temperature for 6 h. The mixture was poured into 100 mL of cooled (0° C.) 2.0 N NaOH. The aqueous layer was extracted with EtOAc (3×400 mL). The combined organic layers were washed with 300 mL of brine, dried over MgSO$_4$, and concentrated under reduced pressure. The crude product was purified using PrepLC (8% of (10% concd $NH_4OH$ in MeOH) in $CH_2Cl_2$).

mp 68–72° C.; $^1H$ NMR (CDCl$_3$) δ 7.76 (d, J=8.9 Hz, 2H), 7.49 (d, J=8.9 Hz, 1H), 7.36 (d, J=8.8 Hz, 2H), 7.31 (d, J=2.4 Hz, 1H), 6.94 (dd, J=8.9 and 2.4 Hz, 1H), 6.78 (d, J=8.8 Hz, 4H), 4.26 (td, J=9.8, 4.1 Hz, 1H), 4.09 (t, J=5.8 Hz, 2H), 3.88 (s, 3H), 2.92 (t, J=5.8 Hz, 2H), 2.69 (m, 7H), 2.50 (m, 2H), 2.17–1.95 (m, 2H), 1.84 (m, 4H), 1.73 (m, 2H), 1.50–1.15 (m, 10H); FDMS 639 (M$^+$); Anal. Calcd for $C_{39}H_{46}N_2O_4S$: C, 73.32; H, 7.26; N, 4.38. Found: C, 73.03; H, 7.13; N, 4.29.

Part E. (±)-6-Hydroxy-2-[4-[2-(1-pyrrolidinyl)ethoxy]phenyl]benzo[b]thiophen-3-yl 4-[[trans-2-(1-Piperidyl)cyclohexyl]oxy]phenyl Ketone Dioxalate.

The title compound was prepared from (±)-6-methoxy-2-[4-[2-(1-pyrrolidinyl)ethoxy]phenyl]benzo[b]thiophen-3-yl 4-[[trans-2-(1-piperidyl)cyclohexyl]oxy]phenyl ketone (Part D) as a yellow solid by essentially following the procedures described in Example 21, Parts B and C.

mp 140–145° C.; $^1H$ NMR (DMSO-d$_6$) δ 7.70 (d, J=8.6 Hz, 2H), 7.38 (d, J=2.2 Hz, 1H), 7.34 (d, J=8.6 Hz, 2H), 7.24 (d, J=8.7 Hz, 1H), 7.06 (d, J=8.7 Hz, 2H), 6.95 (d, J=8.7 Hz, 2H), 6.87 (d, J=10.9 Hz, 1H), 4.69 (m, 1H), 4.25 (m, 2H), 3.50 (m, 2H), 3.28 (m, 5H), 3.09 (m, 2H), 2.93 (m, 2H), 2.07 (m, 2H), 1.91 (m, 4H), 1.80 - 1.20 (m, 12H); FDMS 624 (M$^+$); Anal. Calcd for $C_{38}H_{44}N_2O_4S$·2.87$C_2H_2O_4$: C, 59.48; H, 5.68; N, 3.17. Found: C, 59.45; H, 5.85; N, 3.35.

EXAMPLE 21

Preparation of (±)-6-Hydroxy-3-[4-[[trans-2-(1-piperidyl)cyclohexyl]oxy]benzyl]-2-[4-[2-(1-pyrrolidinyl)ethoxy]phenyl]benzo[b]thiophene Dioxalate.

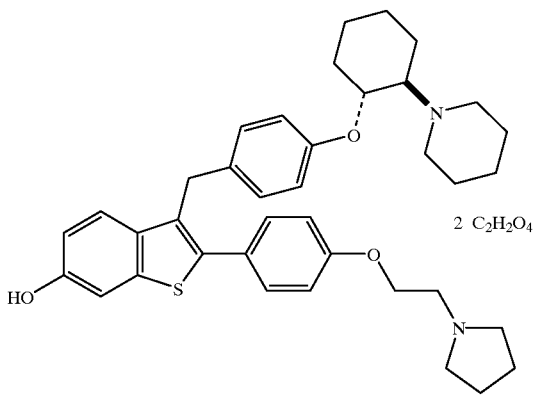

Part A. (±)-6-Methoxy-3-[4-[[trans-2-(1-piperidyl)-cyclohexyl]oxy]benzyl]-2-[4-[2-(1-pyrrolidinyl)ethoxy]phenyl]benzo[b]thiophene.

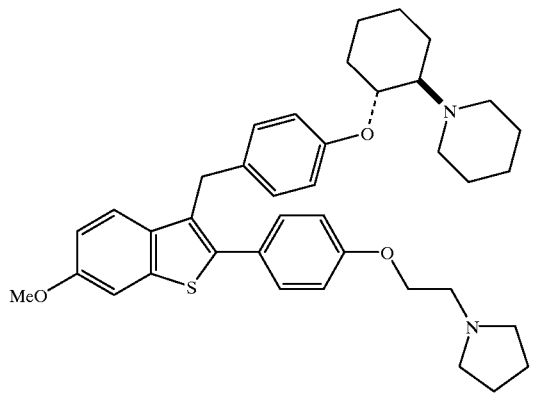

To a solution of 6-methoxy-[2-[4-[2-(1-pyrrolidinyl)ethoxy]phenyl]benzo[b]thiophen-3-yl] 4-[[trans-2-(1-piperidyl)cyclohexyl]oxy]phenyl ketone (Example 20, Part D) (1.340 g, 2.10 mmol) in 21.0 mL of anhydrous THF was added dropwise 2.10 mL (2.10 mmol) of 1.0 M LiAlH$_4$ in THF at 0° C. The reaction mixture was stirred for 1 h and 45 min while allowing the temperature to be raised to 20° C. The reaction was then quenched at 0° C. by addition of 80 μL of H$_2$O, followed by 80 μL of 15% NaOH, and then an additional 240 μL of H$_2$O (Fieser workup). This mixture was then filtered over a pad of silica gel and washed with THF. The filtrate was concentrated to dryness under reduced pressure. The crude alcohol was dissolved in 21.0 mL of anhydrous CH$_2$Cl$_2$ and cooled to 0° C. To this was added 2.30 mL (14.7 mmol) of triethylsilane, and the reaction mixture was stirred for 5 min, followed by a dropwise addition of 1.60 mL (21.0 mmol) of trifluoroacetic acid. The ice bath was removed and the reaction mixture was stirred further for 3 h 45 min before being quenched with 25.0 mL of saturated NaHCO$_3$ at 0° C. The layers were separated and the aqueous layer was extracted with EtOAc (3×200 mL). The combined organic layers were dried over MgSO$_4$, concentrated under reduced pressure, and purified by flash chromatography (silica gel, 57:40:3 hexanes-THF-TEA) to afford 1.251 g (2.00 mmol, 96%) of a clear gel. $^1$H NMR: (CDCl$_3$) δ 7.41 (d, J=8.9 Hz, 2H), 7.40 (d, J=8.8 Hz, 1H), 7.31 (d, J=2.3 Hz, 1H), 7.03 (d, J=8.4 Hz, 2H), 6.94 (d, J=8.8 Hz, 2H), 6.93 (m, 1H), 6.81 (d, J=8.6 Hz, 2H), 4.15 (m, 5H), 3.86 (s, 3H), 2.94 (t, J=5.9 Hz, 2H), 2.85–2.55 (m, 9H), 2.20–2.10 (m, 2H), 1.83 (m, 4H), 1.72 (m, 2H) 1.58–1.48 (m, 4H), 1.42–1.18 (m, 6H); FDMS 625 (M$^+$); Anal. Calcd for C$_{39}$H$_{48}$N$_2$O$_3$S: C, 74.96; H, 7.74; N, 4.48. Found: C, 75.00; H, 7.94; N, 4.35.

Part B. (±)-6-Hydroxy-3-[4-[[trans-2-(1-piperidyl)-cyclohexyl]oxy]benzyl]-2-[4-[2-(1-pyrrolidinyl)ethoxy]phenyl]benzo[b]thiophene.

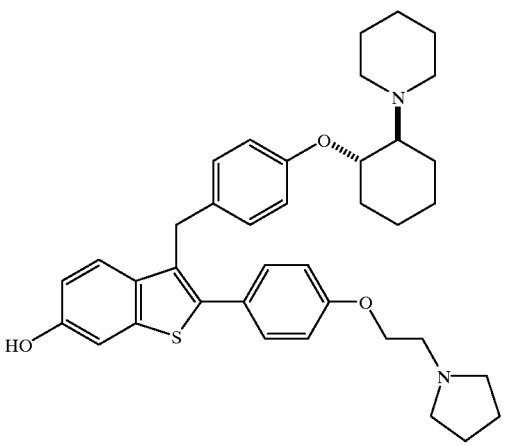

To a solution of 1.150 g (1.84 mmol) (±)-6-methoxy-3-[4-[[trans-2-(1-piperidyl)cyclohexyl]oxy]benzyl]-2-[4-[2-(1-pyrrolidinyl)ethoxy]phenyl]benzo[b]thiophene (Part A) in 20.0 mL of anhydrous dichloroethane at 0° C. was added 1.10 mL (14.7 mmol) of ethanethiol, followed by the addition of aluminum chloride (982 mg, 7.36 mmol). The yellow biphasic reaction mixture was allowed to warm to room temperature and stirred for 3 h. The reaction was quenched at 0° C. with 20 mL of saturated aqueous NaHCO$_3$. The aqueous layer was separated and extracted with EtOAc (3×200 mL). The combined organic layers were washed with 150 mL of brine, dried over MgSO$_4$, and concentrated under reduced pressure. The crude product was purified by using flash chromatography (silica gel, 60:37:3 THF-hexanes-TFA) to afford 1.067 g (1.75 mmol, 95%) of a white solid.

mp 179–182° C.; $^1$H NMR (CDCl$_3$) δ 7.30 (dd, J=8.7, 1.9 Hz, 2H), 7.07 (d, J=2.2 Hz, 1H), 7.01 (d, J=8.6 Hz, 2H), 6.82 (d, J=2.2 Hz, 1H), 6.77 (m, 5H), 4.14 (t, J=5.6 Hz, 2H), 4.12 (buried m, 1H), 4.10 (s, 2H), 3.00 (t, J=5.5 Hz, 2H), 2.81 (m, 5H), 2.69 (m, 4H), 2.14 (m, 2H), 1.87 (m, 4H), 1.71 (m, 2H), 1.58 (m, 3H), 1.38 (m, 3H), 1.26 (m, 4H); FDMS 611 (M$^+$); Anal. Calcd for C$_{38}$H$_{46}$N$_2$O$_3$S: C, 74.71; H, 7.59; N, 4.59. Found: C, 74.92; H, 7.80; N, 4.53.

Part C. (±)-6-Hydroxy-3-[4-[[trans-2-(1-piperidyl)-cyclohexyl]oxy]benzyl]-2-[4-[2-(1-pyrrolidinyl)ethoxy]phenyl]benzo[b]thiophene Dioxalate.

In approximately 4 mL of CHCl$_3$-EtOAc (1:1) was dissolved 14.7 mg (0.164 mmol) of oxalic acid. To this was added dropwise 50.0 mg (0.082 mmol) of (±)-6-hydroxy-3-[4-[[trans-2-(1-piperidyl)cyclohexyl]oxy]benzyl]-2-[4-[2-(1-pyrrolidinyl)ethoxy]phenyl]benzo[b]thiophene (Part C) in 7 mL of CHCl$_3$. A white precipitate was formed, and the slurry was sonicated for 30 min and filtered with EtOAc rinse. The precipitate was dried over P$_2$O$_5$ at 55° C. in a vacuum oven.

mp 163–165 ° C.; $^1$H NMR (DMSO-d$_6$) δ 7.44 (d, J=8.5 Hz, 2H), 7.37 (d, J=8.7 Hz, 1H), 7.27 (s, 1H), 7.09 (d, J=8.6 Hz, 2H), 7.04 (d, J=8.6 Hz, 2H), 6.93 (d, J=8.5 Hz, 2H), 6.81 (dd, J=8.7, 2.1 Hz, 1H), 4.49 (m, 1H), 4.33 (br t, 2H), 4.12

(s, 2H), 3.51 (br t, 2H), 3.28 (m, 5H), 3.15 (m, 2H), 3.01 (m, 2H), 2.10 (m, 2H), 1.92 (m, 4H), 1.75–1.60 (m, 6H), 1.55–1.40 (m, 3H), 1.26 (m, 3H); FDMS 611 (M$^+$); Anal. Calcd for $C_{38}H_{46}N_2O_3S \cdot 2.0C_2H_2O_4 \cdot 0.24CHCl_3$: C, 61.90; H, 6.18; N, 3.42. Found: C, 61.90; H, 5.99; N, 3.37.

EXAMPLE 22
Preparation of (±)-6-Hydroxy-2-[4-[2-(1-pyrrolidinyl) ethoxy]phenyl]benzo[b]thiophen-3-yl 6-[[trans-2-(1-Piperidyl)cyclohexyl]oxy]pyrid-3-yl Ketone.

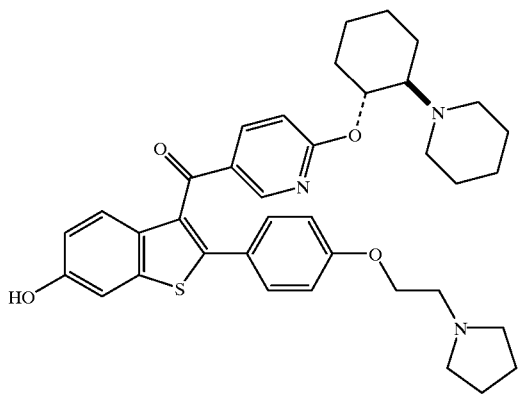

Part A. (±)-6-[[trans-2-(1-Piperidyl)cyclohexyl]oxy]-3-pyridinecarboxylic Acid.

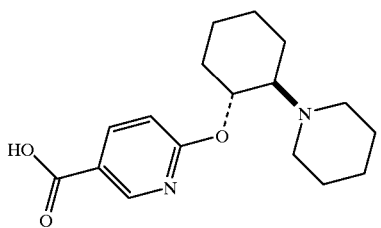

The title compound was prepared from methyl (±)-6-[[trans-2-(1-piperidyl) cyclohexyl]oxy]-3-pyridinecarboxylate as an off-white solid by essentially following the procedure described in Example 20, Part C.

$^1$H NMR (DMSO-d$_6$) δ 10.00 (m, 1H) 8.73 (dd, J=2.4, 0.5 Hz, 1H), 8.21 (dd, J=8.7, 2.4 Hz, 1H), 7.04 (d, J=8.6 Hz, 1H), 5.35 (m, 1H), 3.60 (br t, 1H), 3.49 (br d, J=11.6 Hz, 1H), 3.40 (br d, J=11.4 Hz, 1H), 3.18 (br q, 1H), 2.73 (br q, J=11.2 Hz, 1H), 2.48 (m, 1H), 2.23 (m, 1H), 2.10–1.83 (m, 2H), 1.83–1.58 (m, 6H), 1.45–1.12 (m, 4H).

Part B. (±)-6-Hydroxy-2-[4-[2-(1-pyrrolidinyl)ethoxy]phenyl]benzo[b]thiophen-3-yl 6-[[trans-2-(1-Piperidyl)cyclohexyl]oxy]pyrid-3-yl Ketone.

The title compound was prepared in 29% yield from 6-methoxy-2-[4-[2-(1-pyrrolidinyl)ethoxy]phenyl]benzo[b]-thiophene (Example 1, Part B) and (±)-6-[[trans-2-(1-piperidyl)cyclohexyl]oxy]-3-pyridinecarboxylic acid (Part A) by essentially following the procedures detailed in Example 20, Parts D and E.

$^1$H NMR (CDCl$_3$) δ 8.32 (d, J=2.4 Hz, 1H), 7.70 (dd, J=8.6, 2.4 Hz, 1H), 7.41 (d, J=8.9 Hz, 1H), 7.30 (d, J=2.1 Hz, 1H), 7.06 (d, J=8.6 Hz, 2H), 6.81 (dd, J=8.8, 2.2 Hz, 1H), 6.62 (d, J=8.6 Hz, 2H), 6.44 (d, J=8.6 Hz, 1H), 5.22 (m, 1H), 4.07 (t, J=5.4 Hz, 2H), 3.00 (t, J=5.4 Hz, 2H), 2.87–2.57 (m, 9H), 2.20–2.00 (m, 2H), 1.95–1.65 (m, 6H), 1.60–1.20 (m, 10H); FDMS 626 (M$^+$); Anal. Calcd for $C_{37}H_{43}N_3O_4S \cdot 0.59H_2O$: C, 69.83; H, 7.00; N, 6.60. Found: C, 69.58; H, 6.73; N, 6.99.

EXAMPLE 23
Preparation of (±)-6-Hydroxy-3-[6-[[trans-2-(1-piperidyl) cyclohexyl]oxy]pyrid-3-yl]methyl-2-[4-[2-(1-pyrrolidinyl) ethoxy]phenyl]benzo[b]thiophene Dioxalate.

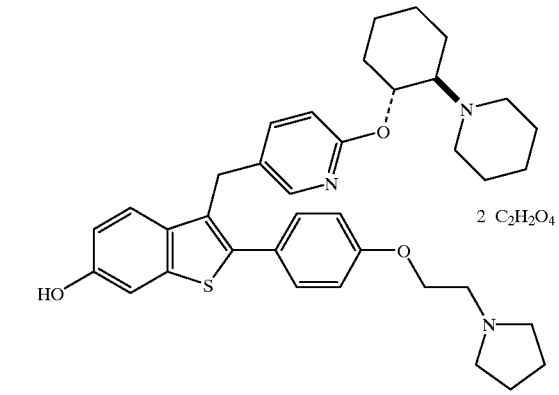

Part A. (±)-6-Hydroxy-3-[6-[[trans-2-(1-piperidyl) cyclohexyl]oxy]pyrid-3-yl]methyl-2-[4-[2-(1-pyrrolidinyl) ethoxy]phenyl]benzo[b]thiophene.

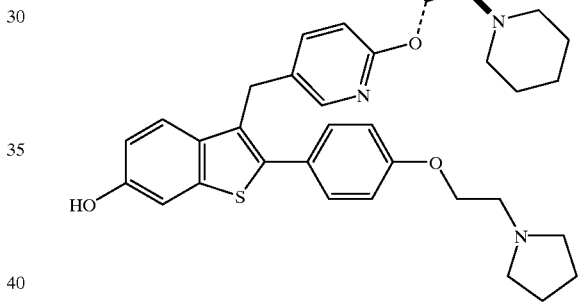

The title compound was prepared in 39% yield from 6-hydroxy-2-[4-[2-(1-pyrrolidinyl)ethoxy]phenyl]benzo[b]-thiophen-3-yl 6-[[trans-2-(1-piperidyl)cyclohexyl]oxy] pyrid-3-yl ketone (Example 22, Part B) by essentially following the procedures detailed in Example 21, Parts A and B.

mp 170–174° C.; $^1$H NMR (CDCl$_3$) δ 7.89 (d, J=2.2 Hz, 1H), 7.31–7.21 (m, 4H), 7.03 (d, J=2.1 Hz, 1H), 6.80 (d, J=8.6 Hz, 3H), 6.54 (d, J=8.5 Hz, 1H), 5.11 (m, 1H), 4.14 (t, J=5.4 Hz, 2H), 4.05 (s, 2H), 2.99 (t, J=5.4 Hz, 2H), 2.80 (m, 5H), 2.59 (m, 4H), 2.16 (m, 2H), 1.87 (m, 4H), 1.69 (m, 3H), 1.43–1.25 (m, 9H); FDMS 611 (M$^+$); Anal. Calcd for $C_{37}H_{45}N_3O_3S$: C, 72.63; H, 7.41, N, 6.87. Found: C, 72.34, H, 7.64, N, 6.61.

Part B. (±)-6-Hydroxy-3-[6-[[trans-2-(1-piperidyl) cyclohexyl]oxy]pyrid-3-yl]methyl-2-[4-[2-(1-pyrrolidinyl) ethoxy]phenyl]benzo[b]thiophene Dioxalate.

The title compound was prepared from (±)-6-hydroxy-3-[6-[[trans-2-(1-piperidyl)cyclohexyl]oxy]pyrid-3-yl] methyl-2-[4-[2-(1-pyrrolidinyl)ethoxy]phenyl]benzo[b] thiophene (Part A) by essentially following the procedures detailed in Example 20, Part C.

mp 128–133° C. (dec); $^1$H NMR (DMSO-d$_6$) δ 7.93 (s, 1H), 7.47 (dd, J=8.7 Hz, 2.7 Hz, 2H), 7.38 (m, 2H), 7.27 (d, J=2.0 Hz, 1H), 7.10 (d, J=8.6 Hz, 2H) 6.83 (d, J=8.6 Hz, 1H), 6.77 (d, J=8.4 Hz, 1H), 5.13 (m, 1H), 4.35 (br t, 2H), 4.14 (s, 2H), 3.56 (br t, 2H), 3.33–3.00 (m, 9H), 2.12 (m, 2H), 1.99–1.94 (m, 4H), 1.75–1.62 (m, 6H), 1.28–1.17 (m, 6H); FDMS 612 (M$^+$) ; Anal. Calcd for $C_{37}H_{45}N_3O_3S \cdot 2.36C_2H_2O_4$: C, 60.79; H, 6.08; N, 5.10. Found: C, 60.76; H, 6.25; N, 5.26.

EXAMPLE 24

Preparation of 2-[4-[2-(1-Pyrrodinyl)ethoxy]phenyl]-3,4-dihydronaphth-1-yl 4-[2-(1-Piperidyl)ethoxy]phenyl Ketone Dioxalate.

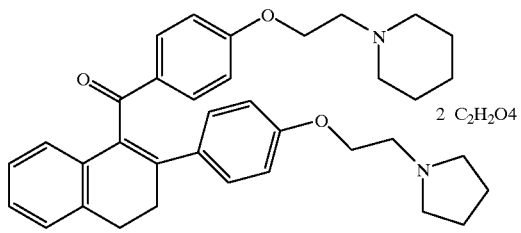

Part A. 2-(4-Hydroxyphenyl)-3,4-dihydronaphth-1-yl 4-[2-(1-Piperidyl)ethoxy]phenyl Ketone.

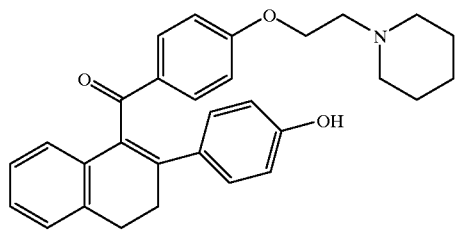

The title compound was prepared in 95% yield from 2-(4-methoxyphenyl)-3,4-dihydronaphth-1-yl 4-[2-(1-piperidyl)ethoxy]phenyl ketone by essentially following the procedure detailed in Example 21, Part B.

mp 83–85° C.; $^1$H NMR (CDCl$_3$) δ 7.75 (d, J=8.7 Hz, 2H), 7.21 (d, J=7.1 Hz, 1H), 7.16–7.05 (m, 4H), 6.94 (d, J=7.8 Hz, 1H), 6.60 (d, J=8.8 Hz, 2H), 6.54 (d, J=8.5 Hz, 2H), 4.01 (t, J=5.6 Hz, 2H), 3.03 (distorted t, 2H), 2.81 (t, J=8.4 Hz, 2H), 2.74 (t, J=5.6 Hz, 2H), 2.53 (br s, 4H), 1.61 (m, 4H), 1.43 (m, 2H); FDMS 453 (M$^+$) ; Anal. Calcd for $C_{30}H_{31}NO_3 \cdot 0.56CH_2Cl_2$: C, 73.24; H, 6.46; N, 2.79. Found: C, 73.27; H, 6.50; N, 2.72.

Part B. 2-[4-[2-(1-Pyrrolidinyl)ethoxy]phenyl]-3,4-dihydronaphth-1-yl 4-[2-(1-Piperidyl)ethoxy]phenyl Ketone Dioxalate.

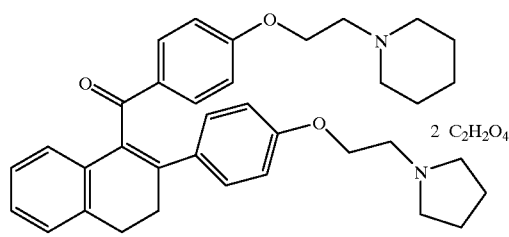

To a solution of 731.0 mg (1.61 mmol) 2-(4-hydroxyphenyl)-3,4-dihydronaphth-1-yl 4-[2-(1-piperidyl)ethoxy]phenyl ketone (Part A) in 16.0 mL of anhydrous DMF at room temperature was added Cs$_2$CO$_3$ (1.575 g, 4.83 mmol), followed by addition of 1-(2-chloroethyl)pyrrolidine hydrochloride (411 mg, 2.42 mmol). The light yellow slurry was then heated to 85° C. and stirred for 3.5 h. The reaction mixture was cooled to room temperature and 80 mL of H$_2$O was added. This mixture was extracted with EtOAc (3×100 mL). The combined organic layers were washed with 100 mL of brine, dried over MgSO$_4$, and concentrated under reduced pressure. The residue was purified by flash chromatography (silica gel, 60:37:3 THF-hexanes-TEA) to afford 821.5 mg (1.49 mmol, 93%) of a yellow gel. The free diamine was then used to prepare the title compound by essentially following the procedure detailed in Example 21, Part C.

mp 93–97° C.; $^1$H NMR (DMSO-d$_6$) δ 7.77 (d, J=8.7 Hz, 2H), 7.26–7.01 (m, 5H), 6.92 (d, J=8.8 Hz, 2H), 6.80 (d, J=8.7 Hz, 2H), 6.68 (d, J=7.7 Hz, 1H), 4.33 (br t, 2H), 4.18 (br t, 2H), 3.45 (m, 2H), 3.36 (m, 2H), 3.25 (m, 4H), 3.13 (m, 4H), 2.99 (br t, 2H), 2.72 (br s, 2H), 1.87 (m, 4H), 1.68 (m, 4H), 1.46 (m, 2H); FDMS 551 (M$^+$) , 641 (M+1.0 C$_2$H$_2$O$_4$); Anal. Calcd for $C_{36}H_{42}N_2O_3 \cdot 2.68C_2H_2O_4$: C, 62.72; H, 6.03; N, 3.54. Found: C, 62.32; H, 5.71; N, 3.64.

EXAMPLE 25

Preparation of 1-[4-[2-(1-Piperidyl)ethoxy]benzyl]-2-[4-[2-(1-pyrrolidinyl)ethoxy]phenyl]-3,4-dihydronaphthalene Dioxalate.

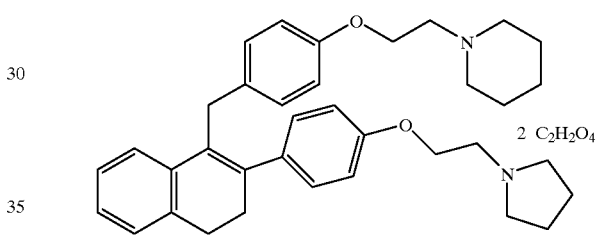

The title compound was prepared in 68% yield from 2-[4-[2-(1-pyrrolidinyl)ethoxy]phenyl]-3,4-dihydronaphth-1-yl 4-[2-(1-piperidyl)ethoxy]phenyl ketone by essentially following the procedures detailed in Example 21, Parts A and C.

mp 140–143° C.; $^1$H NMR (DMSO-d$_6$) δ 7.36 (d, J=7.9 Hz, 1H), 7.19–7.02 (m, 6H), 6.94–6.79 (m, 5H), 4.96 (s, 2H), 4.24 (m, 4H), 3.36–3.30 (m, 7H), 3.15 (m, 4H), 3.05–2.90 (m, 3H), 2.80–2.55 (m, 2H), 1.92 (m, 4H), 1.72 (m, 4H), 1.50 (m, 2H); FDMS 534 (M-2); Anal. Calcd for $C_{36}H_{44}N_2O_2 \cdot 2.0C_2H_2O_4$: C, 67.02; H, 6.75; N, 3.91. Found: C, 67.32; H, 6.69; N, 4.10.

EXAMPLE 26

Preparation of 2-[4-[2-(1-Pyrrolidinyl)ethoxy]phenyl] naphth-1-yl 4-[2-(1-Piperidyl)ethoxy]phenyl Ketone Dioxalate.

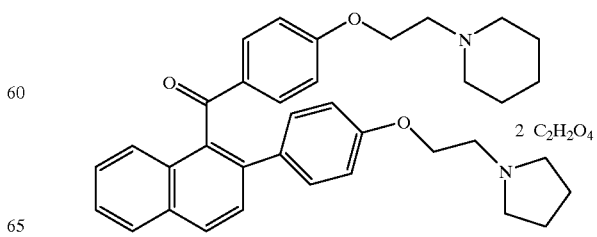

Part A. 2-(4-Hydroxyphenyl)naphth-1-yl 4-[2-(1-Piperidyl)ethoxy]phenyl Ketone.

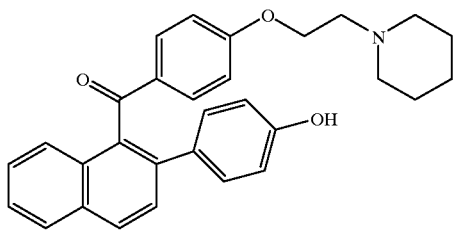

The title compound was prepared in 92% yield from 2-(4-methoxyphenyl)naphth-1-yl 4-[2-(1-piperidyl)ethoxy]phenyl ketone by essentially following the procedure described in Example 21, Part B.

mp 167–170° C.; $^1$H NMR (CDCl$_3$) δ 7.98 (d, J=8.5 Hz, 1H), 7.91 (d, J=8.4 Hz, 1H), 7.70 (d, J=8.0 Hz, 1H), 7.61–7.41 (m, 5H), 7.17 (d, J=8.5 Hz, 2H), 6.69–6.59 (m, 4H), 4.05 (t, J=5.6 Hz, 2H), 2.79 (t, J=5.4 Hz, 2H), 2.58 (br s, 4H), 1.65 (m, 4H), 1.47 (m, 2H); FDMS 451 (M$^+$).

Part B. 2-[4-[2-(1-Pyrrolidinyl)ethoxy]phenyl]naphth-1-yl 4-[2-(1-Piperidyl)ethoxy]phenyl Ketone Dioxalate.

The title compound was prepared from 2-(4-hydroxyphenyl)naphth-1-yl 4-[2-(1-piperidyl)ethoxy]phenyl ketone in 94% yield by essentially following the procedure detailed in Example 3, Part D and Example 21, Part C.

mp 95–100° C.; $^1$H NMR (DMSO-d$_6$) δ 8.11 (d, J=8.6 Hz, 1H), 8.03 (d, J=8.0 Hz, 1H), 7.58–7.40 (m, 6H), 7.29 (d, J=8.5 Hz, 2H), 6.90 (d, J=8.6 Hz, 4H), 4.30 (br t, 2H), 4.21 (br t, 2H), 3.47 (br t, 2H), 3.34 (br t, 2H), 3.27 (br s, 4H), 3.18–3.04 (m, 4H), 1.88 (br s, 4H), 1.67 (m, 4H), 1.46 (m, 2H); FDMS 549 (M$^+$); Anal. Calcd for C$_{36}$H$_{40}$N$_2$O$_3$·2.27C$_2$H$_2$O$_4$: C, 64.66; H, 5.96; N, 3.72. Found: C, 64.22 H, 5.89; N, 3.56.

EXAMPLE 27
Preparation of 1-[4-[2-(1-Piperidyl)ethoxy]benzyl]-2-[4-[2-(1-pyrrolidinyl)ethoxy]phenyl]naphthalene Dioxalate.

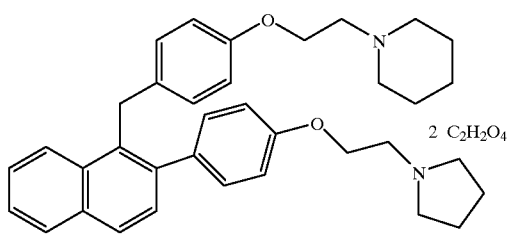

The title compound was prepared in 71% yield from 2-[4-[2-(1-pyrrolidinyl)ethoxy]phenyl]naphth-1-yl 4-[2-(1-piperidyl)ethoxy]phenyl ketone by essentially following the procedures detailed in Example 21, Parts A and C.

mp 184–187° C.; $^1$H NMB. (DMSO-d$_6$) δ 7.96 (d, J=7.7 Hz, 1H), 7.91 (d, J=8.5 Hz, 1H), 7.85 (d, J=7.7 Hz, 1H), 7.50–7.40 (m, 3H), 7.31 (d, J=8.4 Hz, 2H), 7.05 (d, J=8.4 Hz, 2H), 6.92 (d, J=8.5 Hz, 2H), 6.82 (d, J=8.7 Hz, 2H), 4.36 (s, 2H), 4.32 (br t, 2H), 4.20 (br t, 2H), 3.53 (m, 2H), 3.31 (m, 6H), 3.09 (m, 4H), 1.93 (m, 4H), 1.69 (m, 4H), 1.50 (m, 2H); FDMS 535 (M$^+$); Anal. Calcd for C$_{36}$H$_{42}$N$_2$O$_2$·2.0C$_2$H$_2$O$_4$: C, 67.21; H, 6.49; N, 3.92. Found: C, 66.93; H, 6.45; N, 4.05.

EXAMPLE 28
Preparation of 2-[4-[2-(1-Pyrrolidinyl)ethoxy]phenyl]benzo[b]thiophen-3-yl 4-[2-(1-Piperidyl)ethoxy]phenyl Ketone Dioxalate.

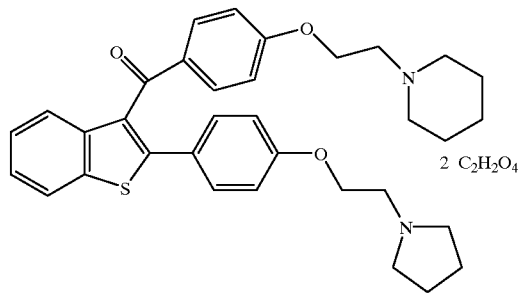

Part A. 2-(4-Methoxyphenyl)benzo[bhthiophen-3-yl 4-Hydroxyphenyl Ketone.

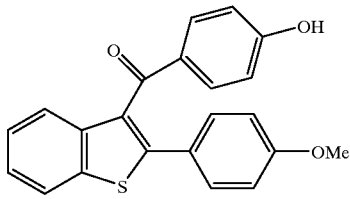

A ~0.5 M solution of sodium thioethoxide was prepared by adding ethanethiol (1.60 mL, 21.4 mmol) to a suspension of 60% NaH dispersion in mineral oil (769 mg, 19.2 mmol) in 40 mL of anhydrous DMF at 0° C. The ice bath was removed and the solution was stirred at room temperature for 30 min. The 0.5 M solution of sodium thioethoxide was then added dropwise to the solution of 4.00 g (10.7 mmol) of 2-(4-methoxyphenyl)benzo[b]thiophen-3-yl 4-methoxyphenyl ketone in 10.0 mL of anhydrous DMF at room temperature. The reaction mixture was heated at 85° C. for 3 h, then allowed to cool to room temperature, and acidified with 20 mL of 1.0 N HCl. To this was added 200 mL of H$_2$O and the mixture was extracted with EtOAc (3×400 mL). The combined organic layers were washed with 200 mL of brine, dried over MgSO$_4$, and concentrated under reduced pressure. The crude product was purified by PrepLC (30% EtOAc in hexanes) to afford 3.017 g of the title compound (8.37 mmol, 78%) as a yellow foam.

mp 76–77° C.; $^1$H NMR (CDCl$_3$) δ 7.85 (m, 1H), 7.72 (d, J=8.7 Hz, 2H), 7.64 (m, 1H), 7.38–7.29 (m, 4H), 6.76 (d, J=8.7 Hz, 2H), 6.68 (d, J=8.7 Hz, 2H), 6.03 (br s, 1H), 3.75 (s, 3H); FDMS 360 (M$^+$); Anal. Calcd for C$_{22}$H$_{16}$O$_3$S: C, 73.31; H, 6.20. Found: C, 73.57; H, 4.60.

Part B. 2-(4-Methoxyphenyl)benzo[b]thiophen-3-yl 4-[2-(1-Piperidyl)ethoxy]phenyl Ketone.

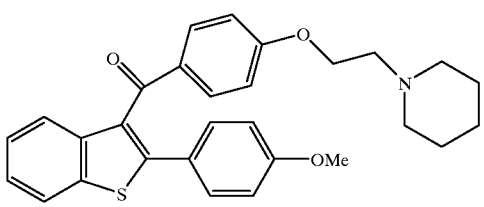

The title compound was prepared using 2-(4-methoxyphenyl)benzo[b]thiophen-3-yl 4-hydroxyphenyl ketone and 1-(2-chloroethyl)piperidine hydrochloride in 81% yield by essentially following the same procedures detailed in Example 24, Part B.

mp 41–44° C.; ¹H NMR (CDCl₃) δ 7.85 (m, 1H), 7.77 (d, J=8.8 Hz, 2H), 7.64 (m, 1H), 7.40–7.33 (m, 4H), 6.77 (d, J=8.6 Hz, 4H), 4.11 (t, J=5.8 Hz, 2H), 3.76 (s, 3H), 2.77 (t, J=5.8 Hz, 2H), 2.51 (br s, 4H), 1.61 (m, 4H), 1.44 (m, 2H); FDMS 471 (M⁺) ; Anal. Calcd for C₂₉H₂₉NO₃S: C, 73.86; H, 6.20, N, 2.97. Found: C, 73.90; H, 6.20; N, 3.14.

Part C. 2-(4-Hydroxyphenyl)benzo[b]thiophen-3-yl 4-[2-(1-Piperidyl)ethoxy]phenyl Ketone.

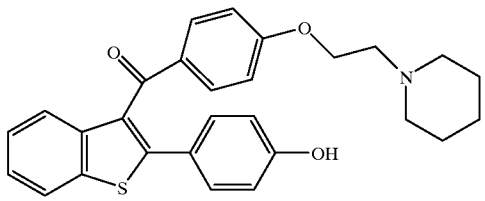

The title compound was prepared from 2-(4-methoxyphenyl)benzo[b]thiophen-3-yl 4-[2-(1-piperidyl)ethoxy]phenyl ketone in 93% yield as a yellow foam by essentially following the same procedure detailed in Example 21, Part B.

mp 100–103° C.; ¹H NMR (CDCl₃) δ 7.84 (m, 1H), 7.70 (m, 1H), 7.68 (d, J=8.9 Hz, 2H), 7.34 (m, 2H), 7.19 (d, J=8.7 Hz, 2H), 6.62 (d, J=8.9 Hz, 2H), 6.58 (d, J=8.6 Hz, 2H), 4.07 (t, J=5.6 Hz, 2H), 2.78 (t, J=5.6 Hz, 2H), 2.57 (br s, 4H), 1.64 (m, 4H), 1.45 (m, 2H); FDMS 457 (M⁺) ; Anal. Calcd for C₂₈H₂₇NO₃S: C, 73.49; H, 5.95; N, 3.06. Found: C, 73.76; H, 5.97; N, 3.07.

Part D. 2-[4-[2-(1-Pyrrolidinyl)ethoxy]phenyl]benzo[b]thiophen-3-yl 4-[2-(1-Piperidyl)ethoxy]phenyl Ketone Dioxalate.

The title compound was prepared in quantitative yield from 2-(4-hydroxyphenyl)benzo[b]thiophen-3-yl 4-[2-(1-piperidyl)ethoxy]phenyl ketone (Part C) by essentially following the procedure detailed in Example 4, Part B, except using 1-(2-hydroxyethyl)pyrrolidine, and Example 21, Part C.

mp 86–90° C.; ¹H NMR (DMSO-d₆) δ 8.06 (d, J=7.8 Hz, 1H), 7.70 (d, J=8.7 Hz, 2H), 7.43–7.35 (m, 5H), 6.96 (d, J=8.9 Hz, 2H), 6.95 (d, J=8.6 Hz, 2H), 4.34 (br t, 2H), 4.25 (br t, 2H), 3.48 (br t, 2H), 3.37 (br t, 2H), 3.27 (m, 4H), 3.13 (m, 4H), 1.89 (m, 4H), 1.68 (m, 4H), 1.47 (m, 2H); FDMS 555 (M⁺) ; Anal. Calcd for C₃₄H₃₈N₂O₃S.2.0C₂H₂O₄: C, 62.11; H, 5.76; N, 3.81. Found: C, 61.81; H, 5.61; N, 3.53.

EXAMPLE 29
Preparation of 3-[4-[2-(1-Piperidyl)ethoxy]benzyl]-2-[4-[2-(1-pyrrolidinyl)ethoxy]phenyl]benzo[b]thiophene Dioxalate.

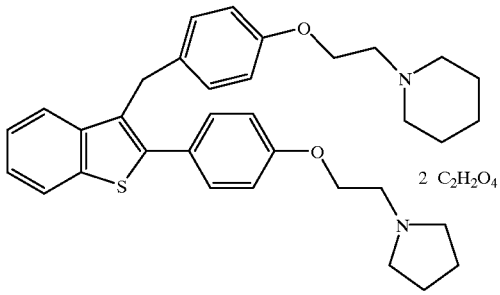

The title compound was prepared in 63% yield from 2-[4-[2-(1-pyrrolidinyl)ethoxy]phenyl)benzo[b]thiophen-3-yl 4-[2-(1-piperidyl)ethoxy]phenyl ketone by essentially following the procedures detailed in Example 21, Parts A and C.

mp 188–191° C.; ¹H NMR (DMSO-d₆) δ 7.96 (m, 1H), 7.55 (m, 1H), 7.50 (d, J=7.9 Hz, 2H), 7.34 (m, 2H), 7.13 (d, J=8.3 Hz, 2H), 7.05 (d, J=8.2 Hz, 2H), 6.88 (d, 8.5 Hz, 2H), 4.34 (br t, 2H), 4.21 (m, 4H), 3.55 (m, 2H), 3.33 (m, 6H), 3.11 (m, 4H), 1.94 (m, 4H), 1.70 (m, 4H), 1.51 (m, 2H); FDMS 541 (M⁺) ; Anal. Calcd for C₃₄H₄₀N₂O₂S.2.0C₂H₂O₄: C, 63.32; H, 6.15; N, 3.89. Found: C, 63.03; H, 6.05; N, 3.81.

EXAMPLE 30
Preparation of 3-[4-[2-(1-Piperidinyl)ethoxy]benzoyl]-2-[4-[2-(1-pyrrolidinyl)ethoxy]phenyl]benzo[b]thiophene-6-carboxamide Dioxalate.

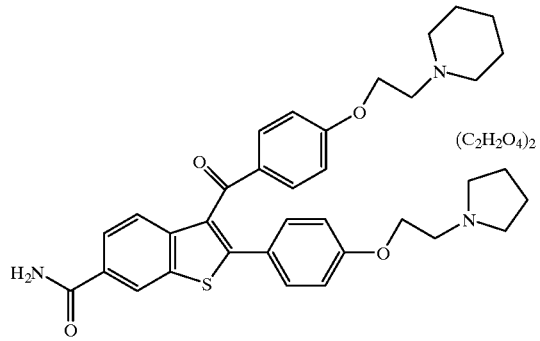

Part A. 2-14-[[(1,1-Dimethylethyl)dimethylsilyl]oxy]phenyl]-6-hydroxybenzo[b]thiophen-3-yl 4-[2-(1-Piperidinyl) ethoxyl phenyl Ketone.

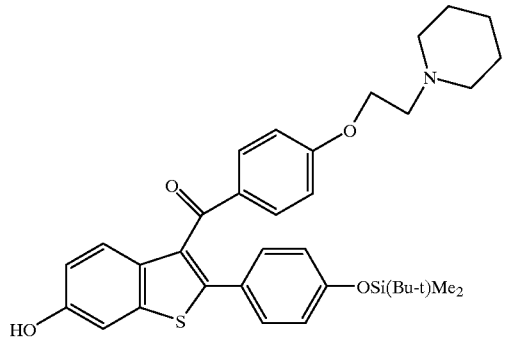

To a solution of 30 g (58.8 mmol) of 6-hydroxy-2-(4-hydroxyphenyl)benzo[b]thiophen-3-yl 4-[2-(1-piperidinyl)ethoxy]phenyl ketone hydrochloride in 120 mL of anhydrous THF and 60 mL of anhydrous DMF was added 20 mL (144 mmol) of anhydrous triethylamine and 9.75 g (64.7 mmol) of tertbutyldimethylsilyl chloride under a nitrogen atmosphere. The reaction mixture was heated at 60° C. in an oil bath for 4 h and then cooled to room temperature. The solution was diluted with 225 mL of toluene, filtered through a medium glass frit, and concentrated at reduced pressure. The residue was purified by PrepLC (0 to 4% MeOH in CH₂Cl₂) to give 6.77 g (11.5 mmol, 20%) of a yellow foam.

¹H NMR (CDCl₃) δ 7.67 (d, J=8.8 Hz, 2H), 7.45 (d, J=8.8 Hz, 1H), 7.23 (m, 3H), 6.83 (d, J=8.8 Hz, 1H), 6.68 (m, 4H), 4.18 (br s, 2H), 2.96 (br s, 2H), 2.72 (br s, 4H), 1.75 (br s, 4H), 1.51 (br s, 2H), 0.93 (s, 9H), 0.12 (s, 6H); high resolution FDMS 588.2648 (M⁺) .

Part B. 2-[4-[[(1,1-Dimethylethyl)dimethylsilyl]oxy]phenyl]-6-[[(trifluoromethyl)sulfonyl]oxy]benzo[b]thiophen-3-yl 4-[2-(1-Piperidinyl)ethoxy]phenyl Ketone.

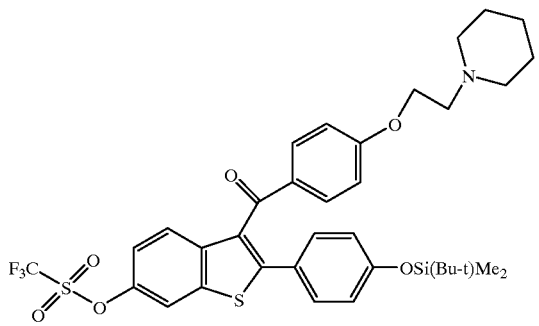

To a solution of 6.0 g (10.2 mmol) of 2-[4-[[(1,1-dimethylethyl)dimethylsilyl]oxy]phenyl]-6-hydroxybenzo[b]thiophen-3-yl 4-[2-(1-piperidinyl)ethoxy]phenyl ketone (Part A) in 60 mL of anhydrous dichloroethane was added 4.13 g (40.8 mmol) of anhydrous triethylamine and 4.01 g (11.2 mmol) of N-phenyltrifluoromethanesulfonimide under a nitrogen atmosphere. The reaction mixture was stirred at room temperature for 4 h and then filtered through a cotton plug and concentrated at reduced pressure. The residue was chromatographed over silica gel (0 to 3% MeOH in $CH_2Cl_2$) to give 7.20 g (10.0 mmol, 98%) of a brown foam.

$^1$H NMR (CDCl$_3$) δ 7.82 (d, J=9.0 Hz, 2H), 7.75 (d, J=8.8 Hz, 2H), 7.32 (m, 3H), 6.79 (d, J=8.8 Hz, 2H), 6.74 (d, J=8.6 Hz, 2H), 4.20 (t, J=5.6 Hz, 2H), 2.91 (t, J=5.7 Hz, 2H), 2.66 (br s, 4H), 1.70 (m, 4H), 1.53 (m, 2H), 0.98 (s, 9H), 0.17 (s, 6H); FDMS 719.7 (M$^+$).

Part C. 2-(4-Hydroxyphenyl)-3-[4-[2-(1-piperidinyl)ethoxy]benzoyl]benzo[b]thiophene-6-carboxylic Acid Methyl Ester.

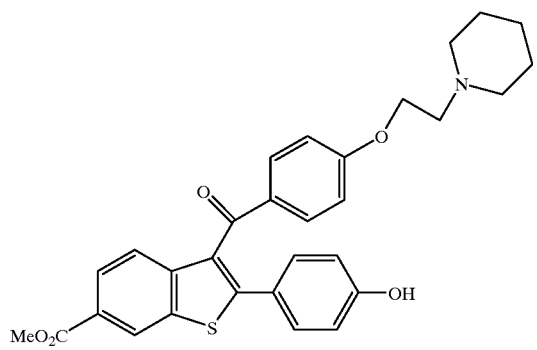

To a solution of 3.7 mL of anhydrous DMF, 1.8 mL of anhydrous triethylamine, and 1.8 mL of anhydrous methanol was added 1.0 g (1.4 mmol) of 2-[4-[[(1,1-dimethylethyl)dimethylsilyl]oxy]phenyl]-6-[[(trifluoromethyl)sulfonyl]oxy]benzo[b]thiophen-3-yl 4-[2-(1-piperidinyl)ethoxy]phenyl ketone (Part B) at room temperature. To this were added 29.4 mg (0.13 mmol) of Pd(II) acetate and 53.8 mg (0.13 mmol) of 1,3-bis(diphenylphosphino)propane, and the flask was evacuated and then filled with carbon monoxide in a balloon. The reaction mixture was heated at 55° C. for 12 h under a carbon monoxide atmosphere. After cooling the reaction mixture to room temperature, the solution was saturated with nitrogen gas and then concentrated at reduced pressure. To this were added 5 mL of THF and 4 mL of 1N HCl, and the solution was stirred at room temperature for 3 h. The reaction mixture was treated with 10 mL of 2N ammonium hydroxide solution for an additional hour at room temperature. The solution was poured into a separatory funnel and the aqueous layer was saturated with sodium chloride and extracted three times with 50 mL portions of THF. The combined organic layers were washed with brine, dried with anhydrous sodium sulfate, and concentrated at reduced pressure. The residue was purified on silica gel (0 to 10% MeOH in $CH_2Cl_2$) to give 578 mg (1.1 mmol, 80%) of an orange foam.

$^1$H NMR (CDCl$_3$) δ 8.62 (s, 1H), 8.07 (d, J=8.5 Hz, 1H), 7.92 (d, J=8.5 Hz, 1H), 7.68 (d, J=8.6 Hz, 2H), 7.22 (d, J=8.2 Hz, 2H), 6.69 (d, J=8.6 Hz, 4H), 4.25 (t, J=5.6 Hz, 2H), 4.01 (s, 3H), 3.07 (t, J=4.3 Hz, 2H), 2.87 (br s, 4H), 1.82 (br s, 4H), 1.59 (br s, 2H); FDMS 516 (M$^+$).

Part D. 3-[4-[2-(1-Piperidinyl)ethoxy]benzoyl]-2-[4-[2-(1-pyrrolidinyl)ethoxy]phenyl]benzo[b]thiophene-6-carboxylic Acid Methyl Ester.

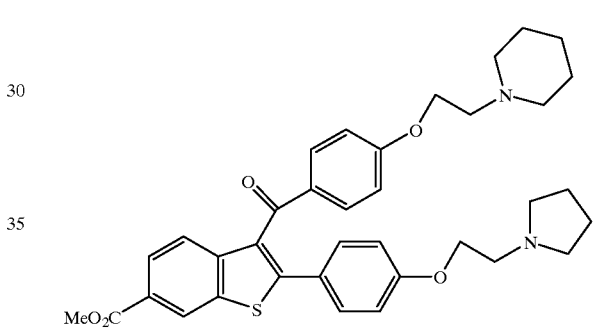

To a solution of 1.5 g (2.9 mmol) of 2-(4-hydroxyphenyl)-3-[4-[2-(1-piperidinyl)ethoxy]benzoyl]benzo[b]thiophene-6-carboxylic acid methyl ester (Part C) and 544 mg (3.2 mmol) of 1-(2-chloroethyl)pyrrolidine hydrochloride in 20 mL of anhydrous DMF was added 2.37 g (7.3 mmol) of cesium carbonate at room temperature under a nitrogen atmosphere. The reaction mixture was heated at 60° C. for 4 h and then cooled to room temperature and diluted with 125 mL of THF and 75 mL of water. The aqueous layer was saturated with sodium chloride and extracted twice with 50 mL portions of THF. The combined organic layers were washed with brine, dried with anhydrous sodium sulfate, and concentrated at reduced pressure. The residue was purified on silica gel (1:1 MeOH/TEA (10%) in THF) to give 1.26 g (2.2 mmol, 77%) of an orange-brown foam.

$^1$H NMR (CDCl$_3$) δ 8.57 (s, 1H), 7.98 (dd, J=8.6, 1.5 Hz, 1H), 7.77 (d, J=8.8 Hz, 2H), 7.66 (d, J=8.5 Hz, 1H), 7.38 (d, J=8.8 Hz, 2H), 6.78 (dd, J=8.7, 6.7 Hz, 4H), 4.18 (m, 4H), 4.01 (s, 3H), 2.86 (t, J=6.0 Hz, 2H), 2.74 (t, J=6.0 Hz, 2H), 2.59 (m, 4H), 2.47 (m, 4H), 1.79 (m, 4H), 1.58 (m, 4H), 1.48 (m, 2H); FDMS 614 (M$^{+1}$).

Part E. 3-[4-[2-(1-Piperidinyl)ethoxy]benzoyl]-2-[4-[2-(1-pyrrolidinyl)ethoxy]phenyl]benzo[b]thiophene-6-carboxamide.

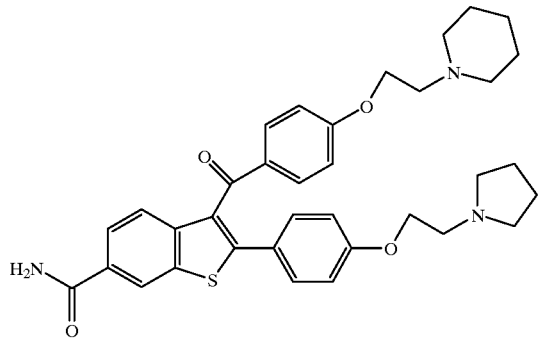

To a solution of 4.37 g (7.1 mmol) of 3-[4-[2-(1-piperidinyl)ethoxy]benzoyl]-2-[4-[2-(1-pyrrolidinyl)ethoxy]phenyl]benzo[b]thiophene-6-carboxylic acid methyl ester (Part D) in 100 mL of methanol was added 35 mL of liquid anhydrous ammonia. The solution was sealed in a shaker and heated to 60° C. for 3 days. The solution was then saturated with nitrogen gas, concentrated at reduced pressure, and chromatographed on silica gel (1:1 TEA/MeOH in THF, 0 to 10%) to give 3.22 g (5.4 mmol, 76%) of a yellow-brown foam.

$^1$H NMR (CDCl$_3$) δ 8.40 (s, 1H), 7.72 (m, 4H), 7.37 (d, J=8.6 Hz, 2H), 6.78 (dd, J=8.1, 2.1 Hz, 4H), 4.07 (m, 4H), 2.86 (t, J=5.6 Hz, 2H), 2.74 (t, J=5.8 Hz, 2H), 2.61 (br s, 4H), 2.48 (br s, 4H), 1.80 (br s, 4H), 1.59 (m, 4H), 1.43 (m, 2H); FDMS 597 (M$^+$).

Part F. 3-[4-[2-(1-Piperidinyl)ethoxy]benzoyl]-2-[4-[2-(1-pyrrolidinyl)ethoxy]phenyl]benzo[b]thiophene-6-carboxamide Dioxalate.

A solution of 3-[4-[2-(1-piperidinyl)ethoxy]benzoyl]-2-[4-[2-(1-pyrrolidinyl)ethoxy]phenyl]benzo[b]thiophene-6-carboxamide (Part E) (131 mg, 0.219 mmol) in EtOAc (8 mL) was treated with a solution of oxalic acid (49.3 mg, 0.548 mmol) in EtOAc (8 mL) to form a white suspension. After filtration and drying, 135 mg (79%) of the title compound was obtained as a white solid.

mp 87.0–93.0° C.; IR (KBr) 3420 (br), 3359 (br), 2681 (br), 1722, 1650, 1599 cm$^{-1}$; $^1$H NMR (DMSO-d$_6$) δ 9.20 (br s, 4H), 8.56 (s, 1H), 8.06 (s, 1H), 7.83 (d, J=8.5 Hz, 1H), 7.70 (d, J=8.3 Hz, 2H), 7.35–7.45 (m, 4H), 6.96 (d, J=8.3 Hz, 4H), 4.26–4.38 (m, 2H), 4.20–4.26 (m, 2H), 3.40–3.50 (m, 2H), 3.30–3.38 (m, 2H), 3.19–3.30 (m, 4H), 3.02–3.18 (m, 4H), 1.82–1.92 (m, 4H), 1.62–1.72 (m, 4H), 1.20–1.48 (m, 2H); FDMS m/e 598 (M$^+$-C$_4$H$_3$O$_8$); Anal. Calcd for C$_{39}$H$_{43}$N$_3$O$_{12}$S: C, 60.22; H, 5.57; N, 5.40; S, 4.12. Found: C, 60.07; H, 5.68; N, 5.18; S, 4.02.

EXAMPLE 31

Preparation of 3-[[4-[2-(1-Piperidinyl)ethoxy]phenyl]methyl]-2-[4-[2-(1-pyrrolidinyl)ethoxy]phenylbenzo[b]thiophene-6-methanamine Dioxalate.

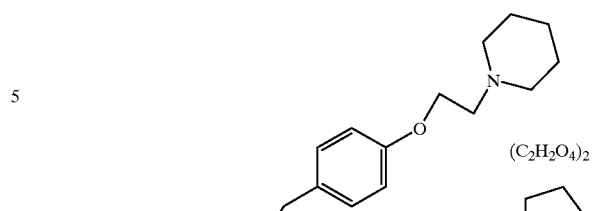

Part A. 3-[4-[2-(1-Piperidinyl)ethoxy]benzoyl]-2-[4-[2-(1-pyrrolidinyl)ethoxy]phenyl]benzol[b]thiophene-6-carbonitrile.

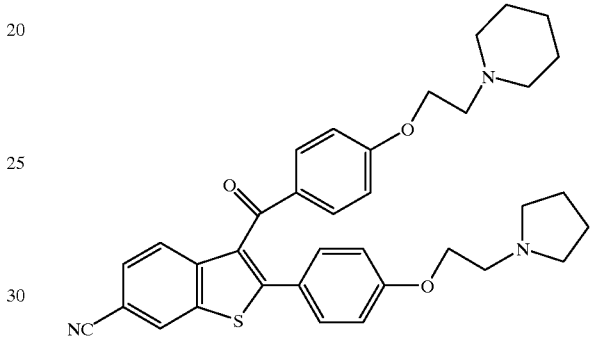

To a solution of 3.1 g (5.2 mmol) of 3-[4-[2-(1-piperidinyl)ethoxy]benzoyl]-2-[4-[2-(1-pyrrolidinyl)ethoxy]phenyl]benzo[b]thiophene-6-carboxamide (Example 30, Part E) in 75 mL of anhydrous THF was added 3.1 g (13.0 mmol) of (methoxycarbonylsulfamoyl)triethylammonium hydroxide (inner salt) at room temperature under a nitrogen atmosphere. The reaction mixture was stirred for 3 days and then filtered through a medium frit, concentrated at reduced pressure, and chromatographed on silica gel (1:1 TEA/MeOH in THF, 0 to 10%) to give 2.70 g (4.7 mmol, 90%) of a brown foam.

$^1$H NMR (CDCl$_3$) δ 8.18 (s, 1H), 7.72 (d, J=8.9 Hz, 3H), 7.56 (d, J=8.1 Hz, 1H), 7.38 (d, J=8.6 Hz, 2H), 6.80 (t, J=8.3 Hz, 4H), 4.22 (br s, 4H), 3.10 (br s, 2H), 2.89 (br s, 6H), 2.64 (br s, 4H), 1.95 (br s, 4H), 1.70 (br s, 4H), 1.43 (br s, 2H); FDMS 580 (M$^+$).

Part B. 6-(Aminomethyl)-α-[4-[2-(1-piperidinyl)ethoxy]phenyl]-2-[4-[2-(1-pyrrolidinyl)ethoxy]phenyl]benzo[b]thiophene-3-methanol.

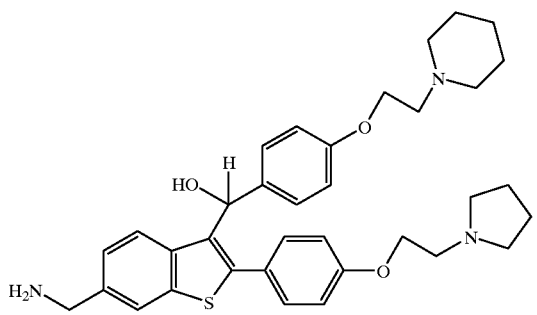

To a solution of 1.35 g (2.3 mmol) of 3-[4-[2-(1-piperidinyl)ethoxy]benzoyl]-2-[4-[2-(1-pyrrolidinyl)

ethoxy]phenyl]benzo[b]thiophene-6-carbonitrile (Part A) in 30 mL of anhydrous THF under a nitrogen atmosphere was added 414 mg (11.6 mmol) of lithium aluminum hydride. The reaction was stirred for 2.5 hours at room temperature and then quenched with 5 mL of ethyl acetate and 5 mL of saturated aqueous potassium sodium tartrate for 16 h. The reaction mixture was poured into 50 mL of water, saturated with sodium chloride, and extracted with three 50 mL portions of THF. The combined organic layers were washed with brine, dried with anhydrous magnesium sulfate, and concentrated to give 1.32 g (95% crude yield) of a brown foam.

$^1$H NMR (CDCl$_3$) δ 7.68 (m, 2H), 7.38 (d, J=8.6 Hz, 2H), 7.31 (d, J=8.6 Hz, 2H), 7.08 (d, J=8.4 Hz, 1H), 6.88 (d, J=8.7 Hz, 2H), 6.81 (d, J=8.7 Hz, 2H), 6.17 (s, 1H), 4.05 (m, 4H), 3.87 (s, 2H), 2.86 (t, J=5.9 Hz, 2H), 2.72 (t, J=6.1 Hz, 2H), 2.57 (br s, 4H), 2.47 (br s, 4H), 1.75 (br s, 4H), 1.57 (m, 4H), 1.43 (br s, 2H).

Part C. 3-[[4-[2-(1-Piperidinyl)ethoxy]phenyl]methyl]-2-[4-[2-(1-pyrrolidinyl)ethoxy]phenyl]benzo[b]thiophene-6-methanamine.

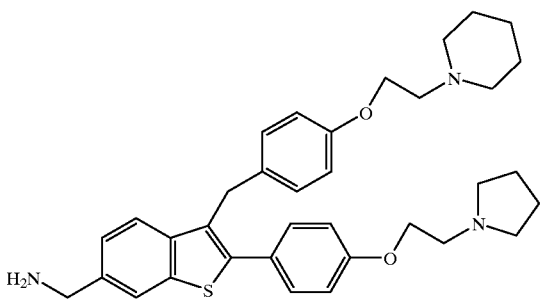

To a solution of 1.32 g (2.3 mmol) of 6-(aminomethyl)-α-[4-[2-(1-piperidinyl)ethoxy]phenyl]-2-[4-[2-(1-pyrrolidinyl)ethoxy]phenyl]benzo[b]thiophene-3-methanol in 40 mL of anhydrous dichloroethane at 0° C. was added 1.84 g (15.8 mmol) of triethylsilane and 2.62 g (23.0 mmol) of trifluoroacetic acid, respectively, under a nitrogen atmosphere. After one hour at 0° C., the reaction was warmed to room temperature and stirred for 24 h. The reaction was quenched with 10 mL of saturated aqueous sodium bicarbonate and poured into 30 mL of water. The aqueous layer was saturated with sodium chloride, separated from the dichloroethane layer, and extracted with three 50 mL portions of THF. The combined organic layers were dried over anhydrous magnesium sulfate and concentrated at reduced pressure to give 786 mg (60% crude yield) of a brown foam. This material was carried on to the salt in Part D.

Part D. 3-[[4-[2-(1-Piperidinyl)ethoxy]phenyl]methyl]-2-[4-[2-(1-pyrrolidinyl)ethoxy]phenyl]benzo[b]thiophene-6-methanamine Dioxalate.

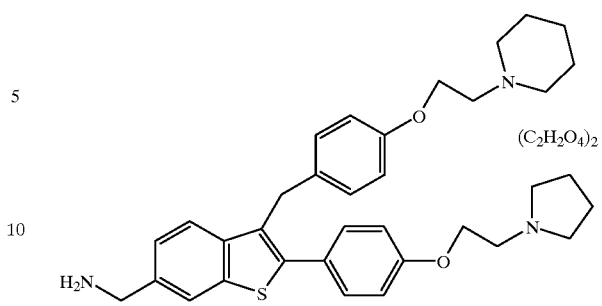

3-[[4-[2-(1-Piperidinyl)ethoxy]phenyl]methyl]-2-[4-[2-(1-pyrrolidinyl)ethoxy]phenyl]benzo[b]thiophene-6-methanamine (Part C) was dissolved in 50 mL of ethyl acetate and added to a solution of 100 mg of oxalic acid in 30 mL of ethyl acetate. After adding 10 mL of ether to the solution, the precipitate was filtered to give 1.05 g (99%) of a white solid.

mp 140–142° C.; $^1$H NMR (DMSO) δ 8.04 (s, 1H), 7.58 (d, J=8.3 Hz, 1H), 7.47 (d, J=8.8 Hz, 2H), 7.41 (d, J=8.3 Hz, 1H), 7.09 (d, J=8.7 Hz, 2H), 6.99 (d, J=8.6 Hz, 2H), 6.83 (d, J=8.6 Hz, 2H), 4.20 (m, 4H), 4.13 (s, 2H), 4.06 (t, J=5.6 Hz, 2H), 3.17 (t, J=5.3 Hz, 2H), 2.92 (br s, 4H), 2.86 (t, J=5.6 Hz, 2H), 2.64 (br s, 4H), 1.81 (br s, 4H), 1.55 (m, 4H), 1.41 (d, J=5.1 Hz, 2H); FDMS 570.4 (M$^+$).

EXAMPLE 32

Preparation of 3-[4-[2-(1-Piperidinyl)ethoxy]phenyl]methyl]-2-[4-[2-(1-pyrrolidinyl)ethoxy]phenyl]benzo[b]thiophene-6-methanol Dioxalate.

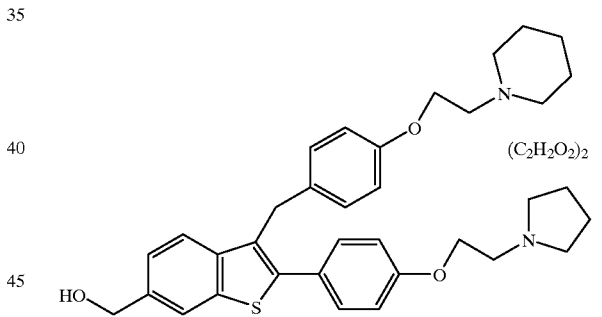

Part A. α(3)-[4-[2-(1-Piperidinyl)ethoxy]phenyl]-2-[4-[2-(1-pyrrolidinyl)ethoxy]phenyl]benzo[b]thiophene-3,6-dimethanol.

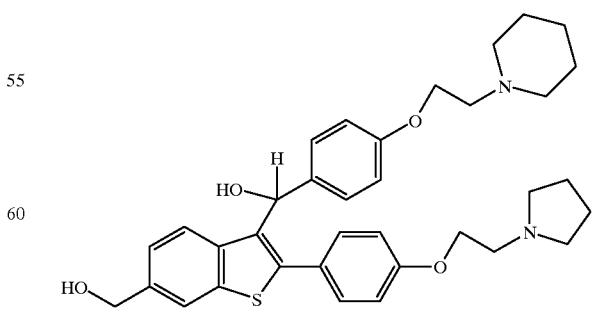

Diisobutylaluminum hydride (1.0 M in toluene, 3.59 mL) was added dropwise to a stirred solution of 3-[4-[2-(1- piperidinyl)ethoxy]benzoyl]-2-[4-[2-(1-pyrrolidinyl) ethoxy]phenyl]benzo[b]thiophene-6-carboxylic acid methyl ester (550 mg, 0.898 mmol) in anhydrous THF (6 mL) at 0° C. under argon. The mixture was stirred at 0° C. for 1.5 h. Methanol (2 mL) and saturated aqueous potassium sodium tartrate solution (15 mL) were sequentially added to the mixture, and the resultant two-layered solution was stirred vigorously at ambient temperature for 2 h. The mixture was extracted with a mixed solvent of ethyl acetate/THF (1:1, 30 mL×2). The combined organic layers were dried over MgSO$_4$, filtered, and concentrated to give 496 mg (crude yield 94%) of the diol as a gum.

$^1$H NMR (CDCl$_3$) δ 7.79 (s, 1H), 7.68 (d, J=8.4 Hz, 1H), 7.36 (d, J=8.5 Hz, 2H), 7.24 (d, J=8.4 Hz, 1H), 7.13–7.19 (m, 2H), 6.84 (d, J=8.6 Hz, 2H), 6.79 (d, J=8.5 Hz, 2H), 6.17 (s, 1H), 4.72 (s, 2H), 3.98–4.08 (m, 4H), 3.25 (br s, 1H), 2.90 (t, J=5.8 Hz, 2H), 2.76 (t, J=5.8 Hz, 2H), 2.60–2.68 (m, 4H), 2.45–2.55 (m, 4H), 1.78–1.85 (m, 4H), 1.55–1.65 (m, 4H), 1.38–1.46 (m, 2H).

Part B. 3-[[4-[2-(1-Piperidinyl)ethoxy]phenyl]methyl]-2-[4-[2-(1-pyrrolidinyl)ethoxy]phenyl]benzo[b]thiophene-6-methanol Dioxalate.

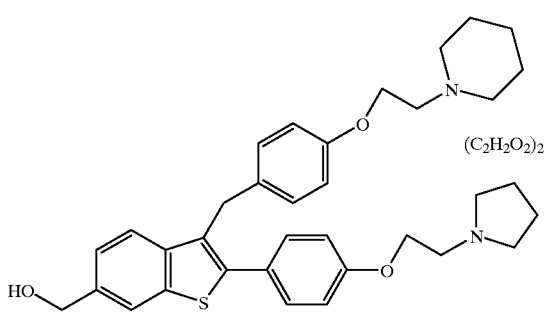

Triethylsilane (0.946 mL, 5.92 mmol) and trifluoroacetic acid (0.652 mL, 8.46 mmol) were added consecutively to a stirred solution of α(3)-[4-[2-(1-piperidinyl)ethoxy]phenyl]-2-[4-[2-(1-pyrrolidinyl)ethoxy]phenyl]benzo[b]thiophene-3,6-dimethanol (Part A) (496 mg, 0.846 mmol) in dry 1,2-dichloroethane (5 mL) at 0° C. under argon atmosphere, and the resultant solution was stirred at 0° C. for 6 h. After dilution with THF (25 mL), the mixture was washed with saturated aqueous NaHCO$_3$ (15 mL) and the aqueous layer was extracted with THEF (15 mL). The combined organic layers were washed with brine (15 mL), dried over MgSO$_4$, filtered, and concentrated. The gummy residue was chromatographed on silica [gradient TEA/i-PrOH (1:2) 0–4% in THF] to isolate 110 mg (23%) of the free base as a gum. The free base was then dissolved in EtOAc (5 mL) and treated with a solution of oxalic acid (39.9 mg, 0.443 mmol) in EtOAc (5 mL) to form a white suspension. After filtration and drying, 120 mg (83%) of the title compound was obtained as a white solid.

mp 102.0–106.0° C.; IR (KBr) 3410 (br), 2700 (br), 1725 cm$^{-1}$; $^1$H NMR (DMSO-d$_6$) δ 1.40–1.50 (m, 2H), 1.60–1.70 (m, 4H), 1.85–1.95 (m, 4H), 3.00–3.18 (m, 4H), 3.22–3.40 (m, 6H), 3.45–3.53 (m, 2H), 4.15 (s, 2H), 4.18–4.25 (m, 2H), 4.25–4.35 (m, 2H), 4.55 (s, 2H), 6.82 (d, J=8.3 Hz, 2H), 6.98 (d, J=8.3 Hz, 2H), 7.07 (d, J=8.5 Hz, 2H), 7.23 (d, J=8.2 Hz, 1H), 7.43 (d, J=8.5 Hz, 2H), 7.46 (d, J=8.2 Hz, 1H), 7.84 (s, 1H), 8.60 (br s, 4H); FDMS m/e 571 (M$^+$-C$_4$H$_3$O$_8$); Anal. Calcd for C$_{39}$H$_{46}$N$_2$O$_{11}$S: C, 62.38; H, 6.17; N, 3.73; S, 4.27. Found: C, 62.63; H, 6.36; N, 3.91; S, 4.07.

EXAMPLE 33

Preparation of 6-Hydroxy-3-[6-[2-(1-pyrrolidinyl)ethoxy]pyrid-3-ylmethyl]-2-[4-[2-(1-pyrrolidinyl)ethoxy]phenyl]benzo[b]thiophene Dioxalate.

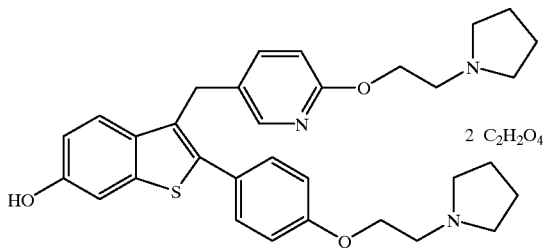

Part A. 6-Methoxy-2-[4-[2-(1-pyrrolidinyl)ethoxy]phenyl]benzo[b]thiophen-3-yl 6-Chloropyrid-3-yl Ketone.

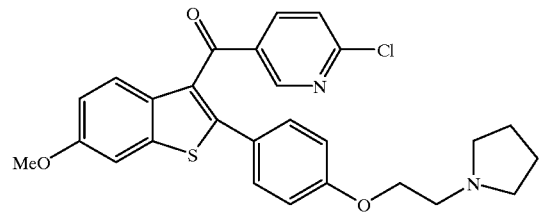

The title compound was prepared from 6-methoxy-2-[4-[2-(1-pyrrolidinyl)ethoxy]phenyl]benzo[b]thiophene (Example 1, Part B) and 6-chloronicotinic acid in 51% yield (based on 6-methoxy-2-[4-[2-(1-pyrrolidinyl)ethoxy]phenyl]benzo[b]thiophene) by essentially following the proceedures described in Example 1, Part C.

Part B. 6-Methoxy-2-[4-[2-(1pyrrolidinyl)ethoxy]phenyl]benzo[b]thiophen-3-yl 6-[2-(1-Pyrrolidinyl)ethoxy]pyrid-3-yl Ketone.

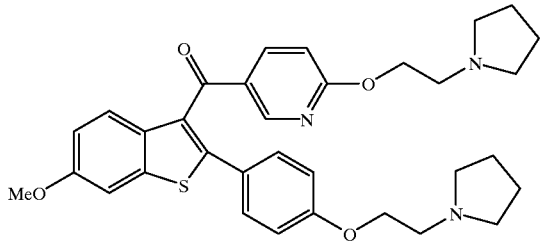

The title compound was prepared in 84% yield from 6-methoxy-2-[4-[2-(1-pyrrolidinyl)ethoxy]phenyl]benzo[b]thiophen-3-yl 6-chloropyrid-3-yl ketone (Part A) and 1-(2-hydroxyethyl)pyrrolidine by essentially following the procedures described in Example 9, Part B.

FDMS 572 (M+1; 100); Anal. Calcd for C$_{33}$H$_{37}$N$_3$O$_4$S: C, 69.33; H, 6.52; N, 7.35. Found: C, 69.10; H, 6.76; N, 7.08.

Part C. 6-Methoxy-3-[6-[2-(1-pyrrolidinyl)ethoxy]pyrid-3-ylmethyl]-2-[4-[2-(1-pyrrolidinyl)ethoxy]phenyl]benzo[b]thiophene Dioxalate Hemihydrate.

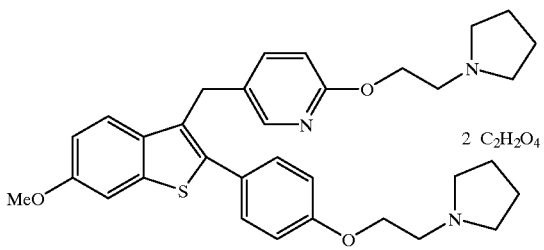

The title was prepared in 37% yield from 6-methoxy-2-[4-[2-(1-pyrrolidinyl)ethoxy]phenyl]benzo[b]thiophen-3-yl 6-[2-(1-pyrrolidinyl)ethoxy]pyrid-3-yl ketone (Part B) by essentially following the procedure described in Example 3, Part E.

FDMS 558 (M+1; 100); Anal. Calcd for $C_{33}H_{39}N_3O_3S \cdot 2C_2H_2O_4 \cdot 0.5 H_2O$: C, 59.51; H, 5.94; N, 5.63. Found: C, 59.39; H, 5.76; N, 5.76.

Part D. 6-Hydroxy-3-[6-[2-(1-pyrrolidinyl) ethoxy]pyrid-3-ylmethyl]-2-[4-[2-(1-pyrrolidinyl) ethoxy]phenyl]benzo[b]thiophene Dioxalate.

The title compound was prepared in 59% yield from 6-methoxy-3-[6-[2-(1-pyrrolidinyl)ethoxy]pyrid-3-ylmethyl]-2-[4-[2-(1-pyrrolidinyl)ethoxy]phenyl]benzo[b]thiophene (Part C) by essentially following the procedure described in Example 1, Part D.

$^1$H NMR (DMSO-$d_6$) δ 7.88 (d, J=1.8 Hz, 1H), 7.43–7.32 (m, 4H), 7.23 (d, J=2.1 Hz, 1H), 7.07 (d, J=8.4 Hz, 2H), 6.78 (dd, J=8.4 and 2.1 Hz, 1H), 6.71 (d, J=8.6 Hz, 1H), 4.42 (t, J=4.9 Hz, 2H), 4.30 (t, J=4.6 Hz, 2H), 4.09 (s, 2H), 3.53 (t, J=4.3 Hz, 2H), 3.46 (t, J=4.6 Hz, 2H), 2.50–2.33 (m, 8H), 1.96–1.73 (m, 8H); FDMS: 544 (M+1; 100).

EXAMPLE 34
Preparation of 6-Hydroxy-3-[4-[(1-pyrrolidinyl)methyl] benzyl]-2-[4-[(1-pyrrolidinyl)methyl]phenyl]benzo[b]thiophene Dioxalate.

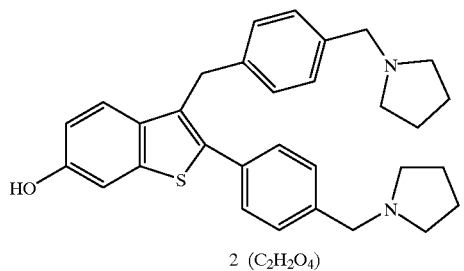

Part A. 1-Bromo-4-[(1-pyrrolidinyl)methyl]benzene.

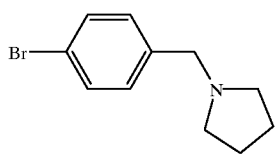

Pyrrolidine (20.0 mL, 0.240 mole) was added to a stirred solution of 4-bromobenzyl bromide (10.0 g, 40.0 mmol) in anhydrous $CH_2Cl_2$ (20 mL) at 0° C. under nitrogen. The resultant solution was allowed to stir at room temperature for 1 h. The reaction mixture was diluted with EtOAc (150 mL) before it was washed with half-saturated aqueous NaHCO$_3$ (50 mL). After drying over MgSO$_4$, filtration, and concentration, the oily residue was chromatographed on silica [20% EtOAc in hexanes, then 10% EtOH/Et$_3$N (2/1) in THF/hexanes (1/1)] to provide 9.02 g of the benzyl pyrrolidine (94%) as an oil.

IR (neat) 2966,1488 cm$^{-1}$; $^1$H NMR (CDCl$_3$) δ 1.79 (br s, 4H), 2.49 (br s, 4H), 3.57 (s, 2H), 7.21 (d, J=8.2 Hz, 2H), 7.43 (d, J=8.2 Hz, 2H);

Part B. 2-Dimethylamino-6-methoxybenzo[b]thiophen-3-yl 4-[(1-Pyrrolidinyl)methyl]phenyl Ketone.

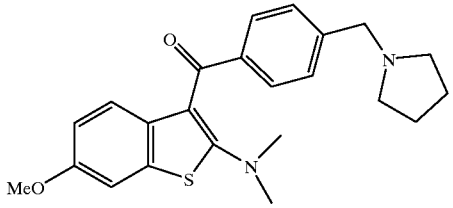

4-(Chloromethyl)benzoyl chloride (105 mg, 0.558 mmol) was added to a stirred solution of 2-dimethylamino-6-methoxybenzo[b]thiophene (105 mg, 0.507 mmol) in chlorobenzene (1 mL) under nitrogen. The resultant mixture was heated in an oil bath at 110° C. for 2.5 h. The mixture was cooled to 0° C., treated with pyrrolidine (5 mL), then allowed to stir at room temperature for 2 h. After dilution with THF (20 mL), the mixture was washed with saturated aqueous NaHCO$_3$ (5 mL). The organic layer was dried over MgSO$_4$, filtered, concentrated, and chromatographed on silica [gradient 20–40% EtOAc in hexanes, then 0–10% EtOH/Et$_3$N (2/1) in THF/hexanes (1/1)] to give 148 mg (74%) of the ketone as a foam.

IR (neat) 2957, 1625, 1603 cm$^{-1}$; $^1$H NMR (CDCl$_3$) δ 1.83 (br s, 4H), 2.53 (br s, 4H), 2.87 (s, 6H), 3.69 (s, 2H), 3.83 (s, 3H), 6.81 (dd, J=9.0 and 3.0 Hz, 1H), 7.12 (d, J=3.0 Hz, 1H), 7.36 (d, J=9.0 Hz, 1 H), 7.41 (d, J=8.1 Hz, 2H), 7.82 (d, J=8.1 Hz, 2H); FDMS m/e 394 (M$^+$).

Part C. 6-Methoxy-2-[4-[(1-pyrrolidinyl)methyl]phenyl] benzo[b]thiophen-3-yl 4-[(1-Pyrrolidinyl)methyl]phenyl Ketone.

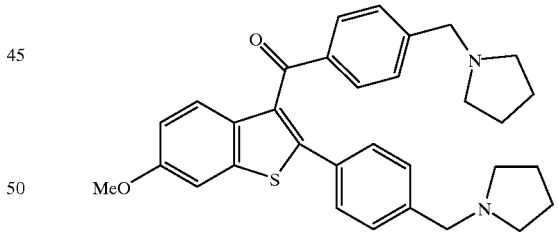

The aryl bromide of Part A (146 mg, 0.608 mmol) was added to a stirred suspension of magnesium ribbons (13.9 mg, 0.570 mmol) in anhydrous THF (2 mL) under argon atmosphere, followed by the addition of a small iodine crytal. The resultant mixture was heated in an oil bath at 60–65° C. for 2 h to form a homogeneous Grignard solution. The Grignard solution was cooled to room temperature before it was added to a stirred solution of the benzothiophene of Part B (150 mg, 0.380 mmol) in anhydrous THF (2 mL) at 0° C. under argon atmosphere. The resultant mixture was stirred at 0° C. for 1.5 h, then quenched with saturated aqueous NH$_4$Cl (3 mL). After extraction with EtOAc (15 mL×2), the combined organic layers were dried over MgSO$_4$, filtered, concentrated, and chromatographed on silica [gradient 0–4% EtOH/Et₃N (2/1) in THF/hexanes (1/1)] to give 170 mg (88%) of the trisubstituted benzothiophene as a foam.

IR (neat) 2964, 1647, 1603 cm$^{-1}$; $^1$H NMR (CDCl₃) δ 1.77 (br s, 8H), 2.40–2.50 (m, 8H), 3.52 (s, 2H), 3.55 (s, 2H), 3.91 (s, 3H), 7.05 (dd, J=8.9 and 2.3 Hz, 1H), 7.17 (d, J=8.1 Hz, 2H), 7.22 (d, J=8.2 Hz, 2H), 7.32 (d, J=8.1 Hz, 2H), 7.34 (d, J=2.3 Hz, 1H) , 7.65 (d, J=8.9 Hz, 1H) , 7.70 (d, J=8.2 Hz, 2H); FDMS m/e 510 (M⁺) .

Part D. 6-Methoxy-3-[4-[(1-pyrrolidinyl)methyl]benzyl]-2-[4-[(1-pyrrolidinyl)methyl]phenyl]benzo[b]thiophene.

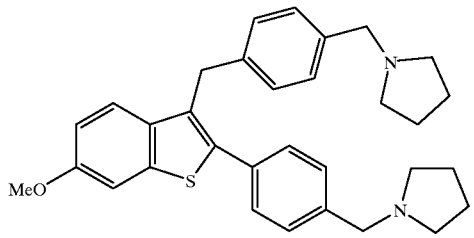

DIBAL-H (0.911 mL, 1 M in toluene) was added to a stirred solution of the ketone of Part C (310 mg, 0.607 mmol) in anhydrous CH₂Cl₂ (4 mL) at 0° C. under nitrogen atmosphere, and the resultant solution was stirred at 0° C. for 40 min. The reaction mixture was treated sequentially with MeOH (0.5 mL) and saturated aqueous Rochelle's salt solution (10 mL), and then the two-layered solution was stirred vigorously at room temperature for 1 h. After extraction with EtOAc (50 mL), the organic layer was dried over MgSO₄, filtered, and concentrated to yield 280 mg of the corresponding alcohol.

The above alcohol was dissolved in anhydrous CH₂Cl₂ (3 mL) and cooled down to 0° C. before it was sequentially treated with Et₃SiH (0.611 mL, 3.83 mmol) and TFA (0.421 mL, 5.46 mmol). The resultant mixture was stirred at 0° C. for 1 h. After cautious treatment with saturated aqueous NaHCO₃ (8 mL), the mixture was allowed to warm to room temperature and extracted with EtOAc (15 mL×2). The combined organic layers were dried over MgSO₄, filtered, concentrated, and chromatographed on silica [gradient 0–4% EtOH/Et₃N (2/1) in THF/hexanes (1/1)] to give 220 mg (81%) of the corresponding methylene compound as a foam.

IR (neat) 2963, 1603 cm$^{-1}$; $^1$H NMR (CDCl₃) δ 1.75–1.87 (m, 8H), 2.45–2.60 (m, 8H), 3.57 (s, 2H), 3.64 (s, 2H), 3.87 (s, 3H), 4.24 (s, 2H), 6.90 (dd, J=8.9 and 2.4 Hz, 1H), 7.09 (d, J=8.0 Hz, 2H), 7.21 (d, J=8.0 Hz, 2H), 7.33 (d, J=2.4 Hz, 1H), 7.35 (d, J=8.2 Hz, 2H), 7.39 (d, J=8.9 Hz, 1H), 7.45 (d, J=8.2 Hz, 2H); FDMS m/e 496 (M⁺) .

Part E. 6-Hydroxy-3-[4-[(1-pyrrolidinyl)methyl]benzyl]-2-[4-[(1-pyrrolidinyl)methyl]phenyl]benzo[b]thiophene Dioxalate.

AlCl₃ (354 mg, 2.66 mmol) was added to a stirred solution of the methoxy benzothiophene (220 mg, 0.443 mmol) in anhydrous CH₂Cl₂ (5 mL) at room temperature under nitrogen atmosphere. The resultant suspension was stirred for 3–5 min before it was treated with EtSH (0.295 mL, 3.99 mmol), and the mixture was stirred for an additional 35 min. After dilution with THF (15 mL), the mixture was cooled to 0° C. and sequentially treated with saturated aqueous NaHCO₃ (15 mL) and saturated aqueous Rochelle's salt solution (10 mL). The two-layered solution was stirred vigorously for 70 min. The organic layer was separated and the aqueous layer was extracted with THF (25 mL×2). The combined organic layers were dried over MgSO₄, filtered, concentrated, and chromatographed on silica [gradient 0–4% EtOH/Et₃N (2/1) in THF/hexanes (1/1)] to give 205 mg (96%) of the hydroxy benzothiophene as a foam.

A solution of oxalic acid (76.5 mg, 0.850 mmol) in EtOAc (4 mL) was added dropwise to a stirred solution of the above hydroxy benzothiophene in EtOAc (4 mL). The resultant white suspension was filtered and the white solid was dried at 80° C. under vacuum to provide 240 mg (85%) of the dioxalate.

IR (neat) 3400–2500 (br), 1721, 1600 cm$^{-1}$; $^1$H NMR (CDCl₃) δ 1.75–1.95 (m, 8H), 2.95–3.20 (m, 8H), 4.17 (s, 2H), 4.21 (s, 2H), 4.26 (s, 2H), 6.81 (dd, J=8.7 and 2.1 Hz, 1H), 7.11 (d, J=7.9 Hz, 2H), 7.28 (d, J=2.1 Hz, 1H), 7.35 (d, J=7.9 Hz, 2H), 7.37 (d, J=8.7 Hz, 1H), 7.50 (d, J=8.1 Hz, 2H), 7.56 (d, J=8.1 Hz, 2H); FDMS m/e 483 (M+1-2C₂H₂O₄); Anal. Calcd for C₃₁H₃₄N₂OS.1.8C₂H₂O₄: C, 64.46; H, 5.88; N, 4.34. Found: C, 64.17; H, 5.92; N, 4.47.

EXAMPLE 35

Preparation of 6-Hydroxy-2-[4-[(4-morpholinyl)methyl]phenyl]benzo[b]thiophen-3-yl 4-[(1-Pyrrolidinyl)methyl]phenyl Ketone Dioxalate.

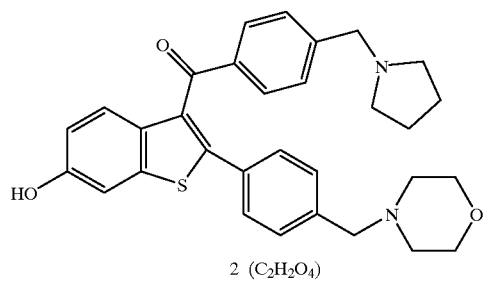

Part A. 4-[(4-Bromophenyl)methyl]morpholine.

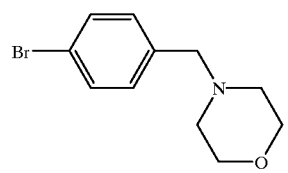

Following the procedure of Example 34, Part A, the benzyl morpholine was obtained as an oil in 100% yield.

IR (KBr) 2803, 1487, 1111 cm$^{-1}$; $^1$H NMR (CDCl₃) δ 2.43 (t, J=4.5 Hz, 4H), 3.45 (s, 2H), 3.71 (t, J=4.5 Hz, 4H), 7.22 (d, J=8.1 Hz, 2H), 7.45 (d, J=8.1 Hz, 2H); FDMS m/e 255 (M⁺, $^{79}$Br) and 257 (M⁺, $^{81}$Br); Anal. Calcd for C₁₁H₁₄BrNO: C, 51.58; H, 5.51; N, 5.47. Found: C, 51.77; H, 5.66; N, 5.68.

Part B. 6-Methoxy-2-[4-[(4-morpholinyl)methyl]phenyl]benzo[b]thiophen-3-yl 4-[(1-Pyrrolidinyl)methyl]phenyl Ketone.

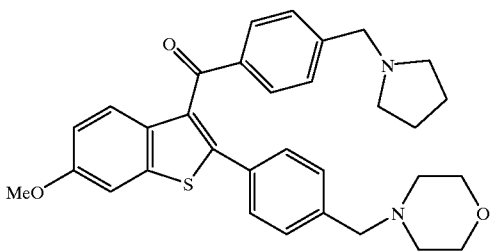

Following the procedure of Example 34, Part C, the trisubstituted benzothiophene was obtained from the above aryl bromide as a foam in 88% yield.

IR (neat) 2954, 1649, 1602 cm$^{-1}$; $^1$H NMR (CDCl$_3$) δ 1.77 br s, 4H), 2.35 (br s, 4H), 2.40 (br s, 4H), 3.39 (s, 2H), 3.56 (s, 2H), 3.68 (t, J=4.2 Hz, 4H) 3.92 (s, 3H), 7.02 (dd, J=8.7 and 2.1 Hz, 1H), 7.14–7.37 (m, 7H), 7.64 (d, 8.7 Hz, 1H), 7.70 (d, 7.8 Hz, 2H); FDMS m/e 527 (M+1).

Part C. 6-Hydroxy-2-[4-1(4-morpholinyl)methyl]phenyl]benzo[b]thiophen-3-yl 4-[(1-Pyrrolidinyl)methyl]phenyl Ketone Dioxalate.

Following the procedure of Example 34, Part E, the hydroxy ketone was obtained as a yellowish solid in 55% yield.

IR (KBr) 3420 (br), 2990 (br), 2830–2200 (br), 1641, 1608 cm$^1$; $^1$H NMR (DMSO-d$_6$) δ 1.79 (br s, 4H), 2.37 (br s, 4H), 2.53 (br s, 4H), 3.39 (s, 2H), 3.60 (s, 2H), 3.68 (t, J=4.2 Hz, 4H), 6.40 (dd, J=8.7 and 2.1 Hz, 1H), 6.69 (d, J=2.1 Hz, 1H), 7.12 (d, J=8.1 Hz, 2H) 7.21–7.25 (m, 4H), 7.43 (d, J=8.7 Hz, 1H), 7.67 (d, J=7.8 Hz, 2H); FDMS m/e 513 (M+1-2C$_2$H$_2$O$_4$).

EXAMPLE 36

Preparation of 6-Hydroxy-2-[4-[(4-morpholinyl)methyl]phenyl]-3-[4-[(1-pyrrolidinyl)methyl]benzyl]benzo[b]thiophene Dioxalate.

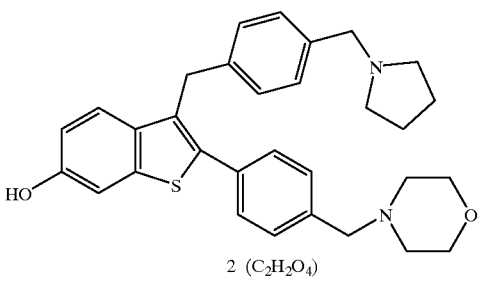

Part A. 6-Methoxy-2-[4-[(4-morpholinyl)methyl]phenyl]-3-[4-[(1-pyrrolidinyl)methyl]benzyl]benzo[b]thiophene.

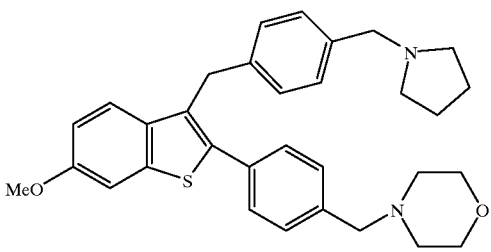

Following the procedure of Example 34, Part D, the methoxy benzothiophene was obtained from the above ketone as a foam in 57% yield.

IR (neat) 2958, 1603 cm$^{-1}$; $^1$H NMR (CDCl$_3$) δ 1.76–1.80 (m, 4H), 2.37–2.50 (m, 8H), 3.53 (s, 2H), 3.57 (s, 2H), 3.73 (t, J=4.8 Hz, 4H) 3.87 (s, 3H), 4.25 (s, 2H), 6.90 (dd, J=8.7 and 2.4 Hz, 1H), 7.10 (d, J=8.1 Hz, 2H), 7.18–7.41 (m, 6H), 7.45 (d, J=8.1 Hz, 2H); FDMS m/e 513 (M+1).

Part B. 6-Hydroxy-2-[4-[(4-morpholinyl)methyl]phenyl]-3-[4-[(1-pyrrolidinyl)methyl]benzyl]benzo[b]thiophene Dioxalate.

Following the procedure of Example 34, Part E, the hydroxy benzothiophene salt was obtained as a white solid in 57% yield.

IR (KBr) 3445 (br), 2950, 2840–2220 (br), 1720, 1630, 1600 cm$^{-1}$; $^1$H NMR (DMSO-d$_6$) δ 1.88 (br s, 4H), 2.56 (br s, 4H), 3.13 (br s, 4H), 3.61 (br s, 4H), 3.70 (s, 2H), 4.22 (br s, 4H), 6.79 (dd, J=8.4 and 2.0 Hz, 1H), 7.13 (d, J=7.5 Hz, 2H), 7.27 (d, J=2.0 Hz, 1H), 7.34–7.44 (m, 7H); FDMS m/e 499 (M+1-2C$_2$H$_2$O$_4$); Anal. Calcd for C$_{31}$H$_{34}$N$_2$O$_2$S.2C$_2$H$_2$O$_4$: C, 61.93; H, 5.64; N, 4.13. Found: C, 62.09; H, 5.77; N, 3.96.

EXAMPLE 37

Preparation of 3-[3-Bromo-4-[(1-pyrrolidinyl)methyl]benzyl]-6-hydroxy-2-[4-[2-(4-morpholinyl)ethoxy]phenyl]benzo[b]thiophene Dioxalate.

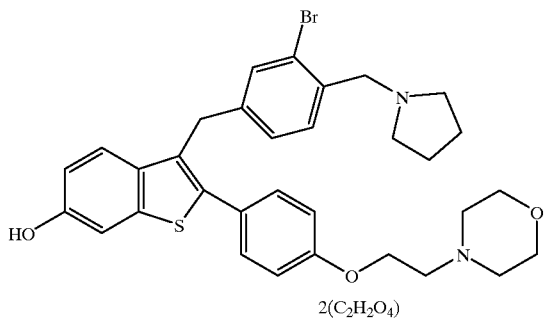

Part A. Methyl 3-Bromo-4-[(1-pyrrolidinyl)methyl]benzoate.

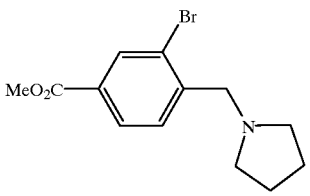

AIBN (79 mg) was added to a stirred suspension of methyl 3-bromo-4-methylbenzoate (11.0 g, 48.0 mmol) and NBS (10.3 g, 57.6 mmol) in CCl$_4$ (400 mL), and the resultant mixture was heated to reflux for 2 h. After cooling to room temperature, the mixture was diluted with hexanes (200 mL) before it was filtered and concentrated to give 14.7 g (crude yield 100%) of methyl 3-bromo-4-(bromomethyl)benzoate.

Part of the crude dibromide (14.7 g) was dissolved in anhydrous CH$_2$Cl$_2$ (60 mL). The solution was cooled to 0° C. and treated with pyrrolidine (9.96 mL, 119 mmol), then it was allowed to stir at room temperature for 2 h. The reaction mixture was diluted with EtOAc (500 mL), washed with half-saturated aqueous NaHCO$_3$ (100 mL), dried over MgSO$_4$, filtered, and concentrated to give an oily residue. The crude product was chromatographed on silica [gradient 0–10% EtOH/Et$_3$N (2/1) in THF/hexanes (1/1)] to provide 6.45 g of the pyrrolidinyl ester (45%) as an oil.

IR (neat) 2953, 1728, 1602 cm$^{-1}$; $^1$H NMR (CDCl$_3$) δ 1.82 (br s, 4H), 2.61 (br s, 4H), 3.77 (s, 2H), 3.92 (s, 3H), 7.59 (d, J=8.0 Hz, 1H), 7.95 (dd, J=8.0 and 1.4 Hz, 1H), 8.20 (d, J=1.4 Hz, 1H); FDMS m/e 297 (M$^+$, $^{79}$Br) and 299(M$^+$, $^{81}$Br).

Part B. 3-Bromo-4-[(1-pyrrolidinyl)methyl]benzoic Acid Hydrochloride.

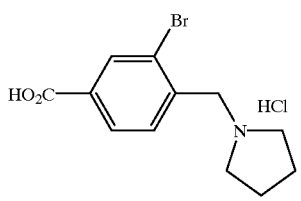

LiOH (32.4 mL, 1 N) was added to a stirred solution of the above ester (6.45 g, 21.6 mmol) in THF (75 mL) / MeOH (25 mL), and the resultant solution was heated in an oil bath at 50° C. for 3 h. After cooling to room temperature, the solution was treated in portions with 5 N HCl (22 mL), and then concentrated at 50° C. under vacuum to give 8.20 g (crude yield 99%) of the benzoic acid as a white solid contaminated with LiCl.

IR (KBr) 3397 (br), 2924, 2679–2000 (br), 1713, 1634, 1464 cm$^{-1}$; $^1$H NMR (DMSO-d$_6$) δ1.94 (br s, 4H), 2.95–3.70 (m, 4H), 4.54 (s, 2H), 7.92 (d, J=8.1 Hz, 1H), 8.10 (s, 1H), 8.12 (d, J=8.1 Hz, 1H).

Part C. 6-Methoxy-2-[4-[2-(4-morpholinyl)ethoxy]phenyl]benzo[b]thiophene.

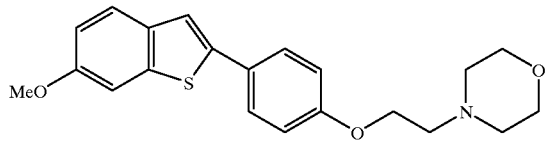

Cs$_2$CO$_3$ (4.89 g, 15.0 mmol) was added to a stirred solution of 2-(4-hydroxyphenyl)-6-methoxybenzo[b]thiophene (1.10 g, 4.29 mmol) and 4-(2-chloroethyl)morpholine hydrochloride (3.20 g, 17.2 mmol) in anhydrous DMF (10 mL). The resultant suspension was heated in an oil bath at 75° C. for 4 h. After cooling to room temperature, the mixture was diluted with EtOAc (60 mL), washed with half-saturated aqueous NaCl solution (20 mL), dried over MgSO$_4$, filtered, and concentrated to give a solid residue. Chromatography on silica [gradient 0–15% EtOH/Et$_3$N (2/1) in THF/hexanes (1/1)] provided 1.43 g of the ether (90%) as a solid.

IR (KBr) 2940, 1606 cm$^{-1}$; $^1$H NMR (CDCl$_3$) δ 2.61 (t, J=4.6 Hz, 4H), 2.84 (t, J=5.7 Hz, 2H), 3.76 (t, J=4.6 Hz, 4H), 3.84 (s, 3H), 4.17 (t, J=5.7 Hz, 2H), 6.96 (d, J=8.6 Hz, 2H), 6.98 (dd, J=8.6 and 2.2 Hz, 1H), 7.30 (d, J=2.2 Hz, 1H), 7.35 (s, 1H), 7.60 (d, L =8.6 Hz, 2H), 7.63 (d, J=8.6 Hz, 1H); FDMS m/e 369 (M$^+$).

Part D. 3-Bromo-4-[(1-pyrrolidinyl)methyl]phenyl 6-Methoxy-2-[4-[2-(4-morpholinyl)ethoxy]phenyl]benzo[b]thiophen-3-yl Ketone.

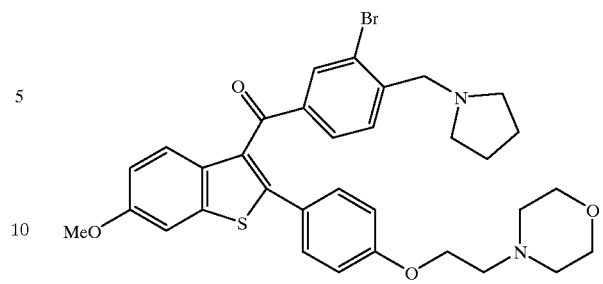

Oxalyl chloride (1.11 mL, 12.7 mmol) was added to a stirred suspension of the above benzothiophene (812 mg, 2.53 mmol) in anhydrous ClCH$_2$CH$_2$Cl (6 mL), followed by the addition of 2 drops of DMF. The suspension was stirred at room temperature under nitrogen atmosphere for 6 h, then it was concentrated to dryness under vacuum at 50° C.

To the crude benzoyl chloride suspended in anhydrous CH$_2$Cl$_2$ (5 mL) was added a solution of the benzothiophene of Part C above (624 mg, 1.69 mmol) in anhydrous CH$_2$Cl$_2$ (10 mL). The mixture was cooled to 0° C., treated with AlCl$_3$ (1.35 g, 10.1 mmol), and stirred for 1 h. THF (10 mL) was added to the mixture at 0° C., followed by the slow, sequential additions of saturated aqueous NaHCO$_3$ (30 mL) and saturated aqueous Rochelle's salt solution (10 mL). Then the two-layered solution was stirred vigorously for 70 min. The organic layer was separated and the aqueous layer was extracted with EtOAc (60 mL×2). The combined organic layers were washed with brine (25 mL), dried over MgSO$_4$, filtered, concentrated, and chromatographed on silica [gradient 0–20% EtOH/Et$_3$N (2/1) in THF/hexanes (1/1)] to give 695 mg (65%) of the ketone as a foam.

IR (neat) 2961, 1645, 1606 cm$^{-1}$; $^1$H NMR (CDCl$_3$) δ 1.80 (br s, 4H), 2.52–2.57 (m, 8H), 2.76 (t, J=5.7 Hz, 2H), 3.66 (s, 2H), 3.72–3.89 (m, 4H), 3.91 (s, 3H), 4.04 (t, J=5.7 Hz, 2H), 6.75 (d, J=8.7 Hz, 2H), 7.20 (dd, J=8.9 and 2.3 Hz, 1H), 7.25–7.30 (m, 2H), 7.34 (d, J=2.3 Hz, 1H), 7.38 (d, J=7.9 Hz, 1H), 7.62 (dd, J=7.9 and 1.6 Hz, 1H), 7.68 (d, J=8.9 Hz, 1H), 7.91 (d, J=1.6 Hz, 1H); FDMS m/e 634 (M$^+$, $^{79}$Br) and 636(M$^+$, $^{81}$Br).

Part E. 3-[3-Bromo-4-[(1-pyrrolidinyl)methyl]benzyl]-6-methoxy-2-[4-[2-(4-morpholinyl)ethoxy]phenyl]benzo[b]thiophene.

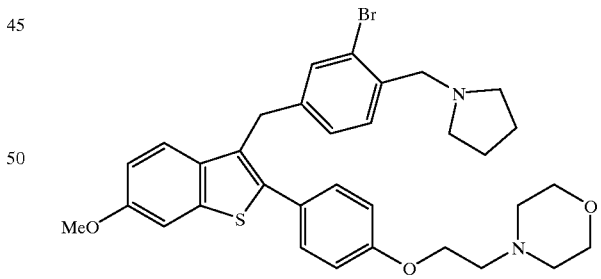

Following the procedure of Example 34, Part D, the corresponding methylene compound was obtained as a foam in 86% yield.

IR (neat) 2958, 1608 cm$^{-1}$; FDMS m/e 621 (M+1, $^{79}$Br) and 623 (M+1, $^{81}$Br).

Part F. 3-[3-Bromo-4-[(1-pyrrolidinyl)methyl]benzyl]-6-hydroxy-2-[4-[2-(4-morpholinyl)ethoxy]phenyl]benzo[b]thiophene Dioxalate.

Following the procedure of Example 34, Part E, the hydroxy benzothiophene salt was obtained as a white solid in 55% yield. FDMS m/e 607 (M+1, $^{79}$Br) and 609 (M+1, $^{81}$Br).

EXAMPLE 38

Preparation of 6-Hydroxy-3-[3-methyl-4-[(1-pyrrolidinyl)methyl]benzyl]-2-[4-[2-(4-morpholinyl)ethoxy]phenyl]benzo[b]thiophene Dioxalate.

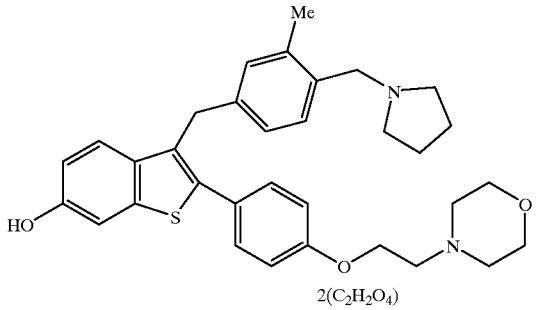

Part A. 6-Methoxy-3-[3-methyl-4-[(1-pyrrolidinyl)methyl]benzyl]-2-[4-[2-(4-morpholinyl)ethoxy]phenyl]benzo[b]thiophene.

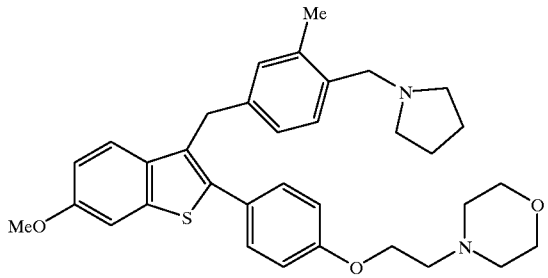

A sealed tube containing a stirred mixture of the aryl bromide of Example 37, Part E, (283 mg, 0.456 mmol), tetramethlytin (0.316 mL, 2.28 mmol), and tetrakis(triphenylphosphine)palladium(0) (16 mg, 0.014 mmol) in o-xylene (5 mL) was heated in an oil bath at 155° C. for 1 h. A black precipitate was formed. The mixture was cooled to room temperature and subjected to chromatography on silica [gradient 0–20% EtOH/Et$_3$N (2/1) in THF/hexanes (1/1)] to give 94 mg (37%, low yield attributed to spill) of the corresponding aryl methyl compound as a foam.

IR (neat) 2957, 1608 cm$^{-1}$; $^1$H NMR (CDCl$_3$) δ 1.78 (br s, 4H), 3.30 (s, 3H), 2.54–2.61 (m, 8H), 2.82 (t, J=5.7 Hz, 2H), 3.57 (s, 2H), 3.75 (t, J=4.5 Hz, 4H), 3.87 (s, 3H), 4.14 (t, J=5.7 Hz, 2H), 4.18 (s, 2H) , 6.88–6.96 (m, 4H), 7.18 (d, J=7.9 Hz, 1H), 7.32–7.44 (m, 5H); FDMS m/e 556 (M$^+$) .

Part B. 6-Hydroxy-3-[3-methyl-4-[(1-pyrrolidinyl)methyl]benzyl]-2-[4-[2-(4-morpholinyl)ethoxy]phenyl]benzo[b]thiophene Dioxalate.

Following the procedure of Example 34, Part E, the hydroxy benzothiophene salt was obtained as a white solid in 55% yield.

IR (KBr) 3455 (br), 2970, 2840–2220 (br), 1723, 1630 (br), 1610 cm$^{-1}$; $^1$H NMR (DMSO-d$_6$) δ 1.79–1.89 (m, 4H), 2.27 (s, 3H), 2.63–2.71 (m, 4H), 2.90–3.12 (m, 6H), 3.55–3.63 (m, 4H), 4.13–4.24 (m, 6H), 6.88–7.04 (m, 5H), 7.28–7.39 (m, 5H); FDMS m/e 543 (M+1).

EXAMPLE 39

Preparation of 6-Hydroxy-2-[4-[2-(1-pyrrolidinyl)ethyl]phenyl]benzo[b]thiophen-3-yl 3-Methyl-4-[(1-pyrrolidinyl)methyl]phenyl Ketone Dioxalate.

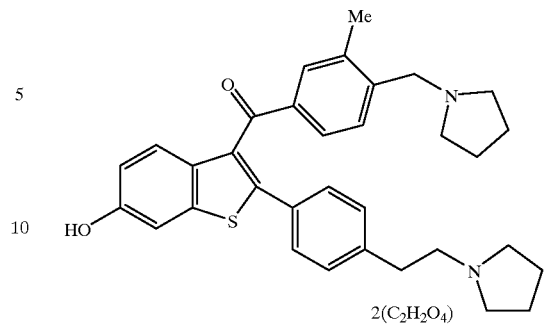

Part A. 1-Bromo-4-[2-(1-pyrrolidinyl)ethyl]benzene.

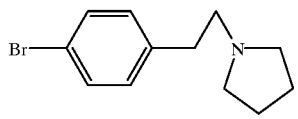

Methanesulfonyl chloride (2.12 mL, 27.4 mmol) was added to a stirred solution of 4-bromophenethyl alcohol (5.00 g, 24.9 mmol) and anhydrous pyridine (2.21 mL, 27.4 mmol) in anhydrous CH$_2$Cl$_2$ (25 mL) at 0° C. under nitrogen atmosphere. Upon the completion of the addition the mixture was allowed to stir at room temperature for 8 h. Then the reaction mixture was cooled to 0° C. and treated with pyrrolidine (10.4 mL, 124 mmol). After stirring at room temperature for 2 h, the mixture was diluted with EtOAc (120 mL), washed with half-saturated NaHCO$_3$ (30 mL), dried over MgSO$_4$, filtered, concentrated, and chromatographed on silica [gradient 0–10% EtOH/Et$_3$N (2/1) in THF/hexanes (1/1)] to give 5.37 g (85%) of the substituted pyrrolidine as an oil.

IR (CHCl$_3$) 2933, 1489 cm$^{-1}$; $^1$H NMR (CDCl$_3$) δ 1.80 (br s, 4H), 2.56 (br s, 4H), 2.64–2.80 (m, 4H), 7.10 (d, J=7.8 Hz, 2H), 7.40 (d, J=7.8 Hz, 2H); FDMS m/e 253 (M$^+$, $^{79}$Br) and 255 (M+, $^{81}$Br).

Part B. 2-Dimethylamino-6-(methoxy)benzo[b]thiophen-3-yl 3-Methyl-4-[(1-pyrrolidinyl)methyl]phenyl Ketone.

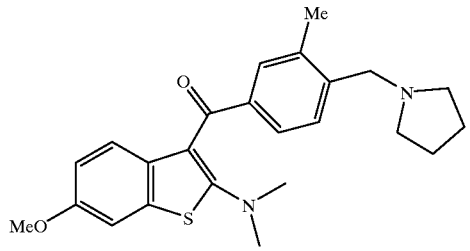

Oxalyl chloride (2.57 mL, 29.5 mmol) was added to a stirred suspension of 3-methyl-4-[(1-pyrrolidinyl)methyl]benzoic acid hydrochloride (1.76 g, 5.90 mmol) in anhydrous ClCH$_2$CH$_2$Cl (12 mL), followed by the addition of 2 drops of DMF. The suspension was stirred at room temperature under nitrogen atmosphere for 6 h, then it was concentrated to dryness under vacuum at 50° C.

To the crude benzoyl chloride obtained and suspended in anhydrous chlorobenzene (10 mL) was added 2-dimethylamino-6-methoxybenzo[b]thiophene (1.02 g, 4.92 mmol. The resultant mixture was heated in an oil bath at 110° C. for 2 h. After cooling to room temperature, the mixture was diluted with EtOAc (80 mL), washed with saturated NaHCO₃ (25 mL), dried over MgSO₄, filtered, concentrated, and chromatographed on silica [gradient 0–10% EtOH/Et₃N (2/1) in THF/hexanes (1/1)] to give 1.50 g (75%) of the ketone as a foam.

IR (CHCl₃) 2950, 1647, 1601 cm⁻¹; ¹H NMR (CDCl₃) δ 1.81 (br s, 4H), 2.39 (s, 3H), 2.56 (br s, 4H), 2.89 (s, 6H), 3.65 (s, 2H), 3.83 (s, 3H), 6.80 (dd, J=9.0 and 2.4 Hz, 1H), 7.12 (d, J=2.4 Hz, 1H), 7.32 (d, J=9.0 Hz, 1H), 7.39 (d, J=8.1 Hz, 1H), 7.63 (d, J=8.1 Hz, 1H), 7.69 (s, 1H); FDMS m/e 408 (M⁺); Anal. Calcd for C₂₄H₂₈N₂O₂S: C, 70.56; H, 6.91; N, 6.86. Found: C, 70.75; H, 7.15; N, 6.91.

Part C. 6-Methoxy-2-[4-[2-(1-pyrrolidinyl)ethyl]phenyl]benzo[b]thiophen-3-yl 3-Methyl-4-[(1-pyrrolidinyl)methyl]phenyl Ketone.

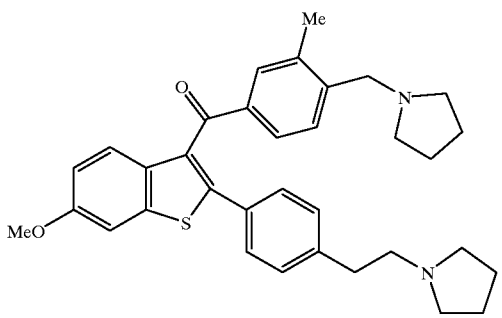

Following the procedure of Example 34, Part C, the trisubstituted benzothiophene was obtained from the aryl bromide of Part A above and the amino benzothiophene of Part B above as a foam in 96% yield.

IR (CHCl₃) 2964, 1647, 1603 cm⁻¹; ¹H NMR (CDCl₃) δ 1.75–1.82 (m, 8H) 2.25 (s, 3H), 2.44 (br s, 4H), 2.51–2.61 (m, 6H), 2.71–2.76 (m, 2H), 3.53 (s, 2H), 3.90 (s, 3H), 6.99 (dd, J=8.7 and 2.1 Hz, 1H), 7.05 (d, J=8.1 Hz, 2H), 7.23 (d, J=7.8 Hz, 1H), 7.29–7.34 (m, 3H), 7.52 (d, J=7.8 Hz, 1H), 7.58 (s, 1H), 7.60 (d, J=8.7 Hz, 1H); FDMS m/e 538 (M+); Anal. Calcd for C₃₄H₃₈N₂O₂S: C, 75.80; H, 7.11; N, 5.20. Found: C, 75.67; H, 7.10; N, 5.25.

Part D. 6-Hydroxy-2-[4-[2-(1-pyrrolidinyl)ethyl]phenyl]benzo[b]thiophen-3-yl 3-Methyl-4-[(1-pyrrolidinyl)methyl]phenyl Ketone Dioxalate.

Following the procedure of Example 34, Part E, the title compound was obtained as a yellowish solid in 77% yield.

IR (KBr) 3420 (br), 2970, 2850–2300 (br), 1721, 1641, 1607 cm⁻¹; ¹H NMR (DMSO-d₆) δ.1.83 (br s, 4H), 1.88 (br s, 4H), 2.26 (s, 3H), 2.81–2.91 (m, 6H), 3.21 (br s, 6H), 4.07 (s, 2H), 6.88 (dd, J=8.7 and 2.1 Hz, 1H), 7.17 (d, J=8.0 Hz, 2H), 7.26 (d, J=8.0 Hz, 2H), 7.33–7.39 (m, 3H), 7.46 (d, J=8.7 Hz, 1H), 7.54 (s, 1H); FDMS m/e 525 (M⁺-2C₂H₂O₄); Anal. Calcd for C₃₃H₃₆N₂O₂S.2C₂H₂O₄: C, 63.05; H, 5.72; N, 3.97. Found: C, 63.24; H, 6.02; N, 4.22.

EXAMPLE 40

Preparation of 6-Hydroxy-3-[3-methyl-4-[(1-pyrrolidinyl)methyl]benzyl]-2-[4-[2-(1-pyrrolidinyl)ethyl]phenyl]benzo[b]thiophene Dioxalate.

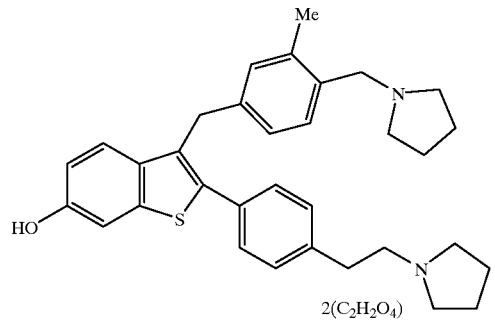

Part A. 6-Methoxy-3-[3-methyl-4-[(1-pyrrolidinyl)ethyl]benzyl]-2-[4-[2-(1-pyrrolidinyl)ethyl]phenyl]benzo[b]thiophene.

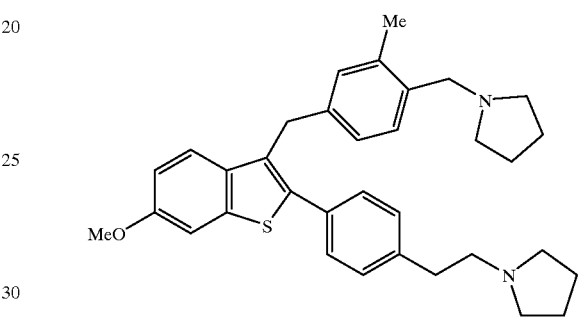

Following the procedure of Example 34, Part D, the methylene compound was obtained from the ketone of Example 39, Part C, as a foam in 67% yield.

IR (KBr) 2953, 1601 cm⁻¹; ¹H NMR (CDCl₃) δ 1.77 (br s, 4H), 1.83 (br s, 4H), 2.29 (s, 3H), 2.51 (br s, 4H), 2.60 (br s, 4H), 2.70–2.75 (m, 2H), 2.85–2.88 (m, 2H), 3.54 (s, 2H), 3.88 (s, 3H), 4.20 (s, 2H), 6.88–6.95 (m, 3H), 7.17 (d, J=7.8 Hz, 1H), 7.24 (d, J=8.1 Hz, 2H), 7.32 (d, J=2.1 Hz, 1H), 7.38–7.45 (m, 3H); FDMS m/e 524 (M⁺); Anal. Calcd for C₃₄H₄₀N₂OS: C, 77.82; H, 7.68; N, 5.34. Found: C, 78.03; H, 7.58; N, 5.54.

Part B. 6-Hydroxy-3-[3-methyl-4-[(1-pyrrolidinyl)methyl]benzyl]-2-[4-[2-(1-pyrrolidinyl)ethyl]phenyl]benzo[b]thiophene Dioxalate.

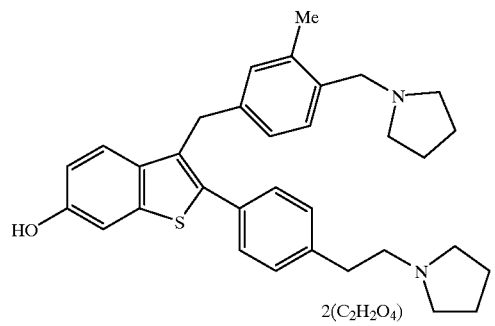

Following the procedure of Example 34, Part D, the hydroxy benzothiophene salt was obtained as a white solid in 73% yield.

IR (KBr) 3420 (br), 2976, 2830–2230 (br), 1722, 1613 cm⁻¹; ¹H NMR (DMSO-d₆) δ 1.81–1.91 (m, 8H), 2.26 (s, 3H), 2.95–3.11 (m, 6H), 3.19–3.35 (m, 6H), 4.15 (s, 2H), 4.17 (s, 2H), 6.79 (dd, J=8.6 and 2.0 Hz, 1H), 6.89 (d, J=8.4 Hz, 1H), 6.99 (s, 1H), 7.26 (d, J=2.0 Hz, 1H), 7.29–7.43 (m, 6H); FDMS m/e 511 (M+1-2C₂H₂O₄); Anal. Calcd for C₃₃H₃₈N₂OS.2C₂H₂O₄: C, 64.33; H, 6.13; N, 4.06. Found: C, 64.42; H, 6.40; N, 4.11.

EXAMPLE 41

Preparation of 6-Hydroxy-2-[4-[2-(1-pyrrolidinyl)ethyl] phenyl]benzo[b]thiophen-3-yl 3-Methoxy-4-[(1-pyrrolidinyl)methyl]phenyl Ketone Dioxalate.

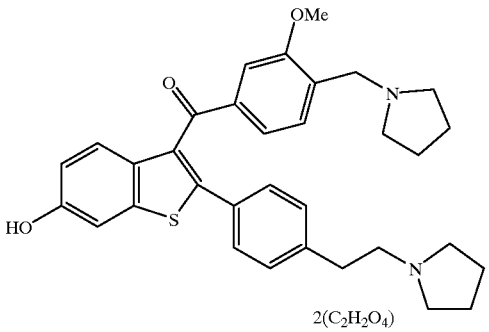

Part A. Methyl 3-Methoxy-4-[(1-pyrrolidinyl)methyl] benzoate.

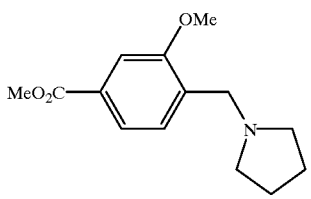

Following the procedure of Example 37, Part A, the substituted pyrrolidine was obtained from methyl 3-methoxy-4-methylbenzoate as an oil in 65% yield.

IR (CHCl₃) 2954, 1716 cm⁻¹; ¹H NMR (CDCl₃) δ 1.95 (br s, 4H), 2.89 (br s, 4H), 3.91 (s, 3H), 3.92 (s, 3H), 3.98 (br t, J=6.8 Hz, 2H), 7.56 (s, 1H), 7.61–7.67 (m, 2H); FDMS m/e 249 (M+).

Part B. 3-Methoxy-4-[(1-pyrrolidinyl)methyl]benzoic Acid Hydrochloride.

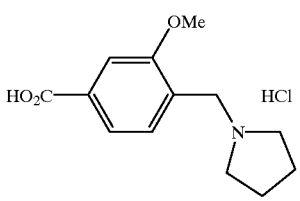

Following the procedure of Example 37, Part B, the acid was obtained from the above ester as a yellowish solid in 65% crude yield.

¹H NMR (DMSO-d₆) δ 1.89–1.94 (br s, 4H), 3.01–3.05 (br s, 2H), 3.26–3.34 (br s, 2H), 3.88 (s, 3H), 4.32 (s, 2H), 7.53 (s, 1H), 7.54 (d, J=7.7 Hz, 1H), 7.70 (d, J=7.7 Hz, 1H); FDMS m/e 235 (M+).

Part C. 6-Benzyloxy-2-(dimethylamino)benzo[b]thiophen-3-yl 3-Methoxy-4-[(1-pyrrolidinyl)methyl]phenyl Ketone.

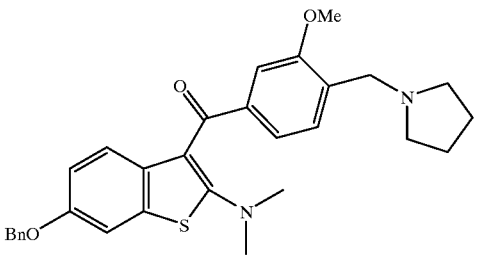

Following the procedure of Example 39, Part B, the ketone was obtained from the above acid and 6-benzyloxy-2-dimethylaminobenzo[b]thiophene as a foam in 81% yield.

IR (CHCl₃) 2970, 1621, 1600 cm⁻¹; ¹H NMR (CDCl₃) δ 1.85 (br s, 4H), 2.70 (br s, 4H), 2.89 (s, 6H), 3.80 (s, 2H), 3.88 (s, 3H), 5.08 (s, 2H), 6.89 (dd, J=8.9 and 2.5 Hz, 1H), 7.20 (d, J=2.3 Hz, 1H), 7.33–7.47 (m, 9H); FDMS m/e 500 (M⁺).

Part D. 6-Benzyloxy-2-[4-[2-(1-pyrrolidinyl)ethyl]phenyl] benzo[b]thiophen-3-yl 3-Methoxy-4-[(1-pyrrolidinyl) methyl]phenyl Ketone.

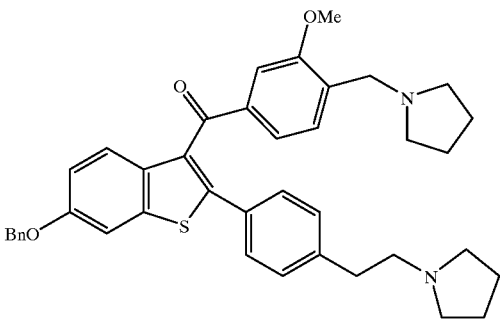

Following the procedure of Example 34, Part C, the trisubstituted benzothiophene was obtained from the dimethylamino compound of Part C as a foam in 81% yield.

IR (CHCl₃) 2965, 1648, 1601 cm⁻¹; ¹H NMR (CDCl₃) δ 1.77–1.82 (m, 8H), 2.52 (br s, 4H), 2.60 (br s, 4H), 2.61–2.67 (m, 2H), 2.75–2.80 (m, 2H), 3.63 (s, 2H), 3.80 (s, 3H), 5.16 (s, 2H), 7.06 (d, J=8.1 Hz, 2+1H superimposed), 7.25–7.50 (m, 11H), 7.61 (d, J=8.9 Hz, 1H); FDMS m/e 631 (M+1).

Part E. 6-Hydroxy-2-[4-[2-(1-pyrrolidinyl)ethyl]phenyl] benzo[b]thiophen-3-yl 3-Methoxy-4-[(1-pyrrolidinyl) methyl]phenyl Ketone Dioxalate.

To a stirred solution of the above benzyloxy benzothiophene (440 mg, 0.698 mmol) in THF (8 mL) under nitrogen atmosphere were sequentially added 10% Pd/C (440 mg) and 25% aqueous HCO₂NH₄ (2 mL). The resultant mixture was stirred under a balloon nitrogen atmosphere for 7 h. After filtration, the filtrate was diluted with EtOAc (50 mL), washed with half-saturated NaCl (15 mL), dried over MgSO₄, filtered, concentrated, and chromatographed on silica [gradient 0–20% EtOH/TEA (2/1) in THF/hexanes (1/1)] to give 225 mg (60%) of the hydroxy benzothiophene as a foam.

A solution of oxalic acid (64.2 mg, 0.712 mmol) in EtOAc (6 mL) was added dropwise to a stirred solution of the hydroxy benzothiophene (175 mg, 0.323 mmol) in THF (4 mL). The resultant white suspension was filtered and the white solid was dried at 60° C. under vacuum to provide 213 mg (91%) of the corresponding dioxalate.

IR (neat) 3450 (br), 2964, 2830–2220, 1719, 1640, 1607 cm$^{-1}$; $^1$H NMR (DMSO-d$_6$) δ 1.83–1.88 (br s, 8H), 2.83–2.93 (m, 6H), 3.18 (br s, 6H), 3.75 (s, 3H), 4.06 (s, 2H), 6.90 (dd, J=8.8 and 2.2 Hz, 1H), 7.15–7.39 (m, 8H), 7.43 (d, J=8.8 Hz, 1H); FDMS m/e 541 (M+1-2C$_2$H$_2$O$_4$); Anal. Calcd for C$_{33}$H$_{36}$N$_2$O$_3$S.2C$_2$H$_2$O$_4$: C, 61.66; H, 5.59; N, 3.89. Found: C, 61.91; H, 5.69; N, 4.00.

EXAMPLE 42

Preparation of 6-Hydroxy-3-[3-methoxy-4-[(1-pyrrolidinyl) methyl]benzyl]-2-[4-[2-(1-pyrrolidinyl)ethyl]phenyl]benzo [b]thiophene Dioxalate.

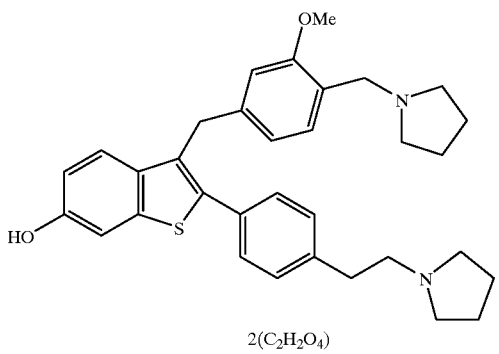

Part A. 6-Benzyloxy-3-[3-methoxy-4-[(1-pyrrolidinyl) methyl]benzyl]-2-[4-[2-(1-pyrrolidinyl)ethyl]phenyl]benzo [b]thiophene.

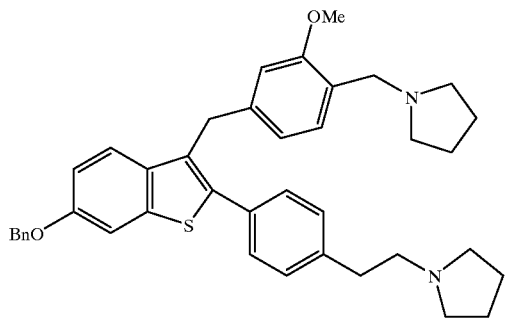

Following the procedure of Example 34, Part D, the methylene compound was obtained from the ketone of Example 41, Part D as a foam in 62% yield.

IR (CHCl$_3$) 2966, 1601 cm$^{-1}$; $^1$H NMR (CDCl$_3$) δ 1.82 (br s, 8H), 2.60 (br s, 8H), 2.68–2.75 (m, 2H), 2.72–2.95 (m, 2H), 3.68 (s, 5H, OCH$_3$ and CH$_2$), 4.22 (s, 2H), 5.13 (S, 2H), 6.64 (s, 1H), 6.71 (d, J=7.5 Hz, 1H), 6.98 (dd, J=8.5 and 2.0 Hz, 1H), 7.23 (br s, 2H), 7.30–7.50 (m, 10H); FDMS m/e 616 (M$^+$). Anal. Calcd for C$_{40}$H$_{44}$N$_2$O$_2$S: C, 77.88; H, 7.19; N, 4.54. Found: C, 77.93; H, 7.22; N, 4.61.

Part B. 6-Hydroxy-3-[3-methoxy-4-[(1-pyrrolidinyl) methyl]benzyl]-2-[4-[2-(1-pyrrolidinyl)ethyl]phenyl]benzo [b]thiophene Dioxalate.

Following the procedure of Example 41, Part E, the title hydroxy benzothiophene salt was obtained from the benzyl ether as a white solid in an overall 65% yield.

IR (KBr) 3420 (br), 2980, 2830–2240 (br), 1720, 1613 cm$^{-1}$; $^1$H NMR (DMSO-d$_6$) δ 1.86–1.93 (m, 8H), 2.96–3.01 (m, 2H), 3.06–3.21 (m, 4H), 3.25–3.50 (m, 6H), 3.70 (s, 3H), 4.14 (s, 2H), 4.20 (s, 2H), 6.60 (d, J=7.9 Hz, 1H), 6.81 (dd, J=8.7 and 2.1 Hz, 1H), 7.26 (d, J=8.2 Hz, 2 + 1H superimposed), 7.36 (d, J=8.2 Hz, 2H) 7.42–7.46 (m, 3H); FDMS m/e 527 (M+1-2C$_2$H$_2$O$_4$); Anal. Calcd for C$_{33}$H$_{38}$N$_2$O$_2$S.1.7C$_2$H$_2$O$_4$: C, 64.31; H, 6.14; N, 4.12. Found: C, 64.25; H, 6.42; N, 4.02.

EXAMPLE 43

Preparation of 6-Hydroxy-2-[4-[2-(1-[(S)-2-hydroxymethyl]pyrrolidinyl]ethyl]phenyl]benzo[b] thiophen-3-yl 3-Methoxy-4-[(1-pyrrolidinyl)methyl]phenyl Ketone Dioxalate.

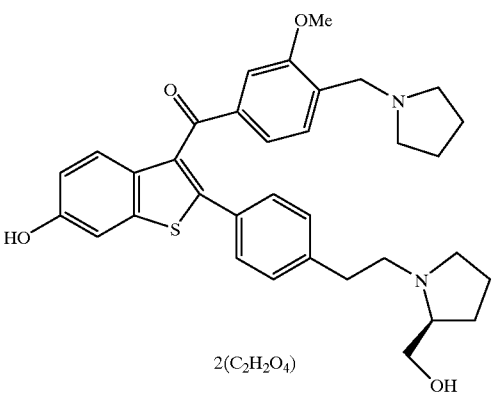

Part A. 1-Bromo-4-[2-(triisopropylsilyloxy)ethyl]benzene.

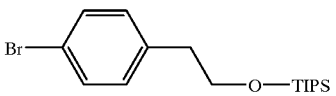

Triisopropylsilyl trifluoromethanesulfonate (35.1 mL, 130 mmol) was added to a stirred solution of 4-bromophenethyl alcohol (20.2 g, 100 mmol) and anhydrous triethylamine (27.8 mL, 200 mmol) in anhydrous CH$_2$Cl$_2$ (200 mL) at room temperature under nitrogen atmosphere. The resultant mixture was stirred for 3 h. After dilution with EtOAc (200 mL), the mixture was washed with a mixed aqeous solution of saturated NaHCO$_3$ (50 mL) and brine (50 mL), dried over MgSO$_4$, filtered, concentrated, and chromatographed on silica (gradient 0–10% EtOAc in hexanes) to give 33.5 g (94%) of the silyl ether as an oil.

IR (CHCl$_3$) 2944, 1489 cm$^{-1}$; $^1$H NMR (CDCl$_3$) δ 1.03 (br s, 3H), 1.39 (br s, 18H), 2.81 (t, J=6.8 Hz, 2H), 3.86 (t, J=6.8 Hz, 2H), 7.11 (d, J=8.2 Hz, 2H), 7.40 (d, J=8.2 Hz, 2H); FDMS m/e 356 (M$^+$. $^{79}$Br) and 358 (M$^+$, $^{81}$Br).

Part B. 6-Benzyloxy-2-[4-(2-hydroxyethyl)phenyl]benzo[b] thiophen-3-yl 3-Methoxy-4-[(1-pyrrolidinyl)methyl]phenyl Ketone.

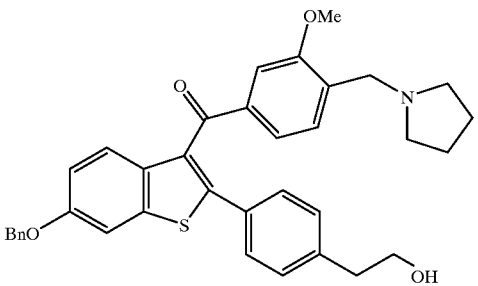

The above silyl ether (571 mg, 1.60 mmol) was added to a stirred suspension of magnesium ribbons (36.4 mg, 1.50 mmol) in anhydrous THF (2 mL) under argon atmosphere, followed by the addition of a small iodine crystal. The mixture was heated in an oil bath at 60–65° C. for 2 h to form a homogeneous Grignard solution. The Grignard solution was cooled to room temperature before it was added to a stirred solution of the compound of Example 41, Part C (500 mg, 1.00 mmol) in anhydrous THF (4 mL) at 0° C. under argon atmosphere. The resultant mixture was stirred at 0° C. for 1.5 h, then quenched with saturated aqueous NH$_4$Cl (5 mL). After extraction with EtOAc (25 mL×2), the combined organic layers were dried over MgSO$_4$, filtered, and concentrated to give a gummy residue (597 mg).

The residue was dissolved in anhydrous THF (5 mL) and treated with tetrabutylammonium fluoride (1.20 mL, 1 M in THF) at room temperature under nitrogen atmosphere. After stirring for 1.5 h, the mixture was concentrated under vacuum and chromatographed on silica [gradient 0–30% EtOH/Et$_3$N (2/1) in THF/hexanes (1/1)] to give 395 mg (68%) of the alcohol as a foam.

IR (CHCl3) 2960, 1646, 1601 cm$^{-1}$; $^1$H NMR (CDCl$_3$) δ 1.80 (br s, 4H), 2.54 (br s, 4H), 2.75 (t, J=6.2 Hz, 2H), 3.59 (s, 2H), 3.74 (t, J=6.2 Hz, 2H), 3.79 (s, 3H), 5.18 (s, 2H), 7.05 (d, J=8.1 Hz, 1H), 7.09–7.50 (m, 13H), 7.74 (d, J=8.9 Hz, 1H); FDMS m/e 578 (M+1); Anal. Calcd for C$_{36}$H$_{35}$NO$_4$S: C, 74.84; H, 6.11; N, 2.42. Found: C, 75.02; H, 6.34; N, 2.50.

Part C. 6-Benzyloxy-2-[4-[2-1-[(S)-2-hydroxymethyl] pyrrolidinyl]ethyl]phenyl]benzo[b]thiophen-3-yl 3-Methoxy-4-[(1-pyrrolidinyl)methyl]phenyl Ketone.

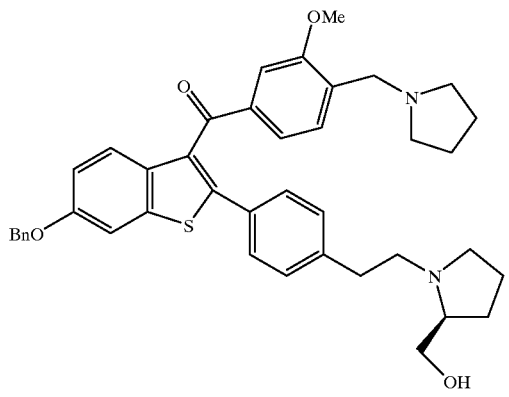

Methanesulfonyl chloride (0.420 mL, 5.43 mmol) was added to a stirred solution of the above alcohol (2.09 g, 3.62 mmol) in anhydrous pyridine (5 mL) at 0° C. under nitrogen atmosphere, and the reaction mixture was allowed to stir at room temperature for 2 h. (S)-Prolinol (1.25 mL, 12.7 mmol) was added and the resultant mixture was heated at 70° C. for 2 h. After dilution with EtOAc (120 mL), the mixture was washed with half-saturated NaHCO$_3$ (30 mL), dried over MgSO$_4$, filtered, concentrated, and chromatographed on silica [gradient 0–25% EtOH/Et$_3$N (2/1) in THF/hexanes (1/1)] to give 2.01 g (84%) of the substituted pyrrolidine a foam.

IR (neat) 3355 (br), 2958, 1646, 1600 cm$^{-1}$; $^1$H NMR (CDCl$_3$) δ 1.63–2.19 (m, 8H), 2.25–2.80 (m, 8H), 2.87 (t, J=7.7 Hz, 2H), 3.15–3.58 (m, 4H), 3.44 (dd, J=11.5 and 3.6 Hz, 1H), 3.60 (dd, J=11.5 and 3.6 Hz, 1H), 3.62 (s, 2H), 3.80 (s, 3H), 7.04–7.08 (m, 3H), 7.23–7.47 (m, 11H), 7.62 (d, J=9.0 Hz, 1H); FDMS m/e 661 (M+1).

Part D. 6-Hydroxy-2-[4-[2-[1-[(S)-2-hydroxymethyl] pyrrolidinyl]ethyl]phenyl3benzo[b]thiophen-3-yl 3-Methoxy-4-[(1-pyrrolidinyl)methyl]phenyl Ketone Dioxalate.

Following the procedure of Example 41-E, the title salt was obtained from the above methoxy benzothiophene as a yellowish solid in an overall 6% yield. The free base of the title compound was unstable.

$^1$H NMR (CD$_3$OD) δ 1.75–2.25 (m, 8H), 2.82–3.05 (m, 2H), 3.15–3.23 (m, 4H), 3.38–3.91 (m, 6H), 3.80 (s, 3H), 4.01–4.13 (m, 1H), 4.28 (s, 2H), 6.92 (br d, J=6.3 Hz, 1H), 7.03–7.37 (m, 8H), 7.56 (m,1H); FDMS m/e 571 (M+1).

EXAMPLE 44

Preparation of 6-Hydroxy-3-[3-methyl-4-[[1-[(S)-2-methoxymethyl]pyrrolidinyl]methyl]benzyl]-2-[4-[2-(1-pyrrolidinyl)ethoxy]phenyl]benzo[b]thiophene Dioxalate.

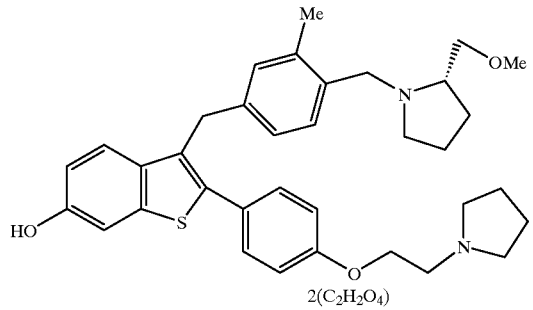

Part A. Methyl 3-Bromo-4-[[1-[(S) -2-methoxymethyl] pyrrolidinyl]methyl]benzoate.

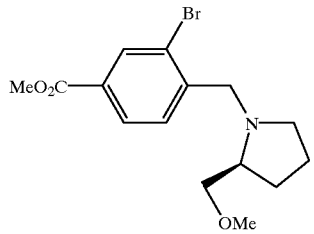

Following the procedure of Example 37, Part A, the substituted pyrrolidine was obtained from methyl 3-bromo-4-methylbenzoate and (S)-2-(methoxymethyl)pyrrolidine as an oil in 63% yield.

IR (neat) 2950, 1727 cm$^{-1}$; FDMS m/e 341 (M$^+$, $^{79}$Br) and 343 (M$^+$, $^{81}$Br); Anal. Calcd for C$_{15}$H$_{20}$BrNO$_3$: C, 52.64; H, 5.89; N, 4.09. Found: C, 52.91; H, 5.93; N, 3.85.

Part B. 3-Bromo-4-[[1-[(S)-2-methoxymethyl]pyrrolidinyl] methyl]benzoic acid hydrochloride.

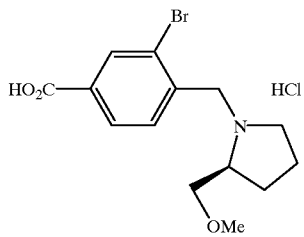

Following the procedure of Example 37, Part B, the acid was obtained from the above ester as a white solid in 100% yield.

$^1$H NMR (DMSO-d$_6$) δ 1.60–1.78 (m, 1H), 1.80–2.05 (m, 2H), 2.08–2.22 (m, 1H), 3.10–3.50 (m, 2H), 3.29 (s, 3H), 3.60–3.65 (m, 1H), 3.75–3.95 (m, 2H), 4.46 (br d, J=13.4

Hz, 1H), 4.76 (d, J=13.4 Hz, 1H), 7.93 (d, J=8.0 Hz, 1H), 8.03 (d, J=8.0 Hz, 1H), 8.12 (s, 1H), 11.15 (br s, 1H), 13.55 (br s,1H).

Part C. 3-Bromo-4-[[1-[(S)-2-methoxymethyl]pyrrolidinyl]methyl]phenyl 2-Dimethylamino-6-methoxybenzo[b]thiophen-3-yl Ketone.

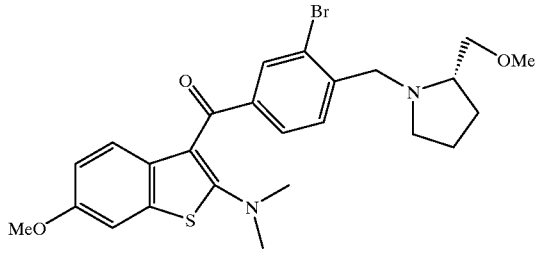

Following the procedure of Example 39, Part B, the ketone was obtained from the above acid as a foam in 75% yield.

IR (neat) 1626, 1544 cm$^{-1}$; FDMS m/e 516 (M$^+$, $^{79}$Br) and 518 (M$^+$, $^{81}$Br); Anal. Calcd for $C_{25}H_{29}BrN_2O_3S$: C, 58.03; H, 5.65; N, 5.41. Found: C, 58.15; H, 5.40; N, 5.29.

Part D. 3-Bromo-4-[[1-[(S) -2-methoxymethyl]pyrrolidinyl]methyl]phenyl 6-Methoxy-2-[4-[2-(1-pyrrolidinyl)ethoxy]phenyl]benzo[b]thiophen-3-yl Ketone.

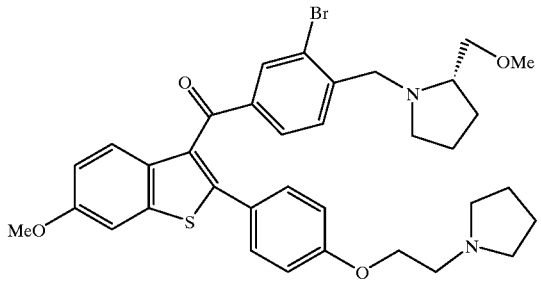

Following the procedure of Example 34, Part C, the trisubstituted benzothiophene was obtained from the above benzothiophene and the corresponding aryl bromide as a foam in 95% yield.

IR (neat) 2962, 1645, 1606 cm$^{-1}$; FDMS m/e 662 (M$^+$, $^{79}$Br) and 664 (M$^+$, $^{81}$Br); Anal. Calcd for $C_{35}H_{39}BrN_2O_4S$: C, 63.34; H, 5.92; N, 4.22. Found: C, 63.18; H, 5.84; N, 4.44.

Part E. 3-[3-Bromo-4-[[1-[(S)-2-methoxymethyl]pyrrolidinyl]methyl]benzyl]-6-methoxy-2-[4-[2-(1-pyrrolidinyl)ethoxy]phenyl]benzo[b]thiophene.

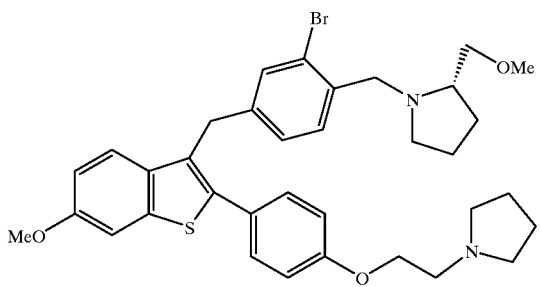

Following the procedure of Example 34, Part D, the methylene compound was obtained from the above ketone as a foam in 79% yield.

IR (neat) 2963, 1607 cm$^{-1}$; FDMS m/e 648 (M$^+$, $^{79}$Br) and 650 (M$^+$, $^{81}$Br); Anal. Calcd for $C_{35}H_{41}BrN_2O_3S$: C, 64.71; H, 6.36; N, 4.31. Found: C, 64.93; H, 6.42; N, 4.35.

Part F. 6-Methoxy-3-[3-methyl-4-[[1-[(S)-2-methoxymethyl]pyrrolidinyl]methyl]benzyl]-2-[4-[2-(1-pyrrolidinyl)ethoxy]phenyl]benzo[b]thiophene.

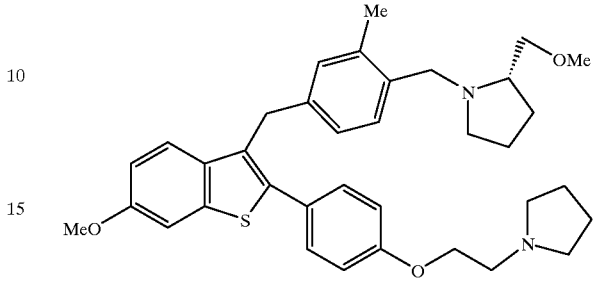

Following the procedure of Example 38, Part A, the aryl methyl compound was obtained from the above aryl bromide as a foam in 85% yield.

IR (neat) 2962, 1608 cm$^{-1}$; FDMS m/e 584 (M$^+$) and 585 (M+1); Anal. Calcd for $C_{36}H_{44}N_2O_3S$: C, 73.94; H, 7.58; N, 4.79. Found: C, 73.84; H. 7.42; N, 4.50.

Part G. 6-Hydroxy-3-[3-methyl-4-[[1-[(S)-2-methoxymethyl]pyrrolidinyl]methyl]benzyl]-2-[4-[2-(1-pyrrolidinyl)ethoxy]phenyl]benzo[b]thiophene Dioxalate.

Following the procedure of Example 34, Part D, a mixture of the free bases of the compounds of this example and the following example were obtained from the above dimethoxy compound. Following conversion to the dioxalate, the title compound was obtained as a white solid in a 2-step yield of 19%.

IR (KBr) 3450–2500 (br), 1718, 1609 cm$^{-1}$; FDMS m/e 571 (M+1-2C$_2$H$_2$O$_4$); Anal. Calcd for $C_{35}H_{42}N_2O_3S.2C_2H_2O_4$: C, 62.39; H, 6.18; N, 3.73. Found: C, 62.61; H, 6.02; N, 3.72.

EXAMPLE 45

Preparation of 6-Hydroxy-3-[3-methyl-4-[[1-[(S)-2-hydroxymethyl]pyrrolidinyl]methyl]benzyl]-2-[4-[2-(1-pyrrolidinyl)ethoxy]phenyl]benzo[b]thiophene Dioxalate.

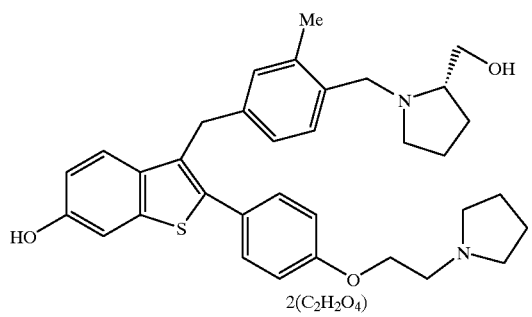

Following separation of the free base in Part G of the above example, the dihydroxy compound was converted into the title dioxalate which was obtained in a white solid in a 2-step yield of 33%.

IR (KBr) 3400–2500 (br), 1721, 1609 cm$^{-1}$; FDMS m/e 557 (M+1-2C$_2$H$_2$O$_4$); Anal. Calcd for $C_{34}H_{40}N_2O_3S.1.6C_2H_2O_4$: C, 62.39; H, 6.18; N. 3.73. Found: C, 62.61; H, 6.02; N, 3.72.

EXAMPLE 46

Preparation of 6-Hydroxy-2-[4-[2-(1-pyrrolidinyl)ethoxy]phenyl]benzo[b]thiophen-3-yl 3-Methyl-4-[(4-morpholinyl)methyl]phenyl Ketone Dioxalate.

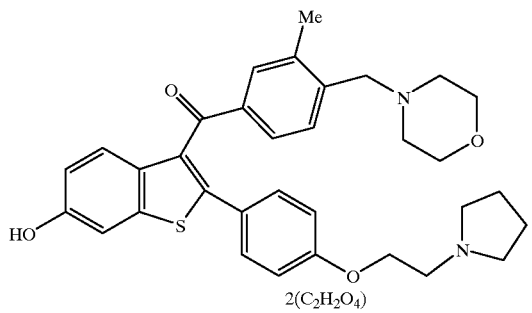

Part A. Methyl 3-Bromo-4-[(4-morpholinyl)methyl] benzoate.

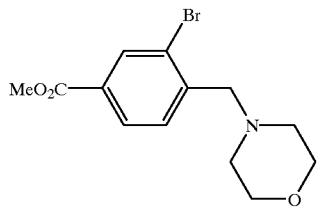

Following the procedure of Example 37, Part A, the substituted morpholine was obtained from methyl 3-bromo-4-methylbenzoate and morpholine as an oil in 53% yield.

IR (neat) 2953, 1727 cm$^{-1}$; $^1$H NMR (CDCl$_3$) δ 2.48–2.60 (m, 4H), 3.63 (s, 2H), 3.70–3.80 (m, 4H), 3.93 (s, 3H), 7.59 (d, J=8.0 Hz, 1H), 7.95 (d, J=8.0 Hz, 1H), 8.23 (s, 1H); FDMS m/e 313 (M$^+$,$^{79}$Br) and 315 (M$^+$,$^{81}$Br); Anal. Calcd for C$_{13}$H$_{16}$BrNO$_3$: C, 49.70; H, 5.13; N, 4.46. Found: C, 49.42; H, 4.98; N, 4.55.

Part B. 3-Bromo-4-[(4-morpholinyl)methyl]benzoic Acid Hydrochloride.

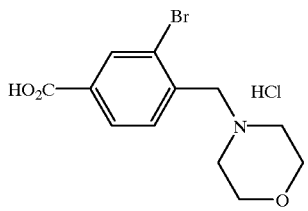

Following the procedure of Example 37, Part B, the acid was obtained from the above ester as a white solid in 100% yield.

$^1$H NMR (DMSO-d$_6$) δ 3.25 (br s, 4H), 3.88 (br s, 4H), 4.51 (s, 2H), 7.93 (d, J=8.0 Hz, 1H), 8.12 (s, 1H), 8.19 (br d, J=8.0 Hz, 1H).

Part C. 3-Bromo-4-[(4-morpholinyl)methyl]phenyl 2-Dimethylamino-6-methoxybenzo[b]thiophen-3-yl Ketone.

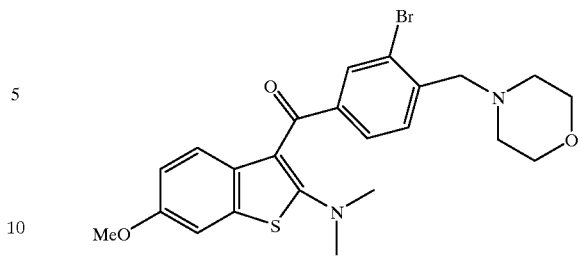

Following the procedure of Example 39, Part C, the ketone was obtained from 2-dimethylamino-6-methoxybenzo[b]thiophene and the above acid as a foam in 80% yield.

IR (neat) 1622, 1540 cm$^{-1}$; $^1$H NMR (CDCl$_3$) δ 2.52–2.60 (m, 4H), 2.89 (s, 6H), 3.65 (s, 2H), 3.72–3.80 (m, 4H), 3.83 (s, 3H), 6.84 (dd, J=8.9 and 2.4 Hz, 1H), 7.13 (d, J=2.4 Hz, 1H), 7.39 (d, J=8.9 Hz, 1H) , 7.58 (d, J=8.0 Hz, 1H), 7.77 (dd, J=8.0 and 1.4 Hz, 1H), 8.05 (d, J=1.4 Hz, 1H); FDMS m/e 488 (M$^+$, $^{79}$Br) and 490 (M$^+$,$^{81}$Br).

Part D. 3-Bromo-4-[(4-morpholinyl)methyl]phenyl 6-Methoxy-2-[4-[2-(1-pyrrolidinyl)ethoxy]phenyl]benzo[b] thiophen-3-yl Ketone.

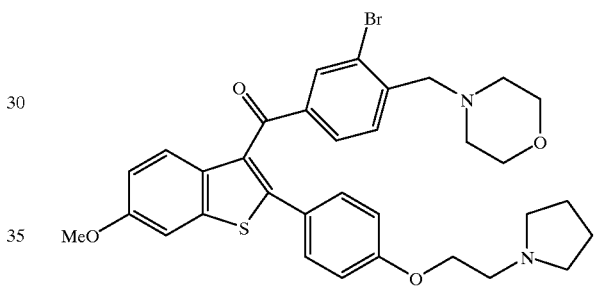

Following the procedure of Example 34, Part C, the trisubstituted benzothiophene was obtained from the corresponding aryl bromide and the above benzothiophene as a foam in 80% yield.

IR (neat) 2959, 1622, 1598 cm$^{-1}$; FDMS m/e 635 (M+1, $^{79}$Br) and 637 (M+1, $^{79}$Br).

Part E. 6-Methoxy-2-[4-[2-(1-pyrrolidinyl)ethoxy]phenyl] benzo[b]thiophen-3-yl 3-Methyl-4-[(4-morpholinyl)methyl] phenyl Ketone.

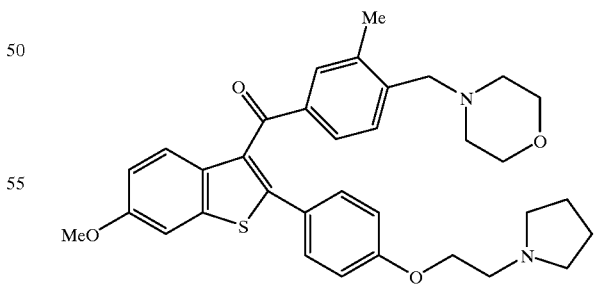

Following the procedure of Example 34, Part E, the aryl methyl compound was obtained from the above aryl bromide as a foam in 76% yield.

IR (neat) 2958, 1643, 1603 cm$^{-1}$; FDMS m/e 570 (M$^+$) .

Part F. 6-Hydroxy-2-[4-[2-(1-pyrrolidinyl)ethoxy]phenyl] benzo[b]thiophen-3-yl 3-Methyl-4-[(4-morpholinyl)methyl] phenyl Ketone Dioxalate.

Following the procedure of Example 34, Part E, the salt of the hydroxy benzothiophene was obtained from the above methoxy benzothiophene as a yellowish solid in a 2-step yield of 69%.

IR (KBr) 3400–2500 (br), 1725, 1639 cm$^{-1}$; FDMS mn/e 557(M+1-2C$_2$H$_2$O$_4$); Anal. Calcd for C$_{33}$H$_{36}$N$_2$O$_4$S.2C$_2$H$_2$O$_4$: C, 60.32; H, 5.47; N, 3.80. Found: C, 60.60; H, 5.53; N, 4.01.

EXAMPLE 47

Preparation of 3-[3-Bromo-4-[(4-morpholinyl)methyl] benzyl]-6-hydroxy-2-[4-[2-(1-pyrrolidinyl)ethoxy]phenyl] benzo[b]thiophene Dioxalate.

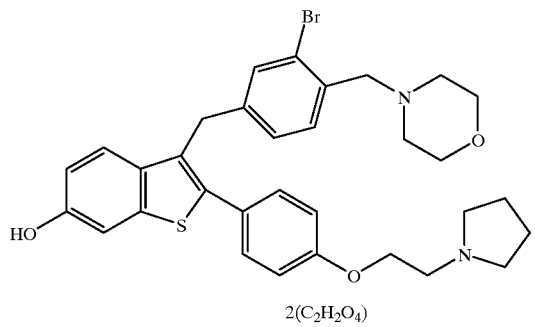

Part A. 3-[3-Bromo-4-[(4-morpholinyl)methyl]benzyl]-6-methoxy-2-[4-[2-(1-pyrrolidinyl)ethoxy3phenyl]benzo[b] thiophene.

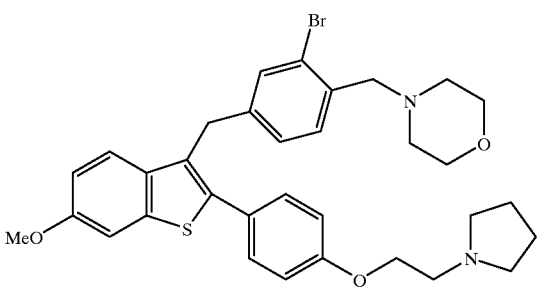

Following the procedure of Example 34, Part D, the methylene compound was obtained from the ketone of Example 46, Part A as a foam in 84% yield.

IR (neat) 2958, 1608 cm$^{-1}$; FDMS m/e 621 (M+1,$^{79}$Br) and 623 (M+1, $^{81}$Br); Anal. Calcd for C$_{33}$H$_{37}$BrN$_2$O$_3$S: C, 63.76; H, 6.00; N, 4.51. Found: C, 63.50; H, 5.82; N, 4.38.
Part B. 3-[3-Bromo-4-[(4-morpholinyl)methyl]benzyl]-6-hydroxy-2-[4-[2-(1-pyrrolidinyl)ethoxy]phenyl]benzo[b] thiophene Dioxalate.

Following the procedure of Example 34, Part E, the title hydroxy benzothiophene salt was obtained from the above methoxy benzothiophene as a white solid in 66% yield.

IR (KBr) 3400–2500 (br), 1721, 1607 cm$^{-1}$; FDMS m/e 607 (M+1-2C$_2$H$_2$O$_4$,$^{79}$Br) and 609 (M+1-2C$_2$H$_2$O$_4$,$^{81}$Br); Anal. Calcd for C$_{32}$H$_{35}$BrN$_2$O$_3$S.1.5C$_2$H$_2$O$_4$: C, 56.61; H, 5.16; N, 3.77. Found: C, 56.70; H, 5.13; N, 3.95.

EXAMPLE 48

Preparation of 6-Hydroxy-3-[3-methyl-4-[(4-morpholinyl) methyl]benzyl]-2-[4-[2-(1-pyrrolidinyl)ethoxy]phenyl] benzo[b]thiophene Dioxalate.

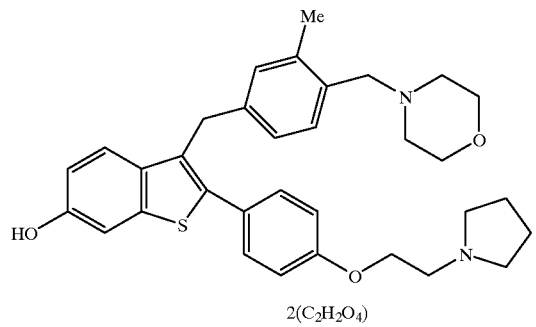

Part A. 6-Methoxy-3-[3-methyl-4-[(4-morpholinyl)methyl] benzyl]-2-[4-[2-(1-pyrrolidinyl)ethoxy]phenyl]benzo[b] thiophene.

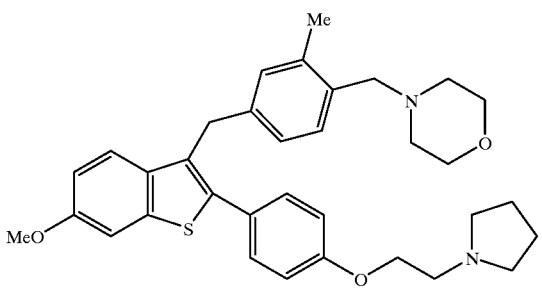

Following the procedure of Example 38, Part A, the aryl methyl compound was obtained from the aryl bromide of Example 47, Part A as a foam in 91% yield.

IR (neat) 2957, 1608 cm$^{-1}$; FDMS m/e 556 (M$^+$).
Part B. 6-Hydroxy-3-[3-methyl-4-[(4-morpholinyl)methyl] benzyl]-2-[4-[2-(1-pyrrolidinyl)ethoxy]phenyl]benzo[b] thiophene Dioxalate.

Following the procedure of Example 34, Part E, the title hydroxy benzothiophene salt was obtained from the above methoxy benzothiophene as a white solid in a 2-step yield of 79%.

IR (KBr) 3400–2500 (br), 1722, 1610 cm$^{-1}$; FDMS m/e 543 (M$^+$-2C$_2$H$_2$O$_4$); Anal. Calcd for C$_{33}$H$_{38}$N$_2$O$_3$S.1.5C$_2$H$_2$O$_4$: C, 63.79; H, 6.10; N, 4.13. Found: C, 63.92; H, 6.15; N, 4.31.

EXAMPLE 49

Preparation of 6-Hydroxy-2-[4-[2-(1-pyrrolidinyl)ethoxy] phenyl]benzo[b]thiophen-3-yl 3-Methoxy-4-[(4-morpholinyl)methyl]phenyl Ketone Dioxalate.

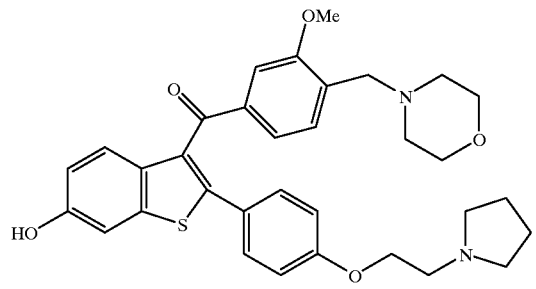

Part A. Methyl 3-Methoxy-4-(4-morpholinyl)benzoate.

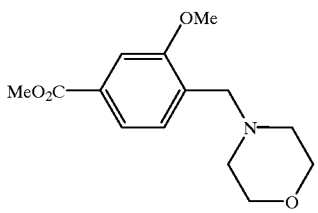

Following the procedure of Example 37, Part A, the substituted morpholine was obtained from methyl 4-methyl-3-methoxybenzoate and morpholine as an oil in 79% yield.

IR (neat) 2953, 1723, 1582 cm$^{-1}$; FDMS m/e 265 (M$^+$) ; Anal. Calcd for $C_{14}H_{19}NO_4$: C, 63.38; H, 7.22; N, 5.28. Found: C, 63.11; H, 7.20; N, 5.50.

Part B. 3-Methoxy-4-(4-morpholinyl)benzoic Acid Hydrochloride.

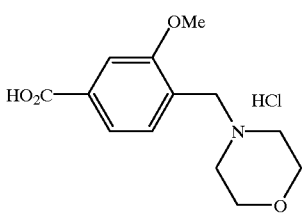

Following the procedure of Example 37, Part B, the acid was obtained from the ester as a white solid in 100% yield.

$^1$H NMR (DMSO-d$_6$) δ 3.05 (br s, 2H), 3.15–3.25 (m, 2H), 3.85 (s, 2H), 3.87 (s, 5H, OCH$_3$ and CH$_2$), 4.29 (s, 2H), 7.52 (s, 1H), 7.53 (d, J=8.0 Hz, 1H), 7.77 (d, J=8.0 Hz, 1H), 11.65 (br s, 1H), 13.15 (br s, 1H).

Part C. 6-Benzyloxy-2-(dimethylamino)benzo[b]thiophen-3-yl 3-Methoxy-4-[(4-morpholinyl)methyl]phenyl Ketone.

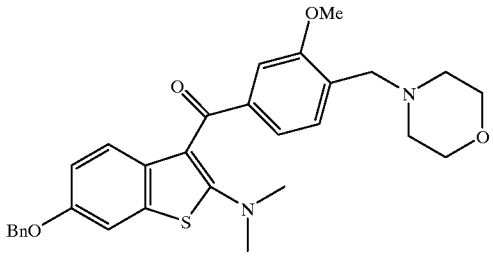

Following the procedure of Example 39, Part B, the ketone was obtained from 6-benzyloxy-2-(dimethylamino)benzo[b]thiophene and the above acid as a foam in 81% yield.

IR (neat) 2954, 1625, 1600 cm$^{-1}$; FDMS m/e 516 (M$^+$) ; Anal. Calcd for $C_{30}H_{32}N_2O_4S$: C, 69.74; H, 6.24; N, 5.42. Found: C, 70.03; H, 6.47; N, 5.44.

Part D. 6-Benzyloxy-2-[4-[2-(1-pyrrolidinyl)ethoxy]phenyl]benzo[b]thiophen-3-yl 3-Methoxy-4-[(4-morpholinyl)methyl]phenyl Ketone.

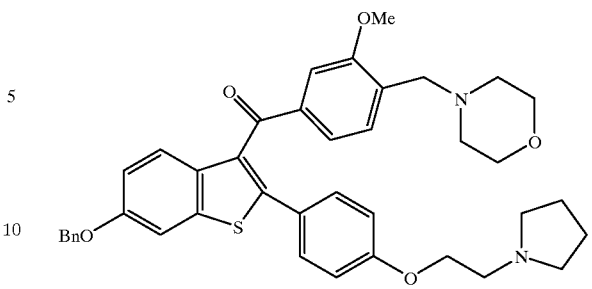

Following the procedure of Example 34, Part C, the trisubstituted benzothiophene was obtained from the corresponding aryl bromide and the above benzothiophene as a foam in 88% yield.

IR (neat) 2961, 1651 cm$^{-1}$; FDMS m/e 662 (M$^+$) and 663 (M+1); Anal. Calcd for $C_{40}H_{42}N_2O_5S$: C, 72.48; H, 6.39; N, 4.23. Found: C, 72.47; H, 6.35; N, 4.43.

Part E. 6-Hydroxy-2-[4-[2-(1-pyrrolidinyl)ethoxy]phenyl]benzo[b]thiophen-3-yl 3-Methoxy-4-[(4-morpholinyl)methyl]phenyl Ketone Dioxalate.

Following the procedure of Example 41, Part E, the salt of the hydroxy benzothiophene was obtained from the above benzyl ether as a yellowish solid in an overall 74% yield.

IR (KBr) 3400–2500 (br), 1722, 1633, 1606 cm$^{-1}$; FDMS m/e 573 (M+1-2C$_2$H$_2$O$_4$); Anal. Calcd for $C_{33}H_{36}N_2O_5S \cdot 2.3C_2H_2O_4$: C, 57.91; H, 5.25; N, 3.59. Found: C, 57.93; H, 5.37; N, 3.78.

EXAMPLE 50

Preparation of 6-Hydroxy-3-[3-methoxy-4-[(4-morpholinyl)methyl]benzyl]-2-[4-[2-(1-pyrrolidinyl)ethoxy]phenyl]benzo[b]thiophene Dioxalate.

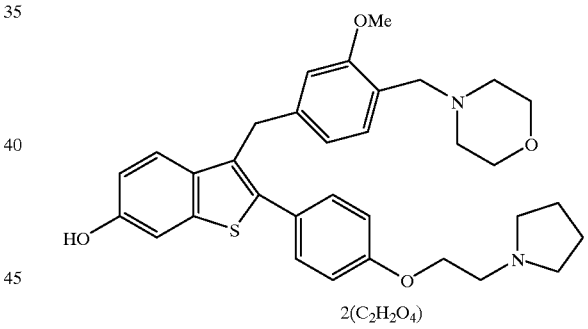

2(C$_2$H$_2$O$_4$)

Part A. 6-Benzyloxy-3-[3-methoxy-4-[(4-morpholinyl)methyl]benzyl]-2-[4-[2-(1-pyrrolidinyl)ethoxy]phenyl]benzo[b]thiophene.

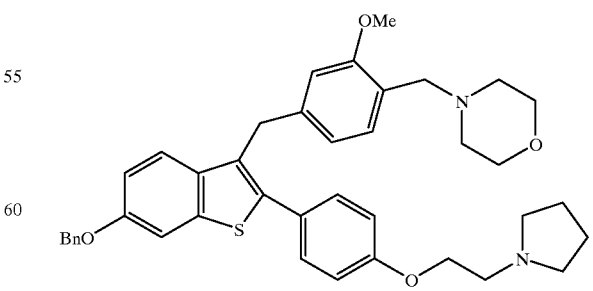

Following the procedure of Example 34, Part D, the methylene compound was obtained from the ketone of Example 49, Part D as a foam in 82% yield.

IR (neat) 2961, 1609 cm$^{-1}$; FDMS m/e 649 (M+1); Anal. Calcd for C$_{40}$H$_{44}$N$_2$O$_4$S: C, 74.04; H, 6.84; N, 4.32. Found: C, 74.30; H, 7.18; N, 4.34.

Part B. 6-Hydroxy-3-[3-methoxy-4-[(4-morpholinyl) methyl]benzyl]-2-[4-[2-(1-pyrrolidinyl)ethoxy]phenyl] benzo[b]thiophene Dioxalate.

Following the procedure of Example 41, Part E, the salt of the hydroxy benzothiophene was obtained from the above benzyl ether as a white solid in an overall 90% yield.

IR (KBr) 3400–2500 (br), 1613 cm$^{-1}$; FDMS m/e 559 (M+1-2C$_2$H$_2$O$_4$); Anal. Calcd for C$_{33}$H$_{38}$N$_2$O$_4$S.1.4C$_2$H$_2$O$_4$: C, 62.79; H, 6.01; N, 4.09. Found: C, 62.73; H, 5.93; N, 4.04.

EXAMPLE 51

Preparation of 6-Hydroxy-2-[4-[2-(1-pyrrolidinyl)ethyl] phenyl]benzo[b]thiophen-3-yl 3-Methoxy-4-[(4-morpholinyl)methyl]phenyl Ketone Dioxalate.

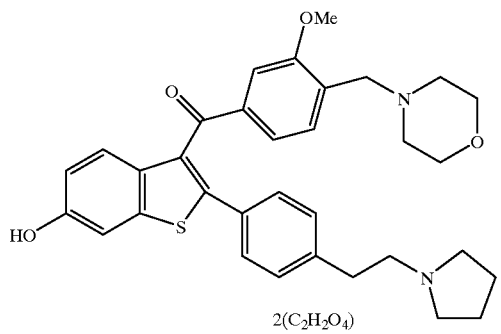

Part A. 6-Benzyloxy-2-[4-[2-(1-pyrrolidinyl)ethyl]phenyl] benzo[b]thiophen-3-yl 3-Methoxy-4-[(4-morpholinyl) methyl]phenyl Ketone.

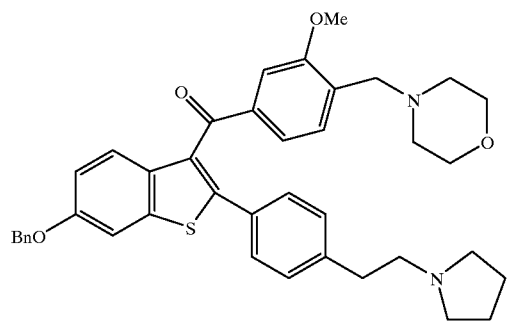

Following the procedure of Example 34, Part C, the trisubstituted benzothiophene was obtained from the aryl bromide of Example 39, Part A and the ketone of Example 49, Part C as a foam in 91% yield.

IR (neat) 3400 (br), 2959, 1651, 1600 cm$^{-1}$; FDMS m/e 646 (M$^+$) ; Anal. Calcd for C$_{40}$H$_{42}$N$_2$O$_4$S: C, 74.27; H, 6.54; N, 4.33. Found: C, 74.09; H, 6.74; N, 4.38.

Part B. 6-Hydroxy-2-[4-[2-(1-pyrrolidinyl)ethyl]phenyl] benzo[b]thiophen-3-yl 3-Methoxy-4-[(4-morpholinyl) methyl]phenyl Ketone Dioxalate.

Following the procedure of Example 41, Part E, the salt of the hydroxy benzothiophene was obtained from the above benzyl ether as a yellowish solid in an overall 83% yield.

IR (KBr) 3400–2500 (br), 1718, 1645 cm$^{-1}$; FDMS m/e 557 (M+1-2C$_2$H$_2$O$_4$); Anal. Calcd for C$_{33}$H$_{36}$N$_2$O$_4$S.2C$_2$H$_2$O$_4$: C, 60.32; H, 10 5.47; N, 3.80. Found: C, 60.06; H, 5.43; N, 4.00.

EXAMPLE 52

Preparation of 6-Hydroxy-3-[3-methoxy-4-[(4-morpholinyl) methyl]benzyl]-2-[4-[2-(1-pyrrolidinyl)ethyl]phenyl]benzo [b]thiophene Dioxalate.

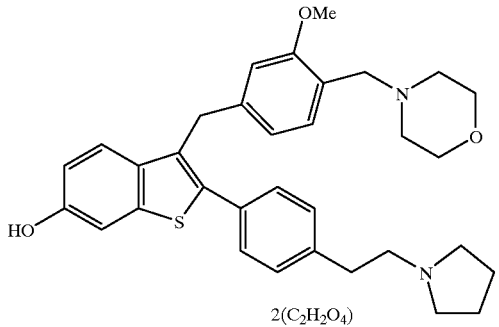

Part A. 6-Benzyloxy-3-[3-methoxy-4-[(4-morpholinyl) methyl]benzyl]-2-[4-[2-(1-pyrrolidinyl)ethyl]phenyl]benzo [b]thiophene.

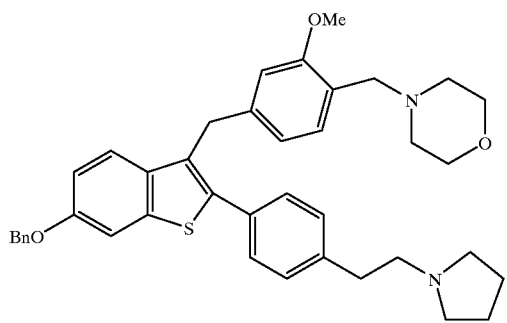

Following the procedure of Example 34, Part D, the methylene compound was obtained from the ketone of Example 51, Part A as a foam in 100% yield.

IR (neat) 2957, 1600 cm$^{-1}$; FDMS m/e 632 (M$^+$) ; Anal. Calcd for C$_{40}$H$_{44}$N$_2$O$_3$S: C, 75.92; H, 7.01; N, 4.43. Found: C, 75.93; H, 7.00; N, 4.39.

Part B. 6-Hydroxy-3-[3-methoxy-4-[(4-morpholinyl) methyl]benzyl]-2-[4-[2-(1-pyrrolidinyl)ethyl]phenyl]benzo [b]thiophene Dioxalate.

Following the procedure of Example 41, Part E, the salt of the hydroxy benzothiophene was obtained from the above benzyl ether as a white solid in an overall 83% yield.

IR (KBr) 3400–2500 (br), 1719, 1612 cm$^{-1}$; FDMS m/e 543 (M+1-2C$_2$H$_2$O$_4$); Anal. Calcd for C$_{33}$H$_{38}$N$_2$O$_3$S.1.7C$_2$H$_2$O$_4$: C, 62.83; H, 6.00; N, 4.03. Found: C, 62.72; H, 6.05; N, 4.16.

EXAMPLE 53

Preparation of 6-Hydroxy-2-[4-[2-[1-[(S)-2-hydroxymethyl]pyrrolidinyl]ethyl]phenyl]benzo[b] thiophen-3-yl 3-Methoxy-4-[(4-morpholinyl)methyl]phenyl Ketone Dioxalate.

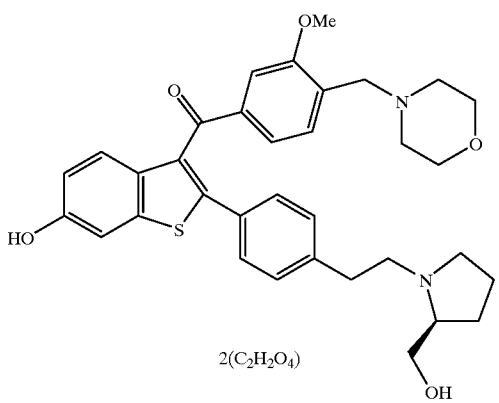

Part A. 6-Benzyloxy-2-[4-(2-hydroxyethyl)phenyl]benzo[b]thiophen-3-yl 3-Methoxy-4-[(4-morpholinyl)methyl]phenyl Ketone.

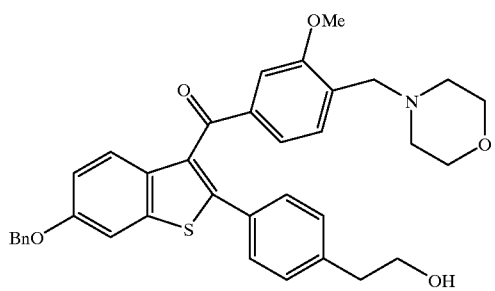

Following the procedure of Example 43, Part A, the trisubstituted benzothiophene was obtained from the ketone of Example 49, Part C as a foam in an overall 95% yield.

IR (neat) 3424 (br), 2936, 1647, 1600 cm$^{-1}$; FDMS m/e 593 (M$^+$); Anal. Calcd for $C_{36}H_{35}NO_5S$: C, 72.83; H, 5.94; N, 2.36. Found: C, 72.66; H, 5.95; N, 2.59.

Part B. 6-Benzyloxy-2-[4-[2-[1-[(S)-2-hydroxymethyl]pyrrolidinyl]ethyl]phenyl]benzo[b]thiophen-3-yl 3-Methoxy-4-[(4-morpholinyl)methyl]phenyl Ketone.

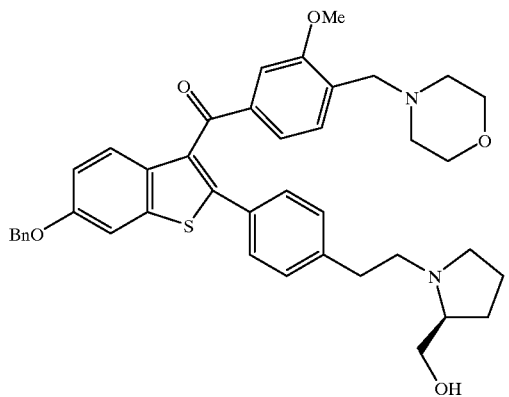

Following the procedure of Example 43, Part B, the substituted prolinol was obtained from the above alcohol and (S)-prolinol as a foam in an overall 43% yield.

IR (neat) 3389 (br), 2954, 1654, 1600 cm$^{-1}$; FDMS m/e 677 (M+1); Anal. Calcd for $C_{41}H_{44}N_2O_5S$: C, 72.75; H, 6.55; N, 4.14. Found: C, 72.78; H, 6.46; N, 4.14.

Part C. 6-Hydroxy-2-[4-[2-[1-[(S)-2-hydroxymethyl]pyrrolidinyl]ethyl]phenyl]benzo[b]thiophen-3-yl 3-Methoxy-4-[(4-morpholinyl)methyl]phenyl Ketone Dioxalate.

Following the procedure of Example 41, Part E, the salt of the hydroxy benzothiophene was obtained from the above benzyl ether as a yellowish solid in an overall 65% yield.

IR (KBr) 3377 (br), 3400–2500 (br), 1718, 1638, 1609 cm$^{-1}$; FDMS m/e 587 (M+1-2$C_2H_2O_4$). Anal. Calcd for $C_{34}H_{38}N_2O_5S \cdot 1.4C_2H_2O_4$: C, 62.01; H, 5.77; N, 3.93. Found: C, 61.99; H, 5.80; N, 4.12.

EXAMPLE 54

Preparation of 6-Hydroxy-2-[4-[2-[1-(S)-2-hydroxymethyl]pyrrolidinyl]ethyl]phenyl]-3-[3-methoxy-4-[(4-morpholinyl)methyl]benzyl]benzo[b]thiophene Dioxalate.

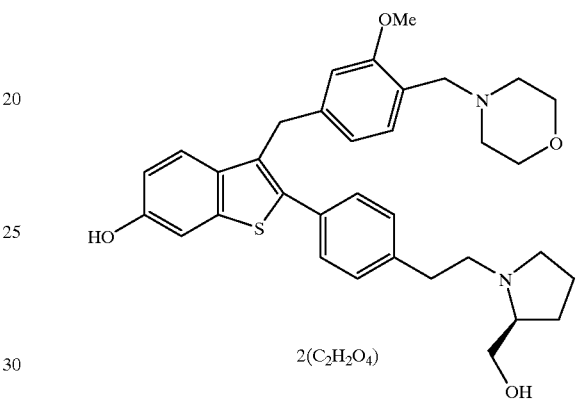

Part A. 6-Benzyloxy-2-[4-[2-[1-[(S)-2-hydroxymethyl]pyrrolidinyl]ethyl]phenyl]-3-[3-methoxy-4-[(4-morpholinyl)methyl]benzyl]benzo[b]thiophene.

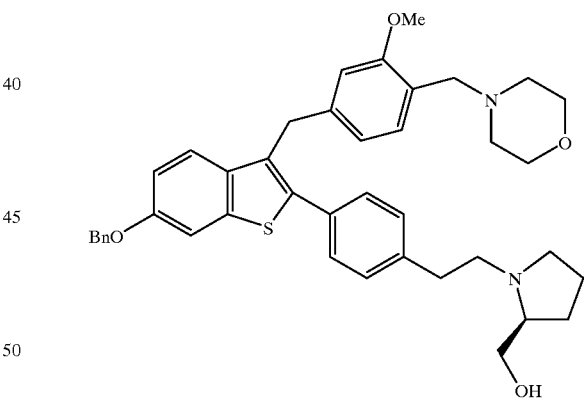

Following the procedure of Example 34, Part D, the methylene compound was obtained from the above ketone as a foam in 88% yield.

IR (neat) 3390 (br), 2955, 1600 cm$^{-1}$; FDMS m/e 663 (M+1). Anal. Calcd for $C_{41}H_{46}N_2O_4S$: C, 74.29; H, 6.99; N, 4.23. Found: C, 74.40; H, 6.97; N. 4.18.

Part B. 6-Hydroxy-2-[4-[2-[1-[(S)-2-hydroxymethyl]pyrrolidinyl]ethyl]phenyl]-3-[3-methoxy-4-[(4-morpholinyl)methyl]benzyl]benzo[b]thiophene Dioxalate.

Following the procedure of Example 41, Part E, the salt of the hydroxy benzothiophene was obtained from the above benzyl ether as a white solid in an overall 73% yield.

IR (KBr) 3376 (br), 3400–2500 (br), 1719, 1612 cm$^{-1}$; FDMS m/e 573 (M+1-2$C_2H_2O_4$). Anal. Calcd for

EXAMPLE 55
Preparation of 6-Hydroxy-2-[4-[2-[1-[(R)-2-hydroxymethyl]pyrrolidinyl]ethyl]phenyl]benzo[b]thiophen-3-yl 3-Methoxy-4-[(4-morpholinyl)methyl]phenyl Ketone Dioxalate.

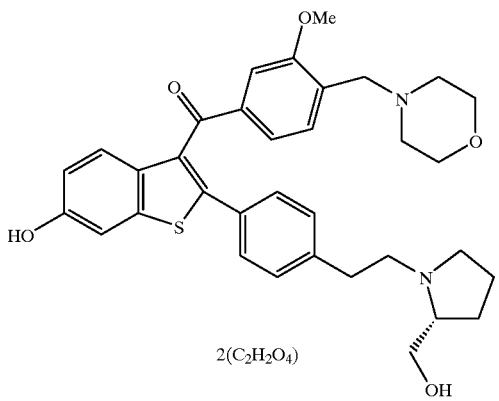

Part A. Preparation of 6-Benzyloxy-2-[4-[2-[1-[(R)-2-hydroxymethyl]pyrrolidinyl]ethyl]phenyl]benzo[b]thiophen-3-yl 3-Methoxy-4-[(4-morpholinyl)methyl]phenyl Ketone.

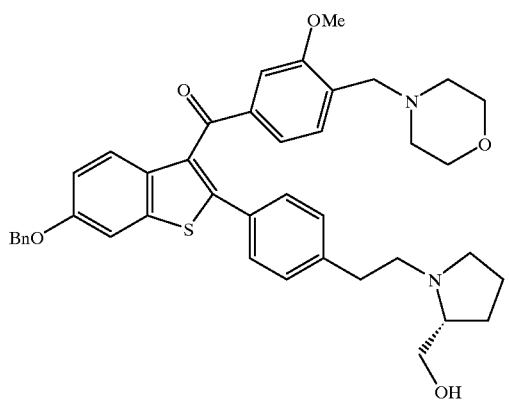

Following the procedure of Example 43, Part C, the substituted prolinol was obtained from the alcohol of Example 53, Part A and (R)-prolinol as a foam in an overall 48% yield.

IR (neat) 3378 (br), 2956, 1648, 1600 cm$^{-1}$; FDMS m/e 677 (M+1) . Anal. Calcd for $C_{41}H_{44}N_2O_5S$: C, 72.75; H, 6.55; N, 4.14. Found: C, 72.96; H, 6.32; N, 4.20.

Part B. 6-Hydroxy-2-[4-[2-[1-[(R)-2-hydroxymethyl]pyrrolidinyl]ethyl]phenyl]benzo[b]thiophen-3-yl 3-Methoxy-4-[(4-morpholinyl)methyl]phenyl Ketone Dioxalate.

Following the procedure of Example 41, Part E, the salt of the hydroxy benzothiophene was obtained from the above benzyl ether as a yellowish solid in an overall 63% yield.

IR (KBr) 3384 (br), 3400–2500 (br), 1719, 1638, 1607 cm$^{-1}$; FDMS m/e 587 (M+1-2C$_2$H$_2$O$_4$). Anal. Calcd for $C_{34}H_{38}N_2O_5S.1.4C_2H_2O_4$: C, 62.01; H, 5.77; N, 3.93. Found: C, 61.73; H, 5.90; N, 4.14.

EXAMPLE 56
Preparation of 6-Hydroxy-2-[4-[2-[1-[(R)-2-hydroxymethyl]pyrrolidinyl]ethyl]phenyl]-3-[3-methoxy-4-[(4-morpholinyl)methyl]benzyl]benzo[b]thiophene Dioxalate.

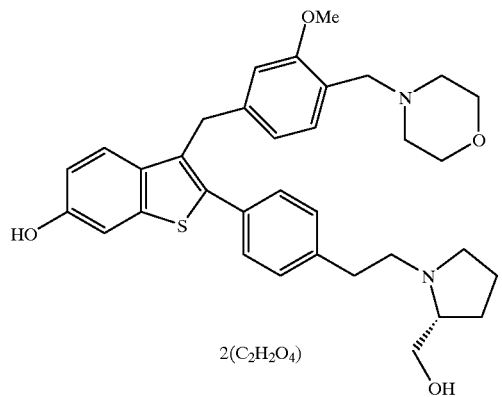

Part A. 6-Benzyloxy-2-[4-[2-[1-[(R)-2-hydroxymethyl]pyrrolidinyl]ethyl]phenyl]-3-[3-methoxy-4-[(4-morpholinyl)methyl]benzyl]benzo[b]thiophene.

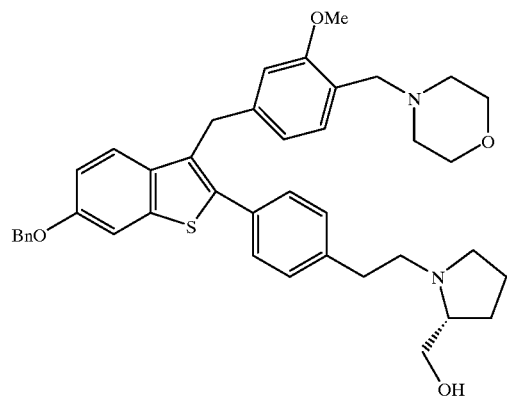

Following the procedure of Example 34, Part D, the methylene compound was obtained from the ketone of Example 55, Part A as a foam in 83% yield.

IR (neat) 3426 (br), 2955, 1600 cm$^{-1}$; FDMS m/e 663 (M+1). Anal. Calcd for $C_{41}H_{46}N_2O_4S$: C, 74.29; H, 6.99; N, 4.23. Found: C, 74.29; H, 6.98; N, 4.33.

Part B. 6-Hydroxy-2-[4-[2-1-[(R) -2-hydroxymethyl]pyrrolidinyl]ethyl]phenyl]-3-[3-methoxy-4-[(4-morpholinyl)methyl]benzyl]benzo[b]thiophene Dioxalate.

Following the procedure of Example 41, Part E, the salt of the hydroxy benzothiophene was obtained from the above benzyl ether as a white solid in an overall 77% yield.

IR (KBr) 3401 (br), 3400–2500 (br), 1718, 1612 cm$^{-1}$; FDMS m/e 573 (M+1-2C$_2$H$_2$O$_4$). Anal. Calcd for $C_{34}H_{40}N_2O_4S.1.5C_2H_2O_4$: C, 62.79; H, 6.12; N, 3.96. Found: C, 62.68; H, 5.88; N, 4.13.

EXAMPLE 57
Preparation of 3,5-Dimethoxy-4-[(1-pyrrolidinyl)methyl]phenyl 6-Hydroxy-2-[4-[2-(1-pyrrolidinyl)ethoxy]phenyl]benzo[b]thiophen-3-yl Ketone.

$C_{34}H_{40}N_2O_4S.1.2C_2H_2O_4$: C, 64.22; H, 6.28; N, 4.11. Found: C, 64.01; H, 6.10; N, 3.97.

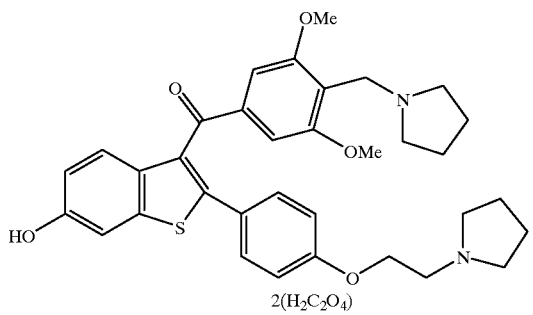

Part A. Methyl 3,5-Dimethoxy-4-[(1-pyrrolidinyl)methyl] benzoate.

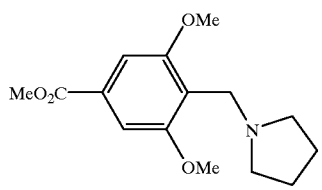

Following the procedure of Example 37, Part A, the substituted pyrrolidine was obtained from methyl 3,5-dimethoxy-4-methylbenzoate and pyrrolidine as an oil in 51% yield.

IR (KBr) 2964, 1721 cm$^{-1}$; FDMS m/e 279 (M$^+$). Anal. Calcd for $C_{15}H_{21}NO_4$: C, 64.50; H, 7.58; N, 5.01. Found: C, 64.56; H, 7.65; N, 5.04.

Part B. 3,5-Dimethoxy-4-[(1-pyrrolidinyl)methyl]benzoic Acid Hydrochloride.

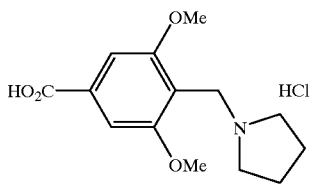

Following the procedure of Example 37, Part B, the acid was obtained from the above ester as a white solid in 100% yield.

$^1$H NMR (DMSO-d$_6$) δ 1.80–2.00 (m, 4H), 3.00 (br s, 2H), 3.32 (br s, 2H), 3.86 (s, 6H), 4.20 (s, 2H), 7.20 (s, 2H).

Part C. 6-Benzyloxy-2-(dimethylamino)benzo[b]thiophen-3-yl 3,5-Dimethoxy-4-[(1-pyrrolidinyl)methyl]phenyl Ketone.

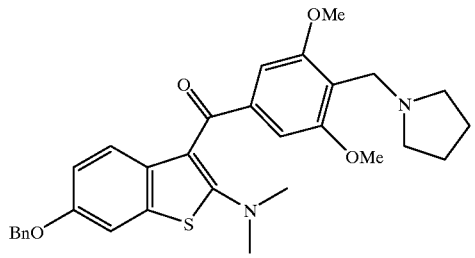

Following the procedure of Example 39, Part C, the ketone was obtained from 6-benzyloxy-2-(dimethylamino) benzo[b]thiophene and the above acid as a foam in 71% yield.

IR (neat) 2957, 1625, 1601 cm$^{-1}$; FDMS m/e 530 (M$^+$).

Part D. 6-Benzyloxy-2-[4-[2-(1-pyrrolidinyl)ethoxy] phenyl]benzo[b]thiophen-3-yl 3,5-Dimethoxy-4-[(1-pyrrolidinyl)methyl]phenyl Ketone.

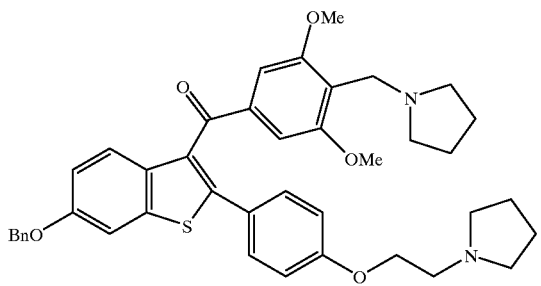

Following the procedure of Example 34, Part C, the ketone was obtained from the corresponding aryl bromide and the above ketone as a foam in 88% yield.

IR (neat) 2957, 1647, 1606 cm$^{-1}$; FDMS m/e 677 (M+1). Anal. Calcd for $C_{41}H_{44}N_2O_5S$: C, 72.75; H, 6.55; N, 4.14. Found: C, 72.55; H, 6.76; N, 4.19.

Part E. 3,5-Dimethoxy-4-[(1-pyrrolidinyl)methyl]phenyl 6-Hydroxy-2-[4-[2-(1-pyrrolidinyl)ethoxy]phenyl]benzo[b] thiophen-3-yl Ketone.

Following the procedure of Example 41, Part E, the salt of the hydroxy benzothiophene was obtained from the above benzyl ether as a yellowish solid in an overall 70% yield.

IR (KBr) 3450–2500 (br), 1720, 1643 cm$^{-1}$; FDMS m/e 587 (M+1-2$C_2H_2O_4$). Anal. Calcd for $C_{34}H_{38}N_2O_5S \cdot 2C_2H_2O_4$: C, 59.52; H, 5.52; N, 3.65. Found: C, 59.71; H, 5.78; N, 3.56.

EXAMPLE 58

Preparation of 3-[3,5-Dimethoxy-4-[(1-pyrrolidinyl)methyl] benzyl]-6-hydroxy-2-[4-[2-(1-pyrrolidinyl)ethoxy]phenyl] benzo[b]thiophene Dioxalate.

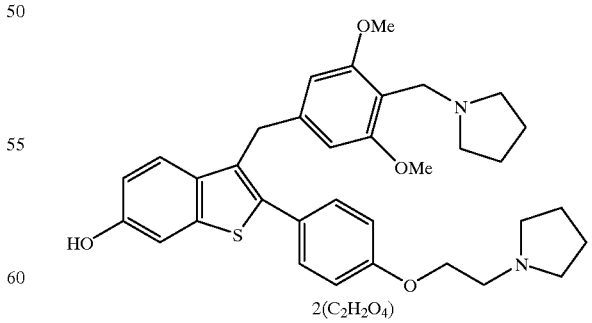

Part A. 6-Benzyloxy-3-[3,5-dimethoxy-4-[(1-pyrrolidinyl) methyl]benzyl]-2-[4-[2-(1-pyrrolidinyl)ethoxy]phenyl] benzo[b]thiophene.

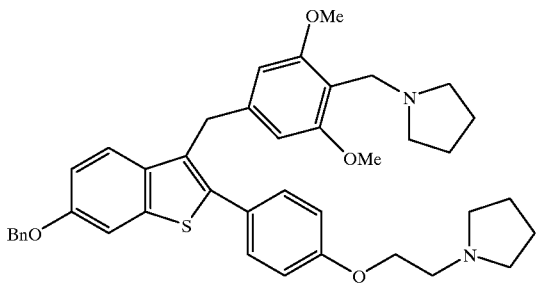

Following the procedure of Example 34, Part D, the methylene compound was obtained from the ketone of Example 57, Part D as a foam in 79% yield.

IR (neat) 2961, 1606 cm$^{-1}$; FDMS m/e 663 (M+1). Anal. Calcd for $C_{41}H_{46}N_2O_4S$: C, 74.29; H, 6.99; N, 4.23. Found: C, 74.48; H, 7.15; N, 4.37.

Part B. 3-[3,5-Dimethoxy-4-[(1-pyrrolidinyl)methyl] benzyl]-6-hydroxy-2-[4-[2-(1-pyrrolidinyl)ethoxy]phenyl] benzo[b]thiophene Dioxalate.

Following the procedure of Example 41, Part E, the salt of the hydroxy benzothiophene was obtained from the above benzyl ether as a white solid in an overall 71% yield.

IR (KBr) 3450–2500 (br), 1721, 1609 cm$^{-1}$; FDMS m/e 573 (M+1−2$C_2H_2O_4$). Anal. Calcd for $C_{34}H_{40}N_2O_4S \cdot 2C_2H_2O_4$: C, 60.63; H, 5.89; N, 3.72. Found: C, 60.92; H, 6.11; N, 3.94.

EXAMPLE 59

Preparation of (±)-6-Hydroxy-3-[4-[[trans-2-(1-pyrrolidinyl)cyclohexyl]oxy]benzyl]-2-[4-[2-(1-pyrrolidinyl)ethoxy]phenyl]benzo[b]thiophene Dioxalate.

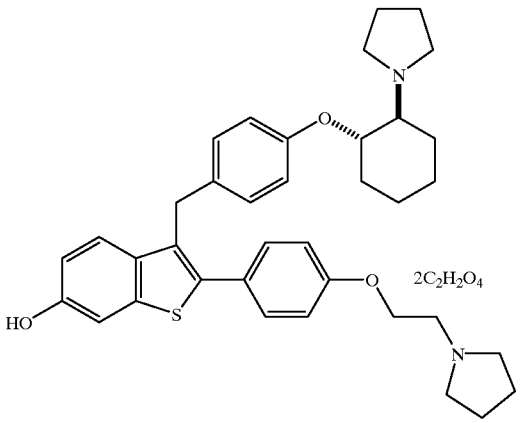

Part A. 6-Methoxy-2-[4-[2-(1-pyrrolidinyl)ethoxy]phenyl] benzo[b]thiophen-3-yl 4-Fluorophenyl Ketone.

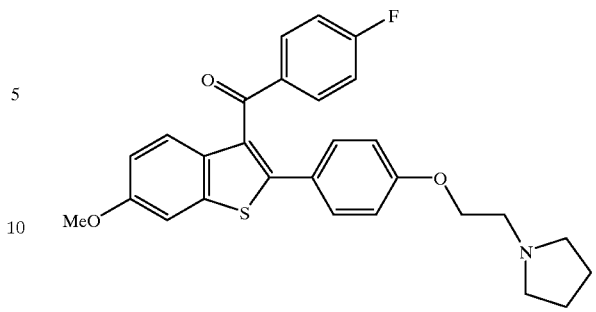

To 671.4 mg of 6-methoxy-2-[4-[2-(1-pyrrolidinyl) ethoxy]phenyl]benzo[b]thiophene (Example 1, Part B) in 10 mL of 1,2-dichloroethane was added 1.114 g of AlCl$_3$ at 0° C., followed by dropwise addition of 0.30 mL of 4-fluorobenzoyl chloride. The deep red solution was stirred at 0° C. for 1 h and then at 0 to 15° C. for 19 h. The reaction was quenched by pouring the reaction mixture into 50 mL of ice-cold 2.0 N NaOH solution. The mixture was then extracted with 3×100 mL of EtOAc which was washed with 50 mL of H$_2$O and brine. Combined organic layers were dried over MgSO$_4$, concentrated, and purified by flash chromatography with 5 v/v % (10% conc NH$_4$OH in MeOH) in CH$_2$Cl$_2$ to give 826.4 mg (92%) of the product ketone as viscous oil.

FDMS 475 (M$^+$) ; Anal Calcd for $C_{28}H_{26}FNO_3S$: C, 70.71; H, 5.51; N, 2.94. Found: C, 70.75; H, 5.58; N, 3.15.

Part B. (±)-6-Methoxy-2-E4-[2-(1-pyrrolidinyl)ethoxy] phenyl]benzo[b]thiophen-3-yl 4-[[trans-2-(1-Pyrrolidinyl) cyclohexyl]oxy]phenyl Ketone.

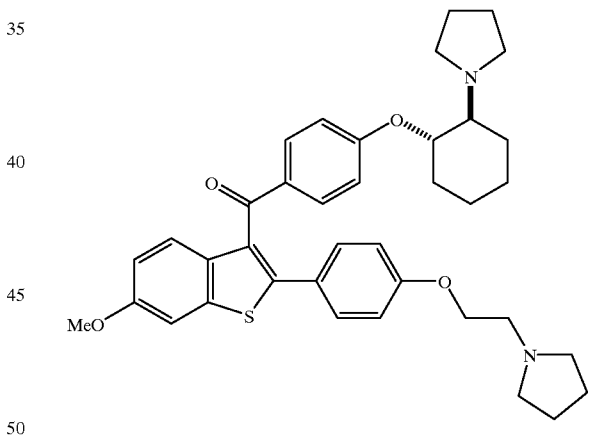

To a suspension of ca. 60 mg of NaH (60% oil dispersion) in 2.0 mL of freshly distilled THF was added 330.9 mg of (±)trans-2-(1-pyrrolidinyl)cyclohexanol in 2.0 mL of THF at room temperature. The mixture was heated at reflux for 45 min, cooled down to room temperature, and then to this was added 0.90 mL of 1.086 M of the fluoride (Part A). The mixture was heated at reflux for 24 h, cooled down, and then the reaction was quenched with 20 mL of H$_2$O. The mixture was extracted with 3×50 mL of EtOAc which was washed with 25 mL of brine. The combined extracts were dried over MgSO$_4$, concentrated, and purified by flash chromatography with 40:5:55 THF-Et$_3$N-hexanes to afford 349.9 mg (57%) of the product along with 49.0 mg (10%) of recovered fluoride. mp 39–47° C.; FDMS 624.9 (M$^+$) , 500.8 (base); Anal. Calcd for $C_{38}H_{44}N_2O_4S$: C, 73.05; H, 7.10; N, 4.48. Found: C, 73.01; H, 7.25; N, 4.21.

Part C. (±)-6-Hydroxy-3-[4-[[trans-2-(1-pyrrolidinyl) cyclohexyl]oxy]benzyl]-2-[4-[2-(1-pyrrolidinyl)ethoxy] phenyl]benzo[b]thiophene Dioxalate.

The title compound was prepared in 36% yield for four steps from the ketone (Part B) by essentially following the procedures detailed in Example 21, Parts A–C. mp>105° C. (decomp?); FDMS 597.1 (M+1); Anal. Calcd for $C_{37}H_{44}N_2O_3S \cdot 2.5C_2H_2O_4$: C, 61.38; H, 6.01; N, 3.41. Found: C, 61.63; H, 5.77; N, 3.01.

EXAMPLE 60

Preparation of (±)-6-Hydroxy-3-[4-[[trans-2-(hexahydro-1H-azepin-1-yl)cyclohexyl]oxy3benzyl]-2-[4-[2-(1-pyrrolidinyl)ethoxy]phenyl]benzo[b]thiophene Dioxalate.

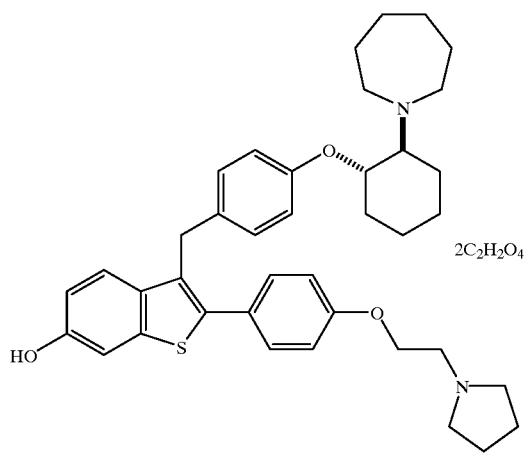

Part A. (±)-6-Methoxy-2-[4-[2-(1-pyrrolidinyl)ethoxy] phenyl]benzo[b]thiophen-3-yl 4-[[trans-2-(Hexahydro-1H-azepin-1-yl)cyclohexyl]oxy]phenyl Ketone.

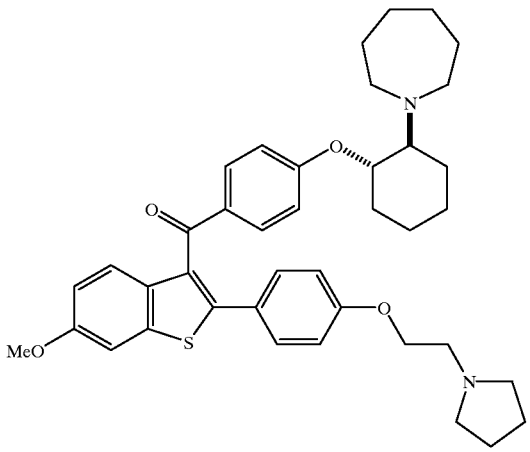

The title compound was prepared in 54% yield from 6-methoxy-2-[4-[2-(1-pyrrolidinyl)ethoxy]phenyl]benzo[b] thiophen-3-yl] 4-fluorophenyl ketone and (±)-trans-2-(hexahydro-1H-azepin-1-yl)cyclohexanol by essentially following the procedures detailed in Example 59, Part B.

mp 43.5–51.5° C.; FDMS 653.1 (M+1); Anal. Calcd for $C_{40}H_{48}N_2O_4S$: C, 73.59; H, 7.41; N, 4.29. Found: C, 73.61; H, 7.61; N, 4.07.

Part B. (±)-6-Hydroxy-3-[4-[[trans-2-(hexahydro-1H-azepin-1-yl)cyclohexyl]oxy]benzyl]-2-[4-[2-(1-pyrrolidinyl)ethoxy]phenyl]benzo[b]thiophene Dioxalate.

The title compound was prepared in 29% yield for four steps from the ketone (Part A) by essentially following the procedures detailed in Example 21, Parts A–C.

mp>114° C. (decomp?); FDMS 625.1 (M+1); Anal. Calcd for $C_{39}H_{48}N_2O_3S \cdot 2.5C_2H_2O_4$: C, 62.18; H, 6.28; N, 3.30. Found: C, 62.02; H, 6.28; N, 3.12.

EXAMPLE 61

Preparation of (±)-6-Hydroxy-3-[4-[[trans-2-(imidazol-1-yl) cyclohexyl]oxy]benzyl]-2-[4-[2-(1-pyrrolidinyl)ethoxy] phenyl]benzo[b]thiophene Dioxalate.

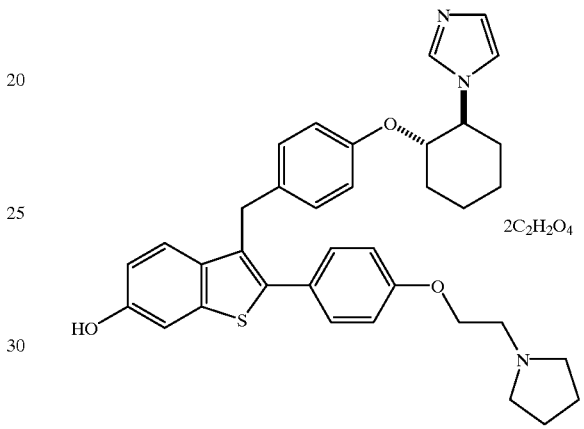

Part A. (±)-trans-2-(Imidazol-1-yl)cyclohexanol.

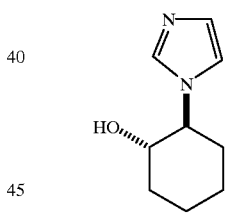

A mixture of 20.18 g of imidazole, 81.95 g of $K_2CO_3$, and 20.0 mL of cyclohexene oxide in ca. 200 mL of $H_2O$ was stirred at room temperature for 19 h, at 100° C. (bath temp.) for 7 h, and then at room temperature overnight. The mixture was extracted with 3×500 mL of EtOAc and 500 mL of $CH_2Cl_2$. The organic layers were washed with 2×300 mL of $H_2O$ and 300 mL of brine. Combined organic layers were dried over $MgSO_4$ and concentrated. The crude product was crystallized from EtOAc to yield 8.57 g (26%) of the crystalline solid.

mp 127–131° C.; FDMS 167 (M+1); Anal Calcd for $C_9H_{14}N_2O \cdot 0.22H2O$: C, 63.52; H. 8.55; N, 16.46. Found: C, 63.63; H, 8.30; N, 16.11.

Part B. (±)-6-Methoxy-2-[4-[2-(1-pyrrolidinyl)ethoxy] phenyl]benzo[b]thiophen-3-yl 4-[[trans-2-(Imidazol-1-yl) cyclohexyl]oxy]phenyl Ketone.

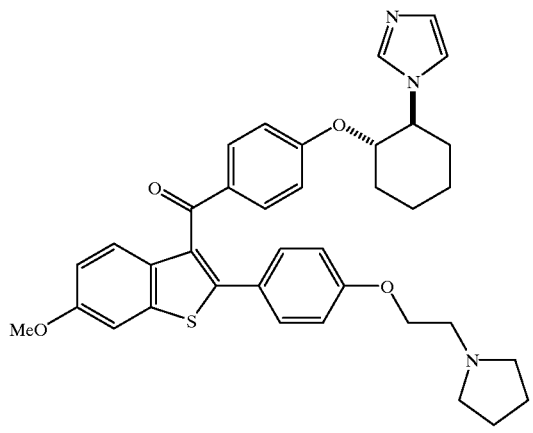

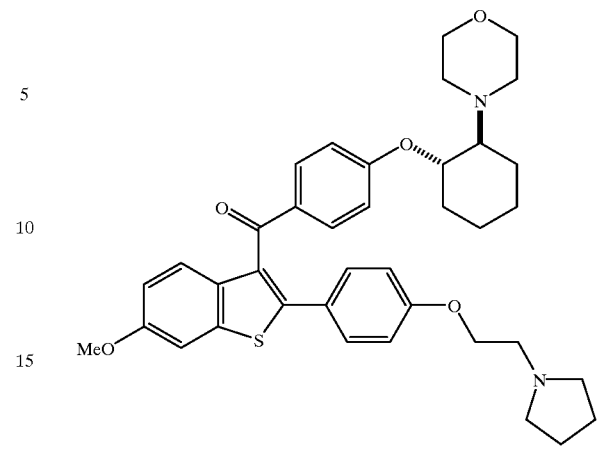

The title compound was prepared in 71% yield from 6-methoxy-2-[4-[2-(1-pyrrolidinyl)ethoxy]phenyl]benzo[b]thiophen-3-yl] 4-fluorophenyl ketone and (±)-trans-2-(imidazol-1-yl)cyclohexanol (Part A) by essentially following the procedures detailed in Example 59, Part B.

mp 68–78° C.; FDMS 622.4 (M+1); Anal. Calcd for $C_{37}H_{39}N_3O_4S \cdot 0.35NH_4OH$: C, 70.09; H, 6.48; N, 7.40. Found: C, 69.75; H, 6.14; N, 7.03.

Part C. (±)-6-Hydroxy-3-[4-[[trans-2-(imidazol-1-yl)cyclohexyl]oxy]benzyl]-2-[4-[2-(1-pyrrolidinyl)ethoxy]phenyl]benzo[b]thiophene Dioxalate.

The title compound was prepared in 81% yield for four steps from the ketone (Part B) by essentially following the procedures detailed in Example 21, Parts A–C.

mp>103° C. (decomp?); FDMS 594 (M+1); Anal. Calcd for $C_{36}H_{39}N_3O_3S \cdot 2.1C_2H_2O_4 \cdot 1.1C_4H_8O_2$: C, 60.89; H, 5.96; N, 4.78. Found: C, 60.49; H, 5.59; N, 4.95.

EXAMPLE 62

Preparation of (±)-6-Hydroxy-3-[4-[[trans-2-(4-morpholinyl)cyclohexyl]oxy]benzyl]-2-[4-[2-(1-pyrrolidinyl)ethoxy]phenyl]benzo[b]thiophene Dioxalate.

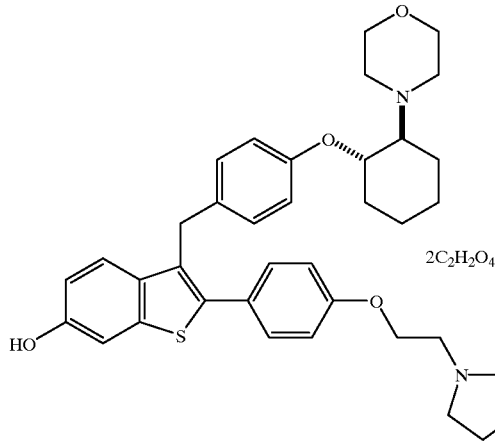

Part A. (±)-6-Methoxy-2-[4-[2-(1-pyrrolidinyl)ethoxy]phenyl]benzo[b]thiophen-3-yl 4-[[trans-2-(4-Morpholinyl)cyclohexyl]oxy]phenyl Ketone.

The title compound was prepared in 80% yield from 6-methoxy-2-[4-[2-(1-pyrrolidinyl)ethoxy]phenyl]benzo[b]thiophen-3-yl] 4-fluorophenyl ketone and (±)-trans-2-(4-morpholinyl)cyclohexanol by essentially following the procedures detailed in Example 59, Part B.

mp 50–57° C.; FDMS 640.6 (M$^+$) ; Anal. Calcd for $C_{38}H_{44}N_2O_5S \cdot 0.14CH_2Cl_2$: C, 70.18; H, 6.84; N, 4.29. Found: C, 70.20; H, 6.82; N, 4.35.

Part B. (±)-6-Hydroxy-3-[4-[[trans-2-(4-morpholinyl)cyclohexyl]oxy]benzyl]-2-[4-[2-(1-pyrrolidinyl)ethoxy]phenyl]benzo[b]thiophene Dioxalate.

The title compound was prepared in 72% yield for four steps from the ketone (Part A) by essentially following the procedures detailed in Example 21, Part A–C.

mp>110° C. (decomp?); FDMS 613.4 (M+1); Anal Calcd for $C_{37}H_{44}N_2O_4S \cdot 2.3C_2H_2O_4 \cdot 1.1C_4H_8O_2$: C, 60.26; H, 6.31; N, 3.06. Found: C, 59.88; H, 5.94; N, 3.00.

EXAMPLE 63

Preparation of (±)-6-Hydroxy-2-[4-[2-(1-pyrrolidinyl)ethoxy]phenyl]benzo[b]thiophen-3-yl] 3-Methoxy-4-[[trans-2-(1-pyrrolidinyl)cyclohexyl]oxy]phenyl Ketone Dioxalate.

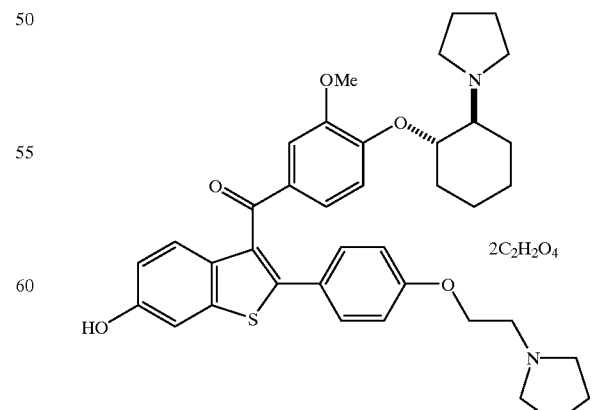

Part A. 3-Methoxy-4-[[trans-2-(1-pyrrolidinyl)cyclohexyl]oxy]benzoic Acid.

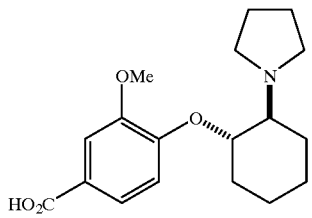

The title compound was prepared in 96% for two steps from methyl vanillate similarly as described in Example 20, Parts B and C.

$^1$H NMR (CDCl$_3$) d 7.68 (m, 2H), 7.17 (d, J=8.8 Hz, 1H), 4.80 (m, 1H), 3.88 (s, 3H), 3.63 (m, 2H), 3.35 (m, 2H), 3.11 (m, 1H), 2.35–1.25 (m, 12H).

Part B. (±)-6-Benzyloxy-2-[4-[2-(1-pyrrolidinyl)ethoxy]phenyl]benzo[b]thiophen-3-yl 3-Methoxy-4-[[trans-2-(1-pyrrolidinyl)cyclohexyl]oxy]phenyl Ketone.

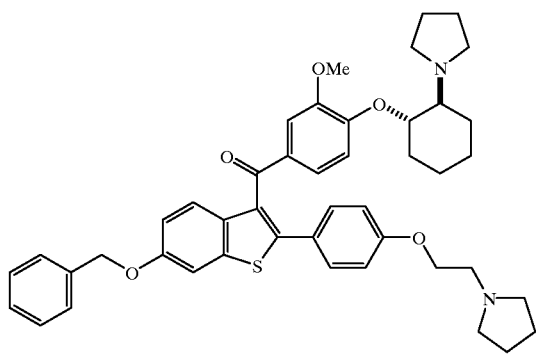

The title compound was prepared in 43% yield for two steps from 6-benzyloxy-2-(dimethylamino)benzo[b]thiophene by essentially following the procedures outlined in Example 41, Part C (but using thionyl chloride to form the acid chloride) and Example 81, Part E.

mp 50–54° C.; FDMS 731.8 (M+1); Anal. Calcd for C$_{45}$H$_{50}$N$_2$O$_5$S: C, 73.94; H, 6.90; N, 3.83. Found: C, 73.73; H, 6.96; N, 4.00.

Part C. (±)-6-Hydroxy-2-[4-[2-(1-pyrrolidinyl)ethoxy]phenyl]benzo[b]thiophen-3-yl 3-Methoxy-4-[[trans-2-(1-pyrrolidinyl)cyclohexyl]oxy]phenyl Ketone Dioxalate.

The title compound was prepared in 12% yield for two steps from (±)-6-benzyloxy-2-[4-[2-(1-pyrrolidinyl)ethoxy]phenyl]benzo[b]thiophen-3-yl [3-methoxy-4-[[trans-2-(1-pyrrolidinyl)cyclohexyl]oxy]phenyl] ketone (Part B) by essentially following the procedures described for debenzylation and oxalate salt formation in Example 81, Part I.

FDMS 641.3 (M+1); Anal. Calcd for C$_{38}$H$_{44}$N$_2$O$_5$S.2C$_2$H$_2$O$_4$: C, 61.45; H, 5.89; N, 3.41. Found: C, 61.27; H, 5.77; N, 3.40.

EXAMPLE 64

Preparation of (±)-6-Hydroxy-3-[3-methoxy-4-[[trans-2-(1-pyrrolidinyl)cyclohexyl]oxy]benzyl]-2-[4-[2-(1-pyrrolidinyl)ethoxy]phenyl]benzo[b]thiophene Dioxalate.

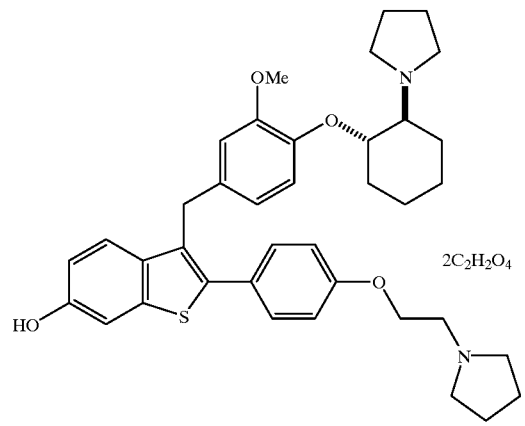

The title compound was prepared in 59% yield for four steps from (±)-6-benzyloxy-2-[4-[2-(1-pyrrolidinyl)ethoxy]phenyl]benzo[b]thiophen-3-yl 3-methoxy-4-[[trans-2-(1-pyrrolidinyl)cyclohexyl]oxy]phenyl ketone (Example 63, Part B) by essentially following the procedures outlined in Example 85, Part B.

FDMS 627.3 (M+1); Anal. Calcd for C$_{38}$H$_{46}$N$_2$O$_4$S.2C$_2$H$_2$O$_4$: C, 62.52; H, 6.25; N, 3.47. Found: C, 62.73; H, 6.18; N, 3.43.

EXAMPLE 65

Preparation of (±)-6-Hydroxy-3-[3-hydroxy-4-[[trans-2-(1-pyrrolidinyl)cyclohexyl]oxy]benzyl]-2-[4-[2-(1-pyrrolidinyl)ethoxy]phenyl]benzo[b]thiophene.

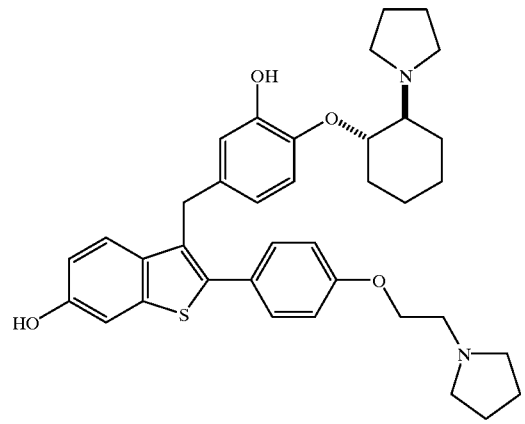

The title compound was prepared in 29% yield from (±)-6-hydroxy-3-[3-methoxy-4-[[trans-2-(1-pyrrolidinyl)cyclohexyl]oxy]benzyl]-2-[4-[2-(1-pyrrolidinyl)ethoxy]phenyl]benzo[b]thiophene (free base of Example 64) by essentially following the procedure outlined in Example 21, Part B.

FDMS 613.3 (M+1).

EXAMPLE 66

Preparation of (±)-6-Hydroxy-2-[4-[2-(1-pyrrolidinyl)ethoxy]phenyl]benzo[b]thiophen-3-yl 3-Fluoro-4-[[trans-2-(1-pyrrolidinyl)cyclohexyl]oxy]phenyl Ketone Dioxalate.

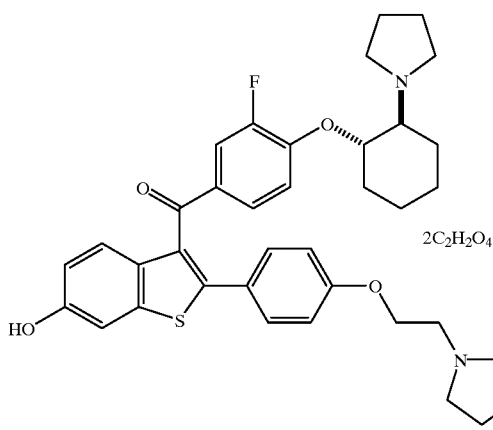

Part A. 6-Benzyloxy-2-(dimethylamino)benzo[b]thiophen-3-yl 3,4-Difluorophenyl Ketone.

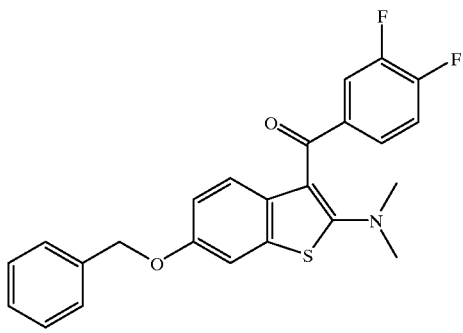

The title compound (oil) was prepared in 95% yield from 6-benzyloxy-2-(dimethylamino)benzo[b]thiophene and 3,4-difluorobenzoyl chloride by essentially following the procedure outlined in Example 81, Part C.

FDMS 423 (M+) ; Anal. Calcd for $C_{24}H_{19}F_2NO_2S$: C, 68.07; H, 4.52; N, 3.31. Found: C, 68.36; H, 4.75; N, 3.37.
Part B. (±)-6-Benzyloxy-2-[4-[2-(1-pyrrolidinyl)ethoxy]phenyl]benzo[b]thiophen-3-yl 3-Fluoro-4-[[trans-2-(1-pyrrolidinyl)cyclohexyl]oxy3phenyl Ketone.

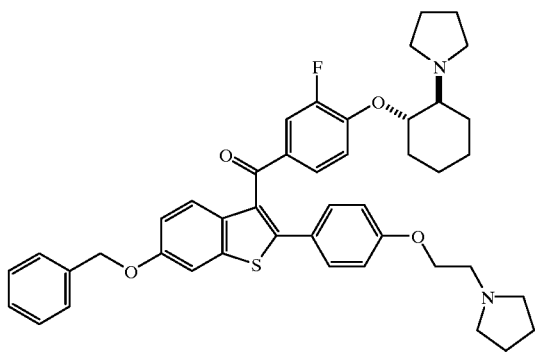

The title compound was prepared in 67% yield for two steps from 6-benzyloxy-2-(dimethylamino)benzo[b]thiophen-3-yl 3,4-difluorophenyl ketone (Part A) similarly as described in Example 59, Part B and Example 81, Part E.

mp 47–51° C.; FDMS 719 (M+1); Anal. Calcd for $C_{44}H_{47}FN_2O_4S$: C, 73.51; H, 6.59; N, 3.90. Found: C, 73.28; H, 6.71; N, 4.01.

Part C. (±)-6-Hydroxy-2-[4-[2-(1-pyrrolidinyl)ethoxy]phenyl]benzo[b]thiophen-3-yl] 3-Fluoro-4-[[trans-2-(1-pyrrolidinyl)cyclohexyl]oxy]phenyl Ketone Dioxalate.

The title compound was obtained in 81% for two steps from the ketone (Part B) via debenzylation and oxalate salt formation as described in Example 81, Part I.

FDMS 629.3 (M+1); Anal. Calcd for $C_{37}H_{41}FN_2O_4S.2C_2H_2O_4$: C, 60.88; H, 5.61; N, 3.46. Found: C, 60.97; H, 5.70; N, 3.59.

EXAMPLE 67

Preparation of (±)-6-Hydroxy-3-[3-fluoro-4-[[trans-2-(1-pyrrolidinyl)cyclohexyl]oxy]benzyl]-2-[4-[2-(1-pyrrolidinyl)ethoxy]phenyl]benzo[b]thiophene Dioxalate.

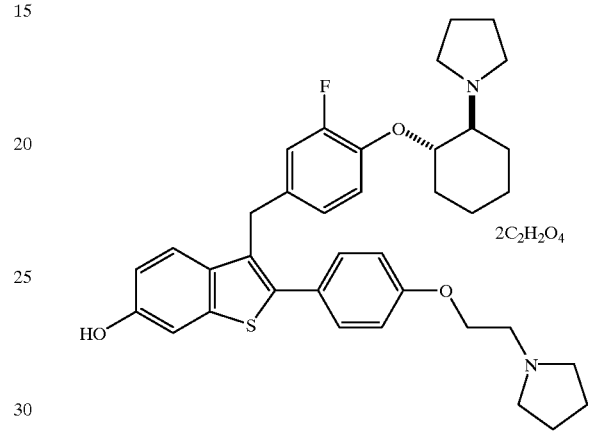

The title compound was prepared in 66% yield for four steps from (±)-6-benzyloxy-2-[4-[2-(1-pyrrolidinyl)ethoxy]phenyl]benzo[b]thiophen-3-yl 3-fluoro-4-[[trans-2-(1-pyrrolidinyl)cyclohexyl]oxy]phenyl ketone (Example 66, Part B) using similar procedures to those of Example 85, Part B.

mp>111° C. (decomp.?); FDMS 614.8 (M+) ; Anal. Calcd for $C_{37}H_{43}FN_2O_3S.2C_2H_2O_4$: C, 61.95; H, 5.96; N, 3.52. Found: C, 61.81; H, 6.16; N, 3.38.

EXAMPLE 68

Preparation of (±)-6-Hydroxy-2-[4-[2-(1-pyrrolidinyl)ethoxy]phenyl]benzo[b]thiophen-3-yl 3-Fluoro-4-[[trans-2-(1-piperidyl)cyclohexyl]oxy]phenyl Ketone Dioxalate.

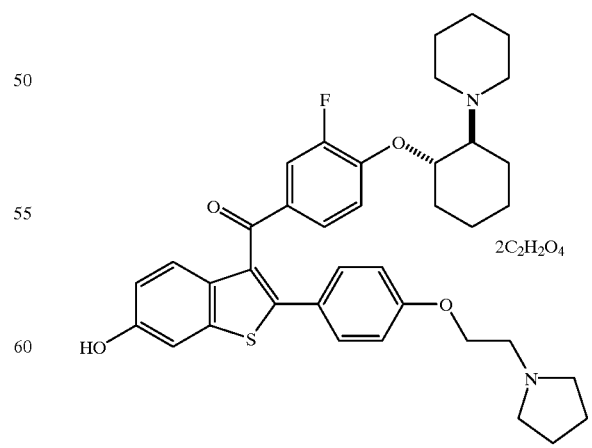

The title compound was prepared in 13% for four steps from 6-benzyloxy-2-(dimethylamino)benzo[b]thiophen-3- yl 3,4-difluorophenyl ketone (Example 66, Part A) using similar methods to those of Example 66, Parts B and C.

FDMS 643.4 (M+1); Anal. Calcd for $C_{38}H_{43}FN_2O_4S \cdot 2C_2H_2O_4$: C, 61.30; H, 5.76; N, 3.41. Found: C, 61.57; H, 5.74; N, 3.59.

EXAMPLE 69

Preparation of (±)-6-Hydroxy-3-[3-fluoro-4-[[trans-2-(1-piperidyl)cyclohexyl]oxy]benzyl]-2-[4-[2-(1-pyrrolidinyl)ethoxy]phenyl]benzo[b]thiophene Dioxalate.

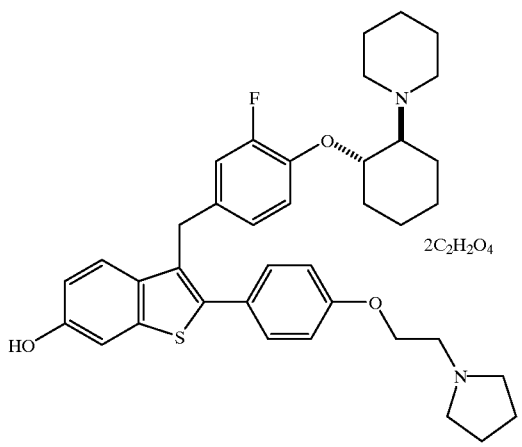

The title compound was prepared in 62% for three steps from (±)-6-benzyloxy-2-[4-[2-(1-pyrrolidinyl)ethoxy]phenyl]benzo[b]thiophen-3-yl 3-fluoro-4-[[trans-2-(1-piperidyl)cyclohexyl]oxy]phenyl ketone (an intermediate in the preparation of Example 68) using procedures similar to those of Example 85, Part B.

FDMS 629.4 (M+1); Anal. Calcd for $C_{38}H_{45}FN_2O_3S \cdot 2C_2H_2O_4 \cdot 1.1C_4H_8O$: C, 62.74; H, 6.56; N, 3.15. Found: C, 63.14; H, 6.27; N, 2.92.

EXAMPLE 70

Preparation of (±)-6-Hydroxy-3-[4-[[trans-2-(1-pyrrolidinyl)cyclohexyl]oxy]-3-(trifluoromethyl)benzyl]-2-[4-[2-(1-pyrrolidinyl)ethoxy]phenyl]benzo[b]thiophene Dioxalate.

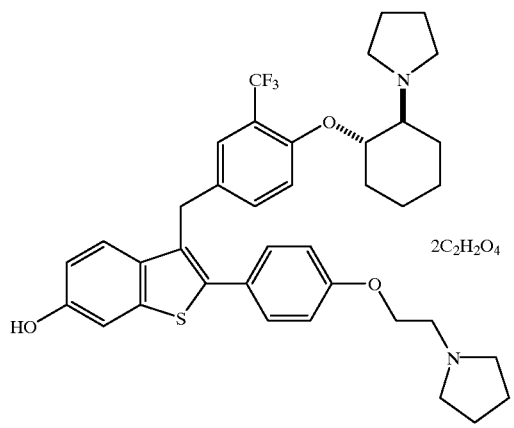

Part A. 6-Benzyloxy-2-(dimethylamino)benzo[b]thiophen-3-yl 4-Fluoro-3-(trifluoromethyl)phenyl Ketone.

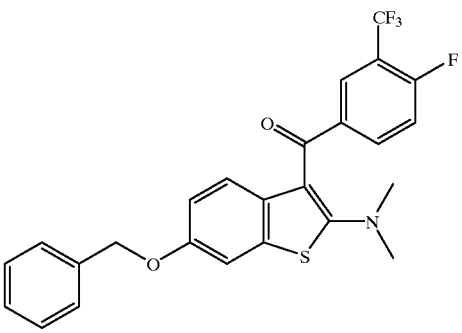

The title compound was prepared in 93% yield from 6-benzyloxy-2-(dimethylamino)benzo[b]thiophene and 4-fluoro-3-(trifluoromethyl)benzoyl chloride by essentially following the procedure outlined in Example 81, Part C, and Example 85, Part B.

mp 164–167° C.; FDMS 473 (M$^+$) ; Anal. Calcd for $C_{25}H_{19}F_4NO_2S$: C, 63.42; H, 4.04; N, 2.96. Found: C, 63.65; H, 4.17; N, 2.81.

Part B. (±)-6-Hydroxy-3-[4-[[trans-2-(1-pyrrolidinyl)-cyclohexyl]oxy]-3-(trifluoromethyl)benzyl]-2-[4-[2-(1-pyrrolidinyl)ethoxy]phenyl]benzo[b]thiophene Dioxalate.

The title compound was prepared in 41% for six steps from 6-benzyloxy-2-(dimethylamino)benzo[b]thiophen-3-yl 4-fluoro-3-(trifluoromethyl)phenyl ketone (Part A) using similar procedures to those of Example 66, Parts B and C.

mp>124° C. (decomp?); FDMS 665.2 (M+1); Anal. Calcd for $C_{38}H_{43}F_3N_2O_3S \cdot 2C_2H_2O_4$: C, 59.71; H, 5.61; N, 3.32. Found: C, 59.48; H, 5.55; N, 3.44.

EXAMPLE 71

Preparation of (±)-6-Hydroxy-5-methoxy-3-[4-[[trans-2-(1-pyrrolidinyl)cyclohexyl]oxy]benzyl]-2-[4-[2-(1-pyrrolidinyl)ethoxy]phenyl]benzo[b]thiophene Dioxalate.

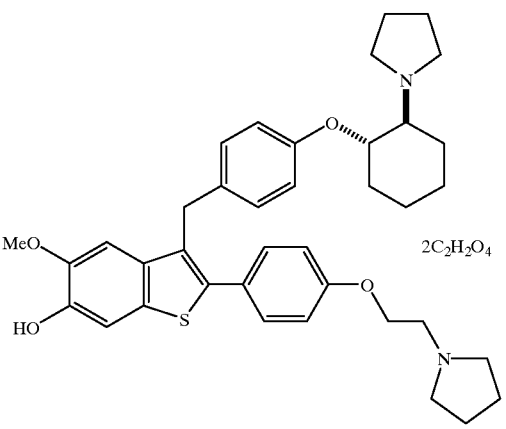

Part A. 6-Benzyloxy-2-dimethylamino-5-methoxybenzo[b]thiophene.

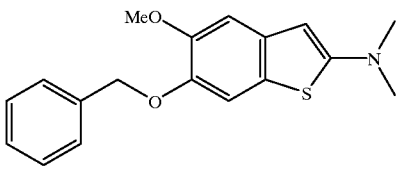

The title compound was prepared in 17% for two steps from 4-benxyloxy-3-methoxybenzaldehyde and N,N-dimethylthioformamide using similar procedures to those of Example 81, Parts A and B.

mp 140–142° C.; FDMS 313 (M+) ; Anal. Calcd for $C_{18}H_{19}NO_2S$: C, 68.98; H, 6.11; N, 4.47. Found: C, 68.81; H, 6.32; N, 4.17.

Part B. (±)-6-Hydroxy-5-methoxy-3-[4-[[trans-2-(1-pyrrolidinyl)cyclohexyl]oxy]benzyl]-2-[4-[2-(1-pyrrolidinyl)ethoxy]phenyl]benzo[b]thiophene Dioxalate.

The title compound was prepared in 37% for seven steps from 6-benzyloxy-2-dimethylamino-5-methoxybenzo[b]thiophene (Part A) using procedures similar to those of Example 70, Parts A and B.

mp>100° C. (decomp?); FDMS 627 (M+1); Anal. Calcd for $C_{38}H_{46}N_2O_4S.2.4C_2H_2O_4.0.6C_4H_8O_2$: C, 60.49; H, 6.31; N, 3.07. Found: C, 60.11; H, 6.11; N, 3.43.

EXAMPLE 72

Preparation of (±)-5-Methoxy-2-[4-[2-(1-pyrrolidinyl)ethoxy]phenyl]benzo[b]thiophen-3-yl 4-[[trans-2-(1-Piperidyl)cyclohexyl]oxy]phenyl Ketone Dioxalate.

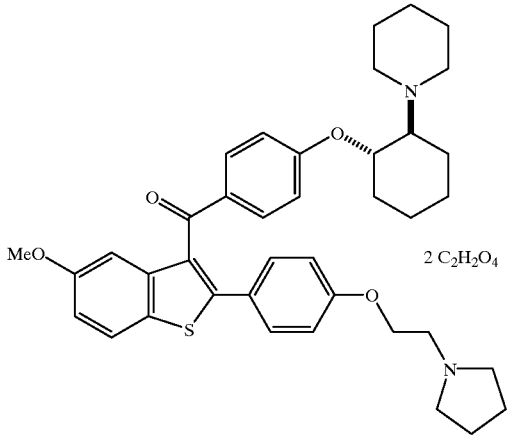

Part A. 5-Methoxybenzo[b]thiophene.

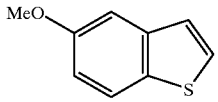

5-Bromobenzo[b]thiophene was prepared in quantitative yield for two steps from 4-bromobenzenethiol and bromoacetaldehyde dimethyl acetal as described in the preparation of 4- and 6-methoxybenzo[b]thiophene (see Example 92, Part A): mp 40–43.5° C; FDMS 212.1 (M-1); Anal. Calcd for $C_8H_5BrS.0.10C_7H_8OS$: C, 46.01; H, 2.57; S, 15.53. Found: C, 46.19; H, 2.49; S, 15.79.

To a solution of 1.8 g of 5-bromobenzo[b]thiophene in 2 mL of anhydrous DMF and 1 mL of MeOH was added 686 mg of NaOMe. The mixture was heated to 110° C. (bath temp), and 121 mg of CuBr was added. The brown suspension was heated at 110° C. for ~2 h and at ~145° C. for 30 min. The reaction was quenched with ca. 50 mL of $H_2O$ and the mixture was extracted with 100 mL of $Et_2O$ (2×), EtOAc (1×), and $CH_2Cl_2$ (1×). The organic layers were washed with 50 mL of brine, combined, dried over $MgSO_4$, concentrated, and flash chromatographed with 3% $Et_2O$-hexanes to afford 894.5 mg (64%) of the title compound along with 168.8 mg (9.4%) of 5-bromobenzo[b]thiophene.

mp 39–41.5° C.; FDMS 164.2 (M+) ; Anal. Calcd for $C_9H_8OS.0.11H_2O$: C, 65.04; H, 4.98; S, 19.29. Found: C, 65.07; H, 4.95; S, 18.96.

Part B. 5-Methoxybenzo[b]thiophene-2-boronic Acid.

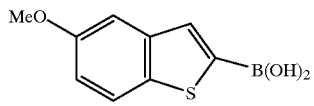

The title compound was prepared in 50% yield by essentially following the procedures in Example 1, Part A from 5-methoxybenzo[b]thiophene (Part A).

mp 226–228° C.; FDMS 569; Anal. Calcd for $C_9H_9BO_3S$: C, 51.96; H, 4.36. Found: C, 51.85; H, 4.15.

Part C. 5-Methoxy-2-[4-[2-(1-pyrrolidinyl)ethoxy]phenyl]benzo[b]thiophene.

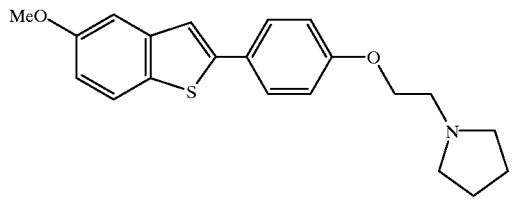

The title compound was prepared in 47% yield by essentially following the procedures in Example 1, Part B, from 5-methoxybenzo[b]thiophene-2-boronic acid (Part B) and 1-(2-(4-bromophenoxy)ethyl)pyrrolidine.

mp 123–126° C.; FDMS 353 (M+) ; Anal. Calcd for $C_{21}H_{23}NO_2S$: C, 71.36; H, 6.56; N, 3.96. Found: C, 71.07; H, 6.44; N, 4.01.

Part D. 4-Fluorophenyl 5-Methoxy-2-[4-[2-(1-pyrrolidinyl)ethoxy]phenyl]benzo[b]thiophen-3-yl Ketone.

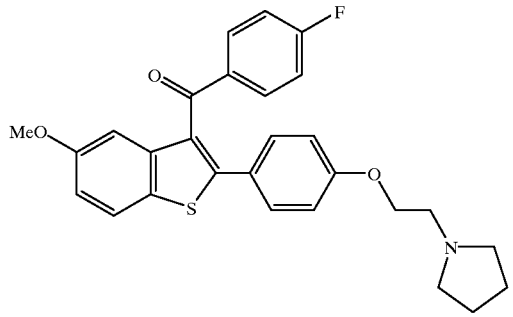

The title compound was prepared by essentially following the procedure detailed in Example 1, Part C, from 5-methoxy-2-[4-[2-(1-pyrrolidinyl)ethoxy]phenyl]benzo[b]thiophene (Part C) and 4-fluorobenzoyl chloride. The crude product was purified by flash chromatography (silica gel, 55:42:3 THF-hexanes-$Et_3N$) to afford 2.11 g (4.44 mmol, 71%) of a yellow semi-solid.

FDMS 475 (M+); Anal. Calcd for $C_{28}H_{26}FNO_3S$: C, 70.72; H, 5.51; N, 2.95. Found: C, 70.50; H, 5.49; N, 2.83.

Part E. (±)-5-Methoxy-2-[4-[2-(1-pyrrolidinyl)ethoxy]phenyl]benzo[b]thiophen-3-yl 4-[[trans-2-(1-Piperidyl)cyclohexyl]oxy]phenyl Ketone.

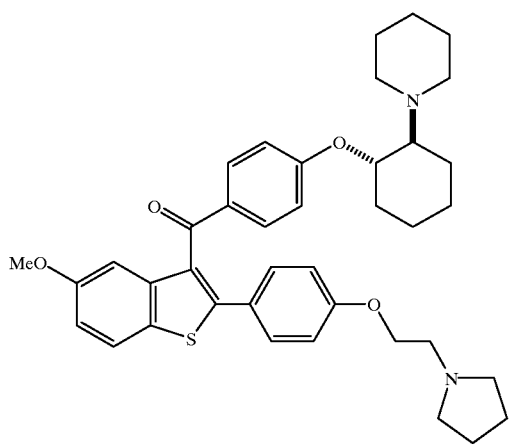

To a slurry of NaH (530 mg, 13.2 mmol, 60% dispersion in mineral oil) in 28 mL of anhydrous DMF was added dropwise 1.61 g (8.77 mmol) of (±)-trans-2-(1-piperidyl)cyclohexanol (Example 20, Part A) in 7 mL of DMF at room temperature over a period of 20 min. A heat gun was applied to the reaction mixture to facilitate alkoxide formation. Slow evolution of hydrogen gas was observed. The slurry was stirred at room temperature for 1 h, and to this was added the 4-fluorophenyl ketone (2.09 g, 4.39 mmol) (Part D) in 8 ml of DMF via a cannula over 10 min period at room temperature. The slurry immediately turned reddish orange. The reaction was carried to completion by stirring overnight (18 h). The reaction was then quenched at 0° C. with slow addition of 75 mL of $H_2O$. The mixture was taken up in EtOAc and partitioned. The aqueous layer was extracted with EtOAc (3×300 mL). The combined organic layers were dried over $MgSO_4$ after washing with 300 mL of brine and then concentrated under reduced pressure. The residue was purified by PrepLC (40:57:3 THF-hexanes-$Et_3N$) to afford 2.24 g (3.51 mmol, 80%) of a yellowish white foam.

mp 63–66° C.; FDMS 639 (M+); Anal. Calcd for $C_{39}H_{46}N_2O_4S$: C, 73.32; H, 7.26; N, 4.38. Found: C, 73.03; H, 7.38; N, 4.20.

Part F. (±)-5-Methoxy-2-[4-[2-(1-pyrrolidinyl)ethoxy]phenyl]benzo[b]thiophen-3-yl 4-[[trans-2-(1-Piperidyl)cyclohexyl]oxy]phenyl Ketone Oxalate.

The title compound was prepared in 97% from the ketone (Part E) by essentially following the procedure outlined in Example 21, Part C.

mp 144–147° C.; FDMS 639.3 (M+); Anal. Calcd for $C_{39}H_{48}N_2O_3S \cdot 2.64C_2H_2O_4$: C, 60.67; H, 5.90; N, 3.20. Found: C, 60.66; H, 5.89; N, 3.24.

EXAMPLE 73

Preparation of (±)-5-Methoxy-3-[4-[[trans-2-(1-piperidyl)cyclohexyl]oxy]benzyl]-2-[4-[2-(1-pyrrolidinyl)ethoxy]phenyl]benzo[b]thiophene Dioxalate.

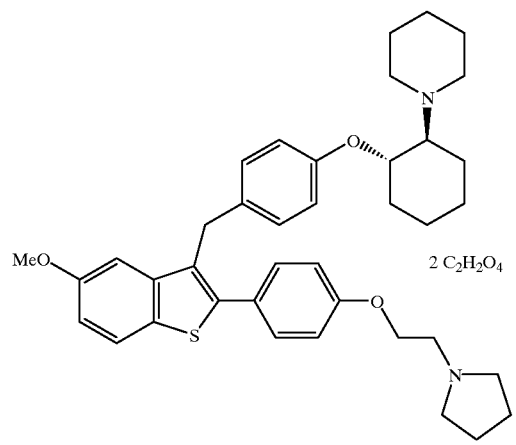

The free base of the compound was prepared in 69% yield from the ketone (Example 72, Part E) by essentially following the procedures detailed in Example 21, Part A. The title compound was prepared by essentially following the procedure outlined in Example 21, Part C.

Free base: mp 53–56° C.; FDMS 625 (M+). Dioxalate: mp 139–145° C.; FDMS 625 (M+); Anal. Calcd for $C_{39}H_{48}N_2O_3S \cdot 2.0C_2H_2O_4$: C, 64.16; H, 6.51; N, 3.48. Found: C, 63.88; H, 6.57; N, 3.41.

EXAMPLE 74

Preparation of (±)-5-Hydroxy-3-[4-[[trans-2-(1-piperidyl)cyclohexyl]oxy]benzyl]-2-[4-[2-(1-pyrrolidinyl)ethoxy]phenyl]benzo[b]thiophene Dioxalate.

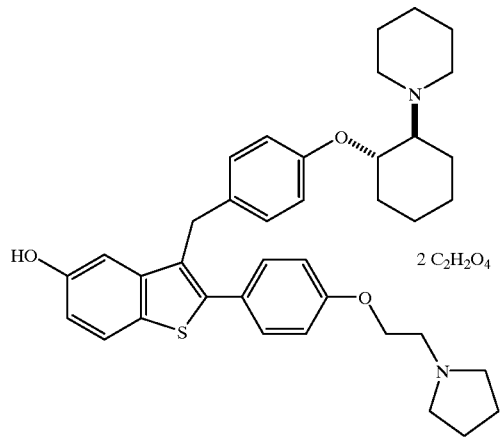

Part A. (±)-5-Hydroxy-3-[4-[[trans-2-(1-piperidyl)cyclohexyl]oxy]benzyl]-2-[4-[2-(1-pyrrolidinyl)ethoxy]phenyl]benzo[b]thiophene.

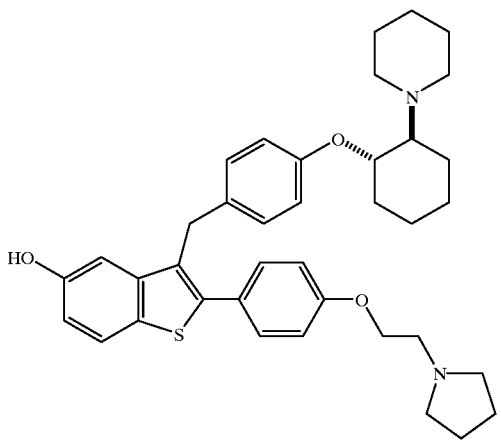

The title compound was prepared in 89% yield from the methoxybenzo[b]thiophene (free base of Example 73) by essentially following the procedures detailed in Example 21, Part B.

mp 103–106° C.; FDMS 610 (M+) ; Anal. Calcd for $C_{38}H_{46}N_2O_3S \cdot 1.48H_2O$: C, 71.59; H, 7.74; N, 4.39. Found: C, 71.59; H, 7.44; N, 4.32.

Part B. (±)-5-Hydroxy-3-[4-[[trans-2-(1-piperidyl)cyclohexyl]oxy]benzyl]-2-[4-[2-(1-pyrrolidinyl)ethoxy]phenyl]benzo[b]thiophene Dioxalate.

The title compound was prepared from the free base by essentially following the procedures detailed in Example 21, Part C.

mp 172–176° C. (dec); FDMS 611 (M+); Anal. Calcd for $C_{38}H_{46}N_2O_3S \cdot 2C_2H_2O_4 \cdot 1.5H_2O$: C, 61.67; H, 6.53; N, 3.42. Found: C, 61.41; H, 6.21; N, 3.40.

EXAMPLE 75

Preparation of (±)-7-Hydroxy-2-[4-[2-(1-pyrrolidinyl)ethoxy]phenyl]benzo[b]thiophen-3-yl 4-[[trans-2-(1-Piperidyl)cyclohexyl]oxy]phenyl Ketone Dioxalate.

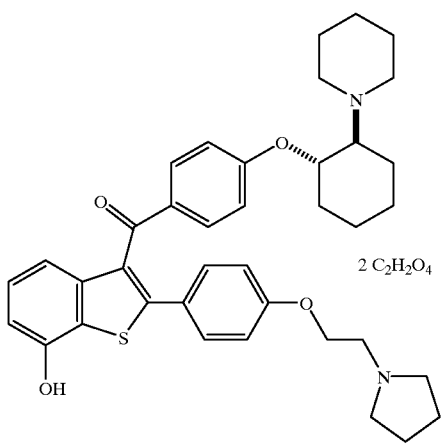

Part A. 2-Methoxybenzenethioacetaldehyde Diethyl Acetal.

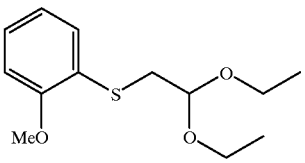

The title compound was prepared in 90% crude yield from 2-methoxybenzenethiol by essentially following the procedures detailed in Graham, S. L., et. al. *J. Med. Chem.* 1989, 32, 2548–2554.

Part B. 7-Methoxybenzo[b]thiophene.

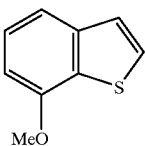

To a biphasic mixture of polyphosphoric acid (PPA; 64.1 g) and 600 mL of dry chlorobenzene heated to reflux at 140° C. was added dropwise 2-methoxybenzenethioacetaldehyde diethyl acetal (Part A) (30.0 g, 117 mmol) in 75 mL of chlorobenzene over a period of 1.5 h. The dark green biphasic mixture was stirred at reflux for an additional 1.5 h. The reaction mixture was cooled to room temperature and the organic layer was decanted off the PPA layer. The PPA layer was cooled to 0° C. and diluted with 500 mL of $H_2O$. This aqueous layer was extracted with $CH_2Cl_2$ (3×100 mL). The combined organic layers were washed with 200 mL of brine, dried over $MgSO_4$ and concentrated under reduced pressure. The residue was purified using a PrepLC with a gradient elution (0 to 7% $Et_2O$ in hexanes) to afford 10.3 g (63.1 mmol, 54%) of a green oil. FDMS 164 (M+) ; Anal. Calcd for $C_9H_8OS \cdot 0.06CH_2Cl_2$: C, 64.27; H, 4.83. Found: C, 64.15; H, 4.81.

Part C. 7-Methoxybenzo[b]thiophene-2-boronic Acid.

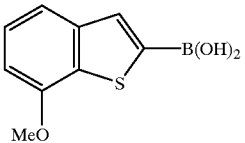

The title compound was prepared in 44% yield (51% SM recovery) by essentially following the procedures in Example 1, Part A from 7-methoxy[b]benzothiophene (Part B).

mp 272–275° C.; FDMS 569; Anal. Calcd for $C_9H_9BO_3S$: C, 51.96; H, 4.36; N, 0.00. Found: C, 51.71; H, 4.15; N, 0.00.

Part D. 7-Methoxy-2-[4-[2-(1-pyrrolidinyl)ethoxy]phenyl]benzo[b]thiophene.

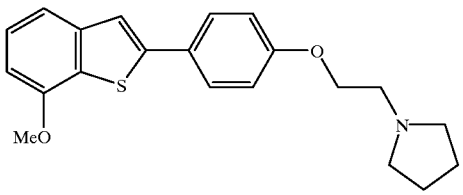

The title compound was prepared in 31% yield by essentially following the procedures outlined in Example 1, Part B from 7-methoxybenzo[b]thiophene-2-boronic acid (Part C).

mp 88–90° C.; FDMS 353 (M+); Anal. Calcd for $C_{21}H_{23}NO_2S$: C, 71.36; H, 6.56; N, 3.96. Found: C, 71.17; H, 6.58; N, 3.83.

Part E. 7-Hydroxy-2-[4-[2-(1-pyrrolidinyl)ethoxy]phenyl]benzo[b]thiophene.

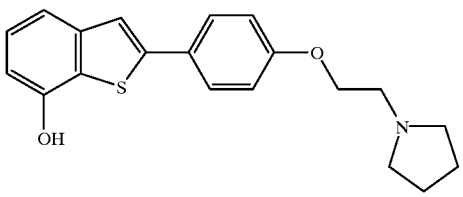

The title compound was prepared by essentially following the procedures outlined in Example 21, Part B from 7-methoxybenzo[b]thiophene (Part D) and recrystallized from EtOAc-hexanes to afford 944 mg (2.78 mmol, 56%) of light orange needle-like crystals.

mp 180–183° C.; FDMS 339 (M+) ; Anal. Calcd for $C_{20}H_{21}NO_2S \cdot 0.3H_2O$: C, 69.66; H, 6.31; N, 4.06. Found: C, 69.62; H, 6.21; N, 4.46.

Part F. 3-(4-Fluorophenyl)carbonyl-2-[4-[2-(1-pyrrolidinyl)ethoxy]phenyl]benzo[b]thiophen-7-yl 4-Fluorobenzoate.

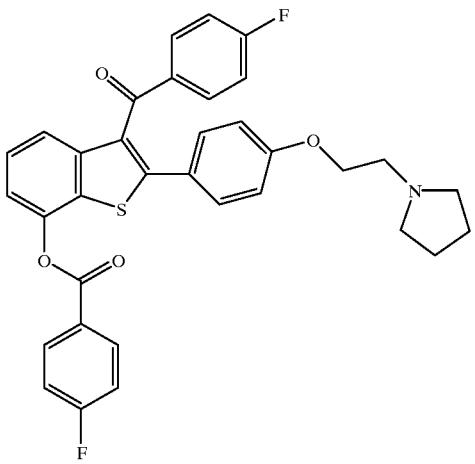

To a slurry of 7-hydroxy-2-[4-[2-(1-pyrrolidinyl)ethoxy]phenyl]benzo[b]thiophene (Part E) (244 mg, 0.808 mmol) in 5.0 mL of anhydrous dichloroethane was added 4-fluorobenzoyl chloride (105 μL, 0.888 mmol) at room temperature. The white slurry was stirred at room temperature for 3 h to form the intermediate ester. The reaction was then cooled to 0° C. and another 105 μL (0.888 mmol) of 4-fluorobenzoyl chloride was added, followed by addition of aluminum chloride (431 mg, 3.23 mmol) which turned the slurry into a dark red homogeneous solution. The reaction was slowly warmed to room temperature over 2 h and then stirred for 2.5 days. The reaction mixture was then poured into 20 mL of ice-cold 2.0 N NaOH solution. The mixture was then taken up in EtOAc and the layers were separated. The aqueous layer was extracted with EtOAc (2×100 mL). The combined organic layers were dried over $MgSO_4$ and concentrated under reduced pressure. The residue was purified by flash chromatography (silica gel, 4%(10% $NH_4OH$ in MeOH)/$CH_2Cl_2$) to afford 408 mg (.700 mmol, 87%) of an off-white foam.

mp 64–68° C.; FDMS 583 (M+) ; Anal. Calcd for $C_{34}H_{27}F_2NO_4S \cdot 0.08CH_2Cl_2$: C, 69.33; H, 4.64; N, 2.37. Found: C, 69.36; H, 4.61; N, 2.01.

Part G. 4-Fluorophenyl 7-Hydroxy-2-[4-[2-(1-pyrrolidinyl)ethoxy]phenyl]benzo[b]thiophen-3-yl Ketone.

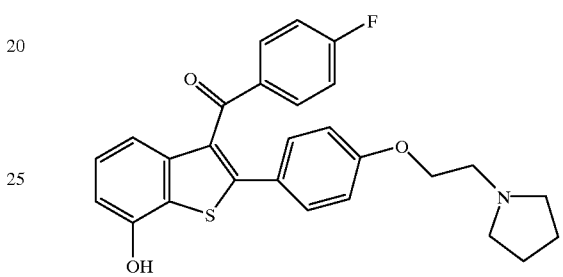

To a slurry of NaH (14.4 mg, 0.171 mmol, 60% dispersion in mineral oil) in 0.5 mL of anhydrous THF (or DMF) was added (±)-trans-2-(1-piperidyl)cyclohexanol in 0.5 mL of THF (or DMF) via a cannula. The reaction mixture was warmed with a heat gun to initialize the alkoxide formation and then stirred at room temperature for 2 h. The slurry was cooled to 0° C. and to this was added dropwise 4-fluorobenzoate (Part F) (100 mg, 0.171 mmol) in 0.5 mL of THF (or DMF). The reaction was stirred at 0° C. for 1 h and then allowed to warm to room temperature while stirring for 45 min. The reaction was quenched at 0° C. with 15 mL of $H_2O$. The aqueous layer was extracted with EtOAc (3×50 mL) and the combined organic layers were dried over $MgSO_4$ and concentrated under reduced pressure. The residue was purified by flash chromatography (silica gel, 70:27:3 THF-hexanes-$Et_3N$) to afford 67.9 mg (0.147 mmol, 86%) of a brown solid.

mp 138–142° C., FDMS 462 (M+); Anal. Calcd for $C_{27}H_{24}FNO_3S \cdot 0.57H_2O$: C, 68.73; H, 5.37; N, 2.97. Found: C, 68.95; H, 5.66; N, 3.30.

Part H. (±)-7-Hydroxy-2-[4-[2-(1-pyrrolidinyl)ethoxy]phenyl]benzo[b]thiophen-3-yl 4-[[trans-2-(1-Piperidyl)cyclohexyl]oxy]phenyl Ketone Dioxalate.

The free base of the title compound was prepared in 18% yield by essentially following the procedures in Example 72, Part E, from 4-fluorophenyl ketone (Part G) and (±)-trans-2-(1-piperidyl)cyclohexanol (Example 20 Part A). The dioxalate was then prepared by essentially following procedures in Example 21, Part C from the free base.

FDMS 625 (M+); Anal. Calcd for $C_{38}H_{44}N_2O_4S \cdot 2.5C_2H_2O_4 \cdot 3.2H_2O$: C, 56.91; H,6.15; N, 3.09. Found: 0, 56.61; H, 5.80; N, 3.47.

EXAMPLE 76

Preparation of (±)-6-Hydroxy-3-[4-[[trans-2-(1-piperidyl)cyclopentylloxy]benzyl]-2-[4-[2-(1-pyrrolidinyl)ethoxy]phenyl]benzo[b]thiophene Dioxalate.

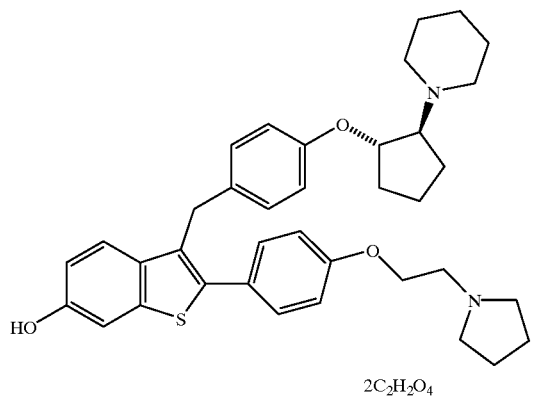

Part A. (±)-trans-2-(1-Piperidyl)cyclopentanol.

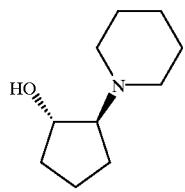

The title compound was prepared in 81% yield from cyclopentene oxide and piperidine by essentially following the procedures outlined in Example 20, Part A.

FDMS 169.1 (M$^+$); Anal. Calcd for $C_{10}H_{19}NO.0.24H_2O$: C, 69.19; H, 11.31; N, 8.07. Found: C, 69.19; H, 11.40; N, 8.21.

Part B. (±)-6-Methoxy-2-[4-[2-(1-pyrrolidinyl)ethoxy] phenyl]benzo[b]thiophen-3-yl 4-1[[(±)-trans-2-(1-Piperidyl) cyclopentyl]oxy]phenyl Ketone.

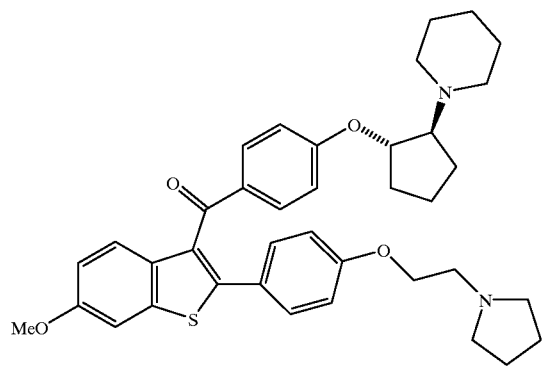

The title compound was prepared in 70% yield by essentially following the procedures outlined in Example 72, Part E, from 4-fluorophenyl 6-methoxy-2-[4-[2-(1-pyrrolidinyl) ethoxy]phenyl]benzo[b]thiophen-3-yl ketone (Example 59, Part A) and (±)-trans-2-(1-piperidyl)cyclopentanol (Part A).

mp 68–72° C.; FDMS 625 (M$^+$); Anal. Calcd for $C_{38}H_{44}N_2O_4S$: C, 73.05; H, 7.10; N, 4.48. Found: C, 73.27; H, 6.96; N, 4.30.

Part C. (±)-6-Methoxy-3-[4-[[trans-2-(1-piperidyl) cyclopentyl]oxy]benzyl]-2-[4-[2-(1-pyrrolidinyl)ethoxy] phenyl]benzo[b]thiophene.

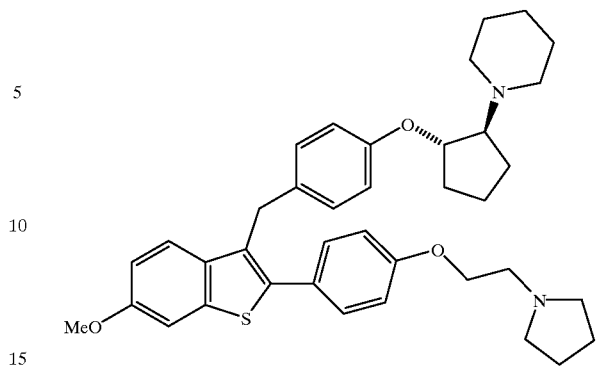

The title compound was prepared in 57% yield from the ketone (Part B) by essentially following the procedures detailed in Example 21, Part A.

mp 61–64° C.; FDMS 611 (M+); Anal Calcd for $C_{38}H_{46}N_2O_3S.0.39H_2O$: C, 73.87; H, 7.63; N, 4.53. Found: C, 73.85; H, 7.53; N, 4.83.

Part D. (±)-6-Hydroxy-3-4-[[trans-2-(1-piperidyl) cyclopentyl]oxy]benzyl]-2-[4-[2-(1-pyrrolidinyl)ethoxy] phenyl]benzo[b]thiophene Dioxalate.

The free base of title compound was prepared in 79% yield from the methoxybenzo[b]thiophene (Part C) by essentially following the procedures detailed in Example 21, Part B.

The title compound was prepared by essentially following the procedures detailed in Example 21, Part C. mp 145–150° C.; FDMS 597 (M$^+$); Anal. Calcd for $C_{37}H_{44}N_2O_3S.2.1C_2H_2O_4.1.6H_2O$: C, 60.74; H, 6.36; N, 3.44. Found: C, 60.41; H, 6.46; N, 3.37.

EXAMPLE 77

Preparation of (±)-3-[4-[trans-2-(Diethylamino)cyclohexyl] oxy]benzyl]-6-hydroxy-2-[4-[2-(1-pyrrolidinyl)ethoxy] phenyl]benzo[b]thiophene Dioxalate.

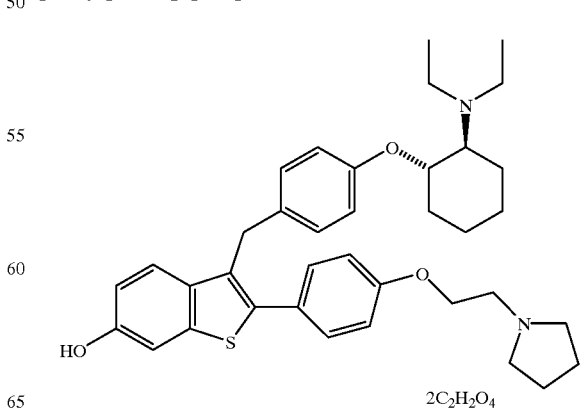

Part A. (±)-trans-2-(Diethylamino)cyclohexanol.

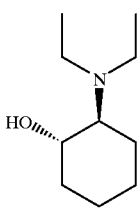

The title compound was prepared from N,N-diethylamine and cyclohexene oxide by essentially following the procedures outlined in Example 20, Part A.

FDMS 171 (M+, base); Anal. Calcd for $C_{10}H_{21}NO \cdot 0.26CH_2Cl_2$: C, 63.73; H, 11.22; N, 7.24. Found: C, 63.80; H, 11.35; N, 7.52.

Part B. (±)-4-[[trans-2-(Diethylamino)cyclohexyl]oxy]phenyl 6-Methoxy-2-[4-[2-(1-pyrrolidinyl)ethoxy]phenyl]benzo[b]thiophen-3-yl Ketone.

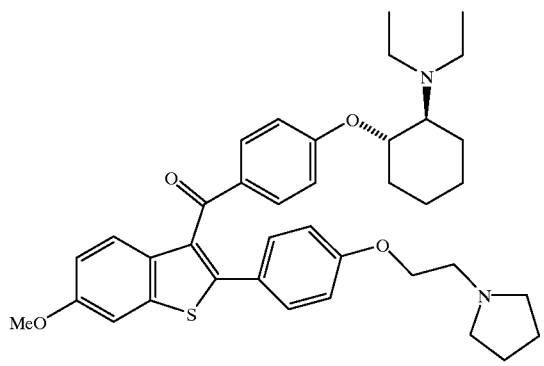

The title compound was prepared in 67% yield by essentially following the procedures outlined in Example 72, Part E, from 4-fluorophenyl 6-methoxy-2-[4-[2-(1-pyrrolidinyl)ethoxy]phenyl]benzo[b]thiophen-3-yl ketone (Example 59, Part A) and (±)-trans-2-(diethylamino)cyclohexanol (Part A).

FDMS 627 (M+) ; Anal. Calcd for $C_{38}H_{46}N_2O_4S$: C, 72.81; H, 7.40; N, 4.47. Found: C, 73.06; H, 7.44; N, 4.65.

Part C. (±)-3-[4-[[trans-2-(Diethylamino)cyclohexyl]oxy]benzyl]-6-methoxy-2-[4-[2-(1-pyrrolidinyl)ethoxy]phenyl]benzo[b]thiophene.

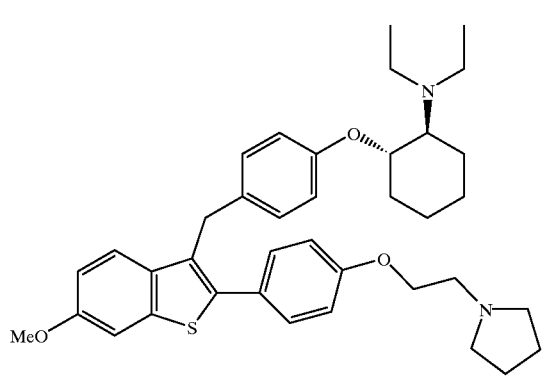

The title compound was prepared in 79% yield from the ketone (Part B) by essentially following the procedures detailed in Example 21, Part A.

FDMS 613 (M+) ; Anal. Calcd for $C_{38}H_{48}N_2O_3S$: C, 74.47; H. 7.89; N, 4.57. Found: C, 74.49; H, 8.18; N, 4.66.

Part D. (±)-3-[4-[[trans-2-(Diethylamino)cyclohexyl]oxy]benzyl]-6-hydroxy-2-[4-[2-(1-pyrrolidinyl)ethoxy]phenyl]benzo[b]thiophene.

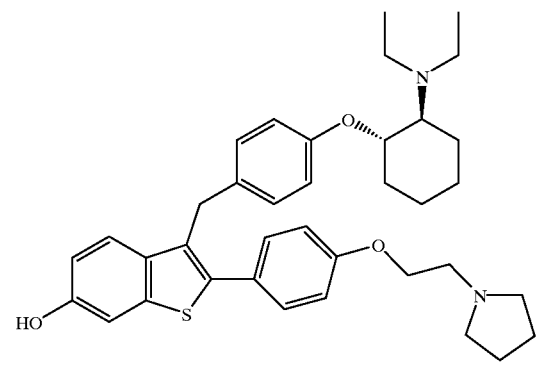

The title compound was prepared in 73% yield from the methoxybenzo[b]thiophene (Part C) by essentially following the procedures detailed in Example 21, Part B.

mp 95–100° C.; FDMS 599 (M+); Anal. Calcd for $C_{37}H_{46}N_2O_3S \cdot O.2CH_2Cl_2$: C, 72.55; H, 7.59; N, 4.55. Found C, 72.21; H, 7.59; N, 4.87.

Part E. (±)-3-[4-[[trans-2-(Diethylamino)cyclohexyl]oxy]benzyl]-6-hydroxy-2-[4-[2-(1-pyrrolidinyl)ethoxy]phenyl]benzo[b]thiophene Dioxalate.

The title compound was prepared from the free base (Part D) by essentially following the procedures detailed in Example 21, Part C.

mp 143–146° C.; FDMS 599 (M+); Anal. Calcd for $C_{37}H_{46}N_2O_3S \cdot 2.0C_2H_2O_4 \cdot 1.8H_2O$: C, 60.64; H, 6.66; N, 3.45. Found: C, 60.63; H, 6.31; N, 3.26.

EXAMPLE 78

Preparation of (±)-3-[4-[[cis-2-(Dimethylamino)cyclohexyl]oxy]benzyl]-6-hydroxy-2-[4-[2-(1-pyrrolidinyl)ethoxy]phenyl]benzo[b]thiophene Dioxalate.

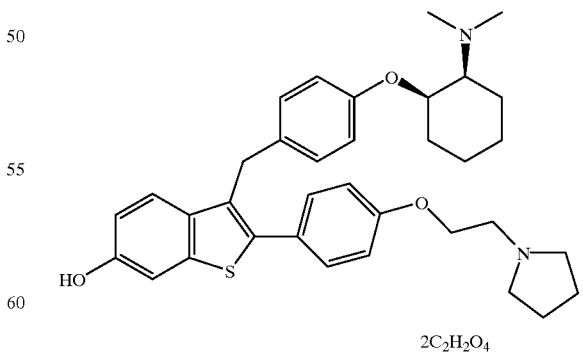

Part A. (±)-4-[cis-2-(Dimethylamino)cyclohexyloxy]phenyl 6-Methoxy-2-[4-[2-(1-pyrrolidinyl)ethoxy]phenyl]benzo[b]thiophen-3-yl Ketone.

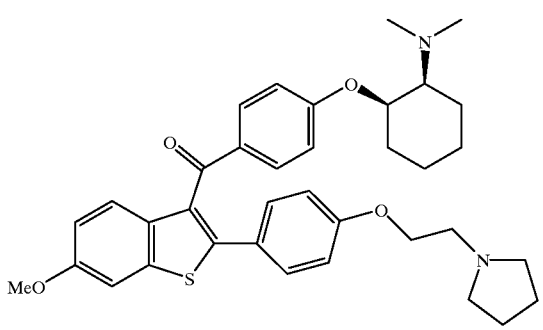

The title compound was prepared in 71% yield by essentially following the procedures outlined in Example 72, Part E, from 4-fluorophenyl 6-methoxy-2-[4-[2-(1-pyrrolidinyl)ethoxy]phenyl]benzo[b]thiophen-3-yl ketone (Example 59, Part A) and (±)-cis-2-(dimethylamino)cyclohexanol.

mp 61–64° C.; FDMS 599 (M+); Anal. Calcd for $C_{36}H_{42}N_2O_4S$: C, 72.21; H, 7.07; N, 4.68. Found: C, 72.15; H, 7.30; N, 4.64.

Part B. (±)-3-[4-[[cis-2-(Dimethylamino)cyclohexyl]oxy]benzyl]-6-methoxy-2-[4-[2-(1-pyrrolidinyl)ethoxy]phenyl]benzo[b]thiophene

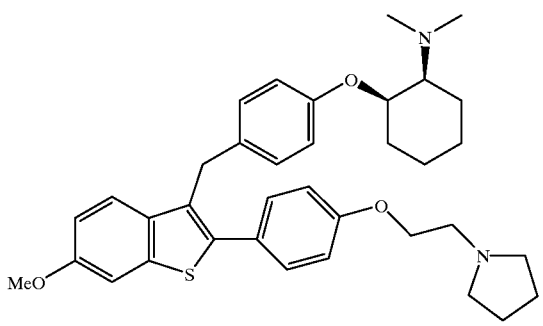

The title compound was prepared in 57% yield from the ketone (Part A) by essentially following the procedures detailed in Example 21, Part A.

FDMS 585 (M+); Anal. Calcd for $C_{36}H_{44}N_2O_3S \cdot 0.27CH_4O$: C, 73.41; H, 7.66; N, 4.72. Found: C, 73.62; H, 7.74; N, 4.32.

Part C. (±)-3-[4-[[cis-2-(Dimethylamino)cyclohexyl]oxy]benzyl]-6-hydroxy-2-[4-[2-(1-pyrrolidinyl)ethoxy]phenyl]benzo[b]thiophene

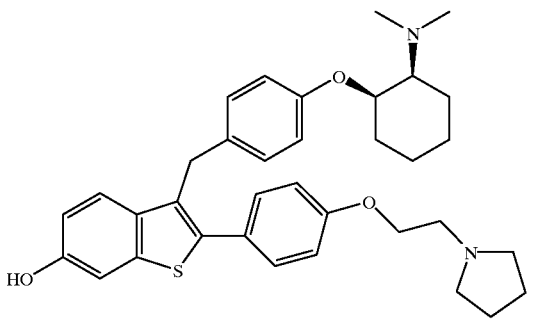

The title compound was prepared in 75% yield from the methoxybenzo[b]thiophene (Part B) by essentially following the procedures detailed in Example 21, Part B.

mp 95–98° C.; FDMS 571 (M+); Anal. Calcd for $C_{35}H_{42}N_2O_3S$: C, 73.65; H, 7.42; N, 4.91. Found C, 73.39; H, 7.63; N, 4.78.

Part D. (±)-3-[4-[[cis-2-(Dimethylamino)cyclohexyl]oxy]benzyl]-6-hydroxy-2-[4-[2-(1-pyrrolidinyl)ethoxy]phenyl]benzo[b]thiophene Dioxalate The title compound was prepared from the free base (Part C) by essentially following the procedures detailed in Example 21, Part C.

mp 103–106° C. (dec.); FDMS 571 (M+); Anal. Calcd for $C_{35}H_{42}N_2O_3S \cdot 2.0C_2H_2O_4 \cdot 1.7H_2O$: C, 59.94; H, 6.37; N, 3.58. Found: C, 59.81; H, 6.09; N, 3.44.

EXAMPLE 79

Preparation of (±)-3-[4-[[trans-2-(Dimethylamino)cyclohexyl]oxy]benzyl]-6-hydroxy-2-[4-[2-(1-pyrrolidinyl)ethoxy]phenyl]benzo[b]thiophene Dioxalate

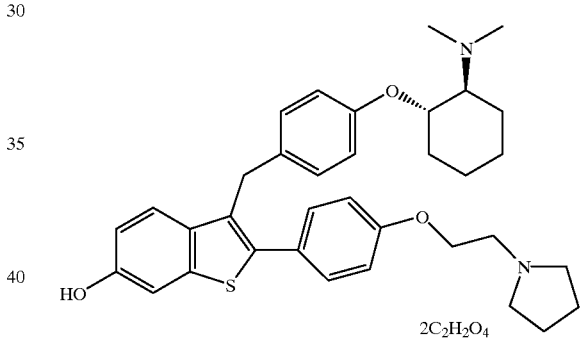

Part A. (±)-trans-2-(Dimethylamino)cyclohexanol

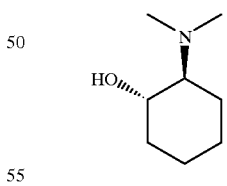

To a solution of cyclohexene oxide (3.64 mL, 36.0 mmol) in 30 mL of dry methanol was added dropwise 2.0 M dimethylamine in THF (15.0 mL, 30.0 mmol). The reaction mixture was stirred at 0° C. for 4 h. The solution was then warmed to room temperature and stirred for 18 h. The reaction mixture was then concentrated under reduced pressure to afford 1.11 g (26% crude yield) of the crude product which was used in the following reaction without purification.

Part B. (±)-4-[[trans-2-(Dimethylamino)cyclohexyl]oxy]phenyl 6-Methoxy-2-[4-[2-(1-pyrrolidinyl)ethoxy]phenyl]benzo[b]thiophen-3-yl Ketone

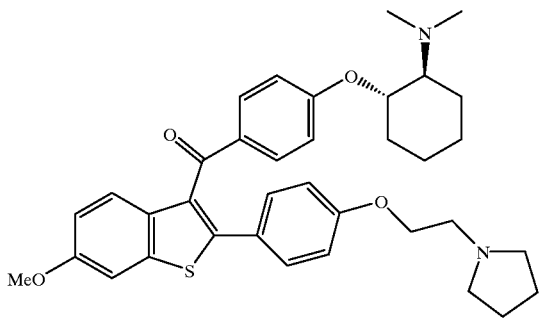

The title compound was prepared in 77% yield by essentially following the procedures outlined in Example 72, Part E, from 4-fluorophenyl 6-methoxy-2-[4-[2-(1-pyrrolidinyl)ethoxy]phenyl]benzo[b]thiophen-3-yl ketone (Example 59, Part A) and (±)-trans-2-(dimethylamino)cyclohexanol (Part A).

mp 65–70° C.; FDMS 599 (M$^+$); Anal. Calcd for $C_{36}H_{42}N_2O_4S$: C, 72.21; H, 7.07; N, 4.68. Found: C, 71.98; H, 6.96; N, 4.44.

Part C. (±)-3-[4-[[trans-2-(Dimethylamino)cyclohexyl]oxy]benzyl]-6-methoxy-2-[4-[2-(1-pyrrolidinyl)ethoxy]phenyl]benzo[b]thiophene

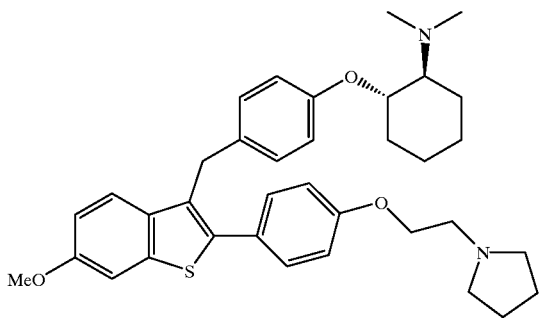

The title compound was prepared in 66% yield from the ketone (Part B) by essentially following the procedures detailed in Example 21, Part A.

mp 58–61° C., FDMS 585 (M$^+$); Anal. Calcd for $C_{36}H_{44}N_2O_3S$: C, 73.94; H, 7.58; N, 4.79. Found: C, 74.19; H, 7.55; N, 5.07.

Part D. (±)-3-[4-[[trans-2-(Dimethylamino)cyclohexyl]oxy]benzyl]-6-hydroxy-2-[4-[2-(1-pyrrolidinyl)ethoxy]phenyl]benzo[b]thiophene

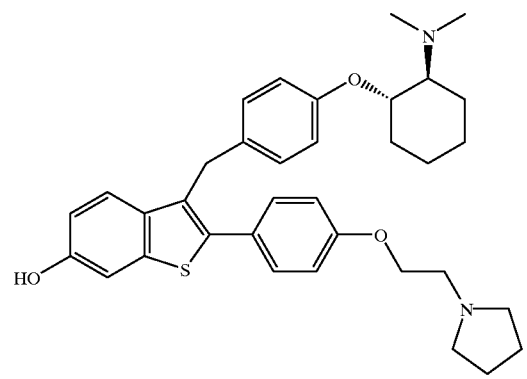

The title compound was prepared in 77% yield from the methoxybenzo[b]thiophene (Part C) by essentially following the procedures detailed in Example 21, Part B.

mp 97–102° C.; FDMS 571 (M$^+$); Anal. Calcd for $C_{35}H_{42}N_2O_3S \cdot 0.19CH_2Cl_2$: C, 72.01; H, 7.28; N, 4.77. Found C, 72.04; H, 7.32; N, 4.43.

Part E. (±)-3-[4-[[trans-2-(Dimethylamino)cyclohexyl]oxy]benzyl]-6-hydroxy-2-[4-[2-(1-pyrrolidinyl)ethoxy]phenyl]benzo[b]thiophene Dioxalate The title compound was prepared from the free base (Part D) by essentially following the procedures detailed in Example 21, Part C.

mp 104–106° C. (dec.); FDMS 571 (M$^+$); Anal. Calcd for $C_{35}H_{42}N_2O_3S \cdot 2.0C_2H_2O_4 \cdot 1.2H_2O$: C, 60.44; H, 6.41; N, 3.51. Found: C, 60.07; H, 6.26; N, 3.21.

EXAMPLE 80

Preparation of (±)-7-Hydroxy-3-[4-[[trans-2-(1-piperidyl)cyclohexyl]oxy]benzyl]-2-[4-[2-(1-pyrrolidinyl)ethoxy]phenyl]benzo[b]thiophene Dioxalate

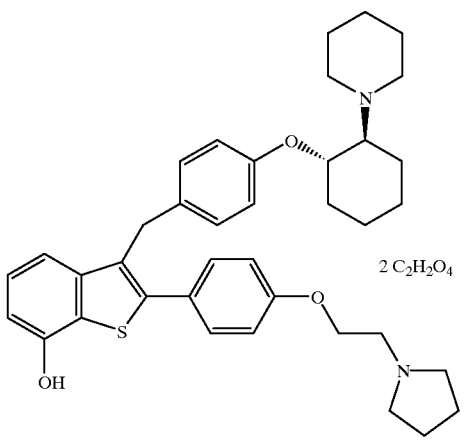

Part A. 4-Fluorophenyl 7-Methoxy-2-[4-[2-(1-pyrrolidinyl) ethoxy]phenyl]benzo[b]thiophen-3-yl Ketone

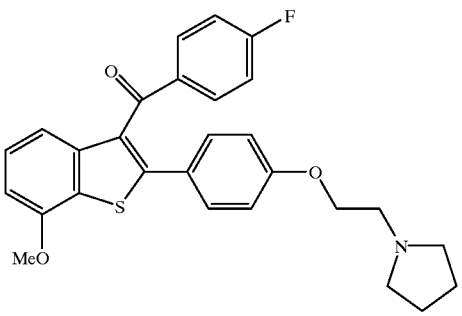

To a suspension of powdered KOH (177 mg, 3.15 mmol) in 1.6 mL of dry DMSO was added 4-fluorophenyl 7-hydroxy-2-[4-[2-(1-pyrrolidinyl)ethoxy]phenyl]benzo[b]thiophen-3-yl ketone (350370) (Example 75, Part G) (364 mg, 0.788 mmol) at room temperature. The reaction mixture turned orange in color. To the alkoxide was added slowly methyl iodide (49 μL, 0.79 mmol) over a period of 15 min. The reaction mixture was then stirred for 1.5 h. Another portion of MeI (20 μL, 0.32 mmol) was added, stirred for 1.5 h., followed by another addition of 20 μL (0.32 mmol) of MeI and stirring for an additional 30 min at room temperature. The rection mixture was then poured into 20 mL of $H_2O$. This mixture was extracted with $CH_2Cl_2$ (3×20 mL). The combined organic layers were washed with $H_2O$ (5×10 mL), dried over $MgSO_4$, and concentrated under reduced pressure. The residue was then purified by flash chromatography (silica gel, 4%[10% $NH_4OH$ in MeOH]/$CH_2Cl_2$) to afford 108 mg (0.226 mmol, 29%) of a white foam.

FDMS 475 ($M^+$); Anal. Calcd for $C_{28}H_{26}FNO_3S$: C, 70.71; H, 5.51; N, 2.94. Found: C, 70.48; H, 5.77; N, 2.72.

Part B. (±)-7-Methoxy-2-[4-[2-(1-pyrrolidinyl)ethoxy] phenyl]benzo[b]thiophen-3-yl 4-[[trans-2-(1-Piperidyl) cyclohexyl]oxy]phenyl Ketone

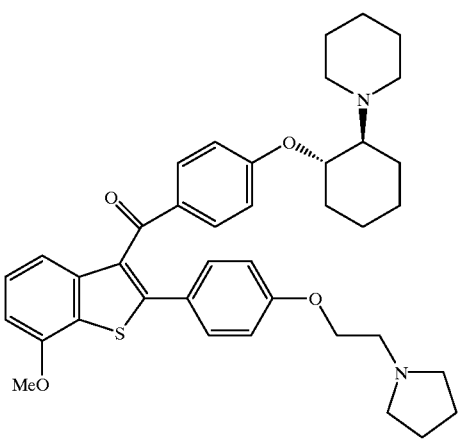

The title compound was prepared in 74% yield by essentially following the procedures outlined in Example 72, Part E, from the 4-fluorophenyl ketone (BZ4-GCY-222) (Part A) and (±)-trans-2-(1-piperidyl)cyclohexanol (Example 20, Part A).

mp 66–69° C.; FDMS 639 (M+); Anal. Calcd for $C_{36}H_{46}N_2O_4S$: C, 73.32; H, 7.26; N, 4.38. Found: C, 73.60; H, 7.53; N, 4.65.

Part C. (±)-7-Methoxy-3-[4-[[trans-2-(1-piperidyl) cyclohexyl]oxy]benzyl]-2-[4-[2-(1-pyrrolidinyl)ethoxy] phenyl]benzo[b]thiophene Dioxalate

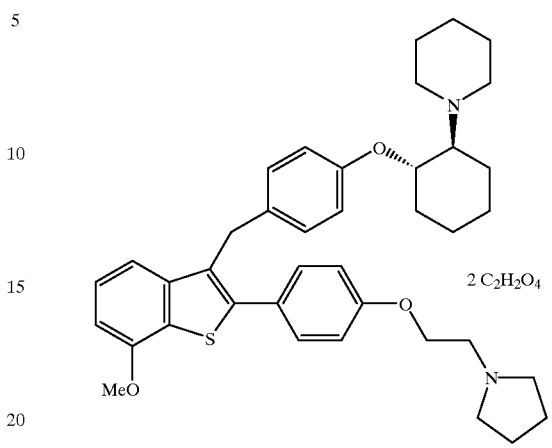

The free base of the title compound was prepared in 63% yield from the ketone (Part B) by essentially following the procedures detailed in Example 21, Part A. The title compound was prepared by essentially following the procedures outlined in Example 21, Part C from the free base obtained.

FDMS 625 (M+), Anal. Calcd for $C_{39}H_{48}N_2O_3S\cdot 2.1C_2H_2O_4\cdot 1.4H_2O$: C, 61.83; H, 6.61; N, 3.34. Found: C, 61.49; H, 6.58; N, 3.44.

Part D. (±)-7-Hydroxy-3-[4-[[trans-2-(1-piperidyl) cyclohexyl]oxy]benzyl]-2-[4-[2-(1-pyrrolidinyl)ethoxy] phenyl]benzo[b]thiophene Dioxalate The free base of the title compound was prepared in 76% yield from the methoxybenzothiophene (free base of Part C) by essentially following the procedures detailed in Example 21, Part B. The title compound was prepared by essentially following the procedures outlined in Example 21, Part C from the free base obtained.

FDMS 611 ($M^+$); Anal. Calcd for $C_{38}H_{46}N_2O_3S\cdot 2.0C_2H_2O_4\cdot 3.3H_2O$: C, 59.35; H, 6.71; N, 3.30. Found: C, 59.33; H, 6.66; N, 3.45.

EXAMPLE 81

Preparation of (±)-3-[4-[[trans-2-(Dimethylamino) cyclohexyl]oxy]-3-methoxybenzyl]-6-hydroxy-2-[4-[2-(1-pyrrolidinyl)ethoxy]phenyl]benzo[b]thiophene Dioxalate

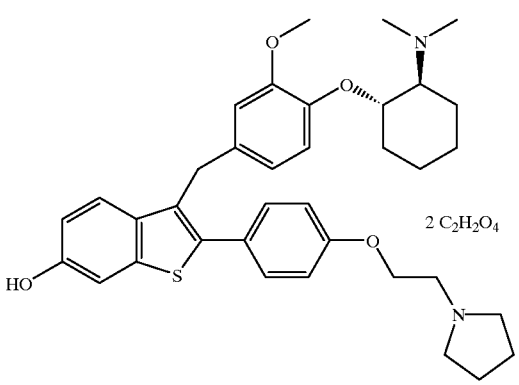

Part A. 4-Benzyloxy-α-hydroxy-N,N-(dimethyl)phenylthioacetamide

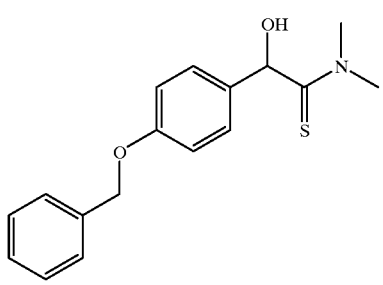

To a solution of distilled diisopropylamine (22.9 mL, 175 mmol) in 400 mL of anhydrous THF at −78° C. was added 1.6 M n-butyllithium in hexanes (100 mL, 160 mmol) over a period of 45 min. The mixture was stirred at −78° C. for 1.5 h. To the solution was cannulated over a period of 1 h a solution of 4-benzyloxybenzaldehyde (30.9 g, 146 mmol) and N,N-dimethylthioformamide (13.7 mL, 160 mmol) in 100 mL of distilled THF. The reaction mixture was stirred at −78° C. for 16 h. The reaction was then quenched with 500 mL of saturated NH$_4$Cl solution. The mixture was extracted with EtOAc (3×1 L), and the combined organic layers were dried over MgSO$_4$ and concentrated under reduced pressure. The residue was then recrystallyzed from EtOAc/hexanes to afford 20.0 g (66.5 mmol, 46%) of an off-white solid.

mp 104–107° C.; FDMS 301 (M+); Anal. Calcd for C$_{17}$H$_{19}$NO$_2$S: C, 67.75; H, 6.35; N, 4.65. Found: C, 67.61; H, 6.37; N, 4.57.

Part B. 6-Benzyloxy-2-(dimethylamino)benzo[b]thiophene

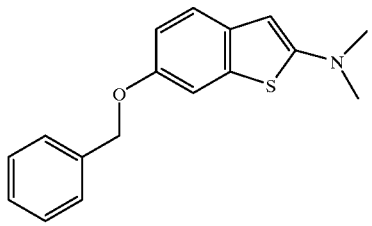

To a solution of thioacetamide (Part A) (500 mg, 1.66 mmol) in 65 mL of dry dichloroethane at room temperature was added dropwise methanesulfonic acid (0.54 ml, 8.3 mmol). The red reaction mixture was stirred for 1.5 h and then poured into 10 mL of saturated aqueous NaHCO$_3$ solution, followed by addition of 3 mL of H$_2$O, and stirred vigorously. The layers were separated and the organic layer was dried over MgSO$_4$ and concentrated under reduced pressure. The residue was then purified by flash chromatography (silica gel, 10% Et$_2$O/hexanes) to afford 327 mg (1.15 mmol, 70%) of a white solid.

mp 78–81° C.; FDMS 283 (M+); Anal. Calcd for C$_{17}$H$_{17}$NOS: C, 72.05; H, 6.05; N, 4.94. Found: C, 72.22; H, 6.15; N, 4.89.

Part C. 6-Benzyloxy-2-(dimethylamino)benzo[b]thiophen-3-yl 3,4-Dimethoxyphenyl Ketone

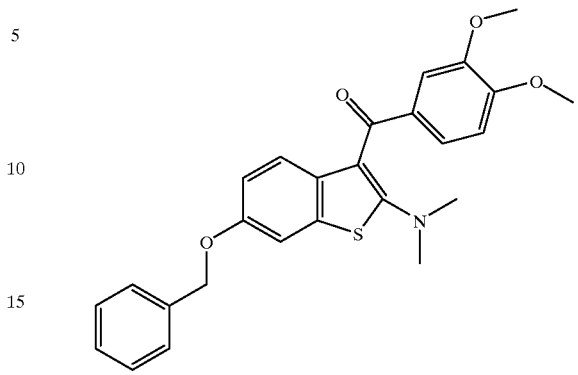

To a solution of 3,4-dimethoxybenzoyl chloride (1.250 g, 6.231 mmol) in 18 mL of chlorobenzene was added 6-benzyloxy-2-(dimethylamino)benzo[b]thiophene (Part B) (1.059 g, 3.738 mmol). The dark blue reaction mixture was then heated to 110° C. and stirred for 17 h by which time the solution turned to brown. The brown solution was then quenched at 0° C. with 30 mL of saturated aqueous NaHCO$_3$ solution and extracted with EtOAc (2×200 mL). The combined organic layers were washed with 200 mL with brine, dried over MgSO$_4$, concentrated under reduced pressure, and purified by flash chromatography (silica gel, 50:50 EtOAc-hexanes) to afford 1.265 g (2.826 mmol, 76%) of a yellow foam.

mp 69–72° C.; FDMS 447 (M+); Anal. Calcd for C$_{26}$H$_{25}$NO$_4$S: C, 69.78; H, 5.63; N, 3.13. Found: C, 69.93; H, 5.77; N, 3.25.

Part D. 4-[2-(1-Pyrrolidinyl)ethoxy]phenyl Magnesium Bromide

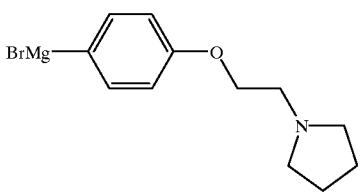

To a solution of 1-[2-(4-bromophenoxy)ethyl]pyrrolidine in 24.1 mL of freshly distilled THF was added 293 mg of magnesium turnings. The mixture was heated at reflux for 3 h or until all the magnesium was consumed to afford ~24.1 mL of 0.48 M Grignard reagent solution.

Part E. 6-Benzyloxy-2-[4-[2-(1-pyrrolidinyl)ethoxy]phenyl] benzo[b]thiophen-3-yl 3,4-Dimethoxyphenyl Ketone

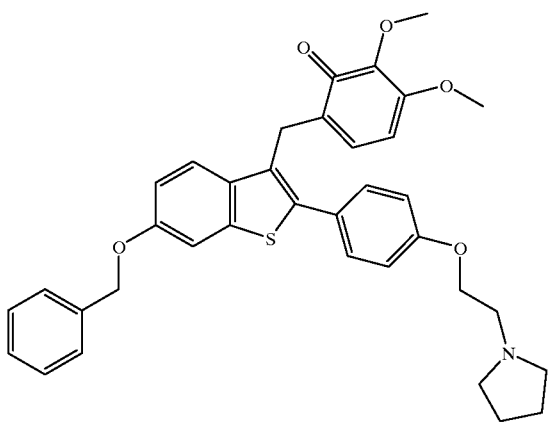

To the dimethylaminobenzo[b]thiophenyl ketone (Part C) (1.237 g, 2.763 mmol) in 30 ml of freshly distilled THF was added dropwise 0.48 M 4-[2-(1-pyrrolidinyl)ethoxy]phenyl magnesium bromide in THF (Part D) (8.63 mL, 4.14 mmol) at 0° C. The resultant bright red solution was stirred at 0° C. for 2 h 15 min. The reaction was quenched at 0° C. with 30 mL of saturated aqueous $NH_4Cl$ solution. The mixture was diluted with 15 mL of $H_2O$ and extracted with EtOAc (2×200 mL). The combined organic layers were dried over $MgSO_4$, concentrated under reduced pressure, and then purified by flash chromatography (silica gel, 60:37:3 THF-hexanes-$Et_3N$) to afford 1.507 g (2.538 mmol, 92%) of a yellow foam.

mp 74–77° C.; FDMS 593 (M+); Anal. Calcd for $C_{36}H_{35}NO_5S$: C, 72.83; H, 5.94; N, 2.36. Found: C, 72.91; H, 5.94; N, 2.62.

Part F. 6-Benzyloxy-2-[4-[2-(1-pyrrolidinyl)ethoxy]phenyl] benzo[b]thiophen-3-yl 4-Hydroxy-3-methoxyphenyl Ketone

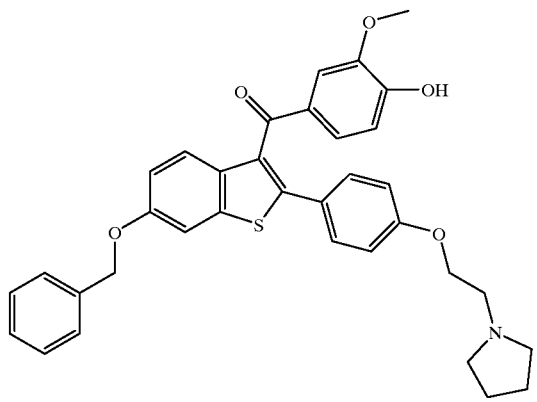

To the 3,4-dimethoxyphenyl ketone (Part E) (1.496 g, 2.519 mmol) in 15 mL of dry DMF was added sodium thioethoxide (848 mg, 10.1 mmol), and the reaction mixture was stirred at 80° C. for 3 h. The mixture was then cooled to 0° C. and quenched with 15 mL of saturated aqueous $NH_4Cl$ solution. This mixture was extracted with $CHCl_3$ (3×150 mL). The combined organic layers were washed with 450 mL of $H_2O$ and 150 mL of brine, dried over $MgSO_4$ and concentrated under reduced pressure. The residue was purified by flash chromatography (silica gel, 6%[10% $NH_4OH$ in MeOH]/$CH_2Cl_2$) to afford 1.251 g (2.159 mmol, 86%) of a yellow foam.

FDMS 579 (M+); Anal. Calcd for $C_{35}H_{33}NO_5S$: C, 72.52; H, 5.74; N, 2.42. Found: C, 72.63; H, 5.73; N, 2.64.

Part G. (±)-6-Benzyloxy-2-[4-[2-(1-pyrrolidinyl)ethoxy]phenyl]benzo[b]thiophen-3-yl 4-[trans-2-(Dimethylamino)cyclohexyl]oxy-3-methoxyphenyl Ketone

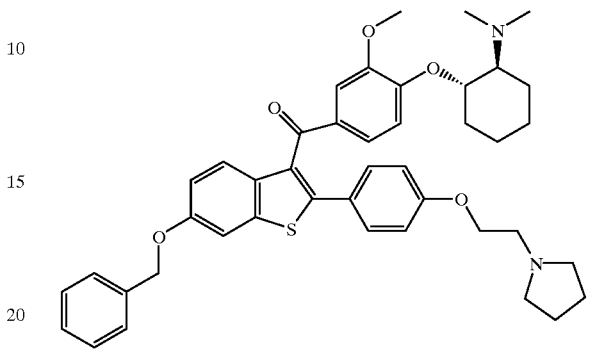

The title compound was prepared in 93% yield by essentially following the procedures outlined in Example 20, Part B from the phenol (Part F) and (±)-trans-2-(dimethylamino)cyclohexanol (Example 79, Part A).

mp 66–69° C.; FDMS 705 (M+); Anal. Calcd for $C_{43}H_{48}N_2O_5S \cdot 0.62NH_5O$: C, 71.08; H, 7.09; N, 5.05. Found: C 70.88; H, 6.76; N, 4.65.

Part H. (±)-6-Benzyloxy-α-[4-[[trans-2-(dimethylamino)cyclohexyl]oxy]-3-methoxyphenyl]-2-[4-[2-(1-pyrrolidinyl)ethoxy]phenyl]benzo[b]thiophene-3-methanol

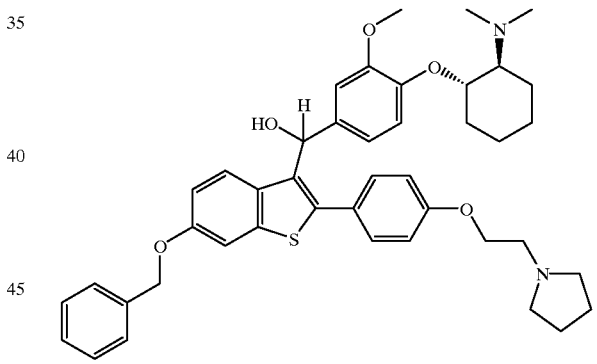

The title compound was prepared in by essentially following the procedures outlined in Example 31, Part B from the ketone (Part G). The crude product was purified by flash chromatography (silica gel, 10%[10% $NH_4OH$ in MeOH]/$CH_2Cl_2$) to afford 418 mg (0.591 mmol, 69%) of a white foam.

FDMS 708 (M+1); Anal. Calcd for $C_{43}H_{50}N_2O_5S \cdot 0.22CH_2Cl_2$: C, 71.54; H, 7.12; N, 3.86. Found: C, 71.52; H, 7.31; N, 4.06.

Part I. (±)-3-[4-[[trans-2-(Dimethylamino)cyclohexyl]oxy]-3-methoxybenzyl]-6-hydroxy-2-[4-[2-(1-pyrrolidinyl)ethoxy]phenyl]benzo[b]thiophene Dioxalate The 6-benzyloxy protected title compound was prepared from the disubstituted methanol (Part H) by essentially following procedures outlined in Example 31, Part C. A slurry of the crude (±)-6-benzyloxy-3-[4-[[trans-2-(dimethylamino)cyclohexyl]oxy]-3-methoxybenzyl]-2-[4-[2-(1-pyrrolidinyl)ethoxy]phenyl]benzo[b]thiophene (374 mg, 0.542 mmol) and Pd/C (10%, 375 mg) in 5.4 mL of a 1:1 mixture of THF-EtOH was stirred under positive hydrogen pressure (from balloon) for 19 h. The reaction mixture was filtered through a pad of diatomaceous earth and washed with THF. The filtrate was then concentrated under reduced pressure and the residue was flash chromatographed (silica gel, 10%[10% NH$_4$OH in MeOH]/CH$_2$Cl$_2$) to afford 200 mg (0.333 mmol, 61% from alcohol) of an off-white foam. The title compound was then prepared by essentially following the procedures outlined in Example 21, Part C from the free base.

mp 167° C. (dec.); FDMS 601 (M+); Anal. Calcd for C$_{36}$H$_{44}$N$_2$O$_4$S·1.83C$_2$H$_2$O$_4$: C, 62.22; H, 6.27; N, 3.66. Found: C, 62.26; H, 6.40; N, 3.28.

EXAMPLE 82

Preparation of (±)-4-[[trans-2-(Dimethylamino) cyclohexyl]oxy]-3-methoxyphenyl 6-Hydroxy-2-[4-[2-(1-pyrrolidinyl)ethoxy]phenyl]benzo[b]thiophen-3-yl Ketone Dioxalate

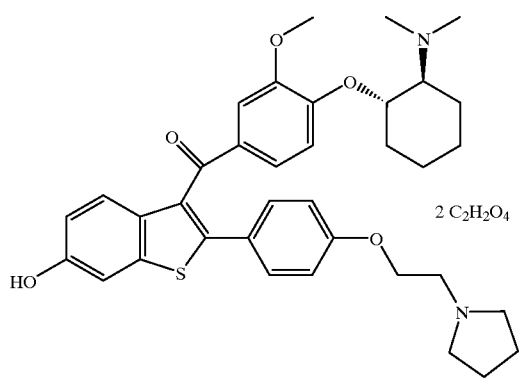

The title compound was prepared from the free base (Example 81, Part G) by essentially following the procedures outlined in Example 81, Part I and Example 21, Part C.

mp 170° C. (dec.); FDMS 615 (M+); Anal. Calcd for C$_{36}$H$_{42}$N$_2$O$_5$S·1.82C$_2$H$_2$O$_4$: C, 61.15; H, 5.91; N, 3.60. Found: C, 61.12; H, 6.05; N, 3.66.

EXAMPLE 83

Preparation of 3-[3-Chloro-4-[(1-pyrrolidinyl) methyl]benzyl]-2-[4-[2-(1-pyrrolidinyl)ethoxy] phenyl]benzo[b]thiophene Dioxalate

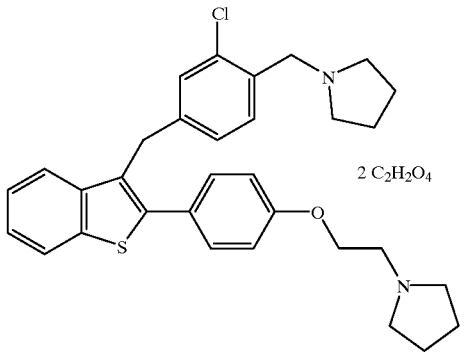

Part A. Methyl 4-Bromomethyl-3-chlorobenzoate

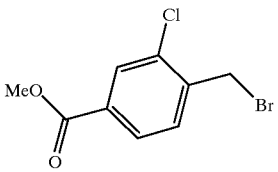

The title compound was prepared in 56% yield by essentially following the procedure outlined in the first part of Example 37, Part A, from methyl 3-chloro-4-methylbenzoate.

FDMS 264 (M+); Anal. Calcd for C$_9$H$_8$BrClO$_2$: C, 41.02; H, 3.06. Found: C, 41.10; H, 3.10.

Part B. Methyl 3-Chloro-4-[(1-pyrrolidinyl)methyl] benzoate

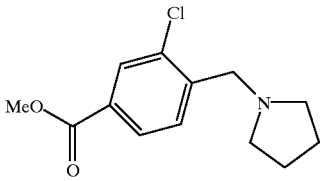

The title compound was prepared in 44% yield by essentially following the procedures outlined in the second part of Example 37, Part A, from methyl 4-bromomethyl-3-chlorobenzoate (Part A).

FDMS 253 (M+); Anal. Calcd for C$_{13}$H$_{16}$ClNO$_2$: C, 61.54; H, 6.36; N, 5.52. Found: C, 61.24; H, 6.11; N, 5.53.

Part C. 3-Chloro-4-[(1-pyrrolidinyl)methyl]benzoic Acid

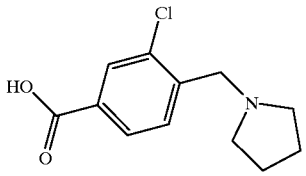

The title compound was prepared in 72% crude yield by essentially following the procedures outlined in Example 20, Part C, from methyl 3-chloro-4-[(1-pyrrolidinyl)methyl] benzoate (Part B). This compound was used without purification.

Part D. 3-Chloro-4-[(1-pyrrolidinyl)methyl]phenyl 2-[4-[2-(1-pyrrolidinyl)ethoxy]phenyl]benzo[b]thiophen-3-yl Ketone Dioxalate

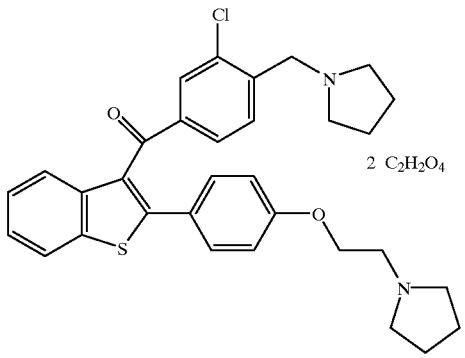

The free base of the title compound was prepared in 55% yield by essentially following the procedures outlined in Example 1, Part C from 2-[4-[2-(1-pyrrolidinyl)ethoxy]phenyl]benzo[b]thiophene (Example 4, Part A) and 3-chloro-4-[(1-pyrrolidiny)lmethyl]benzoic acid (Part C). The title compound was then prepared by essentially following the procedures outlined in Example 21, Part, C from the free base.

mp 97–102° C.; FDMS 544 (M–1); Anal. Calcd for $C_{32}H_{33}ClN_2O_2S \cdot 2.0C_2H_2O_4$: C, 59.62; H, 5.14; N, 3.86. Found: C, 59.41; H, 5.28; N, 3.90.

Part E. 3-[3-Chloro-4-[(1-pyrrolidinyl)methyl]benzyl]-2-[4-[2-(1-pyrrolidinyl)ethoxy]phenyl]benzo[b]thiophene Dioxalate The free base of the title compound was prepared in 57% yield by essentially following the procedures in Example 21, Part A from the ketone (free base of Part D). The title compound was prepared by essentially following the procedures outlined in Example 21, Part C from 3-[3-chloro-4-[(1-pyrrolidinyl)methyl]benzyl]-2-[4-[2-(1-pyrrolidinyl)ethoxy]phenyl]benzo[b]thiophene.

mp 126–130° C. dec.; FDMS 531 (M+); Anal. Calcd for $C_{32}H_{35}ClN_2OS \cdot 2.0C_2H_2O_4$: C, 60.80; H, 5.53; N, 3.94. Found: C, 60.63; H, 5.81; N, 3.87.

EXAMPLE 84

Preparation of 3-[3-Chloro-4-[(1-pyrrolidinyl) methyl]benzyl]-6-hydroxy-2-[4-[2-(1-pyrrolidinyl) ethoxy]phenyl]benzo[b]thiophene Dioxalate

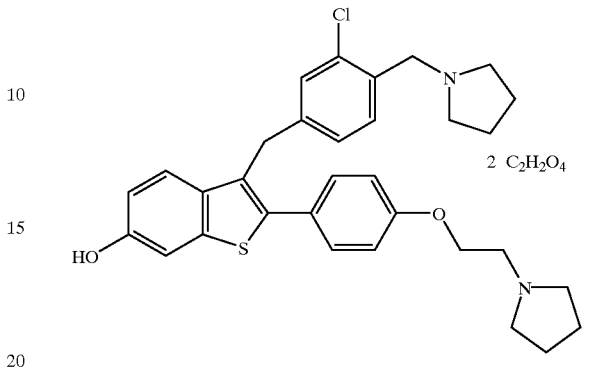

Part A. 6-Benzyloxy-2-(dimethylamino)benzo[b]thiophen-3-yl 3-Chloro-4-[(1-pyrrolidinyl)methyl]phenyl Ketone

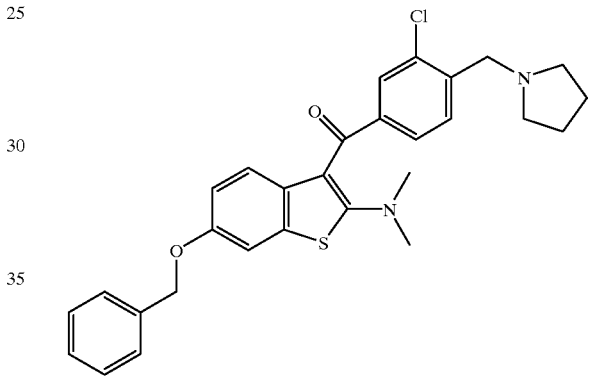

The title compound was prepared in 93% yield by essentially following the procedures outlined in Example 41, Part C (but using thionyl chloride to form the acid chloride) from 6-benzyloxy-2-(dimethylamino)benzo[b]thiophene (Example 81, Part B) and 3-chloro-4-[(1-pyrrolidinyl) methyl]benzoic acid (Example 83, Part C).

FDMS 504 (M–1); Anal Calcd. for $C_{29}H_{29}ClN_2O_2S$: C, 68.96; H, 5.79; N, 5.55. Found: C, 69.00; H, 5.62; N, 5.55.

Part B. 6-Benzyloxy-2-[4-[2-(1-pyrrolidinyl)ethoxy]phenyl] benzo[b]thiophen-3-yl 3-Chloro-4-[(1-pyrrolidinyl)methyl] phenyl Ketone

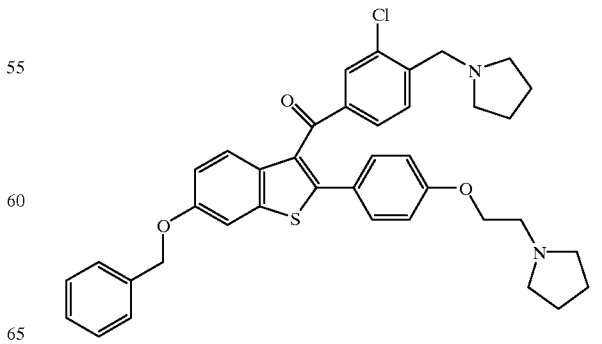

The title compound was prepared in 94% yield by essentially following the procedures in Example 81, Part E, from 4-[2-(1-pyrrolidinyl)ethoxy]phenyl magnesium bromide (Example 81, Part D) and 6-benzyloxy-2-(dimethylamino) benzo[b]thiophen-3-yl 3-chloro-4-[(1-pyrrolidinyl)methyl] phenyl ketone (Part A).

FDMS 651 (M+).

Part C. 3-Chloro-4-[(1-pyrrolidinyl)methyl]phenyl 6-Hydroxy-2-[4-[2-(1-pyrrolidinyl)ethoxy]phenyl]benzo[b]thiophen-3-yl Ketone Dioxalate

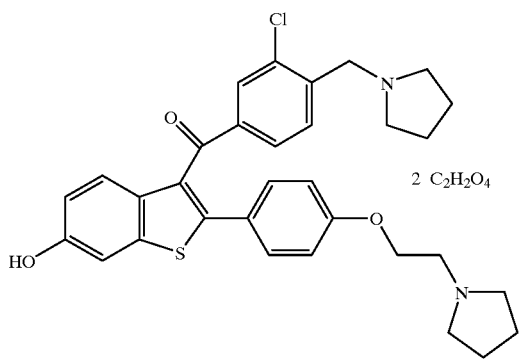

The free base of the title compound was prepared in 71% yield by essentially following the procedures outlined in Example 81, Part I from the ketone. The title compound was prepared by essentially following the procedure outlined in Example 21, Part C.

mp 174–178° C.; FDMS 561 (M+); Anal. Calcd for $C_{32}H_{33}ClN_2O_3S \cdot 1.75C_2H_2O_4$: C, 59.33; H, 5.12; N, 3.78. Found: 59.33; H, 5.27; N, 3.90.

Part D. 3-[3-Chloro-4-[(1-pyrrolidinyl)methyl]benzyl]-6-hydroxy-2-[4-[2-(1-pyrrolidinyl)ethoxy]phenyl]benzo[b]thiophene Dioxalate The free base of the title compound was prepared in 38% yield by essentially following the procedures outlined in Example 21, Part A, from the above ketone (Part C). The title compound was then prepared by essentially following the procedures outlined in Example 21, Part C.

FDMS 547 (M+); Anal. Calcd for $C_{32}H_{35}ClN_2O_2S \cdot 1.66C_2H_2O_4$: C, 60.90; H, 5.54; N, 4.02. Found: C, 60.90; H, 5.72; N 3.99.

EXAMPLE 85

Preparation of (±)-6-Hydroxy-3-[3-methoxy-4-[[trans-2-(1-piperidyl)cyclohexyl]oxy]benzyl]-2-[4-[2-(1-pyrrolidinyl)ethoxy]phenyl]benzo[b]thiophene Dioxalate

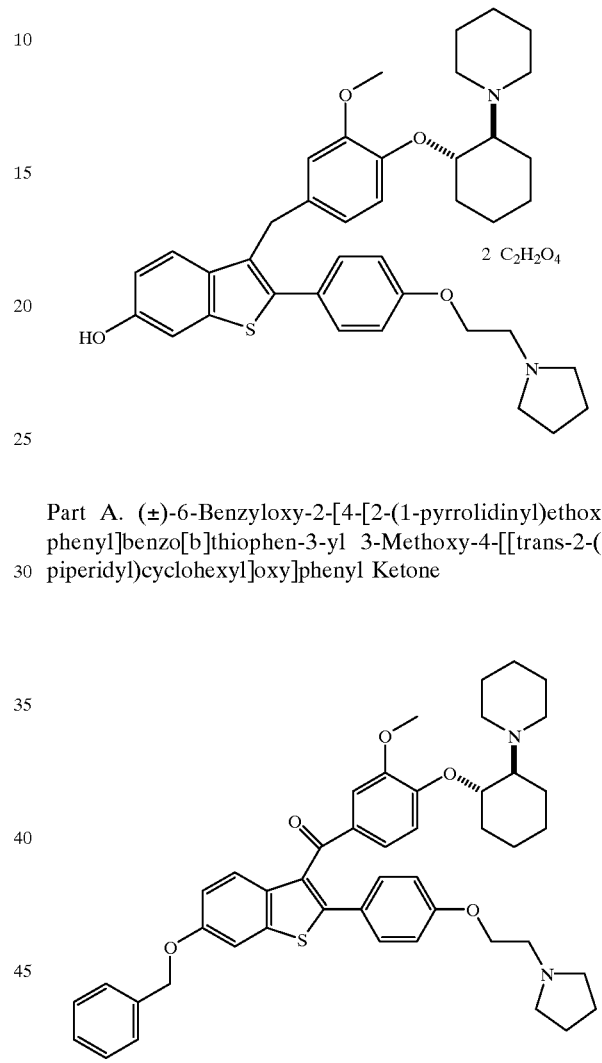

Part A. (±)-6-Benzyloxy-2-[4-[2-(1-pyrrolidinyl)ethoxy]phenyl]benzo[b]thiophen-3-yl 3-Methoxy-4-[[trans-2-(1-piperidyl)cyclohexyl]oxy]phenyl Ketone The title compound was prepared in 72% yield by essentially following the procedures outlined in Example 20, Part B, from 6-benzyloxy-2-[4-[2-(1-pyrrolidinyl)ethoxy]phenyl]benzo[b]thiophen-3-yl 4-hydroxy-3-methoxyphenyl ketone (Example 81, Part F) and (±)-trans-2-(1-piperidyl)cyclohexanol (Example 20, Part A).

FDMS 746 (M+); Anal. Calcd for $C_{46}H_{52}N_2O_5S \cdot 0.19CH_2Cl_2$: C, 72.89; H, 6.94; N, 3.68. Found: C, 72.84; H, 6.98; N, 4.03.

Part B. (±)-6-Hydroxy-3-[3-methoxy-4-[[trans-2-(1-piperidyl)cyclohexyl]oxy]benzyl]-2-[4-[2-(1-pyrrolidinyl)ethoxy]phenyl]benzo[b]thiophene Dioxalate The free base of the title compound was prepared in 46% yield by essentially following the procedures outlined in Example 21, Part A and Example 81, Part I from the ketone (Part A). The title compound was then prepared by essentially following the procedure outlined in Example 21, Part C.

mp 167–171° C. (dec.); FDMS 641 (M+); Anal. Calcd for $C_{39}H_{48}N_2O_4S \cdot 1.88C_2H_2O_4$: C, 63.39; H, 6.44; N, 3.46. Found: C, 63.39; H, 6.61; N, 3.27.

EXAMPLE 86

Preparation of (±)-6-Hydroxy-2-[4-[2-(1-pyrrolidinyl)ethoxy]phenyl]benzo[b]thiophen-3-yl 3-Methoxy-4 -[[trans-2-(1-piperidyl)cyclohexy]loxy]phenyl Ketone Dioxalate

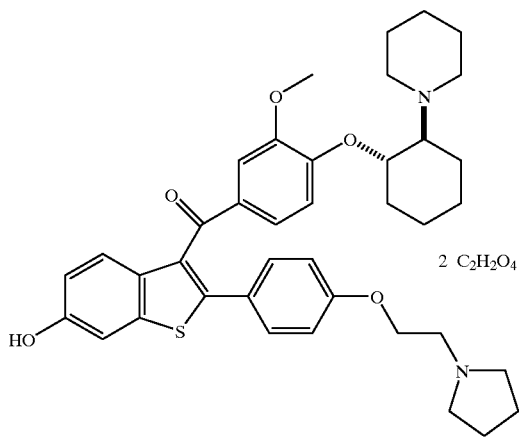

The free base of the title compound was prepared in 41% yield by essentially following the debenzylation procedure in Example 81, Part I, from the ketone (Example 85, Part A). The title compound was then prepared by essentially following the procedures in Example 21, Part C.

mp 151–155° C.; FDMS 655 (M+); Anal. Calcd for $C_{39}H_{46}N_2O_5S \cdot 1.76C_2H_2O_4$: C, 62.79; H, 6.14; N, 3.44. Found: C, 62.56; H, 6.54; N, 3.31.

EXAMPLE 87

Preparation of (±)-3-[[trans-2-(Dimethylamino)cyclohexyl]oxy]isoxazol-5-yl 6-Hydroxy-2-[4-[2-(1-pyrrolidinyl)ethoxy]phenyl]benzo[b]thiophen-3-yl Ketone Dioxalate

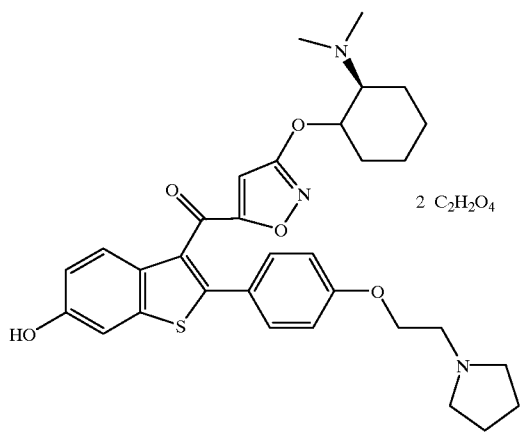

Part A. (±)-Methyl 3-[[trans-2-(Dimethylamino)cyclohexyl]oxy]isoxazole-5-carboxylate

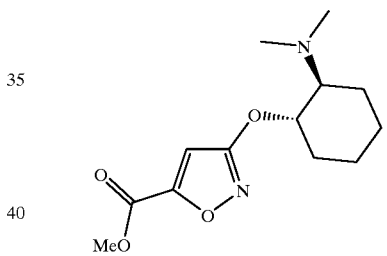

The title compound was prepared in 73% yield by essentially following the procedures outlined in Example 20, Part B from methyl 3-hydroxyisoxazole-5-carboxylate and (±)-trans-2-(dimethylamino)cyclohexanol (Example 79, Part A).

FDMS 268 (M+); Anal. Calcd for $C_{13}H_{20}N_2O_4$: C, 58.19; H, 7.51; N, 10.44. Found: C, 58.31; H, 7.51; N, 10.54.

Part B. (±)-3-[[trans-2-(Dimethylamino)cyclohexyl]oxy]isoxazole-5-carboxylic Acid

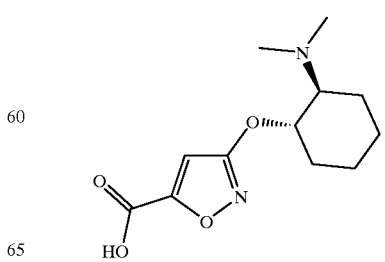

The title compound was prepared by essentially following the procedures outlined in Example 20, Part C, from the ester (Part A).

Part C. (±)-6-Benzyloxy-2-(dimethylamino)benzo[b]thiophen-3-yl 3-[[trans-2-(Dimethylamino)cyclohexyl]oxy]isoxazol-5-yl Ketone

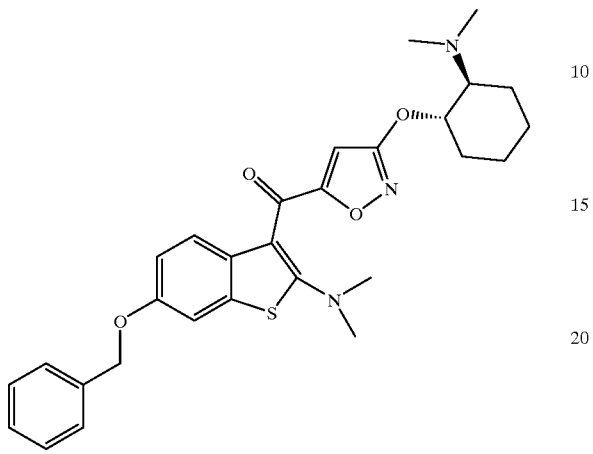

The title compound was prepared in 92% yield by essentially following the procedures outlined in Example 84, Part A from the isoxazole-5-carboxylic acid (Part B) and 6-benzyloxy-2-(dimethylamino)benzo[b]thiophene (Example 81, Part B).

FDMS 519 (M+); Anal. Calcd for $C_{29}H_{33}N_3O_4S \cdot 0.52H_2O$: C, 65.84; H, 6.49; N, 7.94. Found: C, 65.87; H, 6.12; N, 7.56.

Part D. (±)-6-Benzyloxy-2-[4-[2-(1-pyrrolidinyl)ethoxy]phenyl]benzo[b]thiophen-3-yl 3-[[trans-2-(Dimethylamino)cyclohexyl]oxy]isoxazol-5-yl Ketone

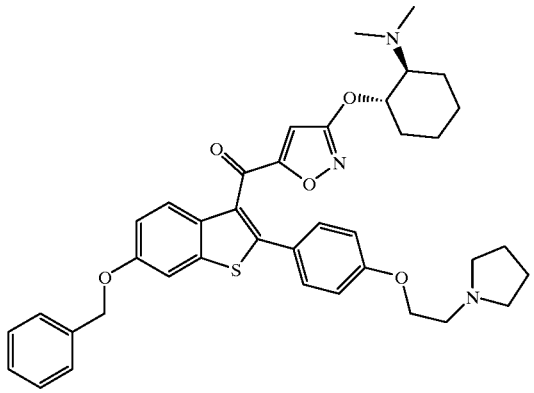

The title compound was prepared in 77% yield by essentially following the procedures outlined in Example 81, Part E from the ketone (Part C) and 4-[2-(1-pyrrolidinyl)ethoxy]phenyl magnesium bromide (Example 81, Part D).

FDMS 666 (M+).

Part E. (±)-3-[[trans-2-(Dimethylamino)cyclohexyl]oxy]isoxazol-5-yl 6-Hydroxy-2-[4-[2-(1-pyrrolidinyl)ethoxy]phenyl]benzo[b]thiophen-3-yl Ketone Dioxalate The free base of the title compound was prepared in 51% yield by essentially following the debenzylation procedure outlined in Example 81, Part I from the ketone (Part D). The title compound was prepared by essentially following the procedures in Example 21, Part C.

FDMS 576 (M+).

EXAMPLE 88

Preparation of 3-[4-[(Dimethylamino)methyl]-3-methoxybenzyl]-6-hydroxy-2-[4-[2-(1-pyrrolidinyl)ethoxy]phenyl]benzo[b]thiophene Dioxalate

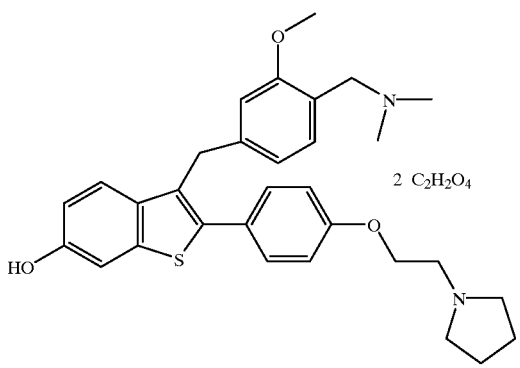

Part A. 4-Allyloxy-α-hydroxy-N,N-dimethylphenylthioacetamide

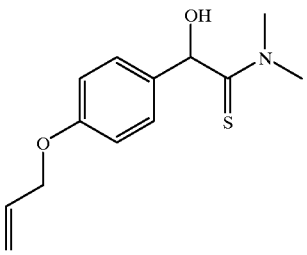

The title compound was prepared in 70% yield by essentially following the procedure in Example 81, Part A from 4-allyloxybenzaldehyde.

FDMS 251 (M+).

Part B. 6-Allyloxy-2-(dimethylamino)benzo[b]thiophene

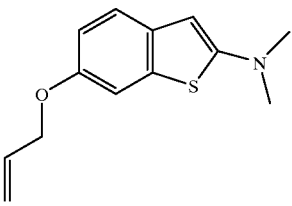

The title compound was prepared in 49% yield by essentially following the procedures outlined in Example 81, Part B from the thioacetamide (Part A).

FDMS 233 (M+); Anal. Calcd for $C_{13}H_{15}NOS$: C, 66.92; H, 6.48; N, 6.00. Found: C, 66.76; H, 6.54; N, 5.82.

Part C. Methyl 4-(Dimethylamino)methyl-3-methoxybenzoate

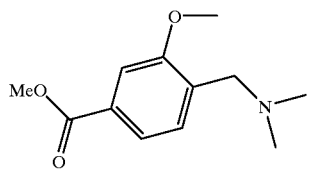

The title compound was prepared in 77% yield by essentially following the procedure outlined in Example 37, Part A from methyl 4-bromomethyl-3-methoxybenzoate (see Example 37, Part A) and dimethylamine.

FDMS 223 (M+); Anal. Calcd. for $C_{12}H_{17}NO_3$: C, 64.55; H, 7.67; N, 6.27. Found: C, 64.52; H, 7.68; N, 6.43.

Part D. 4-(Dimethylamino)methyl-3-methoxybenzoic Acid

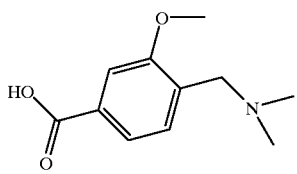

The crude title compound (+30% NaCl by weight) was prepared by essentially following the procedures outlined in Example 20, Part C from the methyl benzoate (Part C).

Part E. 6-Allyloxy-2-(dimethylamino)benzo[b]thiophen-3-yl 4-(Dimethylamino)methyl-3-methoxyphenyl Ketone

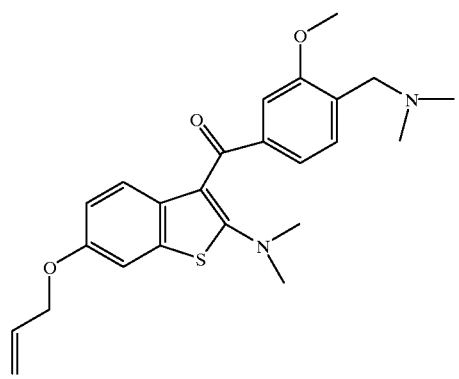

The title compound was prepared in 73% yield (23% SM recovered) by essentially following the procedures outlined in Example 84, Part A from 6-allyloxy-2-(dimethylamino) benzo[b]thiophene (Part B) and 4-(dimethylamino)methyl-3-methoxybenzoic acid (Part D).

FDMS 424 (M+); Anal. Calcd for $C_{24}H_{28}N_2O_3S$: C, 67.90; H, 6.65; N, 6.60. Found: C, 68.18; H, 6.77; N, 6.81.

Part F. 6-Allyloxy-2-[4-[2-(1-pyrrolidinyl)ethoxy]phenyl] benzo[b]thiophen-3-yl 4-(Dimethylamino)methyl-3-methoxyphenyl Ketone

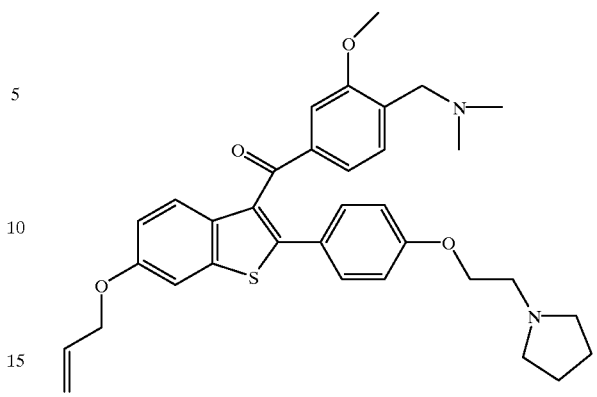

The title compound was prepared in 70% yield by essentially following the procedures outlined in Example 81, Part E from the ketone (Part E) and 4-[2-(1-pyrrolidinyl)ethoxy] phenyl magnesium bromide (Example 81, Part D).

FDMS 570 (M⁺); Anal. Calcd for $C_{34}H_{38}N_2O_4S$: C, 71.55; H, 6.71; N, 4.91. Found: C, 71.30; H, 6.85; N, 4.89.

Part G. 3-[4-(Dimethylamino)methyl-3-methoxybenzyl]-6-hydroxy-2-[4-[2-(1-pyrrolidinyl)ethoxy]phenyl]benzo[b] thiophene Dioxalate Deoxygenation of the ketone (Part F) was accomplished in 57% crude yield by essentially following the procedures outlined in Example 21, Part A.

The free base of the title compound was prepared by stirring a slurry of the above crude product (139 mg, 0.250 mmol), 10% Pd/C (150 mg), and p-toluenesulfonic acid monohydrate (105 mg, 0.551 mmol) in 3 mL of a 5:1 mixture of MeOH-THF solution at reflux for 22 h. The reaction was quenched with 3.5 mL of saturated aqueous NaHCO₃ solution, stirred vigorously for 15 min, and then concentrated to dryness under reduced pressure. The residue was taken up in 200 mL of THF and stirred vigorously for 30 min. The slurry was filtered through a pad of diatomaceous earth and washed with THF. The filtrate was concentrated under reduced pressure and the residue was flash chromatographed (silica gel, 10%[10% NH₄OH in MeOH]/ CH₂Cl₂) to afford 66.7 mg (0.129 mmol, 52%) of a light brown foam. The title compound was prepared by essentially following the procedures outlined in Example 21, Part C.

FDMS 517 (M+); Anal. Calcd for $C_{31}H_{36}N_2O_3S \cdot 2.0C_2H_2O_4 \cdot 0.7H_2O \cdot 1.2C_4H_8O_2$ (Hygroscopic): C, 58.65; H, 6.31; N, 3.44. Found: C, 58.27; H, 6.31; N, 3.41.

EXAMPLE 89

Preparation of 2-[4-[2-(Dimethylamino)ethoxy]
phenyl]-3-[4-(dimethylamino)methyl-3-
methoxybenzyl]-6-hydroxybenzo[b]thiophene
Dioxalate

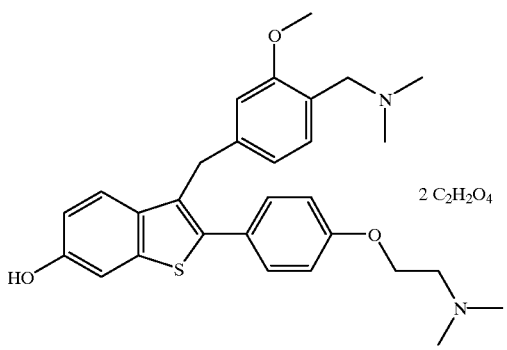

Part A. [2-(4-Chlorophenoxy)ethyl]dimethylamine

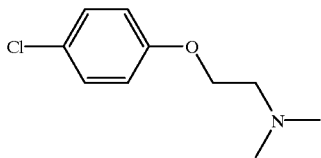

The title compound was prepared in 61% yield (26% SM recovered) by essentially following the procedure outlined in Example 34, Part A from 2-bromoethyl 4-chlorophenyl ether and dimethylamine.

FDMS 199 (M+); Anal. Calcd for $C_{10}H_{14}ClNO$: C, 60.15; H, 7.07; N, 7.01. Found: C, 59.88; H, 7.03; N, 7.22.

Part B. Preparation of 4-[2-(Dimethylamino)ethoxy]phenyl Magnesium Chloride

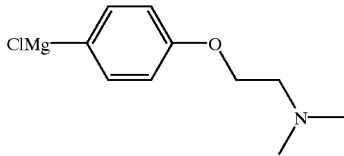

To the chlorobenzene (Part A) in 23.6 mL of freshly distilled THF was added 216 mg of magnesium turnings and a catalytic amount of iodine crystals. The mixture was heated at reflux for 36 h or until all the magnesium was consumed to afford ~23.6 mL of 0.38 M Grignard reagent solution as a milky white suspension.

Part C. 6-Allyloxy-2-[4-[2-(dimethylamino)ethoxy]phenyl] benzo[b]thiophen-3-yl 4-(Dimethylamino)methyl-3-methoxyphenyl Ketone

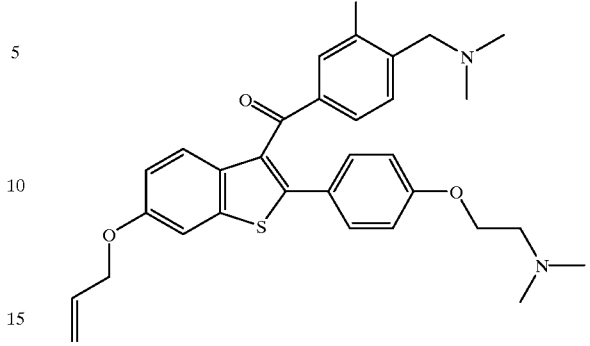

The title compound was prepared in 80% yield by essentially following the procedures outlined in Example 81, Part E from the ketone (Example 88, Part E) and the Grignard reagent (Part B).

FDMS 544 (M+); Anal. Calcd for $C_{32}H_{36}N_2O_4S$: C, 70.56; H, 6.66; N, 5.14. Found: C, 70.33; H, 6.73; N, 5.10.

Part D. 2-[4-[2-(Dimethylamino)ethoxy]phenyl]-3-[4-(dimethylamino)methyl-3-methoxybenzyl]-6-hydroxybenzo[b]thiophene Dioxalate Deoxygenation of the ketone (Part C) was accomplished in 46% by essentially following the procedures outlined in Example 21, Part A.

The free base of the title compound was prepared in 45% yield by essentially following the procedures outlined in Example 88, Part G. The title compound was then prepared by essentially following the procedure outlined in Example 21, Part C.

FDMS 491 (M+); Anal. Calcd for $C_{29}H_{34}N_2O_3S \cdot 2.0C_2H_2O_4 \cdot 1.06C_4H_8O_2$ (Hygroscopic): C, 58.54; H, 6.13; N, 3.67. Found: C, 58.62; H, 6.39; N, 3.79.

EXAMPLE 90

Preparation of 2-[4-[2-(Dimethylamino)ethoxy]
phenyl]-6-hydroxybenzo[b]thiophen-3-yl 4-
(Dimethylamino)methyl-3-methoxyphenyl Ketone
Dioxalate

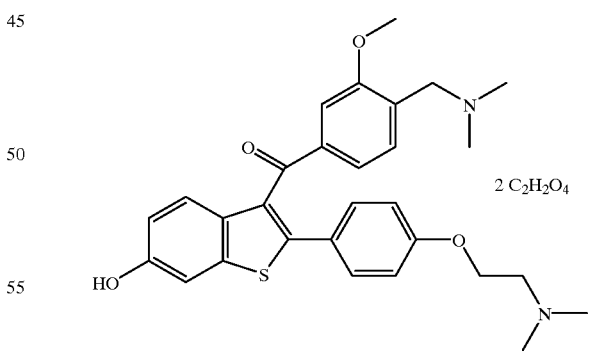

The free base of the title compound was prepared in 37% yield by essentially following the procedures outlined in Example 88, Part G from 6-allyloxy-2-[4-[2-(dimethylamino)ethoxy]phenyl]benzo[b]thiophen-3-yl 4-(dimethylamino)methyl-3-methoxyphenyl ketone (Example 89, Part C). The dioxalate was then prepared by using the procedures from Example 21, Part C from the free base.

FDMS 505 (M+); Anal. Calcd for C$_{29}$H$_{32}$N$_2$O$_4$S·2.0C$_2$H$_2$O$_4$: C, 57.89; H, 5.30; N, 4.09. Found: C, 57.75; H, 5.47; N, 4.13.

EXAMPLE 91

Preparation of 4-(Dimethylamino)methyl-3-methoxyphenyl 6-Hydroxy-2-[4-[2-(1-pyrrolidinyl)ethoxy]phenyl]benzo[b]thiophen-3-yl Ketone Dioxalate

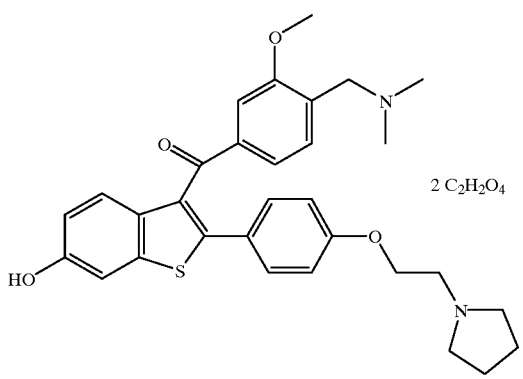

The free base of the title compound was prepared in 81% yield by essentially following the procedures outlined in Example 88, Part G from 6-allyloxy-2-[4-[2-(1-pyrrolidinyl)ethoxy]phenyl]benzo[b]thiophen-3-yl 4-(dimethylamino)methyl-3-methoxyphenyl ketone (Example 88, Part F). The dioxalate was then prepared by using the procedures from Example 21, Part C from the free base.

FDMS 531 (M+); Anal. Calcd for C$_{31}$H$_{34}$N$_2$O$_4$S·2.0C$_2$H$_2$O$_4$: C, 59.15; H, 5.39; N, 3.94. Found: C, 58.96; H, 5.73; N, 4.00.

EXAMPLE 92

Preparation of (±)-4-Hydroxy-3-[4-[[trans-2-(1-piperidyl)cyclohexyl]oxy]benzyl]-2-[4-[2-(1-pyrrolidinyl)ethoxy]phenyl]benzo[b]thiophene Dioxalate

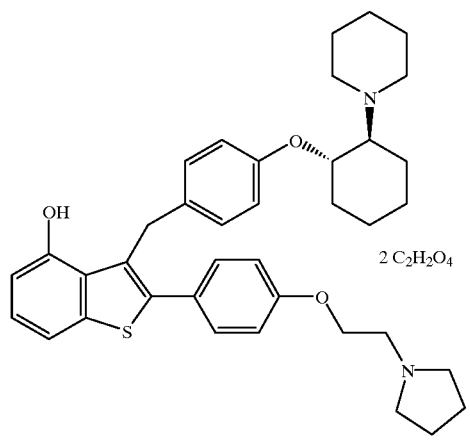

Part A. 4-Methoxybenzo[b]thiophene and 6-Methoxybenzo[b]thiophene

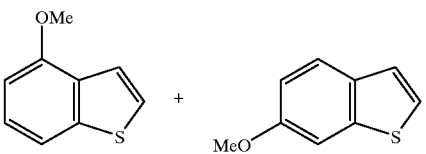

To a mixture of 25.10 g of 3-methoxybenzenethiol and 19.2 mL of bromoacetaldehyde dimethyl acetal in 200 mL of acetone was added 27 g of K$_2$CO$_3$ in one portion at room temperature. The white suspension was stirred vigorously at room temperature for 2 h. The mixture was filtered with thorough ethereal rinse. The filtrate was concentrated, taken up in 500 mL of Et$_2$O, and washed with 300 mL of H$_2$O, 0.5 N KOH, H$_2$O, and brine. The washings were back extracted with Et$_2$O (3×500 mL). Combined organic layers were dried over MgSO$_4$ and concentrated to afford 37.46 g (quantitative) of the crude 3-methoxybenzenethioacetaldehyde dimethyl acetal.

To a heated biphasic solution of 53.9 g of PPA in ca. 500 mL of chlorobenzene at 145° C. (bath temp.) was added dropwise 18.44 g of the crude acetal in ca. 100 mL of chlorobenzene over 4.5 h period. The dark green biphasic solution was heated at reflux with vigorous stirring for another 2 h. After cooling to room temperature, the organic layer was separated, concentrated, taken up in 500 mL of EtOAc, and washed with 300 mL of H$_2$O and brine. The PPA layer was dissolved in ca. 1.0 L of H$_2$O and extracted with EtOAc (4×500 mL). The extracts were washed with 300 mL of H$_2$O and 1:1 mixture of saturated aqueous NaHCO$_3$ and brine. Combined organic layers were dried over MgSO$_4$, concentrated and purified by PrepLC with hexanes to yield 2.40 g of 4-methoxybenzo[b]thiophene and 7.96 g of 6-methoxybenzo[b]thiophene (78% total) which were cleanly separated.

4-methoxybenzothiophene: FDMS 164.0 (M+); Anal. Calcd for C$_9$H$_8$OS: C, 65.82; H, 4.91; S, 19.52. Found: C, 66.01; H, 4.90; S, 19.60.

6-methoxybenzothiophene: FDMS 164.0 (M+).

Part B. 4-Methoxybenzo[b]thiophene-2-boronic Acid

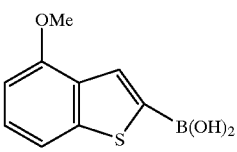

The title compound was prepared in 62% yield by essentially following the procedures in Example 1, Part A from 4-methoxybenzothiophene (Part A).

mp 267–270° C.; FDMS 570.

Part C. 4-Methoxy-2-[4-[2-(1-pyrrolidinyl)ethoxy]phenyl]benzo[b]thiophene

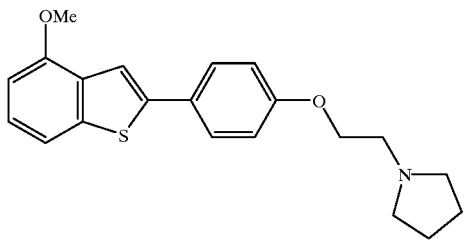

The title compound was prepared in 53% yield by essentially following the procedures outlined in Example 1, Part B from 4-methoxybenzo[b]thiophene-2-boronic acid (Part B).

FDMS 353 (M+).

Part D. 4-Hydroxy-2-[4-[2-(1-pyrrolidinyl)ethoxy]phenyl]benzo[b]thiophene

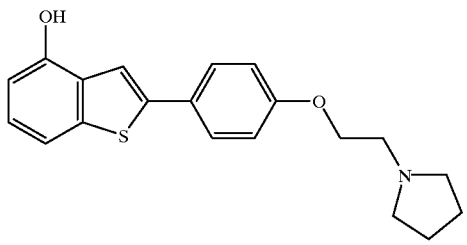

The title compound was prepared by essentially following the procedures outlined in Example 21, Part B from the methoxybenzo[b]thiophene (Part C). Recrystallization from EtOAc-hexanes afforded 712 mg (2.09 mmol, 38%) of off-white needle-like crystals.

mp 191–193° C.; FDMS 339 (M+); Anal. Calcd for $C_{20}H_{21}NO_2S \cdot 0.17H_2O$: C, 70.13; H, 6.28; N, 4.09. Found: C, 69.81; H, 6.10; N, 3.85.

Part E. 2-[4-[2-(1-pyrrolidinyl)ethoxy]phenyl]benzo[b]thiophen-4-yl 4-Fluorobenzoate

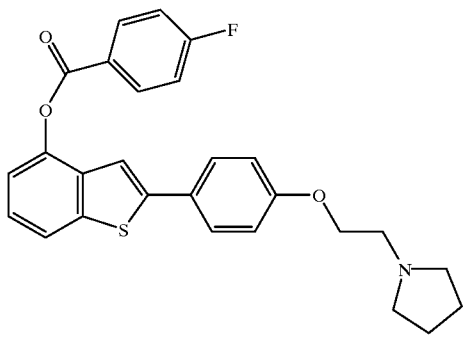

A mixture of 4-hydroxybenzo[b]thiophene (Part D) (607 Mg, 1.79 mmol) and 4-fluorobenzoyl chloride (233 μL, 1.97 mmol) in 10 mL of anhydrous dichloroethane was stirred at room temperature for 18 h. Another portion of 4-fluorobenzoyl chloride (166 μL, 1.48 mmol) was added and the reaction mixture was stirred for 3 days. A third portion of acid chloride (233 μl, 1.97 mmol) was added and the mixture was stirred for an additional 4 h. The reaction was then quenched with 25 mL of satd. $NaHCO_3$ soln, and the mixture was extracted (3×100 mL) with EtOAc. The combined organic layers were washed with 100 mL of brine, dried over $MgSO_4$, concentrated under reduced pressure, and flash chromatographed (silica gel, 5%[10% $NH_4OH$ in MeOH]/$CH_2Cl_2$) to afford 699 mg (1.51 mmol, 85%) of a white solid.

FDMS 461 (M+); Anal. Calcd for $C_{27}H_{24}FNO_3S \cdot 0.16NH_5O$: C, 69.42; H, 5.35; N, 3.48. Found: C, 69.40; H, 5.30; N, 3.65.

Part F. 3-(4-Fluorophenyl)carbonyl-2-[4-[2-(1-Pyrrolidinyl)ethoxy]phenyl]benzo[b]thiophen-4-yl 4-Fluorobenzoate

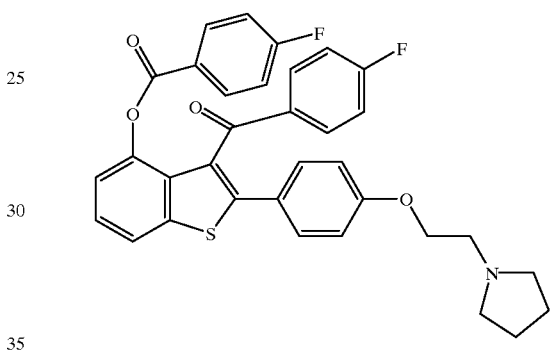

To a solution of 4-fluorobenzoate (Part E) (683 mg, 1.48 mmol) in 10.0 mL of anhydrous dichloroethane was added 4-fluorobenzoyl chloride (192 μL, 1.63 mmol) at room temperature. The reaction mixture was cooled to 0° C., and aluminum chloride (789 mg, 5.92 mmol) was added which turned the slurry into a dark red homogeneous solution. The reaction mixture was slowly warmed to room temperature and then stirred for 24 h. Another portion of aluminum chloride (395 mg, 2.94 mmol) and 4-fluorobenzoyl chloride (95 μL, 0.80 mmol) were added, and the reaction mixture was stirred at room temperature for another 24 h. The reaction mixture was then poured into 25 mL of ice-cold saturated aqueous $NaHCO_3$ solution. The mixture was taken up in EtOAc and the layers were separated. The aqueous layer was extracted with EtOAc (4×150 mL). The combined organic layers were washed with 100 mL of brine, dried over $MgSO_4$, concentrated under reduced pressure, and purified by flash chromatography (MPLC, silica gel, 40:57:3 THF-hexanes-$Et_3N$) to afford 193 mg (0.331 mmol, 22%) of white foam.

mp 58–63° C.; FDMS 583 (M+); Anal. Calcd for $C_{34}H_{27}F_2NO_4S$: C, 69.97; H, 4.66; N, 2.40. Found: C, 70.37; H, 5.00; N, 2.30.

Part G. (±)-4-Hydroxy-2-[4-[2-(1-pyrrolidinyl)ethoxy]phenyl]benzo[b]thiophen-3-yl 4-[[trans-2-(1-Piperidyl)cyclohexyl]oxy]phenyl Ketone

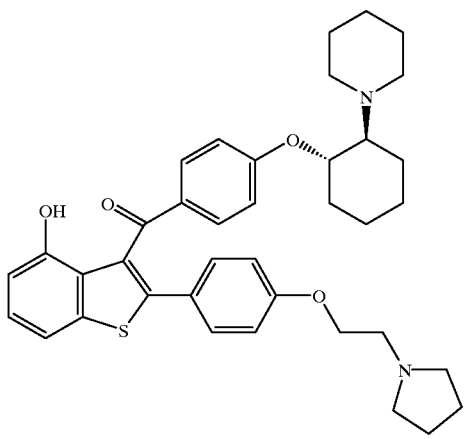

The title compound was prepared in 32% yield by essentially following the procedures in Example 75, Part G, from the 4-fluorobenzoate (Part F) and (±)-trans-2-(1-piperidyl)cyclohexanol (Example 20, Part A).

FDMS 625 (M+); Anal. Calcd for $C_{38}H_{44}N_2O_4S \cdot 2.5C_2H_2O_4 \cdot 3.2H_2O$: C, 56.91; H, 6.15; N, 3.09. Found: C, 56.61; H, 5.80; N, 3.47.

Part H. (±)-4-Hydroxy-3-[4-[[trans-2-(1-piperidyl)cyclohexyl]oxy]benzyl]-2-[4-[2-(1-pyrrolidinyl)ethoxy]phenyl]benzo[b]thiophene

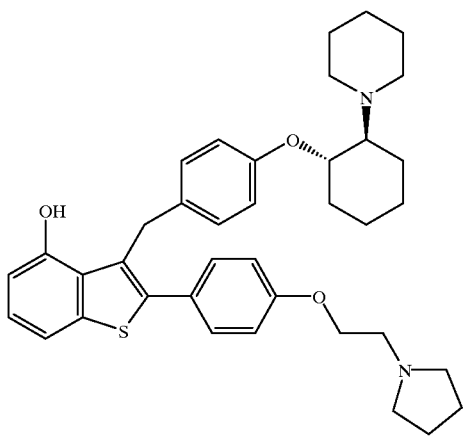

The title compound was prepared in 24% yield by essentially following the procedures outlined in Example 21, Part A from the ketone (Part G).

FDMS 610 (M+).

Part I. (±)-4-Hydroxy-3-[4-[[trans-2-(1-piperidyl)cyclohexyl]oxy]benzyl]-2-[4-[2-(1-pyrrolidinyl)ethoxy]phenyl]benzo[b]thiophene Dioxalate The title compound was prepared by essentially following the procedure outlined in Example 21, Part C from the free base (Part H).

FDMS 611 (M+); Anal. Calcd for $C_{38}H_{46}N_2O_3S \cdot 2.1C_2H_2O_4 \cdot 3.3H_2O$: C, 58.98; H, 6.66; N, 3.26. Found: C, 58.70; H, 6.32; N, 3.28.

EXAMPLE 93

Preparation of 5-Methoxy-3-[3-methoxy-4-[(1-pyrrolidinyl)methyl]benzyl]-2-[4-[2-(1-pyrrolidinyl)ethoxy]phenyl]benzo[b]thiophene Dioxalate

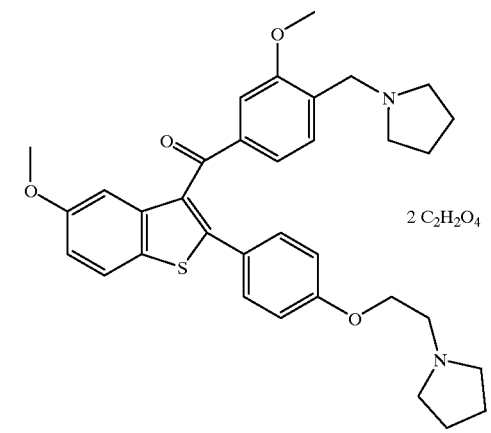

Part A. 5-Methoxy-2-[4-[2-(1-pyrrolidinyl)ethoxy]phenyl]benzo[b]thiophen-3-yl 3-Methoxy-4-[(1-pyrrolidinyl)methyl]phenyl Ketone Dioxalate The free base of the title compound was prepared in 37% yield by essentially following the procedures outlined in Example 41; Part C from 5-methoxy-2-[4-[2-(1-pyrrolidinyl)ethoxy]phenyl]benzo[b]thiophene (Example 71, Part C) and 3-methoxy-4-[(1-pyrrolidinyl)methyl]benzoic acid (Example 41, Part B). The title compound was prepared by essentially following the procedures outlined in Example 21, Part C from the free base.

FDMS 571 (M+); Anal. Calcd for $C_{34}H_{38}N_2O_4S \cdot 2.0C_2H_2O_4 \cdot 0.48C_4H_8O_2$: C, 60.46; H, 5.83; N, 3.53. Found: C, 60.57; H, 6.08; N, 3.58.

Part B. 5-Methoxy-3-[3-methoxy-4-(1-pyrrolidinylmethyl)benzyl]-2-[4-[2-(1-pyrrolidinyl)ethoxy]phenyl]benzo[b]thiophene Dioxalate The free base of the title compound was prepared in 68% yield by essentially following the procedures in Example 21, Part A from the free base of ketone (Part A). The title compound was prepared by essentially following the procedures in Example 21, Part C from the free base.

Free base: FDMS 557 (M+); Anal. Calcd for $C_{34}H_{40}N_2O_3S$: C, 73.35; H, 7.24; N, 5.03. Found: C, 73.49; H, 7.12; N, 5.03. Dioxalate: FDMS 557 (M+); Anal. Calcd

EXAMPLE 94

Preparation of 1-[2-[2-Fluoro-4-[[2-[4-[2-(1-pyrrolidinyl)ethoxy]phenyl]benzo[b]thiophen-3-yl]methyl]phenoxy]ethyl]pyrrolidine Dioxalate

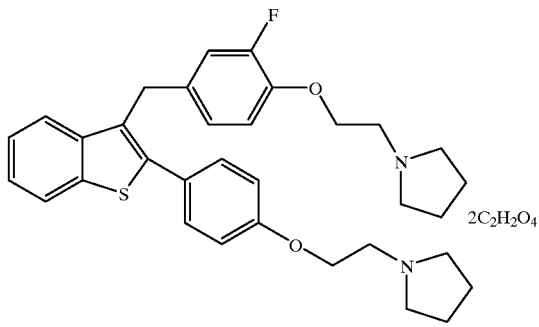

Part A. 3,4-Difluorophenyl 2-[4-[2-(1-Pyrrolidinyl)ethoxy]phenyl]benzo[b]thiophen-3-yl Ketone

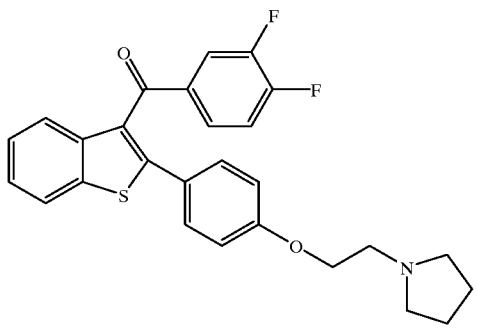

A slurry of 3.23 g (10 mmol) of 2-[4-[2-(1-pyrrolidinyl)ethoxy)phenyl]benzo[b]thiophene in 50 mL of 1,2 dichloroethane was treated with 1.76 g (10 mmol) of 3,4-difluorobenzoyl chloride at 0° C. The mixture was protected from light and 4.4 mL (40 mmol) $TiCl_4$ was added dropwise. The reaction was stirred at 0° C. for 5 h at which time it was quenched by carefully pouring it into 400 mL of saturated aqueous $NaHCO_3$. To this was added EtOAc (200 mL), and the two layers were separated. The aqueous layer was extracted with EtOAc (2×50 mL). The combined organic layers were dried over $Na_2SO_4$ and evaporated in vacuo to give a crude oil which was purified by chromatography ($SiO_2$; 2% MeOH in $CHCl_3$) to afford 1.7 g (3.7 mmol; 37%) of the ketone as a viscous oil.

$^1$H NMR ($CDCl_3$) δ 7.87-7.75 (m, 2 H), 7.63-7.56 (m, 1 H), 7.48-7.31 (m, 3 H), 7.30-7.25 (m, 2 H), 7.03-6.94 (m, 1 H), 6.79-6.75 (m, 2 H), 4.1 (t, 2 H), 2.8 (t, 2 H), 2.7-2.5 (m, 4 H), 1.84-1.80 (m, 4 H); FDMS 463 (M+); Anal. Calcd for $C_{27}H_{23}F_2NO_2S·1.08CHCl_3$: C, 56.93; H, 4.1; N, 2.36. Found: C, 56.90; H, 4.05; N, 2.45.

Part B. 3-Fluoro-4-[2-(1-pyrrolidinyl)ethoxy]phenyl 2-[4-[2-(1-Pyrrolidinyl)ethoxyphenyl]benzo[b]thiophen-3-yl Ketone

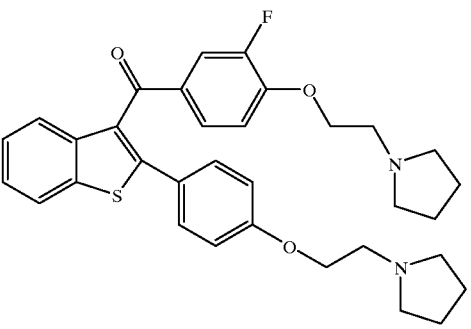

A 60% dispersion of sodium hydride in mineral oil (0.39 g, 9.8 mmol) was rinsed with hexanes and dried under reduced pressure. To this was added 30 mL of dry THF, followed by 1.1 g (9.8 mmol) of 1-(2-hydroxyethyl) pyrrolidine. After gas evolution had ceased, a solution of 2.27 g (4.90 mmol) of the 3,4-difluorophenyl 2-[4-[2-(1-pyrrolidinyl)ethoxy)phenyl]benzo[b]thiophen-3-yl ketone in 30 mL of THF was added. The reaction was stirred under a nitrogen atmosphere for 3 h at ambient temperature after which it was poured into a mixture of 100 mL of brine and 60 mL of EtOAc. The layers were separated and the aqueous layer was extracted with 30 mL of EtOAc. The combined organic layer was washed with brine (2×100 mL), dried over $Na_2SO_4$, and concentrated under reduced pressure to give 3.2 g of an oil. This was purified twice by chromatography ($SiO_2$; 50/45/5% THF/Hex/$Et_3N$; then 5% $CHCl_3$ in MeOH) to afford 1.6 g (2.9 mmol; 58%) of the desired compound as a viscous oil.

$^1$H NMR ($CDCl_3$) δ 7.87-7.84 (m, 1 H), 7.69-7.66 (m, 1 H), 7.58-7.54 (m, 1 H), 7.50-7.47 (m, 1 H), 7.38-7.26 (m, 3 H), 6.81-6.75 (m, 4 H), 4.15 (t, 2 H), 4.06 (t, 2 H), 2.91-2.86 (m, 4 H), 2.62-2.61 (m, 8 H), 1.82-1.77 (m, 8 H); FDMS 461 (M-97), 559 (M+1); Anal. Calcd for $C_{33}H_{35}FN_2O_3S·1.45CHCl_3$: C, 56.54; H, 5.02; N, 3.83. Found: C, 56.45; H, 5.0; N, 3.87.

100 mg was converted to the dioxalate salt. Anal. Calcd for $C_{33}H_{35}FN_2O_3S·2\ C_2H_2O_4·1\ H_2O$: C, 58.72; H, 5.46; N, 3.70. Found: C, 58.46; H, 5.06; N, 3.32.

Part C. 1-[2-[2-Fluoro-4-[[2-[4-[2-(1-pyrrolidinyl)ethoxy]phenyl]benzo[b]thiophen-3-yl]methyl]phenoxy]ethyl]pyrrolidine Dioxalate A solution of 1.1 g (2 mmol) of 3-fluoro-4-[2-(1-pyrrolidinyl)ethoxy]phenyl 2-[4-[2-(1-pyrrolidinyl)ethoxyphenyl]benzo[b]thiophen-3-yl ketone in 25 mL of THF at 0° O C. was treated with 10 mL of 1 M DIBAL-H in hexanes. The reaction was stirred at 0° C. for 30 min and was quenched by the addition of 5 mL of EtOAc and concentrated in vacuo. The resulting residue was immersed in an ice bath, then cautiously treated with 10 mL of TFA, followed by 186 mg (5 mmol) of $NaBH_4$. The reaction was stirred for 2 h, then evaporated in vacuo. The residue was taken up in 50 mL of 5 N NaOH and extracted with $CH_2Cl_2$ (2×30 mL). The combined extracts were dried over $Na_2SO_4$ and evaporated in vacuo to give 900 mg of an oil. Purification by chromatography (MPLC $SiO_2$; 60/35/5 THF/Hex/TEA) afforded 135 mg (0.25 mmol, 12%) of the title compound as an oil which was converted to the dioxalate salt according to the method of Example 1, Part C.

$^1$H NMR ($CDCl_3$) δ 7.95-7.85 (m, 1 H), 7.75-7.7 (m, 1 H), 7.6-7.65 (m, 1 H), 7.55-7.5 (m, 1 H), 7.45-7.38 (m, 4 H), 7.05 (s, 1 H), 6.85-6.8 (m, 2 H), 5.05 (s, 2 H), 4.20 (t, 2 H), 4.1 (t, 2 H), 3.0-2.9 (m, 4 H), 2.7-2.6 (m, 8 H), 1.8–1.9 (m,

8 H); Anal. Calcd for $C_{33}H_{37}FN_2O_2S\cdot1.65\ C_2H_2O_4$: C, 62.89; H, 5.86; N, 4.04. Found: C, 62.93; H, 6.05; N, 4.00.

EXAMPLE 95

Preparation of 1-[2-[4-[[2-[4-[2-(1-Pyrrolidinyl) ethoxy]phenyl]benzo[b]thiophen-3-yl]methyl]-2-trifluoromethylphenoxy]ethyl]pyrrolidine Dioxalate

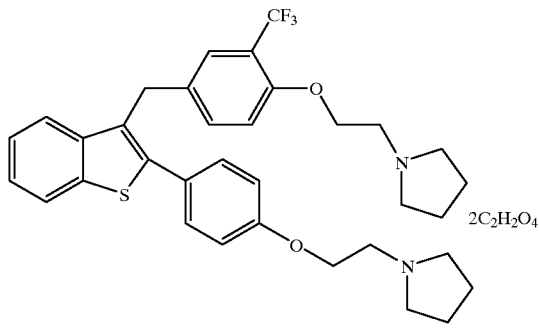

Part A. 4-Fluoro-3-trifluoromethylphenyl 2-[4-[2-(1-Pyrrolidinyl)ethoxy]phenyl]benzo[b]thiophen-3-yl Ketone

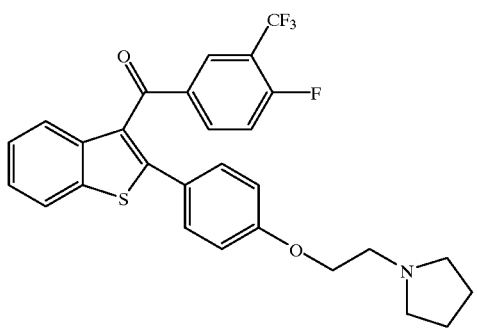

A slurry of 8 g (38.4 mmol) of 4-fluoro-3-trifluoromethyl benzoic acid in 30 mL of dichloromethane and 2 drops of DMF was treated with 6.70 mL (76.9 mmol) of $(COCl)_2$ and the mixture was stirred at ambient temperature for 4 h. The resulting solution was evaporated in vacuo, and the residual oil was distilled under reduced pressure to yield 7.2 g (31.8 mmol, 83%) of the acid chloride as a colorless oil.

A solution of 3.38 g (10.45 mmol) of 2-[4-[2-(1-pyrrolidinyl)ethoxy)phenyl]benzo[b]thiophene was dissolved in 200 mL of 1,2-dichloroethane and treated with 2.4 g (10.45 mmol) of the above acid chloride at 0° C. The reaction was protected from light and 4.4 mL (39.8 mmol) $TiCl_4$ was added dropwise. The reaction was stirred at ambient temperature for 4 h at which time it was quenched by carefully pouring it into 500 mL of saturated aqueous $NaHCO_3$. EtOAc (400 mL) was added and the two layers were separated. The aqueous layer was extracted with EtOAc (2×200 mL). The combined organic layers were dried over $Na_2SO_4$ and evaporated in vacuo to give an oil which was purified by chromatography ($SiO_2$; 78/20/2% Hex/THF/Et$_3$N) to afford 3.64 g (7.1 mmol; 68%) of the ketone as a solid.

$^1$H NMR (CDCl$_3$) δ 7.95-7.85 (m, 3 H), 7.45-7.35 (m, 3 H), 7.30-7.2 (m, 2 H), 7.1-7.00 (m, 1 H), 6.79-6.72 (m, 2 H), 4.05 (t, 2 H), 2.85 (t, 2 H), 2.7-2.5 (m, 4 H), 1.85-1.75 (m, 4 H); FDMS 514 (M+1); Anal. Calcd for $C_{28}H_{23}F_4NO_2S$: C, 65.89; H, 4.51; N, 2.73. Found: C, 65.75; H, 4.68; N, 2.78.

Part B. 2-[4-[2-(1-Pyrrolidinyl)ethoxyphenyl]benzo[b]thiophen-3-yl 4-[2-(1-Pyrrolidinyl)ethoxy]-3-trifluorophenyl Ketone

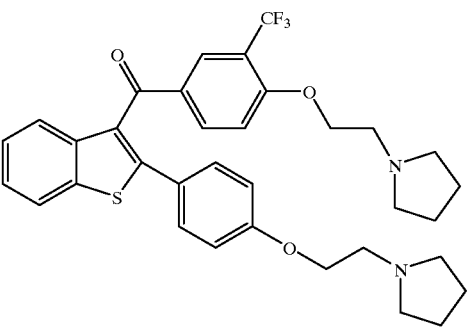

A 60% dispersion of sodium hydride in mineral oil (0.47 g, 11.7 mmol) was rinsed with hexanes and dried under reduced pressure. To this was added 25 mL of dry DMF followed by 1.35 g (11.7 mmol) 1-(2-hydroxyethyl) pyrrolidine. After gas evolution had ceased, a solution of 3 g (5.8 mmol) of 4-fluoro-3-trifluoromethylphenyl 2-[4-[2-(1-pyrrolidinyl)ethoxy]phenyl]benzo[b]thiophen-3-yl ketone in 30 mL of DMF was added. The reaction was stirred under a nitrogen atmosphere overnight at ambient temperature, after which it was poured into a mixture of 100 mL of brine and 60 mL of EtOAc. The layers were separated and the aqueous layer was extracted with 30 mL of EtOAc. The combined organic layer was washed with brine (2×100 mL), dried over $Na_2SO_4$, and concentrated under reduced pressure to 3.8 g of an oil. This was purified by chromatography ($SiO_2$; 5% MeOH/1% $NH_4OH$ in $CHCl_3$) to afford 3.07 g (5 mmol; 87%) of the named compound as a viscous oil.

FDMS 609 (M+1)

412 mg was converted to the dioxalate salt.

$^1$H NMR (DMSO-d$_6$) δ 8.1 (d, 1 H), 8.0-7.9 (m, 2 H), 7.65 (d, 1 H), 7.5-7.4 (m, 2 H), 7.4-7.3 (m, 2 H), 7.15 (d, 1 H), 6.9-7.0 (d, 2 H), 4.55 (bs, 4 H), 4.55-4.4 (m, 2 H), 4.2-4.3 (m, 2 H), 3.4-3.6 (m, 4 H); 3.1-3.3 (m, 8 H), 1.8-1.95 (m, 8 H); Anal. Calcd for $C_{34}H_{35}F_3N_2O_3S\cdot1.5C_2H_2O_4$: C, 59.75; H, 5.15; N, 3.77. Found: C, 59.61; H, 5.16; N, 3.80.

Part C. 1-[2-[4-[[2-[4-[2-(1-Pyrrolidinyl)ethoxy]phenyl] benzo[b]thiophen-3-yl]methyl]-2-trifluoromethylphenoxy] ethyl]pyrrolidine Dioxalate A solution of 1 g (1.64 mmol) of the 2-[4-[2-(1-pyrrolidinyl)ethoxyphenyl]benzo[b]thiophen-3-yl 4-[2-(1-pyrrolidinyl)ethoxy]-3-trifluorophenyl ketone in 30 mL of THF at 0° C. was treated with 9 mL of 1 M DIBAL-H in hexanes. The reaction was stirred at 0° C. for 1 h and was quenched by the addition of 5 mL of EtOAc and concentrated in vacuo. The resulting residue was immersed in an ice bath then cauiously treated with 10 mL of TFA followed by 124 mg (3.30 mmol) of $NaBH_4$. The reaction was stirred for 2 h then evaporated in vacuo. The residue was partitioned between saturated aqueous $NaHCO_3$ (25 mL) and $CHCl_3$ (50 mL). The layers were separated and the aqueous layer was extracted with $CHCl_3$ (3×30 mL). The combined organic layers were dried over $Na_2SO_4$ and evaporated in vacuo to give 1.1 g of an oil. Purification by chromatography ($SiO_2$; 2% MeOH in $CHCl_3$) afforded 353 mg (0.59 mmol 36%) of the title compound as an oil which was converted to the dioxalate salt according to the method of Example 1, Part C.

$^1$H NMR (Free Base-CDCl$_3$) δ 7.84-7.81 (m, 1 H), 7.48-7.45 (m, 1 H), 7.4-7.31 (m, 3 H), 7.31-7.15 (m, 2 H), 7.15-7.11 (m, 1 H), 6.93-6.98 (m, 2 H), 6.82 (d, 1 H), 4.2

(s, 2 H), 4.15-4.1 (m, 4 H), 2.95 (t, 4 H); 2.65-2.55 (m, 8 H), 1.85-1.75 (m, 8 H); Anal. Calcd for $C_{38}H_{41}F_3N_2O_{10}S$: C, 58.91; H, 5.33; N, 3.62. Found: C, 58.80; H, 5.27; N, 3.57.

EXAMPLE 96

Preparation of 3-Nitro-4-[2-(1-pyrrolidinyl)ethoxy] phenyl 2-[4-[2-(1-Pyrrolidinyl)ethoxyphenyl]benzo[b]thiophen-3-yl Ketone Dioxalate

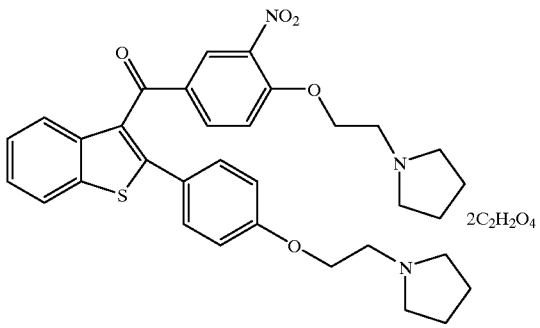

Part A. Methyl 3-Nitro-4-[2-(1-pyrrolidinyl)ethoxy]benzoate Hydrochloride

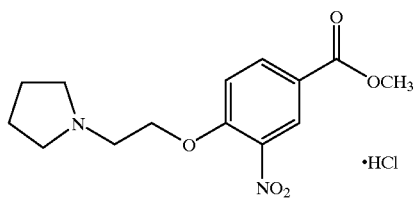

A mixture of 32 g (162.4 mmol) of methyl 4-hydroxy-3-nitrobenzoate, 51.13 g (194.9 mmol) of triphenylphosphine, 22.45 g (194.9 mmol) of 1-(2-hydroxyethylpyrrolidine), and 600 mL of $CH_2Cl_2$ was cooled to 0° C. and treated with 33.95 g of (194.9 mmol) diethyl azodicarboxylate. The cooling bath was removed and the reaction was stirred at ambient temperature for 16 h. It was concentrated to dryness under reduced pressure, mixed with 200 mL of $CHCl_3$ and filtered. The filtrate was chromatographed ($SiO_2$; 3% MeOH in $CHCl_3$) to give 14.63 g of product still contaminated with methyl 4-hydroxy-3-nitrobenzoate. It was dissolved in 200 mL of EtOAc and treated with HCl gas for 2 min. The resulting solid was filtered to yield 11.81 g (36 mmol, 22%) of the HCl salt of the named product.

$^1$H NMR (DMSO-$d_6$) δ 10.85–11 (bs, 1 H), 8.45 (d, 1 H), 8.25 (dd, 1 H), 7.58 (d, 1 H), 4.65 (t, 2 H), 3.9 (s, 3 H), 3.7-3.55 (m, 4 H), 3.05-3.4 (m, 2 H); 2.1-1.8 (m, 4 H); FDMS 294 (M+); Anal. Calcd for $C_{14}H_{18}N_2O_5 \cdot HCl$: C, 50.84; H, 5.79; N, 8.47. Found: C, 50.84; H, 5.70; N, 8.62.

Part B. 3-Nitro-4-[2-(1-pyrrolidinyl)ethoxy]benzoic Acid Hydrochloride

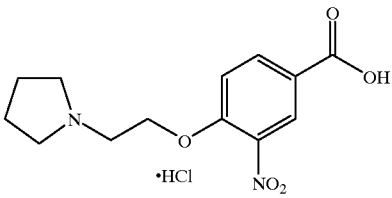

Methyl 3-nitro-4-[2-(1-pyrrolidinyl)ethoxy]benzoate (5.9 g, 20 mmol) was mixed with 60 mL of 5 N aqueous HCl and refluxed 16 h. It was mixed with toluene/EtOH and concentrated under reduced pressure to dryness. The resulting solid was tritrated with hot EtOAc to afford 5.7 g (18 mmol, 90%) of the benzoic acid hydrochloride.

$^1$H NMR (DMSO-$d_6$) δ 8.36 (d, 1 H), 8.22(dd, 1 H), 7.45 (d, 1 H), 4.21 (t, 2 H), 3.65-3.4 (m, 5 H), 3.0–3.2 (m, 3 H), 2.1-1.7 (m, 4 H); FDMS 280 (M+); Anal. Calcd for $C_{13}H_{16}N_2O_5 \cdot HCl \cdot 0.11$ toluene: C, 50.60; H, 5.50; N, 8.47. Found: C, 50.60; H, 5.51; N, 8.57.

Part C. 3-Nitro-4-[2-(1-pyrrolidinyl)ethoxy]phenyl 2-[4-[2-(1-Pyrrolidinyl)ethoxyphenyl]benzo[b]thiophen-3-yl Ketone Dioxalate A mixture of 2 g (6.3 mmol) of 3-nitro-4-[2-(1-pyrrolidinyl)ethoxy]benzoic acid hydrochloride, 20 mL of $SOCl_2$, 50 mL of 1,2-dichloroethane and 2 drops of DMF was heated at reflux for 16 h then evaporated in vacuo to dryness. The resulting solid was dissolved in 50 mL of 1,2-dichloroethane and concentrated under reduced pressure. It was redissolved in 50 mL of 1,2-dichloroethane and treated sequentially with a solution of 2 g (6.2 mmol) of 2-[4-[2-(1-pyrrolidinyl)ethoxy]phenyl]benzo[b]thiophene in 150 mL of 1,2-dichloroethane and 3.3 g (24.7 mmol) of $AlCl_3$ at 0° C. The reaction was protected from light and stirred at 0° C. for 5 h at which time it was quenched by carefully pouring it into 200 mL of vigorously stirred saturated aqueous $NaHCO_3$. A solution of 200 mL of EtOAc and 400 mL of THF was added and the mixture was filtered through diatomaceous earth and the two layers were separated. The aqueous layer was extracted with EtOAc (200 mL). The combined organic layers were washed with brine, dried over $Na_2SO_4$ and evaporated in vacuo to give an oil which was purified by chromatography ($SiO_2$; 10% MeOH in $CHCl_3$) to afford 1.26 g (2.2 mmol; 36%) of the desired compound as an oil. A sample of 200 mg was converted to the dioxalate salt according to the method of Example 1, Part C.

$^1$H NMR (Free Base-$CDCl_3$) δ 8.17 (d, 1 H), 7.93 (dd, 1 H), 7.87 (dd, 1 H), 7.81-7.78 (m, 1 H), 7.41-7.38 (m, 2 H), 7.31-7.27 (m, 2 H), 6.93 (d, 1 H), 6.78-6.75 (m, 2 H), 4.22 (t, 2 H), 4.04 (t, 2 H), 2.92 (t, 2 H), 2.86 (t, 2 H), 2.61-2.58 (m, 8 H), 1.81-1.76 (m, 8 H); FDMS 586 (M+1); Anal. Calcd for $C_{33}H_{35}N_3O_5S \cdot 2C_2H_2O_4$: C, 58.03; H, 5.13; N, 5.49. Found: C, 58.30; H, 5.13; N, 5.74.

EXAMPLE 97

Preparation of 3-Amino-4-[2-(1-pyrrolidinyl)
ethoxy]phenyl 2-[4-[2-(1-Pyrrolidinyl)
ethoxyphenyl]benzo[b]thiophen-3-yl Ketone
Dioxalate

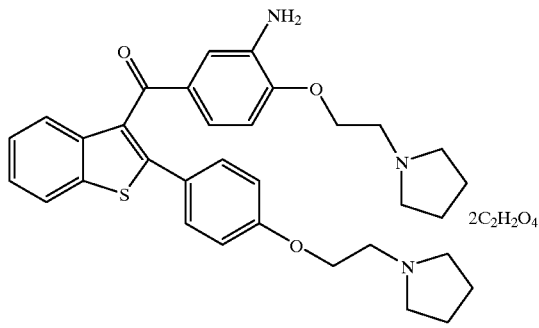

A solution of 3-nitro-4-[2-(1-pyrrolidinyl)ethoxy]phenyl 2-[4-[2-(1-pyrrolidinyl)ethoxyphenyl]benzo[b]thiophen-3-yl ketone (0.57 g 1 mmol) in 10 mL of EtOH and 10 mL of HOAc was hydrogenated in a shaken hydrogenation apparatus for 60 h with 0.5 g of 5% Pd/C and an initial hydrogen pressure of 4.1 bar. The mixture was filtered through diatomaceous earth and concentrated under reduced pressure to an oil. This was partitioned between 10 mL of saturated aqueous $NaHCO_3$ and a 70/30 mixture of EtOAc and MeOH. The organic layer was dried over $Na_2SO_4$ and concentrated in vacuo to an oil which was purified by chromatrography ($SiO_2$; 5% MeOH/1% $NH_4OH$ in $CHCl_3$) to afford 0.26 g (0.47 mmol; 47%) of the title compound as an oil which was converted to the dioxalate salt according to the method of Example 1, Part C.

$^1$H NMR (Free Base-$CDCl_3$) δ 7.82-7.79 (m, 1 H), 7.57-7.55 (m, 1 H), 7.37-7.30 (m, 2 H), 7.29-7.26 (m, 3 H), 7.12-7.08 (m, 1 H), 6.78-6.75 (m, 2 H), 6.58 (d, 1 H), 4.07 (t, 2 H), 4.04 (t, 2 H), 4.00 (bs, 2 H), 2.88-2.81 (m, 4 H), 2.59-2.55 (m, 8 H), 1.79-1.74 (m, 8 H); FDMS 556 (M+1); Anal. Calcd for $C_{33}H_{37}N_3O_3S \cdot 0.6C_2H_2O_4 \cdot 1.8$ MeOH: C, 56.69; H, 5.87; N, 4.95. Found: C, 55.98; H, 5.88; N, 5.24

EXAMPLE 98

Preparation of 1-[2-[2-Nitro-4-[[2-[4-[2-(1-pyrrolidinyl)ethoxy]phenyl]benzo[b]thiophen-3-yl]methyl]phenoxy]ethyl]pyrrolidine Dioxalate

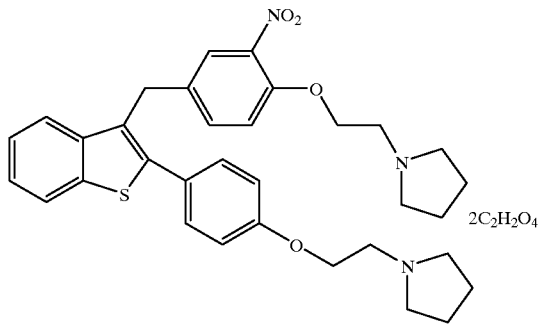

A solution of 5.7 g (9.7 mmol) of 3-nitro-4-[2-(1-pyrrolidinyl)ethoxy]phenyl 2-[4-[2-(1-pyrrolidinyl) ethoxyphenyl]benzo[b]thiophen-3-yl ketone in 200 mL of $CH_2Cl_2$ at 0° C. was treated with 49 mL of 1 M DIBAL-H in hexanes. The reaction was stirred at 0° C. for 1 h then concentrated in vacuo to an oil. The resulting residue was immersed in an ice bath then cautiously treated with 25 mL of TFA dropwise, followed by 736 mg (19.5 mmol) of $NaBH_4$. The reaction was stirred for 30 min then evaporated in vacuo. The residue was partitioned between saturated aqueous $NaHCO_3$ (25 mL) and EtOAc (300 mL). Aqueous 5 N NaOH (50 mL) was added, and the layers were separated. The aqueous layer was extracted with EtOAc (3×100 mL). The combined organic layers were dried over $Na_2SO_4$ and evaporated in vacuo to give 8 g of an oil. Purification by chromatography ($SiO_2$; 2% MeOH in $CHCl_3$) afforded 3.1 g (5.4 mmol 56%) of the title compound as an oil which was converted to the dioxalate salt according to the method of Example 1, Part C.

$^1$H NMR (Free Base-$CDCl_3$) δ 7.85-7.82 (m, 1 H), 7.62 (d, 1 H), 7.46-7.43 (m, 1 H), 7.38-7.29 (m, 4 H), 7.20 (dd, 1 H), 6.97-6.91 (m, 3 H), 4.22 (s, 2 H), 4.19-4.12 (m, 4 H), 2.92 (t, 4 H), 2.65-2.60 (m, 8 H), 1.84-1.76 (m, 8 H); FDMS 572 (M+1); Anal. Calcd for $C_{33}H_{37}N_3O_4S \cdot 2C_2H_2O_4$: C, 59.11; H, 5.50; N, 5.59. Found: C, 59.40; H, 5.46; N, 5.87

EXAMPLE 99

Preparation of 1-[2-[2-Amino-4-[[2-[4-[2-(1-pyrrolidinyl)ethoxy]phenyl]benzo[b]thiophen-3-yl]methyl]phenoxy]ethyl]pyrrolidine Dioxalate

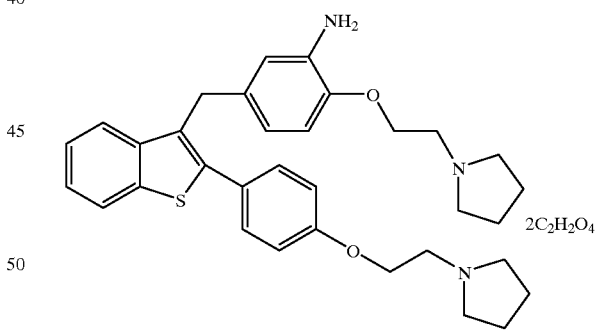

The title compound was prepared in 36% yield from 1-[2-[2-nitro-4-[[2-[4-[2-(1-pyrrolidinyl)ethoxy]phenyl] benzo[b]thiophen-3-yl]methyl]phenoxy]ethyl]pyrrolidine by essentially following the procedure detailed for the preparation of Example 97.

Anal. Calcd for $C_{33}H_{39}N_3O_2S \cdot 2C_2H_2O_4 \cdot 0.95$ MeOH: C, 60.59; H, 6.27; N, 5.59. Found: C, 60.62; H, 6.12; N, 5.30

EXAMPLE 100

Preparation of 3-Bromo-4-[2-(1-pyrrolidinyl)
ethoxy]phenyl 2-[4-[2-(1-Pyrrolidinyl)
ethoxyphenyl]benzo[b]thiophen-3-yl Ketone
Dioxalate

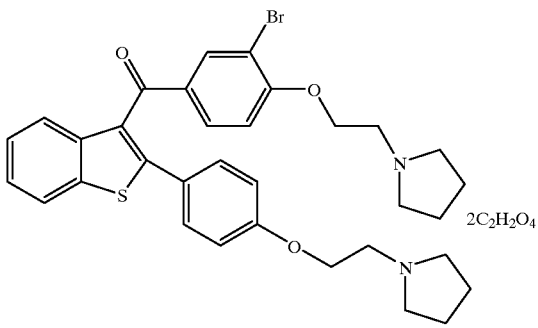

Part A. 3-Bromo-4-methoxyphenyl 2-(4-Methoxyphenyl)
benzo[b]thiophen-3-yl Ketone

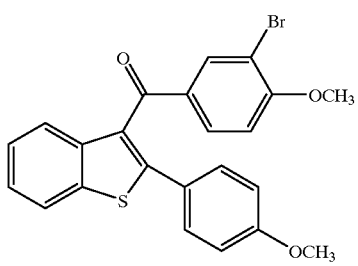

A slurry of 13.35 g (58 mmol) of 3-bromo-4-methoxybenzoic acid in 120 mL of 1,2-dichloroethane and 1 mL of DMF was treated with 8.4 mL (116 mmol) of $SOCl_2$ and the mixture was heated at reflux for 16 h. The resulting solution was evaporated in vacuo to an oil which was mixed with 50 mL of 1,2-dichloroethane and reconcentrated under reduced pessure.

A solution of the above oil in 120 mL of 1,2-dichloroethane was treated with 13.86 g (58 mmol) of 2-[4-methoxy)phenyl]benzo[b]thiophene. The mixture was cooled to 0° C., protected from light and treated with 25 mL (228 mmol) of $TiCl_4$ dropwise. The reaction was stirred at 0° C. for 3 h at which time it was quenched by the careful addition of 100 mL of saturated aqueous $NaHCO_3$. The layers were separated and the organic layer was washed with saturated aqueous $NaHCO_3$. It was dried over $Na_2SO_4$ and evaporated in vacuo to give 28 g of a solid which was purified by chromatography ($SiO_2$; 50% $CHCl_3$ in Hex) to afford 17.13 g (37.81 mmol; 65%) of the ketone as a solid.

$^1$H NMR ($CDCl_3$) δ 8.03 (d, 1 H), 7.88-7.85 (m, 1 H), 7.72-7.67 (m, 2 H), 7.38-7.33 (m, 4 H), 6.81-6.71 (m, 3 H), 3.88 (s, 3 H), 3.76 (s, 3 H).

Part B. 3-Bromo-4-hydroxyphenyl 2-(4-Hydroxyphenyl)
benzo[b]thiophen-3-yl Ketone

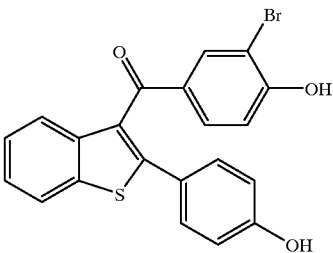

A 0° C. solution of 6.5 g (14.3 mmol) of 3-bromo-4-methoxyphenyl 2-(4-methoxyphenyl)benzo[b]thiophen-3-yl ketone in 300 mL of dichloromethane was treated with 15.3 g (115 mmol) of $AlCl_3$, followed by 17 mL (230 mmol) of ethanethiol. The cold bath was removed and the reaction was stirred at ambient temperature for 3.5 h. The reaction mixture was cooled to 0° C. and poured into cold water. The layers were separated and the aqueous layer was extracted with EtOAc (2×150 mL). The combined organic layers were dried over $Na_2SO_4$ and evaporated to give 5.9 g (13.9 mmol, 97%) of an oil which crystallized out when mixed with $CH_2Cl_2$.

$^1$H NMR (DMSO-$d_6$) δ 11.4 (bs, 2 H), 8.1-8.05 (m, 1 H), 7.8 (d, 1 H), 7.62-7.5 (m, 2 H), 7.45-7.35 (m, 2 H), 7.25 (d, 2 H), 6.85 (d, 1 H), 6.75 (d, 2 H); FDMS 425.8 (M+1).

Part C. 3-Bromo-4-[2-(1-pyrrolidinyl)ethoxy]phenyl 2-[4-[2-(1-Pyrrolidinyl)ethoxyphenyl]benzo[b]thiophen-3-yl Ketone Dioxalate A solution of 1 g (2.4 mmol) of the above bis-hydroxybenzothiophene in 25 mL of DMF was treated with 1.6 g (9.6 mmol) of 1-(2-chloroethyl)pyrrolidine hydrochloride followed by 4.7 g (14.4 mmol) of $Cs_2CO_3$. The mixture was heated to 85° C. for 16 h at which time it was cooled and poured into 100 mL of brine and extracted with EtOAc (3×50 mL). The combined organic layers were dried over $MgSO_4$ and evaporated to give 1.1 g of an oil which was purified by radial chromatography ($SiO_2$; 60:35:5 hexanes-THF-TEA) to afford 0.68 g (1.1 mmol; 46%) of an oil. The oil was converted to the dioxalate salt according to the method of Example 1, Part C.

$^1$H NMR (Free Base-$CDCl_3$) δ 8.31 (d, 1 H), 7.84 (dd, 1 H), 7.71-7.68 (m, 1 H), 7.65 (dd, 1 H), 7.38-7.32 (m, 3 H), 6.98 (s, 1 H), 6.8-6.77 (m, 2 H), 6.69 (d, 1 H), 4.13 (t, 2 H), 4.05 (t, 2 H), 2.93 (t, 2 H), 2.86 (t, 2 H), 2.67-2.57 (m, 8 H), 1.81-1.76 (m, 8 H); FDMS 619 (M+).

EXAMPLE 101

Preparation of 1-[2-[2-Bromo-4-[[2-[4-[2-(1-pyrrolidinyl)ethoxy]phenyl]benzo[b]thiophen-3-yl]methyl]phenoxy]ethyl]pyrrolidine Dioxalate

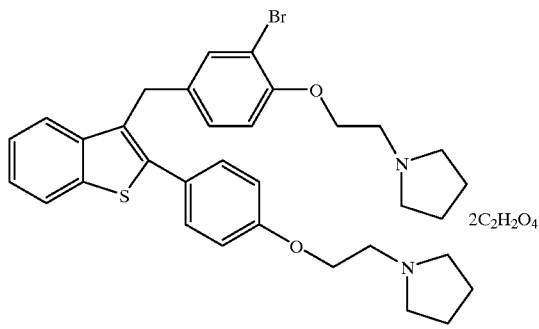

To a solution of 83 mg (2.20 mmol) of LAH in 20 mL of dry THF was added dropwise a solution of 0.68 g (1.1 mmol) of 3-bromo-4-[2-(1-pyrrolidinyl)ethoxy]phenyl 2-[4-[2-(1-pyrrolidinyl)ethoxyphenyl]benzo[b]thiophen-3-yl ketone in 15 mL of dry THF at 0° C. The reaction was stirred at ambient temperature for 2 h then quenched with 5 mL of EtOAc and poured into 100 mL of brine. The mixture was extracted with 150 mL of 20% MeoH in EtOAc. The extracts were dried over $MgSO_4$ and concentrated to 537 mg of an oil.

The resulting oil was mixed with 10 mL of TFA, cooled to 0° C. and treated with 65 mg (1.73 mmol) of $NaBH_4$. The cooling bath was removed and the reaction was stirred for 16 h. It was evaporated in vacuo and partitioned between saturated aqueous $NaHCO_3$ (25 mL) and EtOAc (30 mL). The layers were separated and the aqueous layer was extracted with EtOAc (3×20 mL). The combined organic layers were dried over $MgSO_4$ and evaporated in vacuo to give 450 mg of an oil. Purification by chromatography ($SiO_2$; 1% MeOH/0.5% $NH_4OH$ in $CHCl_3$) afforded 122 mg (0.2 mmol 23%) of the title compound as an oil which was converted to the dioxalate salt according to the method of Example 1, Part C.

FDMS 605 (M+).

EXAMPLE 102

Preparation of 1-[2-[2-Methoxy-4-[[2-[4-[2-(1-pyrrolidinyl)ethoxy]phenyl]benzo[b]thiophen-3-yl]methyl]phenoxy]ethyl]pyrrolidine Dioxalate

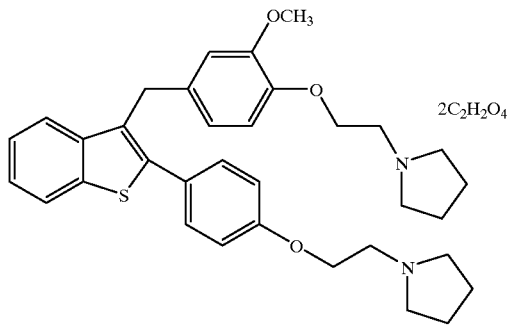

Part A. Methyl 3-Methoxy-4-[2-(1-pyrrolidinyl)ethoxy]benzoate

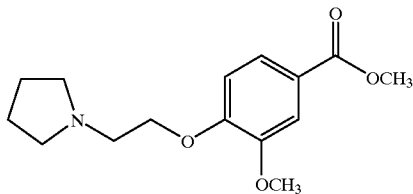

The substituted pyrrolidine was prepared in 94% yield from methyl 4-hydroxy-3-methoxybenzoate and $K_2CO_3$ by essentially following the procedure detailed for the preparation of Example 100, Part C.

$^1$H NMR ($CDCl_3$) δ 7.63 (d, 1 H), 7.53 (s, 1 H), 6.9 (d, 1 H), 4.2 (t, 2 H), 3.89 (s, 3 H), 3.88 (s, 3 H), 2.96 (t, 2 H), 2.64-2.61 (m, 4 H), 1.85-1.75 (m, 4 H); FDMS 279 (M+).

Part B. 3-Methoxy-4-[2-(1-pyrrolidinyl)ethoxy]benzoic Acid Hydrochloride

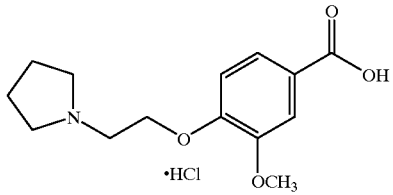

The benzoic acid hydrochloride was prepared in 63% yield from methyl 3-methoxy-4-[2-(1-pyrrolidinyl)ethoxy] benzoate by essentially following the procedure detailed for the preparation of Example 96, Part B.

$^1$H NMR (DMSO-$d_6$) δ 11.27 (bs, 2 H), 7.57 (d, 1 H), 7.55 (s, 1 H), 7.12 (d, 1 H), 4.44 (t, 2 H), 3.82 (s, 3 H), 3.5 (bs, 4 H), 3.1 (bs, 2 H); 1.98 (bs, 2 H), 1.89 (bs, 2 H); Anal. Calcd for $C_{14}H_{19}NO_4$·HCl: C, 55.72; H, 6.68; N, 4.64. Found: C, 56.01; H, 6.88; N, 4.70.

Part C. 3-Methoxy-4-[2-(1-pyrrolidinyl)ethoxy]phenyl 2-[4-[2-(1-Pyrrolidinyl)ethoxyphenylbenzo[b]thiophen-3-yl Ketone

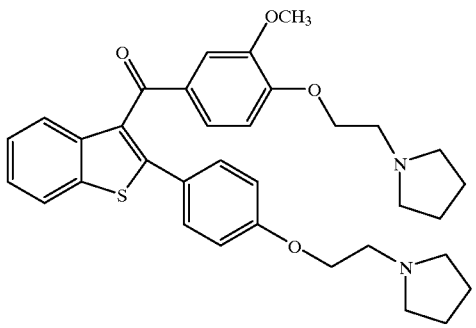

The ketone was prepared in 33% yield from 3-methoxy-4-[2-(1-pyrrolidinyl)ethoxy]benzoic acid hydrochloride by essentially following the procedure detailed for the preparation of Example 96, Part C.

$^1$H NMR (Free Base-$CDCl_3$) δ 7.86-7.83 (m, 1 H), 7.67-7.64 (m, 1 H), 7.49 (d, 1 H), 7.38-7.26 (m, 5 H), 6.8-6.76 (m, 2 H), 6.67 (d, 1 H), 4.12 (t, 2 H), 4.06 (t, 2 H), 3.83 (t, 3 H), 2.94 (t, 2 H), 2.88 (t, 2 H), 2.62-2.58 (m, 8 H), 1.81-1.76 (m, 8 H); FDMS 570 (M+).

Part D. 1-[2-[2-Methoxy-4-[[2-[4-[2-(1-pyrrolidinyl)ethoxy]phenyl]benzo[b]thiophen-3-yl]methyl]phenoxy]ethyl]pyrrolidine Dioxalate The title compound was prepared in 10% yield from 3-methoxy-4-[2-(1-pyrrolidinyl)ethoxy]phenyl 2-[4-[2-(1-pyrrolidinyl)ethoxyphenyl]benzo[b]thiophen-3-yl ketone by essentially following the procedure detailed for the preparation of Example 101.

$^1$H NMR (Free Base-CDCl$_3$) δ 7.98-795 (m, 1 H), 7.64-761 (m, 1 H), 7.50 (d, 2 H), 7.36-7.33 (m, 2 H), 7.12 (d, 2 H), 6.87-6.84 (m, 2 H), 6.51 (d, 1 H), 6.2 (bs, 4 H), 4.34 (t, 2 H), 4.20 (s, 2 H), 4.16 (t, 2 H), 3.68 (s, 3 H), 3.5 (t, 2 H), 2.86 (t, 2 H), 2.67-2.57 (m, 8 H), 2.0-1.9 (m, 8 H); FDMS 557 (M+1); Anal. Calcd for C$_{34}$H$_{40}$N$_2$O$_3$S·2C$_2$H$_2$O$_4$: C, 61.94; H, 6.02; N, 3.80. Found: C, 62.23; H, 6.09; N, 3.89.

EXAMPLE 103

Preparation of 3-Hydroxy-4-[2-(1-pyrrolidinyl)ethoxy]phenyl 2-[4-[2-(1-Pyrrolidinyl)ethoxyphenyl]benzo[b]thiophen-3-yl Ketone Dioxalate

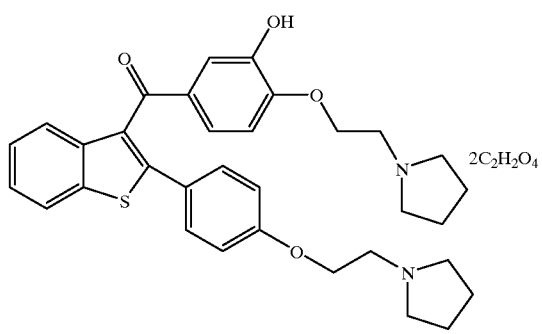

The title compound was prepared in 83% yield from 3-methoxy-4-[2-(1-pyrrolidinyl)ethoxy]phenyl 2-[4-[2-(1-pyrrolidinyl)ethoxyphenyl]benzo[b]thiophen-3-yl ketone by essentially following the procedure detailed for the preparation of Example 100, Part B.

Anal. Calcd for C$_{33}$H$_{36}$N$_2$O$_4$S·2C$_2$H$_2$O$_4$·1.25H$_2$O: C, 58.53; H, 5.64; N, 3.69. Found: C, 58.42; H, 5.27; N, 3.86.

EXAMPLE 104

Preparation of 1-[2-[2-Hydroxy-4-[[2-[4-[2-(1-pyrrolidinyl)ethoxy]phenyl]benzo[b]thiophen-3-yl]methyl]phenoxy]ethyl]pyrrolidine Dioxalate

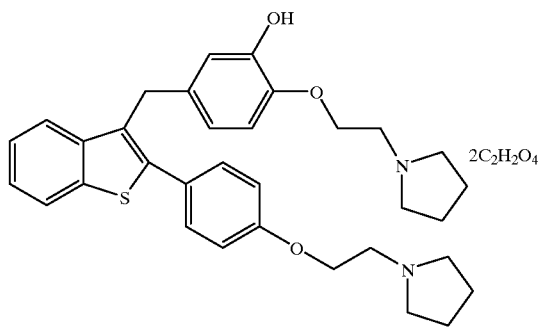

The title compound was prepared in 29% yield from 3-hydroxy-4-[2-(1-pyrrolidinyl)ethoxy]phenyl 2-[4-[2-(1-pyrrolidinyl)ethoxyphenyl]benzo[b]thiophen-3-yl ketone by essentially following the procedure detailed for the preparation of Example 95, Part C.

FDMS 541.9; Anal. Calcd for C$_{33}$H$_{38}$N$_2$O$_3$S·1.75C$_2$H$_2$O$_4$: C, 62.6; H, 5.97; N, 4.00. Found: C, 62.44; H, 6.09; N, 4.11.

EXAMPLE 105

Preparation of 3-Propyl-4-[2-(1-pyrrolidinyl)ethoxy]phenyl 2-[4-[2-(1-Pyrrolidinyl)ethoxyphenyl]benzo[b]thiophen-3-yl Ketone Dioxalate

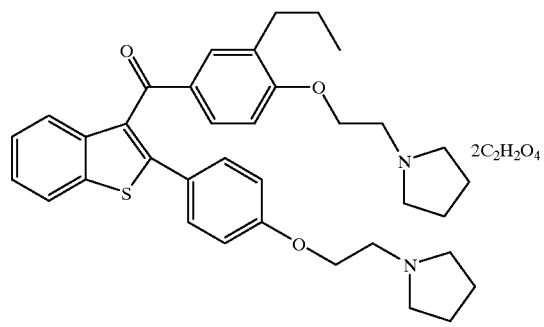

Part A. 2-(4-Methoxyphenyl)benzo[b]thiophen-3-yl 4-Methoxy-3-propylphenyl Ketone

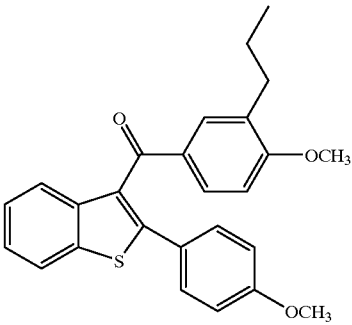

A mixture of 3-bromo-4-methoxyphenyl 2-(4-methoxyphenyl)benzo[b]thiophen-3-yl ketone (1 g, 2.2 mmol), tetrapropyltin (1.6 g, 5.5 mmol), tetrakis(triphenylphosphine)palladium(0) (150 mg, 0.13 mmol) and toluene (20 mL) was heated in a sealed tube at 130° C. for 18 h. The mixture was concentrated under reduced pressure, mixed with 30 mL of diethyl ether and stirred vigorously with 30 mL saturated aqueous KF for 2 h. The layers were separated and the organic layer was dried over MgSO$_4$ then concentrated to dryness. Purification by chromatography (SiO$_2$; 45% ClCH$_2$CH$_2$Cl in Hex) afforded 0.88 g (2.1 mmol 96%) of the propyl compound as a solid.

FDMS 416 (M+); Anal. Calcd for C$_{26}$H$_{24}$O$_3$S·H$_2$O: C, 71.86; H, 6.03. Found: C, 71.46; H, 5.82.

Part B. 2-(4-Hydroxyphenyl)benzo[b]thiophen-3-yl 4-Hydroxy-3-propylphenyl Ketone

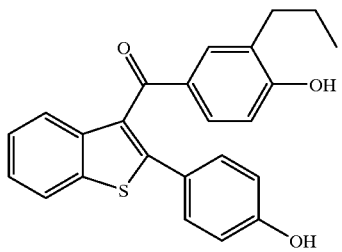

The named compound was prepared in quanitative yield from 2-(4-methoxyphenyl)benzo[b]thiophen-3-yl 4-methoxy-3-propylphenyl ketone by essentially following the procedure detailed for the preparation of Example 100, Part B.

FDMS 388 (M+); Anal. Calcd for $C_{24}H_{20}O_3S \cdot 0.72CHCl_3$: C, 62.69; H, 4.44. Found: C, 62.58; H, 4.4.

Part C. 3-Propyl-4-[2-(1-pyrrolidinyl)ethoxy]phenyl 2-[4-[2-(1-Pyrrolidinyl)ethoxyphenyl]benzo[b]thiophen-3-yl Ketone Dioxalate The title compound was prepared in 69% yield from 3-propyl-4-hydroxyphenyl 2-(4-hydroxyphenyl)benzo[b]thiophen-3-yl ketone by essentially following the procedure detailed for the preparation of Example 100, Part C.

$^1$H NMR (Free base-CDCl$_3$) δ 7.86-7.83 (m, 1 H), 7.67-7.58 (m, 3 H), 7.38-7.32 (m, 4 H), 6.79-6.76 (m, 2 H), 6.66 (d, 1 H), 4.09 (t, 2 H), 4.03 (t, 2 H), 2.89 (t, 2 H), 2.85 (t, 2 H), 2.62-2.59 (m, 8 H), 2.51-2.46 (m, 2 H), 1.79-1.65 (m, 8 H), 1.52-1.44 (m, 2 H), 0.84 (t, 3 H); FDMS 583 (M+1); Anal. Calcd for $C_{36}H_{42}N_2O_3S \cdot 2C_2H_2O_4 \cdot 0.15CCl_4$: C, 71.66; H, 6.99; N, 4.62. Found: C, 71.85; N, 7.23; N, 4.23.

EXAMPLE 106

Preparation of 3-Ethyl-4-[2-(1-pyrrolidinyl)ethoxy]phenyl 2-[4-[2-(1-Pyrrolidinyl)ethoxyphenyl]benzo[b]thiophen-3-yl Ketone Dioxalate

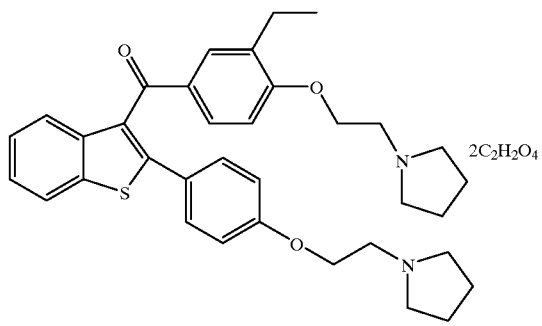

Part A. 3-Ethyl-4-methoxyphenyl 2-(4-Methoxyphenyl)benzo[b]thiophen-3-yl Ketone

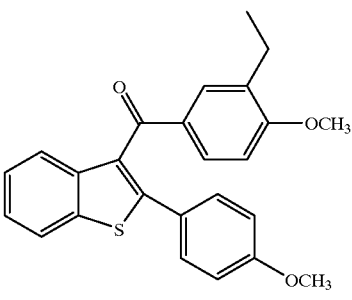

The ethyl compound was prepared in 45% yield from 3-bromo-4-methoxyphenyl 2-(4-methoxyphenyl)benzo[b]thiophen-3-yl ketone and tetraethyltin by essentially following the procedure detailed for the preparation of Example 105, Part A.

Anal. Calcd for $C_{25}H_{22}O_3S$: C, 74.6; H, 5.51. Found: C, 74.9; N, 5.65.

Part B. 3-Ethyl-4-hydroxyphenyl 2-(4-Hydroxyphenyl)benzo[b]thiophen-3-yl Ketone

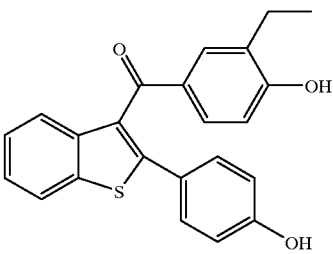

The named compound was prepared in 96% yield from 3-ethyl-4-methoxyphenyl 2-(4-methoxyphenyl)benzo[b]thiophen-3-yl ketone by essentially following the procedure detailed for the preparation of Example 100, Part B.

FDMS 374 (M+); Anal. Calcd for $C_{23}H_{18}O_3S \cdot 0.1CHCl_3$: C, 71.81; H, 4.72. Found: C, 71.92; N, 4.81.

Part C. 3-Ethyl-4-[2-(1-pyrrolidinyl)ethoxy]phenyl 2-[4-[2-(1-Pyrrolidinyl)ethoxyphenyl]benzo[b]thiophen-3-yl Ketone Dioxalate The title compound was prepared in 42% yield from 3-ethyl-4-hydroxyphenyl 2-(4-hydroxyphenyl)benzo[b]thiophen-3-yl ketone by essentially following the procedure detailed for the preparation of Example 100, Part C.

$^1$H NMR (Free base-CDCl$_3$) δ 7.91-7.88 (m, 1 H), 7.73-7.62 (m, 3 H), 7.43-7.35 (m, 4 H), 6.82 (d, 2 H), 6.71 (d, 1 H), 4.15 (t, 2 H), 4.09 (t, 2 H), 2.95 (t, 2 H), 2.90 (t, 2 H), 2.67-2.55 (m, 10 H), 1.9-1.84 (m, 8 H), 1.13 (t, 3 H); FDMS 569 (M+1); Anal. Calcd for $C_{35}H_{40}N_2O_3S \cdot 2C_2H_2O_4$: C, 62.55; H, 5.92; N, 3.74. Found: C, 62.33; H, 5.85; N, 3.74.

EXAMPLE 107

Preparation of 3-Butyl-4-[2-(1-pyrrolidinyl)ethoxy]phenyl 2-[4-[2-(1-Pyrrolidinyl)ethoxyphenyl]benzo[b]thiophen-3-yl Ketone

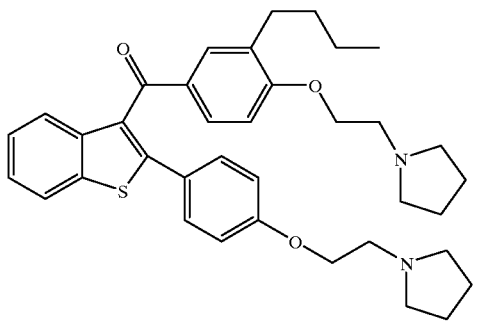

Part A. 3-Butyl-4-methoxyphenyl 2-(4-Methoxyphenyl)benzo[b]thiophen-3-yl Ketone

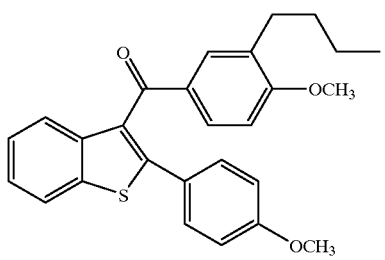

The butyl compound was prepared in 49% yield from 3-bromo-4-methoxyphenyl 2-(4-methoxyphenyl)benzo[b]thiophen-3-yl ketone and tetrabutyltin by essentially following the procedure detailed for the preparation of Example 105, Part A.

FDMS 430 (M+); Anal. Calcd for $C_{27}H_{26}O_3S \cdot 0.25H_2O$: C, 74.54; H, 6.14. Found: C, 74.79; N, 6.32.

Part B. 3-Butyl-4-hydroxyphenyl 2-(4-Hydroxyphenyl)benzo[b]thiophen-3-yl Ketone

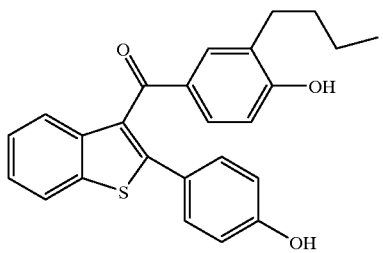

The named compound was prepared in 98% yield from of 3-butyl-4-methoxyphenyl 2-(4-methoxyphenyl)benzo[b]thiophen-3-yl ketone by essentially following the procedure detailed for the preparation of Example 100, Part B.

Anal. Calcd for $C_{25}H_{22}O_3S \cdot 0.5CHCl_3$: C, 66.27; H, 4.91. Found: C, 66.29; N, 4.84.

Part C. 3-Butyl-4-[2-(1-pyrrolidinyl)ethoxy]phenyl 2-[4-[2-(1-Pyrrolidinyl)ethoxyphenyl]benzo[b]thiophen-3-yl Ketone The title compound was prepared in 49% yield from 3-butyl-4-hydroxyphenyl 2-(4-hydroxyphenyl)benzo[b]thiophen-3-yl ketone by essentially following the procedure detailed for the preparation of Example 100, Part C.

$^1$H NMR (Free base-CDCl$_3$) δ 7.86-7.83 (m, 1 H), 7.67-7.58 (m, 3 H), 7.38-7.32 (m, 4 H), 6.79-6.76 (m, 2 H), 6.66 (d, 1 H), 4.09 (t, 2 H), 4.03 (t, 2 H), 2.89 (t, 2 H), 2.85 (t, 2 H), 2.62-2.56 (m, 8 H), 2.50 (t, 2 H), 1.94-1.78 (m, 8 H), 1.46-1.38 (m, 2 H), 1.28-1.2 (m, 2 H), 0.88 (t, 3 H); FDMS 597 (M+1); Anal. Calcd for $C_{37}H_{44}N_2O_3S \cdot 0.7$Hex: C, 75.3; H, 8.25; N, 4.26. Found: C, 75.24; H, 7.90; N, 3.87.

EXAMPLE 108

Preparation of 1-[2-[2-Propyl-4-[[2-[4-[2-(1-pyrrolidinyl)ethoxy]phenyl]benzo[b]thiophen-3-yl]methyl]phenoxy]ethyl]pyrrolidine Dioxalate

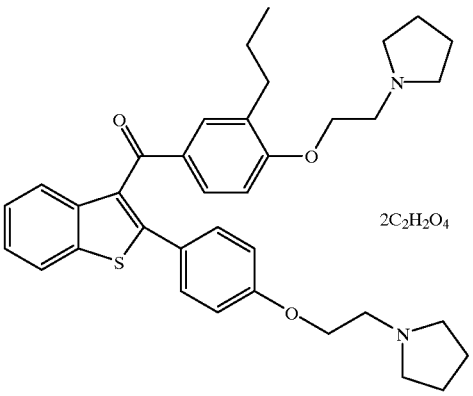

The title compound was prepared in 56% yield from 3-propyl-4-[2-(1-pyrrolidinyl)ethoxy]phenyl 2-[4-[2-(1-pyrrolidinyl)ethoxyphenyl]benzo[b]thiophen-3-yl ketone by essentially following the procedure detailed for the preparation of Example 101.

$^1$H NMR (Free base-CDCl$_3$) δ 7.84-7.81 (m, 1 H), 7.54-7.51 (m, 1 H), 7.44-7.42 (m, 2 H), 7.32-7.24 (m, 3 H), 6.96-6.93 (m, 2 H), 6.87-6.84 (m, 1 H), 6.71-6.68 (m, 1 H), 4.18 (s, 2 H), 4.14 (t, 2 H), 4.05 (t, 2 H), 2.94-2.87 (m, 4 H), 2.63-2.58 (m, 8 H), 2.53 (t, 2 H), 1.84-1.77 (m, 8 H), 1.59-1.51 (m, 2 H), 0.89-0.86 (m, 3 H); FDMS 569 (M+1); Anal. Calcd for $C_{36}H_{44}N_2O_2S \cdot 1.75C_2H_2O_4$: C, 65.7; H, 6.74; N, 3.78. Found: C, 65.99; N, 6.54; N 3.71.

EXAMPLE 109

Preparation of 1-[2-[2-Ethyl-4-[[2-[4-[2-(1-pyrrolidinyl)ethoxy]phenyl]benzo[b]thiophen-3-yl]methyl]phenoxy]ethyl]pyrrolidine Dioxalate

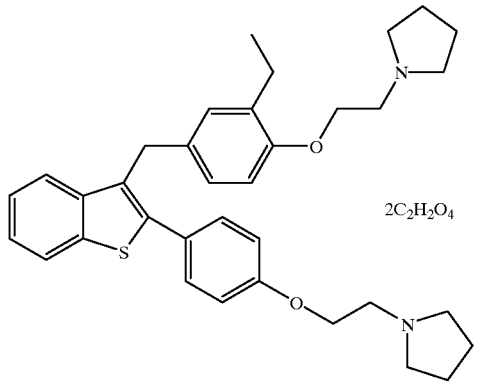

The title compound was prepared in 56% yield from 3-ethyl-4-[2-(1-pyrrolidinyl)ethoxy]phenyl 2-[4-[2-(1-pyrrolidinyl)ethoxyphenyl]benzo[b]thiophen-3-yl ketone by essentially following the procedure detailed for the preparation of Example 101.

$^1$H NMR (Free base-CDCl$_3$) δ 7.84-7.81 (m, 1 H), 7.55-7.51 (m, 1 H), 7.45-7.41 (m, 2 H), 7.30-7.28 (m, 3 H), 6.97-6.93 (m, 2 H), 6.87-6.83 (m, 1 H), 6.73-6.68 (m, 1 H), 4.19 (s, 2 H), 4.14 (t, 2 H), 4.06 (t, 2 H), 2.94-2.87 (m, 4 H), 2.65-2.55 (m, 10 H), 1.84-1.79 (m, 8 H), 1.14 (s, 3 H); Exact Mass Calcd for $C_{35}H_{42}N_2O_2S$: 555.3045. Found: 555.3057.

EXAMPLE 110

Preparation of 1-[2-[2-Butyl-4-[[2-[4-[2-(1-pyrrolidinyl)ethoxy]phenyl]benzo[b]thiophen-3-yl]methyl]phenoxy]ethyl]pyrrolidine Dioxalate

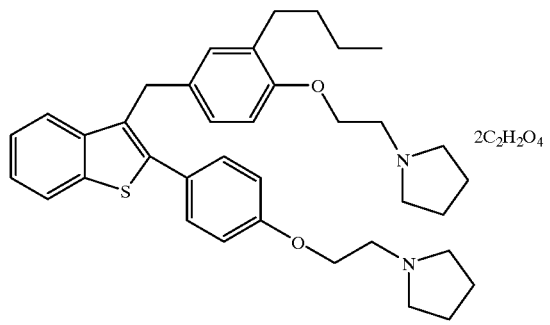

The title compound was prepared in 64% yield from 3-butyl-4-[2-(1-pyrrolidinyl)ethoxy]phenyl 2-[4-[2-(1-pyrrolidinyl)ethoxyphenyl]benzo[b]thiophen-3-yl ketone by essentially following the procedure detailed for the preparation of Example 101.

$^1$H NMR (DMSO-d$_6$) δ 7.98-7.94 (m, 1 H), 7.58-7.5 (m, 1 H), 7.47 (d, 2 H), 7.34-7.32 (m, 2 H), 7.1 (d, 2 H), 6.9 (s, 1 H), 6.8 (s, 2 H) 4.5 (bs, 4 H), 4.35 (t, 2 H), 4.21 (t, 2 H), 4.17 (s, 2 H), 3.54-3.50 (m, 4 H), 3.4-3.2 (m, 8 H), 2.5-2.45 (m, 2 H), 1.93-1.85 (m, 8 H), 1.44-1.39 (m, 2 H), 1.26-1.21 (m, 2 H), 1.17 (t, 3 H); FDMS 582 (M+1); Anal. Calcd for $C_{37}H_{46}N_2O_2S\cdot1.75C_2H_2O_4$: C, 65.7; H, 6.74; N, 3.78. Found: C, 65.99; N, 6.54; N 3.71.

EXAMPLE 111

Preparation of 1-[2-[2-Acetamido-4-[[2-[4-[2-(1-pyrrolidinyl)ethoxy]phenyl]benzo[b]thiophen-3-yl]methyl]phenoxy]ethyl]pyrrolidine Dioxalate

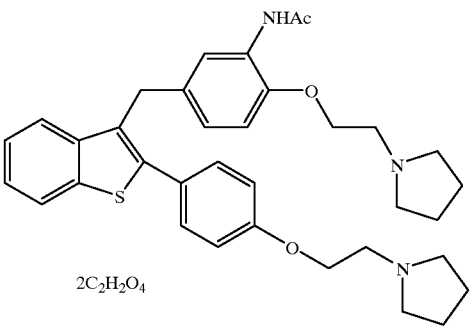

1-[2-[2-Amino-4-[[2-[4-[2-(1-pyrrolidinyl)ethoxy]phenyl]benzo[b]thiophen-3-yl]methyl]phenoxy]ethyl]pyrrolidine (178 mg, 0.33 mmol) was treated with 2 mL of acetic anhydride and 2 mL of pyridine. This was stirred at ambient temperature for 16 h and concentrated under reduced pressure. The resulting oil was mixed with toluene and reconcentrated to dryness. Purification by chromatography (SiO$_2$; 95/5% THF/Et$_3$N) afforded 70 mg (0.12 mmol 36%) of the title compound as an oil which was converted to the dioxalate salt according to the method of Example 1, Part C.

$^1$H NMR (Free base-CDCl$_3$) δ 8.93 (s, 1 H), 8.33 (d, 1 H), 7.82-7.79 (m, 1 H), 7.54-7.50 (m, 1 H), 7.46-7.43 (m, 2 H), 7.28-7.24 (m, 2 H), 6.96-6.93 (m, 2 H), 6.73 (d, 1 H), 6.62 (d, 1 H), 4.22 (s, 2 H), 4.13 (t, 2 H), 4.08 (t, 2 H), 2.91 (t, 2 H), 2.77 (t, 2 H), 2.63-2.61 (m, 8 H), 2.17 (s, 3 H), 1.84-1.79 (m, 8 H); FDMS 584 (M+1); Anal. Calcd for $C_{35}H_{41}N_3O_3S\cdot2C_2H_2O_4$: C, 61.32; H, 5.94; N, 5.50. Found: C, 61.59; H, 5.98; N, 5.59.

EXAMPLE 112

Preparation of 1-[2-[2-Ethylamino-4-[[2-[4-[2-(1-pyrrolidinyl)ethoxy]phenyl]benzo[b]thiophen-3-yl]methyl]phenoxy]ethyl]pyrrolidine Dioxalate

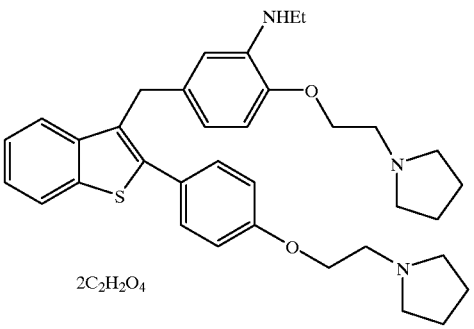

1-[2-[2-Acetamido-4-[[2-[4-[2-(1-pyrrolidinyl)ethoxy]phenyl]benzo[b]thiophen-3-yl]methyl]phenoxy]ethyl]pyrrolidine (600 mg, 1.1 mmol) was dissolved in 20 mL of dry THF and added to a mixture of 20 mL of THF and 84 mg (2.2 mmol) of LAH. The reaction was heated at reflux for 3 h then quenched with 5 mL of EtOAc. To this was added 25 mL of saturated aqueous potassium sodium tartrate. The mixture was stirred for 30 min and extracted with EtOAc (3×30 mL). The combined organic layer was dried over Na$_2$SO$_4$ and concentrated under reduced pressure to 450 mg of an oil which was purified by chromatrography (SiO$_2$; 5% MeOH/1% NH$_4$OH in CHCl$_3$) to afford 55 mg (0.1 mmol; 9%) of the title compound as an oil which was converted to the dioxalate salt according to the method of Example 1, Part C.

$^1$H NMR (Free base-CDCl$_3$) δ 7.82-7.80 (m, 1 H), 7.59-7.55 (m, 1 H), 7.47-7.44 (m, 2 H), 7.29-7.27 (m, 2 H), 6.96-6.93 (m, 2 H), 6.62 (d, 1 H), 6.44 (d, 1 H), 6.34 (dd, 1 H), 4.22 (bs, 1 H), 4.17 (s, 2 H), 4.13 (t, 2 H), 4.07 (t, 2 H), 3.05 (q, 2 H), 2.94-2.86 (m, 4 H), 2.65-2.59 (m, 8 H), 1.84-1.77 (m, 8 H), 1.21 (t, 3 H); FDMS 572 (M+3); Anal. Calcd for C$_{35}$H$_{43}$N$_3$O$_2$S·2C$_2$H$_2$O$_4$: C, 62.47; H, 6.32; N, 5.60. Found: C, 62.46; H, 6.19; N, 5.43.

EXAMPLE 113

Preparation of 1-[2-[2-Methanesulfonamido-4-[[2-[4-[2-(1-pyrrolidinyl)ethoxy]phenyl]benzo[b]thiophen-3-yl]methyl]phenoxy]ethyl]pyrrolidine Dioxalate

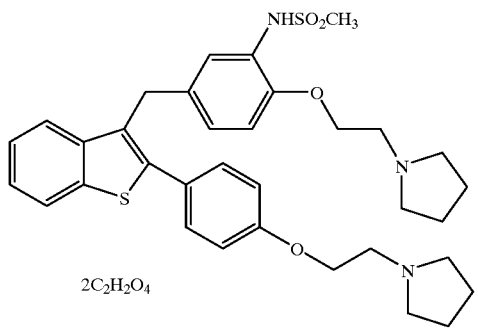

A solution of 1-[2-[2-amino-4-[[2-[4-[2-(1-pyrrolidinyl)ethoxy]phenyl]benzo[b]thiophen-3-yl]methyl]phenoxy]ethyl]pyrrolidine (750 mg, 1.4 mmol) in 25 mL of CH$_2$Cl$_2$ at 0° C. was treated with 159 mg (107 mL, 1.4 mmol) of methanesulfonyl chloride. The reaction was stirred at 0° C. for 8 h then concentrated under vaccuum. The residue was purified by chromatrography (SiO$_2$; 5% MeOH/1% NH$_4$OH in CHCl$_3$) to afford 447 mg (0.72 mmol; 52%) of the title compound as an oil which was converted to the dioxalate salt according to the method of Example 1, Part C.

$^1$H NMR (Free base-CDCl$_3$) δ 7.84-7.81 (m, 1 H), 7.55-7.53 (m, 1 H), 7.52-7.41 (m, 3 H), 7.30-7.27 (m, 3 H), 6.98-6.94 (m, 2 H), 6.85 (d, 1 H), 6.76 (dd, 1 H), 4.21 (s, 2 H), 4.15 (s, 2 H), 4.09 (t, 2 H), 2.93 (t, 2 H), 2.82 (s, 3 H), 2.65-2.60 (m, 10 H), 1.89-1.84 (m, 4 H), 1.83-1.80 (m, 4 H); FDMS 619 (M+); Anal. Calcd for C$_{34}$H$_{41}$N$_3$O$_4$S$_2$·2C$_2$H$_2$O$_4$·1H$_2$O·0.1EtOAc: C, 55.79; H, 5.83; N, 5.08. Found: C, 56.01; H, 5.98; N, 4.71.

EXAMPLE 114

Preparation of 1-[2-[2-Phenylsulfonamido-4-[[2-[4-[2-(1-pyrrolidinyl)ethoxy]phenyl]benzo[b]thiophen-3-yl]methyl]phenoxy]ethyl]pyrrolidine Dioxalate

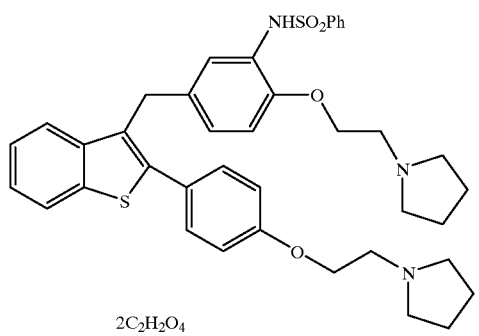

This compound was prepared in 35% yield from phenylsulfonyl chloride and 1-[2-[2-amino-4-[[2-[4-[2-(1-pyrrolidinyl)ethoxy]phenyl]benzo[b]thiophen-3-yl]methyl]phenoxy]ethyl]pyrrolidine by essentially following the procedure detailed for the preparation of Example 113.

$^1$H NMR (Free base-CDCl$_3$) δ 8.1 (bs, 1 H), 7.84-7.81 (m, 1 H), 7.58-7.54 (m, 2 H), 7.49-7.35 (m, 5 H), 7.31-7.21 (m, 4 H), 6.98-6.95 (m, 2 H), 6.72–6.78 (m, 2 H), 4.17-4.12 (m, 4 H), 3.92 (t, 2 H), 2.92 (t, 2 H), 265-2.54 (m, 10 H), 1.94-193 (m, 4 H), 1.83-1.79 (m, 4 H); FDMS 682 (M+1); Anal. Calcd for C$_{39}$H$_{43}$N$_3$O$_4$S$_2$·1.5C$_2$H$_2$O$_4$·0.2H$_2$O: C, 61.48; H, 5.70; N, 5.12. Found: C, 61.25; H, 6.05; N, 4.97.

EXAMPLE 115

Preparation of 2-[4-(2-Aminoethoxy)phenyl]-6-hydroxy-3-[3-methyl-4-[(1-pyrrolidinyl)methyl]benzyl]benzo[b]thiophene Dioxalate

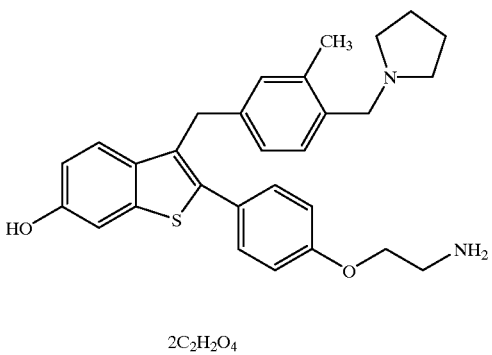

Part A. 4-(6-Methoxybenzo[b]thiophen-2-yl)phenyl Triisopropylsilyl Ether

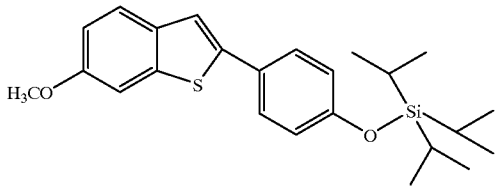

A solution of 6-methoxy-2-(4-hydroxyphenyl)benzo[b]thiophene (16 g, 62.4 mmol) in 160 mL of dry DMF was treated with Et₃N (12.6 g, 124.8 mmol) at 0° C. To this was added in a dropwise manner 28.7 g (93.6 mmol) of triisopropyl trifluoromethanesulfonate. The cooling bath was removed and the reaction mixture was stirred at ambient temperature for 2 h before being poured into 200 mL of saturated aqueous NaHCO₃ and 300 mL of brine. This was extracted with 10% EtOAc in hexanes (3×200 mL). The combined extracts were washed with brine (2×300 mL), dried over MgSO₄ and concentrated under reduced pressure to give 32 g of an oil which was purified by chromatrography (SiO₂; 5% EtOAc in Hexanes) to yield 12.3 g (29.8 mmol, 48%) of the silyl ether as a white solid.

FDMS 412 (M+); Anal. Calcd for C₂₄H₃₂O₂SSi·0.65EtOAc: C, 68.50; H, 8.18. Found: C, 68.55; H, 8.16.

Part B. 6-Methoxy-2-[4-[(triisopropylsilyl)oxy]phenyl]benzo[b]thiophen-3-yl 3-Methyl-4-[(1-pyrrolidinyl)methyl]phenyl Ketone

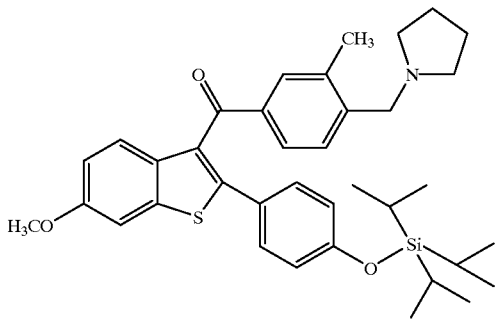

The ketone was prepared in 83% yield from the above benzothiophene, TiCl₄, and 3-methyl-4-[(1-pyrrolidinyl)methyl]benzoic acid hydrochloride by essentially following the procedure detailed for the preparation of Example 96, Part C.

FDMS 613 (M+); Anal. Calcd for C₃₇H₄₇NO₃SSi·0.23CHCl₃: C, 69.5; H, 7.40; N, 2.18. Found: C, 69.43; H, 7.48; N, 2.34.

Part C. 2-(4-Hydoxyphenyl)-6-methoxybenzo[b]thiophen-3-yl 3-Methyl-4-[(1-pyrrolidinyl)methyl]phenyl Ketone

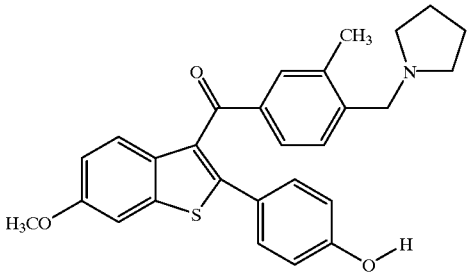

A solution of the above silyl ether (5.23 g, 8.5 mmol) in THF (50 mL) was treated with a 1 M THF solution of tetrabutylammonium fluoride (8.5 mL) at ambient temperature. The reaction was stirred for 16 h, concentrated in vacuo, mixed with CHCl₃ and purified by chromatography (SiO₂; 2.5% MeOH in CHCl₃) to afford 3.8 g (8.3 mmol, 98%) of the phenoxy product as an oil.

¹H NMR (Free base-CDCl₃) δ 7.65 (d, 1 H), 7.53 (s, 1 H), 7.48 (d, 1 H), 7.32 (d, 1 H), 7.21-7.16 (m, 3 H), 6.99-6.97 (m, 1 H), 6.57 (d, 2 H), 5.75 (bs, 1 H), 3.89 (s, 3 H), 3.59 (s, 2 H), 2.6-2.5 (m, 4 H), 2.25 (s, 3 H), 1.85-1.78 (m, 4 H).

Part D. 2-(4-Hydroxyphenyl)-6-methoxy-3-[3-methyl-4-[(1-pyrrolidinyl)methyl]benzyl]benzo[b]thiophene

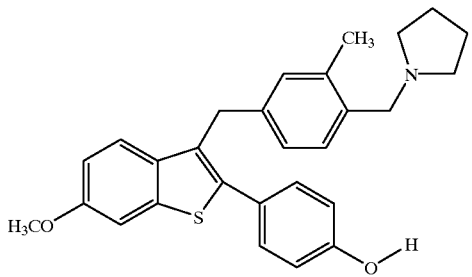

A solution of the above ketone (4 g, 8.7 mmol) in THF (100 mL) was cooled to 0° C. under N₂ and treated with a 1 M solution of LAH in THF (17.4 mL). The bath was removed and the reaction was stirred at ambient temperature for 2 h. It was quenched by the dropwise addition of 500 mL of H₂O at 0° C., followed by 200 mL of EtOAc and 50 g diatomaceous earth. The mixture was filtered, the layers were separated, and the organic layer was dried over MgSO₄ and concentrated to give 4 g of the benzyl alcohol.

The foam was dissolved in 100 mL of ClCH₂CH₂Cl and cooled to 0° C. under N₂. The colorless solution was treated with 5.1 g (43.5 mmol) of Et₃SiH and 10 g (87.4 mmol) of TFA. The reaction was stirred at 0° C. for 1 h then quenched with 50 mL of saturated aqueous NaHCO₃. The layers were separated and the aqueous layer was extracted with 100 mL of CH₂Cl₂. The combined organic layer was dried over MgSO₄ and concentrated to an oil. Purification by chromatography (SiO₂; 65/30/5% Hex/THF/Et₃N) afforded 3.5 g (7.9 mmol 91%) of the methylene compound as a foam.

¹H NMR (Free base-DMSO-d₆) δ 7.55 (d, 1 H), 7.4 (d, 1 H), 7.36 (d, 2 H), 7.1 (d, 1 H), 6.95-6.80 (m, 5 H), 4.15 (s, 2 H), 3.80 (s, 3 H), 3.4 (s, 2 H), 3.3 (bs, 1 H), 2.43-2.30 (m, 4 H), 2.20 (s, 3 H), 1.65-1.60 (m, 4 H); FDMS 443 (M+).

Part E. 6-Methoxy-3-[3-methyl-4-[(1-pyrrolidinyl)methyl]benzyl]-2-[4-[2-(phthalimido)ethoxy]phenyl]benzo[b]thiophene

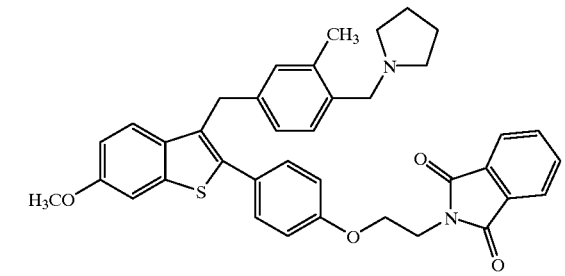

The named compound was prepared in 29% yield from 2-(4-hydroxyphenyl)-6-methoxy-3-[3-methyl-4-[(1-pyrrolidinyl)methyl]benzyl]benzo[b]thiophene and hydroxyethylphthalimide by essentially following the procedure detailed for the preparation of Example 20, Part B.

FDMS 616 (M+); Anal. Calcd for C₃₈H₃₆N₂O₄S·1.2H₂O: C, 71.49; H, 6.06; N, 4.39. Found: C, 71.58; H, 6.10; N, 4.36.

Part F. 6-Hydroxy-3-[3-methyl-4-[(1-pyrrolidinyl)methyl]benzyl]-2-[4-[2-(phthalimidyl)ethoxy]phenyl]benzo[b]thiophene Dioxalate

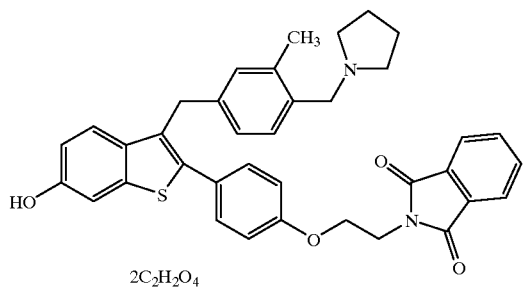

2C₂H₂O₄

This compound was prepared in 52% yield from the above 6-methoxybenzo[b]thiophene by essentially following the procedure detailed for the preparation of Example 1, Part D.

¹H NMR (Free base-CDCl₃) δ 7.88-7.84 (m, 2 H), 7.74-7.71 (m, 2 H), 7.34-7.29 (m, 2 H), 7.19-7.15 (m, 2 H), 7.1 (d, 1 H), 6.92 (s, 1 H), 6.88-6.84 (m, 3 H), 6.41-6.37 (m, 1 H), 4.24 (t, 2 H), 4.14-4.10 (m, 3 H), 3.61 (s, 2 H), 2.69-2.61 (m, 6 H), 2.27 (s, 3 H), 1.80-1.79 (m, 4 H); FDMS 603 (M+1).

Part G. 2-[4-(2-Aminoethoxy)phenyl]-6-hydroxy-3-[3-methyl-4-[(1-pyrrolidinyl)methyl]benzyl]benzo[b]thiophene Dioxalate A mixture of the above phthalimide (0.4 g, 0.66 mmol) and 1 mL hydrazine hydrate in 50 mL of EtOH was heated at reflux for 1 h then concentrated to dryness under reduced pressure. The residue was mixed with 50 mL of 1 N aqueous NaOH and 50 mL of 10% MeOH in EtOAc. The layers were separated and the aqueous layer was extracted with 25 mL of 10% MeOH in EtOAc. The combined organic layer was dried over MgSO₄, concentrated to dryness and purified by chromatography (SiO₂; 5% MeOH, 1% NH₄OH in CHCl₃) to afford 230 mg (0.49 mmol, 74%) of the title product as a solid which was converted to its dioxalate salt according to the method of Example 1, Part C.

¹H NMR (Free base-CDCl₃) δ 8.3 (s, 1 H), 7.39 (d, 1 H), 7.37-7.2 (m, 3 H), 7.05 (d, 1 H), 7.0 (d, 2 H), 6.85 (s, 1 H), 6.82-6.7 (m, 2 H), 4.08 (s, 2 H), 3.94 (t, 2 H), 3.41 (s, 2 H), 3.34 (bs, 2 H), 2.88 (t, 2 H), 2.39-2.35 (m, 4 H), 2.18 (s, 3 H), 1.65-1.6 (m, 4 H); FDMS 472 (M+).

EXAMPLE 116

Preparation of (R)-6-Hydroxy-2-[4-[2-hydroxy-3-(1-pyrrolidinyl)propoxy]phenyl]-3-[3-methyl-4-[(1-pyrrolidinyl)methyl]benzyl]benzo[b]thiophene Dioxalate

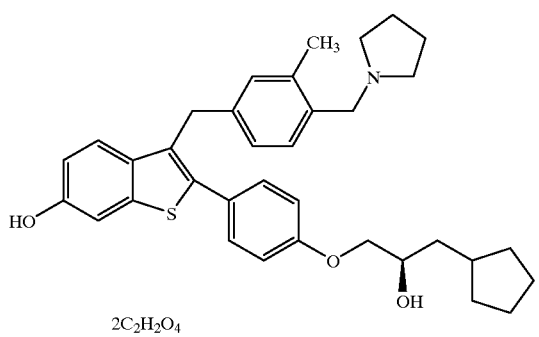

2C₂H₂O₄

Part A. (2R)-2-[4-(Glycidyloxy)phenyl]-6-methoxy-3-[3-methyl-4-[(1-pyrrolidinyl)methyl]benzyl]benzo[b]thiophene

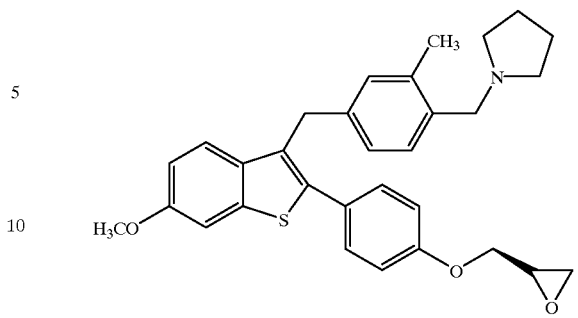

A 60% dispersion of sodium hydride (141 mg, 3.5 mmol) was rinsed with hexanes under a nitrogen atmosphere and dried under reduced pressure. To this was added a solution of the hydroxyphenylbenzo[b]thiophene of Example 115, Part C (1.3 g, 2.9 mmol) in 30 mL of dry DMF and stirred for 1 h at ambient temperature. The mixture was treated with (2R)-(−)-glycidyl-3-nitrobenzenesulfonate, then stirred for 16 h at ambient temperature. The reaction was poured into a mixture of 50 mL of saturated aqueous NaHCO₃, 100 mL of saturated aqueous NaCl and 100 mL of H₂O. It was extracted with EtOAc (3×100 mL). The extracts were washed with brine, dried over MgSO₄, concentrated under reduced pressure and purified by chromatography to give 1.2 g (2.4 mmol, 81%) of the product as an oil.

¹H NMR (Free base-CDCl₃) δ 7.45-7.38 (m, 5 H), 7.33 (d, 1 H), 7.18 (d, 1 H), 6.97-6.88 (m, 3 H), 4.23-4.18 (m, 1 H), 4.18 (s, 2 H), 4.02-3.96 (m, 1 H), 3.88 (m, 3 H), 3.55 (s, 2 H), 3.39-3.37 (m, 1 H), 2.95-2.92 (m, 1 H), 2.79-2.71 (m, 1 H), 2.55-2.49 (m, 4 H), 2.3 (s, 3 H), 1.8-1.76 (m, 4 H).

Part B. (R)-2-[4-[2-Hydroxy-3-(1-pyrrolidinyl)propoxy]phenyl]-6-methoxy-3-[3-methyl-4-[(1-pyrrolidinyl)methyl]benzyl]benzo[b]thiophene

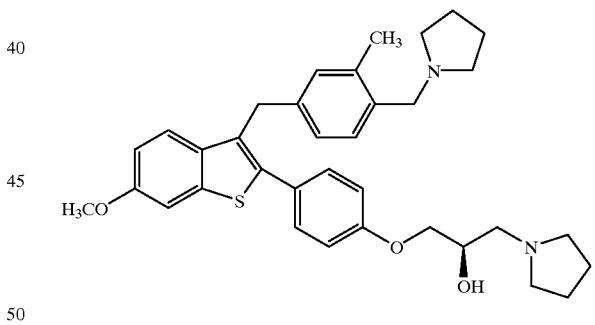

The above (2R)-[(glycidyloxy)phenyl]benzo[b]thiophene (1.18 g, 2.4 mmol) was mixed with pyrrolidine (338 mg, 4.8 mmol) and MeOH (50 mL). The mixture was heated at reflux for 6 h, concentrated to an oil and purified by chromatography (SiO₂; 30% THF/5% Et₃N in hexanes) to afford 1 g of the named product as an oil.

Part C. (R)-6-Hydroxy-2-[4-[2-hydroxy-3-(1-pyrrolidinyl)propoxy]phenyl]-3-[3-methyl-4-[(1-pyrrolidinyl)methyl]benzyl]benzo[b]thiophene Dioxalate The title compound was prepared in 61% yield from the above methoxybenzo[b]thiophene by essentially following the procedure detailed for the preparation of Example 115, Parts F and G.

¹H NMR (DMSO-d₆) δ 7.4-6.7 (m, 11 H), 4.3-3.9 (m, 9 H), 3.4-3.2 (m, 7 H), 3.2-2.29 (m, 4 H), 2.25 (s, 3 H), 2.00-1.7 (m, 10 H); FDMS 557 (M+1).

EXAMPLE 117

Preparation of 1-[2-[4-[[5-Fluoro-6-hydroxy-2-[4-[2-(1-pyrrolidinyl)ethoxy]phenyl]benzo[b]thiophen-3-yl]methyl]phenoxy]ethyl]pyrrolidine Dioxalate

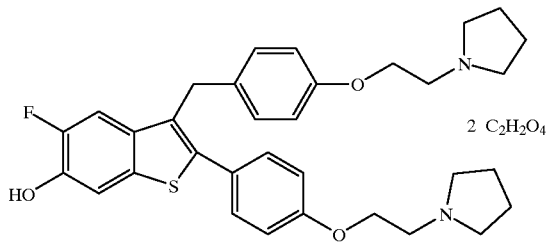

Part A. N,N-Dimethyl-3-fluoro-4-methoxy-α-hydroxyphenylthioacetamide

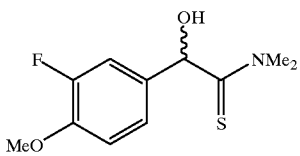

A −78° C. solution of 18.7 mL (142.7 mmol) of diisopropylamine in 100 mL of THF was treated with 89.0 mL (1.6 M in hexanes; 142.2 mmol) of n-BuLi. The reaction mixture was stirred at −78° C. for 15 min and at 0° C. for 0.5 h. After cooling back to −78° C., a solution of 20.0 g (129.7 mmol) of 3-fluoro-4-anisaldehyde and 12.2 mL (143.6 mmol) of N,N-dimethylthioformamide in 100 mL of THF was added slowly. After complete addition, the reaction was stirred at −78° C. for 15 min and was quenched with a solution of 15 mL of HOAc in 100 mL of MeOH. The mixture was concentrated in vacuo and the residue was partitioned between 250 mL of saturated aqueous NaHCO$_3$ and 250 mL of EtOAc. The organic layer was separated and the aqueous layer was extracted with EtOAc (2×100 mL). The combined organic layers were dried over Na$_2$SO$_4$, filtered, and concentrated in vacuo to give 22.4 g of an oily solid. Trituration with Et$_2$O afforded 16.21 g (66.6 mmol; 51%) of the title compound as a light yellow solid.

Anal. Calcd for C$_{11}$H$_{14}$FNO$_2$S: C, 54.30; H, 5.80; N, 5.76. Found: C, 54.00; H, 5.86; N, 5.77.

Part B. 2-Dimethylamino-5-fluoro-6-methoxybenzo[b]thiophene

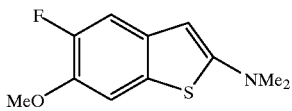

A solution of 16.6 g (68.2 mmol) of N,N-dimethyl-3-fluoro-4-methoxy-2-hydroxyphenylthioacetamide (Part A) in 400 mL of CH$_2$Cl$_2$ was treated with 22.0 mL (339.0 mmol) of MeSO$_3$H in a dropwise manner. The reaction was stirred at room temperature for 4 h, was cooled to 0° C., and was quenched by the careful addition of 500 mL of saturated aqueous NaHCO$_3$. The two layers were separated and the aqueous layer was extracted with EtOAc (5×200 mL). The combined organic layers were washed with 500 mL of saturated aqueous NaHCO$_3$ and 500 mL of H$_2$O, dried over Na$_2$SO$_4$, and filitered. Evaporation of the solvent in vacuo afforded 21.4 g of an oil which was purified by flash chormatography (SiO$_2$; gradient of 10% then 20% EtOAc in hexanes) to give 2.87 g (12.7 mmol; 19%) of the title compound as a light pink solid.

FDMS 225 (M+); Anal. Calcd for C$_{11}$H$_{12}$FNOS: C, 58.65; H, 5.37; N, 6.22. Found: C, 58.37; H, 5.42; N, 6.17.

Part C. 2-Dimethylamino-5-fluoro-6-methoxybenzo[b]thiophene-3-yl 4-Nitrophenyl Ketone

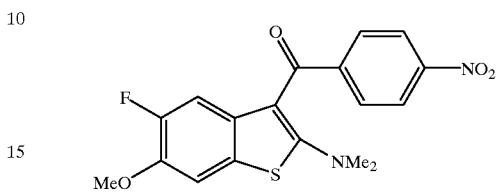

A solution of 1.08 g (4.82 mmol) of 2-dimethylamino-5-fluoro-6-methoxybenzo[b]thiophene (Part B) in 15 mL of chlorobenzene was treated with 0.99 g (5.31 mmol) of 4-nitrobenzoyl chloride. The reaction was stirred at room temperature for 17 h and was diluted with 100 mL of EtOAc. The solution was washed sequentially with 2 N aqueous NaOH (2×50 mL), H$_2$O (50 mL) and brine (50 mL), then dried over Na$_2$SO$_4$, and filtered. Evaporation of the solvent in vacuo afforded 2.1 g of a dark solid which was purified by flash chromatography (SiO$_2$; gradient of 10% then 20% then 40% EtOAc in hexanes) to give 0.27 g of starting material and 1.25 g (3.34 mmol; 93% based on consumed starting material) of the title compound.

FDMS 374 (M+); Anal. Calcd for C$_{18}$H$_{15}$FN$_2$O$_4$S: C, 57.75; H, 4.04; N, 7.48. Found: C, 58.04; H, 3.98; N, 7.50.

Part D. 2-Dimethylamino-5-fluoro-6-methoxybenzo[b]thiophen-3-yl 4-[2-(1-Pyrrolidinyl)ethoxy]phenyl Ketone

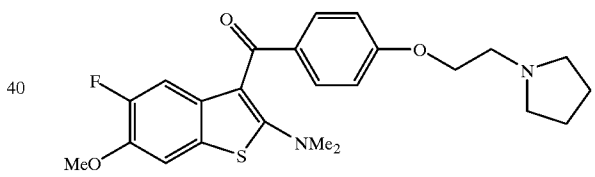

A mixture of 2.0 g (5.34 mmol) of 2-dimethylamino-5-fluoro-6-methoxybenzo[b]thiophene-3-yl 4-nitrophenyl ketone (Part C) and 1.4 g (60% dispersion in mineral oil; 35.0 mmol; washed with hexanes) of NaH in 60 mL of DMF was treated with a solution of 3.75 mL (32.1 mmol) of 1-(2-hydroxyethyl)pyrrolidine in 10 mL of DMF in such rate to control the effervescence. After complete addition, the reaction was stirred at room temperature for 1 h and was quenched by the careful addition of 5 mL of MeOH. The mixture was diluted with 200 mL of EtOAc and was poured into 200 mL of H$_2$O. The two layers were separated and the organic phase was washed with H$_2$O (2×100 mL) and brine (100 mL). The organic phase was dried over K$_2$CO$_3$, filtered, and concentrated in vacuo to give 5.21 g of an amber oil. Purification by flash chromatography (SiO$_2$; gradient of 2% then 5% MeOH in CH$_2$Cl$_2$) afforded 2.10 g (4.74 mmol; 89%) of the title compound as a bright yellow oil.

FDMS 442 (M+); Anal. Calcd for C$_{24}$H$_{27}$FN$_2$O$_3$S: C, 65.14; H, 6.15; N, 6.33. Found: C, 65.08; H, 6.43; N, 6.29.

Part E. 5-Fluoro-6-methoxy-2-[4-[2-(1-pyrrolidinyl)ethoxy]phenyl]benzo[b]thiophen-3-yl 4-[2-(1-Pyrrolidinyl)ethoxy]phenyl Ketone Dioxalate

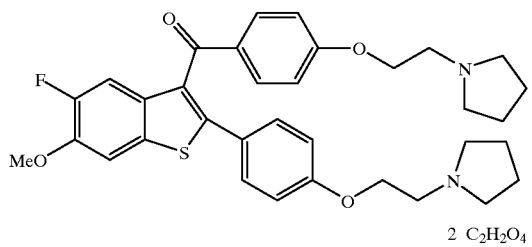

Magnesium turnings (69 gm; 2.84 mmol) were placed in a 3-neck round bottom equipped with a stir bar, nitrogen inlet, dropping funnel and reflux condenser and flame-dried under a stream of nitrogen. THF (5 mL) was added to the reaction vessel followed by a solution of 732 mg (2.71 mg) of 1-[2-(4-bromophenoxy)ethyl]pyrrolidine and a small $I_2$ crystal. The vessel contents were heated to mild reflux for 7 h at which time all the Mg had been consumed. The reaction was cooled to 0° C. and was added via a cannula to a 0° C. solution of 1.00 g (2.26 mmol) of 2-dimethylamino-5-fluoro-6-methoxybenzo[b]thiophene-3-yl 4-[2-(1-pyrrolidinyl)ethoxy]phenyl ketone (Part D) in 10 mL of THF. The mixture was stirred at 0° C. for 16 h, was quenched with 10 mL of $H_2O$, and was acidified to pH 7–8 with 1 N aqueous HCl. The mixture was extracted with $CH_2Cl_2$ (4×100 mL). The combined organic extracts were washed with $H_2O$, dried over $K_2CO_3$, filtered, and concentrated in vacuo to give 1.53 g of an oil. Purification by flash chromatography ($SiO_2$; 4:11:84 TEA/THF/hexanes) afforded 1.18 g (2.12 mmol; 78%) of the title compound as an oil. A sample was converted to the dioxalate salt according to the method described in Example 1, Part C.

FDMS 589 (M+1); Anal. Calcd for $C_{34}H_{37}FN_2O_4S\cdot2 C_2H_2O_4$: C, 57.22; H, 5.18; N, 3.51. Found: C, 57.48; H, 5.42; N, 3.54.

Part F. 5-Fluoro-6-hydroxy-2-[4-[2-(1-pyrrolidinyl)ethoxy]phenyl]benzo[b]thiophen-3-yl 4-[2-(1-Pyrrolidinyl)ethoxy]phenyl Ketone Dioxalate

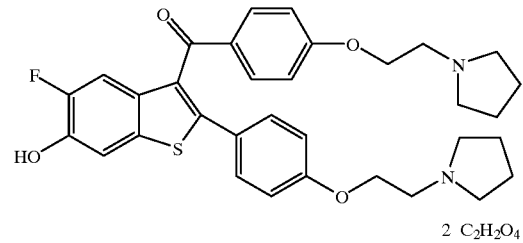

By essentially following the procedures outlined in Example 1, Part D, the title compound was prepared in 61% yield starting from 5-fluoro-6-methoxy-2-[4-[2-(1-pyrrolidinyl)ethoxy]phenyl]benzo[b]thiophen-3-yl 4-[2-(1-pyrrolidinyl)ethoxy]phenyl ketone (Part E). A sample was converted to the dioxalate salt according to the method described in Example 1, Part C.

FDMS 575 (M+1); Anal. Calcd for $C_{33}H_{35}FN_2O_4S\cdot2 C_2H_2O_4$: C, 61.49; H, 5.44; N, 3.88. Found: C, 61.30; H, 5.67; N, 4.09.

Part G. 1-[2-[4-[[5-Fluoro-6-Hydroxy-2-[4-[2-(1-pyrrolidinyl)ethoxy]phenyl]benzo[b]thiophen-3-yl]methyl]phenoxy]ethyl]pyrrolidine Dioxalate The title compound was prepared in 64% yield from 5-fluoro-6-hydroxy-2-[4-[2-(1-pyrrolidinyl)ethoxy]phenyl]benzo[b]thiophen-3-yl 4-[2-(1-pyrrolidinyl)ethoxy]phenyl ketone (Part F) by essentially following the procedure detailed in Example 3, Part E. A sample was converted to the dioxalate salt according to the method described in Example 1, Part C.

FDMS 561 (M+1); Anal. Calcd for $C_{33}H_{37}FN_2O_3S\cdot2 C_2H_2O_4$: C, 59.99; H, 5.58; N, 3.78. Found: C, 59.76; H, 5.67; N, 3.68.

EXAMPLE 118

Preparation of (±)-5-Fluoro-6-hydroxy-3-[4-[[trans-2-(1-piperidyl)cyclohexyl]oxy]benzyl]-2-[4-[2-(1-pyrrolidinyl)ethoxy]phenyl]benzo[b]thiophene Dioxalate

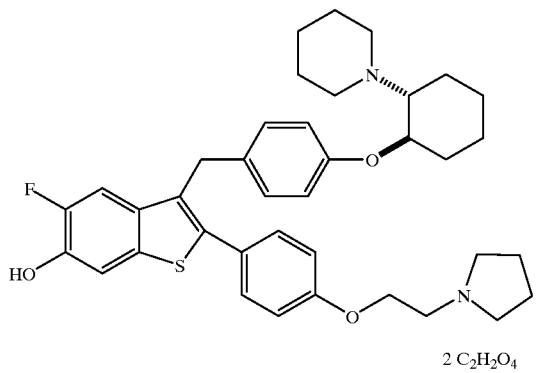

Part A. 2-Dimethylamino-5-fluoro-6-methoxybenzo[b]thiophene-3-yl 4-[[trans-2-(1-Piperidyl)cyclohexyl]oxy]phenyl Ketone

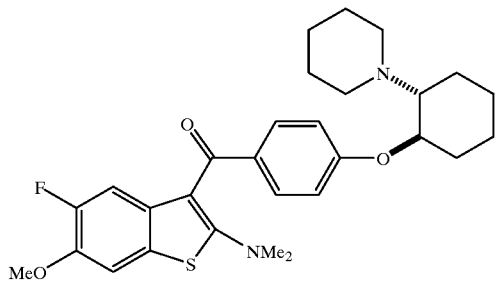

The title compound was prepared in 51% from 2-dimethylamino-5-fluoro-6-methoxybenzo[b]thiophene-3-yl 4-nitrophenyl ketone (Example 117, Part C) and (±)-trans-2-(1-piperidyl)cyclohexanol by essentially following the procedure detailed in Example 117, Part D.

FDMS 510 (M+); Anal. Calcd for $C_{29}H_{35}FN_2O_3S$: C, 68.21; H, 6.91; N, 5.49. Found: C, 68.32; H, 7.18; N, 5.39.

Part B. (±)-5-Fluoro-6-methoxy-2-[4-[2-(1-pyrrolidinyl)ethoxy]phenyl]benzo[b]thiophen-3-yl 4-[[trans-2-(1-Piperidyl)cyclohexyl]oxy]phenyl Ketone Dioxalate

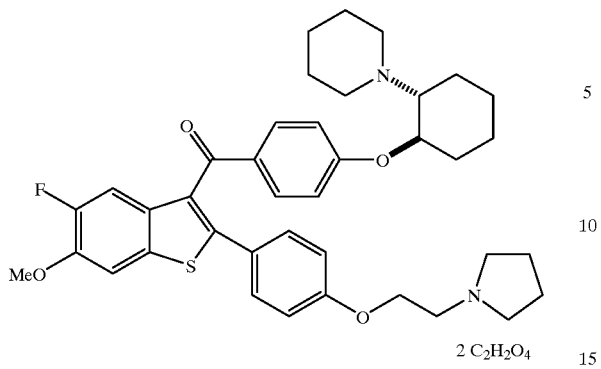

2 C₂H₂O₄

The title compound was prepared in 72% yield (based on consumed starting material) from 2-dimethylamino-5-fluoro-6-methoxybenzo[b]thiophene-3-yl 4-[[trans-2-(1-piperidyl)cyclohexyl]oxy]phenyl ketone (Part A) by essentially following the procedure detailed in Example 117, Part E. A sample was converted to the dioxalate salt according to the method described in Example 1, Part C.

FDMS 657 (M+1); Anal. Calcd for $C_{39}H_{45}FN_2O_4S \cdot 2 C_2H_2O_4$: C, 61.71; H, 5.90; N, 3.35. Found: C, 61.45; H, 6.07; N, 3.63.

Part C. (±)-5-Fluoro-6-hydroxy-2-[4-[2-(1-pyrrolidinyl)ethoxy]phenyl]benzo[b]thiophen-3-yl 4-[[trans-2-(1-Piperidyl)cyclohexyl]oxy]phenyl Ketone Dioxalate

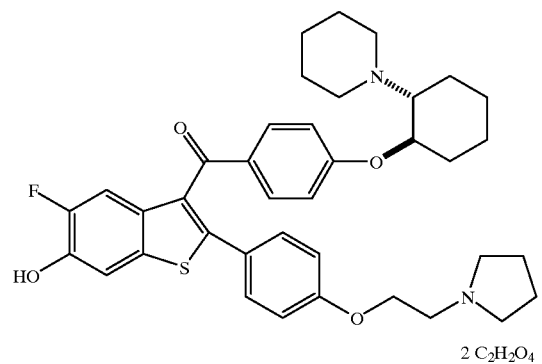

2 C₂H₂O₄

The title compound was prepared in 70% yield from (±)-5-fluoro-6-methoxy-2-[4-[2-(1-pyrrolidinyl)ethoxy]phenyl]benzo[b]thiophen-3-yl 4-[[trans-2-(1-piperidyl)cyclohexyl]oxy]phenyl ketone (Part B) by essentially following the procedure detailed in Example 1, Part D. A sample was converted to the dioxalate salt according to the method described in Example 1, Part C.

FDMS 643 (M+1); Anal. Calcd for $C_{38}H_{43}FN_2O_4S \cdot 2 C_2H_2O_4$: C, 61.30; H, 5.76; N, 3.40. Found: C, 61.04; H, 5.84; N, 3.45.

Part D. (±)-5-Fluoro-6-hydroxy-3-[4-[[trans-2-(1-piperidyl)cyclohexyl]oxy]benzyl]-2-[4-[2-(1-pyrrolidinyl)ethoxy]phenyl]benzo[b]thiophene Dioxalate The title compound was prepared in 70% yield from (±)-5-fluoro-6-hydroxy-2-[4-[2-(1-pyrrolidinyl)ethoxy]phenyl]benzo[b]thiophen-3-yl 4-[[trans-2-(1-piperidyl)cyclohexyl]oxy]phenyl ketone (Part C) by essentially following the procedure detailed in Example 3, Part E. A sample was converted to the dioxalate salt according to the method described in Example 1, Part C.

FDMS 629 (M+1); Anal. Calcd for $C_{38}H_{45}FN_2O_3S \cdot 2 C_2H_2O_4$: C, 62.36; H, 6.11; N, 3.46. Found: C, 62.60; H, 6.11; N, 3.50.

EXAMPLE 119

Preparation of 1-[2-[4-[[2-[4-[2-(1-pyrrolidinyl)ethoxy]phenyl]benzofuran-3-yl]methyl]phenoxy]ethyl]pyrrolidine Dioxalate

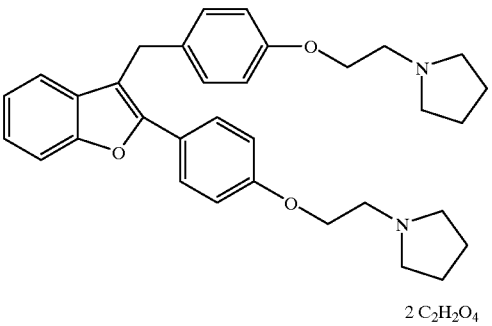

2 C₂H₂O₄

Part A. 2-(4-Methoxyphenyl)benzofuran

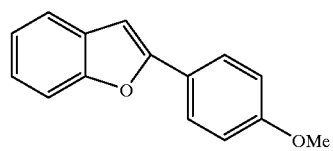

A solution of 46.0 g (0.39 mole) of benzofuran in 100 mL of Et₂O was treated with 0.40 mol (1.6 M in hexanes) of n-BuLi at such a rate as to keep the reaction temperature below 25° C. The mixture was stirred for 15 min and was added to a 10° C. solution of 57.2 g (0.40 mole) of CuBr in 100 mL of Et₂O at a rate so as to keep the reaction temperature below 10° C. The mixture was allowed to reach room temperature over 0.5 h and was treated with a solution of 93.6 g of iodoanisole in 300 mL of pyridine. The mixture was heated to 110° C. for 3 h, allowing the Et₂O to boil off. The reaction mixture was concentrated in vacuo and the residue was dissolved in 3 L of EtOAc. The organic layer was washed several times with 2 N aqueous HCl and once with H₂O, dried over MgSO₄, and filtered. Concentration in vacuo afforded a residue which was recrystallized from MeOH to afford 44.5 g of the title compound as a solid.

mp 145–147° C.

Part B. 2-(4-Methoxyphenyl)benzofuran-3-yl 4-[2-(1-Pyrrolidinyl)ethoxy]phenyl Ketone

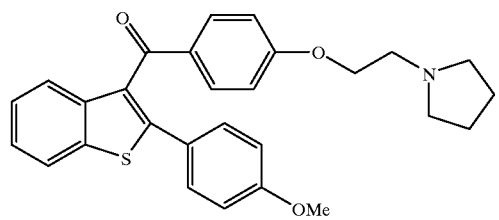

The title compound was prepared in 79% yield from 2-(4-methoxyphenyl)benzofuran (Part A) and 4-[2-(1-pyrrolidinyl)ethoxy]benzoic acid hydrochloride by essentially following the procedure detailed in Example 1, Part C.

mp 92–95° C.; FDMS 441 (M+);

Part C. 2-(4-Hydroxyphenyl)benzofuran-3-yl 4-[2-(1-Pyrrolidinyl)ethoxy]phenyl Ketone

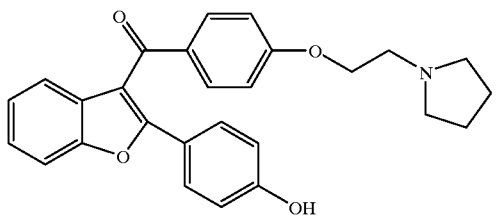

By essentially following the procedures described in Example 1, Part D, the title compound was prepared in 81% yield from 2-(4-methoxyphenyl)benzofuran-2-yl 4-[2-(1-pyrrolidinyl)ethoxy]phenyl ketone (Part B).

FDMS 427 (M+); Anal. Calcd for $C_{27}H_{25}NO_4$: C, 75.86; H, 5.89; N, 3.38. Found: C, 75.59; H, 5.96; N, 3.47.

Part D. 2-[4-[2-(1-Pyrrolidinyl)ethoxy]phenyl]benzofuran-3-yl 4-[2-(1-Pyrrolidinyl)ethoxy]phenyl Ketone Dioxalate

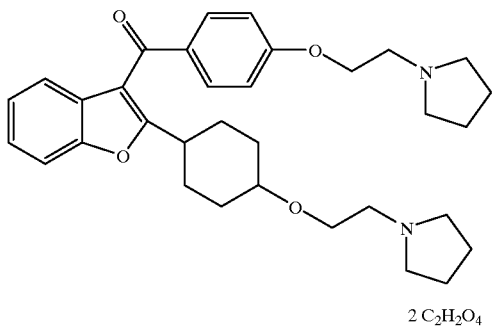

By essentially following the procedure described in Example 3, Part D, the title compound was prepared in 76% yield from 2-(4-hydroxyphenyl)benzofuran-3-yl 4-[2-(1-pyrrolidinyl)ethoxy]phenyl ketone (Part D) and 1-(2-chloroethyl)pyrrolidine hydrochloride. A sample was converted to the dioxalate salt according to the method described in Example 1, Part C.

FDMS 525 (M+1). Anal. Calcd for $C_{33}H_{36}N_2O_4 \cdot 2 C_2H_2O_4$ C, 63.06; H, 5.72 N, 3.98. Found: C, 62.66 H, 5.75; N, 4.06.

Part E. 1-[2-[4-[[2-[4-[2-(1-pyrrolidinyl)ethoxy]phenyl] benzofuran-3-yl]methyl]phenoxy]ethyl]pyrrolidine Dioxalate By essentially following the procedure detailed in Example 3, Part E, the title compound was prepared in 82% yield from 2-[4-[2-(1-pyrrolidinyl)ethoxy]phenyl] benzofuran-3-yl 4-[2-(1-pyrrolidinyl)ethoxy]phenyl ketone (Part D). A sample was converted to the dioxalate salt according to the method described in Example 1, Part C.

FDMS 511 (M+1); Anal. Calcd for $C_{33}H_{38}N_2O_3 \cdot 2 C_2H_2O_4 \cdot H_2O$ C, 62.70; H, 6.26 N, 3.95. Found: C, 62.83 H, 6.13; N, 3.98.

EXAMPLE 120

Preparation of N-[4-[6-Hydroxy-3-[[3-methyl-4-[(1-pyrrolidinyl)methyl]phenyl]methyl]benzo[b]thiphen-2-yl]phenyl]-α-(1-pyrrolidinyl)acetamide Dioxalate

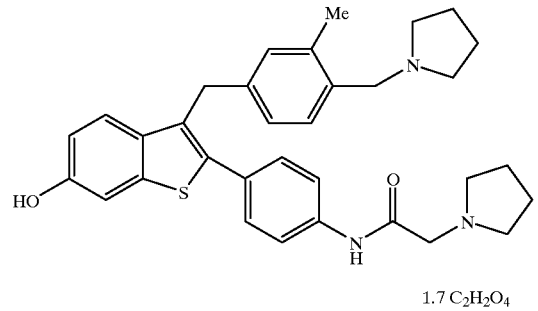

Part A. N-(4-Bromophenyl)-α-chloroacetamide

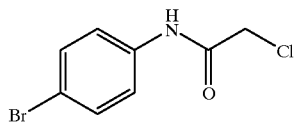

A mixture of 8.60 g (0.05 mol) of 4-bromoaniline, 10.60 g (0.10 mol) of $Na_2CO_3$, and 6.78 g (0.06 mol) of chloroacetyl chloride in 100 mL of acetone was stirred at ambient temperature for 3 h. The mixture was concentrated in vacuo, and the residue was partitioned between EtOAc and $H_2O$. The organic layer was separated, washed with $H_2O$, dried over $Na_2SO_4$, filtered, and evaporated in vacuo to give 11.4 g of analytically pure title compound as light crystals.

FDMS 248 (M+); Anal. Calcd for $C_8H_7BrClNO$: C, 38.67; H, 2.84; N, 5.64. Found: C, 38.45; H, 2.83; N, 5.56.

Part B. N-(4-Bromophenyl)-α-(1-Pyrrolidinyl)acetamide

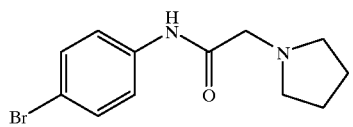

A solution of 5.0 g (0.02 mol) of N-(4-bromophenyl)-α-chloroacetamide (Part A) and 5.05 mL (0.06 mol) of pyrrolidine in 100 mL of THF was stirred overnight at ambient temperature. The mixture was concentrated in vacuo and the residue was partitioned between $H_2O$ and EtOAc. The organic layer was separated, washed with $H_2O$, dried over $Na_2SO_4$, filtered, and evaporated in vacuo to afford 5.74 g of analytically pure title compound as crystals.

mp 60–63° C.; Anal. Calcd for $C_{12}H_{15}BrN_2O$: C, 50.90; H, 5.34; N, 9.89. Found: C, 50.62; H, 5.39; N, 9.74.

Part C. N-[4-(6-Methoxybenzo[b]thiophen-2-yl)phenyl]-α-(1-pyrrolidinyl)acetamide

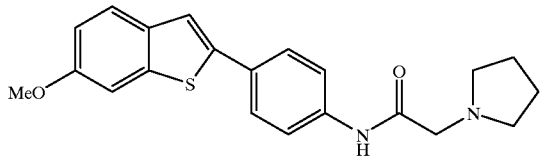

By essentially following the procedures described in Example 1, Part B, the title compound was prepared in 97% yield from N-(4-bromophenyl)-α-(1-pyrrolidinyl)acetamide (Part B) and 6-methoxybenzo[b]thiophene-2-boronic acid (Example 1, Part A).

IR (CHCl$_3$) 1684; FDMS 366 (M+).

Part D. N-[4-[6-Methoxy-3-[[3-methyl-4-[(1-pyrrolidinyl)methyl]phenyl]carbonyl]benzo[b]thiophen-2-yl]phenyl]-α-(1-pyrrolidinyl)acetamide Dioxalate

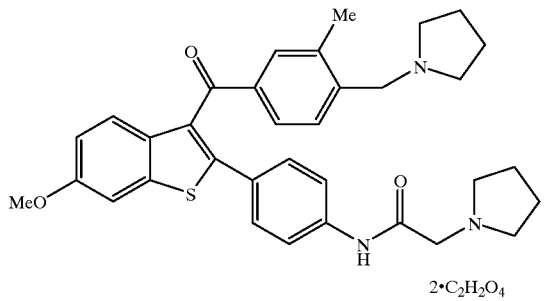

By essentially following the procedures described in Example 1, Part C, the title compound was prepared in 68% yield from the product of Part C and 3-methyl-4-[(1-pyrrolidinyl)methyl]benzoic acid. A sample was converted to the dioxalate salt according to the method described in Example 1, Part C.

IR (CHCl$_3$) 1701, 1640; FDMS 567 (M+). Anal. Calcd for C$_{34}$H$_{37}$N$_3$O$_3$S·2 C$_2$H$_2$O$_4$ C, 61.03; H, 5.53 N, 5.62. Found: C, 60.99 H, 5.72; N, 5.38.

Part E. N-[4-[6-Hydroxy-3-[[3-methyl-4-[(1-pyrrolidinyl)methyl]phenyl]carbonyl]benzo[b]thiophen-2-yl]phenyl]-α-(1-pyrrolidinyl)acetamide By essentially following the procedures described in Example 1, Part D, the title compound was prepared from the product of Part D. A sample was converted to the oxalate salt according to the method described in Example 1, Part C.

FDMS 554 (M+1). Anal. Calcd for C$_{33}$H$_{35}$N$_3$O$_3$S·1.7 C$_2$H$_2$O$_4$ C, 61.86; H, 5.48 N, 5.95. Found: C, 62.15 H, 5.47; N, 5.78.

Part F. N-[4-[6-Hydroxy-3-[[3-methyl-4-[(1-pyrrolidinyl)methyl]phenyl]methyl]benzo[b]thiophen-2-yl]phenyl]-α-(1-pyrrolidinyl)acetamide Dioxalate By essentially following the procedures described in Example 3, Part E, the title compound was prepared from the product of Part E above. A sample was converted to the dioxalate salt according to the method described in Example 1, Part C.

IR (KBr) 1696, 1607; FDMS 540 (M+1). Anal. Calcd for C$_{33}$H$_{37}$N$_3$O$_2$S·1.7 C$_2$H$_2$O$_4$ C, 61.86; H, 5.48 N, 5.95. Found: C, 62.15 H, 5.47; N, 5.78.

EXAMPLE 121

Preparation of 1-[2-[4-[3-[[4-[1-Ethyl-2-(1-pyrrolidinyl)ethoxy]phenyl]methyl]benzo[b]thiophen-2-yl]phenoxy]ethyl]pyrrolidine Dioxalate

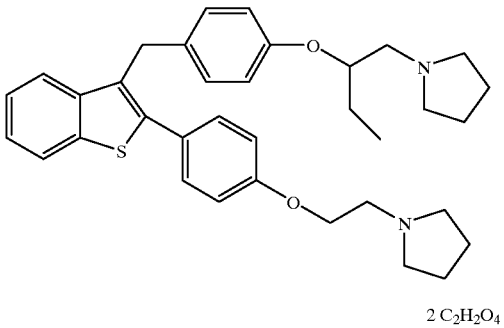

Part A. 1-(1-Pyrrolidinyl)butan-2-ol

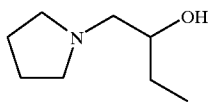

A mixture of 2.6 mL (31.1 mmol) of pyrrolidine and 21.6 g (156.3 mmol) of K$_2$CO$_3$ in 100 mL of DMF was treated with 4.7 g (3.20 mL; 90% tech. grade; 28.2 mmol) of 1-bromo-2-butanone and the reaction was stirred at ambient temperature for 2 h. The mixture was filtered and concentrated in vacuo. The residue was taken up in 100 mL of 1 N aqueous HCl and the solution was washed with 100 mL of EtOAc. The aqueous layer was basified to pH 13 with solid KOH and was extracted with EtOAc (3×100 mL). The combined organic extracts were dried over K$_2$CO$_3$, filtered, and concentrated in vacuo to give 1.6 g of an oil. The oil was taken up in 100 mL of THF and the solution was treated with 860 mg (22.7 mmol) of LiAlH$_4$ at room temperature for 3 h, and then quenched by the sequential addition of 60 mL of H$_2$O, 60 mL of 2 N aqueous NaOH, and 60 mL of H$_2$O at 0° C. The mixture was filtered through diatomaceous earth, and the organic solvent was evaporated in vacuo. The aqueous layer was extracted with EtOAc (4×100 mL). The combined organic layers were dried over K$_2$CO$_3$, filtered, and concentrated in vacuo to give 1.40 g of an oil. Purification by flash chromatography (SiO$_2$; 3% MeOH in CHCl$_3$ saturated with NH$_4$OH) afforded 0.95 g of the title compound as an oil.

FDMS 144 (M+1); Anal. Calcd for C$_8$H$_{17}$NO: C, 67.09; H, 11.96; N, 9.78. Found: C, 67.34; H, 12.07; N, 10.08.

Part B. 4-[1-Ethyl-2-(1-pyrrolidinyl)ethoxy]phenyl 2-[4-[2-(1-Pyrrolidinyl)ethoxy]phenyl]benzo[b]thiophen-3-yl Ketone Dioxalate

209

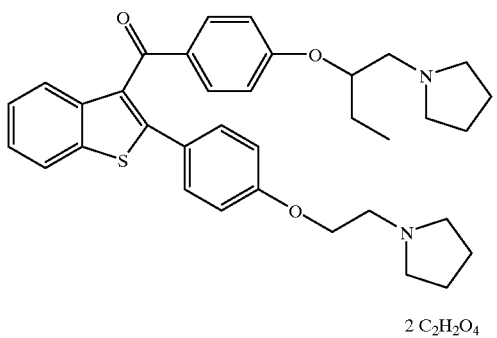

2 C₂H₂O₄

A 0° C. mixture of 75.0 mg (1.88 mmol) of NaH and 550 mg (1.23 mmol) of 4-fluorophenyl 2-[4-[2-(1-pyrrolidinyl) ethoxy]phenyl]benzo[b]thien-3-yl ketone in 10 mL of DMF was treated with a solution of 190 mg (1.33 mmol) of the alcohol from Part A above in 5 mL of DMF at 60° C. for 13 h. After cooling to room temperature, the mixture was poured into 100 mL of brine and extracted with EtOAc (3×100 mL). The combined organic layers were washed with H₂O (2×100 mL) and brine (100 mL), dried over K₂CO₃, filtered, and concentrated in vacuo to give 780 mg of an oil. Purification by radial chromatography (SiO₂; 5% MeOH in CHCl₃ saturated with NH₄OH) afforded 210 mg (0.37 mmol; 30%) of the title compound as an oil. A sample was converted to the dioxalate salt according to the method described in Example 1, Part C.

FDMS 659 (M+1+C₂H₂O₄); Anal. Calcd for C₃₅H₄₀N₂O₃S.2 C₂H₂O₄: C, 62.55; H, 5.92; N, 3.74. Found: C, 62.32; H, 6.15; N, 3.51.

Part C. 1-[2-[4-[3-[[4-[1-Ethyl-2-(1-pyrrolidinyl)ethoxy] phenyl]methyl]benzo[b]thiophen-2-yl]phenoxy]ethyl] pyrrolidine Dioxalate A 0° C. solution of the ketone from Part B (135 mg, 0.237 mmol) in 2.5 mL of anhydrous THF was treated with DIBAL-H (593 µL, 0.593 mmol, 1.0 M solution in toluene) dropwise via a syringe. After 1 h at 0° C., the excess DIBAL-H was quenched with excess MeOH (approximately 1 mL). A solution of 5 mL of saturated Na⁺K⁺ tartrate and 5 mL of EtOAc were added, and the biphasic mixture was vigorously stirred for 1.5 h at ambient temperature. The layers were separated, and the aqueous layer was extracted with EtOAc (2×10 mL). The combined organic layers were dried over Na₂SO₄, filtered, and concentrated in vacuo. The crude product was dissolved in 2.5 mL of 1,2-dichloroethane and Et₃SiH (183 µL, 2.37 mmol). Upon cooling to 0° C., TFA (265 µL, 1.66 mmol) was added in a dropwise fashion. After 1.5 h, the reaction mixture was poured into 50 mL of saturated aqueous NaHCO₃ solution. The aqueous phase was extracted with EtOAc (2×50 mL). The combined organic layers were dried over Na₂SO₄, filtered and concentrated in vacuo. Purification by radial chromatography (SiO₂; gradient 2.5% to 5% MeOH in CHCl₃, saturated with NH₄OH) afforded 62 mg (0.112 mmol; 47%) of a yellow oil. The free base was converted to the title dioxalate salt according to the conditions described in Example 1, Part C.

FDMS 555 (M+1); Anal. calcd for C₃₅H₄₂N₂O₂S·2C₂H₂O₄: C, 63.74; H, 6.31; N, 3.81. Found: C, 63.52; H, 6.26; N, 3.73.

210

EXAMPLE 122

Preparation of 1-[2-[4-[3-[[4-[2-(1-Pyrrolidinyl) butoxy]]phenyl]methyl]benzo[b]thiophen-2-yl] phenoxy]ethyl]pyrrolidine Dioxalate

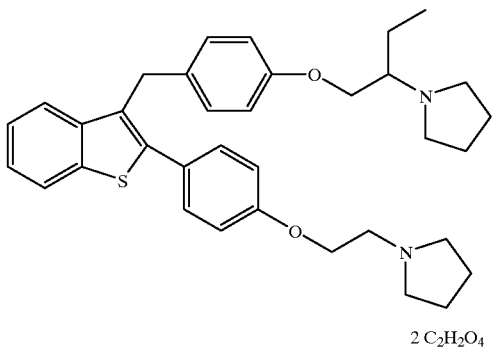

2 C₂H₂O₄

Part A. 2-(1-Pyrrolidinyl)butanol

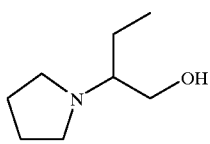

The title compound was prepared in 64% yield for 2 steps from pyrrolidine and ethyl 2-bromobutyrate by essentially following the procedure detailed in Example 121, Part A.

FDMS 144 (M+1); Anal. Calcd for C₈H₁₇NO: C, 67.09; H, 11.96; N, 9.78. Found: C, 66.23; H, 11.36; N, 9.58.

Part B. 4-[2-(1-Pyrrolidinyl)butoxy]phenyl 2-[4-[2-(1-Pyrrolidinyl)ethoxy]phenyl]benzo[b]thiophen-3-yl Ketone Dioxalate

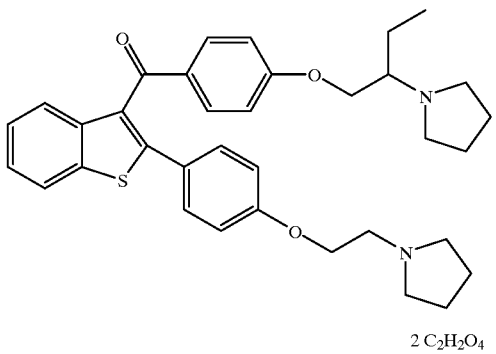

2 C₂H₂O₄

The title compound was prepared in 59% yield from the product of Part A and 4-fluorophenyl 2-[4-[2-(1-pyrrolidinyl)ethoxy]phenyl]benzo[b]thien-3-yl ketone by essentially following the procedure detailed in Example 121, Part B. A sample was converted to the dioxalate salt according to the method described in Example 1, Part C.

FDMS 569 (M+1); Anal. Calcd for C₃₅H₄₀N₂O₃S·2 C₂H₂O₄: C, 62.55; H, 5.92; N, 3.74. Found: C, 62.39; H, 5.80; N, 3.59.

Part C. 1-[2-[4-[3-[[4-[2-(1-pyrrolidinyl)butoxy]]phenyl] methyl]benzo[b]thiophen-2-yl]phenoxy]ethyl]pyrrolidine Dioxalate The title compound was prepared from the free base of the ketone from Part C in 76% yield by essentially following the procedure described in Example 121, Part C.

FDMS 555 (M+1); Anal. calcd for $C_{35}H_{42}N_2O_2S\cdot 2C_2H_2O_4$: C, 63.74; H, 6.31; N, 3.81. Found: C, 63.64; H, 6.07; N, 3.70.

EXAMPLE 123

Preparation of 1-[2-[[5-[6-Hydroxy-3-[[3-methoxy-4-[(1-pyrrolidinyl)methyl]phenyl]methyl]benzo[b]thiophen-2-yl]pyrid-2-yl]oxy]ethyl]pyrrolidine Dioxalate

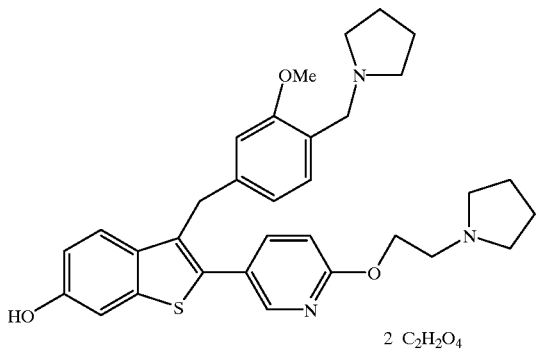

Part A. 6-Benzyloxy-2-[6-[2-(1-pyrrolidinyl)ethoxy]pyrid-3-yl]benzo[b]thiophen-3-yl 3-Methoxy-4-[(1-pyrrolidinyl)methyl]phenyl Ketone

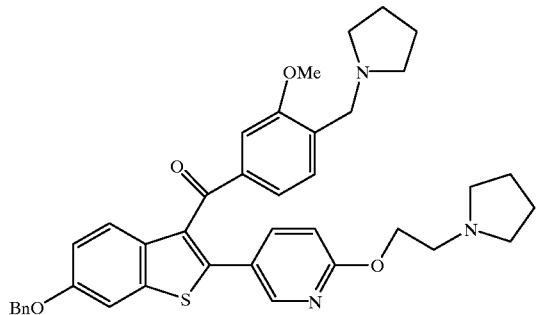

A −78° C. solution of 5-bromopyrid-2-yl 2-(1-pyrrolidinyl)ethyl ether (3.25 g, 12.0 mmol) in 40 mL of anhydrous THF was treated with n-BuLi (8.1 mL, 13.0 mmol, 1.6 M in hexanes). After 1 h, a slurry of $MgBr_2$ [freshly prepared from Mg (365 mg, 15.0 mmol) and 1.3 mL of 1,2-dibromoethane] in 20 mL of anhydrous THF was added. The reaction mixture was stirred at −78° C. for an additional 10 min, and then the cold bath was removed. After 45 min, the Grignard reagent was added dropwise via a cannula to a solution of 6-benzyloxy-2-(dimethylamino)benzo[b]thiophen-3-yl 3-methoxy-4-[(1-pyrrolidinyl)methyl]phenyl ketone (5 g, 10.0 mmol) in 50 mL of THF at 0° C. The resulting mixture was stirred for 2 h at 0° C. and then was allowed to warm to ambient temperature. After 5 h, the reaction mixture was poured into 200 mL of saturated aqueous $NH_4Cl$. The layers were separated, and the aqueous phase was extracted with $CHCl_3$ (3×50 mL). The combined organic phases were dried over $Na_2SO_4$, filtered, and concentrated in vacuo. Purification by PrepLC ($SiO_2$; gradient of 85:10:5 hexanes-THF-TEA to 75:20:5 hexanes-THF-TEA) afforded 2.9 g (4.48 mmol; 45%) of the title product as a viscous orange oil.

FAB HRMS: m/e, calcd for $C_{39}H_{42}N_3O_4S$: 648.2896; Found: 648.2889 (M+1).

Part B. 6-Hydroxy-2-[6-[2-(1-pyrrolidinyl)ethoxy]pyrid-3-yl]benzo[b]thiophen-3-yl 3-Methoxy-4-[(1-pyrrolidinyl)methyl]phenyl Ketone Dioxalate

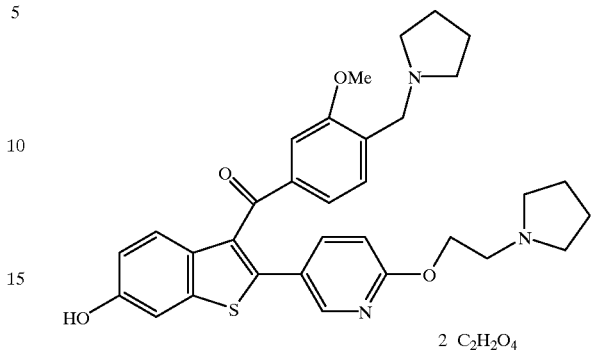

The ketone (2.9 g; 4.48 mmol) from Part A in 40 mL of THF at ambient temperature was treated with 20 mL of ammonium formate (25% aqueous) and 10% Pd/C (2.9 g). Three additional 20 mL aliquots of 25% ammonium formate were added over 12 h. The reaction mixture was filtered through a pad of diatomaceous earth, rinsing well with $CHCl_3$. The layers were separated, and the aqueous layer was extracted with $CHCl_3$ (2×25 mL). The combined organic layers were dried over $Na_2SO_4$, filtered, and concentrated in vacuo to give 2.08 g of the crude product as a yellow foam. Purification by radial chromatography ($SiO_2$; gradient of 75:20:5 hexanes-THF-TEA to 60:35:5 hexanes-THF-TEA) yielded 1.23 g (2.21 mmol; 48%) of a pale yellow foam. A sample of the free base was converted to the title dioxalate salt according to the procedure outlined in Example 1, part C.

FDMS 558 (M+1); Anal. calcd for $C_{32}H_{35}N_3O_4S\cdot 2C_2H_2O_4$: C, 58.61; H, 5.32; N, 5.70. Found: C, 58.76; H, 5.36; N, 5.80.

Part C. 1-[2-[[5-[6-Hydroxy-3-[[3-methoxy-4-[(1-pyrrolidinyl)methyl]phenyl]methyl]benzo[b]thiophen-2-yl]pyrid-2-yl]oxy]ethyl]pyrrolidine Dioxalate DIBAL-H (4.6 mL, 4.6 mmol, 1.0 M solution in toluene) was added dropwise via a syringe to a 0° C. solution of the ketone (Part B; 1.02 g, 1.83 mmol) in 20 mL of anhydrous THF. After 45 min, the excess DIBAL-H was quenched with excess MeOH (approximately 1 mL). A solution of 30 mL of saturated $Na^+K^+$ tartrate and 30 mL of EtOAc were added, and the biphasic mixture was vigorously stirred overnight at ambient temperature. The layers were separated, and the aqueous layer was extracted with EtOAc (20 mL). The combined organic layers were dried over $K_2CO_3$, filtered, and concentrated to an off-white foam. The crude benzyl alcohol (1.1 g) was taken up in 20 mL of 1,2-dichloroethane. $Et_3SiH$ (2 mL, 12.8 mmol) was added, and the resulting mixture was cooled to 0° C. After 5 min, the solution was treated with TFA (1.4 mL, 18.3 mmol). A gummy precipitate formed immediately, so the reaction mixture was allowed to warm to ambient temperature in order to re-dissolve the gum. After 3 h, the reaction mixture was poured into 100 mL of saturated aqueous $NaHCO_3$ solution. Upon addition of 50 mL of EtOAc, the product gummed out; 15 ml MeOH and 50 ml of $CHCl_3$ were added to solubilize the product. The aqueous phase was extracted with $CHCl_3$ (3×50 mL). The combined organic layers were dried over $K_2CO_3$, filtered, and concentrated in vacuo. Purification by radial chromatography gave 673 mg (1.24 mmol; 68%) of a white foam. The free base in 10 mL of THF was converted to the title dioxalate salt by treatment with oxalic acid (230 mg, 2.55 mmol) in 5 mL EtOAc. The white solid was filtered and dried in vacuo to give the title compound.

FDMS 544 (M+1); Anal. calcd for $C_{32}H_{37}N_3O_3S \cdot 2C_2H_2O_4$: C, 59.74; H, 5.71; N, 5.81. Found: C, 59.46; H, 5.70; N, 5.72.

EXAMPLE 124

Preparation of 1-[2-[[5-[6-Hydroxy-3-[[3-methyl-4-[(1-pyrrolidinyl)methyl]phenyl]methyl]benzo[b]thiophen-2-yl]pyrid-2-yloxy]ethyl]pyrrolidine Dioxalate

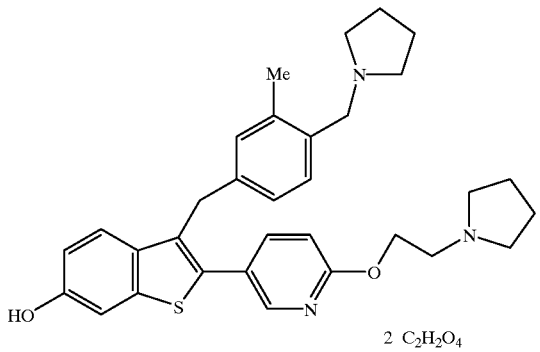

Part A. Methyl 3-Methyl-4-[(1-pyrrolidinyl)methyl] benzoate

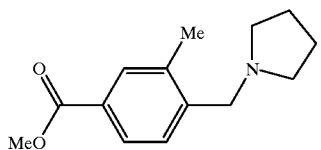

A solution of methyl 3-bromo-4-[(1-pyrrolidinyl)methyl] benzoate (16 g, 53.7 mmol) in 110 mL of toluene was treated with Pd(PPh₃)₄ (3.1 g, 2.68 mmol) and tetramethyltin (22.3 mL, 161.1 mmol). The resulting mixture was heated at 135–140° C. for 36 hr in a sealed tube. After cooling to ambient temperature, the reaction mixture was filtered through diatomaceous earth and concentrated in vacuo. The crude brown residue was purified by PrepLC (SiO₂; 97:2:1 hexanes-THF-TEA) to afford 11.4 g (48.9 mmol; 91%) of the title compound as a slightly yellow oil.

FDMS 233 (M⁺); Anal. calcd for $C_{14}H_{19}NO_2$: C, 72.08; H, 8.21; N, 6.00. Found: C, 72.29; H, 8.17; N, 5.91.

Part B. 3-Methyl-4-[(1-pyrrolidinyl)methyl]benzoic Acid Hydrochloride

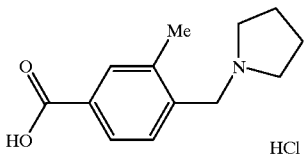

A solution of methyl 3-methyl-4-[(1-pyrrolidinyl)methyl] benzoate (16 g, 68.6 mmol) in 250 mL of 1 N HCl was heated at reflux overnight (13 hr). After cooling to ambient temperature, the aqueous solution was extracted with EtOAc (150 mL). The aqueous layer was concentrated by rotary evaporation to give 16.8 g (65.7 mmol; 96%) of the title acid as a white solid.

FDMS 219 (M⁺); Anal. calcd for $C_{13}H_{17}NO_2 \cdot HCl$: C, 61.06; H, 6.70; N, 5.48. Found: C, 61.22; H, 6.93; N, 5.37.

Part C. 6-Benzyloxy-2-(dimethylamino)benzo[b]thiophen-3-yl 3-Methyl-4-(1-pyrrolidinylmethyl)phenyl Ketone

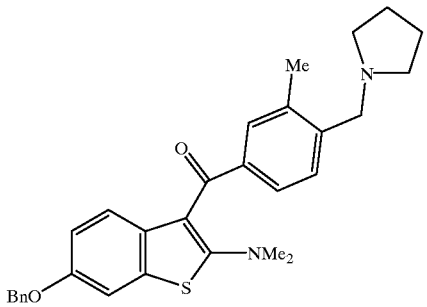

The title compound was prepared from 3-methyl-4-[(1-pyrrolidinyl)methyl]benzoic acid HCl (Part B) in 80% yield as a brilliant orange solid by essentially following the procedure described in Example 39, Part B.

FDMS 484 (M⁺); Anal. calcd for $C_{30}H_{32}N_2O_2S \cdot HCl$: C, 69.15; H, 6.38; N, 5.38. Found: C, 69.36; H, 6.39; N, 5.42.

Part D. 6-Benzyloxy-2-[6-[2-(1-pyrrolidinyl)ethoxy]pyrid-3-yl]benzo[b]thiophen-3-yl 3-Methyl-4-[(1-pyrrolidinyl)methyl]phenyl Ketone

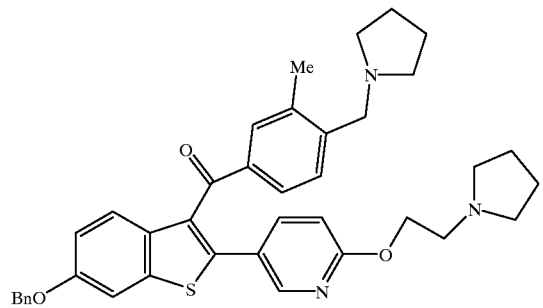

The title compound was prepared from 6-benzyloxy-2-(dimethylamino)benzo[b]thiophen-3-yl 3-methyl-4-[(1-pyrrolidinyl)methyl]phenyl ketone (Part C) in 32% yield by essentially following the procedure detailed in Example 123, Part A.

$^1$H NMR (CDCl₃) δ 8.19 (d, J=2.4 Hz, 1 H), 7.34–7.64 (m, 9 H), 7.25 (s, 1 H), 7.07 (dd, J=8.9, 2.2 Hz, 1 H), 6.99 (s, 1 H), 6.62 (d, J=8.6 Hz, 1 H), 5.15 (s, 2 H), 4.37 (t, J=5.9 Hz, 2 H), 3.55 (s, 2 H), 2.83 (t, J=5.9 Hz, 2 H), 2.54–2.59 (br m, 4 H), 2.46–2.52 (br m, 4 H), 2.28 (s, 3 H), 1.76–1.82 (br m, 8 H); FAB HRMS: m/e, calcd for $C_{39}H_{42}N_3O_3S$: 632.2947; Found: 632.2955 (M+1).

Part E. 1-[2-[[5-[6-Benzyloxy-3-[[3-methyl-4-[(1-pyrrolidinyl)methyl]phenyl]methyl]benzo[b]thiophen-2-yl]pyrid-2-yl]oxy]ethyl]pyrrolidine

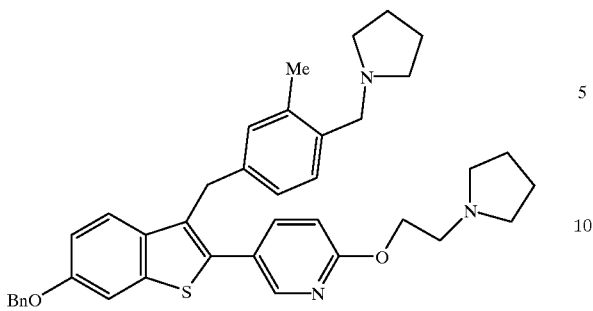

The title compound was prepared from the above ketone (Part D) in 47% yield by essentially following the procedure detailed in Example 123, Part C.

FDMS 618 (M+1); Anal. calcd for $C_{39}H_{43}N_3O_2S$: C, 75.82; H, 7.02; N, 6.80. Found: C, 75.64; H, 6.79; N, 6.77.

Part F. 1-[2-[[5-[6-Hydroxy-3-[[3-methyl-4-[(1-pyrrolidinyl)methyl]phenyl]methyl]benzo[b]thiophen-2-yl]pyrid-2-yl]oxy]ethyl]pyrrolidine Dioxalate The title compound was prepared from the above benzyloxy compound (Part B) in 54% yield by essentially following the procedure described in Example 123, Part B.

FDMS 528 (M+1); Anal. calcd for $C_{32}H_{37}N_3O_2S \cdot 2C_2H_2O_4$: C, 61.09; H, 5.84; N, 5.94. Found: C, 61.04; H, 5.98; N, 5.85.

EXAMPLE 125

Preparation of 6-Hydroxy-2-[6-[2-(1-pyrrolidinyl)ethoxy]pyrid-3-yl]benzo[b]thiophen-3-yl 3-Methyl-4-[(1-pyrrolidinyl)methyl]phenyl Ketone Dioxalate

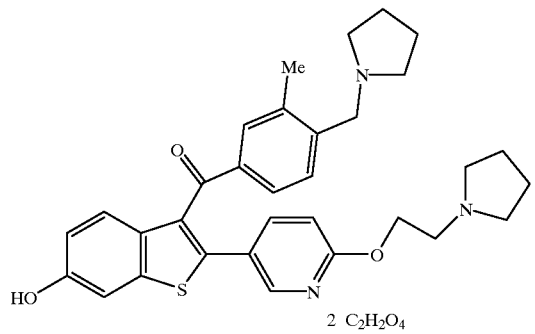

A solution of 6-benzyloxy-2-[6-[2-(1-pyrrolidinyl)ethoxy]pyrid-3-yl]benzo[b]thiophen-3-yl 3-methyl-4-[(1-pyrrolidinyl)methyl]phenyl ketone (265 mg; 0.419 mmol) from Example 124, Part D in 4 mL of 1:1 THF/EtOH was treated with 10% Pd/C (265 mg) for 11 h at ambient temperature under an atmosphere of $H_2$. The catalyst was filtered off and replaced with a fresh portion of 10% Pd/C (265 mg). The reaction mixture was allowed to stir for an additional 12 h under $H_2$ and then it was filtered through a diatomaceous earth pad. The filtrate was concentrated in vacuo to give 170 mg of the crude product as a yellow foam. Purification by radial chromatography (SiO$_2$; gradient of 2.5% to 7.5% MeOH/CHCl$_3$, saturated with NH$_4$OH) afforded 75.6 mg (0.140 mmol; 33%) of a pale yellow foam which was converted to the title dioxalate salt according to the procedure outlined in Example 1, Part C.

FDMS 542 (M+1); Anal. calcd for $C_{32}H_{35}N_3O_3S \cdot 2C_2H_2O_4$: C, 59.91; H, 5.45; N, 5.82. Found: C, 60.16; H, 5.53; N, 5.73.

EXAMPLE 126

Preparation of 1-[2-[2-Methyl-4-[6-hydroxy-3-[[3-methyl-4-[(1-pyrrolidinyl)methyl]phenyl]methyl]benzo[b]thiophen-2-yl]phenoxy]ethyl]pyrrolidine Dioxalate

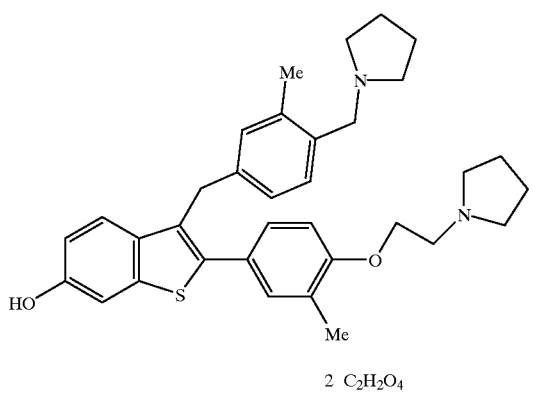

Part A. 4-Bromo-2-methylphenyl 2-(1-Pyrrolidinyl)ethyl Ether

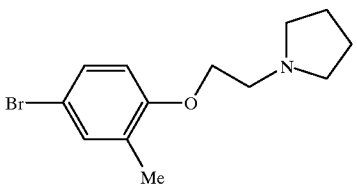

4-Bromo-2-methylphenol (10 g, 53.5 mmol) and 1-(2-chloroethyl)pyrrolidine HCl (11 g, 64.7 mmol) were heated at 80° C. in 500 mL of DMF in the presence of $K_2CO_3$ (22 g, 159.2 mmol) for 16 h. After cooling, the crude product was filtered and concentrated in vacuo. The brown oily residue was purified by PrepLC (SiO$_2$; gradient of 90:8:2 to 85:10:5 hexanes-THF-TEA) to afford 11.25 g (39.6 mmol; 74%) of the title compound as a clear, colorless oil.

FDMS 283 (M-1), 285 (M+1); Anal. calcd for $C_{13}H_{18}BrNO$: C, 54.94; H, 6.38; N, 4.93. Found: C, 55.11; H, 6.16; N, 5.03.

Part B. 6-Benzyloxy-2-[3-methyl-4-[2-(1-pyrrolidinyl)ethoxy]phenyl]benzo[b]thiophen-3-yl 3-Methyl-4-[(1-pyrrolidinyl)methyl]phenyl Ketone

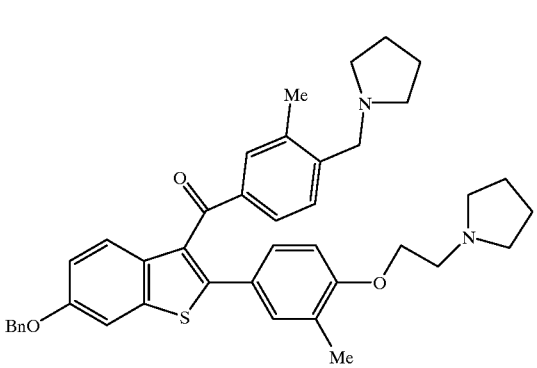

The title compound was prepared from 6-benzyloxy-2-(dimethylamino)benzo[b]thiophen-3-yl 3-methyl-4-[(1-pyrrolidinyl)methyl]phenyl ketone (Example 124, Part C)

and 4-bromo-2-methylphenyl 2-(1-pyrrolidinyl)ethyl ether (Part A) in 59% yield after PrepLC (SiO$_2$; gradient of 85:10:5 to 75:20:5 hexanes-THF-TEA) by essentially following the procedure detailed in Example 123, Part A.

FDMS:644 (M$^+$); Anal. calcd for C$_{41}$H$_{44}$N$_2$O$_3$S: C, 76.36; H, 6.88; N, 4.34. Found: C, 76.48; H, 7.13; N, 4.16.

Part C. 6-Hydroxy-2-[3-methyl-4-[2-(1-pyrrolidinyl) ethoxy]phenyl]benzo[b]thiophen-3-yl 3-Methyl-4-[(1-pyrrolidinyl)methyl]phenyl Ketone Dioxalate

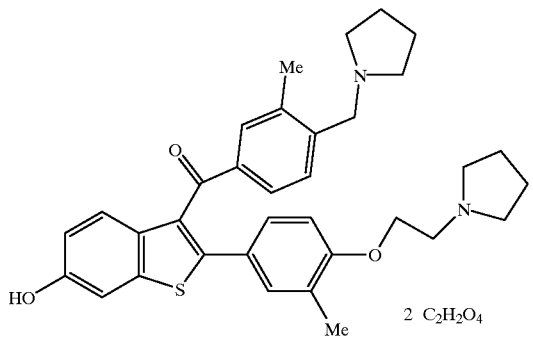

The title compound was prepared from the ketone (Part B) in 66% yield after radial chromatography (SiO$_2$; gradient of 1% to 2% MeOH in CHCl$_3$, saturated with NH$_4$OH) by essentially following the procedure detailed in Example 123, Part B.

FDMS 555 (M+1); Anal. calcd for C$_{34}$H$_{38}$N$_2$O$_3$S·2C$_2$H$_2$O$_4$: C, 62.11; H, 5.76; N, 3.81. Found: C, 61.91; H, 5.92; N, 3.62.

Part D. 1-[2-[2-methyl-4-[6-hydroxy-3-[[3-methyl-4-[(1-pyrrolidinyl)methyl]phenyl]methyl]benzo[b]thiophen-2-yl] phenoxy]ethyl]pyrrolidine Dioxalate The title compound was prepared from the ketone (Part C) in 62% yield after radial chromatography (SiO$_2$; gradient of 1% to 2% MeOH in CHCl$_3$, saturated with NH$_4$OH) by essentially following the procedure detailed in Example 123, Part C.

FDMS 541 (M+1); Anal. calcd for C$_{34}$H$_{40}$N$_2$O$_2$S·2C$_2$H$_2$O$_4$: C, 63.32; H, 6.15; N, 3.89. Found: C, 63.26; H, 6.39; N, 3.96.

EXAMPLE 127

Preparation of 1-[[4-[6-Hydroxy-2-[3-methoxy-4-[2-(1-pyrrolidinyl)ethoxy]phenyl]benzo[b]thiophen-3-yl]methyl-2-methylphenyl]methyl]pyrrolidine Dioxalate

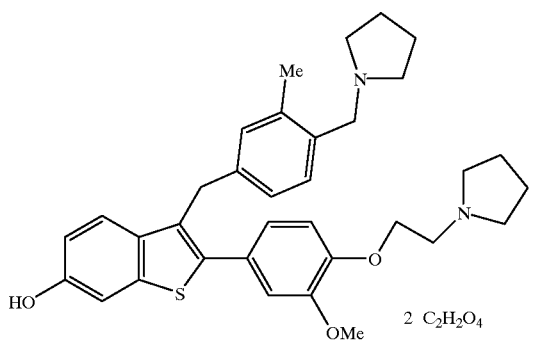

Part A. 4-Bromo-2-methoxyphenyl 2-(1-Pyrrolidinyl)ethyl Ether

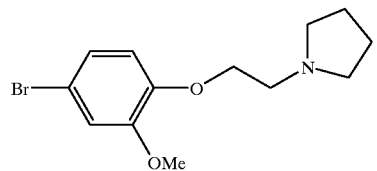

The title compound was prepared from 4-bromoguaiacol (4-bromo-2-methoxyphenol) in 67% yield by essentially following the procedure outlined in Example 126, Part A.

FDMS 299 (M−1), 301 (M+1); Anal. calcd for C$_{13}$H$_{18}$BrNO$_2$: C, 52.01; H, 6.04; N, 4.67. Found: C, 52.24; H, 5.97; N, 4.62.

Part B. 6-Benzyloxy-2-[3-methoxy-4-[2-(1-pyrrolidinyl) ethoxy]phenyl]benzo[b]thiophen-3-yl 3-Methyl-4-[(1-pyrrolidinyl)methyl]phenyl Ketone

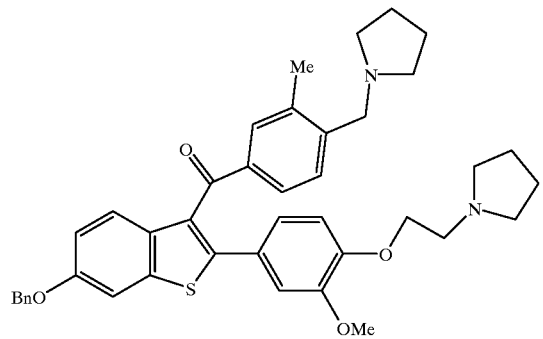

The title compound was prepared from 6-benzyloxy-2-(dimethylamino)benzo[b]thiophen-3-yl 3-methyl-4-[(1-pyrrolidinyl)methyl]phenyl ketone (Example 124, Part C) and 4-bromo-2-methoxyphenyl 2-(1-pyrrolidinyl)ethyl ether (Part A) in 30% yield after PrepLC (SiO$_2$; gradient of 80:15:5 to 70:25:5 hexanes-THF-TEA) by essentially following the procedure detailed in Example 123, Part A.

$^1$H NMR (CDCl$_3$) δ 7.67 (d, J=8.9 Hz, 1 H), 7.63 (s, 1 H), 7.39–7.58 (m, 7 H), 7.27 (d, J=8.0 Hz, 1 H), 7.11 (dd, J=9.0, 2.3, 1 H), 7.00 (d, J=1.9 Hz, 1 H), 6.89 (d, J=1.8 Hz, 1 H), 6.78 (d, J=8.4 Hz, 1 H), 5.20 (s, 2 H), 4.12 (t, J=6.5 Hz, 2 H), 3.73 (s, 3 H), 3.57 (s, 2 H), 2.93 (t, J=6.6 Hz, 2 H), 2.62–2.66 (br m, 4 H), 2.48–2.54 (br m, 4 H), 2.29 (s, 3 H), 1.80–1.84 (br m, 8 H); FAB HRMS: m/e, calcd for C$_{41}$H$_{45}$N$_2$O$_4$S: 661.3100; Found: 661.3107 (M+1).

Part C. 6-Hydroxy-2-[3-methoxy-4-[2-(1-pyrrolidinyl) ethoxy]phenyl]benzo[b]thiophen-3-yl 3-Methyl-4-[(1-pyrrolidinyl)methyl]phenyl Ketone

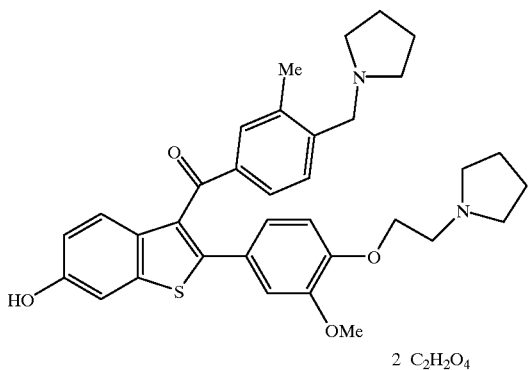

The title compound was prepared from the ketone (Part B) in 56% yield after radial chromatography (SiO$_2$; gradient of 1% to 2% MeOH in CHCl$_3$, saturated with NH$_4$OH) by essentially following the procedure outlined in Example 123, Part B.

FDMS 571 (M+1); Anal. calcd for C$_{34}$H$_{38}$N$_2$O$_4$S·2C$_2$H$_2$O$_4$: C, 60.79; H, 5.64; N, 3.73. Found: C, 60.60; H, 5.48; N, 3.63.

Part D. 1-[[4-[6-Hydroxy-2-[3-methoxy-4-[2-(1-pyrrolidinyl)ethoxy]phenyl]benzo[b]thiophen-3-yl]methyl-2-methylphenyl]methyl]pyrrolidine Dioxalate The title compound was prepared from the ketone (Part C) in 77% yield after radial chromatography (SiO$_2$; gradient of 1% to 2% MeOH in CHCl$_3$, saturated with NH$_4$OH) by essentially following the procedure described in Example 123, Part C.

FDMS 557 (M+1); Anal. calcd for C$_{34}$H$_{40}$N$_2$O$_3$S·2C$_2$H$_2$O$_4$: C, 61.94; H, 6.02; N, 3.80. Found: C, 61.65; H, 5.93; N, 3.84.

EXAMPLE 128

Preparation of 1-[2-[2-Hydroxy-4-[6-hydroxy-3-[3-methyl-4-[(1-pyrrolidinyl)methyl]benzyl]benzo[b]thiophen-2-yl]phenoxy]ethyl]pyrrolidine Dioxalate

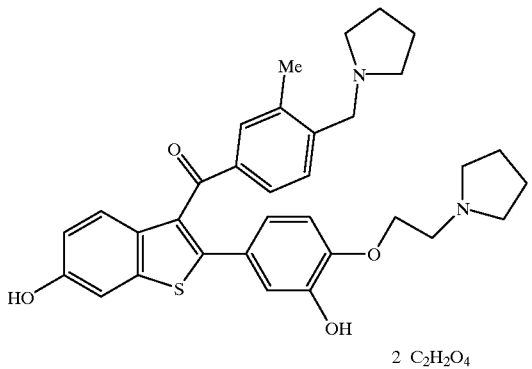

A solution of 1-[[4-[6-hydroxy-2-[3-methoxy-4-[2-(1-pyrrolidinyl)ethoxy]phenyl]benzo[b]thiophen-3-yl]methyl-2-methylphenyl]methyl]pyrrolidine (Example 127, Part D; 182 mg, 0.327 mmol) in 5 mL of 1,2-dichloroethane was cooled to 0° C. and treated with EtSH (195 μL, 2.62 mmol) followed by AlCl$_3$ (262 mg, 1.96 mmol). The resulting mixture was allowed to warm to ambient temperature. After 16 h, the reaction mixture was poured into 10 mL of saturated aqueous NaHCO$_3$ solution. The aqueous layer was extracted with 5% MeOH/CHCl$_3$ (3×10 mL). The combined organic layers were dried over Na$_2$SO$_4$, filtered, and concentrated under reduced pressure. Purification by radial chromatography (SiO$_2$; gradient of 1% to 4% MeOH in CHCl$_3$, saturated with NH$_4$OH) gave 96 mg (0.177 mmol; 54%) of a white foam. Subsequent dioxalate salt formation as described in Example 1, Part C afforded the title compound as a white solid.

FDMS 543 (M+1); Anal. calcd for C$_{33}$H$_{38}$N$_2$O$_3$S·2C$_2$H$_2$O$_4$: C, 61.48; H, 5.86; N, 3.88. Found: C, 61.36; H, 5.77; N, 3.85.

EXAMPLE 129

Preparation of 1-[2-[4-[3-[4-[3-(1-Pyrrolidinyl)-1-propynyl]benzyl]benzo[b]thiophen-2-yl]phenoxy]ethyl]pyrrolidine Dioxalate

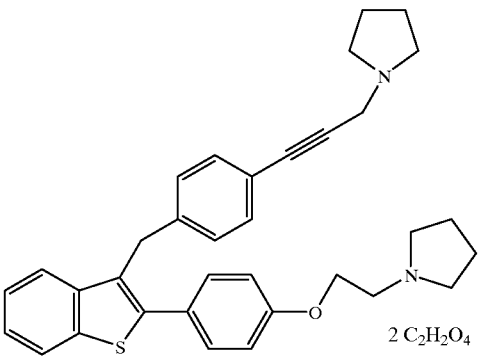

Part A. 4-Iodophenyl 2-[4-[2-(1-Pyrrolidinyl)ethoxy]phenyl]benzo[b]thiophen-3-yl Ketone

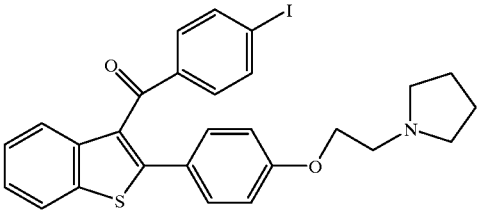

A slurry of 4-iodobenzoic acid (7.67 g, 30.9 mmol) in 300 mL of 1,2-dichloroethane and 2 drops of DMF was treated with SOCl$_2$ (11.3 mL, 154.6 mmol). The resulting mixture was heated at reflux overnight. The clear solution was evaporated in vacuo, then the solid residue was resuspended in 1,2-dichloroethane and reconcentrated. The crude acid chloride was dissolved in 300 mL of 1,2-dichloroethane, and 2-[4-[2-(1-pyrrolidinyl)ethoxy]phenyl]benzo[b]thiophene (5.0 g, 15.5 mmol) was added. The solution was cooled to 0° C. and treated with TiCl$_4$ (8.5 mL, 77.3 mmol). After 5.5 h, the reaction mixture was carefully poured into 600 mL of saturated aqueous NaHCO$_3$. The layers were separated, and the aqueous phase was extracted with CHCl$_3$ (3×300 mL). The combined organic phases were dried over Na$_2$SO$_4$, filtered, and concentrated in vacuo. Purification by PrepLC (SiO$_2$; 1% MeOH in CHCl$_3$, saturated with NH$_4$OH) afforded 6.79 g (12.3 mmol; 79%) of the title product as a yellow foam.

FDMS 553 (M$^+$); Anal. calcd for C$_{27}$H$_{24}$INO$_2$S: C, 58.59; H, 4.37; N, 2.53. Found: C, 58.32; H, 4.28; N, 2.46.

Part B. 4-[3-Hydroxy-1-propynyl]phenyl 2-[4-[2-(1-Pyrrolidinyl)ethoxy]phenyl]benzo[b]thiophen-3-yl Ketone

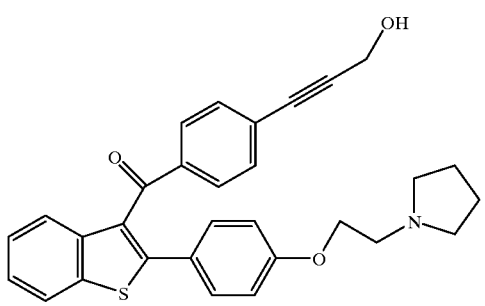

A solution of 4-iodophenyl 2-[4-[2-(1-pyrrolidinyl) ethoxy]phenyl]benzo[b]thiophen-3-yl ketone (Part A; 5.0 g, 9.0 mmol) was treated with propargyl alcohol (1.05 mL, 18.1 mmol) and Pd(PPh$_3$)$_2$Cl$_2$ (190 mg, 0.27 mmol). The reaction vessel was covered with aluminum foil to keep out light, and CuI (35 mg, 0.18 mmol) was added. After stirring overnight at ambient temperature, the reaction mixture was filtered over diatomaceous earth and concentrated in vacuo. Purification by flash chromatography (SiO$_2$; 4% MeOH in CHCl$_3$, saturated with NH$_4$OH) gave 4.32 g (8.97 mmol; quantitative) of the title product as a light brown foam.

$^1$H NMR (CDCl$_3$) δ 7.98 (d, J=9.0 Hz, 1 H), 7.86 (d, J=8.7 Hz, 1 H), 7.54 (d, J=8.3 Hz, 2 H), 7.38–7.42 (m, 3 H), 7.16–7.22 (m, 3 H), 6.66 (d, J=8.7 Hz, 2 H), 4.95 (br, 1 H), 4.41 (s, 2 H), 4.11 (t, J=5.4 Hz, 2 H), 2.98 (t, J=5.4 Hz, 2 H), 2.76 (br m, 4 H), 1.87 (br m, 4 H); FAB HRMS: m/e, calcd for C$_{30}$H$_{28}$NO$_3$S: 482.1790; Found: 482.1779 (M+1).

Part C. 4-[3-(1-Pyrrolidinyl)-1-propynyl]phenyl 2-[4-[2-(1-Pyrrolidinyl)ethoxy]phenyl]benzo[b]thiophen-3-yl Ketone Dioxalate

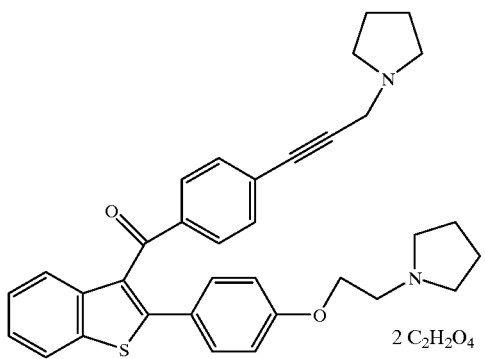

TEA (70 μL, 0.51 mmol) was added to a 0° C. suspension of the ketone (Part B; 4.9 g, 10.2 mmol) and K$_2$CO$_3$ (1.7 g, 12.2 mmol) in 70 mL of CH$_2$Cl$_2$. After 5 min, the reaction mixture was treated with methanesulfonyl chloride (945 μL, 12.2 mmol). After 1 h at 0° C., pyrrolidine (4.24 mL; 50.9 mmol) was quickly added. After stirring 16 h at ambient temperature, the reaction mixture was poured into 100 mL of brine. The aqueous layer was extracted with EtOAc (3×100 mL). The combined organic layers were dried over Na$_2$SO$_4$, filtered, and concentrated under reduced pressure. Purification by PrepLC (SiO$_2$; gradient of 80:15:5 to 60:35:5 hexanes-THF-TEA) afforded 3.0 g (5.61 mmol; 51%) of a light brown foam. A sample of the free base was converted to the title dioxalate salt according to the conditions outlined in Example 1, Part C.

FDMS 534 (M$^+$); Anal. calcd for C$_{34}$H$_{34}$N$_2$O$_2$S·2C$_2$H$_2$O$_4$: C, 63.85; H, 5.36; N, 3.92. Found: C, 63.61; H, 5.55; N, 4.01.

Part D. 1-[2-[4-[3-[4-[3-(1-Pyrrolidinyl)-1-propynyl] benzyl]benzo[b]thiophen-2-yl]phenoxy]ethyl]pyrrolidine Dioxalate The title compound was prepared from the ketone (Part C) in 76% yield by essentially following the procedure described in Example 133, Part C.

$^1$H NMR (CDCl$_3$) δ 7.83 (d, J=7.8 Hz, 1H), 7.46 (d, J=7.8 Hz, 1H), 7.38 (d, J=8.7 Hz, 2H), 7.29–7.33 (m, 4H), 7.07 (d, J=8.1, 2H), 6.94 (d, J=8.7 Hz, 2H), 4.24 (s, 2H), 4.14 (t, J=6.0 Hz, 2H), 3.61 (s, 2H), 2.93 (t, J=5.9 Hz, 2H), 2.65–2.68 (br m, 8H), 1.8–1.84 (br m, 8H); FDMS 521 (M+1); Anal. calcd for C$_{34}$H$_{36}$N$_2$OS·2C$_2$H$_2$O$_4$·0.2H$_2$O: C, 64.79; H, 5.78; N, 3.98. Found: C, 64.42; H, 5.42; N, 3.77.

EXAMPLE 130

Preparation of (E)-1-[2-[4-[3-[4-[3-(1-Pyrrolidinyl)-1-propenyl]benzyl]benzo[b]thiophen-2-yl]phenoxy]-ethyl]pyrrolidine Dioxalate.

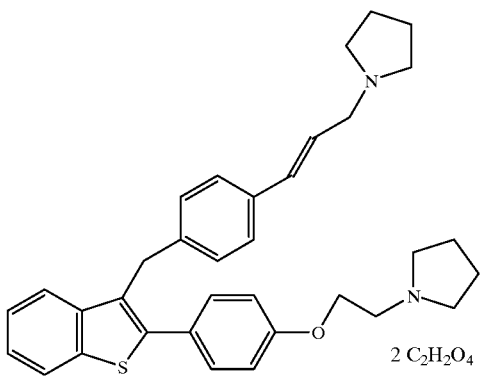

A solution of 1-[2-[4-[3-[4-[3-(1-pyrrolidinyl)-1-propynyl]benzyl]benzo[b]thiophen-2-yl]phenoxy]ethyl]-pyrrolidine (Example 129, Part D; 95 mg, 0.182 mmol) in 1.5 mL of toluene was treated with DIBAL-H (455 mL, 0.455 mmol; 1M in toluene). The resulting mixture was heated at 40° C. for 3 h. The reaction mixture was cooled to 0° C. and quenched with excess MeOH. Saturated K$^+$Na$^+$ tartrate solution and EtOAc (10 mL each) were added, and the biphasic mixture was vigorously stirred for 2 h. The layers were separated, and the aqueous layer was extracted with EtOAc (10 mL). The combined organic layers were dried over Na$_2$SO$_4$, filtered, and concentrated. Purification by radial chromatography (SiO$_2$; 98:1.5:0.5 CHCl$_3$—MeOH—NH$_4$OH) afforded 42 mg (0.80 mmol, 44%) of a pale yellow oil which was converted to the dioxalate salt according to the methods detailed in Example 1, Part C.

$^1$H NMR (CDCl$_3$) δ 7.83 (d, J=7.0 Hz, 1H), 7.49 (d, J=7.0 Hz, 1H), 7.42 (d, J=7.0 Hz, 2H), 7.26–7.32 (m, 4H), 7.09 (d, J=8.0 Hz, 2H), 6.95 (d, J=8.7 Hz, 2H), 6.50 (d, J=15.9 Hz, 1H), 6.29 (dt, J=15.9, 6.5 Hz, 1H), 4.25 (s, 2H), 4.13 (t, J=5.9 Hz, 2H), 3.24 (d, J=6.5 Hz, 2H), 2.91 (t, J=5.9 Hz, 2H), 2.61 (br m, 4H), 2.54 (br m, 4H), 1.82 (br m, 8H); Anal. calcd for C$_{34}$H$_{38}$N$_2$OS·2C$_2$H$_2$O$_4$·0.5H$_2$O: C, 64.11; H, 6.09; N, 3.94. Found: C, 64.11; H, 6.00; N, 4.08; FAB HRMS: m/e, calcd for C$_{34}$H$_{39}$N$_2$OS: 523.2783; Found: 523.2774 (M+1).

EXAMPLE 131

Preparation of (Z)-1-[2-[4-[3-[4-[3-(1-Pyrrolidinyl)-1-propenyl]benzyl]benzo [b]thiophen-2-yl]phenoxy]-ethyl]pyrrolidine Dioxalate.

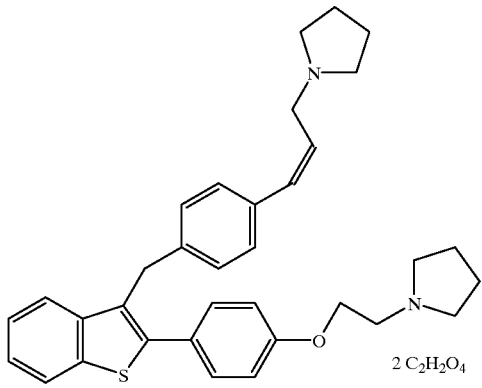

2 C₂H₂O₄

A solution of 1-[2-[4-[3-[4-[3-(1-pyrrolidinyl)-1-propynyl]benzyl]benzo[b]thiophen-2-yl]phenoxy]ethyl]-pyrrolidine (Example 129, Part D; 300 mg, 0.576 mmol) in 40 mL of pyridine was treated with a slurry of Lindlar catalyst (Pd/CaCO₃, Pb poisoned; 100 mg) in 10 mL of pyridine. The resulting mixture was stirred under an atmospheric pressure of H₂ at room temperature for 3 h. The reaction mixture was filtered through a pad of diatomaceous earth and concentrated in vacuo. Purification by radial chromatography (SiO₂, 5% MeOH in CHCl₃, saturated with NH₄OH) gave 185 mg (0.354 mmol, 61%) of a yellow oil which was converted to the dioxalate salt according to the procedure described in Example 1, Part C.

¹H NMR (CDCl₃) δ 7.83 (d, J=6.6 Hz, 1H), 7.52 (d, J=6.8 Hz, 1H), 7.43 (d, J=8.6 Hz, 2H), 7.27–7.30 (m, 2H), 7.11–7.18 (m, 4H), 6.95 (d, J=8.7 Hz, 2H), 6.46 (d, J=11.8 Hz, 1H), 5.81 (dt, J=11.8, 5.9 Hz, 1H), 4.27 (s, 2H), 4.13 (t, J=6.0 Hz, 2H), 3.40 (d, J=6.1 Hz, 2H), 2.92 (t, J=5.9 Hz, 2H), 2.64 (br m, 4H), 2.57 (br m, 4H), 1.76–1.84 (br m, 8H); Anal. calcd for C₃₄H₃₈N₂OS·1.6C₂H₂O₄: C, 67.01; H, 6.23; N, 4.20. Found: C, 66.95; H, 6.07; N, 3.88; FAB HRMS: m/e, calcd for C₃₄H₃₉N₂OS: 523.2783; Found: 523.2779 (M+1).

EXAMPLE 132

Preparation of 1-[2-14-[3-[4-[2-(Ethylamino) ethoxy]-benzyl]benzo[b]thiophen-2-yl]phenoxy] ethyl]pyrrolidine Dioxalate.

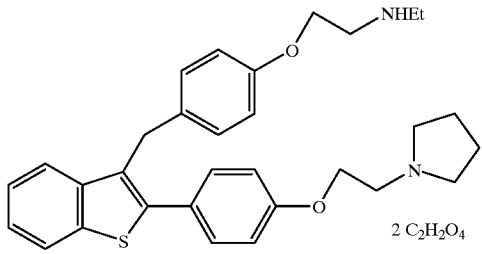

2 C₂H₂O₄

Part A. 4-Fluorophenyl 2-[4-[2-(1-Pyrrolidinyl)-ethoxy]phenyl]benzo[b]thiophen-3-yl Ketone.

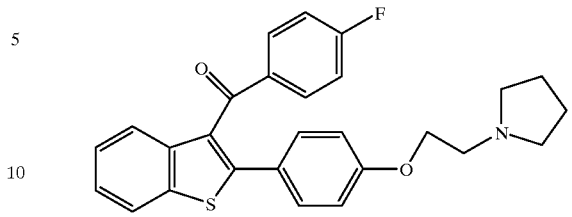

The title compound was prepared in 65% yield from 2-[4-[2- (1-pyrrolidinyl)ethoxy]phenyl]benzo[b]thiophene and 4-fluorobenzoyl chloride by essentially following the procedure detailed in Example 129, Part A.

FAB HRMS: m/e, calcd for C₂₇H₂₅FNO₂S: 446.1590; Found: 446.1597 (M+1).

Part B. 4-[2-(Ethylamino)ethoxy]phenyl 2-[4-[2-(1-Pyrrolidinyl)ethoxy]phenyl]benzo[b]thiophen-3-yl Ketone Dioxalate.

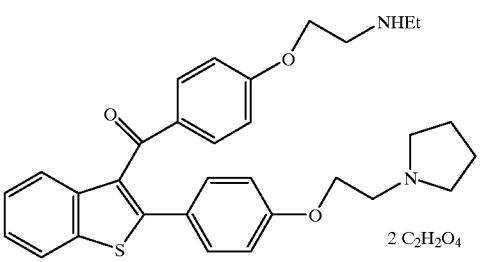

2 C₂H₂O₄

NaH (108 mg, 4.49 mmol), rinsed with hexanes and dried, was added to a solution of 4-fluorophenyl 2-[4-[2-(1-pyrrolidinyl)ethoxy]phenyl]benzo [b]thiophen-3-yl ketone (1.0 g, 2.24 mmol; Part A) in 20 mL of DMF. To the resulting mixture was added dropwise at 0° C. 2-ethylaminoethanol (440 μL, 4.49 mmol) via a syringe. After the foaming had subsided, the reaction mixture was warmed to ambient temperature and allowed to stir overnight. The reaction mixture was poured into 50 mL of brine. The layers were separated and the aqueous layer was extracted with EtOAc (2×50 mL). The combined organic phases were washed with H₂O (2×50 mL) and brine (50 mL), filtered, and concentrated under reduced pressure. Radial chromatography (SiO₂; gradient of 85:10:5 to 70:25:5 hexanes-THF-TEA) afforded 587 mg (1.14 mmol; 42%) of a pale yellow oil. A sample of the purified free base was converted to the title dioxalate salt according to the conditions described in Example 1, Part C.

FDMS 515 (M+1); Anal. calcd for C₃₁H₃₄N₂O₃S·2C₂H₂O₄: C, 60.51; H, 5.51; N, 4.03. Found: C, 60.21; H, 5.40; N, 4.18.

Part C. 1-[2-[4-[3-[4-[2-(Ethylamino)ethoxy]benzyl]-benzo[b]thiophen-2-yl]phenoxy]ethyl]pyrrolidine Dioxalate.

A 0° C. solution of 4-[2-(ethylamino)ethoxy]phenyl 2-[4-[2-(1-pyrrolidinyl)ethoxy]phenyl]benzo[b]thiophen-3-yl ketone (390 mg, 0.758 mmol; Part B) in 5 mL of anhydrous THF was treated with DIBAL-H (1.5 mL, 1.52 mmol, 1M solution in toluene) dropwise via a syringe. After 1 h at 0° C., the excess DIBAL-H was quenched with excess MeOH (approximately 1 mL), 5 mL of saturated Na+K+tartrate and S mL of EtOAc were added, and the biphasic mixture was vigorously stirred for 1.5 h at ambient temperature. The layers were separated, and the aqueous layer was extracted with EtOAc (2×10 mL). The combined organic layers were dried over Na$_2$SO$_4$, filtered and concentrated in vacuo. The crude residue was dissolved in 5 mL of 1,2-dichloroethane and Et$_3$SiH (848 μL, 5.31 mmol). Upon cooling to 0° C., TFA (584 μL, 7.58 mmol) was added in a dropwise fashion. After 1.5 h, the reaction mixture was poured into 50 mL of saturated aqueous NaHCO$_3$ solution. The aqueous phase was extracted with EtOAc (2×50 mL). The combined organic layers were dried over Na$_2$SO$_4$, filtered and concentrated in vacuo. Purification by radial chromatography (SiO$_2$; gradient of 90:8:2 to 85:10:5 hexanes-THF-TEA) afforded 175 mg (0.35 mmol; 42%) of a yellow oil. The free base was converted to the title dioxalate salt according to the conditions described in Example 1, Part C.

FDMS 501 (M+1); Anal. calcd for C$_{31}$H$_{36}$N$_2$O$_2$S·2C$_2$H$_2$O$_4$: C, 61.75; H, 5.92; N, 4.12. Found: C, 61.49; H, 5.83; N, 3.98.

EXAMPLE 133

Preparation of 1-[2-[4-[3-[4-[2-(Dimethylamino)-ethoxy]benzyl]benzo[b]thiophen-2-yl]phenoxy]ethyl]-pyrrolidine Dioxalate.

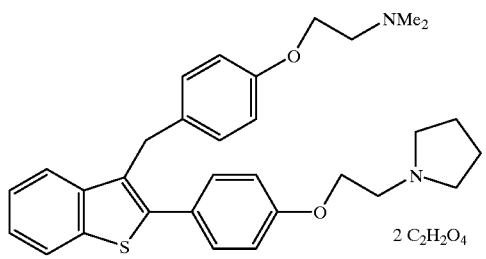

Part A. 4-[2-(Dimethylamino)ethoxy]phenyl 2-[4-2-(1-Pyrrolidinyl)ethoxy]phenyl]benzo[b]thiophen-3-yl Ketone Dioxalate.

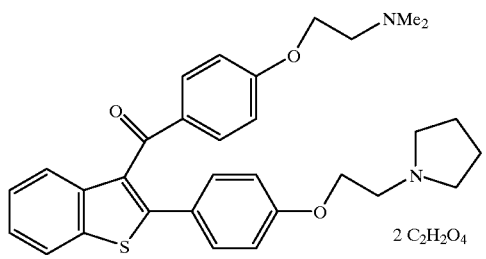

The title compound was prepared from 4-fluorophenyl 2-[4-[2-(1-pyrrolidinyl)ethoxy]phenyl]benzo[b]thiophen-3-yl ketone (Example 132, Part A) and 2-(dimethylamino) ethanol in 55% yield after radial chromatography (SiO$_2$; gradient of 98:1.5:0.5 to 95:4:1 CHCl$_3$-MeOH-NH$_4$OH) by essentially following the procedure described in Example 132, Part B.

FDMS 515 (M+1); Anal. calcd for C$_{31}$H$_{34}$N$_2$O$_3$S·2C$_2$H$_2$O$_4$: C, 60.51; H, 5.51; N, 4.03. Found: C, 60.32; H, 5.48; N, 4.01.

Part B. 1-[2-[4-[3-[4-[2-(Dimethylamino)ethoxy]-benzyl]benzo[b]thiophen-2-yl]phenoxy]ethyl]pyrrolidine Dioxalate.

The title compound was prepared from 4-[2-(dimethylamino)ethoxy]phenyl 2-[4-[2-(1-pyrrolidinyl) ethoxy]phenyl]-benzo[b]thiophen-3-yl ketone (Part A) in 67% yield after radial chromatography (SiO$_2$; 98:1.5:0.5 CHCl$_3$—MeOH—NH$_4$OH) by essentially following the procedure described in Example 132, Part C.

FDMS 501 (M+1); Anal. calcd for C$_{31}$H$_{36}$N$_2$O$_2$S·2C$_2$H$_2$O$_4$: C, 61.75; H, 5.92; N, 4.12. Found: C, 61.88; H, 5.93; N, 4.11.

EXAMPLE 134

Preparation of 1-[2-[4-[3-[4-[2-(Diisopropylamino)-ethoxy]-benzyl]benzo[b]thiophen-2-yl]phenoxy]ethyl]-pyrrolidine Dioxalate.

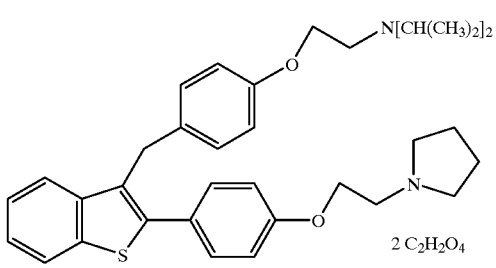

Part A. 4-[2-(Diisopropylamino)ethoxylphenyl 2-[4-[2-(1-Pyrrolidinyl)ethoxy]phenyl]benzo[b]thiophen-3-yl Ketone Dioxalate.

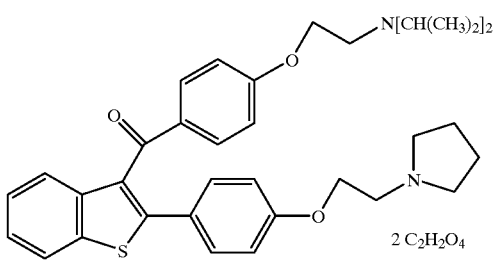

The title compound was prepared in 62% yield from 4-fluorophenyl 2-[4-[2-(1-pyrrolidinyl)ethoxy]phenyl]-benzo[b]thiophen-3-yl ketone (Example 132, Part A) and 2-(diisopropylamino)ethanol by essentially following the procedure detailed in Example 132, Part B.

FDMS 571 (M+1); Anal. calcd for C$_{35}$H$_{42}$N$_2$O$_3$S·2C$_2$H$_2$O$_4$: C, 62.39; H, 6.18; N, 3.73. Found: C, 62.10; H, 5.99; N, 3.82.

Part B. 1-[2-[4-[3-[4-[2-(Diisopropylamino)ethoxy]-benzyl] benzo[b]thiophen-2-yl]phenoxy]ethyl]pyrrolidine Dioxalate.

The title compound was prepared from 4-[2-(diisopropylamino)ethoxy]phenyl 2-[4-[2-(1-pyrrolidinyl) ethoxy]phenyl]-benzo[b]thiophen-3-yl ketone (Part A) in 74% by essentially following the procedure described in Example 132, Part C.

FDMS 557 (M+1); Anal. calcd for C$_{35}$H$_{44}$N$_2$O$_2$S·2C$_2$H$_2$O$_4$: C, 63.57; H, 6.57; N, 3.80. Found: C, 63.30; H, 6.40; N, 3.81.

EXAMPLE 135

Preparation of 1-[2-[4-[3-[4-[2-(Dibutylamino) ethoxy]-benzyl]benzo[b]thiophen-2-yl]phenoxy] ethyl]pyrrolidine Dioxalate.

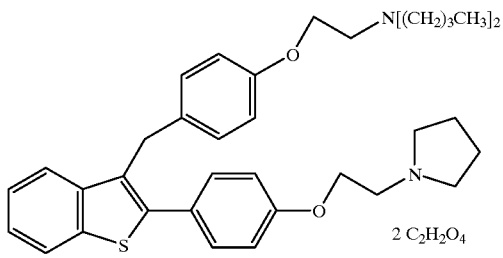

Part A. 4-[2-(Dibutylamino)ethoxy3phenyl 2-14-[2-(1-Pyrrolidinyl)ethoxy]phenyl]benzo[b]thiophen-3-yl Ketone Dioxalate.

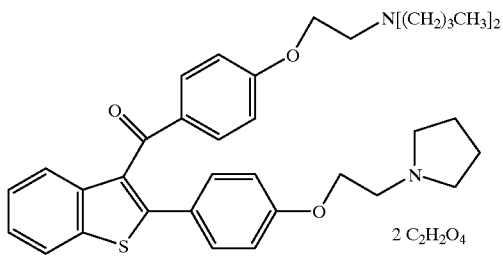

The title compound was prepared in 52% yield from 4-fluorophenyl 2-[4-[2-(1-pyrrolidinyl)ethoxy]phenyl]-benzo[b]thiophen-3-yl ketone (Example 132, Part A) and 2-(dibutylamino)ethanol by essentially following the procedure detailed in Example 132, Part B.

FDMS 599 (M+1); Anal. calcd for $C_{37}H_{46}N_2O_3S \cdot 2C_2H_2O_4$: C, 63.22; H, 6.47; N, 3.60. Found: C, 63.19; H, 6.26; N, 3.52.

Part B. 1-[2-14-[3-[4-[2-(Dibutylamino)ethoxy]-benzyl]benzo[b]thiophen-2-yl]phenoxy]ethyl]pyrrolidine Dioxalate.

The title compound was prepared from 4-[2-(dibutylamino)ethoxylphenyl 2-[4-[2-(1-pyrrolidinyl) ethoxy]phenyl]-benzo[b]thiophen-3-yl ketone (Part A) in 71% by essentially following the procedure described in Example 132, Part C.

FDMS 585 (M+1); Anal. calcd for $C_{37}H_{48}N_2O2S \cdot 2C_2H_2O_4$: C, 64.38; H, 6.85; N, 3.66. Found: C, 64.09; H, 7.01; N, 3.83.

EXAMPLE 136

Preparation of 1-[2-[4-[7-Fluoro-6-hydroxy-3-[4-[2-(1-pyrrolidinyl)ethoxy]benzyl]benzo[b]thiophen-2-yl]-phenoxy]ethyl]pyrrolidine Dioxalate.

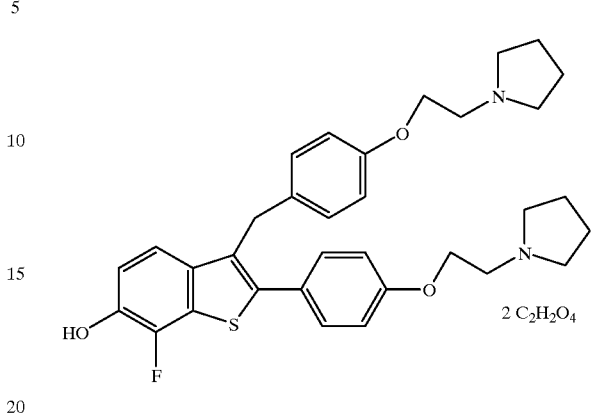

Part A. 2-(4-tert-Butoxyphenyl)-6-methoxybenzo[b]thiophene.

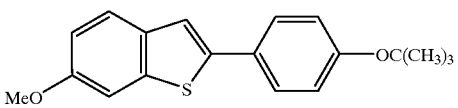

A solution of 6-methoxybenzo[b]thiophene-2-boronic acid (8.87 g, 42.6 mmol) and 4-tert-butoxybromobenzene (US 540851; 10.25 g, 44.7 mmol) in 400 mL of THF was treated with Pd(PPh$_3$)$_4$ (1.9 g, 1.64 mmol) and 45 mL of 2N aqueous Na$_2$CO$_3$. The reaction vessel was covered with aluminum foil to keep out light, and the mixture was heated at reflux overnight. After cooling to ambient temperature, the layers were separated, and the aqueous layer was extracted with EtOAc (3×50 mL). The combined organic layers were dried over MgSO$_4$, filtered, and concentrated under reduced pressure. The crude residue was purified by PrepLC (SiO$_2$, 5% THF in hexanes) to give 8.8 g (28.2 mmol; 66%) of the title product as a white powder.

FAB HRMS: m/e, calcd for $C_{19}H_{20}O_2S$: 312.1184; Found: 312.1188 (M$^+$).

Part B. 2-(4-tert-Butoxyphenyl)-7-fluoro-6-methoxybenzo[b]thiophene.

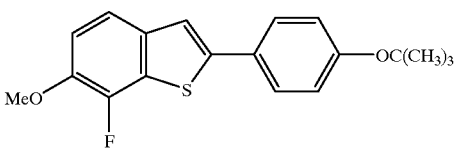

n-BuLi (18 mL, 1.6M in hexanes) was added dropwise to a solution of 2-(4-tert-butoxyphenyl)-6-methoxybenzo[b]-thiophene (Part A; 4.5 g, 14.4 mmol) in 60 mL of anhydrous THF at −78° C. After 30 min, the reaction mixture was warmed to 0° C. and stirred for an additional 1 h. The lithiated benzothiophene was then recooled to −78° C., and a solution of N-fluorodibenzenesulfonamide (9.1 g, 28.8 mmol) in 10 mL of anhydrous THF was quickly added. After 20 min, the reaction mixture was allowed to gradually warm over 1 h. Excess MeOH was added, and the reaction mixture was partitioned between 1N NaOH and EtOAc (50 mL each). The layers were separated, and the aqueous layer was extracted with EtOAc (3×50 mL). The combined organic layers were washed with brine, dried over MgSO$_4$, filtered, and concentrated under reduced pressure. The crude residue was purified by PrepLC (SiO$_2$; hexanes) to give 3.12 g of a mixture of the fluorinated product and the starting benzothiophene (approximately 2.5:1 by $^1$H NMR) as a white powder. A small sample of the title product was purified so the site of fluorination could be verified.

$^1$H NMR (CDCl$_3$) δ 7.58 (2H at 2,6-H), 7.36 (C-3-H), 7.44 (C-4-H), 7.08 (C-5-H), 7.04 (2H at 3,5-Ph), 3.97 (C-6-OCH$_3$), 1.40 (-OC(CH$_3$)3 at 4-Ph); FAB HRMS: m/e, calcd for C$_{19}$H$_{19}$FO$_2$S: 330.1090; Found: 330.1097 (M$^+$).

Part C. 7-Fluoro-2-(4-hydroxyphenyl)-6-methoxybenzo[b]thiophene.

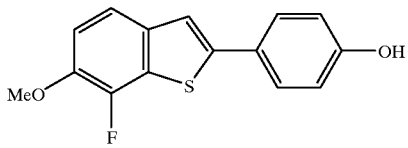

The mixture of 2-(4-tert-butoxyphenyl)-7-fluoro-6-methoxybenzo[b]thiophene and 2-(4-tert-butoxyphenyl)-6-methoxybenzo[b]thiophene (Part B; 3.12 g) in 45 mL of 2,2,2-trifluorethanol at −5° C. was treated with triflic acid (45 μL, 0.51 mmol). After 1 h, the reaction mixture was partitioned between 1N NaOH and CH$_2$Cl$_2$ (50 mL each). The layers were separated, and the aqueous layer was extracted with CH$_2$Cl$_2$ (3×50 mL). The combined organic layers were washed with brine, dried over MgSO$_4$, filtered and concentrated in vacuo. The crude residue was purified by flash chromatography (SiO$_2$; gradient of 5% to 20% THF in hexanes) to give 859 mg of the title compound as a white powder.

FAB HRMS: m/e, calcd for C$_{15}$H$_{11}$FO$_2$S: 274.0464; Found: 274.0468 (M$^+$).

Part D. 7-Fluoro-6-methoxy-2-[4-[2-(1-pyrrolidinyl)-ethoxy]phenyl]benzo[b]thiophene.

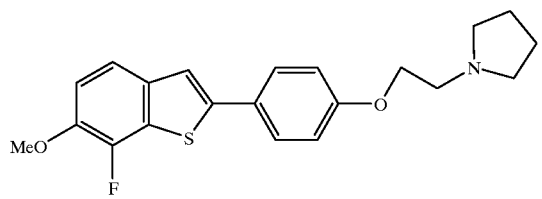

A solution of 7-fluoro-2-[4-hydroxyphenyl]-6-methoxybenzo[b]thiophene (Part C; 550 mg, 2.0 mmol), 1-(2-chloroethyl)pyrrolidine hydrochloride (375 mg, 2.2 mmol) and Cs$_2$CO$_3$ (1.65 g, 5.0 mmol) in 20 mL of DMF was heated at 80° C. for 5 h. The reaction mixture was cooled to ambient temperature and poured into saturated aqueous NaHCO$_3$ solution (20 mL). The aqueous layer was extracted with EtOAc (2×20 mL). The combined organics were washed with H$_2$O (2×50 mL) and brine (50 mL), dried over Na$_2$SO$_4$, filtered, and concentrated. Purification by radial chromatography (SiO$_2$; 2% MeOH in CHCl$_3$, saturated with NH$_4$OH) afforded 598 mg (1.61 mmol; 80%) of the title compound as a yellow oil.

FDMS 371 (M$^+$). Anal. calcd for C$_{21}$H$_{22}$FNO$_2$S: C, 67.90; H, 5.97; N, 3.77. Found: C, 68.07; H, 5.78; N, 3.73.

Part E. 7-Fluoro-6-methoxy-2-14-[2-(1-pyrrolidinyl)-ethoxy]phenyl]benzo[1]thiophen-3-yl 4-Fluorophenyl Ketone.

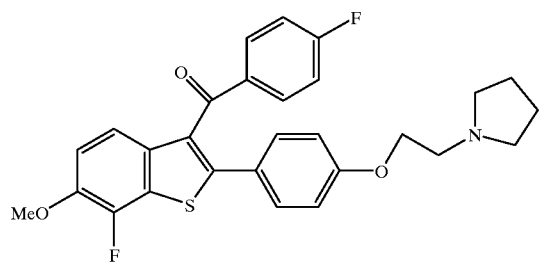

The title compound was prepared in 41% yield from 7-fluoro-6-methoxy-2-[4-[2-(1-pyrrolidinyl)ethoxy]phenyl]-benzo[b]thiophene (Part D) and 4-fluorobenzoyl chloride by essentially following the procedure outlined in Example 129, Part A.

FAB HRMS: m/e, calcd for C$_{28}$H$_{26}$F$_2$NO$_3$S: 494.1601; Found: 494.1604 (M+1).

Part F. 7-Fluoro-6-methoxy-2-[4-[2-(1-pyrrolidinyl)-ethoxy]phenyl]benzo[b]thiophen-3-yl 4-[2-(1-Pyrrolidinyl)ethoxy]phenyl Ketone.

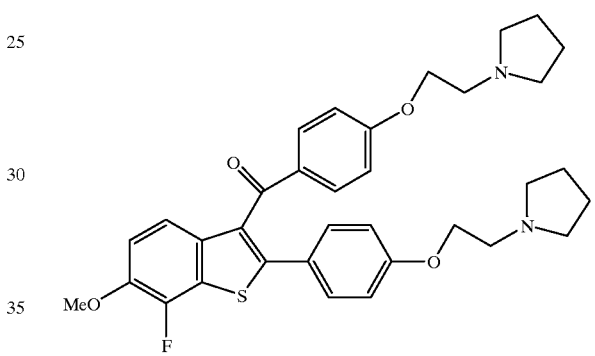

The title compound was prepared in 28% yield from 7-fluoro-6-methoxy-2-[4-[2-(1-pyrrolidinyl)ethoxy]phenyl]-benzo[b]thiophen-3-yl 4-fluorophenyl ketone (Part E) by essentially following the procedure detailed in Example 132, Part B.

FDMS 589 (M+1).

Part G. 7-Fluoro-6-hydroxy-2-[4-[2-(1-pyrrolidinyl)-ethoxy]phenyl]benzo[b]thiophen-3-yl 4-[2-(1-Pyrrolidinyl)ethoxy]phenyl Ketone Dioxalate.

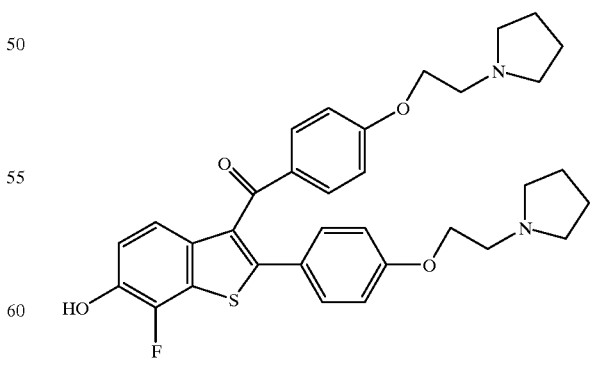

A solution of 7-fluoro-6-methoxy-2-[4-[2-(1-pyrrolidinyl)ethoxy]phenyl]benzo[b]thiophen-3-yl 4-[2-(1-pyrrolidinyl)ethoxy]phenyl ketone (Part F; 130 mg, 0.221 mmol) in 5 mL of 1,2-dichloroethane at 0° C. was treated with boron tribromide (884 μL, 0.884 mmol). After 6 h, the black reaction mixture was poured into saturated aqueous NaHCO₃ (20 mL). The aqueous phase was extracted with CHCl₃ (3×20 mL). The combined organics were dried over Na₂SO₄, filtered and concentrated. Radial chromatography (SiO₂, 5% MeOH in CHCl₃, saturated with NH₄OH) afforded 95.3 mg (0.166 mmol; 75%) of a bright yellow foam. The title dioxalate salt was prepared by essentially following the procedure outlined in Example 1, Part C. FDMS 575 (M+1); Anal. calcd for C₃₃H₃₅FN₂O₄S·2C₂H₂O₄: C, 58.87; H, 5.21; N, 3.71. Found: C, 59.11; H, 5.23; N, 3.73.

Part H. 1-[2-[4-[7-Fluoro-6-hydroxy-3-[4-[2-(1-pyrrolidinyl)ethoxy]benzyl]benzo[b]thiophen-2-yl]phenoxy]-ethyl]pyrrolidine Dioxalate.

The title compound was prepared from 7-fluoro-6-hydroxy-2-[4-[2-(1-pyrrolidinyl)ethoxy]phenyl]benzo[b]thiophen-3-yl 4-[2-(1-pyrrolidinyl)ethoxy]phenyl ketone (Part G) in 49% yield by essentially following the procedure described in Example 132, Part C.
Anal. calcd for C₃₃H₃₇FN₂O₃S·1.75C₂H₂O₄: C, 61.03; H, 5.68; N, 3.90. Found: C, 60.89; H, 5.76; N, 3.75; FAB HRMS: m/e, calcd for C₃₃H₃₈FN₂O₃S: 561.2587; Found: 561.2581 (M+1).

EXAMPLE 137

Preparation of 3-Bromo-4-[(1-pyrrolidinyl)methyl]-phenyl 6-Hydroxy-2-[4-[2-(1-pyrrolidinyl)ethoxy]-phenyl]benzo[b]thiophen-3-yl Ketone Dioxalate.

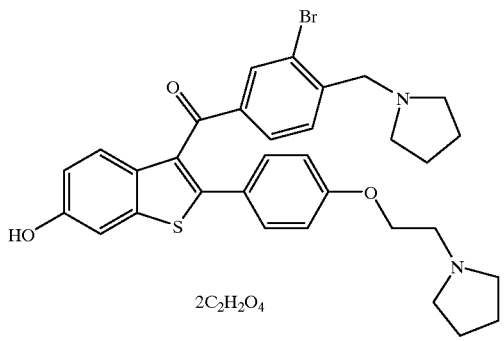

Part A. Methyl 3-Bromo-4-(bromomethyl)benzoate.

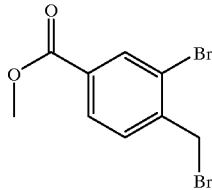

Methyl 3-bromo-4-methylbenzoate (23.3 g; 97 mmol) and 20.8 g (117 mmol) of NBS were combined in 210 mL of CCl₄ and heated to reflux. AIBN (0.8 g; 5.9 mmol) was added and the resultant mixture was heated at reflux for 4 h. After cooling to room temperature, the mixture was filtered and concentrated. The product (13.4 g; 43% yield) was isolated by flash chromatography on silica gel eluting with a gradient of 0–5% EtOAc/hexanes as a white crystalline solid.
¹H NMR (CDCl₃) δ 8.24 (s, 1H), 7.96 (d, J=8.0 Hz, 1H), 7.54 (d, J=8.0 Hz, 1H), 4.62 (s, 2H), 3.94 (s, 3H); FDMS 307

M+); Anal. Calcd for C₉H₈Br2O₂: C, 35.10; H, 2.62. Found: C, 34,99; H, 2.64.

Part B. Methyl 3-Bromo-4-[(1-pyrrolidinyl)methyl]-benzoate.

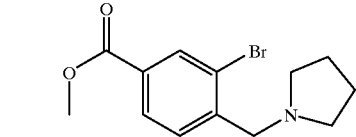

Methyl 3-bromo-4-bromomethylbenzoate (0.61 g; 2.0 mmol) (Part A) was dissolved in THF (10 mL) and pyrrolidine (0.66 mL; 7.9 mmol) was added at room temperature. The mixture was stirred overnight at room temperature, then poured into 80 mL of saturated aqueous aqueous sodium bicarbonate. Extraction as carried out with EtOAc (3×35 mL). The combined organics were washed with brine and dried by passage through sodium sulfate. The product was isolated as a colorless oil (0.46g; 80% yield) by flash chromatography on silica gel eluting with EtOAc.
¹H NMR (CDCl₃) δ 8.19 (s, 1H), 7.94 (d, J=8.0 Hz, 1H), 7.57 (d, J=8.0 Hz, 1H), 3.91 (s, 3H), 3.76 (s, 2H), 2.59 (m, 4H), 1.81 (m, 4H)

Part C. 3-Bromo-4-[(1-pyrrolidinyl)methyl]phenyl 6-Methoxy-2-[4-[2-(1-pyrrolidinyl)ethoxy]phenyl]-benzo[b]thiophen-3-yl Ketone.

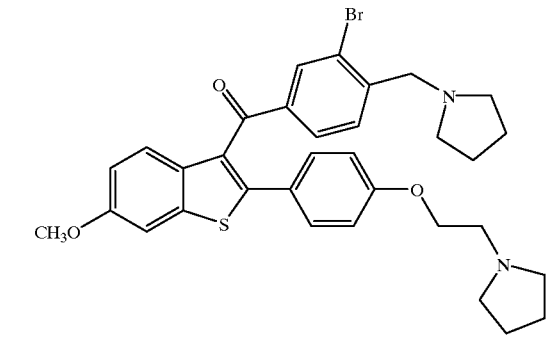

A mixture of methyl 3-bromo-4-(1-pyrrolidinylmethyl)-benzoate (0.59 g; 1.99 mmol) (Part B) in 5 mL of a solution of THF/methanol/H₂O (3:1:1 by volume) and LiOH (0.10 g; 2.38 mmol) was stirred at room temperature overnight. The mixture was concentrated under reduced pressure, dissolved in 5 mL of THF, and acidified with conc HCl. The carboxylic acid was obtained by concentration under reduced pressure, dried in vacuo and converted to the acid chloride without purification. The acid chloride was formed by stirring together the carboxylic acid and 15 mL of SOCl₂ with 6 drops of DMF at room temperature overnight. Excess SOCl₂ was stripped off and its trace was azeotopically removed with 10 mL of benzene under reduced pressure. The acid chloride was placed under high vacuum for 0.5 h, dissolved in dichloroethane (20 mL), treated with 6-methoxy-2-[4-[2-(1-pyrrolidinyl)ethoxy]phenyl]benzo[b]thiophene (Example 1, Part B) (0.47g; 1.33 mmol) and AlCl₃ (1.1 g; 8.0 mmol) at 0° C. for 2 h, and then poured into 80 mL of saturated aqueous aqueous NaHCO₃. After stirring for 1 h, extraction was carried out with EtOAc. The combined organics were washed with brine and dried by passage through NaSO4. The product was isolated as a yellow oil (0.45g; 55% yield) by flash chromatography on silica gel, eluting with EtOAc (95)/Et₃N(5).

¹H NMR (CDCl₃) δ 7.90 (s, 1H), 7.70 (d, J=9.0 Hz, 1H), 7.61 (d, J=8.0 Hz, 1H), 7.35 (d, J=8.0 Hz, 1H), 7.33 (s, 1H), 7.26 (d, J=8.3, 2H), 7.02 (d, J=9.0 Hz, 1H), 6.75 (d, J=8.7 Hz, 2H), 4.03 (t, J=6.0 Hz, 2H), 3.90 (s, 3H), 3.70 (s, 2H), 2.85 (t, J=6.0 Hz, 2H), 2.60 (t, J=6.2 Hz, 4H), 2.51 (t, J=6.2 Hz, 4H), 1.80 (m, 8H); FDMS 620 (M+1); Anal. Calcd for C₃₃H₃₅BrN2O3S: C, 63.97; H, 5.69; N, 4.52. Found: C, 63.89; H, 5.69, N, 4.38.

Part D. 3-Bromo-4-[(1-pyrrolidinyl)methyl]phenyl 6-Hydroxy-2-[4-[2-(1-pyrrolidinyl)ethoxy]phenyl]-benzo[b]thiophen-3-yl Ketone.

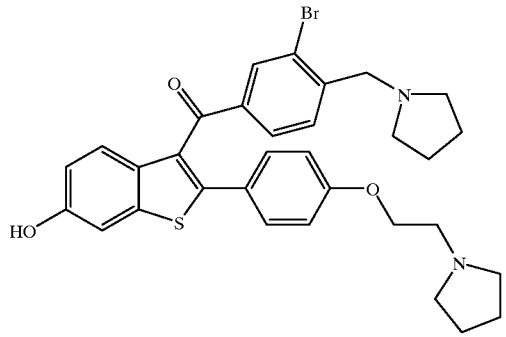

4-[3-Bromo-4-[(1-pyrrolidinyl)methyl]phenyl 6-methoxy-2-[4-[2-(1-pyrrolidinyl)ethoxy]phenyl]benzo[b]thiophen-3-yl ketone (34 mg; 0.055 mmol) (Part D) was dissolved in dichloroethane (5 mL) in a flame-dried, argon-filled flask, and cooled in an ice-water bath. Ethanethiol (0.16 mL; 2.2 mmol) was added, followed by 0.15 g (1.1 mmol) of aluminum chloride. The resultant slurry was stirred in the cold for 2 h. Saturated aqueous sodium bicarbonate (20 mL) was added, and stirring was continued for 2 h. Extraction was carried out with EtOAc (4×25 mL) and the combined organics were washed with brine and dried by passage through sodium sulfate. The product was isolated as a yellow oil (19 mg; 57% yield) by flash chromatography on silica gel, eluting with a gradient of EtOAc(100–90%)/Et₃N(0–5%)/MeOH(0–5%).

¹H NMR (CDCl₃) δ 7.85 (s, 1H), 7.58 (d, J=9.0 Hz, 1H), 7.55 (d, J=8.0 Hz, 1H), 7.32 (d, J=8.0 Hz, 1H), 7.11 (s, 1H), 6.95 (d, J=8.4, 2H), 6.87 (d, J=9.0 Hz, 1H), 6.48 (d, J=8.6 Hz, 2H), 4.06 (t, J=6.0 Hz, 2H), 3.69 (s, 2H), 3.06 (t, J=6.0 Hz, 2H), 2.90 (br s, 4H), 2.58 (br s, 4H), 1.94 (br s, 4H), 1.81 (br s, 4H); FDMS 605 (M+).

Part E. 3-Bromo-4-[(1-pyrrolidinyl)methyl]phenyl 6-Hydroxy-2-[4-[2-(1-pyrrolidinyl)ethoxy]phenyl]-benzo[b]thiophen-3-yl Ketone Dioxalate.

4-[3-Bromo-4-[(1-pyrrolidinyl)methyl]phenyl 6-hydroxy-2-[4-[2-(1-pyrrolidinyl)ethoxy]phenyl]benzo[b]thiophen-3-yl ketone (Part E) (19 mg; 31 μmol), was dissolved in 3 mL of ethyl acetate. Oxalic acid (7 mg; 79 μmol) in 1 mL of EtOAc was added. The resultant slurry was subjected to centrifugation and the supernatant was decanted. Fresh EtOAc (4 mL) was added and the process was repeated two more times. The solid product was dried in vacuo overnight.

EXAMPLE 138

Preparation of 3-[3-Bromo-4-[(1-pyrrolidinyl)methyl]-benzyl]-6-hydroxy-2-[4-[2-(1-pyrrolidinyl)ethoxy]-phenyl]benzo[b]thiophene Dioxalate Hydrate.

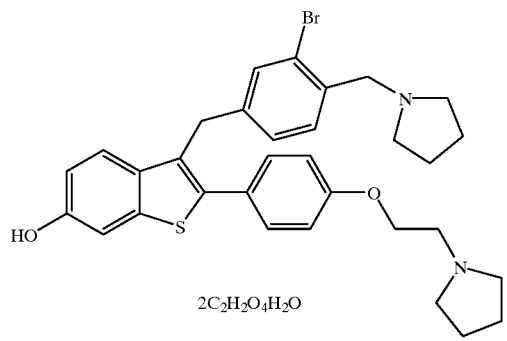

2C₂H₂O₄H₂O

Part A. 3-[3-Bromo-4-[(1-pyrrolidinyl)methyl]benzyl]-6-methoxy-2-[4-[2-(1-pyrrolidinyl)ethoxy]phenyl]-benzo[b]thiophene.

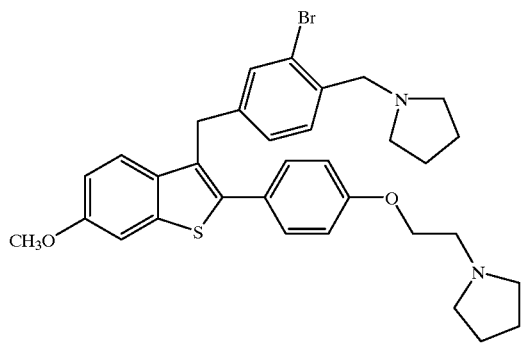

To 4-[3-bromo-4-[(1-pyrrolidinyl)methyl]phenyl 6-methoxy-2-[4-[2-(1-pyrrolidinyl)ethoxy]phenyl]benzo-[b]thiophen-3-yl ketone (Example 137; part C) (0.2 g; 0.32 mmol) in 3.0 mL of THF was added 18.4 mg (0.48 mmol) of LAH at 0° C. The bath was removed and the mixture was stirred for 1 h. Hydrolysis was effected by addition of 1 drop of water, 1 drop of 5N NaOH, and 3 drops of water, followed by stirring for 1 h. The mixture was filtered, the filtrate was concentrated and, the intermediate carbinol was dried in vacuo for 25 min. The carbinol was dissolved in methylene chloride (3.0 mL) under argon atmosphere and cooled in an ice-water bath. Triethylsilane (0.36 mL; 2.26 mmol) was added, followed by dropwise addition of 0.25 mL (3.23 mmol) of TFA. Upon completion of addition of TFA, the bath was removed and stirring was continued for 2 h. Saturated aqueous sodium bicarbonate (25 mL) was added, and extraction was carried out with EtOAc. The combined organics were washed with brine and dried by passage through sodium sulfate. The title compound (0.14 g; 72% yield) was isolated as a colorless oil by flash chromatography on silica gel eluting with a gradient of EtOAc (100–95%)/Et₃N(0–5%).

¹H NMR (CDCl₃) δ 7.34 (m, 6H), 7.03 (d, J=9.0 Hz, 1H), 6.95 (m, 3H), 4.16 (t, J=6.0 Hz, 2H), 3.90 (s, 3H), 3.70 (s, 2H), 2.95 (t, J=6.0 Hz, 2H), 2.65 (br s, 4H), 2.60 (br s, 4H), 1.82 (m, 8H); FDMS 605 (M⁺).

Part B. 3-[3-Bromo-4-[(1-pyrrolidinyl)methyl]benzyl]-6-hydroxy-2-[4-[2-(1-pyrrolidinyl)ethoxy]phenyl]-benzo[b]thiophene.

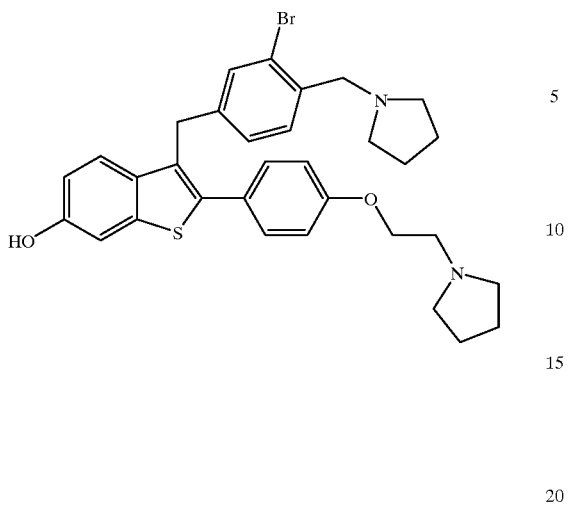

3-[3-Bromo-4-[(1-pyrrolidinyl)methyl]benzyl]-6-methoxy-2-[4-[2-(1-pyrrolidinyl)ethoxy]phenyl]benzo[b]thiophene (0.32 g; 0.53 mmol)(Part A) was dissolved in 9.0 mL of dichloroethane under an argon atmosphere and cooled in an ice-water bath. To this was added ethanethiol (0.78 mL; 10.56 mmol) and 0.70 g (5.28 mmol) of aluminum chloride, and the mixture was stirred in the cold bath for 1 h. Brine (80 mL) was added to the mixture, and stirring was continued while warming to room temperature for 1 h. Extraction was carried out with dichloromethane (4×75 mL). The combined organics were dried by passage through sodium sulfate. The title compound (0.23 g; 74% yield) was isolated as a white crystalline solid by flash chromatography on silica gel eluting with a gradient of EtOAc(100–85%)/Et$_3$N(0–5%)/MeOH(0–10%).

$^1$H NMR (CDCl$_3$) δ 7.34 (m, 5H), 7.14 (s, 1H), 7.06 (d, J=8.0 Hz, 1H), 7.00 (d, J=9.0 Hz, 2H), 6.80 (d, J=9.0 Hz, 1H), 4.12 (br t, J=6.0 Hz, 2H), 3.78 (s, 2H), 3.02 (s, 2H), 2.95 (t, J=6.0 Hz, 2H), 2.79 (br s, 4H), 2.63 (br s, 4H), 1.82 (m, 4H), 1.79 (m, 4H); FDMS 591 (M$^+$); Anal. Calcd for C$_{32}$H$_{35}$BrN$_2$O$_2$S: C, 64.97; H, 5.96; N, 4.74. Found: C, 64.69; H, 5.96; N, 4.64.

Part C. 3- [3-Bromo-4-[ (-pyrrolidinyl)methyl]benzyl]-6-hydroxy-2- [4- [2-(1-pyrrolidinyl)ethoxy]phenyl]-benzo[b]thiophene Dioxalate Hydrate.

The title compound was prepared from 3-[3-bromo-4-{(1-pyrrolidinyl)methyl]benzyl]-6-hydroxy-2-[4-[2-(1-pyrrolidinyl)ethoxy]phenyl]benzo[b]thiophene (Part B) using essentially the procedure of Example 137, Part E.

mp 190–192° C.; Anal. Calcd for C$_{32}$H$_{35}$BrN$_2$O$_2$S·C$_2$H$_2$O$_4$·H$_2$O: C, 54.75; H, 5.23; N, 3.55. Found: C, 54.89; H, 5.02; N, 3.66.

EXAMPLE 139

Preparation of 3-[3-Methoxy-4-[(1-pyrrolidinyl)-methyl]benzyl]-2-[4-[2-(1-pyrrolidinyl)ethoxy]phenyl]-benzo[b]thiophene Dioxalate Hydrate.

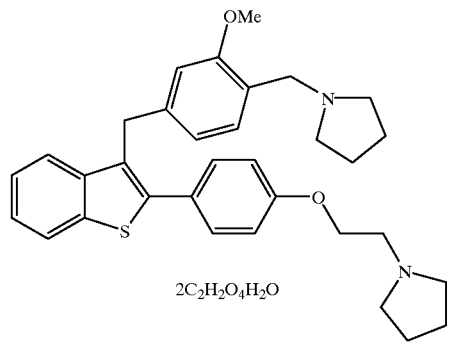

Part A. Methyl 4-Bromomethyl-3-methoxybenzoate.

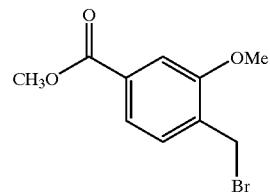

By essentially following the procedure used to prepare Example 137, Part A, the title compound was prepared from methyl 3-methoxy-4-methylbenzoate in 82% yield as a white crystalline solid. The product was purified by crystallization from EtOAc/hexanes rather than chromatography.

$^1$H NMR (CDCl$_3$) δ 7.63 (d, J=7.6 Hz, 1H), 7.58 (S, 1H), 7.41 (d, J=7.9 Hz, 1H), 4.56 (S, 2H), 3.98 (S, 3H), 3.94 (S, 3H); FDMS 528 (M+).

Part B. Methyl 3-Methoxy-4-[(1-pyrrolidinyl)methyl]-benzoate.

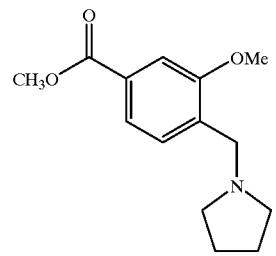

By essentially following the procedure used to prepare Example 137, Part B, the title compound was prepared from methyl 4-bromomethyl-3-methoxybenzoate (Part A) in 85% yield as a pale yellow oil.

$^1$H NMR (CDCl$_3$) δ 7.62 (d, J=7.8 Hz, 1H), 7.51 (s, 1H), 7.43 (d, J=7.7 Hz, 1H), 3.90 (s, 3H), 3.87 (s, 3H), 3.69 (s, 2H), 2.57 (m, 4H), 1.79 (m, 4H).

Part C. 4-[3-Methoxy-4-[(1-pyrrolidinyl)methyl]phenyl 2-[4-[2-(1-pyrrolidinyl)ethoxy]phenyl]benzo[b]thiophen-3-yl Ketone.

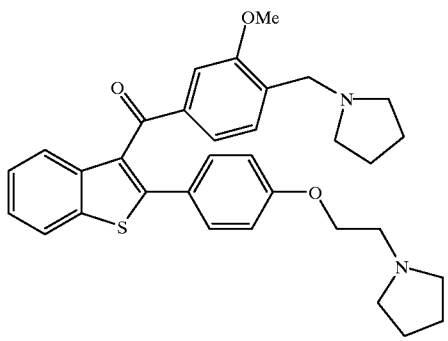

By essentially following the procedure used to prepare Example 137, Part C, the title compound was prepared from methyl 3-methoxy-4-[(1-pyrrolidinyl)methyl]benzoate (Part B) and 1-[2-[4-(benzo[b]thiophen-2-yl)phenoxy]ethyl] pyrrolidine (Example 4, Part A) in 51% yield as a yellow foam. The flash chromatography was carried out by eluting with a gradient of EtOAc(100–90%)/Et$_3$N(0–5%)/MeOH (0–5%).
$^1$H NMR (CDCl$_3$) δ 7.86 (m, 1H), 7.71 (m, 1H), 7.41 (s, 1H), 7.35 (m, 6H) 6.76 (d, J=5.0 Hz, 2H), 4.03 (t, J=5.9 Hz, 2H), 3.79 (s, 3H), 3.61 (s, 2H), 2.85 (t, J=6.0 Hz, 2H), 2.61 (br s, 4H), 2.57 (br s, 4H), 1.78 (m, 8H); FDMS 541 (M+1).
Part D. 3-[3-Methoxy-4-1(1-pyrrolidinyl)methyl]-benzyl]-2-[4-[2-(1-pyrrolidinyl)ethoxy]phenyl]-benzo[b]thiophene.

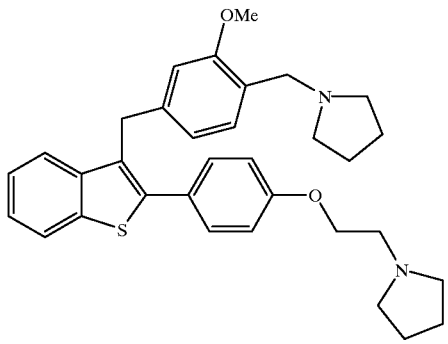

By essentially following the procedure used to prepare Example 138, Part A, the title compound was prepared from 4-[3-methoxy-4-[(1-pyrrolidinyl)methyl]phenyl 2-[4-[2-(1-pyrrolidinyl)ethoxy]phenyl]benzo[b]thiophen-3-yl ketone (Part C) in 53% yield as a yellow foam. The flash chromatography was carried out by eluting with a gradient of EtOAc(100–90%)/Et$_3$N(0–5%)/MeOH(0–5%).
$^1$H NMR (CDCl$_3$) δ 7.81 (m, 1H), 7.52 (m, 1H), 7.43 (d, J=8.7 Hz, 2H), 7.29 (m, 2H), 7.19 (d, J=7.6 Hz, 1H), 6.95 (d, J=8.7 Hz, 2H), 6.69 (d, J=7.9 Hz, 1H), 6.65 (s, 1H), 4.24 (s, 2H), 4.13 (t, J=6.0 Hz, 2H), 3.68 (s, 3H), 3.61 (s, 2H), 2.91 (t, J=6.0 Hz, 2H), 2.61 (br s, 4H), 2.55 (br s, 4H), 1.79 (m, 8H); FDMS 526 (M+).
Part E. 3-[3-Methoxy-4-[(1-pyrrolidinyl)methyl]-benzyl]-2-[4-[2-(1-pyrrolidinyl)ethoxy3phenyl]-benzo[b]thiophene Dioxalate Hydrate.

The title compound was prepared from 3-[3-methoxy-4-[(1-pyrrolidinyl)methyl]benzyl]-2-[4-[2-(1-pyrrolidinyl) ethoxy]-phenyl]benzo[b]thiophene (Part D) using essentially the procedure of Example 137, Part E.

FDMS 527 (M+1); Anal. Calcd for C$_{33}$H$_{38}$N$_2$O$_2$S·2C$_2$H$_2$O$_4$·H$_2$O: C, 61.31; H, 6.12; N, 3.86. Found: C, 61.01; H, 5.66; N, 3.66.

EXAMPLE 140

Preparation of 2-[4-[2-(1-Pyrrolidinyl)ethoxy] phenyl]-3-[4-[2-(1-pyrrolidinyl)ethyl]benzyl]benzo [b]thiophene Dioxalate.

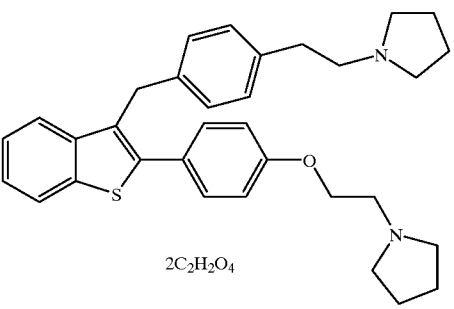

By essentially following the procedure used to prepare Example 138, Part A, the title compound was prepared 2-[4-[2-(1-pyrrolidinyl)ethoxy]phenyl]benzo[b]thiophen-3-yl 4-[2-(1-pyrrolidinyl)ethyl]phenyl ketone (Example 7, Part C) in 56% yield. The flash chromatography was carried out by eluting with a gradient of EtOAc(100–90%)/Et$_3$N (0–5%)/MeOH(0–5%). The dioxalate was formed by treatment of the free base with oxalic acid according to Example 137, Part E.
FDMS 511 (M+1); Anal. Calcd for C$_{33}$H$_{38}$N$_2$OS·2C$_2$H$_2$O$_4$: C, 64–33; H, 6.13; N, 4.06. Found: C, 64.17; H, 6.05; N, 4.14.

EXAMPLE 141

Preparation of 2-[4-12-(1-Pyrrolidinyl)ethoxy] phenyl]-3-14-[(1-pyrrolidinyl)methyl]benzyl]benzo [b]thiophene Dioxalate.

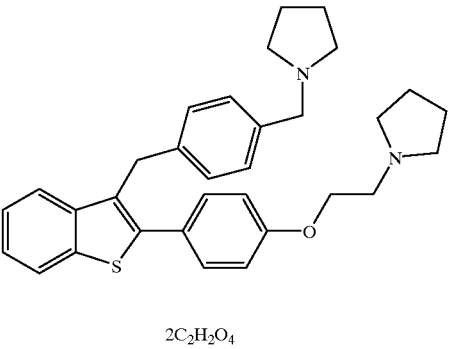

By essentially following the procedure used to prepare Example 138, Part A, the title compound was prepared from 2-[4-[2-(1-pyrrolidinyl)ethoxy]phenyl]benzo[b]thiophen-3-yl 4-[(1-pyrrolidinyl)methyl]phenyl ketone (prepared as in Example 6, Part C) in 60% yield. The flash chromatography was carried out by eluting with a gradient of EtOAc (100–90%)/Et$_3$N(0–5%)/MeOH(0–5%). Conversion to the dioxalate was effected as in Example 137, Part E.
FDMS 497 (M+); Anal. Calcd for C$_{32}$H$_{36}$N$_2$OS·2C$_2$H$_2$O$_4$: C, 63.89; H, 5.96; N, 4.14. Found: C, 63.65; H, 6.09; N, 4.39.

EXAMPLE 142

Preparation of 3-[3-Bromo-4-[(dimethylamino)methyl]-benzyl]-6-hydroxy-2-[4-[2-(1-pyrrolidinyl)ethoxy]-phenyl]benzo[b]thiophene Dioxalate Dihydrate.

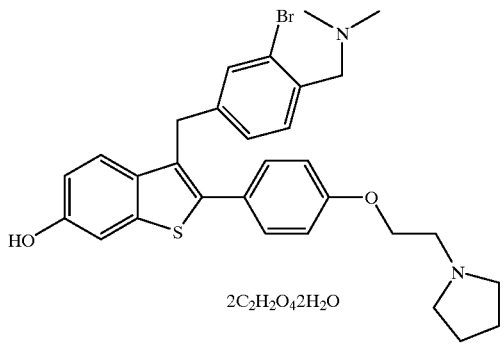

Part A. Methyl 3-Bromo-4-[(dimethylamino)methyl]-benzoate.

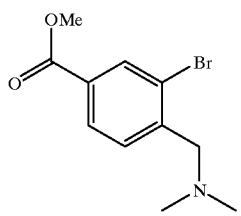

By following essentially the procedure of Example 137, Part B. the title compound was prepared from methyl 3-bromo-4-bromomethylbenzoate (Example 137, Part A) and dimethylamine (40%), in 70% yield. The flash chromatography was carried out by eluting with a gradient of hexanes(100–80%)/EtOAc(0–20%).
$^1$H NMR (CDCl$_3$) δ 8.19 (s, 1H), 7.92 (d, J=8.0 Hz, 1H), 7.51 (d, J=8.0 Hz, 1H), 3.89 (s, 3H), 3.53 (s, 2H), 2.29 (s, 6H); FDMS 271 (M+)

Part B. 3-Bromo-4-[(dimethylamino)methyl3phenyl 6-Methoxy-2-[4-[2-(1-pyrrolidinyl)ethoxy]phenyl]-benzo[b]thiophen-3-yl Ketone.

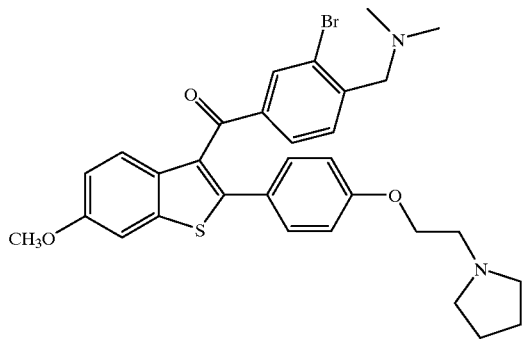

By essentially following the procedure used to prepare Example 137, Part C, the title compound was prepared from methyl 3-bromo-4-[(dimethylamino)methyl]benzoate (Part A) and 6-methoxy-2-[4-[2-(1-pyrrolidinyl)ethoxy]phenyl]benzo[b]-thiophene (Example 1, Part B) in 66% yield.

$^1$H NMR (CDCl$_3$) δ 7.88 (s, 1H), 7.72 (d, J=8.9 Hz,1H), 7.60 (d, J=9.6 Hz, 1H), 7.27 (m, 4H), 7.00 (d, J=9.0 Hz, 1H), 3.99 (t, J=5.9 Hz, 2H), 3.88 (s, 3H), 3.43 (s, 2H), 2.83 (t, J=5.9 Hz, 2H), 2.58 (br s, 4H), 2.20 (s, 6H), 1.79 (m, 4H).

Part C. 3-[3-Bromo-4-[(dimethylamino)methyl]benzyl]-6-methoxy-2-14-[2-(1-pyrrolidinyl)ethoxy]phenyl]-benzo[b]thiophene.

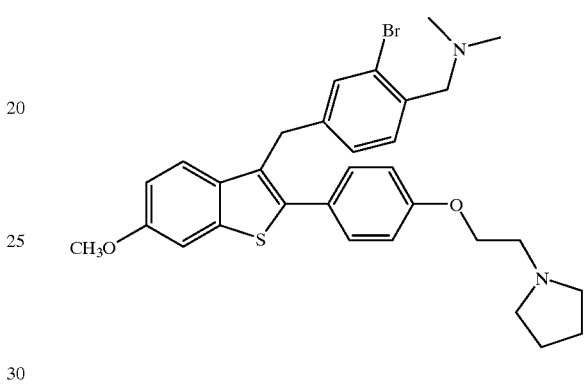

The title compound was prepared from 3-bromo-4-[(dimethylamino)methyl]phenyl 6-methoxy-2-[4-[2-(1-pyrrolidinyl)ethoxy]phenyl]benzo[b]thiophen-3-yl ketone (Part B) essentially by the procedure used for Example 138, Part A in 73% yield. The flash chromatography was carried out by elution with a gradient of EtOAc(100–90%)/Et$_3$N (0–5%)/MeOH(0–5%).

$^1$H NMR (CDCl$_3$) δ 7.35 (m, 4H), 7.27 (m, 2H), 7.04 (d, J=7.9 Hz, 1H), 6.95 (d, J=8.8 Hz, 2H), 6.91 (d, J=8.9 Hz, 1H), 4.16 (s+d, J=6.0, 4H), 3.87 (s, 3H), 3.47 (s, 2H), 2.94 (t, J=6.0 Hz, 2H), 2.66 (br s, 4H), 2.29 (s, 6H), 1.83 (m, 4H).

Part D. 3-[3-Bromo-4-[(dimethylamino)methyl]benzyl]-6-hydroxy-2-[4-[2-(1-pyrrolidinyl)ethoxy]phenyl]-benzo[b]thiophene Dioxalate.

The title compound was prepared from 3-[3-bromo-4-[(dimethylamino)methyl]benzyl]-6-methoxy-2-[4-[2-(1-pyrrolidinyl)ethoxy]phenyl]benzo[b]thiophene (Part C) essentially by the method of Example 138, Part B in 84% yield. Conversion to the dioxalate was effected essentially by the procedure of Example 137, Part E.

FDMS 565 (M+); Anal. Calcd for C$_{30}$H$_{33}$BrN$_2$O$_2$S·2C$_2$H$_2$O$_4$·2H$_2$O: C, 52.24; H, 5.29; N, 3.58. Found: C, 51.85; H, 4.84; N, 3.46.

EXAMPLE 143

Preparation of 3-[3-Bromo-4-[2-(1-pyrrolidinyl)-ethoxy3benzyl]-6-hydroxy-2-[4-[2-(1-pyrrolidinyl)-ethoxy]phenyl]benzo[b]thiophene Dioxalate Hydrate.

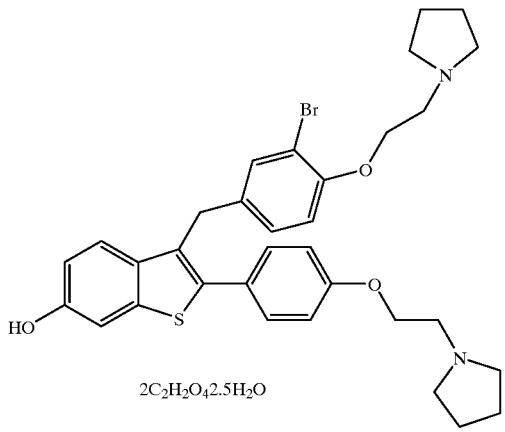

2C₂H₂O₄·2.5H₂O

Part A. 3-Bromo-4-[2-(1-pyrrolidinyl)ethoxy]phenyl 6-Methoxy-2-[4-[2-(1-pyrrolidinyl)ethoxy]phenyl]-benzo[b]thiophen-3-yl Ketone.

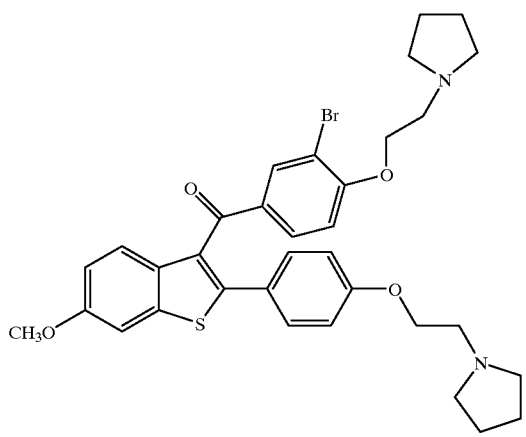

3-Bromo-4-fluorobenzoic acid (0.66 g; 3.0 mmol) and 1.57 mL (18.0 mmol) of oxalyl chloride in 10 mL of dichloromethane in a flask protected from moisture by a calcium chloride filled drying tube was stirred at room temperature for 24 h. The mixture was concentrated under reduced pressure to a white solid acid chloride. The crude acid chloride was dissolved in 50 mL of dichloroethane in an argon atmosphere, To this was added at 0° C. 6-methoxy-2-[4-[2-(1-pyrrolidinyl)ethoxy]phenyl]benzo[b]thiophene (Example 1, Part B)(0.72 g; 2.0 mmol) and 1.6 g (12.0 mmol) of aluminum chloride. The mixture was stirred in the cold for 4 h, then poured into 200 mL of saturated aqueous sodium bicarbonate, and stirred for 1 h. Extraction was carried out with EtOAc (4×50 mL) and the combined organics were washed with brine and dried by passage through sodium sulfate. The mixture was subjected to flash chromatography on silica gel, eluting with a gradient of EtOAc(100–90%)/Et₃N(0–5%)/MeOH(0–5%) to afford 3-bromo-4-fluorophenyl 6-methoxy-2-[4-[2-(1-pyrrolidinyl)-ethoxy]phenyl]benzo[b]thiophen-3-yl ketone contaminated with starting benzothiophene. This mixture was used without further purification.

Sodium hydride (95 mg of a 60% suspension in mineral oil; 2.4 mmol) was suspended in 2 mL of DMF in a flame-dried, argon-filled flask and stirred for about 5 min. 1-(2-Hydroxyethyl)pyrrolidine (0.23 mL; 2.0 mmol) was added and the mixture was stirred for 15 min. 3-Bromo-4-fluorophenyl 6-methoxy-2-[4-[2-(1-pyrrolidinyl)ethoxy]phenyl]benzo[b]-thiophen-3-yl ketone in 3 mL of DMF was then added. The mixture was stirred for 4 h at room temperature, then poured into water (25 mL), and extracted with EtOAc (4×25 mL). The combined organics were washed with brine and dried over magnesium sulfate. The title compound (135 mg; 10% yield) was isolated by flash chromatography on silica gel eluting with a gradient of EtOAc(100–90%)/Et₃N(0–5%)/MeOH(0–5%).

¹H NMR (CDCl₃) δ 7.90 (s, 1H), 7.65 (d, J=9.0 Hz, 1H)), 7.46 (d, J=8.0 Hz, 1H), 7.35 (d, J=8.0 Hz, 1H), 7.33 (d, J=9.0 Hz, 1H), 6.82 (d, 4H), 6.65 (d, J=9.0 Hz, 1H), 4.17 (t, J=5.8 Hz, 2H), 4.06 (t, J - 5.7 Hz, 2H), 3.88 (s, 3H), 3.04 (t, J=5.8 Hz, 2H), 2.97 (t, J=5.9 Hz, 2H), 2.79 (br s, 4H), 2.70 (br s, 4H), 1.84 (m, 8H). FDMS 650 (M+1).

Part B. 3-[3-Bromo-4-[2-(1-pyrrolidinyl)ethoxy]-benzyl]-6-methoxy-2-[4-[2-(1-pyrrolidinyl)ethoxy]-phenyl]benzo[b]thiophene.

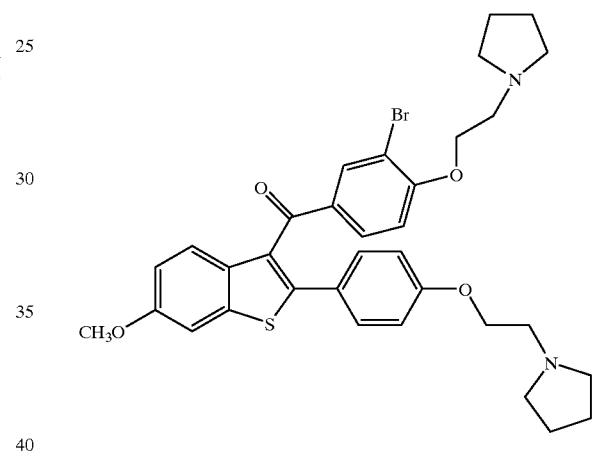

By essentially following the procedure used to prepare Example 138, Part A, the title compound was prepared from 3-bromo-4-[2-(1-pyrrolidinyl)ethoxy]phenyl 6-methoxy-2-[4-[2-(1-pyrrolidinyl)ethoxy]phenyl]benzo[b]thiophen-3-yl ketone (Part A) in 51% yield. The flash chromatography was carried out by eluting with a gradient of EtOAc(100–90%)/Et₃N(0–5%)/MeOH(0–5%). Conversion to the dioxalate was effected as in Example 137, Part E.

¹H NMR (CDCl₃) δ 7.35 (m, 5H), 6.95 (m, 4H), 6.77 (d, J=8.5 Hz, 1H), 4.17 (m, 6H), 3.88 (s, 3H), 3.04 (t, J=5.8 Hz, 2H), 2.97 (t, J=5.9 Hz, 2H), 2.79 (br s, 4H), 2.70 (br s, 4H), 1.84 (m, 8H).

Part C. 3-[3-Bromo-4-[2-(1-pyrrolidinyl)ethoxy]]-benzyl]-6-hydroxy-2-[4-[2-(1-pyrrolidinyl)ethoxy]-phenyl]benzo[b] thiophene Dioxalate Hydrate.

The title compound was prepared from 3-[3-bromo-4-[2-(1-pyrrolidinyl)ethoxy]benzyl]-6-methoxy-2-[4-[2-(1-pyrrolidinyl)ethoxy]phenyl]benzo[b]thiophene (Part B) essentially by the method of Example 138, Part B in 15% yield. Conversion to the dioxalate was effected essentially by the procedure of Example 137, Part E.

¹H NMR (CDCl₃) δ 7.23 (m, 5H), 6.84 (t, J=8.6 Hz, 2H), 6.73 (d, J=8.8 Hz, 2H), 6.62 (d, J=8.5 Hz, 1H), 4.16 (m, 4H), 4.04 (s, 2H), 3.19 (d, J=5.2 Hz, 2H), 3.04 (m, 8H), 2.94 (br s, 4H), 1.94 (m, 8H); FDMS 622 (M+1); Anal. Calcd for C₃₃H₃₇BrN₂O₃S·2C₂H₂O₄·2.5H₂O: C, 52.48; H, 5.48; N, 3.31. Found: C, 52.27; H. 5.20; N, 3.34.

EXAMPLE 144

Preparation of 6-Hydroxy-2-[4-[2-(1-pyrrolidinyl)-ethoxy]phenyl]-3-[[5-[(1-pyrrolidinyl)methyl]pyrazin-2-yl]methyl]benzo[b]thiophene Dioxalate.

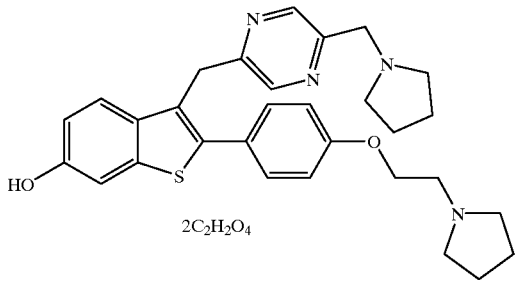

2C₂H₂O₄

Part A. Methyl 5-(Bromomethyl)pyrazine-2-carboxylate.

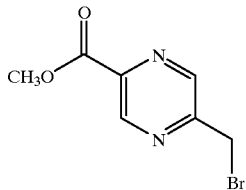

By essentially following the procedure used to prepare Example 137, Part A, the title compound was prepared from 5-methylpyridazine-2-carboxylic acid methyl ester in 82% yield as a white crystalline solid. The product was purified by crystallization from EtOAc/hexanes rather than chromatography.

$^1$H NMR (CDCl$_3$) δ 9.23 (s, 1H), 8.80 (s, 1H), 4.59 (s, 2H), 4.03 (s, 3H); FDMS 231 (M$^+$).

Part B. Methyl 5-[(1-Pyrrolidinyl)methyl]pyrazine-2-carboxylate.

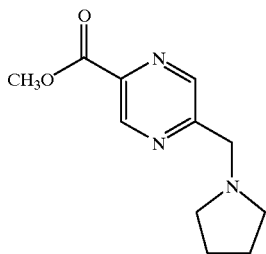

By essentially following the procedure used to prepare Example 137, Part B, the title compound was prepared from methyl 5-(bromomethyl)pyrazine-2-carboxylate (Part A) and pyrrolidine in 85% yield as a pale yellow oil. The mixture was subjected to flash chromatography on silica gel, eluting with a gradient of EtOAc(100–95%)/Et$_3$N(0–5%).

$^1$H NMR (CDCl$_3$) δ 9.23 (s, 1H), 8.78 (s, 1H), 4.03 (s, 3H), 3.90 (s, 2H), 2.59 (br s, 4H), 1.82 (br s, 4H).

Part C. 6-Methoxy-2-[4-[2-(1-pyrrolidinyl)ethoxy]-phenyl]benzo[b]thiophen-3-yl 5-[(1-Pyrrolidinyl)-methyl]pyrazin-2-yl Ketone.

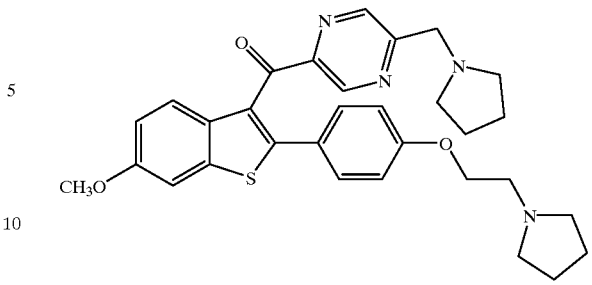

By essentially following the procedure used to prepare Example 137, Part C, the title compound was prepared from methyl 5-[(1-pyrrolidinyl)methyl]pyridazine-2-carboxylate (Part B) and 6-methoxy-2-[4-[2-(1-pyrrolidinyl)ethoxy]-phenyl]benzo[b]thiophene (Example 1, Part B) in 15% yield. The flash chromatography was carried out by eluting with a gradient of EtOAc(100–90%)/Et$_3$N(0–5%)/MeOH (0–5%).

$^1$H NMR (CDCl$_3$) δ 8.88 (s, 1H), 8.34 (s, 1H), 8.03 (d, J=9.1 Hz, 1H), 7.33 (s, 1H), 7.19 (d, J=8.4 Hz, 2H), 7.09 (d, J=8.8 Hz, 1H), 6.68 (d, J=8.6 Hz, 2H), 3.99 (t, J=5.9 Hz, 2H), 3.91 (s, 3H), 3.73 (s, 2H), 2.86 (t, J=5.9 Hz, 2H), 2.62 (br s, 4H), 2.42 (br s, 4H), 1.79 (m, 8H); FDMS 542 (M+).

Part D. 6-Methoxy-2-[4-[2-(i-pyrrolidinyl)ethoxy]-phenyl]-3-[[5-[(1-pyrrolidinyl)methyl3pyrazin-2-yl]-methyl]benzo[b]thiophene.

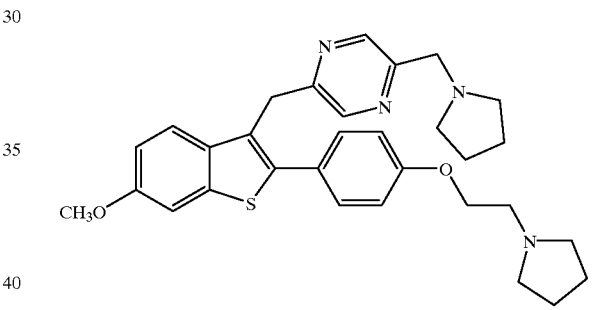

By essentially following the procedure used to prepare Example 138, Part A, the title compound was prepared from 6-methoxy-2-[4-[2-(1-pyrrolidinyl)ethoxy]phenyl]benzo[b]-thiophen-3-yl 5-[(1-pyrrolidinyl)methyl]pyridazin-2-yl ketone (Part C) in 30% yield. The flash chromatography was carried out by eluting with a gradient of EtOAc(100–85%)/Et$_3$N(0–5%)/MeOH(0–10%). Conversion to the dioxalate was effected as in Example 137, Part E.

$^1$H NMR (CDCl$_3$) δ 8.55 (s, 1H), 8.23 (s, 1H), 7.47 (d, J=8.6 Hz, 3H), 7.31 (s, 1H), 6.95 (m, 3H), 4.38 (s, 2H), 4.14 (t, J=5.7 Hz, 2H), 3.87 (s, 3H), 3.75 (s, 2H), 3.00 (t, J=5.8 Hz, 2H), 2.71 (br s, 4H), 2.56 (br s, 4H), 1.83 (br s, 8H).

Part E. 6-Hydroxy-2-[4-[2-(1-pyrrolidinyl)ethoxy]-phenyl]-3-[[5-[(1-pyrrolidinyl)methyl]pyrazin-2-yl]-methyl]benzo[b]thiophene Dioxalate.

By essentially following the procedure used to prepare Example 138, Part B, the title compound was prepared from 6-methoxy-2-[4-[2-(1-pyrrolidinyl)ethoxy]phenyl]-3-[[5-[(1-pyrrolidinyl)methyl]pyrazin-2-yl]methyl]benzo[b]thiophene (Part D) in 24% yield. The flash chromatography was carried out by eluting with a gradient of EtOAc (100–85%)/Et$_3$N(0–5%)/MeOH(0–10%). Conversion to the dioxalate was effected as in Example 137, Part E.

1H NMR (CDCl$_3$) δ 8.53 (s, 1H), 8.20 (s, 1H), 7.36 (m, 3H), 6.97 (s, 1H), 6.83 (d, J=8.6 Hz, 2H), 6.76 (d, J=8.5 Hz, 1H), 4.33 (s, 2H), 4.16 (t, J=5.3 Hz, 2H), 3.75 (s, 2H), 3.01 (t, J=5.2 Hz, 2H), 2.82 (br s, 4H), 2.56 (br s, 4H), 1.88 (br s, 4H), 1.79 (br s, 4H); FDMS 515 (M+1).

EXAMPLE 145

Preparation of 4-[4-(1-Pyrrolidinyl)butoxy]phenyl 2-[4-[2-(1-Pyrrolidinyl)ethoxy]phenyl]benzo[b]thiophen-3-yl Ketone Dioxalate Hydrate.

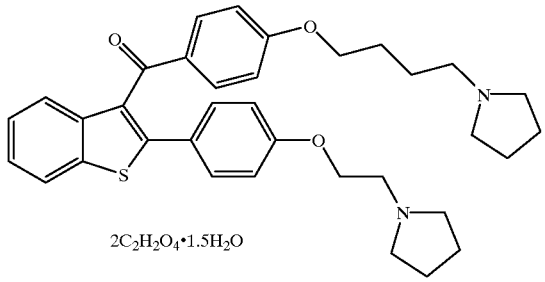

2C₂H₂O₄·1.5H₂O

Part A. 4-Fluorophenyl 2-[4-[2-(1-Pyrrolidinyl)-ethoxy]phenyl]benzo[b]thiophen-3-yl Ketone.

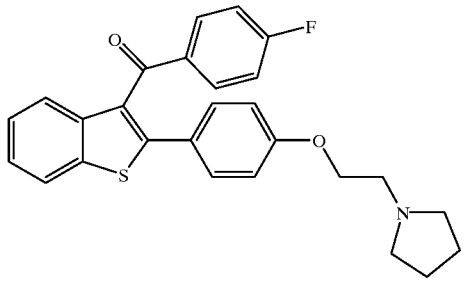

In a flame-dried, argon-filled flask were combined 1-[2-[4-(benzo[b]thiophen-2-yl)phenoxy]ethyl]pyrrolidine (Example 4, Part A) (3.54g; 11.0 mmol) and 2.6g (16.4 mmol) of 4-fluorobenzoyl chloride in 130 mL of dichloromethane. The mixture was cooled in an ice-water bath and protected from light with aluminum foil. Titanium tetrachloride (8.3 g; 43.8 mmol) was added dropwise. The mixture was stirred overnight while allowed to warm to room temperature. The mixture was poured into a rapidly stirred solution of 300 mL of saturated aqueous sodium bicarbonate. After stirring for 1 h, the mixture was transferred to a separatory funnel with 200 mL of water and extracted with dichloromethane (2×150 mL). The combined organics were dried by passage through sodium sulfate. The title compound was isolated as a yellow oil (4.4g; 90% yield) by preparation HPLC using PrepLC, eluting with hexanes/THF/Et₃N (75:20:5).
1H NMR (CDCl₃) δ 8.55 (s, 1H), 8.23 (s, 1H), 7.47 (d, J=8.6 Hz, 3H), 7.31 (s, 1H), 6.95 (m, 3H), 4.38 (s, 2H), 4.14 (t, J=5.7 Hz, 2H), 3.87 (s, 3H), 3.75 (s, 2H), 3.00 (t, J=5.8 Hz, 2H), 2.71 (br s, 4H), 2.56 (br s, 4H), 1.83 (br s, 8H); FDMS 445 (M⁺).

Part B. 4-(1-Pyrrolidinyl)butanol.

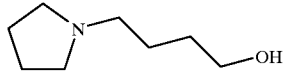

4-Oxo-4-(1-pyrrolidinyl)butyric acid (0.30 g; 1.75 mmol) in 10 mL of THF in an argon-filled flask was treated with lithium aluminum hydride (0.17 g; 4.38 mmol) at 70° C. for 4 h. After cooling the mixture to room temperature, hydrolysis was effected by addition of 0.17 mL each of water and 5 N NaOH, followed by 0.51 mL of water. Stirring was continued for 0.5 h. The mixture was filtered and concentrated under reduced pressure to give the title compound as a colorless oil (0.21g; 84% yield).
¹H NMR (CDCl₃) δ 8.55 3.55 (m, 2H), 2.54 (m, 4H), 2.47 (m, 2H), 1.78 (m, 4H), 1.66 (m, 4H).

Part C. 4-[4-(1-Pyrrolidinyl)butoxy]phenyl 2-[4-[2-(1-Pyrrolidinyl)ethoxy]phenyl]benzo b]thiophen-3-yl Ketone Dioxalate Hydrate.

Sodium hydride (49 mg of 60% NaH in mineral oil; 1.23 mmol) was suspended in 3 mL of dry DMF in a flame-dried, argon-filled flask. After stirring for 15 min, a solution of 4-(1-pyrrolidinyl)butanol (Part B) in 1 mL of dry DMF was added. After stirring for 15 min and gas evolution had ceased, 4-fluorophenyl 2-[4-[2-(1-pyrrolidinyl)ethoxy]-phenyl]benzo[b]thiophen-3-yl ketone (Part A)(0.2g; 0.49 mmol) in 1 mL of dry DMF was added. The mixture was stirred at room temperature for 5 h, then poured into 25 mL of water. Extraction was carried out with EtOAc (4×25 mL). The combined organics were washed with brine and dried by passage through sodium sulfate. The title compound (0.18 g; 66% yield) was isolated as a colorless oil by flash chromatography on silica gel, eluting with a gradient of EtOAc (100–85%)/Et₃N(0–5%)/MeOH(0–10%). Conversion to the dioxalate was effected as in Example 137, Part E.
FDMS 569 (M+1); Anal. Calcd for C₃₅H₄₀N₂O₃S·2C₂H₂O₄·1.5H₂O: C, 60.37; H, 6.11; N, 3.61. Found: C, 60.01; H, 5.92; N, 3.66.

EXAMPLE 146

Preparation of 3-[4-[(1-Pyrrolidinyl)butoxy]]benzyl]-2-[4-[2-(1-pyrrolidinyl)ethoxy]phenyl]benzo[b]-thiophene Dioxalate Hydrate.

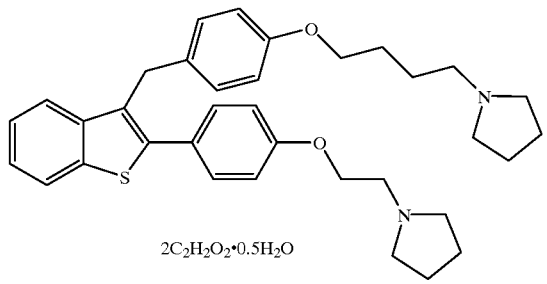

2C₂H₂O₂·0.5H₂O

The title compound was prepared from 4-[4-(1-pyrrolidinyl)butoxy]phenyl 2-[4-[2-(1-pyrrolidinyl)ethoxy]-phenyl]benzo[b]thiophen-3-yl ketone (Example 145, Part C) essentially by application of the procedure used for Example 138, Part A in 65% yield. The flash chromatography was carried out by elution with a gradient of EtOAc(100–90%)/Et₃N(0–5%)/MeOH(0–5%). Conversion to the dioxalate was effected as in Example 137, Part E.
FDMS 554 (M+); Anal. Calcd for C₃₅H₄₂N₂O₂S·2C₂H₂O₄·0.5H₂O: C, 62.97; H, 6.37; N, 3.77. Found: C, 62.91; H, 6.10; N, 3.64.

EXAMPLE 147

Preparation of 2-[4-[2-(1-Pyrrolidinyl)ethoxy]phenyl]benzo[b]thiophen-3-yl 4-[[2-(1-Pyrrolidinyl)ethyl]-amino]phenyl Ketone Trioxalate Hydrate.

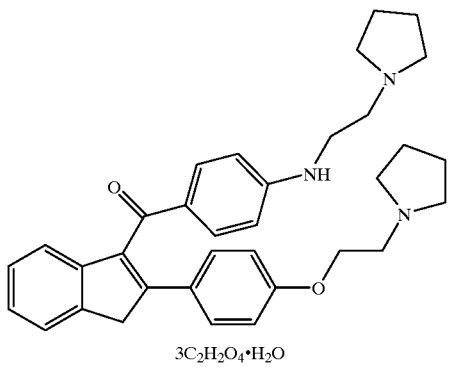

3C$_2$H$_2$O$_4$·H$_2$O

4-Fluorophenyl 2-[4-[2-(1-pyrrolidinyl)ethoxy]phenyl]-benzo[b]thiophen-3-yl ketone (Example 145, Part A) (1.1 g; 2.5 mmol) was combined with 1.6 mL (12.3 mmol) of 1-(2-aminoethyl)pyrrolidine and 1.0 g (7.4 mmol) of potassium carbonate in 2 mL of dry DMF. The mixture was heated in an oil bath maintained at 130° C. for 18 h. After cooling to room temperature, the mixture was poured into 150 mL of water and stirred for 0.5 h. The product was isolated by filtration and washed with fresh water. The title compound (0.9 g; 68% yield) was purified by flash chromatography on silica gel, eluting with a gradient of hexanes(75–15%)/Et$_3$N (5%)/THF(20–80%). Conversion to the trioxalate was effected as in Example 137, Part E.

FDMS 540 (M+1); Anal. Calcd for C$_{33}$H$_{37}$N$_3$O$_2$S·3C$_2$H$_2$O$_4$·H$_2$O: C, 56.58; H, 5.48; N, 5.08. Found: C, 56.94; H, 5.60; N, 6.55.

EXAMPLE 148

Preparation of 2-[4-[2-(1-Pyrrolidinyl)ethoxy3phenyl]-[4-[[2-(1-pyrrolidinyl)ethyl]amino]benzyl]benzo[b]-thiophene Trioxalate Hydrate.

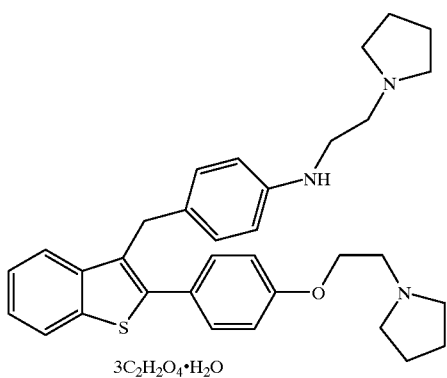

3C$_2$H$_2$O$_4$·H$_2$O

The title compound was prepared from 2-[4-[2-(1-pyrrolidinyl)ethoxy]phenyl]benzo[b]thiophen-3-yl 4-[[2-(1-pyrrolidinyl)ethyl]amino]phenyl ketone (Example 147) essentially by application of the procedure used for Example 138, Part A in 76% yield. The flash chromatography was carried out by elution with a gradient of hexanes(55–15%)/ Et$_3$N(5%)/THF(40–80%). Conversion to the trioxalate was effected as in Example 137, Part E.

FDMS 526 (M+1); Anal. Calcd for C$_{33}$H$_{39}$N$_3$OS·3C$_2$H$_2$O$_4$·H$_2$O: C, 57.56; H, 5.82; N, 5.16. Found: C, 57.34; H, 5.96; N, 4.76.

EXAMPLE 149

Preparation of 2-[4-[2-(1-Pyrrolidinyl)ethoxy]-phenyl]benzo[b]thiophen-3-yl 4-[[2-(1-Pyrrolidinyl)-ethyl]thio]phenyl Ketone Dioxalate Hydrate.

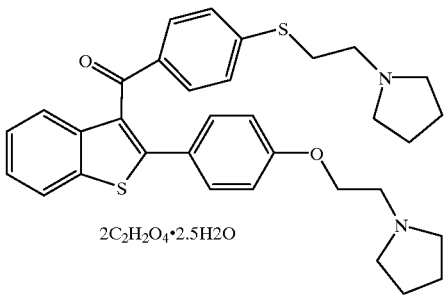

2C$_2$H$_2$O$_4$·2.5H2O

Part A. 2-(1-Pyrrolidinyl)ethanethiol.

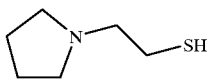

Pyrrolidine (6.85g; 96 mmol) and 8.1 g (135 mmol) of ethylene sulfide in 40 mL of dioxane were heated under reflux for 6 h, then distilled under reduced pressure to give the title compound (7.0g; 55% yield) as a colorless liquid.

$^1$H NMR (CDCl$_3$) δ 2.56 (m, 2H), 2.43 (m, 4H), 1.72 (m, 4H); FDMS 130 (M+1).

Part B. 2-[4-[2-(1-Pyrrolidinyl)ethoxy3phenyl]-benzo[b]thiophen-3-yl 4- [2-(1-Pyrrolidinyl)ethyl]-thio]phenyl Ketone Dioxalate Hydrate.

The title compound was prepared from 4-fluorophenyl 2-[4-[2-(1-pyrrolidinyl)ethoxy]phenyl]benzo[b]thiophen-3-yl ketone (Example 145, Part A) and 2-(1-pyrrolidinyl)-ethanethiol (Part A) essentially by application of the procedure used for Example 145, Part C in 73% yield. The flash chromatography was carried out by elution with a gradient of EtOAc(100–90%)/Et$_3$N(0–5%)/MeOH(0–5%). Conversion to the dioxalate was effected as in Example 137, Part E.

FDMS 557 (M+1); Anal. Calcd for C$_{33}$H$_{36}$N$_2$O$_2$S2-2C$_2$H$_2$O$_4$·2.5H$_2$O: C, 56.84; H, 5.80; N, 3.58. Found: C, 56.63; H, 5.47; N, 3.84.

EXAMPLE 150

Preparation of 2-[4-[2-(1-Pyrrolidinyl)ethoxy]phenyl]-3-[4-[[2-(1-pyrrolidinyl)ethyl]thiol]benzyl]benzo[b]-thiophene Dioxalate Hydrate.

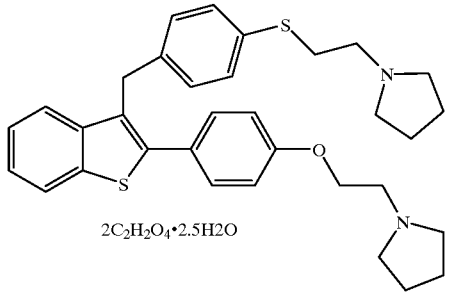

2C₂H₂O₄·2.5H2O

The title compound was prepared from 2-[4-[2-(1-pyrrolidinyl)ethoxy]phenyl]benzo[b]thiophen-3-yl 4-[[2-(1-pyrrolidinyl)ethyl]thio]phenyl ketone (Example 149, Part B) essentially by application of the procedure used for Example 138, Part A in 77% yield. The flash chromatography was carried out by elution with a gradient of EtOAc(100–90%)/Et₃N(0–5%)/MeOH(0–5%). Conversion to the dioxalate was effected as in Example 362485, Part E.
FDMS 543 (M+1); Anal. Calcd for C₃₃H₃₈N₂OS₂·2C₂H₂O₄·2.5H₂O: C, 59.25; H, 5.72; N, 3.45. Found: C, 58.88; H, 5.67; N, 3.32.

EXAMPLE 151

Preparation of 2-[4-[2-(1-Pyrrolidinyl)ethoxy]phenyl]-3-[4-[3-(1-pyrrolidinyl)propoxy]]benzyl3benzo[b]thiophene Trioxalate.

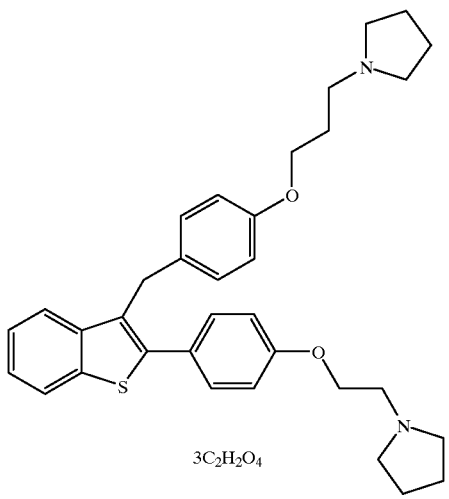

3C₂H₂O₄

The title compound was prepared from 2-[4-[2-(1-pyrrolidinyl)ethoxy]phenyl]benzo[b]thiophen-3-yl 4-[3-(1-pyrrolidinyl)propoxy]phenyl ketone (Example 4) essentially by application of the procedure used for Example 138, Part A in 21% yield. The flash chromatography was carried out by elution with a gradient of EtOAc(100–90%)/Et₃N(0–5%)/MeOH(0–5%). Conversion to the trioxalate was effected as in Example 137, Part E.
FDMS 541 (M+1); Anal. Calcd for C₃₄H₄₀N₂O₂S·3C₂H₂O₄: C, 59.25; H, 5.72; N, 3.45. Found: C, 58.88; H, 5.67; N, 3.32.

EXAMPLE 152

Preparation of 4-[2-(1-Methylpyrrolidin-2-yl)ethoxy]-phenyl 2-[4-[2-(1-pyrrolidinyl)ethoxy]phenyl]benzo[b]-thiophen-3-yl Ketone Dioxalate Hydrate.

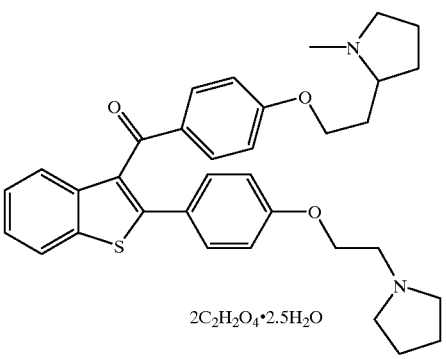

2C₂H₂O₄·2.5H₂O

The title compound was prepared from 4-fluorophenyl 2-[4-[2-(1-pyrrolidinyl)ethoxy]phenyl]benzo[b]thiophen-3-yl ketone (Example 145, Part A) and 2-(1-methylpyrrolidin-2-yl)ethanol essentially by application of the procedure used for Example 145, Part C in 12% yield. The flash chromatography was carried out by elution with a gradient of EtOAc(100–90%)/Et₃N(0–5%)/MeOH(0–5%). Conversion to the dioxalate was effected as in Example 137, Part E.
FDMS 555 (M+); Anal. Calcd for C₃₄H₃₈N₂O₃S·2C₂H₂O₄·2.5H₂O: C, 58.53; H, 6.07; N, 3.59. Found: C, 58.26; H, 5.80; N, 3.50.

EXAMPLE 153

Preparation of 3-[4-[2-(1-Methylpyrrolidin-2-yl)-ethoxy]benzyl]-2-[4-[2-(1-pyrrolidinyl)ethoxy3phenyl]-benzo[b]thiophene Dioxalate.

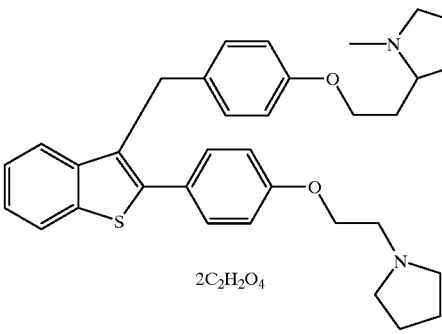

2C₂H₂O₄

The title compound was prepared from 4-[2-(1-methylpyrrolidin-2-yl)ethoxy]phenyl 2-[4-[2-(1-pyrrolidinyl)-ethoxy]phenyl]benzo[b]thiophen-3-yl ketone (Example 152) essentially by application of the procedure used for Example 138, Part A in 69% yield. The flash chromatography was carried out by elution with a gradient of EtOAc(100–90%)/Et₃N(0–5%)/MeOH(0–5%). Conversion to the dioxalate was effected as in Example 137, Part E.
FDMS 541 (M+); Anal. Calcd for C₃₄H₃₈N₂O₃S·3C₂H₂O₄: C, 59.25; H, 5.72; N, 3.45. Found: C, 58.93; H, 5.57; N, 3.07.

EXAMPLE 154

Preparation of 4-[2-(1-Methylpyrrolidin-3-yl)ethoxy]-phenyl 2-[4-[2-(1-Pyrrolidinyl)ethoxy]phenyl]benzo[b]-thiophen-3-yl Ketone Dioxalate Hydrate.

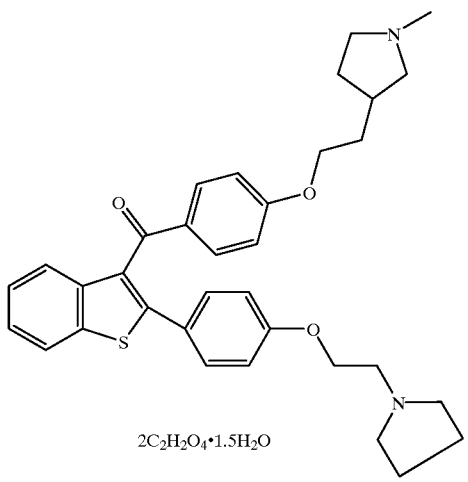

2C₂H₂O₄·1.5H₂O

The title compound was prepared from 4-fluorophenyl 2-[4-[2-(1-pyrrolidinyl)ethoxy]phenyl]benzo[b]thiophen-3-yl ketone (Example 145, Part A) and 2-(1-methylpyrrolidin-3-el)ethanol (R. Lukes, M. Ferles and O. Strouf, *Coll. Czech. Chem. Comm.*, 24, 212–219 (1959)) essentially by application of the procedure used for Example 145, Part C in 23% yield. The flash chromatography was carried out by elution with a gradient of EtOAc(100–90%)/Et₃N(0–5%)/MeOH (0–5%). Conversion to the dioxalate was effected as in Example 137, Part E.
FDMS 554 (M⁺); Anal. Calcd for C₃₄H₃₈N2O3S.2C₂H₂O₄·1.5H₂O: C, 59.91; H, 5.95; N, 3.68. Found: C, 59.56; H, 5.48; N, 3.59.

EXAMPLE 155

Preparation of 3-[4-E2-(1-Methylpyrrolidin-3-yl)-ethoxy]benzyl]-2-[4-[2-(1-pyrrolidinyl)ethoxy]phenyl]-benzo[b]thiophene Dioxalate Dihydrate.

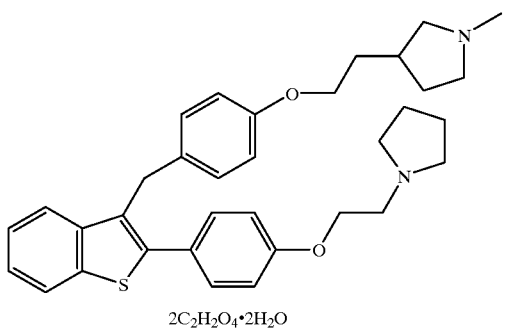

2C₂H₂O₄·2H₂O

The title compound was prepared from 4-[2-(1-methylpyrrolidin-3-yl)ethoxy]phenyl 2-[4-[2-(1-pyrrolidinyl)-ethoxy]phenyl]benzo[b]thiophen-3-yl ketone (Example 154) essentially by application of the procedure used for Example 138, Part A in 63% yield. The flash chromatography was carried out by elution with a gradient of EtOAc(100–90%)/Et₃N(0–5%)/MeOH(0–5%). Conversion to the dioxalate was effected as in Example 137, Part E.

FDMS 540 (M+); Anal. Calcd for C₃₄H₃₈N₂O₃S·2C₂H₂O₄·2H₂O: C, 60.30; H, 6.39; N, 3.70. Found: C, 60.60; H, 6.01; N, 3.61.

EXAMPLE 156

Preparation of 2-[4-[2-(1-Pyrrolidinyl)ethoxy]phenyl]-benzo[b]thiophen-3-yl (S)-4-[2-[(1-Pyrrolidinyl)-methyl]pyrrolidin-1-yl]phenyl Ketone Trioxalate.

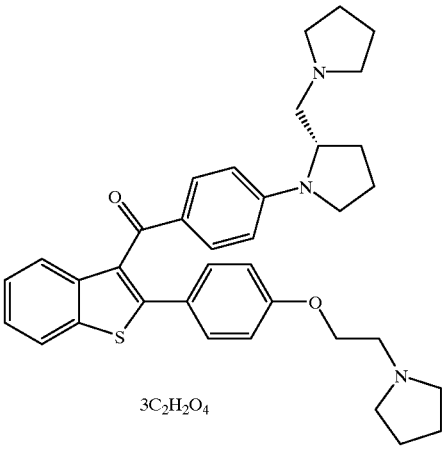

3C₂H₂O₄

The title compound was prepared from 4-fluorophenyl 2-[4-[2-(1-pyrrolidinyl)ethoxy]phenyl]benzo[b]thiophen-3-yl ketone (Example 145, Part A) and (S)-(+)-1-(2-pyrrolidinylmethyl)pyrrolidine essentially by application of the procedure used for Example 145, Part C in 19% yield. The flash chromatography was carried out by elution with a gradient of EtOAc(100–90%)/Et₃N(0–5%)/MeOH(0–5%). Conversion to the trioxalate was effected as in Example 137, Part E.

FDMS 579 (M⁺); Anal. Calcd for C₃₆H₄₁N3O2S·3C₂H₂O₄: C, 59.36; H, 5.57; N, 4.94. Found: C, 59.21; H, 5.76; N, 5.17.

EXAMPLE 157

Preparation of (S)-2-[4-[2-(1-Pyrrolidinyl)ethoxy3-phenyl]-3-[4-[2-[(1-pyrrolidinyl)methyl]pyrrolidin-1-yl]benzylbenzo[b]thiophene Trioxalate.

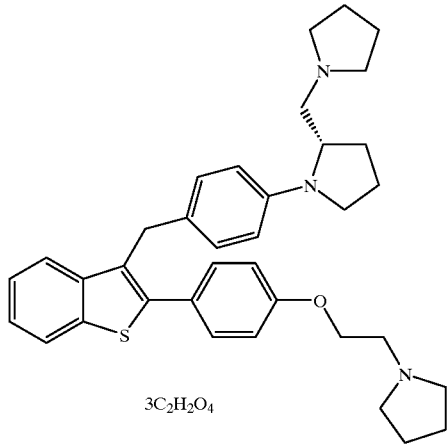

3C₂H₂O₄

The title compound was prepared from 2-[4-[2-(1-pyrrolidinyl) ethoxy]phenyl]benzo[b]thiophen-3-yl (S) -4-[2-[(1-pyrrolidinyl)methyl]pyrrolidin-1-yl]phenyl ketone (Example 156) essentially by application of the procedure used for Example 138, Part A in 69% yield. The flash chromatography was carried out by elution with a gradient of EtOAc(100–90%)/Et₃N(0–5%)/MeOH(0–5%). Conversion to the trioxalate was effected as in Example 137, Part E.

FDMS 565 (M+); Anal. Calcd for $C_{36}H_{41}N_3O_2S \cdot 3C_2H_2O_4$: C, 59.36; H, 5.57; N, 4.94. Found: C, 59.21; H, 5.76; N, 5.17.

EXAMPLE 158

Preparation of 6-Hydroxy-3-[3-methyl-4-[(1-pyrrolidinyl)methyl]benzyl]-2-[4-[2-(1-pyrrolidinyl)-ethoxy]phenyl]benzo[b]thiophene Dioxalate.

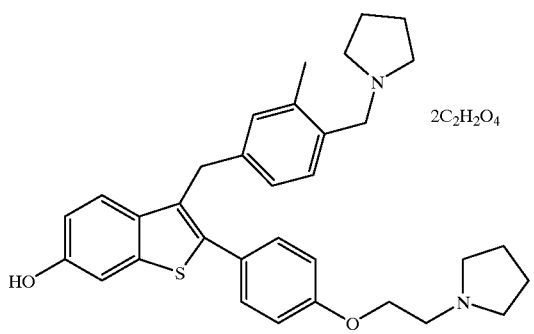

2C₂H₂O₄

Part A. 6-Methoxy-3-[3-methyl-4-[(1-pyrrolidinyl)-methyl]benzyl]-2-[4-[2-(1-pyrrolidinyl)ethoxy]phenyl]-benzo[b]thiophene.

3-[3-Bromo-4-[(1-pyrrolidinyl)methyl]benzyl]-6-methoxy-2-[4-[2-(1-pyrrolidinyl)ethoxy]phenyl]benzo[b]thiophene (Example 138, Part A) (93 mg, 0.15 mmol) in toluene (2 mL) in a pressure tube was treated with tetrakis (triphenylphosphine)palladium (0) (17 mg,) and tetramethyltin (0.2 mL) at ambient temperature. The mixture was flushed with argon and allowed to stir in the dark in the sealed tube at 130° C. for 25 h. The cooled reaction mixture was directly fractionated through flash chromatography with 5% triethylamine in ethyl acetate to afford the title compound as a colorless oil (61 mg, 73%) after the solvent removal.

¹H NMR (CDCl₃): δ 7.42 (d, 1H), 7.39 (d, 2H), 7.32 (d, 1H), 7.18 (d, 1H), 6.95 (d, 2H), 6.90 (m, 3H), 4.18 (s, 2H), 4.14 (t, 2H), 3.87 (s, 3H), 3.55 (s, 2H), 2.92 (t, 2H), 2.64 (m, 4H), 2.51 (m, 4H), 2.30 (s, 3H), 1.83 (m, 4H), 1.77 (m, 4H)

Part B. 6-Hydroxy-3-[3-methyl-4-[(1-pyrrolidinyl)-methyl]benzyl]-2-[4-[2-(1-pyrrolidinyl)ethoxy]phenyl]-benzo[b]thiophene Dioxalate.

6-Methoxy-3-[3-methyl-4-[(1-pyrrolidinyl)methyl]benzyl]-2-[4-[2-(1-pyrrolidinyl)ethoxy]phenyl]benzo[b]thiophene (61 mg, 0.11 mmol) in dichloroethane (2 mL) at ambient temperature was treated with ethanethiol (0.2 mL) and aluminum chloride (190 mg) sequentially at 0° C. under argon for 2 h before quenching with saturated aqueous sodium bicarbonate solution (10 mL). The stirring was allowed to continue for 1 h at ambient temperature. The resulting mixture was diluted with saturated aqueous sodium bicarbonate solution (50 mL) and extracted with dichloromethane (50 mL×3). The combined organic layers were dried (Na₂SO₄), concentrated under reduced pressure, and purified by chromatography with Et₃N:MeOH:EtOAc (5:5:90) to afford the title compound as a white foam (55 mg, 92%). The dioxalate salt was formed according to the method of Example 137, Part E.

¹H NMR (free base, CDCl₃): δ 7.30 (d, 2H), 7.25 (d, 1H), 7.18 (d, 1H), 7.06 (s, 1H), 6.93 (s, 1H), 6.90 (d, 1H), 6.80 (d, 2H), 6.68 (d, 1H), 4.13 (s and t, 4H), 3.60 (s, 2H), 3.00 (t, 2H), 2.80 (m, 4H), 2.59 (m, 4H), 2.28 (s, 3H), 1.89 (m, 4H), 1.80 (m, 4H); FDMS; m/e 527.0 (M+H⁺); Anal. Calc for $C_{33}H_{38}N_2O_2S \cdot 2C_2H_2O_4$: C, 62.87; H, 5.99; N, 3.96. Found: C, 62.68; H, 6.25; N, 3.91.

In general, the following Example 159–177 were prepared and characterized in the form of the free base as described below; then the compounds were converted into their respective dioxalate salts according to the method of Example 137, Part E prior to pharmacological evaluation.

EXAMPLE 159

6-Hydroxy-2-[4-[2-(1-pyrrolidinyl)ethoxy]phenyl]benzo-[b]thiophen-3-yl 3-Methyl-4-1(1-pyrrolidinyl)methyl]-phenyl Ketone.

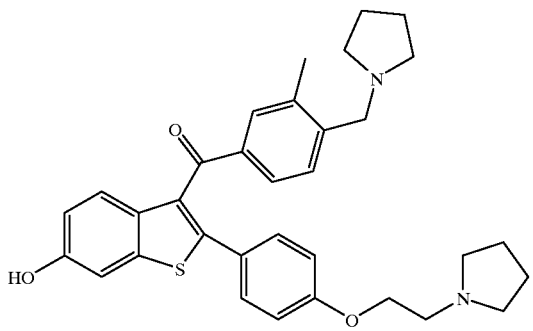

To a solution of 6-hydroxy-2-14-[2-(1-pyrrolidinyl)-ethoxy]phenyl]benzo[b]thiophen-3-yl 3-bromo-4-[(1-pyrrolidinyl)methyl]phenyl ketone (Example 137, Part D) (81 mg, 0.13 mmol) in DMF (2 mL) in a pressure tube were added tetrakis(triphenylphosphine)palladium(0) (18 mg) and tetramethyltin (0.3 mL) sequentially, followed by flushing with argon. The mixture was allowed to stir in the sealed pressure tube at 135° C. for 23 h in dark. The cooled reaction mixture was fractionated directly through flash chromatography with Et₃N:MeOH:EtOAc (5:10:85) to afford the title compound (32 mg, 44%).

¹H NMR (CDCl₃): 6 7.56 (s, 1H), 7.54 (d, 1H), 7.50 (d, 1H), 7.20 (d, 2H), 7.18 (d, 1H), 6.89 (m, 1H), 6.80 (m, 1H), 6.62 (d, 2H), 4.07 (t, 2H), 3.53 (s, 2H), 2.95 (t, 2H), 2.90 (m, 4H), 2.47 (m, 4H), 2.23 (s, 3H), 1.87 (m, 4H), 1.75 (m, 4H); FDMS m/e: 541.3 (M+H⁺).

EXAMPLE 160

Preparation of 6-Hydroxy-2-[4-[2-(1-pyrrolidinyl)-ethoxy]phenyl]-3-[4-[(1-pyrrolidinyl)methyl]benzyl]-benzo[b]thiophene.

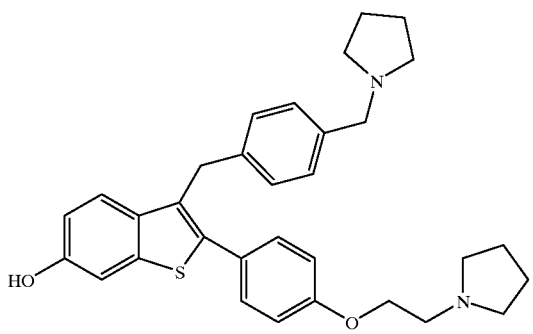

Part A. 6-Methoxy-2-[4-[2-(1-pyrrolidinyl)ethoxy]-phenyl]-3-[4-[(1-pyrrolidinyl)methyl1benzyl]benzo[b]-thiophene.

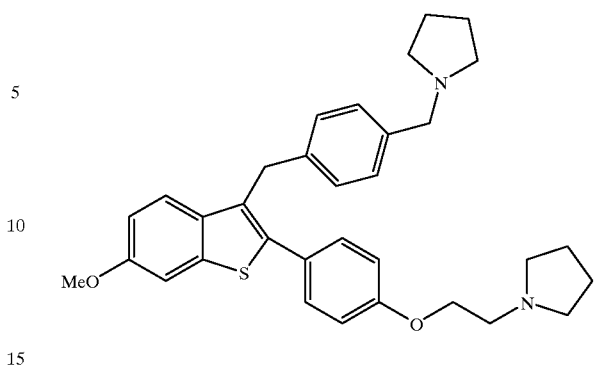

To a solution of 3-[3-bromo-4-[(1-pyrrolidinyl)methyl]-benzyl]-6-methoxy-2-[4-[2-(1-pyrrolidinyl)ethoxy]phenyl]-benzo[b]thiophene (100 mg, 0.16 mmol) in THF (2 mL) at −60° C. under argon was added a solution of n-butyllithium in hexanes (1.6M, 0.2 mL) and the mixture was stirred at −60° C. for 20 min. The reaction was quenched with 0.5 mL of MeOH and allowed to warm up to ambient temperature. The mixture was then concentrated under reduced pressure and fractionated by flash chromatography with Et₃N:MeOH:EtOAc (3:3:94) to afford the product (35 mg, 40%).

¹H NMR (CDCl₃): δ 7.41 (d, 2H), 7.35 (d, 1H), 7.31 (s, 1H), 7.23 (d, 2H), 7.12 (d, 2H), 6.95 (d, 2H), 6.90 (d, 1H), 4.22 (s, 2H), 4.15 (t, 2H), 3.90 (s, 3H), 3.60 (s, 2H), 2.95 (t, 2H), 2.67 (m, 4H), 2.55 (m, 4H), 1.86 (m, 8H); FDMS m/e: 526.3 (M⁺)

Part B. 6-Hydroxy-2-[4-[2-(1-pyrrolidinyl)ethoxy]-phenyl]-3-[4-[(1-pyrrolidinyl)methyl]benzyl]benzo[b]-thiophene.
6-Methoxy-2-[4-[2-(1-pyrrolidinyl)ethoxy]phenyl]-3-[4-[(1-pyrrolidinyl)methyl]benzyl]benzo[b]thiophene (35 mg, 0.066 mmol) in dichloroethane (2 mL) at 0° C. under argon was treated with ethanethiol (0.1 mL) and aluminum chloride (98 mg) for 3 h before quenching with saturated aqueous sodium bicarbonate solution (5 mL). The stirring was allowed to continue for 1 h at ambient temperature. The resulting mixture was diluted with saturated aqueous sodium bicarbonate solution (50 mL) and extracted with dichloromethane (50 mL×3). The combined organic layers were dried (Na2SO4) and concentrated under reduced pressure. Chromatography with Et₃N:MeOH:EtOAc (5:5:90) afforded the title compound as a white foam (25 mg, 73%).

¹H NMR (CD₃OD): δ 7.30 (d, 2H), 7.21 (d, 1H), 7.20 (d, 2H), 7.04 (d, 2H), 7.02 (d, 1H), 6.78 (d, 2H), 6.68 (dd, 1H), 4.17 (s, 2H), 4.16 (t, 2H), 2.98 (t, 2H), 2.69 (m, 4H), 2.60 (m, 4H), 1.94 (m, 4H), 1.89 (m, 4H); FDMS mle: 513 (M+H+).

EXAMPLE 161

Preparation of 3-[3-Cyano-4-[(1-pyrrolidinyl) methyl]-benzyl]-6-hydroxy-2-[4-[2-(1-pyrrolidinyl) ethoxy]-phenyl]benzo[b]thiophene.

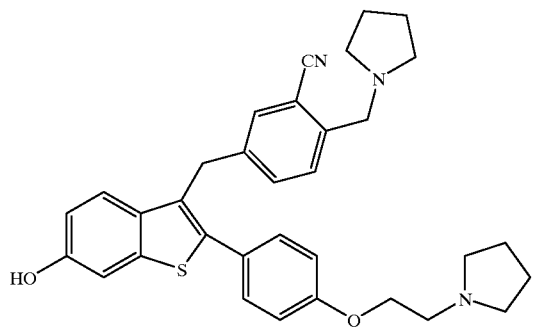

Part A. 3-[3-Cyano-4-1(1-pyrrolidinyl)methyl]benzyl]-6-methoxy-2-[4-[2-(1-pyrrolidinyl)ethoxy]phenyl]benzo-[b]thiophene.

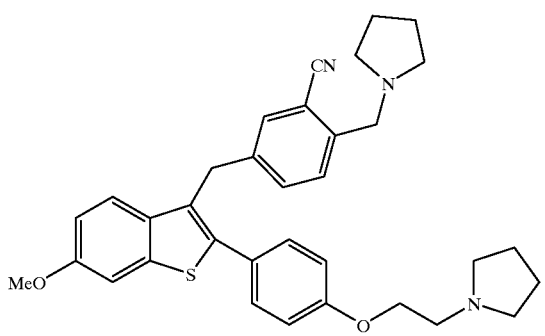

A suspension of 3-[3-bromo-4-[(1-pyrrolidinyl)]methyl]-benzyl]-6-methoxy-2-[4-[2-(1-pyrrolidinyl)ethoxy]phenyl]-benzo[b]thiophene (158 mg, 0.26 mmol) and copper(I) cyanide (40 mg) in 1-methyl-2-pyrrolidinone (3 mL) was allowed to stir at 200° C. under nitrogen for 5 h. The cooled reaction mixture was diluted with brine (50 mL) and extracted with EtOAc (50 mL×3). The combined organic layers were dried with sodium sulfate and concentrated under reduced pressure. Flash chromatography of the residue with Et$_3$N:MeOH:EtOAc (5:5:90) afforded the product (64 mg, 44%).
1H NMR (CDCl$_3$): 6 7.45 (d, 1H), 7.35 (m, 4H), 7.29 (d, 2H), 6.94 (d, 2H), 6.91 (d ,1H), 4.22 (s, 2H), 4.16 (t, 2H), 3.89 (s, 3H), 3.79 (s, 2H), 2.94 (t, 2H), 2.66 (m, 4H), 2.56 (m, 4H), 1.80 (m, 8H); FDMS m/e: 552 (M+H+).
Part B. 3-[3-Cyano-4-[(1-pyrrolidinyl)methyl]benzyl]-6-hydroxy-2-[4-[2-(1-pyrrolidinyl)ethoxy]phenyl]benzo-[b] thiophene.

3-[3-Cyano-4-[(1-pyrrolidinyl)methyl]benzyl]-6-methoxy-2-[4-[2-(1-pyrrolidinyl)ethoxy]phenyl]benzo[b] thiophene (60 mg, 0.11 mmol) in dichloroethane (4 mL) at 0° C. under argon was treated with ethanethiol (0.1 mL) and aluminum chloride (100 mg) for 3 h before quenching with saturated aqueous sodium bicarbonate solution (10 mL). The stirring was allowed to continue for 1 h at ambient temperature. The resulting mixture was diluted with saturated aqueous sodium bicarbonate solution (50 mL) and extracted with dichloromethane (50 mL×3). The combined organic layers were dried (Na$_2$SO$_4$) and concentrated under reduced pressure. Chromatography with Et$_3$N:MeOH:EtOAc (5:5:90) afforded the title compound as a white foam (40 mg, 68%).

$^1$H NMR (CDCl$_3$): δ 7.43 (d, 1H), 7.33 (s, 1H), 7.27 (d, 1H), 7.25 (d, 2H), 7.24 (d, 1H), 7.04 (s, 1H), 6.82 (d, 2H), 6.79 (d, 1H), 4.14 (t, 2H), 4.13 (s, 2H), 3.79 (s, 2H), 3.03 (t, 2H), 2.85 (m, 4H), 2.55 (m, 4H), 1.90 (m, 4H), 1.86 (m, 4H); FDMS m/e: 538 (M+H+).

EXAMPLE 162

Preparation of 3-[3-Aminomethyl-4-[(1-pyrrolidinyl)-methyl]benzyl]-6-hydroxy-2-[4-[2-(1-pyrrolidinyl)-ethoxy]phenyl]benzo[b]thiophene.

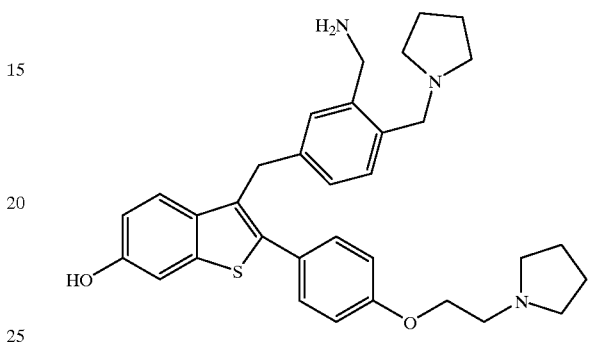

To 3-[3-cyano-4-[(1-pyrrolidinyl)methyl]benzyl]-6-hydroxy-2-[4-[2-(1-pyrrolidinyl)ethoxy]phenyl]benzo[b]-thiophene (29 mg, 0.054 mmol) in THF (2 mL) at 0° C. under argon was added lithium aluminum hydride (14 mg) in one portion. The resulting mixture was allowed to stir at ambient temperature for 7 h before quenching with water (2 mL) and 1.0M sodium hydroxide (1 mL). The stirring was continued for 30 min. The mixture was further diluted with brine (50 mL) and extracted with dichloromethane (50 mL×3). The combined organic layers were dried with sodium sulfate and concentrated under reduced pressure. Chromatography with NH$_4$OH:MeOH:EtOAc (5:10:85) afforded the product (7 mg, 24%).
$^1$H NMR (CDCl$_3$): δ 7.28–6.68 (m, 10H), 4.15 (m, 4H), 3.80 (s, 2H), 3.58 (s, 2H), 2.94 (t, 2H), 2.84 (m, 2H), 2.70 (m, 4H), 2.48 (m, 4H), 1.93 (m, 4H), 1.70 (m, 4H); FDMS m/e: 542.3 (M+H$^+$).

EXAMPLE 163

Preparation of 6-Hydroxy-2-[4-[2-(1-pyrrolidinyl)-ethoxy]phenyl]benzo[b]thiophen-3-yl 3-Methoxy-4-[(1-pyrrolidinyl)methyl]phenyl Ketone.

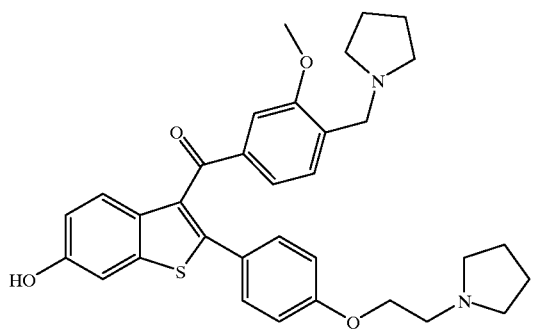

Part A. 6-Benzyloxy-2-(dimethylamino)benzo[b]thiophen-3-yl 3-Methoxy-4-[(1-pyrrolidinyl)methyl]phenyl Ketone.

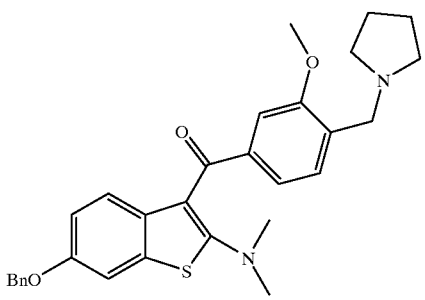

A solution of 6-benzyloxy-2-(dimethylamino)benzo[b]-thiophene (2.5 g, 8.8 mmol) and 3-methoxy-4-[(1-pyrrolidinyl)methyl]benzoyl chloride (3.0 g, 1.3 equiv) in chlorobenzene (30 mL) was heated at 135 OC under nitrogen for 2 h. The cooled reaction mixture was diluted with brine (100 mL), neutralized with NaOH solution (5.0M), and extracted with dichloromethane (100 mL×3). The combined organic layers were dried with sodium sulfate and concentrated under reduced pressure. Chromatography with Et$_3$N:EtOAc (5:95) afforded the product as a brown oil (3.7 g, 84%).

$^1$H NMR (CDCl$_3$): δ 7.5–6.9 (m, 11H), 5.10 (s, 2H), 3.90 (s, 3H), 3.71 (s, 2H), 2.91 (s, 6H), 2.60 (m, 4H), 1.83 (m, 4H): FDMS m/e: 500.0 (M$^+$).

Part B. 6-Benzyloxy-2-[4-[2-(1-pyrrolidinyl)ethoxy]-phenyl]benzo[b]thiophen-3-yl 3-Methoxy-4-[(1-pyrrolidinyl)methyl]phenyl Ketone.

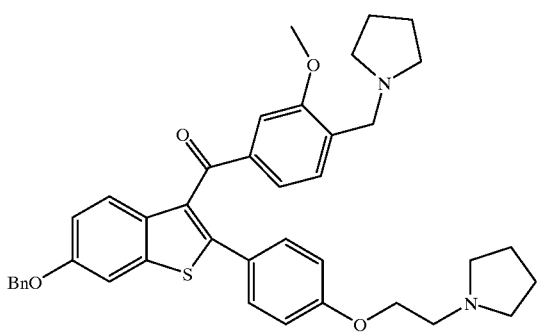

Magnesium turnings (0.3 g) were placed in a two-neck 100 mL round-bottom flask fitted with a reflux condenser and a magnetic stir bar. The whole apparatus was flame-dried and allowed to cool to ambient temperature. Dry THF (22 mL) and a small crystal of iodine was then introduced, followed by slow addition of 1-[2-(4-bromophenoxy)ethyl] pyrrolidine (2.75 mL) while stirring at ambient temperature. The reaction mixture was allowed to warm to a gentle reflux for 2 h or until the magnesium turnings were completely consumed to give a 0.5M solution of the Grignard reagent. This freshly prepared Grignard solution (7 mL) was added slowly to a stirring solution of 6-benzyloxy-2-(dimethylamino)benzo[b]-thiophen-3-yl 3-methoxy-4-[(1-pyrrolidinyl)methyl]phenyl ketone (1.1 g, 2.2 mmol) in THF (5.0 mL) at 0° C. under argon. The resulting mixture was stirred at 0° C. for 2 h before quenching with saturated aqueous NH$_4$Cl solution (50 mL) and extraction with CH$_2$Cl$_2$ (50 mL×3). The combined organic layers were dried with sodium sulfate and concentrated under reduced pressure. Chromatography with Et$_3$N:MeOH:EtOAC (5:5:90) afforded the product as a colorless oil (1.33 g, 93%).

$^1$H NMR (CDCl$_3$): δ 7.60 (d, 1H), 7.47–7.00 (m, 12H), 6.75 (d, 2H), 5.16 (s, 2H), 4.03 (t, 2H), 3.79 (s, 3H), 3.62 (s, 2H), 2.86 (t, 2H), 2.59 (m, 4H), 2.49 (m, 4H), 1.80 (m, 8H).

Part C. 6-Hydroxy-2-[4-[2-(1-pyrrolidinyl)ethoxy]-phenyl]benzo[b]thiophen-3-yl 3-Methoxy-4-[(1-pyrrolidinyl)methyl]phenyl Ketone.

6-Benzyloxy-2-[4-[2-(1-pyrrolidinyl)ethoxy]phenyl]benzo-[b]thiophen-3-yl 3-methoxy-4-[(1-pyrrolidinyl)methyl]phenyl ketone (105 mg, 0.16 mmol) in THF (5.0 mL) was treated sequentially with a solution of ammonium formate (25% in H$_2$O, 3 mL) and 10% palladium on carbon (50 mg) at ambient temperature. The resulting mixture was stirred at ambient temperature under argon for 9 h before filtration through diatomaceous earth followed by rinsing with dichloromethane and methanol. The filtrate was extracted with dichloromethane (30 mL×3) which extracts were washed with water (50 mL). The combined organic layers were dried with sodium sulfate and concentrated under reduced pressure. Chromatography with Et$_3$N:MeOH:EtOAc (5:10:85) afforded the product as a yellow solid (80 mg, 88%).

$^1$H NMR (CDCl$_3$): δ 7.56 (d, 2H), 7.32 (s, 1H), 7.24 (d, 1H), 7.20 (d, 1H), 7.15 (d, 2H), 6.98 (s, 1H), 6.79 (d ,1H), 6.60 (d, 2H), 4.08 (t, 2H), 3.80 (s, 2H), 3.75 (s, 3H), 3.01 (t, 2H), 2.99 (m, 4H), 2.82 (m, 4H), 1.87 (m, 8H); FDMS m/e: 557.1 (M+H$^+$).

EXAMPLE 164

Preparation of 6-Hydroxy-3-[3-methoxy-4-[(1-pyrrolidinyl)methyl]benzyl]-2-[4-[2-(1-pyrrolidinyl)-ethoxy]phenyl]benzo[b]thiophene.

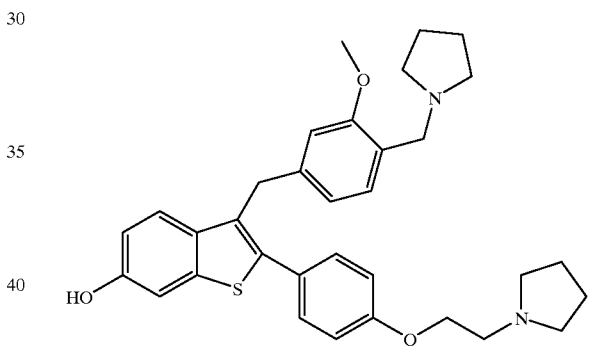

6-Hydroxy-2-[4-[2-(1-pyrrolidinyl)ethoxy]phenyl]benzo-[b]thiophen-3-yl 3-methoxy-4-[(1-pyrrolidinyl)methyl] phenyl ketone (368006, 1.17 g, 2.10 mmol) in dry THF (40 mL) at 0° C. under argon was treated with lithium aluminum hydride (164 mg) for 1 h, then quenched with water(1 mL) and sodium hydroxide (1.0M, 3 mL). Stirring continued for 30 min. The reaction mixture was diluted with brine (100 mL) and extracted with dichloromethane (100 mL×3). The combined organic layers were dried with sodium sulfate and concentrated in vacuo to give a white foam-like material. This material was dissolved in dichloromethane (30 mL), treated with triethylsilane (3.0 mL), cooled to 0° C. under argon, and followed by slow addition of trifluroacetic acid (2.5 mL). The resulting mixture was stirred at 0° C. for 2 h and then concentrated under reduced pressure. The residue was extracted with dichloromethane (50 mL×3) which extracts were washed with saturated aqueous sodium bicarbonate (100 mL). The combined organic layers were dried with sodium sulfate and concentrated. Chromatography with Et$_3$N:MeOH:EtOAc (5:10:85) afforded the product as a white solid (0.87 g, 76%).

$^1$H NMR (CDCl$_3$): δ 7.32 (d, 2H) , 7.24 (d, 1H), 7.23 (d, 1H), 7.21 (s, 1H), 6.84 (d, 2H), 6.68 (d, 1H), 6.62 (s, 1H), 6.59 (d, 1H), 4.16 (s, 2H), 4.14 (t, 2H), 3.80 (s, 2H), 3.58 (s, 3H), 2.98 (t, 2H), 2.78 (m, 4H), 2.74 (m, 4H), 1.86 (m, 8H); FDMS m/e: 543.1 (M+H+).

EXAMPLE 165

Preparation of 6-Hydroxy-3-[3-hydroxy-4-[(1-pyrrolidinyl)methyl]benzyl]-2-[4-[2-(1-pyrrolidinyl)-ethoxy]phenyl3benzo[b]thiophene.

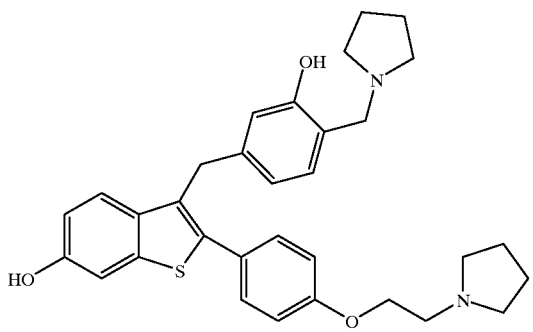

6-Hydroxy-3-[3-methoxy-4-[(1-pyrrolidinyl)methyl]-benzyl]-2-[4-[2-(1-pyrrolidinyl)ethoxy]phenyl]benzo[b]-thiophene (65 mg, 0.12 mmol) in dichloroethane (3 mL) was treated with ethanethiol (0.2 mL) and aluminum chloride (160 mg) at 0° C. for 2 h before quenching with saturated aqueous sodium bicarbonate solution (5 mL). The stirring was continued for 1 h at ambient temperature. The mixture was diluted with saturated aqueous sodium bicarbonate solution (50 mL) and extracted with dichloromethane (50 mL×3). The combined organic layers were dried (Na$_2$SO$_4$) and concentrated under reduced pressure. Chromatography with Et$_3$N:MeOH:EtOAc (5:5:90) afforded the title compound as a white foam (60 mg, 95%).

$^1$H NMR (CDCl$_3$): δ 7.33 (d, 1H), 7.31 (d, 2H), 7.08 (s, 1H), 6.82 (d, 1H), 6.80 (d, 1H), 6.77 (d, 2H), 6.63 (s, 1H), 6.52 (d, 1H), 4.15 (t, 2H), 4.01 (s, 2H), 3.76 (s, 2H), 3.06 (t, 2H), 2.88 (m, 4H), 2.61 (m, 4H), 1.91 (m, 4H), 1.83 (m,4H); FDMS m/e: 528 (M$^+$).

EXAMPLE 166

Preparation of 2-[4-(2-Aminoethoxy)phenyl]-6-hydroxy-3-[3-methoxy-4-[(1-pyrrolidinyl)methyl]benzyl]benzo[b]thiophene.

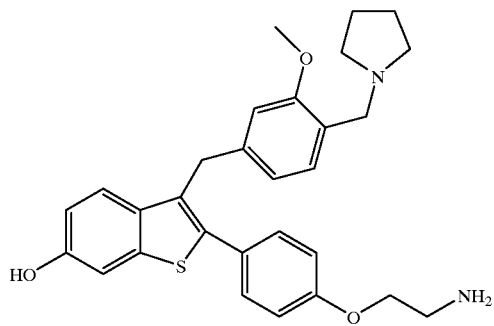

Part A. 4-Bromophenyl Triisopropylsilyl Ether.

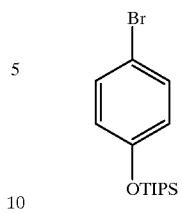

To 4-bromophenol (6.1 g, 35 mmol) and imidazole (2.6 g) in DMF (30 mL) at ambient temperature was added slowly triisopropylsilyl trifluoromethanesulfonate (10.5 mL) while stirring. The resulting mixture was stirred at ambient temperature for 1 h before dilution with water (200 mL) and extraction with EtOAc (100 mL×3). The combined organic layers were dried with sodium sulfate and concentrated under reduced pressure. Chromatography with EtOAc-hexanes (0–5% gradient elusion) afforded the product as a colorless oil (11.2 g, 96%).

$^1$H NMR (CDCl$_3$): δ 7.32 (d, J=9.1 Hz, 2H), 6.77 (d, J=9.1 Hz, 2H), 1.23 (m, 3H), 1.10 (d, J=7.0 Hz, 18H); FDMS m/e: 330 (M+H$^+$).

Part B. 6-Benzyloxy-2-[4-hydroxyphenyl]benzo[b]-thiophen-3-yl 3-Methoxy-4-[(1-pyrrolidinyl)methyl]-phenyl Ketone.

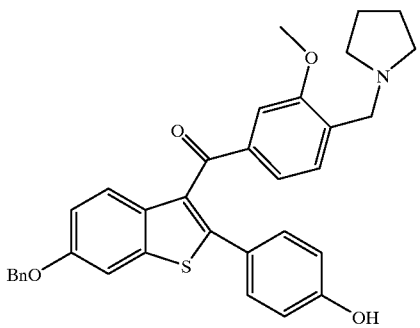

Magnesium turnings (0.24 g) were placed in a two-neck 100 mL round-bottom flask fitted with a reflux condenser and a magnetic stir bar. The whole apparatus was flame-dried and allowed to cool to ambient temperature. Dry THF (17 mL) and a small crystal of iodine were then introduced followed by slow addition of 4-bromophenyl triisopropyl-silyl ether (3.5 g) while stirring at ambient temperature. The reaction mixture was warmed to a gentle reflux for 1 h or until the magnesium turnings were completely consumed to give a 0.5M solution of the Grignard reagent. This freshly prepared Grignard solution (15 mL) was added slowly to a stirring solution of 6-benzyloxy-2-(dimethylamino)benzo[b]thiophen-3-yl 3-methoxy-4-[(1-pyrrolidinyl)methyl]phenyl ketone (2.5 g, 5.0 mmol) in THF (15.0 mL) at 0° C. under argon. The mixture was stirred at 0° C. for 2 h before quenching with saturated aqueous NH$_4$Cl solution (50 mL) and extraction with CH$_2$Cl$_2$ (50 mL×3). The combined organic layers were dried with sodium sulfate and concentrated under reduced pressure. Chromatography with EtOAc afforded a oily brown material as the major fraction. This material was dissolved in THF (25 mL), treated with a solution of tetrabutylammonium fluoride (1.0M in THF, 6 mL) at ambient temperature for 1 h, and then concentrated under reduced pressure. Chromatography with Et$_3$N:MeOH:EtOAc (5:10:85) afforded the title compound as a yellow foam (2.75 g, 100%).

¹H NMR (CDCl₃): δ 7.75 (d, 1H), 7.52–7.30 (m, 6H), 7.20 (d, 2H), 7.20–7.08 (m, 4H), 6.60 (d, 2H), 5.18 (s, 2H), 3.70 (s, 5H), 2.68 (m, 4H), 1.85 (m, 4H).

Part C. 6-Benzyloxy-2-(4-hydroxyphenyl)-3-[3-methoxy-4-[(1-pyrrolidinyl)methyl]benzyl]benzo b]thiophene.

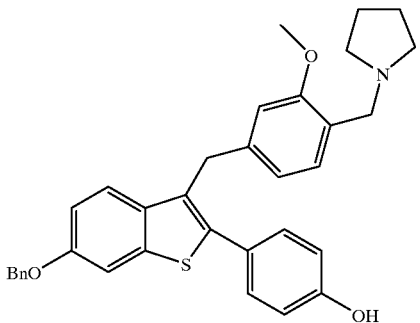

6-Benzyloxy-2-(4-hydroxyphenyl)benzo[b]thiophen-3-yl 3-methoxy-4-[(1-pyrrolidinyl)methyl]phenyl ketone (2.75 g, 5.0 mmol) in THF (25 mL) was treated with lithium aluminum hydride (420 mg) at 0° C. for 2 h, then quenched with water (1 mL) and sodium hydroxide (1.0M, 3 mL). Stirring was continued for 45 min. The reaction mixture was diluted with brine (100 mL) and extracted with dichloromethane (100 mL×3). The combined organic layers were dried with sodium sulfate and concentrated in vacuo to give a white foam-like material. This material was dissolved in dichloromethane (50 mL), treated with triethylsilane (6.0 mL) and trifluroacetic acid (5.0 mL) at 0° C. for 2 h, and concentrated under reduced pressure. The residue was extracted with dichloromethane (100 mL×3) which was washed with saturated aqueous sodium bicarbonate (100 mL). The combined organic layers were dried with sodium sulfate and concentrated. Chromatography with Et₃N:MeOH:EtOAc (5:5:90) afforded the product as a white solid (2.1 g, 78%).

¹H NMR (CDCl₃): δ 7.50–7.27 (m, 9H), 7.15 (d, 1H), 6.96 (d, 1H), 6.69 (d, 2H), 6.65 (d, 1H), 6.55 (s, 1H), 5.12 (s, 2H), 4.18 (s, 2H), 3.71 (s, 2H), 3.57 (s, 3H), 2.70 (m, 4H), 1.83 (m, 4H); FDMS m/e: 536 (M+H⁺).

Part D. 2-[4-(2-Amino-2-oxoethoxy)phenyl]-6-benzyloxy-3-[3-methoxy-4-[(1-pyrrolidinyl)methyl]-benzyl]benzo[b]thiophene.

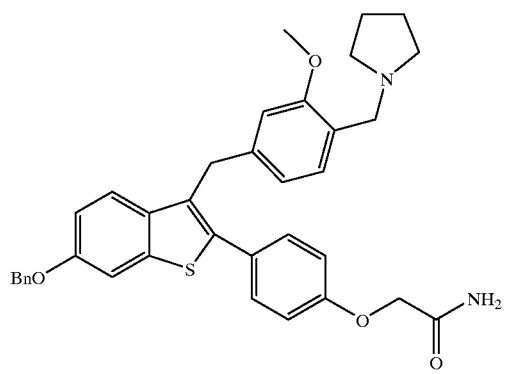

A suspension of 6-benzyloxy-2-(4-hydroxyphenyl)-3-[3-methoxy-4-[(1-pyrrolidinyl)methyl]benzyl]benzo[b]thiophene (154 mg, 0.29 mmol) and cesium carbonate (536 mg) in DMF (4 mL) was treated with 2-chloroacetamide (106 mg) at ambient temperature then heated at 90° C. under nitrogen for 2 h. The cooled reaction mixture was diluted with brine (50 mL) and extracted with EtOAc (30 mL×3). The combined organic layers were dried with sodium sulfate and concentrated under reduced pressure. Chromatography with Et₃N:MeOH:EtOAc (5:10:85) afforded the product (93 mg, 54%).

¹H NMR (CDCl₃): δ 7.60–7.27 (m, 9H), 7.20 (d, 1H), 7.02 (d, 1H), 6.95 (d, 2H), 6.70 (d, 1H), 6.65 (s, 1H), 6.55 (bs, 1H), 5.90 (bs, 1H), 5.12 (s, 2H), 4.52 (s, 2H), 4.23 (s, 2H), 3.70 (s, 3H), 3.63 (s, 2H), 2.62 (m, 4H), 1.80 (m, 4H).

Part E. 2-[4-(2-Aminoethoxy)phenyl]-6-hydroxy-3-[3-methoxy-4-[(1-pyrrolidinyl)methyl]benzyl]benzo[b]-thiophene.

To 2-[4-(2-amino-2-oxoethoxy)phenyl]-6-benzyloxy-3-[3-methoxy-4-[(1-pyrrolidinyl)methyl]benzyl]benzo[b] thiophene (93 mg, 0.15 mmol) in THF (5 mL) was added lithium aluminum hydride (57 mg) at ambient temperature and the mixture was stirred under argon at 65° C. for 24 h. The reaction was quenched with water (1 mL) and sodium hydroxide solution (1.0 M, 1 mL) while stirring continued for 30 min. The mixture was then diluted with brine (50 mL) and extracted with dichloromethane (30 mL×3). The combined organic layers were dried with sodium sulfate and concentrated in vacuo. The crude reduction product was dissolved in THF (5 mL) and treated with a 25% aqueous solution of ammonium formate (2 mL) and palladium on carbon (10%, 100 mg) at ambient temperature under argon for 6 h before filtration through diatomaceous earth followed by rinsing with dichloromethane and methanol. The filtrate was extracted with dichloromethane (30 mL×3) which was washed with water (50 mL). The combined organic layers were dried with sodium sulfate and concentrated under reduced pressure. Chromatography with NH₄OH:MeOH:EtOAc (3:7:90) afforded the product as a white solid (24 mg, 31%).

¹H NMR (CDCl₃): δ 7.37(d, J=8.6 Hz,2H) , 7.20 (d, J=8.8 Hz, 1H), 7.15 (d, J=7.5 Hz, 1H), 7.04 (s, 2H), 6.89 (d, J=8.6 Hz, 1H), 6.65 (d, J=7.5 Hz, 1H), 6.61 (s, 1H), 6.47 (d, J=8.6 Hz, 1H), 4.16 (s, 2H), 4.02 (t, J=5.0 Hz, 2H), 3.67 (s, 2H), 3.54 (s, 3H), 3.14 (t, J=5.0 Hz, 2H), 2.64 (m, 4H), 1.80 (m, 4H); FDMS m/e: 489 (M+H⁺).

EXAMPLE 167

Preparation of 0-[4-[6-Hydroxy-3-[3-methoxy-4-[(1-pyrrolidinyl)methyl3benzyl]benzo[b]thiophen-2-yl]-phenyl]-L-serine Methyl Ester.

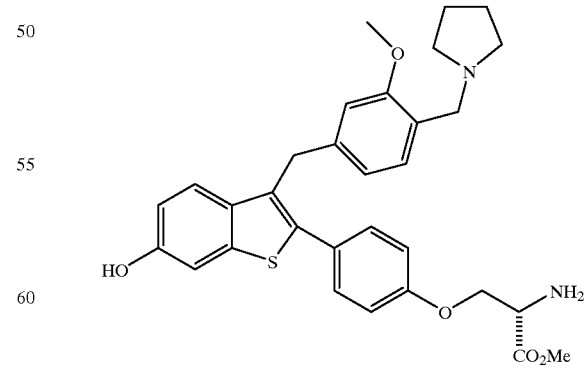

Part A. N-(Triphenylmethyl)-0-14-[6-benzyloxy-3-[3-methoxy-4-[(1-pyrrolidinyl)methyl]benzyl]benzo[b]-thiophen-2-yl]phenyl]-L-serine Methyl Ester.

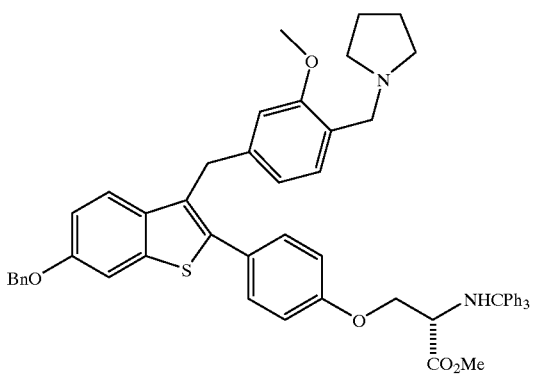

To a stirring solution of 6-benzyloxy-2-(4-hydroxyphenyl)-[3-methoxy-4-[(1-pyrrolidinyl)methyl]benzyl]-benzo[b]thiophene (359 mg, 0.67 mmol), triphenylphosphine (300 mg) and N-trityl-L-serine methyl ester (392 mg) in THF (6 mL) at 0° C. was added diethyl azodicarboxylate (0.18 mL) over 5 min. The mixture was stirred at ambient temperature under argon for 24 h before concentration under reduced pressure. Chromatography with EtOAc followed by $Et_3N$:MeOH:EtOAc (5:5:90) afforded the product (165 mg, 19%).

$^1$H NMR (CDCl$_3$): δ 7.80–7.20 (m, 25H), 7.02 (d, 1H), 6.92 (d, 2H), 6.72(d, 1H), 6.67 (s, 1H), 5.15 (s, 2H), 4.23 (s, 2H), 4.35–4.05 (m, 2H), 3.80 (m, 1H), 3.70 (s, 3H), 3.65 (s, 2H), 3.28 (s, 3H), 2.97 (d, 1H), 2.56 (m, 4H), 1.80 (m, 4H).

Part B. 0-[4-[6-Hydroxy-3-[3-methoxy-4-[(1-pyrrolidinyl)methyl]benzyl]benzo[b]thiophen-2-yl]-phenyl]-L-serine Methyl Ester.

N-(Triphenylmethyl)-0-[4-[6-benzyloxy-3-[3-methoxy-4-[(1-pyrrolidinyl)methyl]benzyl]benzo[b]thiophen-2-yl]phenyl]-L-serine methyl ester (165 mg, 0.18 mmol) in dichloromethane (5 mL) was treated with triethylsilane (0.3 mL) and trifluoroacetic acid (0.3 mL) at ambient temperature for 30 min. The solvent and excess reagents were removed under reduced pressure. The residue was dissolved in THF (3 mL) and treated with an aqueous solution of ammonium formate (25%, 2 mL) and palladium on carbon (10%, 50 mg) at ambient temperature for 21 h before filtration through diatomaceous earth with dichloromethane and methanol rinse. The filtrate was extracted with dichloromethane(30 mL×3) which was washed with water (50 mL). The combined organic layers were dried with sodium sulfate and concentrated under reduced pressure. Chromatography with $NH_4OH$:MeOH:EtOAc (3:7:90) afforded the product as a white solid (26 mg, 25%).

$^1$H NMR (CDCl$_3$): δ 7.36 (d, J=8.6 Hz, 2H) , 7.19 (d, J=8.3 Hz, 1H), 7.17 (d, J=6.7 Hz, 1H), 7.09 (s, 1H), 6.90 (d, J=8.6 Hz, 2H), 6.65 (d, J=6.8 Hz, 1H), 6.61 (s, 1H), 6.52 (d, J=6.8 Hz, 1H) 4.26 (m, 2H), 4.16 (s, 2H), 3.87 (m, 1H), 3.78 (s, 3H), 3.54 (s, 2H), 2.76 (m, 4H), 1.85 (m, 4H); FDMS m/e: 547.0 (M+H$^+$).

EXAMPLE 168

Preparation of (S)-2-Amino-3-[4-[6-hydroxy-3-[3-methoxy-4-[(1-pyrrolidinyl)methyl]benzyl]benzo[b]-thiophen-2-yl]phenoxy]propanol.

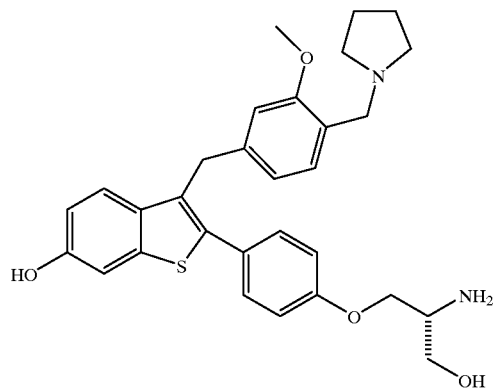

0-[4-[6-Hydroxy-3-[3-methoxy-4-[(1-pyrrolidinyl)methyl]-benzyl]benzo[b]thiophen-2-yl]phenyl]-L-serine methyl ester (25 mg, 0.045 mmol) in THF:CH$_2$Cl$_2$ (3:1, 4 mL) was treated with lithium aluminum hydride (12 mg) at ambient temperature under argon for 3 h. The reaction was quenched with water (0.5 mL) and sodium hydroxide solution (1.0M, 1 mL) and stirred for 30 more min before dilution with water (50 mL) and extracting with ethyl acetate (50 mL×3). The combined organic layers were dried with sodium sulfate and concentrated under reduced pressure. Preparative thin layer chromatography with $Et_3N$:MeOH:EtOAc (10:20:70) afforded the product as a white solid (8 mg, 34%).

$^1$H NMR (CD30D) : δ 7.50 (d, J=8.6 Hz, 2H) , 7.46 (d, J=8.3 Hz, 1H), 7.31 (s, 1H), 7.26 (d, 1H), 7.12 (d, J=8.6 Hz, 2H), 6.91 (d, J=6.8 Hz, 1H), 6.88 (s, 1H), 6.79 (d, J=6.8 Hz, 1H) 4.31 (s, 2H), 4.18 (m, 1H), 4.07 (m, 1H), 3.95 (s, 2H), 3.90 (s, 3H), 3.76 (m, 2H), 3.32 (m, 1H), 2.94 (m, 4H), 1.98 (m, 4H); FDMS m/e: 519.1 (M+H$^+$).

EXAMPLE 169

Preparation of 3-[4-(Aminomethyl)benzyl]-2-[4-[2-(1-pyrrolidinyl)ethoxy]phenyl]benzo[b]thiophene.

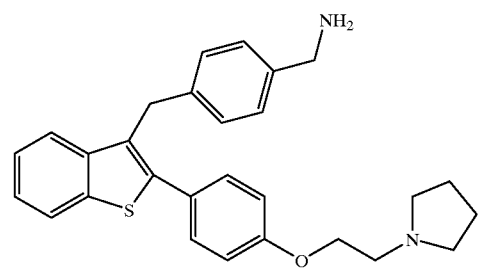

Part A. 4-Bromophenyl 2-[4-[2-(1-Pyrrolidinyl)-ethoxy]phenyl]benzo[b]thiophen-3-yl Ketone.

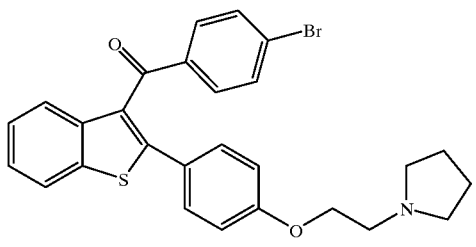

To a solution of 1-[2-[4-(benzo[b]thiophen-2-yl)-phenoxy]ethyl]pyrrolidine (650 mg, 2.0 mmol) and 4-bromobenzoyl chloride (657 mg, 1.5 equiv) in dichloromethane (25 mL) at 0° C. in dark was added TiCl$_4$ (1.0 mL, neat) slowly under argon. The resulting mixture was stirred at ambient temperature for 4 h before being transferred carefully to a stirring solution of saturated aqueous NaHCO$_3$ (100 mL). After stirring for 30 min, the mixture was extracted with CH$_2$Cl$_2$ (3×100 mL). The combined organic layers were dried (Na2SO4) and concentrated under reduced pressure. Chromatography with Et$_3$N:MeOH:EtOAc (4:4:92) afforded the product (940 mg, 92%).

$^1$H NMR (CDCl$_3$): δ 7.90 (m, 1H), 7.84 (m, 1H), 7.63 (d, 2H), 7.43 (d, 2H), 7.42 (d, 2H), 7.33 (d, 2H), 6.80 (d, 2H), 4.09 (t, 2H), 2.90 (t, 2H), 2.64 (m, 4H), 1.85 (m, 4H).

Part B. 3-(4-Bromobenzyl)-2-[4-[2-(1-pyrrolidinyl)-ethoxy]phenyl]benzo[b]thiophene.

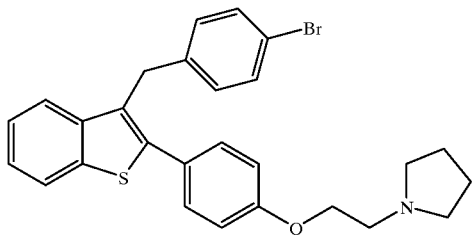

4-Bromophenyl 2-[4-[2-(1-pyrrolidinyl)ethoxy]phenyl]-benzo[b]thiophen-3-yl ketone (430 mg, 0.85 mmol) in THF (7 mL) was treated with lithium aluminum hydride (65 mg) at 0° C. for 2 h, and then the reaction was quenched with water (1 mL) and sodium hydroxide (1.0M, 3 mL). Stirring continued for 30 min. The reaction mixture was diluted with brine (50 mL) and extracted with dichloromethane (3×50 mL). The combined organic layers were dried with sodium sulfate and concentrated in vacuo to give a white foam-like material. This material was dissolved in dichloromethane (5 mL), treated with triethylsilane (0.8 mL) and trifluroacetic acid (0.8 mL) at 0° C. for 3.5 h, and concentrated under reduced pressure. The residue was extracted with dichloromethane (50 mL×3) which was washed with saturated aqueous sodium bicarbonate (50 mL). The combined organic layers were dried with sodium sulfate and concentrated. Chromatography with Et$_3$N:MeOH:EtOAc (4:4:92) afforded the product (302 mg, 72%).

$^1$H NMR (CDCl$_3$): δ 7.87 (d, 1H), 7.55–7.27 (m, 7H), 7.05 (d, 2H), 6.96 (d, 2H), 4.21 (s, 2H), 4.15 (t, 2H), 2.95 (t, 3H), 2.70 (m, 4H), 1.83 (m, 4H).

Part C. 3-(4-Cyanobenzyl)-2-[4-[2-(1-pyrrolidinyl)-ethoxy]phenyl]benzo[b]thiophene.

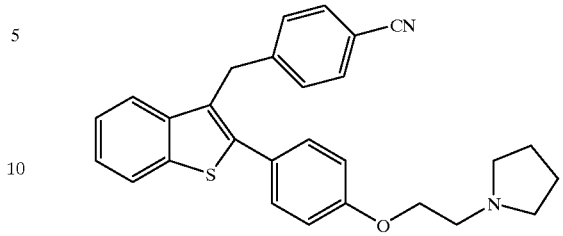

3-(4-Bromobenzyl)-2-[4-[2-(1-pyrrolidinyl)ethoxy]-phenyl]benzo[b]thiophene (300 mg, 0.61 mmol) in DMF (5 mL) was treated with CUCN (135 mg) at reflux for 3 h. The cooled reaction mixture was extracted with EtOAc (3×50 mL), with water (50 mL) washing. The combined organic layers were dried (Na$_2$SO$_4$) and concentrated under reduced pressure. Chromatography with Et$_3$N:MeOH:EtOAc (5:5:90) afforded the product (90 mg, 34%).

$^1$H NMR (CDCl$_3$): δ 7.88 (d, 1H), 7.54 (d, 1H), 7.50–7.30 (m, 8H), 6.96 (d, 2H), 4.33 (s, 2H), 4.15 (t, 2H), 2.95 (t, 2H), 2.65 (m, 4H), 1.83 (m, 4H).

Part D. 3-[4-(Aminomethyl)benzyl]-2-[4-[2-(1-pyrrolidinyl)ethoxy]phenyl]benzo[b]thiophene.

3-(4-Cyanobenzyl)-2-[4-[2-(1-pyrrolidinyl)ethoxy]-phenyl]benzo[b]thiophene (50 mg, 0.114 mmol) in THF (2 mL) was treated with lithium aluminum hydride (40 mg) at ambient temperature under argon for 1 h. The reaction was quenched with water (0.5 mL) and a solution of NaOH (1.0M, 0.5 mL). The stirring was continued for 15 min. The resulting mixture was diluted with brine (30 mL) and extracted with CH$_2$Cl$_2$ (3 x 30 mL). The combined organic layers were dried (Na$_2$SO$_4$) and concentrated under reduced pressure. Chromatography with Et$_3$N:MeOH:EtOAc (10:40:50) afforded the product (19 mg, 37%).

$^1$H NMR (CDCl$_3$): δ 7.86 (d, 1H), 7.51 (d, 1H), 7.41 (d, 2H), 7.28 (m, 2H), 7.23 (d, 2H), 7.12 (d, 2H), 6.94 (d, 2H), 4.60 (bs, 2H), 4.51 (s, 2H), 4.22 (m, 2H), 3.87 (s, 2H), 3.10 (m, 2H), 2.86 (m, 4H), 1.92 (m, 4H); FDMS m/e: 443 (M+H$^+$).

EXAMPLE 170

Preparation of 4-[(1-Ethylpyrrolidin-3-yl)oxy] phenyl 2-[4-[2-(1-Pyrrolidinyl)ethoxy]phenyl]benzo [b]thiophen-3-yl Ketone.

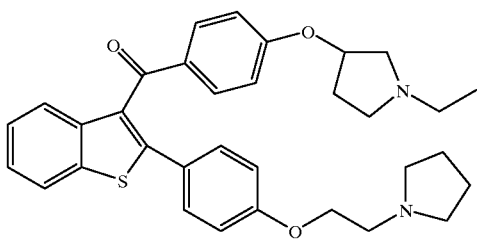

Sodium hydride (60% oil dispersion, 38 mg) was suspended in DMF (1 mL) and stirred at ambient temperature for 15 min under argon before 1-ethyl-3-pyrrolidinol (92 μL) was added. After stirring for 15 min, 4-fluorophenyl 2-[4-[2-(1-pyrrolidinyl)ethoxy]phenyl]benzo[b]thiophen-3-yl ketone (223 mg) in 1 mL of DMF was introduced and the resulting solution was stirred at ambient temperature for 4 h. The reaction mixture was diluted with brine (50 mL) and extracted with EtOAc (3×50 mL). The combined organic layers were dried (Na$_2$SO$_4$) and concentrated under reduced pressure. Chromatography with Et₃N:MeOH:EtOAc (5:5:90) afforded the product as a colorless oil (171 mg, 63%).

¹H NMR (CDCl₃): δ 7.85 (m, 1H), 7.75 (d, 2H), 7.65 (m, 1H), 7.35 (d, 2H), 7.32 (m, 2H), 6.78 (d, 2H), 6.71 (d, 2H), 4.80 (m, 1H), 4.03 (t, 2H), 2.85 (t, 2H), 2.80 (m, 2H), 2.60 (m, 4H), 2.50 (m, 4H), 2.28 (m, 1H), 1.92 (m, 1H), 1.08 (t, 3H).

EXAMPLES 171–173

The following compounds were prepared by the procedure described for Example 170, but using 1-ethylpiperidin-3-ol, 1-methylpiperidine-2-methanol, and 2-piperidinemethanol, respectively.

EXAMPLE 171

4-[(1-Ethylpiperidin-3-yl)oxy]phenyl 2-[4-[2-(1-Pyrrolidinyl)ethoxy]phenyl]benzo[b]thiophen-3-yl Ketone.
FDMS m/e: 555 (M+H⁺).

EXAMPLE 172

4-[(1-Methylpiperidin-2-yl)methoxy]-phenyl 2-[4-[2-(1-Pyrrolidinyl)ethoxy3phenyl]benzo[b]-thiophen-3-yl Ketone.
FDMS m/e: 555 (M+H⁺).

EXAMPLE 173

4-[(2-Piperidinyl)methoxy3phenyl 2-[4-[2-(1-Pyrrolidinyl)ethoxy]phenyl]benzo b]thiophen-3-yl Ketone.
FDMS m/e: 541 (M+H⁺).

EXAMPLE 174

Preparation of 4-[(1-Ethylpyrrolidin-3-yl)oxy] benzyl-2-[4-[2-(1-pyrrolidinyl)ethoxy]phenyl]benzo [b]-thiophene.

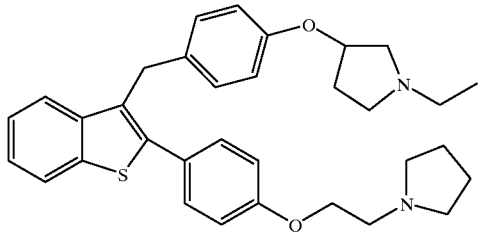

The ketone of Example 170 (112 mg, 0.20 mmol) in THF (3 mL) was treated with lithium aluminum hydride (25 mg) at 0° C. for 1 h, then quenched with water (1 mL) and sodium hydroxide (5.0M, 1 mL). Stirring continued for 20 min. The reaction mixture was diluted with brine (50 mL) and extracted with dichloromethane (3×50 mL). The combined organic layers were dried with sodium sulfate and concentrated in vacuo to give a white foam-like material. This material was dissolved in dichloromethane (5 mL), treated with triethylsilane (0.25 mL) and trifluroacetic acid (0.20 mL) at 0° C. for 1 h, and then concentrated under reduced pressure. The residue was extracted with dichloromethane (50 mL×3) which was washed with saturated aqueous sodium bicarbonate (50 mL). The combined organic layers were dried over sodium sulfate and concentrated. Chromatography with Et₃N:MeOH:EtOAc (5:5:90) afforded the product as a colorless oil (87 mg, 78%).

¹H NMR (CDCl₃): δ 7.81 (m, 1H), 7.50 (m, 1H), 7.40 (d, 2H), 7.29 (m, 2H), 7.02 (d, 2H), 6.92 (d, 2H), 6.78 (d, 2H), 4.78 (m, 1H), 4.20 (s, 2H), 4.13 (t, 2H), 2.95 (t, 3H), 2.88 (m, 1H), 2.77 (m, 1H), 2.63 (m, 4H), 2.52 (m, 4H), 2.27 (m, 1H), 1.97 (m, 1H), 1.83 (m, 4H), 1.13 (t, 3H).

EXAMPLES 175–177

The following compounds were prepared from the corresponding ketones of Examples 171–173 by using the procedure described for Example 174.

EXAMPLE 175:

4-[(1-Ethylpiperidin-3-yl)oxy]benzyl-2-[4-[2-(1-pyrrolidinyl)ethoxy]phenyl]benzo[b]thiophene.
FDMS m/e: 541 (M+H⁺).

EXAMPLE 176:

4–1(1-Methylpiperidin-2-yl)methoxy]-benzyl-2-[4-[2-(1-pyrrolidinyl)ethoxy]phenyl]benzo[b]-thiophene.
FDMS m/e: 541 (M+H⁺).

EXAMPLE 177:

4-[(2-Piperidinyl)methoxy]benzyl-2-[4-[2-(1-pyrrolidinyl)ethoxy]phenyl]benzo[b]thiophene.
FDMS m/e: 527 (M+H⁺).

EXAMPLE 178

Preparation of 6-Hydroxy-2-[4-[2-[2-(S)-(hydroxymethyl)pyrrolidin-1-yl]ethoxy]phenyl]-benzo[b]thiophen-3-yl 3-Methoxy-4-[(4-morpholinyl)-methyl]phenyl Ketone Dioxalate.

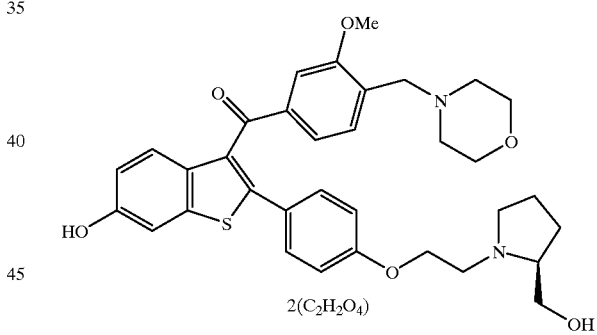

Part A. 2-(4-Bromophenyl)ethanol Triisopropylsilyl Ether.

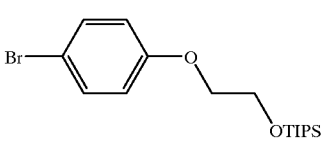

Triisopropylsilyl trifluoromethanesulfonate (24.4 mL, 90.7 mmol) was added to a stirred solution of 2-(4-bromophenoxy)ethanol (15.1 g, 69.8 mmol) and anhydrous triethylamine (19.4 mL, 140 mmol) in anhydrous CH₂Cl₂ (30 mL) at 0° C. under nitrogen atmosphere. The resultant mixture was stirred for 1 h. The mixture was washed with saturated NaHCO₃ (25 mL), extracted with EtOAc (3×75 mL), dried over MgSO₄, filtered, concentrated, and chromatographed on silica (10% CH₂Cl₂ in hexanes) to give 23.4 g (90%) of the silyl ether as a colorless liquid.

IR (thin film) 2944, 1489 cm$^{-1}$; FDMS mle 372 (M$^+$, $^{79}$Br) and 374 (M$^+$, $^{81}$Br). Anal. Calcd. for C$_{17}$H$_{29}$BrO$_2$Si: C, 54.68; H, 7.83. Found: C, 54.97; H, 7.55.

Part B. 6-Benzyloxy-2-[4-[2-(hydroxy)ethoxy]phenyl]-benzo[b]thiophen-3-yl 3-Methoxy-4-[(4-morpholinyl)-methyl]phenyl Ketone.

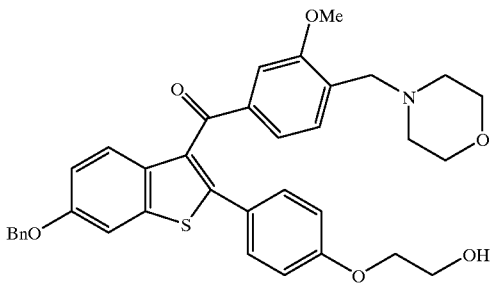

The above silyl ether (2.71 g, 7.26 mmol) was added to a stirred suspension of magnesium ribbons (164 mg, 6.77 mmol) in anhydrous THF (4 mL) under argon atmosphere, followed by the addition of a small iodine chip. The resultant mixture was heated in an oil bath at 60–65° C. for 1.5 h to form a homogeneous Grignard solution. The Grignard solution was cooled to room temperature and diluted with anhydrous THF (10 mL) before it was added to a stirred solution of the benzothiophene of Example 49, Part C, (2.50 g, 4.84 mmol) in anhydrous THF (10 mL) at 0° C. under argon atmosphere. The resultant mixture was stirred at 0° C. for 1.5 h, then quenched with saturated aqueous NH$_4$Cl (15 mL). After -extraction with EtOAc (70 mL×2), the combined organic layers were dried over MgSO$_4$, filtered, and concentrated to give a gummy residue which was dissolved in anhydrous THF (25 mL) and treated with tetrabutylammonium fluoride (5.80 mL, 1M in THF) at room temperature under nitrogen atmosphere. After stirring for 1 h, the mixture was concentrated under vacuum; the residue was chromatographed on silica [gradient 0–30% MeOH/Et$_3$N (2/1) in EtOAc] to give 2.61 g (88%) of the keto-alcohol as a foam. IR (neat) 3426 (br), 1646, 1605 cm$^{-1}$; FDMS m/e 609 (M$^+$); Anal. Calcd. for C$_{36}$H$_{35}$NO$_6$S: C, 70.91; H, 5.79; N, 2.30. Found: C, 70.63; H, 5.65; N, 2.04.

Part C. 6-Benzyloxy-2-[4-[2-[2-(S)-(hydroxymethyl)-pyrrolidin-1-yl]ethoxy]phenyl3benzo[b]thiophen-3-yl 3-Methoxy-4-[(4-morpholinyl)methyl]phenyl Ketone.

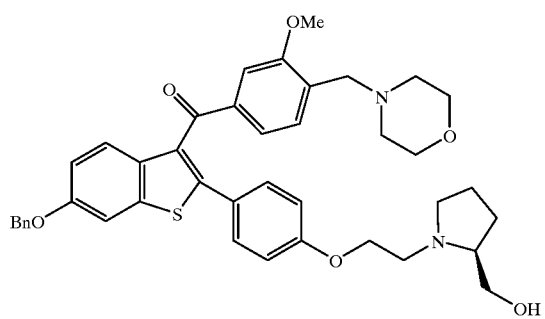

Methanesulfonyl chloride (0.210 mL, 2.71 mmol) was added to a stirred solution of the above keto-alcohol (1.27 g, 2.08 nmol) in anhydrous pyridine (4 mL) at 0° C. under nitrogen atmosphere, the reaction mixture was allowed to stir at 0° C. for 40 min. (S)-Prolinol (0.616 mL, 6.24 mmol) was added and the resultant mixture was heated at 85° C. for 2 h. At room temperature, the mixture was diluted with EtOAc (80 mL), washed with brine (30 mL), dried over MgSO$_4$, filtered, concentrated, and chromatographed on silica [gradient 0–15% EtOH/Et$_3$N (2/1) in EtOAc] to give 448 mg (31%) of the substituted prolinol as a foam.

IR (neat) 3426 (br), 1646, 1605 cm$^{-1}$; FDMS m/e 693 (M$^+$+1); Anal. Calcd. for C$_{41}$H$_{44}$N$_2$O$_6$S: C, 71.07; H, 6.40; N, 4.04. Found: C, 70.77; H, 6.28; N, 3.93.

Part D. 6-Hydroxy-2-[4-[2-[2-(S)-(hydroxymethyl)-pyrrolidin-1-yl]ethyloxy]phenyl]benzo[b]thiophen-3-yl 3-Methoxy-4-[(4-morpholinyl)methyl]phenyl Ketone Dioxalate.

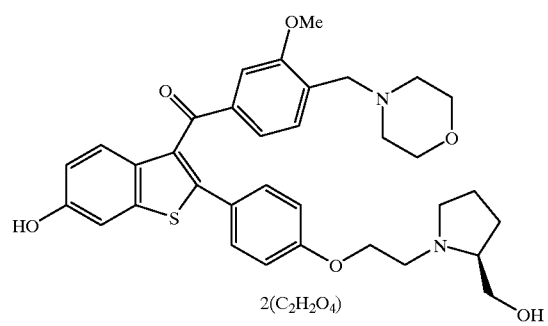

To a stirred solution of the above benzyloxy compound (400 mg, 0.577 mmol) in THF (16 mL) under nitrogen atmosphere were sequentially added 10% Pd/C (400 mg) and 25% aqueous HCO$_2$NH$_4$ (2 mL). The resultant mixture was stirred under a balloon nitrogen atmosphere for 5 h. After filtration, the filtrate was diluted with EtOAc (50 mL), washed with half-saturated NaCl (15 mL), dried over MgSO$_4$, filtered, concentrated, and chromatographed on silica [gradient 0–30% EtOH/Et$_3$N (2/1) in EtOAc] to give 260 mg (75%) of the corresponding hydroxy-benzothiophene as a foam.

A solution of oxalic acid (73.2 mg, 0.812 mmol) in EtOAc (6 mL) was added dropwise to a stirred solution of the hydroxy-benzothiophene (245 mg, 0.406 mmol) in EtOAc (4 mL). The resultant white suspension was filtered and the white solid was dried at 60° C. under vacuum to provide 275 mg (87%) of the title salt as a yellowish solid.

Free base: IR (neat) 3224 (br), 1642, 1605 cm$^{-1}$; FDMS m/e 603 (M$^+$+1); Anal. Calcd. for C$_{34}$H$_{38}$N$_2$O$_6$S: C, 67.75; H, 6.35; N, 4.65. Found: C, 67.97; H, 6.61; N, 4.82. Oxalate salt: IR (KBr) 3400–2500 (br), 1719, 1703, 1639, 1605 cm$^{-1}$; FDMS m/e 602 (M$^+$−2[C$_2$H$_2$O$_4$]); Anal. Calcd. for C$_{34}$H$_{38}$N$_2$O$_6$S·1.3(C$_2$H$_2$O$_4$): C, 61.07; H, 5.69; N, 3.89. Found: C, 61.06; H, 5.42; N, 3.86.

EXAMPLE 179

Preparation of 6-Hydroxy-2-[4-[2-[2-(S)-(hydroxymethyl)pyrrolidin-1-yl]ethoxy]phenyl]-3-[3-methoxy-4-[(4-morpholinyl)methyl]benzyl]benzo[b]thiophene Dioxalate.

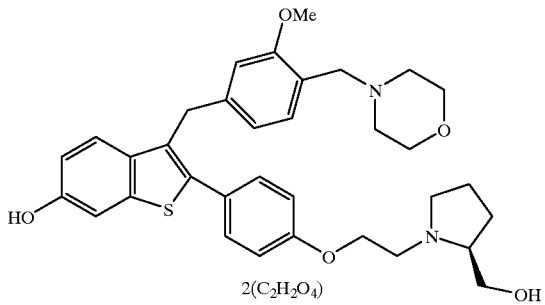

Part A. 6-Benzyloxy-2-[4-[2-[2-(S)-(hydroxymethyl)-pyrrolidin-1-yl]ethyloxy]phenyl3-3-[3-methoxy-4-[(4-morpholinyl)methyl]benzyl]benzo[b]thiophene.

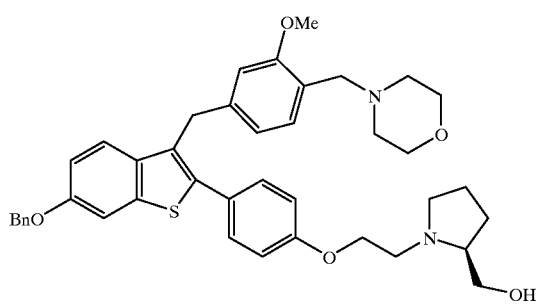

DIBAL-H (1.66 mL, 1M in toluene) was added to a stirred solution of the ketone of Example 178, Part C (460 mg, 0.664 mmol) in anhydrous $CH_2Cl_2$ (4 mL) at 0° C. under nitrogen atmosphere, and the resultant solution was stirred at 0° C. for 50 min. The reaction mixture was treated sequentially with MeOH (0.5 mL) and saturated aqueous Rochelle's salt solution (10 mL), and the two-layered solution was stirred vigorously at room temperature for 1 h. After extraction with EtOAc (50 mL), the organic layer was dried over $MgSO_4$, filtered, and concentrated to yield the corresponding diol.

The above diol was dissolved in anhydrous $CH_2Cl_2$ (5 mL) and cooled down to 0 OC before it was sequentially treated with $Et_3SiH$ (0.743 mL, 4.65 mmol) and TFA (0.511 mL, 6.64 mmol). The resultant mixture was stirred at 0° C. for 1 h. After cautious treatment with saturated aqueous $NaHCO_3$ to neutralize TFA, the mixture was allowed to warm to room temperature where it was extracted with EtOAc (20 mL×2). The combined organic layers were dried over $MgSO_4$, filtered, concentrated, and chromatographed on silica [gradient 0–15% $EtOH/Et_3N$ (2/1) in EtOAc] to give 387 mg (86%) of the benzyl compound as a foam.

IR (neat) 3401 (br), 1609 $cm^{-1}$; FDMS m/e 679 ($M^+$+1); Anal. Calcd. for $C_4lH_{46}N_2O_5S$: C, 72.54; H, 6.83; N, 4.13. Found: C, 72.44; H, 6.64; N, 4.00.

B. 6-Hydroxy-2-[4-[2-[2-(S)-(hydroxymethyl)-pyrrolidin-1-yl]ethoxy3phenyl]-3-[3-methoxy-4-[(4-morpholinyl)methyl]benzyl]benzo[b]thiophene Dioxalate.

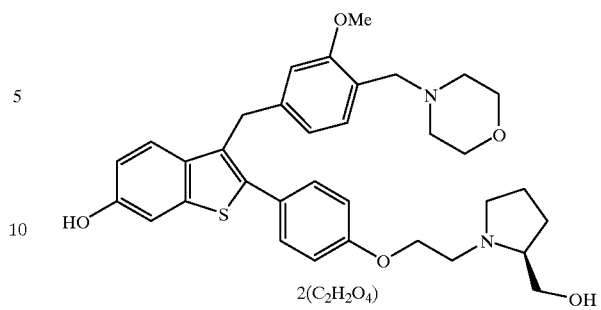

Following the procedure described in Example 178, Part D, the salt of the hydroxybenzothiazole was obtained from the above benzyloxybenzothiazole as a white solid in an overall 67% yield.

IR (KBr) 3400–2500 (br), 1721, 1610 $cm^{-1}$; FDMS m/e 588 ($M^+$–$2[C_2H_2O_4]$); Anal. Calcd. for $C_{34}H_{40}N_2O_5S\cdot1.7$ ($C_2H_2O_4$): C, 60.55; H, 5.90; N, 3.78. Found: C, 60.66; H, 5.69; N, 3.78.

EXAMPLE 180

Preparation of 6-Hydroxy-2-[4-[2-[2-(S)-(hydroxymethyl)pyrrolidin-1-yl]ethoxy]phenyl]benzo[b]thiophen-3-yl 3-Methoxy-4-[(1-pyrrolidinyl)methyl]phenyl Ketone.

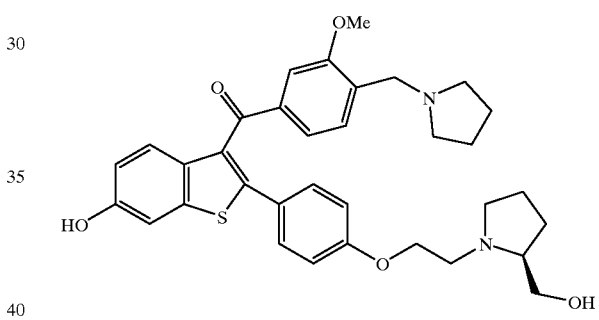

Part A. 6-Benzyloxy-2-[4-[2-(hydroxy)ethoxy]phenyl]-benzo[b]thiophen-3-yl 3-Methoxy-4-[(1-pyrrolidinyl)-methyl]phenyl Ketone.

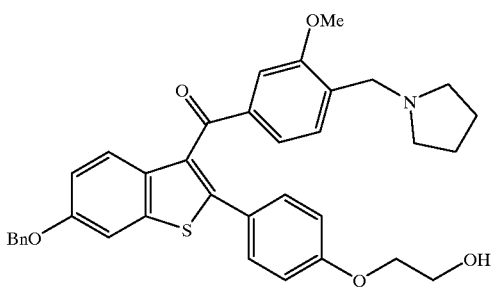

Following the procedure as described in Example 178, Part B, the ketone was obtained from the bromide of Example 178, Part A, and the benzothiophene of Example 41, Part C, as a foam in an overall 73% yield.

IR (neat) 3364 (br), 1651, 1605 $cm^{-1}$; FDMS m/e 593 ($M^+$); Anal. Calcd. for $C_{36}H_{35}NO_5S$: C, 72.83; H, 5.94; N, 2.36. Found: C, 72.68; H, 5.89; N, 2.44.

Part B. 6-Benzyloxy-2-[4-[2-[2-(S)-(hydroxymethyl)-pyrrolidin-1-yl]ethoxy]phenyl]benzo[b]thiophen-3-yl 3-Methoxy-4-1(1-pyrrolidinyl)methyl]phenyl Ketone.

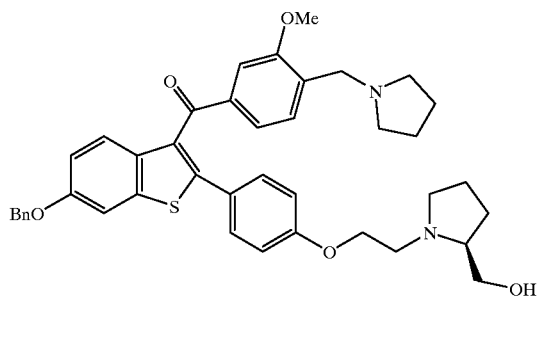

Anhydrous triethylamine (1.52 mL, 10.9 mmol) and methanesulfonyl chloride (0.48 mL, 6.20 mmol) were sequentially added to a stirred solution of the above alcohol (2.16 g, 3.64 mmol) in anhydrous pyridine (6 mL) at 0° C. under a nitrogen atmosphere. The reaction mixture was allowed to stir at 0° C. for 2 h. (S)-Prolinol (2.16 mL, 21.8 mmol) was added and the resultant mixture was heated at 70° C. for 3 h. After dilution with EtOAc (100 mL) and 50 mL distilled water, the mixture was extracted with EtOAc (2×50 mL). The combined organics were washed with water (2×50 mL) followed by washing with saturated NaCl (2×25 mL), dried over MgSO$_4$, filtered, concentrated, and chromatographed on silica (10% Et$_3$N in hexanes and 20% 2:1 EtOH:Et$_3$N 30% THF in 50% EtOAc) to give 1.17 g (47%) of the substituted prolinol as a yellow foam.

IR (thin film) 3530 (br), 2965, 1646, 1607 cm$^{-1}$; FDMS m/e 677 (M$^+$+1). Anal. Calcd. for C$_{41}$H$_{44}$N$_2$O$_5$S: C, 72.75; H, 6.55; N, 4.14. Found: C, 72.47; H, 6.56; N, 4.14.

Part C. 6-Hydroxy-2-[4-[2-[2-(S)-(hydroxymethyl)-pyrrolidin-1-yl]ethoxy]phenyl]benzo[b]thiophen-3-yl 3-Methoxy-4-[(1-pyrrolidinyl)methyl]phenyl Ketone.

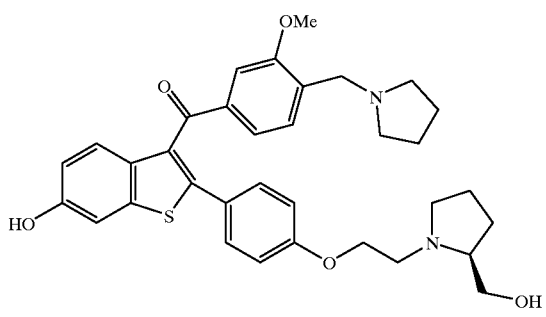

Following the debenzylation procedure described in Example 178, Part D, the hydroxy-benzothiophene was obtained from the above benzyloxy-benzothiophene. Column chromatography on silica [gradient 0–2% EtOH/Et$_3$N (2/1) 20% EtOAc in hexanes; then 2–10% EtOH/Et$_3$N (2/1) 10–20% THF in hexanes] gave 57 mg (15%) of the product as a yellow solid.

IR (thin film) 3450 (br), 2962, 1647, 1605 cm-$^1$; FDMS m/e 587 (M$^+$+1).

EXAMPLE 181

Preparation of 6-Hydroxy-2-[4-[2-[2-(S)-(hydroxymethyl)pyrrolidin-1-yl]ethoxy]phenyl]-3-[3-methoxy-4-[(1-pyrrolidinyl)methyl]benzyl] benzo[b]thiophene Dioxalate.

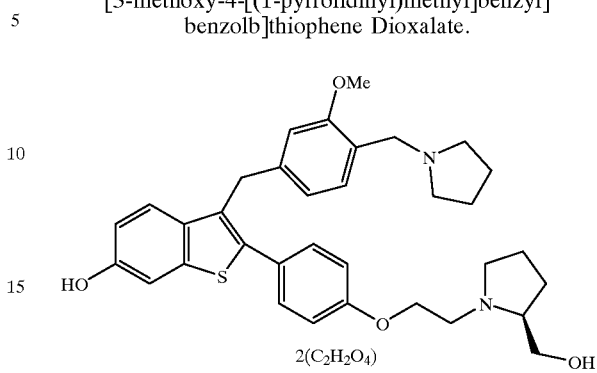

Part A. 6-Benzyloxy-2-[4-[2-[2-(S)-(hydroxymethyl)-pyrrolidin-1-yl]ethoxy]phenyl]-3-[3-methoxy-4-[(1-pyrrolidinyl)methyl]benzyl]benzo[b]thiophene.

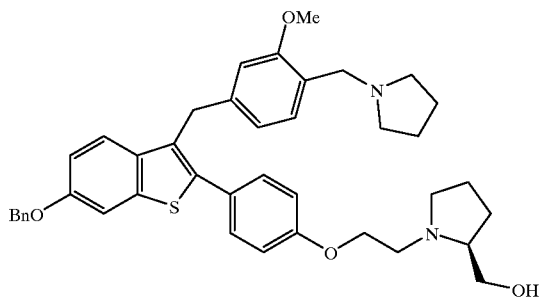

Following the procedure described in Example 179, Part A, the benzyl compound was obtained from the ketone of Example 180, Part B,. Column chromatography on silica [gradient 0–5% EtOH/Et$_3$N (2/1) 10–25% THF in hexanes] gave 373 mg (54%) of the product as an off-white foam.
IR (thin film) 3520 (br), 2963, 1609 cm$^{-1}$; FDMS m/e 663 (M$^+$+1). Anal. Calcd. for C$_{41}$H$_{46}$N$_2$O$_4$S: C, 74.29; H, 6.99; N, 4.23. Found: C, 74.49; H, 6.86; N, 4.29.
Part B. 6-Hydroxy-2-[4-[2-[2-(S)-(hydroxymethyl)-pyrrolidin-1-yl]ethoxy3phenyl]-3-[3-methoxy-4-[(1-pyrrolidinyl)methyl]benzyl]benzo b]thiophene.

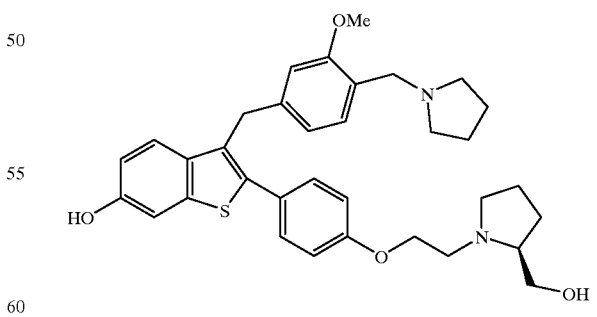

Following the debenzylation procedure described in Example 178, Part D, the hydroxy-benzothiophene compound was obtained from the above benzyloxy-benzothiophene. Column chromatography on silica [gradient 0–10% EtOH/Et$_3$N (2/1) 30–60% THF in hexanes] gave 269 mg (89%) of the product as an off-white foam.

IR (thin film) 3021 (br), 2967, 1610 cm$^{-1}$; FDMS m/e 573 (M$^+$+1). Anal. Calcd. for $C_{34}H_{40}N_2O_4S$: C, 71.30; H, 7.04; N, 4.89. Found: C, 71.23; H, 7.13; N, 4.82.

C. 6-Hydroxy-2-[4-12-[2-(S)-(hydroxymethyl)-pyrrolidin-1-yl]ethoxy]phenyl]-3-[3-methoxy-4-1(1-pyrrolidinyl) methyl]benzyl]benzo[b]thiophene Dioxalate.

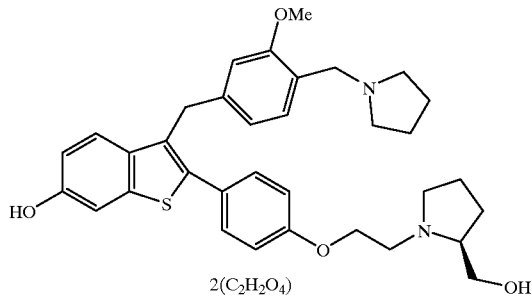

Following the procedure described in Example 178, Part D, the salt was obtained from the above compound as a white solid in a 70% yield.

IR (KBr) 3380 (br), 3300–2200 (br), 1610 (br) cm$^{-1}$; Anal. Calcd. for $C_{34}H_{40}N_2O_4S \cdot 0.90(C_2H_2O_4)$: C, 65.77; H, 6.44; N, 4.28. Found: C, 66.09; H, 6.05; N, 4.32.

EXAMPLE 182

Preparation of 6-Fluoro-2-[4-[2-(1-pyrrolidinyl)-ethoxy]phenyl3benzo[b]thiophen-3-yl 3-Methoxy-4-[(1-pyrrolidinyl)methyl]phenyl Ketone Dioxalate.

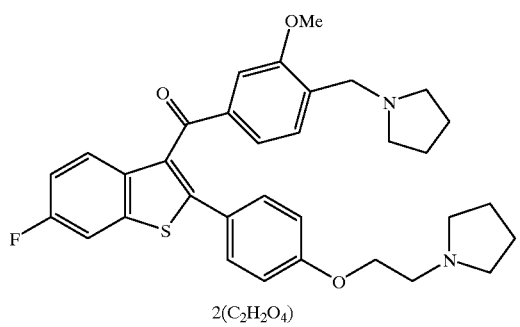

Part A. 6-Fluoro-2-(4-hydroxyphenyl)benzo[b]thiophene.

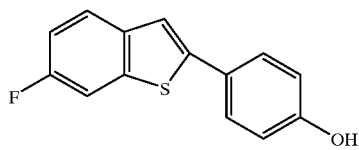

AlCl$_3$ (1.76 g, 13.2 mmol) was added to a stirred solution of (1.14 g, 4.41 mmol) in anhydrous CH$_2$Cl$_2$ (22 mL) at room temperature under nitrogen atmosphere. The resultant suspension was stirred for 3–5 min before it was treated with EtSH (1.30 mL, 17.6 mmol), and the mixture was stirred for an additional 60 min. After dilution with THF (20 mL), the mixture was cooled to 0° C. and treated with saturated aqueous Rochelle's salt solution (25 mL). The two-layered solution was stirred vigorously for 40 min. The organic layer was separated and the aqueous layer was extracted with THF (25 mL). The combined organic layers were washed with brine (15 mL), dried over MgSO$_4$, filtered, concentrated, and chromatographed on silica (CH$_2$Cl$_2$) to give a 660 mg (61%) of the substituted phenol as a white solid, which was recrystalized from CH$_2$Cl$_2$/hexane.

IR (KBr) 3402 (br), 1610 cm$^{-1}$; FDMS m/e 244 (M$^+$).

Part B. 6-Fluoro-2-[4-[2-(1-pyrrolidinyl)ethoxy]-phenyl]benzo[b]thiophene.

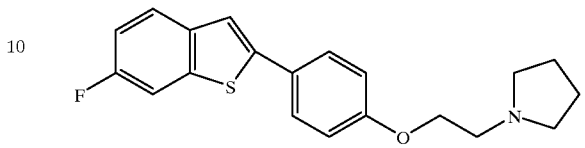

Cs$_2$CO$_3$ (1.87 g, 5.73 mmol) was added to a stirred solution of the above phenol (0.560 g, 2.29 mmol) and N-(2-chloroethyl)pyrrolidine hydrochloride (0.467 g, 2.75 mmol) in anhydrous DMF (5 mL), the resultant suspension was heated in an oil bath at 70° C. for 7 h. At room temperature, the mixture was diluted with water (10 mL), and the suspension was stirred for 10 min. After filtration and vacuum drying, 712 mg (91%) of the ether was obtained as a solid.

IR (KBr) 1604 cm$^{-1}$; FDMS m/e 341 (M$^+$); Anal. Calcd. for $C_{20}H_{20}FNOS$: C,70.35; H, 5.90; N, 4.10. Found: C,70.21; H, 5.80; N, 3.84.

Part C. 6-Fluoro-2-[4-[2-(1-pyrrolidinyl)ethoxy]-phenyl]benzo[b]thiophen-3-yl 3-Methoxy-4-[(1-pyrrolidinyl)methyl]phenyl Ketone.

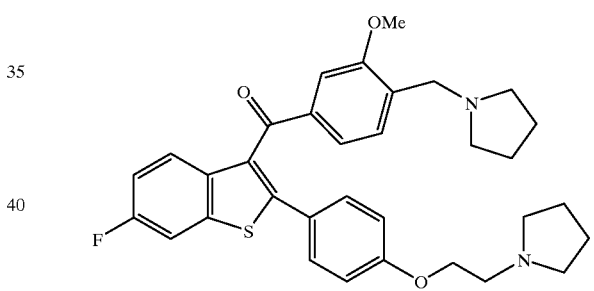

Oxalyl chloride (1.26 mL, 14.4 mmol) was added to a stirred suspension of the acid of Example 49, Part B, (451 mg, 1.44 mmol) in anhydrous CH$_2$Cl$_2$ (5 mL), followed by the addition of 2 drops of DMF. The suspension was stirred at room temperature under nitrogen atmosphere for 6 h, then it was concentrated to dryness under vacuum.

To the crude benzoyl chloride suspended in anhydrous CH$_2$Cl$_2$ (5 mL) was added the ether of Part B above, (350 mg, 1.03 mmol), followed by the addition of TiCl$_4$ (0.566 mL, 5.15 mmol). The mixture was stirred at room temperature for 15 h. Then the mixture was cooled to 0° C. before it was treated sequentially with THF (20 mL) and 2N LiCH (25 mL). The two-layered solution was stirred vigorously for 20 min. The organic layer was separated and the aqueous layer was extracted with EtOAc (25 mL). The combined organic layers were washed with brine (15 mL), dried over MgSO$_4$, filtered, concentrated, and chromatographed on silica (gradient 0–10% NEt3 in EtOAc) to give a 280 mg (65%) of the ketone as a foam.

Part D. 6-Fluoro-2-[4-[2-(1-pyrrolidinyl)ethoxy]-phenyl]benzo[b]thiophen-3-yl 3-Methoxy-4-[(1-pyrrolidinyl)methyl]phenyl Ketone Dioxalate.

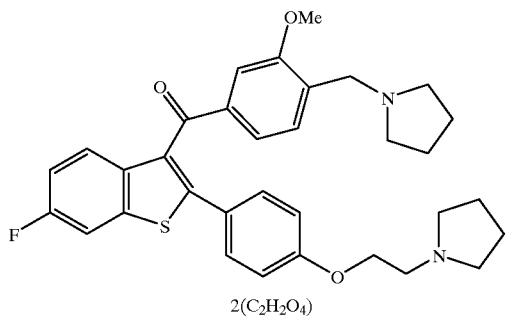

2(C₂H₂O₄)

Following the procedure described in Example 178, Part D, the salt was obtained from the above ketone as a yellowish solid in an 86% yield.
IR (KBr) 3400–2500 (br), 1718, 1640, 1606 cm$^{-1}$; Anal. Calcd. for $C_{33}H_{35}FN_2O_3S \cdot 2(C_2H_2O_4)$: C,60.15; H, 5.32; N, 3.79. Found: C,60.36; H, 5.29; N, 3.52.

EXAMPLE 183

Preparation of 6-Fluoro-3-[3-methoxy-4-[(1-pyrrolidinyl)methyl]benzyl]-2-[4-[2-(1-pyrrolidinyl)-ethoxy]phenyl]benzo[b]thiophene Dioxalate.

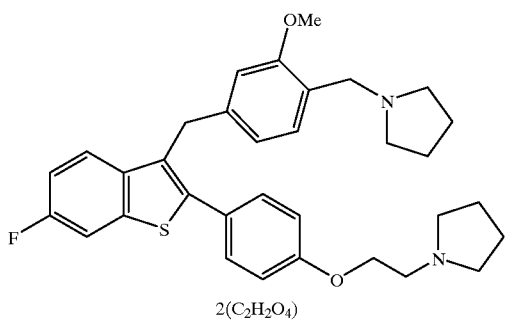

2(C₂H₂O₄)

Part A. 6-Fluoro-3-[3-methoxy-4-[(1-pyrrolidinyl)-methyl]benzyl]-2-[4-[2-(1-pyrrolidinyl)ethoxy]phenyl]-benzo[b]thiophene.

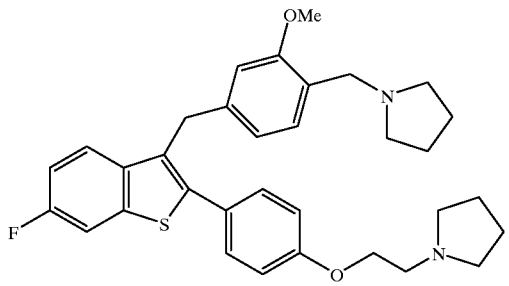

Following the procedure described in Example 179, Part A, the benzyl compound was obtained from the ketone of Example 182, Part C, as a foam in an overall 77% yield.
IR (neat) 1606 cm$^{-1}$; FDMS m/e 545 (M$^+$+1).
Part B. 6-Fluoro-3-[3-methoxy-4-[(1-pyrrolidinyl)-methyl]benzyl]-2-[4-[2-(1-pyrrolidinyl)ethoxy]phenyl]-benzo[b]thiophene Dioxalate.

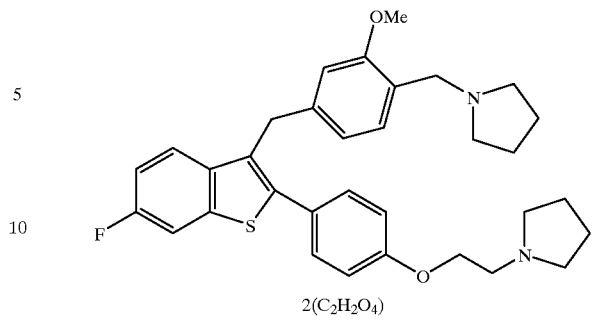

2(C₂H₂O₄)

Following the procedure described in Example 178, Part D, the salt was obtained from the above compound as a white solid in a 96% yield.
IR (KBr) 3400–2500 (br), 1718, 1610 cm$^{-1}$; FDMS m/e 545 (M$^+$+1–2[C₂H₂O₄]) ; Anal. Calcd. for $C_{33}H_{37}FN_2O_2S \cdot 1.7$ (C₂H₂O₄) : C,62.66; H, 5.84; N, 4.01. Found: C,62.65; H, 5.70; N, 3.74.

EXAMPLE 184

Preparation of 3-Methoxy-4-[(4-morpholinyl) methyl]-phenyl 2-[4-[2-(1-Pyrrolidinyl)ethyloxy] phenyl]-benzo[b]thiophen-3-yl Ketone Dioxalate.

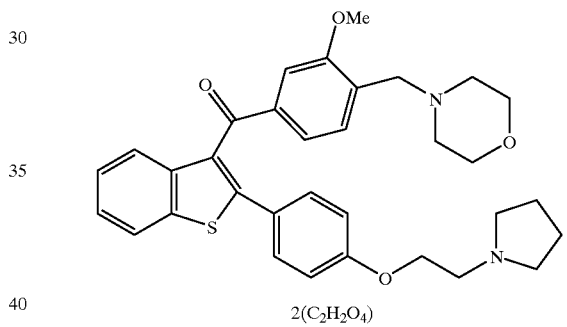

2(C₂H₂O₄)

Part A. 2-(Dimethylamino)benzo[b]thiophen-$^3$-yl 3-Methoxy-4-1(4-morpholinyl)methyl]phenyl Ketone.

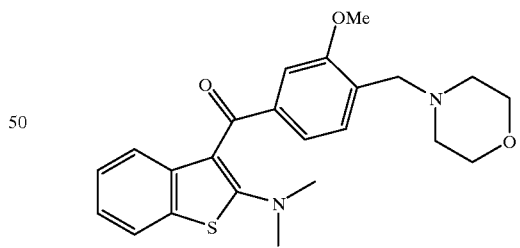

Following the procedure of Example 49, Part C, except using anhydrous dichloromethane as the solvent to prepare the benzoyl chloride, the amino-ketone was obtained from 2-dimethylaminobenzo[b]thiophene [Vesterager et al., Tetrahedron, (1973), 29, 321–329] and the acid of Example 49, Part B. Column chromatography on silica [gradient 0–2% Et₃N 100–98% EtOAc] gave 7.99 g (77%) of the amino-ketone as an yellow foam.
IR (neat) 2953 (br), 1636 cm$^{-1}$; FDMS m/e 410 (M$^+$); Anal. Calcd. for $C_{23}H_{26}N_2O_3S$: C, 67.29; H, 6.38; N, 6.82. Found: C, 67.09; H, 6.36; N, 6.60.

Part B. 3-Methoxy-4-[(4-morpholinyl)methyl]phenyl 2-[4-[2-(1-Pyrrolidinyl)ethoxy]phenyl]benzo[b]thiophen-3-yl Ketone.

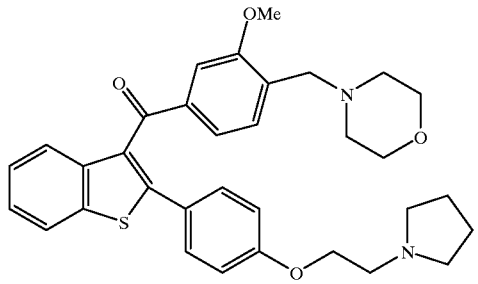

Following the procedure of Example 49, Part D, the ketone was obtained from the above amino-ketone and 1-[2-(4-bromophenoxy)ethyl]pyrrolidine. Column chromatography on silica [100% EtOAc, then gradient 5–10% EtOH/Et$_3$N (2/1) 95–90% EtOAc] gave 1.30 g (96%) of the ketone as a yellow foam.

IR (neat) 2957, 1646, 1606 cm$^{-1}$; Anal. Calcd. for C$_{33}$H$_{36}$N$_2$O$_4$S: C, 71.20; H, 6.52; N, 5.03. Found: C, 71.28; H, 6.61; N, 5.24.

Part C. 3-Methoxy-4-[(4-morpholinyl)methyl]phenyl 2-[4-[2-(1-Pyrrolidinyl)ethyloxy]phenyl]benzo[b]thiophen-3-yl Ketone Dioxalate.

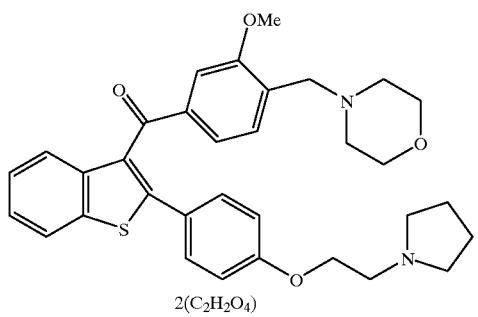

Following the procedure described in Example 178, Part D, the salt was obtained from the above diamine as a yellow solid in a 96% yield.

IR (KBr) 2850–2200 (br), 1723, 1644, 1606 cm$^{-1}$; FDMS m/e 557 (M$^+$+1–2[C$_2$H$_2$O$_4$]); Anal. Calcd. for C$_{33}$H$_{36}$N$_2$O$_4$S·2.0(C$_2$H$_2$O$_4$): C, 60.32; H, 5.47; N, 3.80. Found: C, 60.53; H, 5.48; N, 3.66.

EXAMPLE 185

Preparation of 3-[3-Methoxy-4-[(4-morpholinyl)methyl]-benzyl]-2-[4-[2-(1-pyrrolidinyl)ethoxy]phenyl]-benzo[b]thiophene Dioxalate.

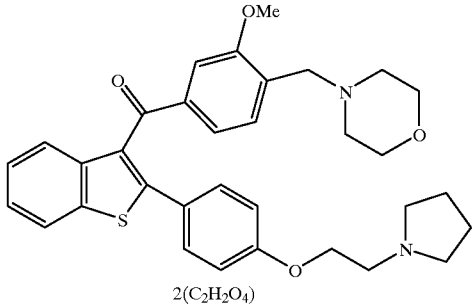

Part A. 3-[3-Methoxy-4-1(4-morpholinyl)methyl]-benzyl]-2-[4-[2-(1-pyrrolidinyl)ethoxy]phenyl]-benzo[b]thiophene.

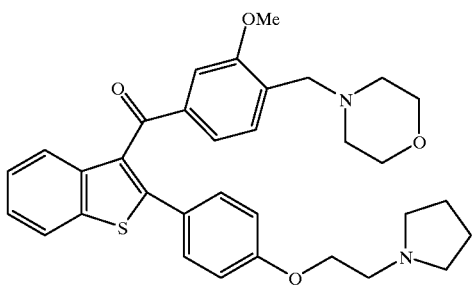

Following the procedure of Example 179, Part A, the benzyl compound was obtained from the ketone of Example 184, Part B. Column chromatography on silica [gradient 0–5% Et$_3$N in EtOAc] gave 553 mg (95%) of the product as a colorless oil.

IR (thin film) 2964, 1609 cm$^{-1}$; FDMS m/e 542 (M$^+$); Anal. Calcd. for C$_{33}$H$_{38}$N$_2$O$_3$S: C, 73.03; H, 7.05; N, 5.16. Found: C, 73.29; H, 6.85; N, 4.97.

Part B. 3-[3-Methoxy-4-[(4-morpholinyl)methyl]-benzyl3-2-[4-[2-(1-pyrrolidinyl)ethoxy]phenyl]-benzo[b]thiophene Dioxalate.

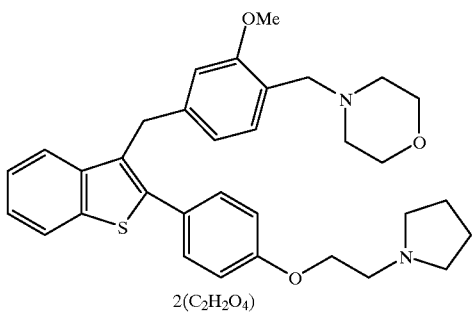

Following the procedure described in Example 179, Part A, the salt was obtained from the above diamine as a white solid in a 98% yield.

IR (KBr) 3450 (br), 2850–2200 (br), 1730, 1611 cm$^{-1}$; FDMS mle 588 (M$^+$+1–2[C$_2$H$_2$O$_4$]); Anal. Calcd. for C$_{33}$H$_{38}$N$_2$O$_3$S·2(C$_2$H$_2$O$_4$): C, 61.48; H, 5.86; N, 3.88. Found: C, 61.37; H, 5.91; N, 3.78.

EXAMPLE 186

Preparation of 3-Methoxy-4-[(4-morpholinyl)-methyl]phenyl 2-[4-[2-(1-Pyrrolidinyl)ethyl]phenyl]-benzo[b]thiophen-3-yl Ketone Dioxalate.

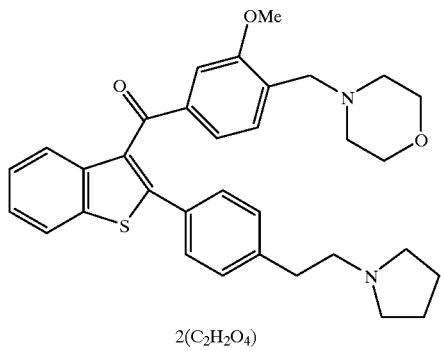

2(C$_2$H$_2$O$_4$)

Part A. 3-Methoxy-4-[(4-morpholinyl)methyl3phenyl 2-[4-[2-(1-Pyrrolidinyl)ethyl]phenyl]benzo[b]thiophen-3-yl Ketone.

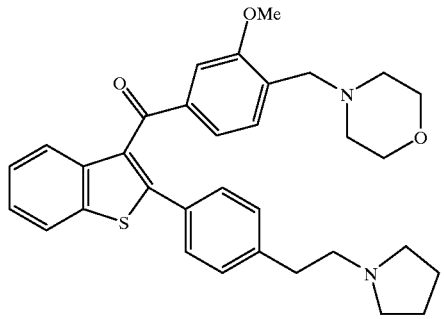

Following the procedure described in Example 184, Part B, the ketone was obtained from the amino-ketone of Example 184, Part A and the aryl bromide of Example 39, part A. Column chromatography on silica [gradient 0–25% EtOH 0–3% Et$_3$N in EtOAc] gave 1.22 g (92%) of the diamine as a orange foam.

IR (KBr) 3440 (br), 2952, 1651, 1600 cm$^{-1}$; FDMS m/e 540 (M$^+$).

B. 3-Methoxy-4-[(4-morpholinyl)methyl]phenyl 2-[4-[2-(1-Pyrrolidinyl)ethyl]phenyl]benzo[b]thiophen-3-yl Ketone Dioxalate.

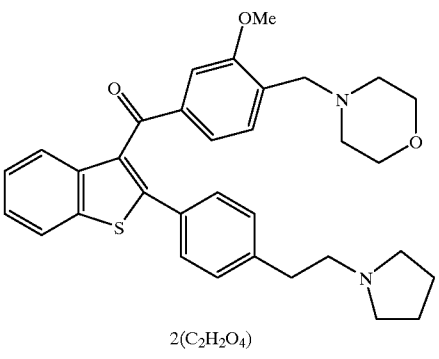

2(C$_2$H$_2$O$_4$)

Following the procedure described in Example 178, Part D, the salt was obtained from the above diamine as an orange solid in a 89% yield.

IR (KBr) 3450 (br), 2850–2200 (br), 1722 (br), 1646, 1608 cm$^{-1}$; FDMS m/e 540 (M$^+$–2[C$_2$H$_2$O$_4$]); Anal. Calcd. for C$_{33}$H$_{36}$N$_2$O$_3$S·2(C$_2$H$_2$O$_4$): C, 61.60; H, 5.59; N, 3.89. Found: C, 61.90; H, 5.33; N, 3.96.

EXAMPLE 187

Preparation of 3-[3-Methoxy-4-[(4-morpholinyl)methyl3-benzyl]-2-[4-[2-(1-pyrrolidinyl)ethyl3phenylbenzo[b]-thiophene Dioxalate.

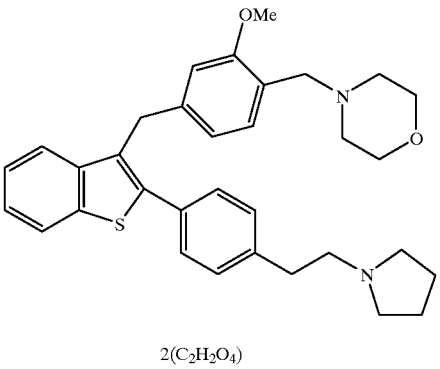

2(C$_2$H$_2$O$_4$)

Part A. 3-[3-Methoxy-4-[(4-morpholinyl)methyl]-benzyl]-2-[4-[2-(1-pyrrolidinyl)ethyl]phenyl]benzo[b]-thiophene.

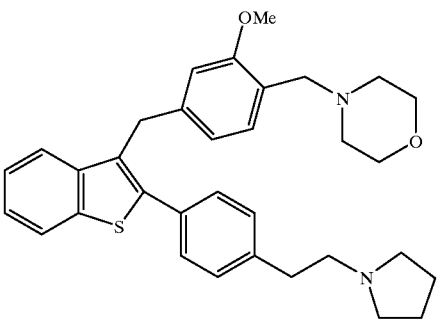

Following the procedure described in Example 179, Part A, the benzyl compound was obtained from the ketone of Example 186, Part A. Column chromatography on silica [gradient 0–5% Et$_3$N in EtOAc] gave 577 mg (64%) of the diamine as a yellow oil.

IR (thin film) 2964, 1611 cm$^{-1}$; FDMS m/e 526 (M$^+$).

Part B. 3-[3-Methoxy-4-[(4-morpholinyl)methyl]-benzyl3-2-[4-[2-(1-pyrrolidinyl)ethyl]phenyl]-benzo[b]thiophene Dioxalate.

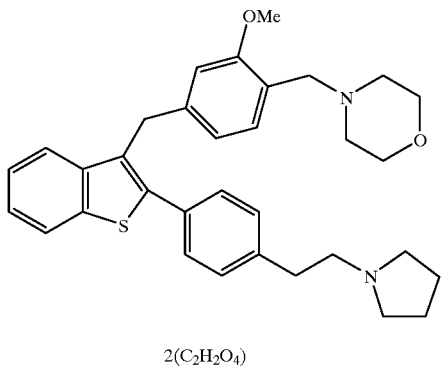

2(C₂H₂O₄)

Following the procedure described in Example 178, Part D, the salt was obtained from the above diamine as an orange solid in a 99% yield.
IR (KBr) 3450 (br), 2850–2200 (br), 1733 (br), 1612 cm⁻¹; FDMS m/e 526 (M⁺−2[C₂H₂O₄]); Anal. Calcd. for C₃₃H₃₈N₂O₂S·2(C₂H₂O₄): C, 62.88; H, 5.99; N, 3.96. Found: C, 63.17; H, 6.04; N, 3.98.

EXAMPLE 188

Preparation of 1-[2-[4-[3-[[4-[2-methyl-2-(1-pyrrolidinyl)propoxy]]phenyl]methyl]benzo[b]thiophen-2-yl]-phenoxy]ethyl]pyrrolidine Dioxalate.

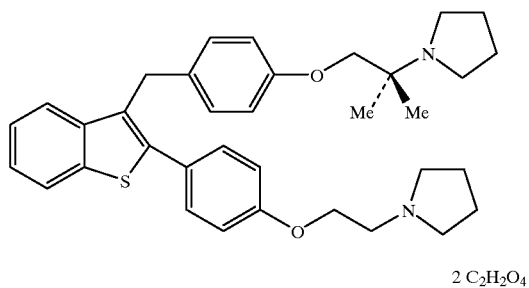

2 C₂H₂O₄

Part A. 2-Methyl-2-(1-pyrrolidinyl)propanol.

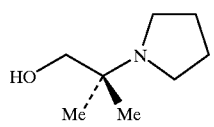

A solution of 2-amino-2-methyl-1-propanol (15 g, 168.3 mmol), 1,4-dibromobutane (18.2 g, 84.1 mmol), and K₂CO₃ (48.8 g, 353.4 mmol) in 1 L of THF was heated at 60° C. for 4.5 days. After cooling to ambient temperature, the reaction mixture was filtered and concentrated in vacuo. Flash chromatography (SiO₂, 94:4:2 EtOAc/MeOH/TEA) afforded 8.21 g (57.3 mmol; 34%) of the title product as a pale yellow oil. A small sample was dissolved in EtOAc and treated with one equivalent of oxalic acid in a method similar to Example 1, Part C.
FDMS 143 (M⁺); Anal. Calcd. for C₈H₁₇NO·C₂H₂O₄·0.1H₂O: C, 51.49; H, 8.21; N, 6.00. Found: C, 50.95; H, 8.00; N, 5.88.

Part B. 4-[2-Methyl-2-(1-pyrrolidinyl)propoxy]phenyl 2-[4-[2-(1-Pyrrolidinyl)ethoxy3phenyl]-benzo[b]thiophen-3-yl Ketone Dioxalate.

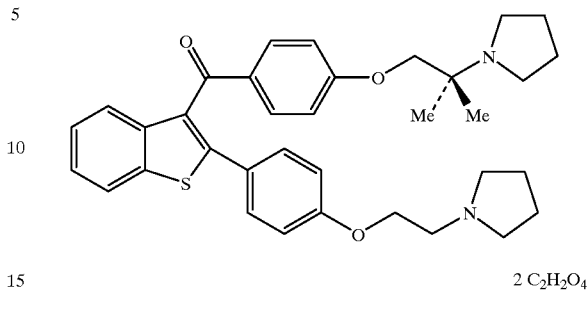

2 C₂H₂O₄

A 0° C. slurry of 4-fluorophenyl 2-[4-[2-(1-pyrrolidinyl)ethoxy]phenyl]benzo[b]thiophen-3-yl ketone (500 mg, 1.12 mmol; Example 132, Part A) and NaH (94 mg, 2.35 mmol) in 6 mL of DMF was treated with a solution of 2-methyl-2-(1-pyrrolidinyl)propanol (321 mg, 2.24 mmol; Part A) in 4 mL of DMF in a dropwise manner. The reaction mixture was allowed to warm to room temperature and stir for 4 h before quenching in 25 mL of brine. The layers were separated, and the aqueous phase was extracted with CHCl₃ (3×20 mL). The combined organic layers were dried over K₂CO₃, filtered and concentrated in vacuo. Radial chromatography (SiO₂; gradient of 97:2:1 to 94:4:2 EtOAc/MeOH/TEA) afforded 527 mg (0.927 mmol; 83 %) of the title product. A small sample was converted to the dioxalate salt in a method similar to Example 1, Part C.
FDMS 569 (M+1); Anal. Calcd. for C₃₅H₄₀N₂O₃S·2C₂H₂O₄: C, 62.55; H, 5.92; N, 3.74. Found: C, 62.47; H, 5.85; N, 3.64.

Part C. 1-[2-[4-[3-[[4-[2-Methyl-2-(1-pyrrolidinyl)-propoxy]]phenyl]methyl]benzo[b]thiophen-2-yl]phenoxy]-ethyl]pyrrolidine Dioxalate.

DIBAL-H (2.0 mL, 2.0 mmol, 1M solution in toluene) was added dropwise via syringe to a 0° C. solution of the ketone from Part B (450 mg, 0.791 mmol) in 10 mL of anhydrous THF. After 1 h the remaining DIBAL-H was quenched with excess MeOH (approximately 1 mL). 15 mL of saturated Na⁺K⁺ tartrate and 15 mL of EtOAc were added, and the biphasic mixture was vigorously stirred overnight at ambient temperature. The layers were separated, and the aqueous layer was extracted with EtOAc (20 mL). The combined organic layers were dried over K₂CO₃, filtered and concentrated to an off-white foam. The crude benzyl alcohol was taken up in 10 mL of 1,2-dichloroethane. Et₃SiH (0.88 mL, 5.5 mmol) was added, and the resulting mixture was cooled to 0° C. After 5 min, the solution was treated with TFA (0.61 mL, 7.9 mmol). After 2.5 h, the reaction mixture was poured into 25 mL of saturated aqueous NaHCO₃ solution. The aqueous layer was extracted with CHCl₃ (3×25 mL). The combined organic layers were dried over K₂CO₃, filtered and concentrated in vacuo. Purification by radial chromatography (SiO₂; gradient of 97:2:1 to 94:4:2 EtOAc/MeOH/TEA) gave 414 mg (0.746 mmol; 94%) of a white foam. The free base was converted to the title dioxalate salt by a method similar to Example 1, Part C.
FDMS 555 (M+1); Anal. Calcd. for C₃₅H₄₂N₂O₂S·2C₂H₂O₄: C, 63.74; H, 6.31; N, 3.81. Found: C, 63.94; H, 6.25; N, 3.89.

EXAMPLE 189

Preparation of (R,S)-1-[2-[4-[3-[[4-[2-(1-Pyrrolidinyl)propoxy]]phenyl]methyl]benzo[b]thiophen-2-yl]-phenoxy]ethyl]pyrrolidine Dioxalate.

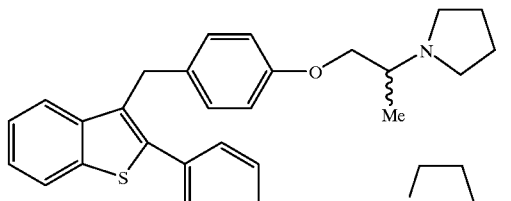

Part A. (R,S) -2-(1-Pyrrolidinyl)propanol.

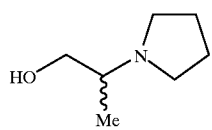

The title compound was prepared in 42% yield from DL-2-amino-1-propanol by essentially following the procedure detailed in Example 188, Part A.
FDMS 129 (M+); Anal. Calcd. for $C_7H_{15}NO \cdot C_2H_2O_4$: C, 49.31; H, 7.82; N, 6.39. Found: C, 49.42; H, 7.87; N, 6.27.
Part B. (R,S) -4- [2-(1-Pyrrolidinyl)propoxy]phenyl 2-[4-[2-(1-Pyrrolidinyl)ethoxy]phenyl]-benzo[b]thiophen-3-yl Ketone Dioxalate.

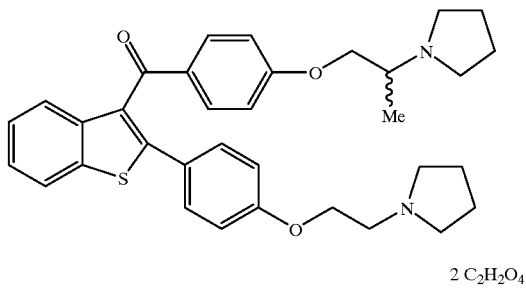

The title compound was prepared from 4-fluorophenyl 2-[4-[2-(1-pyrrolidinyl) ethoxy]phenyl]benzo[b]thiophen-3-yl ketone (Example 132, Part A) and the alcohol from Part A above in 73% yield by essentially following the procedure described in Example 188, Part B.
FDMS 555 (M+1); Anal. Calcd. for $C_{34}H_{38}N_2O_3S \cdot 2C_2H_2O_4$: C, 62.11; H, 5.76; N, 3.81. Found: C, 61.95; H, 5.79; N, 3.92.
Part C. Preparation of (R,S)-1-[2-[4-[3-[14-[2-(1-Pyrrolidinyl)propoxy]]phenyl]methyl]benzo[b]thiophen-2-yl]phenoxy3ethyl]pyrrolidine Dioxalate.

The title compound was prepared from the ketone from Part B in 94% yield by essentially following the procedure detailed in Example 188, Part C.
FDMS 541 (M+1); Anal. Calcd. for $C_{34}H_{40}N_2O_2S \cdot 2C_2H_2O_4$: C, 63.32; H, 6.15; N, 3.89. Found: C, 63.10; H, 6.12; N, 3.90.

EXAMPLE 190

Preparation of (S)-1-[2-[4-[3-[[4-[2-(1-Pyrrolidinyl)-propoxy]]phenyl]methyl]benzo[b]thiophen-2-yl]phenoxy]-ethyl]pyrrolidine Dioxalate.

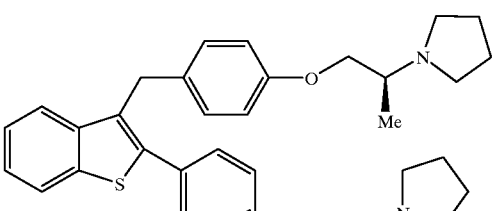

Part A. (S)-2- (1-Pyrrolidinyl)propanol.

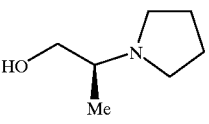

The title compound was prepared in 34% yield from (S)-2-amino-1-propanol by essentially following the procedure detailed in Example 188, Part A.
FDMS 129 (M+); $[\alpha]^{20}_{365}$ +6 (c. 0.0103, MeOH); Anal. Calcd. for $C_7H_{15}NO \cdot C_2H_2O_4$: C, 49.31; H, 7.82; N, 6.39. Found: C, 49.41; H, 7.93; N, 6.30.
Part B. (S)-4-[2-(1-Pyrrolidinyl)propoxylphenyl 2-[4-[2-(1-Pyrrolidinyl)ethoxy]phenyl]benzo[b]thiophen-3-yl Ketone Dioxalate.

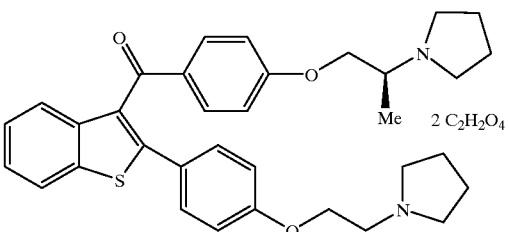

The title compound was prepared from 4-fluorophenyl 2-[4-[2-(1-pyrrolidinyl)ethoxy]phenyl]benzo[b]thiophen-3-yl ketone (Example 132, Part A) and the alcohol from Part A above in 86% yield by essentially following the procedure described in Example 188, Part B.
FDMS 555 (M+1); Anal. Calcd. for $C_{34}H_{38}N_2O_3S \cdot 2C_2H_2O_4$: C, 62.11; H, 5.76; N, 3.81. Found: C, 61.92; H, 5.79; N, 3.96.
Part C. (S)-1-[2-[4-[3-[[4-[2-(1-Pyrrolidinyl)-propoxyl]phenyl]methyl]benzo[b]thiophen-2-yl]-phenoxy]ethyl]pyrrolidine.

The title compound was prepared from the ketone from Part B in 94% yield by essentially following the procedure detailed in Example 188, Part C.
FDMS 541 (M+1); $[\alpha]^{20}_{365}$ +13 (c. 0.0063, MeOH); Anal. Calcd. for $C_{34}H_{40}N_2O_2S \cdot 2C_2H_2O_4$: C, 63.32; H, 6.15; N, 3.89. Found: C, 63.22; H, 5.96; N, 3.93.

EXAMPLE 191

Preparation of (R)-1-[2-[4-[3-[[4-[2-(1-Pyrrolidinyl)-propoxy]]phenyl]methyl]benzo[b]thiophen-2-yl]phenoxy]-ethyl]pyrrolidine Dioxalate.

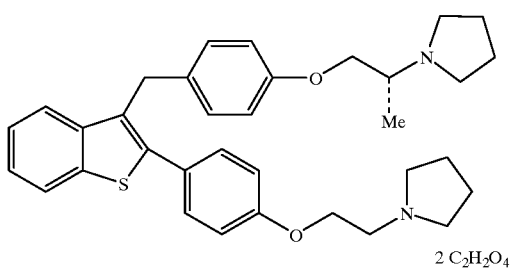

Part A. (R)-2-(1-pyrrolidinyl)propanol.

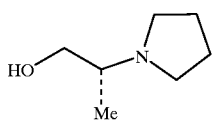

The title compound was prepared in 37% yield from (R)-2-amino-1-propanol by essentially following the procedure detailed in Example 188, Part A.

FDMS 129 (M+); [α]$^{20}_{365}$ −6 (c. 0.0102, MeOH); Anal. Calcd. for $C_7H15NO \cdot C_2H_2O_4$: C, 49.31; H, 7.82; N, 6.39. Found: C, 49.30; H, 7.64; N, 6.35.

Part B. (R)-4-[2-(1-Pyrrolidinyl)propoxy]phenyl 2-[4-[2-(1-Pyrrolidinyl)ethoxy]phenyl]benzo[b]thiophen-3-yl Ketone Dioxalate.

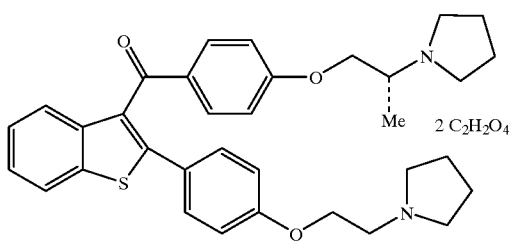

The title compound was prepared from 4-fluorophenyl 2-[4-[2-(1-pyrrolidinyl)ethoxy]phenyl]benzo[b]thiophen-3-yl ketone (Example 132, Part A) and the alcohol from Part A above in 96% yield by essentially following the procedure described in Example 188, Part B.

FDMS 555 (M+1); Anal. Calcd. for $C_{34}H_{38}N_2O_3S \cdot 2C_2H_2O_4$: C, 62.11; H, 5.76; N, 3.81. Found: C, 61.97; H, 5.79; N, 3.98.

Part C. (R)-1-[2-[4-[3-[[4-[2-(1-Pyrrolidinyl)-propoxy]]phenyl]methyl]benzo[b]thiophen-2-yl]-phenoxy]ethyl]pyrrolidine Dioxalate.

The title compound was prepared from the ketone from Part B in 80% yield by essentially following the procedure detailed in Example 188, Part C.

FDMS 541 (M+1); [α]$^{20}_{365}$ −11 (c. 0.0066, MeOH); Anal. Calcd. for $C_{34}H_{40}N_2O_2S \cdot 2C_2H_2O_4$: C, 63.32; H, 6.15; N, 3.89. Found: C, 63.36; H, 6.14; N, 3.88.

EXAMPLE 192

Preparation of 1-[2-[2-Methoxy-4-[[6-hydroxy-2-[4-[2-(1-pyrrolidinyl)ethoxy]phenyl]benzo[b]thiophen-3-yl]-methyl]phenoxy]ethyl]pyrrolidine.

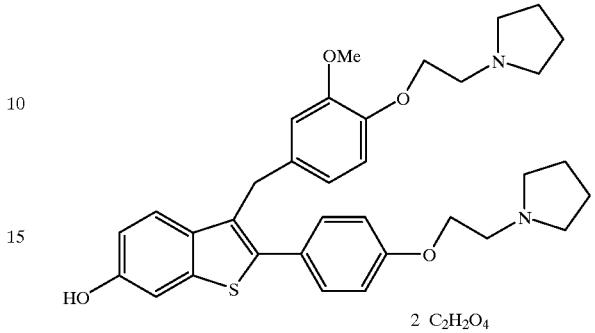

Part A. 3-Methoxy-4-triisopropylsilyloxybenzoic Acid.

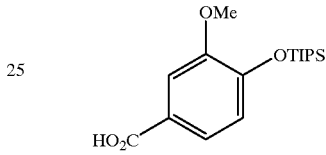

A 0° C. solution of vanillic acid (20 g; 119 mmol) in 550 mL of dry DMF and 33 mL of TEA was treated with TIPS-triflate (48 mL; 179 mmol) dropwise via a syringe. After 15 min, the reaction mixture was allowed to warm to ambient temperature. After stirring overnight, the reaction mixture was poured into 500 mL of saturated $NaHCO_3$ (aq) and 300 mL of EtOAc. The aqueous layer was extracted with EtOAc (3×200 mL). The combined organic layers were washed with $H_2O$ (300 mL), dried over $MgSO_4$, filtered and concentrated in vacuo. Purification by PrepLC ($SiO_2$, 5% EtOAc in hexanes) afforded 22.5 g (69.3 mmol; 58%) of the title compound as fluffy white crystals.

FDMS 324 (M+); Anal. Calcd. for $C_{17}H_{28}O_4Si$: C, 62.92; H, 8.70. Found: C, 62.70; H, 8.81.

Part B. 6-Benzyloxy-2-(dimethylamino)benzo[b]thiophen-3-yl 3-Methoxy-4-triisopropylsilyloxyphenyl Ketone.

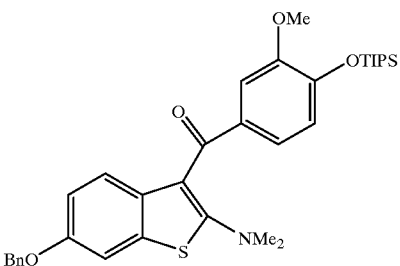

A slurry of 3-methoxy-4-triisopropylsilyloxybenzoic acid (9.75 g, 30 mmol; Part A) in 300 mL of dichloroethane and 1 drop of DMF was treated with oxalyl chloride (13.1 mL, 150 mmol) and stirred overnight at ambient temperature. The reaction mixture was concentrated in vacuo and suspended in 300 mL of chlorobenzene. 6-Benzyloxy-2-(N,N-dimethylamino)-benzo[b]thiophene (8.5 g, 30 mmol) was added, and the resulting mixture was heated at 105° C. for 5 h. After cooling to ambient temperature, the reaction mixture was poured into 500 mL of saturated aqueous NaHCO₃ solution. The aqueous layer was extracted with CHCl₃ (3×150 mL). The combined organics were dried over K₂CO₃, filtered and concentrated in vacuo. Purification by flash chromatography (SiO₂; gradient of 5% to 10% EtOAc in hexanes) afforded 6.05 g (10.3 mmol; 34%) of the title compound.
FDMS 589 (M⁺); Anal. Calcd. for C₃₄H₄₃NO₄SSi: C, 69.23; H, 7.35; N, 2.37. Found: C, 69.54; H, 7.40; N, 2.32.
Part C. 6-Benzyloxy-2-[4-[2-(1-pyrrolidinyl)ethoxy]-phenyl]benzo[b]thiophen-3-yl 3-Methoxy-4-triisopropyl-silyloxyphenyl Ketone.

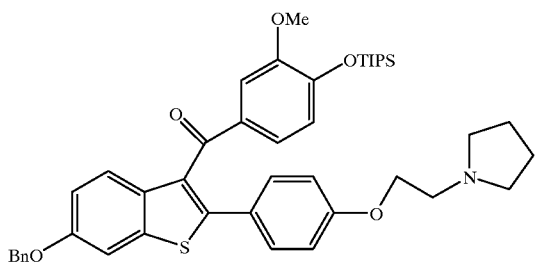

A suspension of 1-[2-(4-bromophenoxy)ethyl]pyrrolidine (3.1 mL, 15 mmol), Mg° (365 mg, 15 mmol) and a small crystal of I2 in 20 mL of dry THF was heated at 60° C. for 1 h. The resulting solution was added via cannula to a 0° C. solution of 6-benzyloxy-2-[4-[2-(1-pyrrolidinyl)ethoxy]phenyl]-benzo[b]thiophen-3-yl 3-methoxy-4-triisopropylsilyloxyphenyl ketone (5.75 g, 9.75 mmol; Part B) in 100 mL of dry THF. After 2.5 h, the reaction mixture was poured into 200 mL of saturated NH₄Cl solution. The aqueous layer was extracted with CHCl₃ (3×150 mL). The combined organics were dried over K₂CO₃, filtered and concentrated in vacuo. Purification by PrepLC (SiO₂; gradient of 90:8:2 to 75:20:5 hex/THF/TEA) afforded 4.89 g (6.65 mmol; 68%) of the title compound.
FDMS 736 (M+1); Anal. Calcd. for C₄₄H₅₃NO₅SSi: C, 71.80; H, 7.26; N, 1.90. Found: C, 71.55; H, 7.11; N, 1.81.
Part D. 6-Benzyloxy-2-[4-[2-(1-pyrrolidinyl)ethoxy]-phenyl]benzo[b]thiophen-3-yl 3-Methoxy-4-hydroxyphenyl Ketone.

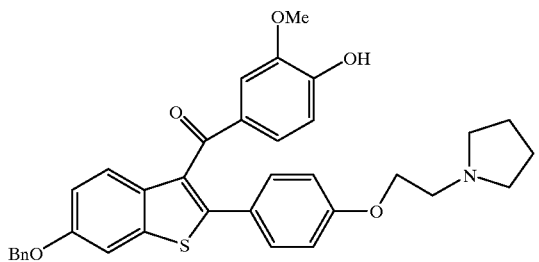

A solution of 6-benzyloxy-2-[4-[2-(1-pyrrolidinyl)-ethoxy]phenyl]benzo[b]thiophen-3-yl 3-methoxy-4-triisopropylsilyloxyphenyl ketone (Part C; 4.89 g; 6.64 mmol) in 65 mL of dry THF was treated with tetrabutylammonium fluoride (1M solution in THF; 7.3 mL) in a dropwise fashion. After 10 min, the reaction mixture was poured into 100 mL of saturated NaHCO₃ (aq). The aqueous layer was extracted with EtOAc (3×50 mL). The combined organic layers were dried over K₂CO₃, filtered and concentrated in vacuo to give a quantitative yield of the title compound as a orange foam. An analytical sample was purified by radial chromatography (SiO₂; gradient of 1% to 3% MeOH in CHCl₃).

FDMS 580 (M+1); Anal. Calcd. for C₃₅H₃₃NO₅S·0.5H₂O: C, 71.41; H, 5.82; N, 2.38. Found: C, 71.61; H, 5.71; N, 2.41.
Part E. 6-Benzyloxy-3-[(3-methoxy-4-hydroxyphenyl)-methyl]-2-[4-[2-(1-pyrrolidinyl)ethoxy]phenyl]-benzo[b] thiophene.

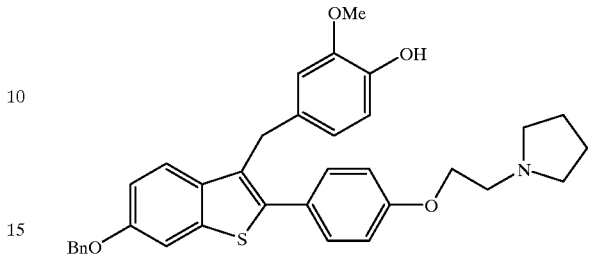

A 0° C. solution of 6-benzyloxy-2-[4-[2-(1-pyrrolidinyl) ethoxy]phenyl]benzo[b]thiophen-3-yl 3-methoxy-4-hydroxyphenyl ketone (Part D; 3.85 g, 6.64 mmol) in 100 mL of anhydrous THF was treated with DIBAL-H (17 mL, 1M solution in toluene) dropwise via syringe. After 1 hr at 0° C., the remaining DIBAL-H was quenched with excess MeOH. 100 mL of saturated Na⁺K⁺ tartrate and 50 mL of EtOAc were added, and the biphasic mixture was vigorously stirred for 1.5 hr at ambient temperature. The layers were separated, and the aqueous layer was extracted with EtOAc (2×100 mL). The combined organic layers were dried over K₂CO₃, filtered and concentrated in vacuo. The crude residue was dissolved in 100 mL of 1,2-dichloroethane, and Et₃SiH (9.4 mL, 58.7 mmol) was added. Upon cooling to 0° C., TFA (6.5 mL, 83.8 mmol) was added in a dropwise fashion. After 1.5 hr, the reaction mixture was poured into 300 mL of saturated NaHCO₃ solution. The aqueous phase was extracted with EtOAc (2×150 mL). The combined organic layers were dried over K₂CO₃, filtered and concentrated in vacuo. Purification by PrepLC (SiO₂; gradient of 0.5% to 2% MeOH in CHCl₃, saturated with NH₄OH) afforded 3.1 g (5.48 mmol; 83%) of a white solid.
FDMS 566 (M+1); Anal. Calcd. for C₃₅H₃₅NO₄S: C, 74.31; H, 6.24; N, 2.48. Found: C, 74,11; H, 6.32; N, 2.46.
Part F. 1-[2-[2-Methoxy-4-[[6-benzyloxy-2-[4-[2-(1-pyrrolidinyl)ethoxy]phenyl]benzo[b]thiophen-3-yl]-methyl] phenoxy]ethyl]pyrrolidine.

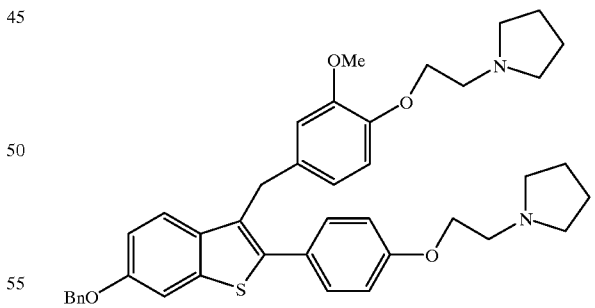

The title compound was prepared in 30% yield from 6-benzyloxy-3-[(3-methoxy-4-hydroxyphenyl)methyl]-2-[4-[2-(1-pyrrolidinyl)ethoxy]phenyl]benzo[b]thiophene (Part E) and 1-(2-chloroethyl)pyrrolidine hydrochloride by a method similar to that outlined in Example 188, Part A.
FAB HRMS: m/e, calcd for C₄₁H₄₇N₂O₄S: 663.3257; Found: 663.3264 (M+1).
Part G. 1-[2-[2-Methoxy-4-[[6-hydroxy-2-[4-[2-(1-pyrrolidinyl)ethoxy]phenyl]benzotb]thiophen-3-yl1-methyl]phenoxy]ethyl]pyrrolidine Dioxalate.

A slurry of 1-[2-[2-methoxy-4-[[6-benzyloxy-2-[4-[2-(1-pyrrolidinyl)ethoxy]phenyl]benzo[b]thiophen-3-yl]-methyl]phenoxy]ethyl]pyrrolidine (Part F; 65 mg, 0,098 mmol) and 10% Pd/C (65 mg) in 2 mL of THF and 0.135 mL of 25% aq. $NH_4^+HCO_2^-$ was vigorously stirred for 6 h at ambient temperature. The reaction mixture was filtered through a pad of diatomaceous earth, and the layers were separated. The aqueous layer was extracted with $CHCl_3$ (3×15 mL). The combined organic layers were dried over $K_2CO_3$, filtered and concentrated in vacuo. Radial chromatography ($SiO_2$; gradient of 1% to 3% MeOH in $CHCl_3$, saturated with $NH_4OH$) gave 36.5 mg (0.064 mmol; 64%) of the free base which was converted to the dioxalate salt according to the procedure outlined in Example 1, Part C.

FAB HRMS: m/e, calcd for $C_{34}H_{41}N_2O_4S$: 573.2787; Found: 573.2780 (M+1)

EXAMPLE 193

Preparation of 1-[2-[4-[6-Hydroxy-3-[[3-methoxy-4-[2-(1-pyrrolidinyl)butyloxy]phenyl]methyl]benzo[b]thiophen-2-yl]phenoxy]ethyl]pyrrolidine Dioxalate.

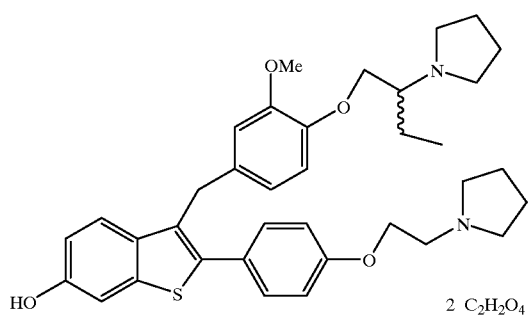

Part A. 1-[2-[4-[6-Benzyloxy-3-[[3-methoxy-4-[2-(1-pyrrolidinyl)butyloxy]phenyl]methyl]benzo[b]thiophen-2-yl]phenoxy]ethyl]pyrrolidine.

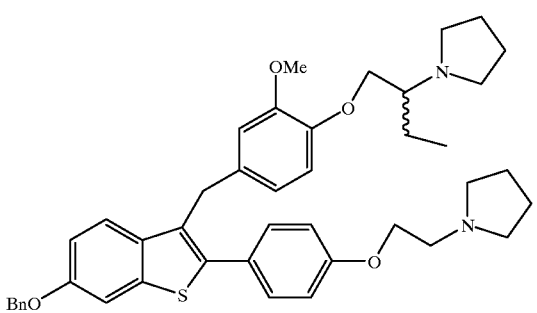

A 0° C. solution of 6-benzyloxy-3-[(3-methoxy-4-hydroxyphenyl)-2-[4-[2-(1-pyrrolidinyl)ethoxy]phenyl]-benzo[b]thiophene (430 mg, 0.76 mmol; Example 192, Part E), $PPh_3$ (240 mg, 0.912 mmol) and 2-(1-pyrrolidinyl)butanol (131 mg, 0.912 mmol; Example 122, Part A) in 7 mL of $CH_2Cl_2$ was treated with diethyl azodicarboxylate (0.144 mL, 0.912 mmol) in a dropwise fashion. The resulting mixture was allowed to warm to ambient temperature and stir overnight. The reaction mixture was poured into 20 mL of $H_2O$. The layers were separated, and the aqueous layer was extracted with $CHCl_3$ (3×20 mL). The combined organic layers were dried over $K_2CO_3$, filtered and concentrated in vacuo. Radial chromatography ($SiO_2$; gradient of 97:2:1 to 94:4:2 EtOAc/MeOH/TEA) gave 45 mg (0.065 mmol; 9%) of the title compound.

FAB HRMS: m/e, calcd for $C_{43}H_{51}N_2O_4S$: 690.3570; Found: 690.3582 (M+1).

Part B. 1-[2-[4-[6-Hydroxy-3-[[3-methoxy-4-[2-(1-pyrrolidinyl)butyloxy]phenyl]methyl]benzo[b]thiophen-2-yl]phenoxy]ethyl]pyrrolidine Dioxalate.

The title compound was prepared in 62% yield from the product of Part A by a method similar to that described in Example 192, Part G.

FAB HRMS: m/e, calcd for $C_{36}H_{45}N_2O_4S$: 601.3100; Found: 601.3105 (M+1)

EXAMPLE 194

Preparation of 1-[2-[4-[6-Hydroxy-3-[[3-methoxy-4-[2-(1-pyrrolidinyl)propoxy]phenyl]methyl]benzo[b]thiophen-2-yl]phenoxy]ethyl]pyrrolidine Dioxalate.

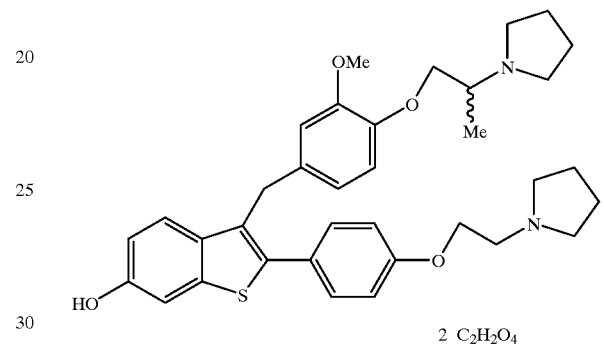

Part A. 1-[2-[4-[6-Benzyloxy-3-[[3-methoxy-4-[2-(1-pyrrolidinyl)propoxy]phenyl]methyl]benzo[b]thiophen-2-yl]phenoxy]ethyl]pyrrolidine.

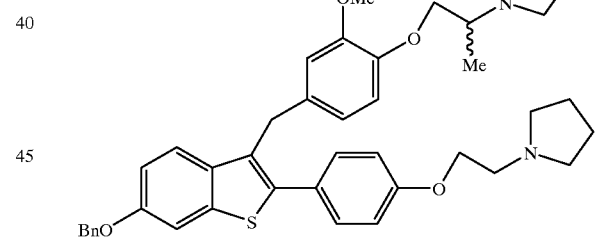

The title compound was prepared in 27% yield from 6-benzyloxy-3-[(3-methoxy-4-hydroxyphenyl)-2-[4-[2-(1-pyrrolidinyl)ethoxy]phenyl]benzo[b]thiophene (Example 192, Part E) and (R,S)-2-(1-pyrrolidinyl)propanol (Example 189, Part A) by a essentially following the procedure outlined in Example 193, Part A.

FDMS 677 (M+1); Anal. Calcd. for $C_{42}H_{48}N_2O_4S$: C, 74.52; H, 7.15; N, 4.14. Found: C, 74.33; H, 6.92; N, 4.34.

Part B. 1-[2-[4-[6-Hydroxy-3-[[3-methoxy-4-[2-(1-pyrrolidinyl)propoxy]phenyl]methyl]-benzo[b]thiophen-2-yl]phenoxy]ethyl]pyrrolidine Dioxalate.

The title compound was prepared in 37% yield from the product of Part A by a method similar to that described in Example 192, Part G.

FDMS 587 (M+1); Anal. Calcd. for $C_{35}H_{42}N_2O_4S \cdot 1.8C_2H_2O_4$: C, 61.91; H, 6.14; N, 3.74. Found: C, 61.99; H, 6.10; N, 3.85.

EXAMPLE 195

Preparation of 1-[2-[4-[6-Hydroxy-3-[[3-methoxy-4-[2-methyl-2-(1-pyrrolidinyl)propoxy]phenyl]methyl]-benzo[b]thiophen-2-yl]phenoxy]ethyl] pyrrolidine Dioxalate.

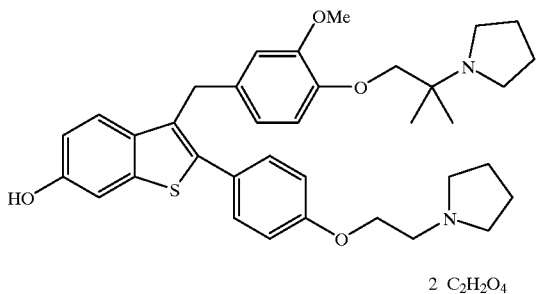

Part A. Methyl 3-Methoxy-4-12-methyl-2-(1-pyrrolidinyl) propoxy]benzoate.

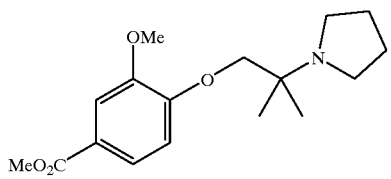

The title compound was prepared in 17% yield from methyl vanillate and 2-methyl-2-(1-pyrrolidinyl)propanol (Example 188, Part A) by a essentially following the procedure outlined in Example 193, Part A.

FDMS 307 (M$^+$); Anal. Calcd. for $C_{17}H_{25}NO_4$: C, 66.43; H, 8.20; N, 4.56. Found: C, 66.27; H, 7.97; N, 4.68.

Part B. 3-Methoxy-4-[2-methyl-2-(1-pyrrolidinyl)-propoxy] benzoic Acid.

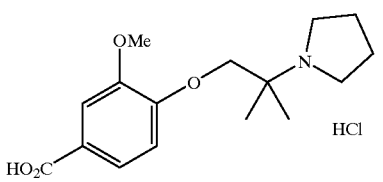

The ester from Part A (1.7 g, 5.53 mmol) was heated at 95° C. in 25 mL of 1N HCl overnight. The solution was allowed to cool to room temperature, then it was extracted with EtOAc (1×25 mL). The aqueous layer was concentrated in vacuo to give 1.8 g (5.46 mmol; 99%) of the title hydrochloride salt as a white powder.

FDMS 294 (M+1); Anal. Calcd. for $C_{16}H_{23}NO_4$·1.3HCl: C, 56.40; H, 7.19; N, 4.11. Found: C, 56.28; H, 6.93; N, 4.32.

Part C. 6-Benzyloxy-2-dimethylaminobenzo[b]thiophen-3-yl 3-Methoxy-4-[2-methyl-2-(1-pyrrolidinyl)propoxy]-phenyl Ketone.

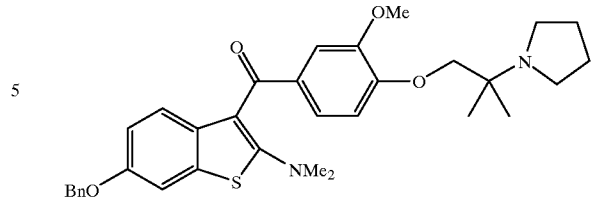

The title compound was prepared in 42% yield from the amino acid from Part B and 6-benzyloxy-2-(N,N-dimethylamino)-benzo[b]thiophene by a essentially following the procedure outlined in Example 192, Part B. A small sample was converted to the oxalate salt for analytical analysis.

FDMS 558 (M$^+$); Anal. Calcd. for $C_{33}H_{38}N_2O_4S$·1$C_2H_2O_4$·0.5$C_4H_8O_2$ (EtOAc): C, 64.14; H, 6.40; N, 4.04. Found: C, 63.87; H, 6.24; N, 3.68.

Part D. 6-Benzyloxy-2-[4-[2-(1-pyrrolidinyl)ethoxy]-phenyl]benzo[b]thiophen-3-yl 3-Methoxy-4-[2-methyl-2-(1-pyrrolidinyl)propoxy]phenyl Ketone.

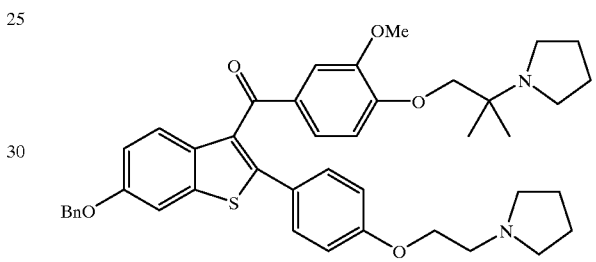

The title compound was prepared from the product of Part C in 33% yield according to the procedure detailed in Example 192, Part C.

FDMS 705 (M+1).

Part E. 6-Hydroxy-2-[4-[2-(1-pyrrolidinyl)ethoxy]-phenyl]benzo[b]thiophen-3-yl 3-Methoxy-4-[2-methyl-2-(1-pyrrolidinyl)propoxy]phenyl Ketone Dioxalate.

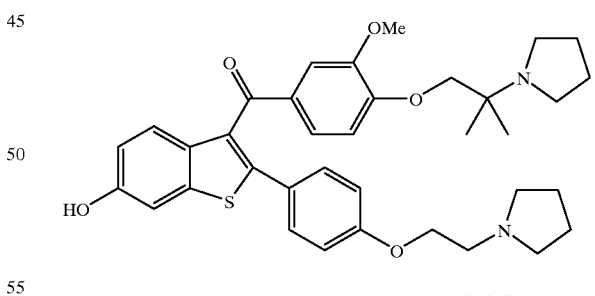

The title compound was prepared in 63% yield from the product of Part D by a essentially following the procedure described in Example 192, Part G.

FDMS 615 (M+1); Anal. Calcd. for $C_{36}H_{42}N_2O_5S$·2$C_2H_2O_4$·1$H_2O$: C, 59.10; H, 5.95; N, 3.45. Found: C, 58.89; H, 5.84; N, 3.36.

Part F. 1-[2-[4-[6-Hydroxy-3-[[3-methoxy-4-[2-methyl-2-(1-pyrrolidinyl)propoxy]phenyl]methyl]-benzo[b]thiophen-2-yl]phenoxy]ethyl]pyrrolidine Dioxalate.

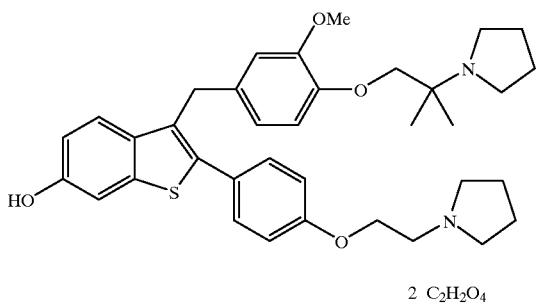

The title compound was prepared in 83% yield from the free base of Part D by a essentially following the procedure outlined in Example 188, Part C.
FDMS 601 (M+1); Anal. Calcd. for $C_{36}H_{44}N_2O_4S \cdot 2C_2H_2O_4 \cdot 1H_2O$: C, 60.14; H, 6.31; N, 3.51. Found: C, 60.43; H, 6.35; N, 3.51.

EXAMPLE 196

Preparation of (R)-2-[4-(2-Aminopropoxy)phenyl]-3-[4-[2-(1-pyrrolidinyl)ethoxy]benzyl]benzo[b]thiophene Dioxalate.

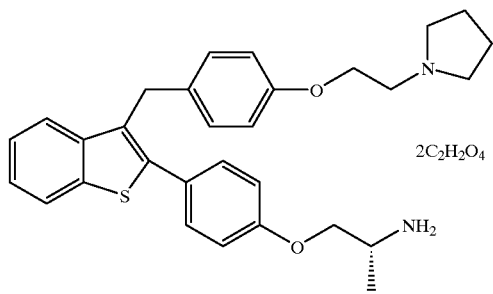

Part A. 2-(4-Hydroxyphenyl)-3-[4-[2-(1-pyrrolidinyl)ethoxy]benzyl]benzo[b]thiophene.

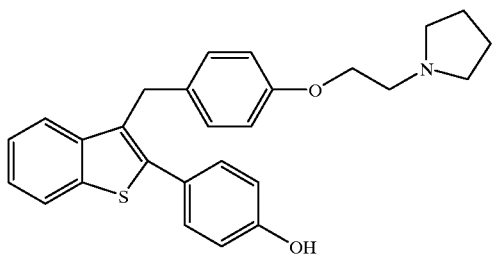

A 0° C. solution of 7.40 g (16.7 mmol) of 2-(4-hydroxyphenyl)benzo[b]thiophen-3-yl 4-[2-(1-pyrrolidinyl)ethoxy]-phenyl ketone (Example 15, Part B) in 500 mL of THF was treated with 67.0 mL of a solution of DIBAL-H (1N in toluene; 67 mmol). The reaction was stirred at 0° C. for 1 hr and was quenched by the careful addition of 50 mL of MeOH. Saturated aq. sodium/potassium tartrate (200 mL) and EtOAc (200 mL) were added and the reaction stirred vigorously for 1 h. The two layers were separated and the aqueous layer was extracted with EtOAc (3×200 mL). The combined organic layers were dried ($K_2CO_3$), filtered and concentrated in vacuo. The residue was taken up in dichloroethane (300 mL). The solution was cooled to 0° C. and was treated with 20.0 mL (125 mmol) of triethylsilane followed by 13.0 mL (168 mmol) of trifluoroacetic acid. The reaction was stirred at 0° C. for 1 hr and was poured into 250 mL of sat'd aq. $NaHCO_3$. The two layers were separated and the organic layer was dried ($K_2CO_3$), filtered, and concentrated in vacuo to give 6.53 g of a foam. Flash chromatography ($SiO_2$; 25% THF: 5% TEA: 70% hexanes) afforded 5.45 g (12.7 mmol; 76%) of the title compound as a foam.
$^1H$ NMR (DMSO-$d_6$) δ 9.77 (s, 1H), 7.90 (d, J=8.8 Hz, 1H), 7.93–7.87 (m, 1H), 7.32–7.24 (m, 4H), 6.97 (d, J=8.7 Hz, 2H), 6.86–6.75 (m, 4H), 4.13 (s, 2H), 3.97 (t, J=5.8 Hz, 2H), 2.87–2.78 (m, 2H), 2.61–2.52 (m, 4H), 1.69–1.61 (m, 4H).
Part B. (R)-(−)-N-t-Boc-2-Amino-1-propanol.

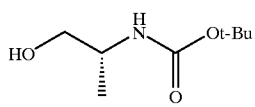

A solution of 2.00 g (26.6 mmol) of (R)-(−)-2-amino-1-propanol in 27 mL of dioxane and 27 mL of 1.0N aq NaOH was treated with a solution of 5.81 g (26.6 mmol) of di-t-butyl dicarbonate in 5 mL of THF. The reaction was stirred overnight and was concentrated in vacuo. The residue was purified by flash chromatography ($SiO_2$; 40% EtOAc in hexanes) to afford 4.38 g (25.0 mmol; 94%) of the title compound as a paste.
FDMS 176 (M+1); Anal. calcd for $C_8H_{17}NO_3$: C, 54.84; H, 9.78; N, 7.99. Found: C, 54.88; H, 9.61; N, 8.05.
Part C. (R)-2-[4-[2-(t-Butyloxycarbonylamino)-propoxy]phenyl]-3-[4-[2-(1-pyrrolidinyl)ethoxy]-benzyl]benzo[b]thiophene Oxalate.

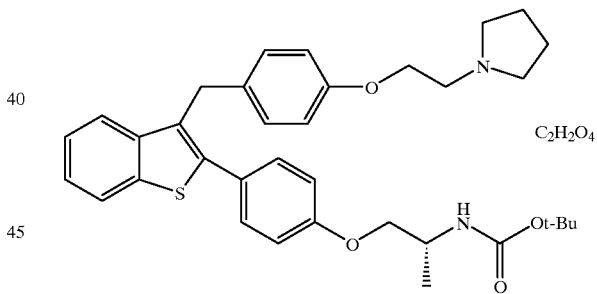

By essentially following the conditions described in Example 20, Part B, adding the diethyl azodicarboxylate to a mixture of triphenylphospine, 2-(4-hydroxyphenyl)-3-[4-[2-(1-pyrrolidinyl)ethoxy]benzyl]benzo[b]thiophene (Part A) and (R)-(−)-N-t-Boc-2-amino-1-propanol (Part B) in THF at 0° C. and stirring the reaction mixture at ambient temperature about 16 h, the free base of the title compound was prepared as a foam in 65% yield following flash chromatography ($SiO_2$; 1% then 3% then 5% MeOH in $CHCl_3$ sat'd with $NH_4OH$). The foam was taken up in a minimal amount of MeOH and treated with a solution of oxalic acid in MeOH to provide the oxalate salt.
FDMS 587 (M+1); Anal. calcd for $C_{35}H_{42}N_2O_4S \cdot 1.3C_2H_2O_4$: C, 64.16; H, 6.39; N, 3.98. Found: C, 64.08; H, 6.59; N, 3.82.
Part D. (R)-2-[4-(2-Aminopropoxy)phenyl]-3-[4-[2-(1-pyrrolidinyl)ethoxy]benzyl]benzo[b]thiophene Dioxalate.

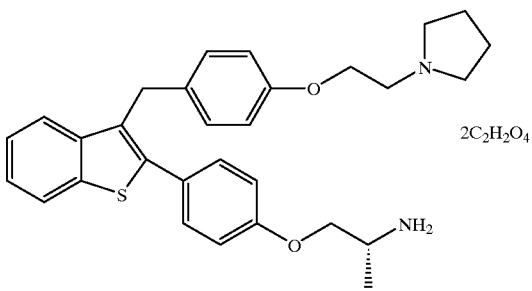

A solution of 0.46 g (0.78 mmol) of the above urethane (Part C) in 10 mL of $CH_2Cl_2$ was treated with 0.42 mL (3.86 mmol) of anisole followed by 0.60 mL (7.79 mmol) of TFA. The reaction was stirred for 3 h and was concentrated in vacuo. The residue was subjected to radial chromatography ($SiO_2$; 10% MeOH in $CHCl_3$ sat'd with $NH_4OH$) to afford 216 mg of the free base of the title compound as an oil. The product was taken up in a minimal amount of MeOH and treated with a solution of oxalic acid in MeOH to provide the oxalate salt following evaporation.

FDMS 487 (M+1); Anal. calcd for $C_{34}H_{38}N_2O_{10}S$: C, 61.25; H, 5.75; N, 4.20. Found: C, 60.98; H, 5.66; N, 4.00.

EXAMPLE 197

Preparation of 2-[4-(2-Aminoethoxy)phenyl]-3-[4-[2-(1-pyrrolidinyl)ethoxy]benzyl]benzo[b]thiophene Dihydrochloride.

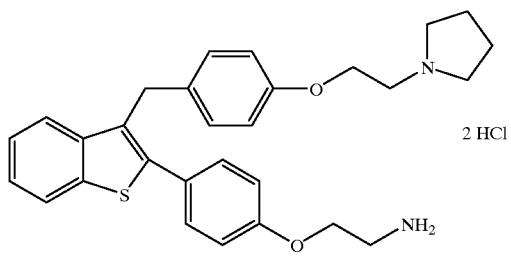

Part A. 2-[4-[2-(t-Butyloxycarbonylamino)ethoxy]-phenyl]-3-[4-[2-(1-pyrrolidinyl)ethoxy]benzyl]-benzo[b]thiophene Oxalate.

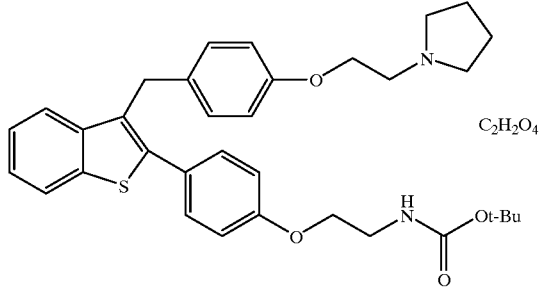

By essentially following the conditions described in Example 196, Part C, the free base of the title compound was prepared as a foam from 2-(4-hydroxyphenyl)-3-[4-[2-(1-pyrrolidinyl)ethoxy]benzyl]benzo[b]thiophene (Example 196; Part A) and N-t-Boc-aminoethanol in 54% yield following flash chromatography ($SiO_2$; 2% then 5% MeOH in $CHCl_3$ sat'd with $NH_4OH$). The product was converted to the oxalate salt according to the method described in Example 196, Part C.

FDMS 487 (M+1); Anal. Calcd for $C_{34}H_{38}N_2O_{10}S$: C, 61.25; H, 5.75; N, 4.20. Found: C, 60.98; H, 5.66; N, 4.00.

Part B. 2-[4-(2-Aminoethoxy)phenyl]-3-[4-[2-(1-pyrrolidinyl)ethoxy]benzyl]benzo[b]thiophene Dihydrochloride.

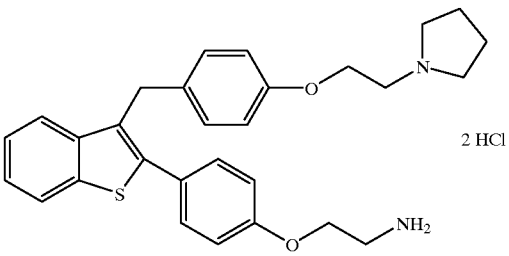

A solution of 1.20 g (2.10 mmol) of the above urethane (Part B) in 5.0 mL of anisole was treated with 10.0 mL of TFA. The reaction was stirred overnight and was concentrated in vacuo. The residue was partitioned between 50 mL of 1N aq HCl and 50 mL of hexanes. The aqueous layer was separated, washed with hexanes (2×50 mL) and EtOAc (2×50 mL), and lyopholized to afford 964 mg (1.77 mmol; 84%) of the title compound. FDMS 487 (M+1); Anal. Calcd for $C_{29}H_{32}N_2O_2S$. 2 HCl: C, 63.84; H, 6.28; N, 5.13. Found: C, 64.14; H, 6.33; N, 5.11.

EXAMPLE 198

Preparation of 2-[4-[2-(1-Imidazolyl)ethoxy]phenyl]-3-[4-[2-(1-pyrrolidinyl)ethoxy]benzyl]benzo[b]thiophene Dioxalate.

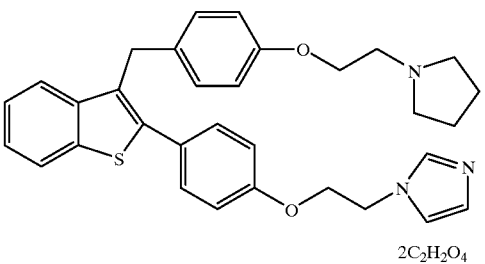

By essentially following the procedure described in Example 3, Part D, the free base of the title compound was prepared from 2-(4-hydroxyphenyl)-3-[4-[2-(1-pyrrolidinyl)-ethoxy]benzyl]benzo[b]thiophene (Example 196; Part A) and 1-(2-chloroethyl)imidazole in 53% yield following radial chromatography ($SiO_2$; 45% THF and 5% TEA in hexanes then 4% MeOH in $CHCl_3$ sat'd with $NH_4OH$). The product was converted to the oxalate salt by the conditions described in Example 196, Part D.

FDMS 524 (M+1); Anal. calcd for $C_{32}H_{33}N_3O_2S.1.5C_2H_2O_4$: C, 63.82; H, 5.51 N, 6.38. Found: C, 64.08; H, 5.51; N, 6.55.

EXAMPLE 199

Preparation of 1-[2-[4-[6-Hydroxy-3-[4-[2-(1-pyrrolidinyl)ethoxy]benzyl]benzo[b]thiophen-2-yl]phenoxy]-ethyl]pyrrolidine Dioxalate

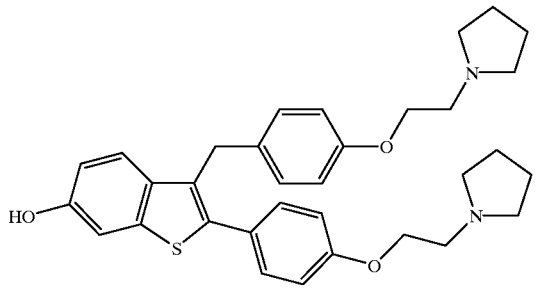

Part A. 2-[4-[2-(1-Pyrrolidinyl)ethoxy]phenyl]-6-triisopropylsilyloxybenzo[b]thiophen-3-yl 4-[2-(1-Pyrrolidinyl)ethoxy]phenyl Ketone

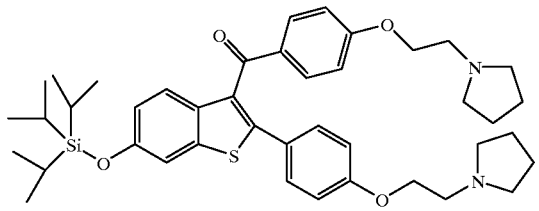

6-Methoxy-2-[4-[2-(1-pyrrolidinyl)-ethoxy]phenyl]-benzo[b]thiophen-3-yl 4-[2-(1-pyrrolidinyl)ethoxy]phenyl ketone, (Example 1, Part C, 8.2 g, 14.37 mmol) was dissolved in 500 mL ClCH$_2$CH$_2$Cl and cooled to 0° C. under N$_2$. This solution was treated sequentially with AlCl$_3$ (15.32 g, 115 mmol) then EtSH (8.9 g, 143.7 mmol). After removing the cooling bath, the mixture was stirred 2 h before recooling to 0° C. and quenching with 100 mL 5N NaOH dropwise. Addition of 200 mL saturated aqueous NaHCO$_3$ and 200 mL H$_2$O gave a precipitate which was filtered through diatomaceous earth. The layers of the filtrate were separated before rinsing the solid with 300 mL n-butanol which was combined with the organic layer. The aqueous layer was saturated with NaCl and extracted four times with 150 mL n-butanol. The combined organic layer was dried over MgSO$_4$ and concentrated under vacuum to 11.5 g gummy solid.

The above solid was dissolved in 30 mL dry DMF, mixed with Et$_3$N (2.9 g, 28.74 mmol) and cooled to 0° C. This was treated with triisopropylsilyl triflate, stirred at ambient temperature for 2 h then quenched with 250 mL brine. The mixture was extracted three times with 75 mL EtOAc and the combined extracts were washed three times with 200 mL brine. Drying over MgSO$_4$ and concentration in vaccuo gave 16 g of an oil which was purified by chromatography (SiO$_2$, THF-Hexanes-Et$_3$N 25/73/2 then CHCl$_3$/MeOH 50/50) to recover 9.21 g (12.9 mmol, 90%) of an oil.

FDMS 713 (M$^+$); $^1$H NMR (CDCl$_3$) δ 7.77 (d, 2H), 7.50 (d, 1H), 7.4–7.32 (m, 3H), 6.95–6.90 (m, 1H), 6.8–6.75 (m, 4H), 4.14–4.09 (m, 4H), 2.93–2.89 (m, 4H), 2.63–2.58 (m, 8H), 1.82–1.79 (m, 8H), 1.31–1.23 (m, 3H), 1.14–1.09 (m, 18H); Anal. Calcd for C$_{42}$H$_{56}$N$_2$O$_4$SSi: C, 70.74; H, 7.92; N, 3.93. Found: C, 70.95; H, 7.88; N, 3.88.

Part B. α-[4-[2-(1-Pyrrolidinyl)ethoxy]phenyl]-2-[4-[2-(1-pyrrolidinyl)ethoxy]phenyl]-6-triisopropylsilyloxybenzo[b]thiophen-3-methanol.

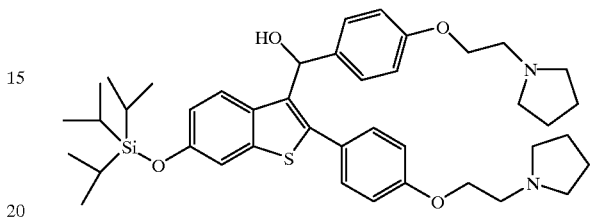

The above ketone (9 g, 12.6 mmol) was dissolved in 200 mL dry THF and cooled to 0° C. under N$_2$. This was treated with 12 mL 1M LiAlH$_4$ in THF and stirred at 0° C. for 1 h after which it was quenched sequentially with 0.5 mL H$_2$O, 0.5 mL 15% NaOH and 2.5 mL H$_2$O. Filtration through diatomaceous earth and concentration to dryness yielded 8.04 g (11.25 mmol, 89%) of a foam.

FDMS 715 (M$^+$); $^1$H NMR (CDCl$_3$) δ 7.53 (d, 1H), 7.39 (d, 2H), 7.32 (d, 2H), 7.28 (d, 1H), 6.91 (d, 2H), 6.86 (d, 2H), 6.81–6.77 (m, 1H), 6.16 (s, 1H), 4.14–4.09 (m, 4H), 2.93–2.89 (m, 4H), 2.85 (bs, 1H), 2.68–2.63 (m, 8H), 1.81–1.79 (m, 8H), 1.31–1.23 (m, 3H), 1.14–1.09 (m, 18H).

Part C. 1-[2-[4-[6-Hydroxy-3-[4-[2-(1-pyrrolidinyl)-ethoxy]benzyl]benzo[b]thiophen-2-yl]phenoxylethyl]-pyrrolidine Dioxalate.

A solution of the above alcohol (1.0 g, 1.4 mmol) in 40 mL ClCH$_2$CH$_2$Cl was cooled to 0° C. and treated with triethyl silane (1.13 g, 9.8 mmol) followed by trifluoroacetic acid (1.6 g, 14 mmol). The reaction was stirred at 0° C. for 2 h, then quenched with 35 mL saturated aqueous NaHCO$_3$. The layers were separated and the aqueous layer was extracted twice with 25 mL CHCl$_3$. The combined organic layer was dried over MgSO$_4$ and concentrated to 1.4 g oil.

The oil was redissolved in 25 mL THF, cooled to 0° C. and treated with 2 mL 1M tetrabutylammonium fluoride in THF. After 15 min, the mixture was concentrated to dryness and partitioned between 50 mL H$_2$O and 50 mL 10% MeOH in EtOAc. The aqueous layer was extracted twice with 50 mL 10% MeOH in EtOAc. The combined organic layer was dried over MgSO$_4$, concentrated to dryness and purified by chromatography (SiO$_2$; 2.5% MeOH in CHCl$_3$). There was recovered 488 mg (0.9 mmol, 64%) which was converted to its dioxalate salt.

FDMS 543 (M+1); $^1$H NMR (CDCl$_3$-Free base) δ 7.31–7.27 (m, 3H), 7.06–6.98 (m, 3H), 6.82–6.72 (m, 5H), 4.15–4.04 (m, 6H), 3.6 (bs, 1H), 2.98–2.91 (m, 4H), 2.89–2.75 (m, 4H), 2.73–2.66 (m, 4H), 1.86–1.82 (m, 8H); Anal. Calcd for C$_{33}$H$_{38}$N$_2$O$_3$S·1.75C$_2$H$_2$O: C, 62.6; H, 5.97; N, 4.00. Found: C, 62.94; H, 6.06; N, 4.21.

EXAMPLE 200

Preparation of 1-[2-[4-[6-Hydroxy-5-methyl-3-[4-[2-(1-pyrrolidinyl)ethoxy]benzyl]benzo[b]thiophen-2-yl]-phenoxy]ethyl]pyrrolidine Dioxalate.

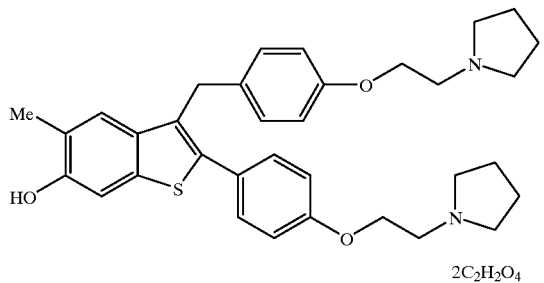

Part A. N,N-Dimethyl-4-methoxy-3-methyl-α-hydroxy-phenylthioacetamide.

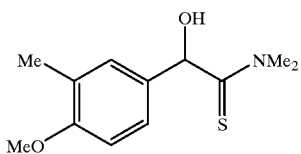

A −78° C. solution of 19.2 mL (137 mmol) of diisopropylamine in 200 mL of THF was treated with 92 mL of n-BuLi (1.6M in hexanes; 147 mmol). The mixture was stirred at −78° C. for 15 min and at 0° C. for 30 min. The mixture was cooled to −78° C. and was treated with a solution of 20.0 g (133.2 mmol) of 3-methyl-p-anisaldehyde and 12.5 mL (147 mmol) of N,N-dimethylthioformamide in 100 mL of THF. The reaction was stirred for 45 min and was quenched by the addition of a solution of 50 mL of ACOH in 100 mL of MeOH. The mixture was allowed to warm to 0° C. and was concentrated in vacuo. The oil was partitioned between H$_2$O and EtOAc (200 mL each). The organic layer was separated and was washed sequentially with 200 mL of sat'd aq NaHCO$_3$, 200 mL of H$_2$O, and 200 mL brine. The solution was dried over Na$_2$SO$_4$, filtered and concentrated in vacuo to give 21.4 g of an oil. Purification by MPLC (SiO$_2$; 10% then 25% EtOAc in hexanes) gave 17.1 g (71.4 mmol; 54%) of the title compound as a orange solid.
IR (CHCl$_3$) 3008, 1608, 1528, 1503, 1386, 1253, 1134, 1060, 1035 cm$^{-1}$; FDMS 239 (M$^+$); Anal. Calcd for C$_{12}$H$_{17}$NO$_2$S: C, 60.22; H, 7.16; N, 5.85. Found: C, 60.50; H, 6.99; N, 5.92.

Part B. 6-Methoxy-5-methyl-2-(N,N-dimethylamino)-benzo[b]thiophene.

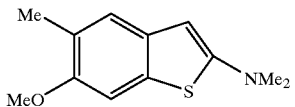

A solution of 17.1 g (71.4 rnmol) of the above thioacetamide (Part A) in 450 mL of CH$_2$Cl$_2$ was treated with 23 mL of MeSO$_3$H and the mixture stirred at room temperature for 4 h. The reaction was cooled to 0° C. and was quenched with 400 mL of sat'd aq NaHCO$_3$H. The two layers were separated and the aqueous layer extracted with EtOAc (3×200 mL). The combined organic layers were washed with sat'd aq NaHCO$_3$ (200 mL), H20 (200 mL), and brine (200 mL).

The organic layer was dried over Na$_2$SO$_4$, filtered and concentrated in vaycuo to give 12.5 g of an oil. Purification by MPLC (SiO$_2$; 15% EtOAc in hexanes) gave 7.45g (33.7 mmol; 47%) of the title compound as a orange solid.

$^1$H NMR (DMSO-d$_6$) d 7.22 (s, 1H), 7.15 (s, 1H), 5.90 (s, 1H), 3.74 (s, 3H), 2.89 (s, 6H), 2.14 (s, 3H); IR (CHCl$_3$) 1565, 1482, 1469, 1433, 1262, 1055 cm$^{-1}$; FDMS 221 (M$^+$).

Part C. 6-Methoxy-5-methyl-2-(N,N-dimethylamino)-benzo[b]thiophen-3-yl 4-[2-(1-Pyrrolidinyl)ethoxy]-phenyl Ketone.

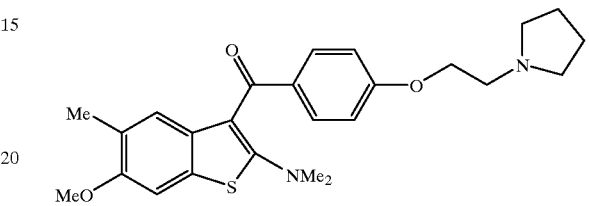

By essentially following the conditions described in Example 192, Part B, the title compound was prepared from the above aminobenzothiophene (Part B) and 4-[2-(1-pyrrolidinyl)ethoxy]benzoyl chloride.

IR (CHCl$_3$) 1598, 1475, 1425, 1255, 1161 cm$^{-1}$; FDMS 438 (M$^+$); Anal. Calcd for C$_{25}$H$_{30}$N$_2$O$_3$S: C, 68.46; H, 6.89; N, 6.39. Found: C, 68.69; H, 6.89; N, 6.21.

Part D. 6-Methoxy-5-methyl-2-[4-[2-(1-pyrrolidinyl)-ethoxy]phenyl]benzo[b]thiophen-3-yl 4-[2-(1-Pyrrolidinyl)ethoxy]phenyl Ketone Dioxalate.

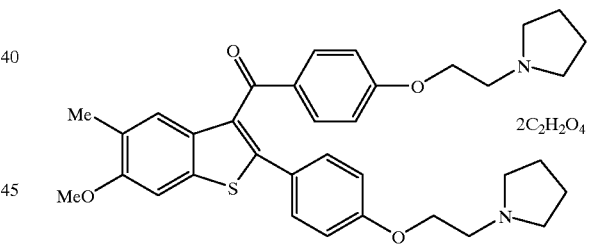

By essentially following the conditions described in Example 192, Part C the free base of the title compound was prepared as an oil from the above ketone (Part C) and 4-[2-(1-pyrrolidinyl)ethoxy]bromobenzene in 85% yield following flash chromatography (35% then 45%, 50% 55% THF with 5% TEA in hexanes). The product was converted to the dioxalate salt according to the procedure described in Example 1, Part C.

IR (KBr) 1720, 1641, 1598, 1470, 1251, 1169, 1041, 720 cm$^{-1}$; FDMS 585 (M+1); Anal. Calcd for C$_{35}$H$_{40}$N$_2$O$_4$S. 2 C$_2$H$_2$O$_4$. 0.6 H$_2$O: C, 60.39; H, 5.87; N, 3.61. Found: C, 60.07; H, 5.62; N, 3.75.

Part E. 6-Hydroxy-5-methyl-2-[4-[2-(1-pyrrolidinyl)-ethoxy]phenyl]benzo[b]thiophen-3-yl 4-[2-(i-Pyrrolidinyl)ethoxy]phenyl Ketone Dioxalate.

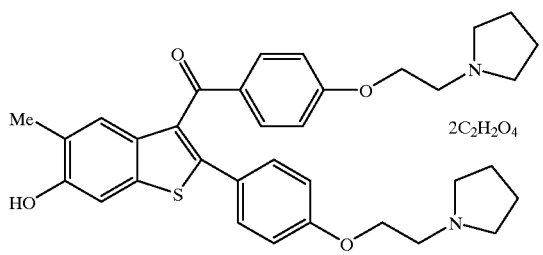

By essentially following the conditions described in the first step of Example 199, Part A, the free base of the title compound was prepared as an oil from the above methoxy-ketone (Part D) in 78% yield following radial chromatography (1% then 2% MeOH in CHCl₃ sat'd with NH₄OH). The product was converted to the dioxalate salt according to the procedure described in Example 1, Part C.

IR (KBr) 3415, 1719, 1598, 1462, 1251, 1168, 721 cm$^{-1}$; FDMS 571 (M+1); Anal. Calcd for $C_{34}H_{38}N_2O_4S$. 2 $C_2H_2O_4$. 0.2 $H_2O$: C, 60.50; H, 5.66; N, 3.71. Found: C, 60.15; H, 5.49; N, 3.79.

Part F. 1-[2-[4-[6-Hydroxy-5-methyl-3-[4-[2-(1-pyrrolidinyl)ethoxy]benzyl]benzo[b]thiophen-2-yl]phenoxy]-ethyl]pyrrolidine Dioxalate.

By essentially following the conditions described in Example 192, Part E, the free base of the title compound was prepared as a foam from the above ketone (Part E) in 68% yield following radial chromatography (1% MeOH in CHCl₃ sat'd with NH₄OH). The product was converted to the dioxalate salt according to the procedure described in Example 1, Part C.

IR (KBr) 3418, 1719, 1703, 1609, 1508, 1465, 1404, 1240, 721 cm$^{-1}$; FDMS 557 (M+1); Anal. Calcd for $C_{34}H_{40}N_2O_7S$. 2 $C_2H_2O_4$: C, 61.94; H, 6.02; N, 3.80. Found: C, 61.69; H, 5.87; N, 3.97.

EXAMPLE 201

Preparation of 6-Methoxy-3–13-methoxy-4-(1-pyrrolidinylmethyl)benzyl]-2-[4-[2-(1-pyrrolidinyl)ethoxy]-phenyl]benzo[b]thiophene Dioxalate.

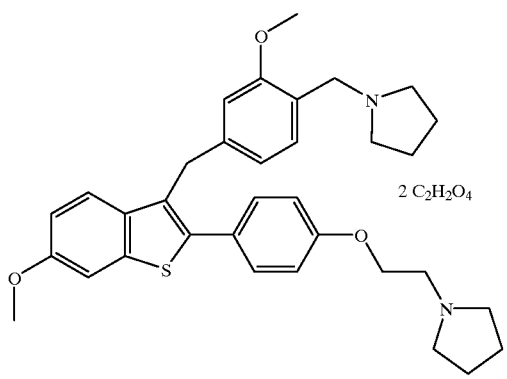

Part A. 6-Methoxy-2-[4-[2-(1-pyrrolidinyl)ethoxy]-phenyl]benzo[b]thiophen-3-yl 3-Methoxy-4-(1-pyrrolidinylmethyl)phenyl Ketone.

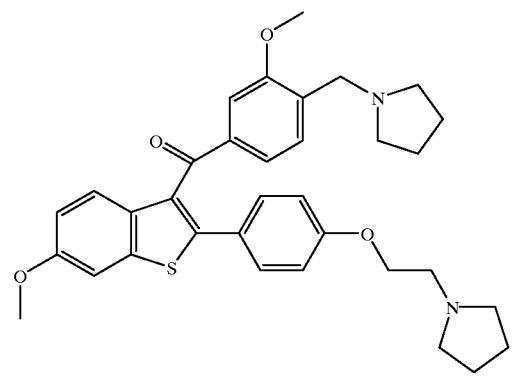

To a mixture of (210 mg, 0.37 mmol) of 6-hydroxy-2-[4-[2-(1-pyrrolidinyl)ethoxy]phenyl]benzo[b]thiophen-3-yl 3-methoxy-4-(1-pyrrolidinylmethyl)phenyl ketone (Example 163, Part C) in 2.0 mL of MeOH/CH₃CN solution (1:9 ratio) was added (0.091 mL, 0.52 mmol) of diisopropylethylamine and (0.26 mL, 0.52 mmol) 2M (trimethylsilyl)diazomethane in hexanes at room temperature. The reaction was stirred for 24 h. Another portion (0.20 mL, 0.40 mmol) of 2M (trimethylsilyl)diazomethane in hexanes was added along with 0.5 mL of MeOH, and the solution was stirred at room temperature for 24 h. Another portion (0.10 mL, 0.20 mmol) of 2M (trimethylsilyl) diazomethane in hexanes was added, and the solution was stirred at room temperature for 24 h. The reaction mixture was concentrated to dryness under reduced pressure and then taken up in 30 mL of $H_2O$ and washed with 25 mL of $H_2O$ and 1:1 satd. NaHCO₃-brine solution which were back extracted with $CH_2Cl_2$ (3×30 mL) and EtOAc (1×30 mL). The combined organic layers were dried over MgSO₄ and concentrated under reduced pressure. Purification by flash chromatography (silica gel, 7%[10% conc NH₄OH in MeOH]/CH₂Cl₂) afforded 92 mg (43%) of a yellow foam. FDMS 571 (M$^+$); Anal. Calcd for $C_{34}H_{38}N_2O_4S·0.40CH_2Cl_2$: C, 68.33; H, 6.47; N, 4.63. Found: C, 68.44; H, 6.42; N, 4.83.

Part B. 6-Methoxy-3-[3-methoxy-4-(1-pyrrolidinylmethyl)benzyl]-2-[4-[2-(1-pyrrolidinyl)ethoxy]phenyl]-benzo[b]thiophene Dioxalate.

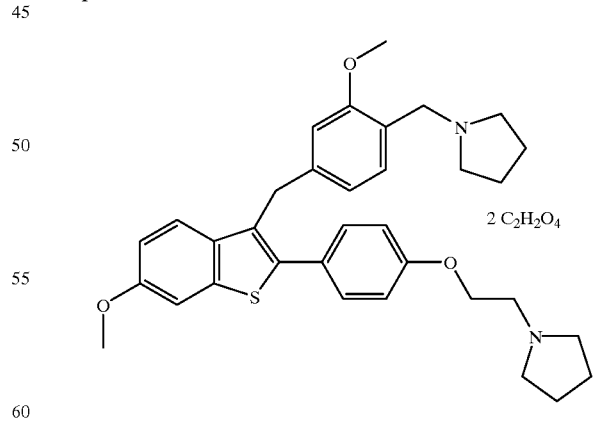

The free base of the title compound was prepared in 40% yield by essentially following the procedures outlined in Example 21, Part A, from 6-methoxy-2-[4-[2-(1-pyrrolidinyl)-ethoxy]phenyl]benzo[b]thiophen-3-yl 3-methoxy-4-(1-pyrrolidinylmethyl)phenyl ketone (Part A). The dioxalate salt was prepared by essentially following the procedures in Example 1, Part C. FDMS 557 (M+); Anal. calcd for $C_{34}H_{40}N_2O_3S \cdot 2C_2H_2O_4$: C, 61.94; H, 6.02; N, 3.80. Found: C, 62.15; H, 6.12; N, 3.88.

EXAMPLE 202

Preparation of 6-Hydroxy-3-[3-(N,N-dimethylamino)-4-(1-pyrrolidinylmethyl)benzyl]-2-[4-[2-(1-pyrrolidinyl)ethoxy]phenyl]benzo[b]thiophene Dioxalate.

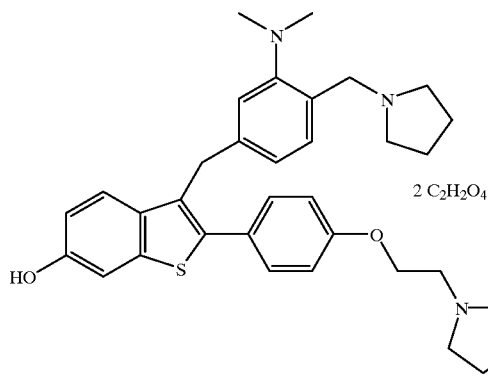

Part A. Methyl 4-Bromomethyl-3-nitrobenzoate.

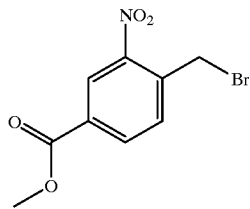

The title compound was prepared in 52% yield by essentially following the procedures outlined in Example 37, Part A, from methyl 4-methyl-3-nitrobenzoate.

FDMS 273 (M–1); Anal. calcd for $C_9H_8BrNO_4$: C, 39.44; H, 2.94; N, 5.11. Found: C, 39.65; H, 3.13; N, 5.00.

Part B. Methyl 4-(1-Pyrrolidinylmethyl)-3-nitrobenzoate.

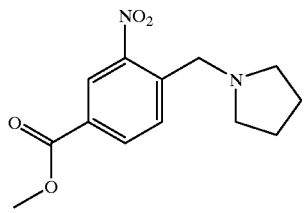

The title compound was prepared in 23% yield by essentially following the procedures outlined in Example 34, Part A, from methyl 4-bromomethyl-3-nitrobenzoate (Part A, above) and pyrrolidine.

FDMS 264 (M+); Anal. Calcd for $C_{13}H_{16}N_2O_4$: C, 59.08; H, 6.10; N, 10.60. Found: C, 59.00; H, 5.90; N, 10.83.

Part C. 3-Nitro-4-[(1-pyrrolidinyl)methyl]benzoic Acid.

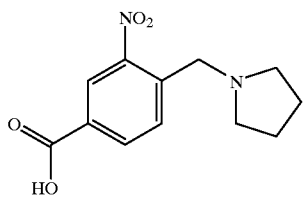

The title compound was prepared in quantitative yield by essentially following the procedures outlined in Example 20, Part C, from methyl 4-(1-pyrrolidinylmethyl)-3-nitrobenzoate (Part B, above).

$^1$HNMR (DMSO-$d_6$) d 8.33 (d, J=1.4 Hz, 1H), 8.18 (dd, J=1.4 Hz, 8.0 Hz, 1H), 7.83 (d, J=8.0 Hz, 1H), 4.00 (s, 2H), 2.52 (m, 4H), 1.70 (m, 4H); FDMS 250 (M+).

Part D. 6-Benzyloxy-2-(dimethylamino)benzo[b]thiophen-3-yl 3-Nitro-4-(1-pyrrolidinylmethyl)phenyl Ketone.

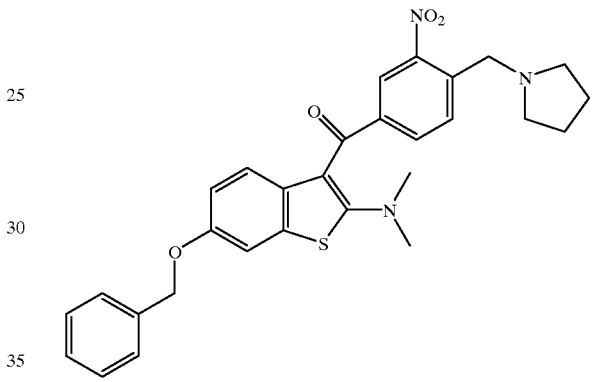

The title compound was prepared in 70% yield by essentially following the procedures outlined in Example 39, Part B (except using thionyl chloride instead of oxalyl chloride) from 3-nitro-4-[(1-pyrrolidinyl)methyl]benzoic acid (Part C, above) and 6-benzyloxy-2-(dimethylamino)-benzo[b]thiophene (Example 81, Part B).

FDMS 515 (M+); Anal. calcd for $C_{29}H_{29}N_3O_4S$: C, 67.55; H, 5.67; N, 8.15. Found: C, 67.71; H, 5.65; N, 7.93.

Part E. 6-Benzyloxy-2-(dimethylamino)benzo[b]thiophen-3-yl 3-Amino-4-(1-pyrrolidinylmethyl)phenyl Ketone.

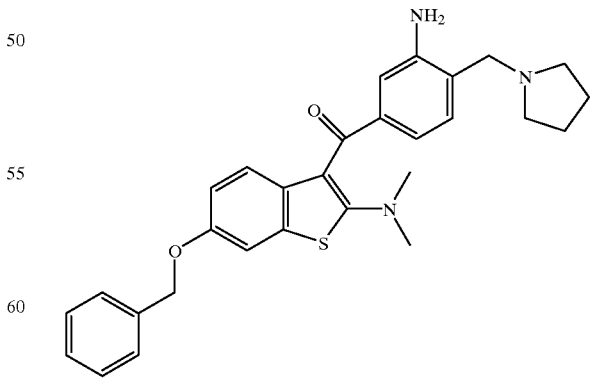

The 492 mg (0.955 mmol) of 6-benzyloxy-2-(dimethylamino)benzo[b]thiophen-3-yl 3-nitro-4-(1-pyrrolidinylmethyl)phenyl ketone (Part D, above) was dissolved in 21 mL of an EtOH/MeOH mixture (5:2 ratio). To the reaction mixture was added 1.07 g (4.77 mmol) of stannous chloride dihydrate. The reaction mixture was heated to 75° C. and to the solution was added 18.1 mg of sodium borohydride dissolved in 10 mL of EtOH/MeOH mixture (7:3 ratio). The solution was added dropwise via syringe over 25 min. The reaction mixture was stirred at 75° C. for 1.5 h. The reaction was then allowed to cool to room temperature. and was then poured into 20 mL of chilled (0° C.) water. The mixture was neutralized by adding 4 mL of 2N NaOH solution and then concentrated under reduced pressure to a volume of ~30 mL. This mixture was extracted with EtOAc (4×100 mL). The combined organic layers were dried over $MgSO_4$ and concentrated under reduced pressure to afford 451 mg (97% crude yield) as a orange foam.

FDMS 485 (M$^+$); Anal. calcd for $C_{29}H_{31}N_3O_2S·0.26CH_2Cl_2$: C, 69.22; H, 6.26; N, 8.28. Found: C, 69.37; H, 6.29; N, 7.90.

Part F. 6-Benzyloxy-2-dimethylamino)benzo[b]thiophen-3-yl 3-(Dimethylamino)-4-(1-pyrrolidinylmethyl)phenyl Ketone.

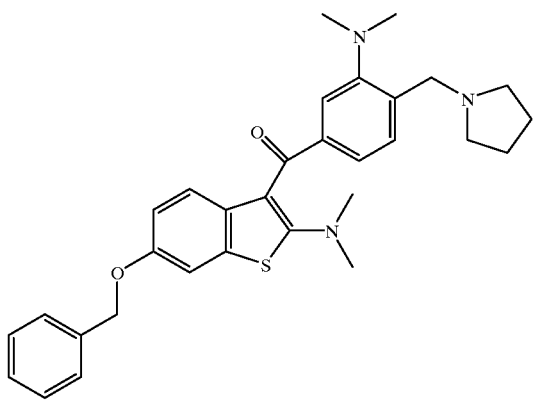

The 430 mg of 6-benzyloxy-2-(dimethylamino)-benzo[b]thiophen-3-yl 3-amino-4-(1-pyrrolidinylmethyl)phenyl ketone (Part E) was dissolved in 6.0 mL of THF. To the solution was added 234 mg of finely crushed sodium borohydride. The slurry was added dropwise to a mixture of 0.40 mL of 40% aqueous formaldehyde and 0.71 mL of 3M $H_2SO_4$ cooled to 0° C. After the addition solid NaOH was added to basify the solution. The layers were separated and the aqueous layer was extracted with EtOAc (2×25 mL). The combined organic layers were washed with brine (1×25 mL) and dried over $MgSO_4$. The residue was purified by flash chromatography (silica gel, 3% to 5%[10% conc $NH_4OH$/MeOH]/$CH_2Cl_2$) to afford 192 mg (0.373 mmol, 42%) of a yellow foam. FDMS 513 (M$^+$); Anal. calcd for $C_{31}H_{35}N_3O_2S$: C, 72.48; H, 6.87; N, 8.18. Found: C, 72.28; H, 6.73; N, 8.14.

Part G. 6-Benzyloxy-2-[4-[2-(1-pyrrolidinyl)ethoxy]-phenyl]benzo[b thiophen-3-yl 3-(Dimethylamino)-4-(1-pyrrolidinylmethyl)phenyl Ketone.

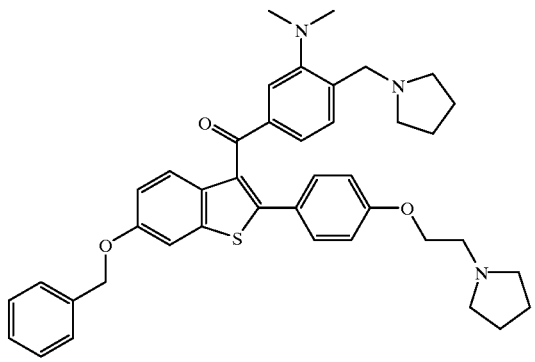

The title compound was prepared in 79% yield by essentially following the procedures outlined in Example 81, Part E, from 6-benzyloxy-2-(dimethylamino) benzo [b] thiophen-3-yl 3 -(dimethylamino) -4-(1-pyrrolidinylmethyl) phenyl ketone (Part F) and 4-[2-(1-pyrrolidinyl)ethoxy] phenyl magnesium bromide (Example 81, Part D).

FDMS 659 (M$^+$); Anal. calcd for $C_{41}H_{45}N_3O_3S·0.5H_2O$: C, 73.33; H, 6.78; N, 6.28. Found: C, 73.63; H, 6.94; N, 6.26.

Part H. 6-Hydroxy-3-[3-(dimethylamino)-4-(1-pyrrolidinylmethyl)benzyl] -2-[4-[2-(1-pyrrolidinyl)ethoxy]-phenyl]benzo [b]thiophene.

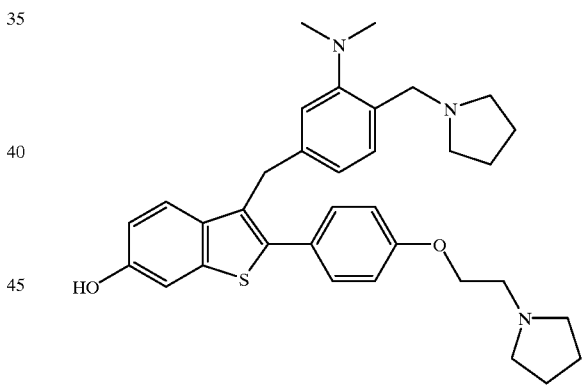

The title compound was prepared in 68% yield by essentially following the procedures outlined in Example 21, Part A and Example 163, Part C from 6-benzyloxy-2-[4-[2-(1-pyrrolidinyl)ethoxy]phenyl]benzo[b]thiophen-3-yl 3-(dimethylamino)-4-(1-pyrrolidinylmethyl)phenyl ketone (Part G).

FDMS 556 (M$^+$); Anal. calcd for $C_{34}H_{41}N_3O_2S$: C, 72.86; H, 7.47; N, 7.50. Found: C, 72.90; H, 7.50; N, 7.15.

Part I. 6-Hydroxy-3-[3-(dimethylamino)-4-(1-pyrrolidinylmethyl)benzyl]-2-[4-[2-(1-pyrrolidinyl)ethoxy]-phenyl]benzo[b]thiophene Dioxalate.

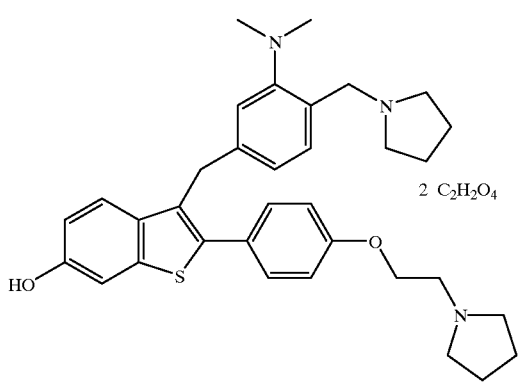

The title compound was prepared in 57% yield by essentially following the procedures outlined in Example 1, Part C from 6-hydroxy-3-[3-(dimethylamino)-4-(1-pyrrolidinylmethyl)benzyl]-2-[4-[2-(1-pyrrolidinyl)ethoxy]phenyl]-benzo[b]thiophene (Part H).

mp 124° C. (dec.); FDMS 556 (M⁺); Anal. calcd for $C_{34}H_{41}N_3O_2S \cdot 1.5C_2H_2O_4$: C, 64.33; H, 6.42; N, 6.08. Found: C, 64.38; H, 6.58; N, 5.76.

EXAMPLE 203

Preparation of 6-Hydroxy-3-[3-(methylamino)-4-(1-pyrrolidinylmethyl)benzyl]-2-[4-[2-(1-pyrrolidinyl)ethoxy3phenyl]benzo[b]thiophene.

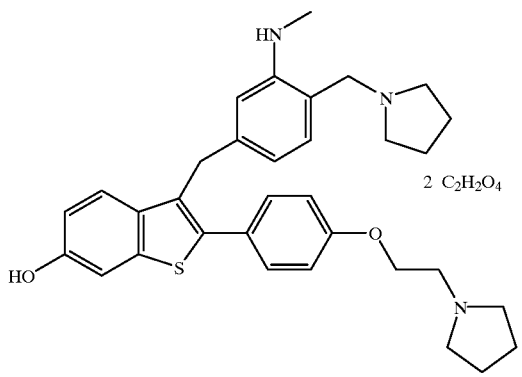

Part A. 4-Methyl-3-methylamino benzoic Acid.

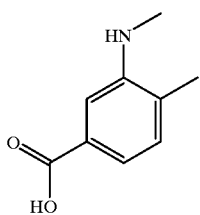

The title compound was prepared in 63% yield from 4-methyl-3-aminobenzoic acid by following the procedure cited in Ito, K., Sekiya, S. Chem. Pharm. Bull. 1966, 14(9), 1007–1009.

mp 167–169° C.; FDMS 165 (M⁺); Anal. calcd for $C_9H_{11}NO_2$: C, 65.44; H, 6.71; N, 8.48. Found: C, 65.16; H, 6.71; N, 8.37.

Part B. Methyl 4-Methyl-3-[(methoxycarbonyl)-(methyl)amino]benzoate.

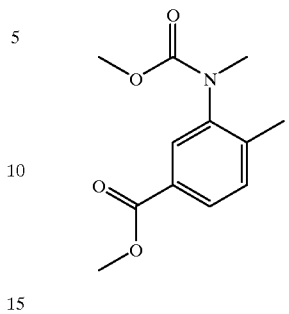

The 3.38 g of 4-methyl-3-methylamino benzoic acid (Part A) was dissolved in 150 mL of MeOH. To the solution was added 2 mL of conc. $H_2SO_4$. The reaction mixture was heated to reflux and stirred for 32 h. The mixture was concentrated to 10 mL under reduced pressure and diluted with 500 mL of EtOAc and basified at 0° C. with 60 mL of conc. sodium bicarbonate solution. The layers were separated and the aqueous layer was extracted (1×500 mL) with EtOAc. The combined organic layers were washed with brine (1×350 mL) and dried over $MgSO_4$ and concentrated under reduced pressure to yield 87% of the crude ester as a yellow oil. The 3.18 g of the ester was then dissolved in 350 mL of acetone. To the mixture was added 5.97 g of $K_2CO_3$ followed by the addition of 5.48 mL of methyl chloroformate. The reaction mixture was heated to reflux and stirred vigorously for 2.5 h. The reaction was cooled to room temperature and diluted with 250 mL of water. The mixture was extracted with EtOAc (2×500 mL). The combined organic layers were washed with brine (1×300 mL) and dried over $MgSO_4$ and concentrated under reduced pressure. Purification by PrepLC (silica gel, $CH_2Cl_2$) afforded 3.88 g (16.3 mmol, 80% yield from the benzoic acid) of yellow oil. FDMS 237 (M⁺); Anal. calcd for $C_{12}H_{15}NO_4$: C, 60.75; H, 6.37; N, 5.90. Found: C, 60.55; H, 6.12; N, 6.11.

Part C. Methyl 4-Bromomethyl-3-[(methoxycarbonyl)-(methyl)amino]benzoate.

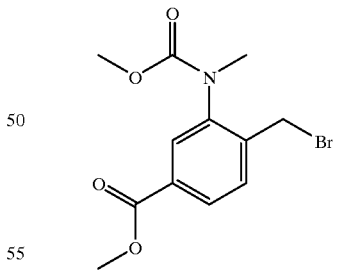

The title compound was prepared in 50% yield by essentially following the procedures outlined in Example 37, Part A from methyl 4-methyl-3-[(methoxycarbonyl)(methyl)-amino]benzoate (Part B).

mp 99–102° C.; FDMS 315 (M⁺); Anal. calcd for $C_{12}H_{14}BrNO_4$: C, 45.59; H, 4.46; N, 4.43. Found: C, 45.34; H, 4.45; N, 4.22.

Part D. Methyl 4-(1-Pyrrolidinyl)methyl-3-[(methoxycarbonyl)(methyl)amino]benzoate.

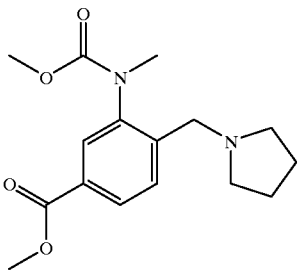

The title compound was prepared in (100% crude yield) by essentially following the procedures outlined in Example 37, Part A from 4-bromomethyl-3-[(methoxycarbonyl)(methyl)amino]-benzoate (Part C).
$^1$HNMR (CDCl$_3$) d 7.94 (d, J=6.0 Hz, 1H), 7.74 (s, 1H), 7.66 (d, J=6.0 Hz, 1H), 3.92 (s, 3H), 3.61 (s, 3H), 3.54 (s, 2H), 3.22 (s, 3H), 2.48 (m, 4H), 1.78 (m, 4H); FDMS 305 (M$^+$)
Part E. 3-[(Methoxycarbonyl)(methyl)aminol -4-[(1-pyrrolidinyl)methyl]benzoic Acid.

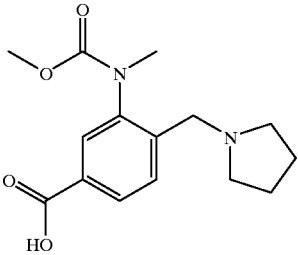

The title compound was prepared in (100% crude yield) by essentially following the procedures outlined in Example 20, Part C from methyl 4-(1-pyrrolidinyl)methyl-3-[(methoxycarbonyl)(methyl)amino]benzoate (Part D).
$^1$HNMR (DMSO-d$_6$) d 7.86 (dd, J=1.4 Hz, 8.0 Hz, 1H), 7.71 (s, 1H), 7.64 (d, J=8.0 Hz, 1H), 3.54 (s, 2H), 3.49 (s, 3H), 3.13 (s, 3H), 2.47 (m, 4H), 1.72 (m, 4H); FDMS 292 (M$^+$).
Part F. 6-Benzyloxy-2-dimethylaminobenzo[b]thiophen-3-yl 3-[(Methoxycarbonyl)(methyl)amino]-4-(1-pyrrolidinylmethyl)phenyl] Ketone.

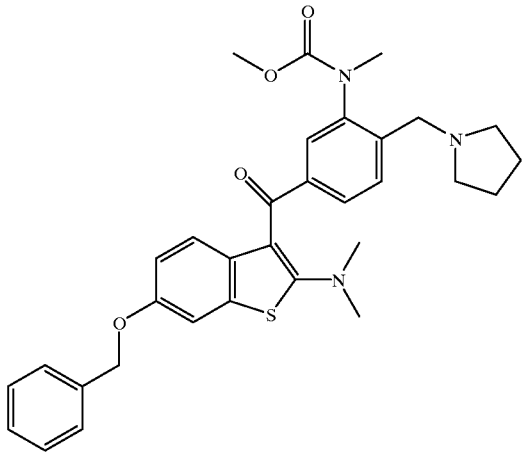

The title compound was prepared in 62% yield by essentially following the procedures outlined in Example 39, Part B (except using thionyl chloride instead of oxalyl chloride) from 3-[(methoxycarbonyl)(methyl)amino]-4-[(1-pyrrolidinyl)methyl]benzoic acid (Part E).
FDMS 557 (M$^+$); Anal. calcd for C$_{32}$H$_{35}$N$_3$O$_4$S: C, 68.92; H, 6.33; N, 7.53. Found: C, 68.85; H, 6.24; N, 7.37.
Part G. 6-Benzyloxy-2-[4-[2-(1-pyrrolidinyl)ethoxy]-phenyl]benzo[b]thiophen-3-yl 3-[(methoxycarbonyl)-(methyl)amino]-4-(1-pyrrolidinylmethyl)phenyl].

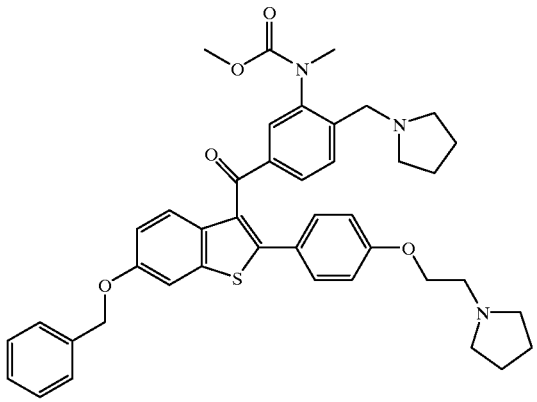

The title compound was prepared in 60% yield by essentially following the procedures outlined in Example 81, Part E from 6-benzyloxy-2-dimethylaminobenzo[b]thiophen-3-yl 3-[(methoxycarbonyl)(methyl)amino]-4-(1-pyrrolidinylmethyl)-phenyl] ketone (Part F) and 4-[2-(1-pyrrolidinyl)-ethoxy]phenyl magnesium bromide (Example 81, Part D).
mp 67–72° C.; FDMS 703 (M$^+$); Anal. calcd for C$_{42}$H$_{45}$N$_3$O$_5$S: C, 71.67; H, 6.44; N, 5.97. Found: C, 71.79; H, 6.68; N, 5.75.
Part H. 6-Benzyloxy-2-[4-[2-(1-pyrrolidinyl)ethoxy]-phenyl]benzo[b]thiophen-3-yl 3-Methylamino-4-(1-pyrrolidinylmethyl)phenyl Ketone.

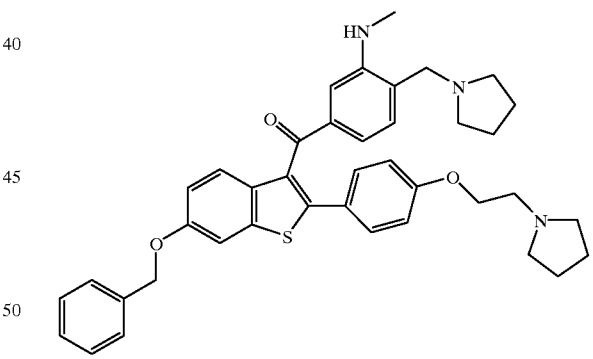

The 379 mg of 6-benzyloxy-2-[4-[2-(1-pyrrolidinyl)-ethoxy]phenyl]benzo[b]thiophen-3-yl 3-[(methoxycarbonyl)-(methyl)amino]-4-(1-pyrrolidinylmethyl)phenyl ketone (Part G) was dissolved in 5.5 mL of dry CH$_2$Cl$_2$. To the solution was added 0.31 mL of trimethylsilyl iodide. The reaction mixture was stirred for 5.5 h. The reaction was quenched with 0.3 mL of MEOH and the mixture was concentrated to dryness under reduced pressure. Purification by flash chromatography (silica gel, 5% to 8%[10% conc NH$_4$OH/MeOH]/CH$_2$Cl$_2$) afforded 130 mg (0.201 mmol, 37%) of a yellow foam.
FDMS 645 (M$^+$); Anal. Calcd for C$_{40}$H$_{43}$N$_3$O$_3$S·0.21CH$_2$Cl$_2$: C, 72.77; H, 6.59; N, 6.33. Found: C, 72.77; H, 6.60; N, 6.21.

Part I. 6-Hydroxy-3-[3-(methylamino)-4-(1-pyrrolidinylmethyl)benzyl]-2-[4-[2-(1-pyrrolidinyl)ethoxy]-phenyl]benzo[b]thiophene Dioxalate.

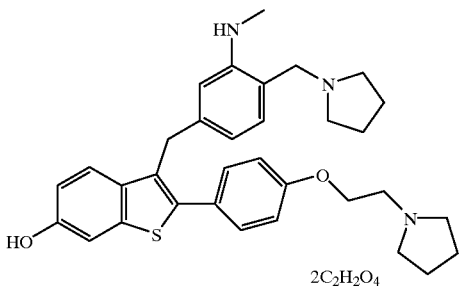

The title compound was prepared in 41% yield by essentially following the procedures outlined in Example 21, Part A, and Example 163, Part C; and formation of the dioxalate salt from Example 1, Part C, from 6-benzyloxy-2-[4-[2-(1-pyrrolidinyl)ethoxy]phenyl]benzo[b]thiophen-3-yl 3-methylamino-4-(1-pyrrolidinylmethyl)phenyl ketone (Part H).
FDMS 541 (M$^+$); Anal. Calcd for $C_{33}H_{39}N_3O_2S \cdot 1.5C_2H_2O_4 \cdot 0.6C_4H_8O_2$: C, 63.21; H, 6.46; N, 5.76. Found: C, 63.54; H, 6.49; N, 5.41.

EXAMPLE 204

Preparation of 6-Hydroxy-2-[4-[2-(1-pyrrolidinyl)-ethoxy]phenyl]benzo[b]thiophen-3-yl 3-(Methylamino)-4-(1-pyrrolidinylmethyl)phenyl Ketone Dioxalate.

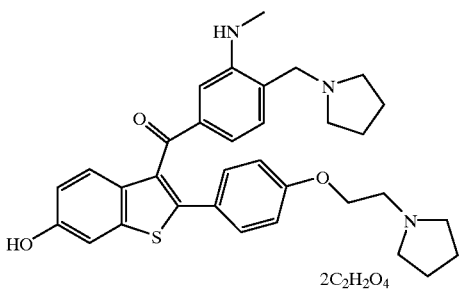

Part A. 6-Hydroxy-2-[4-[2-(1-pyrrolidinyl)ethoxy]-phenyl]benzo[b]thiophen-3-yl 3-(Methylamino)-4-(1-pyrrolidinylmethyl)phenyl Ketone.

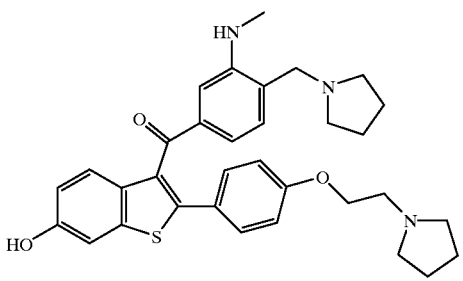

The title compound was prepared in 84% yield by essentially following the procedures outlined in Example 163, Part C from 6-benzyloxy-2-[4-[2-(1-pyrrolidinyl)ethoxy]-phenyl]benzo[b]thiophen-3-yl 3-methylamino-4-(1-pyrrolidinylmethyl)phenyl ketone (Example 203, Part H).

FDMS 555 (M$^+$); Anal. calcd for $C_{33}H_{37}N_3O_3S \cdot 0.13CH_2Cl_2$: C, 70.21; H, 6.63; N, 7.41. Found: C, 70.21; H, 6.70; N, 7.23.

Part B. 6-Hydroxy-2-[4-[2-(1-pyrrolidinyl)ethoxy]-phenyl]benzo[b]thiophen-3-yl 3-(Methylamino)-4-(1-pyrrolidinylmethyl)phenyl Ketone Dioxalate.

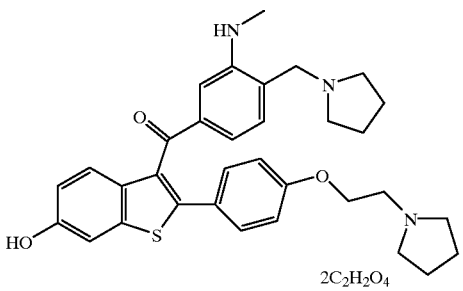

The title compound was prepared in 79% yield by essentially following the procedures outlined in Example 1, Part C from 6-hydroxy-2-[4-[2-(1-pyrrolidinyl)ethoxy]phenyl]-benzo[b]thiophen-3-yl 3-(methylamino)-4-(1-pyrrolidinylmethyl)phenyl ketone (Part A).
FDMS 555 (M$^+$); Anal. calcd for $C_{33}H_{37}N_3O_3S \cdot 1.6C_2H_2O_4 \cdot 0.5C_4H_8O_2$: C, 61.68; H, 5.99; N, 5.65. Found: C, 62.00; H, 6.10; N, 5.65.

EXAMPLE 205

Preparation of 6-Hydroxy-2-[3-hydroxymethyl-4-[2-(1-pyrrolidinyl)ethoxy]phenyl]benzo[b]thiophen-3-yl 3-Methoxy-4-(4-morpholinylmethyl)phenyl Ketone Dioxalate.

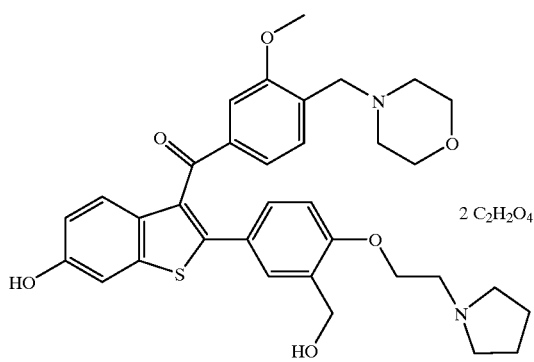

Part A. 1-[2-(2-Hydroxymethyl-4-bromophenoxy)ethyl]-pyrrolidine.

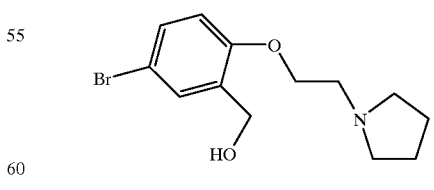

The title compound was prepared in 52% yield by essentially following the procedures outlined in Example 3, Part D, from 1-(2-chloroethyl)pyrrolidine hydrochloride and 5-bromo-2-hydroxybenzyl alcohol.
FDMS 301 (M$^+$); Anal. calcd for $C_{13}H_{18}BrNO_2$: C, 52.01; H, 6.04; N, 4.66. Found: C, 52.04; H, 6.22; N, 4.50.

Part B. 1-[2-(2-t-Butyldimethylsilyloxymethyl-4-bromophenoxy)ethyl]pyrrolidine.

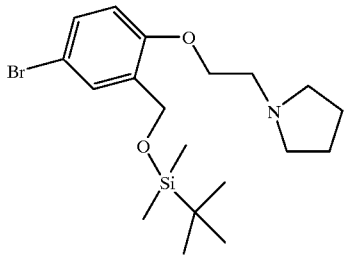

To a solution of (500 mg, 1.67 mmol) 1-[2-(2-hydroxymethyl-4-bromophenoxy)ethyl]pyrrolidine (Part A) in 5.5 mL of anhydrous DMF was added 377 mg of t-butyldimethylsilyl chloride followed by addition of 113 mg of imidazole. The reaction mixture was stirred at room temperature for 30 h. To the reaction was added 6 mL of water. The mixture was extracted with EtOAc (3×60 mL). The combined organic layers were dried over $MgSO_4$ and concentrated to dryness. The residue was azeotroped with xylenes to remove any DMF present. Purification by flash chromatography (silica gel, 3% to 4%[10% conc $NH_4OH$ in MeOH]/$CH_2Cl_2$) afforded 528 mg (1.27 mmol, 77%) of a yellow oil.

FDMS 413 ($M^+$); Anal. calcd for $C_{19}H_{32}BrNO_2Si$: C, 55.06; H, 7.78; N, 3.38. Found: C, 55.29; H, 7.99; N, 3.38.

Part C. 6-Benzyloxy-2-[3-t-butyldimethylsilyloxy-methyl-4-[2-(1-pyrrolidinyl)ethoxy3phenyl]-benzo[b]thiophen-3-yl 3-Methoxy-4-(1-pyrrolidinylmethyl)phenyl Ketone.

To a solution of (142 mg, 0.343 mmol) 1-[2-(2-t-butyldimethylsilyloxymethyl-4-bromophenoxy)ethyl] pyrrolidine (Part B) in 15 mL of freshly distilled THF cooled to −78° C. was added 0.24 mL of n-BuLi. The solution was stirred at −78° C. for 1 h 20 min. To the solution was added 1.0 mL of freshly prepared $MgBr_2$ (prepared by reacting 54 mL of dibromoethane with 13 mg of etched magnesium ribbon in 1.0 mL of THF) via cannula at −78° C. and stirred for 10 min. The ice bath was removed and the solution was stirred at room temperature for 30 min. The Grignard reagent was then added dropwise via a cannula to (177 mg, 0.343 mmol) 6-benzyloxy-2-(dimethylamino)benzo[b] thiophen-3-yl 3-methoxy-4-[(4-morpholinyl)methyl]phenyl ketone (Example 49, Part C) dissolved in 1.0 mL of THF at room temperature. The reaction was stirred for 5.5 h. The reaction was quenched by adding 4 mL of satd. $NH_4Cl$ solution. The mixture was then extracted with EtOAc (2×40 mL). The combined organic layers were dried over $MgSO_4$ and concentrated under reduced pressure. Purification by flash chromatography (silica gel, 46:46:8 $CHCl_3$-Hexanes-2M $NH_3$ in MeOH) afforded 30.8 mg (0.0381 mmol, 11%) of a yellow foam.

$^1$HNMR ($CDCl_3$) d 7.62 (d, J=8.9 Hz, 1H), 7.55 (s, 1H), 7.33–7.48 (m, 6H), 7.21–7.29 (m, 3H), 7.17 (dd, J=2.4 Hz, 8.4 Hz, 1H), 7.05 (dd, J=2.3 Hz, 8.9 Hz, 1H), 6.61 (d, J=8.5 Hz, 1H), 5.15 (s, 2H), 4.64 (s, 2H), 4.05 (t, J=5.8 Hz, 2H), 3.76 (s, 3H), 3.68 (t, J=4.4 Hz, 4H), 3.48 (s, 2H), 2.87 (dist t, 2H), 2.63 (m, 4H), 2.39 (t, J=4.4 Hz, 4H), 1.81 (m, 4H), 0.95 (s, 9H), 0.08 (s, 6H); FDMS 807 ($M^+$)

Part D. 6-Hydroxy-2-[3-hydroxymethyl-4-[2-(1-pyrrolidinyl)ethoxy]phenyl]benzo[b]thiophen-3-yl 3-Methoxy-4-(4-morpholinylmethyl) phenyl Ketone.

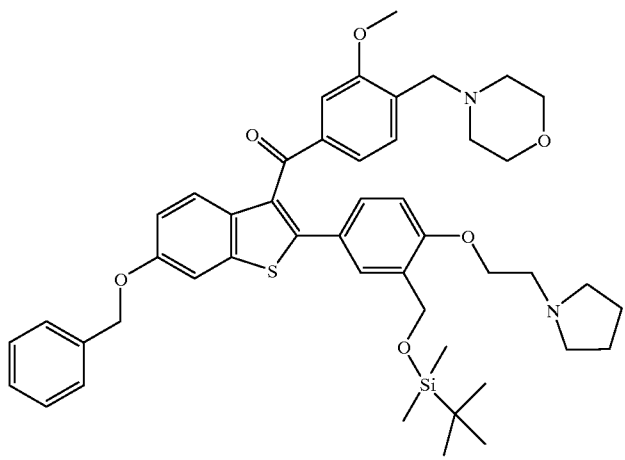

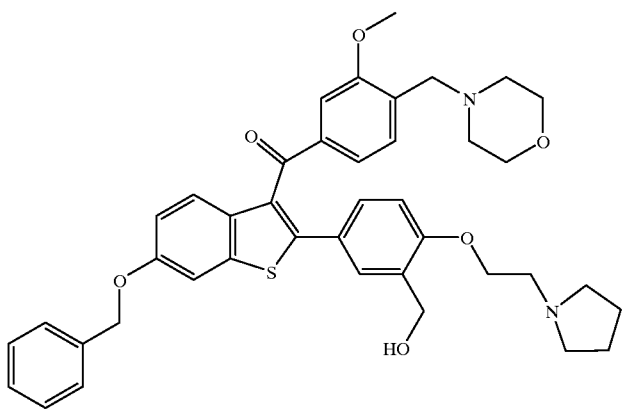

The (30.8 mg, 0.0381 mmol) 6-benzyloxy-2-[3-t-butyl-dimethylsilyloxymethyl-4-[2-(1-pyrrolidinyl)ethoxy]phenyl]-benzo[b]thiophen-3-yl 3-methoxy-4-(1-pyrrolidinylmethyl)-phenyl ketone (Part C) was dissolved in 0.5 mL of 1N tetrabutylammonium fluoride in THF. The solution was stirred at room temperature for 1 h. To the reaction mixture was added 1.0 mL of water and diluted with 15 mL of EtOAc. The layers were separated and the aqueous layer was extracted (1×10 mL) with EtOAc. The combined organic layers were dried over $MgSO_4$ and concentrated under reduced pressure. Purification by flash chromatography (silica gel, 80:17:3 THF-Hexanes-$Et_3N$) afforded 5.7 mg (0.0082 mmol, 22%) of a yellow oil.

$^1$HNMR ($CDCl_3$) d 7.63 (d, J=8.9 Hz, 1H), 7.36–7.48 (m, 7H), 7.22–7.30 (m, 4H), 7.17 (dd, J=2.4 Hz, 8.4 Hz, 1H), 7.07 (dd, J=2.3 Hz, 8.9 Hz, 1H), 6.72 (d, J=8.4 Hz, 1H), 5.15 (s, 2H), 4.48 (s, 2H), 4.17 (dist t, 2H), 3.77 (s, 3H), 3.69 (t, J=4.6 Hz, 4H), 3.49 (s, 2H), 2.85 (dist t, 2H), 2.64 (m, 4H), 2.40 (dist t, J=4.4 Hz, 4H), 1.82 (m, 4H); FDMS 693 (M$^+$)

Part E. 6-Hydroxy-2-[3-hydroxymethyl-4-[2-(1-pyrrolidinyl)ethoxy]phenyl]benzo b]thiophen-3-yl 3-Methoxy-4-(4-morpholinylmethyl)phenyl Ketone Dioxalate.

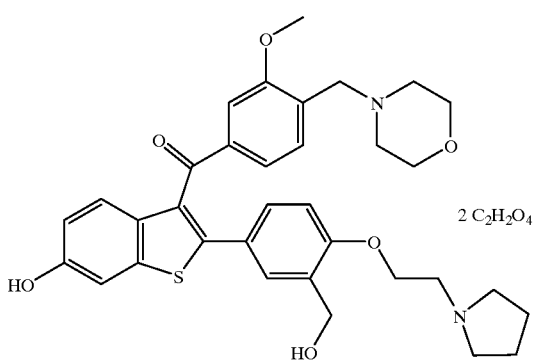

The title compound was prepared in 57% yield by essentially following the procedures outlined in Example 163, Part C, from 6-hydroxy-2-[3-hydroxymethyl[4-[2-(1-pyrrolidinyl)ethoxy]phenyl]benzo[b]thiophen-3-yl 3-methoxy-4-(4-morpholinylmethyl)phenyl ketone (Part D). The dioxalate salt was then prepared by essentially following the procedures outlined in Example 1, Part C.

Free Base: $^1$HNMR ($CDCl_3$) d 7.54 (d, J=8.8 Hz, 1H), 7.30 (s, 1H), 7.14 (m, 4H), 7.05 (s, 1H), 6.81 (d, J=8.8 Hz, 1H), 6.62 (d, J=8.1 Hz, 1H), 4.39 (s, 2H), 4.18 (dist t, 2H), 3.73 (s, 3H), 3.68 (dist t, 4H), 3.49 (s, 2H), 2.95 (dist t, 2H), 2.79 (m, 4H), 2.39 (dist t, 4H), 1.91 (m, 4H); FDMS 603 (M$^+$).

EXAMPLE 206

Preparation of 6-Hydroxy-2-[3-benzyloxymethyl-4-[2-(1-pyrrolidinyl)ethoxy]phenyl]benzo[b]thiophen-3-yl 3-Methoxy-4-(4-morpholinylmethyl)phenyl Ketone Dioxalate.

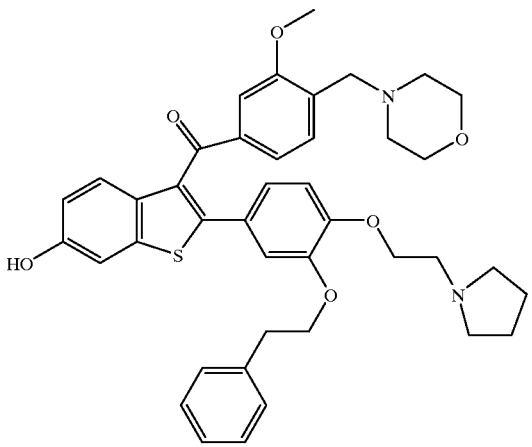

Part A. 1-[2-(2-Benzyloxymethyl-4-bromophenoxy)-ethyl]pyrrolidine.

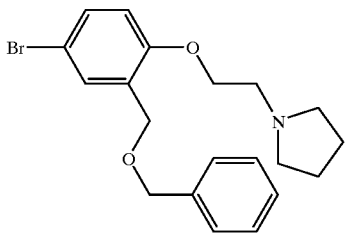

To a solution containing (1.00 g, 3.33 mmol) 1-[2-(2-hydroxymethyl-4-bromophenoxy)ethyl]pyrrolidine (Example 205, Part A) in 65 mL of anhydrous DMF was added 173 mg of NaH (60% dispersion in mineral spirits). The dropwise of addition of (0.40 mL, 3.33 mmol) benzyl bromide and (12.0 mg, 0.0333 mmol) of tetrabutylammonium iodide followed. The reaction was stirred at room temperature. for 1.5 h. The reaction was quenched by the addition of 100 mL of water. The mixture was extracted with EtOAc (3×500 mL). The combined organic layers were washed with brine (1×300 mL) and dried over MgSO$_4$ and concentrated under reduced pressure and azeotroped with xylenes to remove residual DMF. Purification by flash chromatography (silica gel, 3.5% to 5.5%[10% conc NH$_4$OH in MeOH]/CH$_2$Cl$_2$) afforded 660 mg (1.69 mmol, 51%) of a yellow oil.

FDMS 390 (M$^+$); Anal. calcd for C$_{20}$H$_{24}$BrNO$_2$: C, 61.54; H, 6.20; N, 3.58. Found: C, 61.36; H, 6.41; N, 3.52.

Part B. 6-Benzyloxy-2-[3-benzyloxymethyl-4-[2-(1-pyrrolidinyl)ethoxy]phenyl]benzo[b]thiophen-3-yl 3-Methoxy-4-(4-morpholinylmethyl)phenyl Ketone.

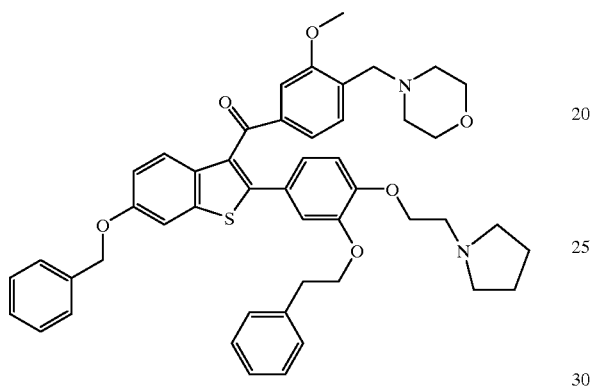

The title compound was prepared in 11% yield by essentially following the procedures outlined in Example 81, Part E, from 6-benzyloxy-2-(dimethylamino)benzo[b]thiophen-3-yl 3-methoxy-4-[(4-morpholinyl)methyl]phenyl ketone (Example 49, Part C) and 1-[2-(2-benzyloxymethyl-4-bromophenoxy)-ethyl]pyrrolidine (Part A).

$^1$HNMR (CDCl$_3$) d 7.63 (d, J=8.9 Hz, 1H), 7.19–7.49 (m, 16H), 7.06 (dd, J=2.4 Hz, 8.9 Hz, 1H), 6.68 (d, J=8.5 Hz, 1H), 5.15 (s, 2H), 4.48 (s, 2H), 4.46 (s, 2H), 4.05 (t, J=5.9 Hz, 2H), 3.70 (s, 3H), 3.65 (t, J=4.5 Hz, 4H), 3.45 (s, 2H), 2.85 (dist t, 2H), 2.60 (m, 4H), 2.37 (t, J=4.5 Hz, 4H), 1.77 (m, 4H).

Part C. 6-Hydroxy-2-[3-benzyloxymethyl-4-[2-(1-pyrrolidinyl)ethoxy]phenyl]benzo[b]thiophen-3-yl 3-Methoxy-4-(4-morpholinylmethyl)phenyl Ketone.

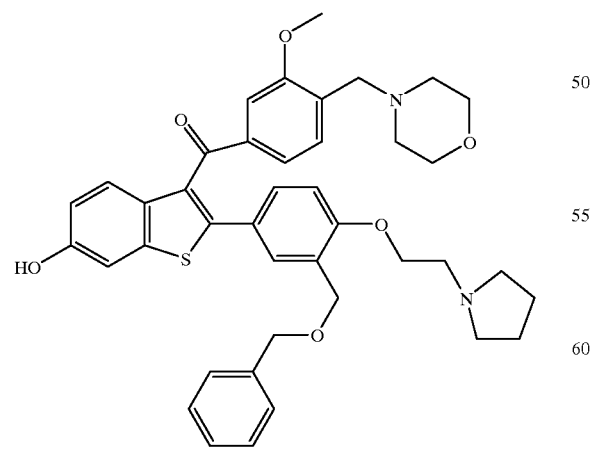

The title compound was prepared in 89% yield by essentially following the procedures outlined in Example 163, Part C, from 6-benzyloxy-2-[3-benzyloxymethyl-4-[2-(1-pyrrolidinyl)ethoxy]phenyl]benzo[b]thiophen-3-yl 3-methoxy-4-(4-morpholinylmethyl)phenyl ketone (Part B).

mp 87–90° C.; FDMS 693 (M$^+$); Anal. calcd for C$_{41}$H$_{44}$N$_2$O$_6$S·0.91H$_2$O: C, 69.43; H, 6.51; N, 3.95. Found: C, 69.43; H, 6.43; N, 3.95.

EXAMPLE 207

Preparation of 5-Hydroxy-2-[4-[2-(1-pyrrolidinyl)-ethoxy]phenyl]benzo[b]thiophen-3-yl 3-Methoxy-4-[(1-pyrrolidinyl)methyl]phenyl Ketone.

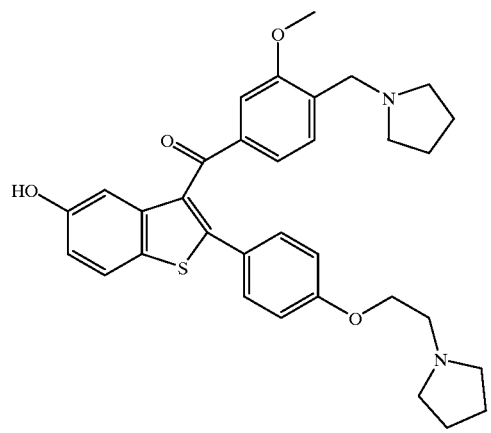

Part A. 2-[4-[2-(1-Pyrrolidinyl)ethoxy]phenyl-5-(trifluoromethylsulfonyloxy)benzo[b]thiophene.

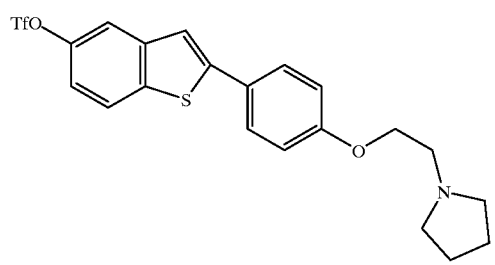

The title compound was prepared from 5-methoxy-[2-[4-[2-(1-pyrrolidinyl)ethoxy]phenyl]benzo[b]thiophene in 56% yield for 2 steps via demethylation previously described and triflate formation by a conventional method.

mp 95–99° C.; FDMS 470.9 (M+); Anal. Calcd for C$_{21}$H$_{20}$F$_3$NO$_4$S$_2$·0.6C$_4$H$_8$O: C, 54.60; H, 4.86; N, 2.73. Found: C, 54.95; H, 4.54; N, 2.72.

Part B. 2-[4-[2-(1-Pyrrolidinyl)ethoxy]phenyl-5-(trifluoromethylsulfonyloxy)benzo[b]thiophen-3-yl 3-Methoxy-4-[(1-pyrrolidinyl)methyl]phenyl Ketone.

323

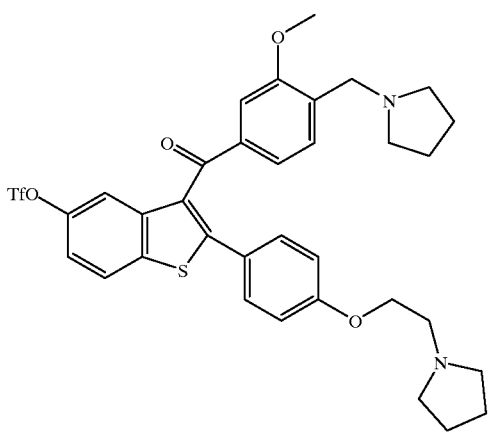

The title compound was prepared in 61% yield from the benzo[b]thiophene Part A) via a Friedel-Craft acylation reaction previously described.

FDMS 674 (M+); Anal. Calcd for $C_{33}H_{33}F_3N_2O_6S_2$: C, 58.74; H, 4.93; N, 4.15. Found: C, 58.74; H, 4.93; N, 3.96.

Part C. 5-Hydroxy-2-[4-[2-(1-pyrrolidinyl)ethoxy]-phenyl]benzo[b]thiophen-3-yl 3-Methoxy-4-[(1-pyrrolidinyl)methyl]phenyl Ketone.

A mixture of 769.4 mg (1.1 mmol) of the above triflate, 0.45 mL of MeOH, and 464 mg (3.4 mmol) of $K_2CO_3$ in 10 mL of anhydrous DMF was purged with CO gas under a positive pressure of a double-layered balloon for 10–15 min. To this was added 13 mg (0.056 mmol) of $Pd(OAc)_2$ and 30 mg (0.11 mmol) of $PPh_3$, and the reaction mixture was purged with CO gas for another 5 min. The mixture was then heated at 65° C. (bath temp) over the weekend (~3 days). The mixture was filtered through a pad of diatomaceous earth with EtOAc rinse. The filtrate was treated with 25 mL of saturated aqueous $NH_4Cl$. This was then taken up in 100 mL of EtOAc and washed with saturated aqueous $NaHCO_3$, $H_2O$, and brine (75 mL each). The aqueous layers were backextracted with EtOAc (100 mL×2). Combined organic layers were dried over $MgSO_4$, concentrated, and purified by flash chromatography with 8:92 (10% conc $NH_4OH$ in MeOH)-$CH_2Cl_2$ to afford a 27% yield of the title compound, instead of an expected carbonylation product.

FDMS 557.1 (M+1); Anal. Calcd for $C_{33}H_{36}N_2O_4S \cdot 0.3CH_2Cl_2$: C, 68.70; H, 6.34; N, 4.81. Found: C, 68.61; H, 6.38; N, 4.67.

324

EXAMPLE 208

Preparation of 3-[4-[(Diethylamino)methyl]-3-methoxybenzyl]-6-hydroxy-2-[4-[2-(1-pyrrolidinyl)ethoxy]-phenyl]benzo[b]thiophene Dioxalate Dihydrate.

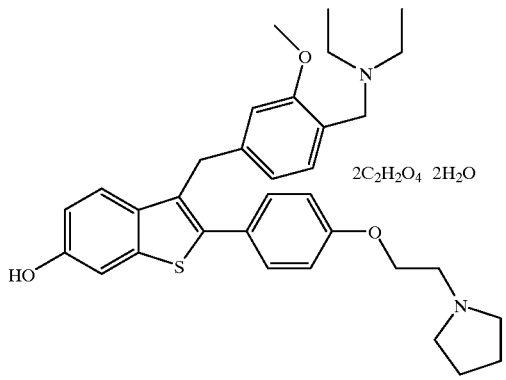

Part A. Methyl 4-(Diethylamino)methyl-3-methoxybenzoate.

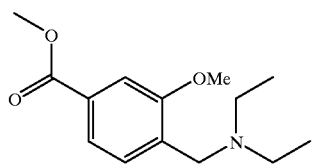

By following essentially the procedure of Example 137, Part B, the amino-ester was prepared from diethylamine and methyl 4-bromomethyl-3-methoxybenzoate (Example 139, Part A) in 79% yield.

$^1$H NMR (CDCl$_3$) δ 7.63 (d, J=7.9 Hz, 2H), 7.53 (d, J=7.7 Hz, 2H), 7.51 (s, 1H), 3.92 (s, 3H), 3.89 (s, 3H), 3.62 (s, 2H), 2.55 (q, J=7.1 Hz, 4H), 1.06 (t, J=7.1 Hz, 6H).

Part B. 6-Benzyloxy-2-dimethylaminobenzo[b]thiophen-3-yl 4-[(Diethylamino)methyl]-3-methoxyphenyl Ketone.

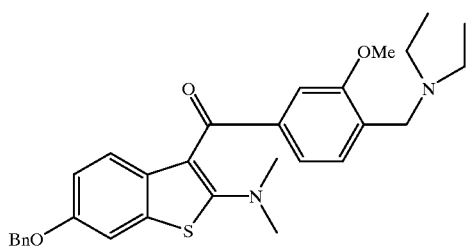

Methyl 4-(diethylamino)methyl-3-methoxybenzoate (0.39 g; 1.6 mmol) was dissolved in 5 mL of a mixture of THF/MeOH/H$_2$O (3:1:1). LiOH (72 mg; 1.1 eq) was added, and the resultant mixture stirred overnight at room temperature. The mixture was neutralized with conc HCl, and the solvent removed under reduced pressure. The crude 4-(diethylamino)methyl-3-methoxybenzoic acid hydrochloride was dried in vacuo for 2 h, and used without purification.

The 4-(diethylamino)methyl-3-methoxybenzoic acid hydrochloride was dissolved in 10 mL of SOCl2 with 3 drops of DMF, and heated under reflux for 2 h. After cooling, the excess SOCl₂ was removed under reduced pressure, and the crude acid chloride hydrochloride dried in vacuo for 2 h, and used without purification.

The acid chloride was combined with 6-benzyloxy-2-dimethylaminobenzo[b]thiophene (0.9 eq) (Example 81, Part B) in chlorobenzene (8 mL), and heated under reflux for 2 h, then cooled and concentrated under reduced pressure. The title compound was isolated (0.61 g; 73% yield overall) as a viscous yellow oil by flash chromatography on silica gel, eluting with a gradient of EtOAc(100–95%)/Et3N (0–5%).

¹H NMR (CDCl₃) δ 7.5–7.3 (m, 9H), 7.19 (s, 1H), 6.88 (d, J=6.5, 1H), 5.08 (s, 2H), 3.85 (s, 3H), 3.65 (s, 2H), 2.88 (s, 6H), 2.56 (q, J=7.0 Hz, 4H), 1.05 (t, J=7.0 Hz, 6H). Anal. calc'd for $C_{30}H_{34}N_2O_3S$: C, 71,68; H, 6.82; N, 5.57. Found: C, 71.95; H, 6.94; N, 5.76. FDMS 502 (M).

Part C. 6-Benzyloxy-2-[4-[2-(1-pyrrolidinyl)ethoxy]-phenyl]benzo[b]thiophen-3-yl 4-[(Diethylamino)methyl]-3-methoxyphenyl Ketone.

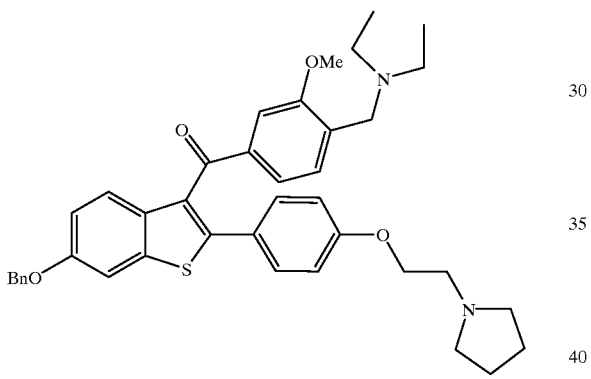

The Grignard reagent 4-[2-(1-pyrrolidinyl)ethoxy]phenyl-magnesium bromide was generated in THF from bromo-4-[2-(1-pyrrolidinyl)ethoxy]benzene and magnesium (0.9 eq).

The above 6-benzyloxy-2-dimethylaminobenzo[b]thiophene (Part B) (0.61 g; 1.21 mmol) was dissolved in THF (7 mL) under a nitrogen atmosphere, and cooled in an ice-water bath. The Grignard reagent (1.3 eq) was added and stirring continued in the cold for 2.5 h. To the reaction mixture was added 40 mL of saturated NH₄Cl, and extraction was carried out with CH₂Cl₂. The combined organics were dried by passage through Na₂SO₄. The title compound was isolated as a yellow oil (0.45 g; 57% yield) by flash chromatography on silica gel, eluting with a gradient of hexanes(50–20%)/EtOAc(50–75%)/Et3N(0–5%).

¹H NMR (CDCl₃) δ 7.62 (d, J=8.9 Hz, 1H), 7.5–7.3 (m, 11H), 7.07 (d, J=8.3 Hz, 1H), 6.75 (d, J=8.3 Hz, 2H), 5.16 (s, 2H), 4.03 (t, J=6.0 Hz, 2H), 3.79 (s, 3H), 3.54 (s, 2H), 2.85 (t, J=6.0 Hz, 2H), 2.60 (br s, 4H), 2.47 (q, J=7.1 Hz, 4H), 1.80 (br s, 4H), 1.00 (t, J=7.2 Hz, 6H). Anal. calc'd for $C_{40}H_{44}N_2O_4S \cdot H_2O$: C, 72.04; H, 6.95; N, 4.20. Found: C, 72.19; H, 6.74; N, 4.29. FDMS 648 (M).

Part D. 6-Benzyloxy-3-[4-[(Diethylamino)methyl]-3-methoxybenzyl]-2-[4-(2-(1-pyrrolidinyl)ethoxy]-phenyl]benzo[b]thiophene.

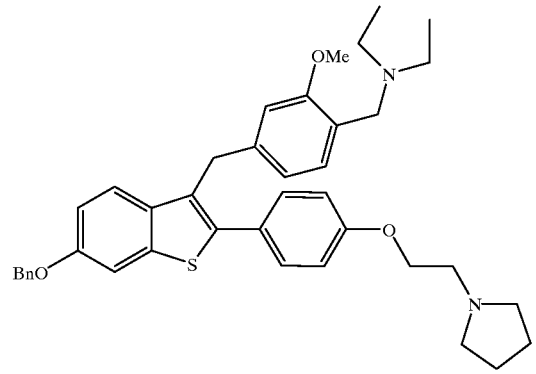

Following essentially the procedure of Example 138, Part A, the title compound was produced from the above ketone (Part C) in 68% yield. Purification was carried out by flash chromatography on silica gel, eluting with a gradient of hexanes(50–20%)/EtOAc(50–75%)/Et₃N(0–5%).

¹H NMR (CDCl₃) δ 7.5–7.2 (m, 10H), 6.94 (t, J=8.6 Hz, 3H), 6.66 (m, 2H), 5.12 (S, 2H), 4.20 (S, 2H), 4.12 (t, J=6.0 Hz, 2H), 3.68 (S, 3H), 3.53 (S, 2H), 2.90 (t, J=6.0 Hz, 2H), 2.62 (br s, 4H), 2.54 (q, J=7.1 Hz, 4H), 1.81 (br s, 4H), 1.04 (t, J=7.2 Hz, 6H). FDMS 635.1 (M+1).

Part E. 3-[4-[(Diethylamino)methyl]-3-methoxybenzyl]-6-hydroxy-2-[4-[2-(1-pyrrolidinyl)ethoxy]phenyl]-benzo[b]thiophene Dioxalate Dihydrate.

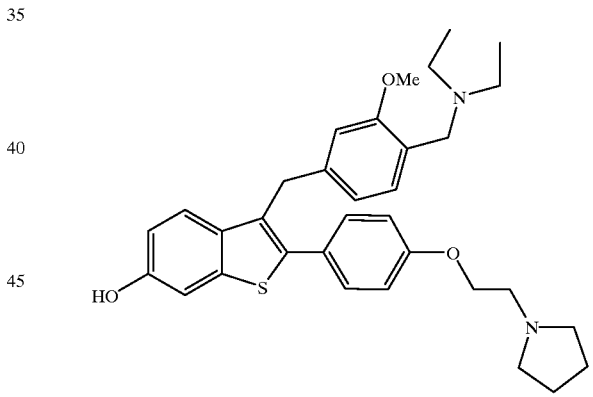

The above benzyloxy compound (Part D) (0.26g; 0.41 mmol) was dissolved in 5 mL of THF and treated with 4 mL of 25% aqueous HCO₂NH₄ and 0.3 g of 10% Pd on charcoal catalyst. The mixture was stirred at room temperature overnight, filtered through diatomaceous earth, and washed well with THF. Water was added and extraction carried out with CH₂Cl₂ (4×25 mL). The combined organics were dried by passage through Na₂SO₄. The title compound (70 mg; 31% yield) was isolated by flash chromatography on silica gel, eluting with a gradient of EtOAc(100–95%)/Et₃N (0–5%).

Anal. calc'd for $C_{33}H_{40}N_2O_3S \cdot C_2H_2O_4 \cdot 2.25H_2O$: C, 58.07; H, 6.39; N, 3.66. Found: C, 57.98; H, 6.00; N, 3.40. FDMS 544.9 (M+1).

EXAMPLE 209

Preparation of 2-[4-(2-Aminoethyl)phenyl]-6-hydroxy-3-[3-methoxy-4-[(1-pyrrolidinyl)methyl]benzyl]-benzo[b]thiophene Dioxalate.

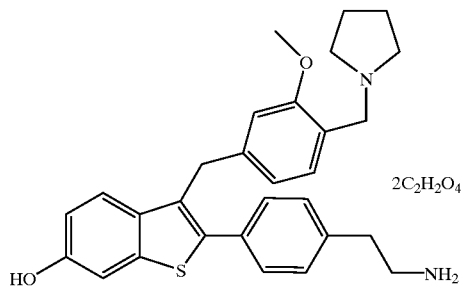

Part A. 6-Benzyloxy-2-dimethylaminobenzo[b]thiophen-3-yl 3-Methoxy-4-[(1-pyrrolidinyl)methyl]phenyl Ketone.

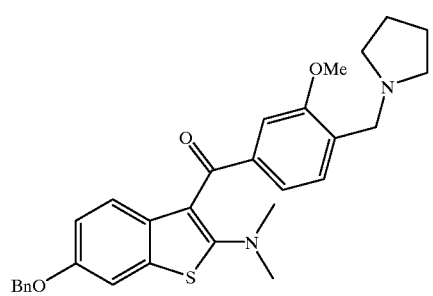

Following essentially the procedure of Example 208, Part B, the title compound was prepared from methyl 3-methoxy-4-[(1-pyrrolidinyl)methyl]benzoate (Example 139, Part B) and 6-benzyloxy-2-dimethylaminobenzo[b]thiophene in 80% yield.
$^1$H NMR (CDCl$_3$) δ 7.45–7.32 (m, 9H), 7.19 (s, 1H), 6.88 (d, J=8.9, 1H), 5.08 (s, 2H), 3.88 (s, 3H), 3.73 (s, 2H), 2.89 (s, 6H), 2.60 (br s, 4H), 1.81 (br s, 4H). FDMS 500.0 (M).

Part B. 2-[4-(2-Aminoethyl)phenyl]-6-benzyloxybenzo[b]thiophen-3-yl 3-Methoxy-4-[(1-pyrrolidinyl)methyl]phenyl Ketone.

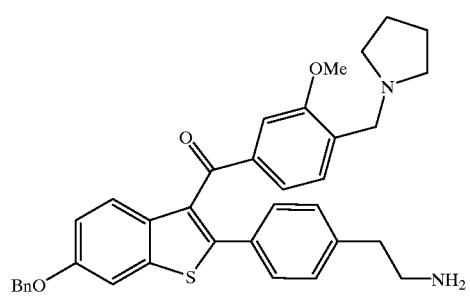

4-(2-Aminoethyl)bromobenzene (1.7 g; 8.4 mmol) and 2.3 mL (2 eq) of ET$_3$N were combined with 3 mL of anhydrous DMF in a flame-dried, argon-filled flask. 1,2-Bis(chlorodimethyl-silyl)ethane was added in 3.0 mL of DMF. The mixture was stirred at room temperature for 2 h. The mixture was filtered through a sintered glass funnel, and concentrated under reduced pressure. The colorless oil subsequently crystallized.

The protected bromobenzene derivative was converted to the corresponding Grignard reagent. Magnesium (33 mg; 1.35 mmol) was placed in a flask which was subsequently flame-dried and filled with argon. Anhydrous THF (3 mL) and the protected aminoarylbromide were added with a small crystal of I$_2$. The mixture was heated under reflux for 3 h. The resulting reagent was used without purification.

The above aminobenzothiophene (Part A) (4.10 g; 8.2 mmol) was dissolved in anhydrous THF in a flame-dried, argon-filled flask, and cooled in an ice-water bath. The Grignard reagent prepared above (1.5 eq) was added dropwise. The mixture was stirred in the cold for 1 h, then saturated NH$_4$Cl was added, and extraction was carried out with CH$_2$Cl$_2$. The combined organics were dried by passage through Na$_2$SO$_4$. The product (4.2 g of yellow oil; 89% yield) was purified by flash chromatography on silica gel, eluting with a gradient of EtOAc(100–85%)/ET$_3$N(0–5%)/NH$_4$OH(0–5%).

$^1$H NMR (CDCl3) δ 7.63 (d, J=8.9 Hz, 1H), 7.5–7.2 (m, 11H), 7.05 (m, 3H), 5.16 (s, 2H), 3.79 (s, 3H), 3.61 (s, 2H), 2.89 (t, J=6.6 Hz, 2H), 2.67 (t, J=6.7 Hz, 2H), 2.50 (br s, 4H), 1.77 (br s, 4H), 1.40 (br s, 2H). FDMS 577.1 (M+1).

Part C. 2-[4-(2-Aminoethyl)phenyl]-6-benzyloxy-3-[3-methoxy-4-[(1-pyrrolidinyl)methyl]benzyl]-benzo[b]thiophene.

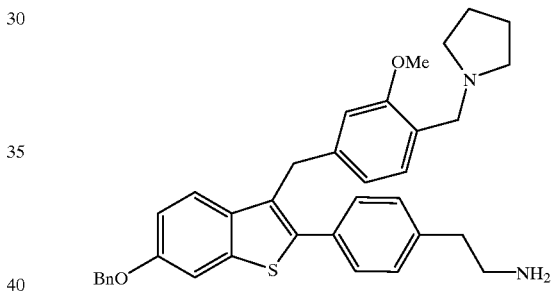

Following essentially the procedure of Example 138, Part A, the title compound was prepared from the above ketone (Part B) in 59% yield. Purification was carried out by flash chromatography on silica gel, eluting with a gradient of EtOAc(100–85%)/MeOH(0–10%)/NH$_4$OH(0–5%).

$^1$H NMR (CDCl$_3$) δ 7.47–7.33 (m, 9H), 7.23 (m, 3H), 6.98 (d, J=8.7 Hz, 1H), 6.69 (d, J=7.6 Hz, 1H), 6.65 (s, 1H), 5.13 (s, 2H), 4.23 (s, 2H), 3.69 (s, 3H), 3.63 (s, 2H), 2.98 (t, J=6.8 Hz, 2H), 2.77 (t, J=6.8 Hz, 2H), 2.57 (br s, 4H), 1.79 (br s, 4H). FDMS 563.1 (M+1).

Part D. 2-[4-(2-Aminoethyl)phenyl]-6-hydroxy-3-[3-methoxy-4-[(1-pyrrolidinyl)methyllbenzyl]-enzo[b]thiophene Dioxalate.

By following essentially the procedure of Example 208, Part E, the title compound was prepared from the benzyloxy compound of Part C, above, in 63% yield.

Anal. calc'd for C$_{29}$H$_{32}$N$_2$O$_2$S·2C$_2$H$_2$O$_4$: C, 73.0; H, 6.87; N, 5.87. Found: C, 72.77; H, 6.81; N, 5.49. FDMS 473.1 (M+1).

EXAMPLE 210

Preparation of 6-Hydroxy-3-[3-methoxy-4-(1-pyrrolidinylmethyl)benzyl]-2-[4-[(2-dimethylamino-1-oxo-ethyl)amino]phenyl]benzo[b]thiophene.

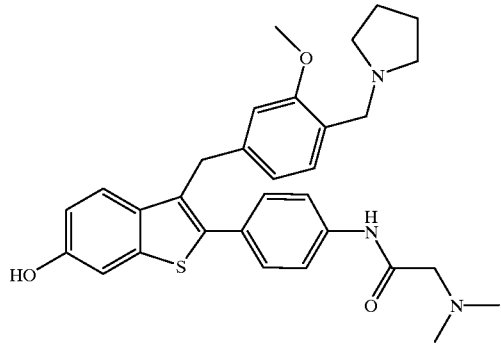

Part A. 6-Benzyloxy-2-[4-[bis(trimethylsilyl)amino]-phenyl]benzo b]thiophen-3-yl 3-Methoxy-4-[(1-pyrrolidinyl)methyl]phenyl Ketone.

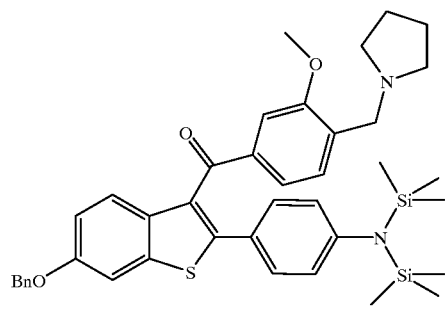

Magnesium turnings (0.25 g) were placed in a two-neck 100 mL round-bottom flask fitted with a reflux condenser and a magnetic stir bar. The whole apparatus was flame-dried and allowed to cool to ambient temperature. Dry THF (17 mL) and a small crystal of iodine were then introduced followed by slow addition of 4-bromo-N,N-bis(trimethylylsilyl)aniline (3.36 g) while stirring at ambient temperature. The reaction mixture was warmed to a gentle reflux for 1.5 h or until magnesium turnings were completely consumed to give a 0.5M solution of the Grignard reagent. This freshly prepared Grignard solution (15 mL) was added slowly to a stirring solution of 6-benzyloxy-2-(dimethylamino)benzo[b]thiophen-3-yl 3-methoxy-4-[(1-pyrrolidinyl)methyl]phenyl ketone (Example 41, Part C; 2.48 g, 5.0 mmol) in THF (15.0 mL) at 0° C. under argon. The mixture was stirred at 0° C. for 3 h before quenched with saturated aqueous NH$_4$Cl solution (50 mL) and extracted with CH$_2$Cl$_2$ (50 mL×3). The combined organic layers were dried with sodium sulfate and concentrated under reduced pressure. Chromatography with EtOAc-hexane (0–100% gradient elution) afforded the title compound (0.73 g).

FDMS m/e: found 693(M$^+$); $^1$H NMR(CDCl$_3$): δ 7.74(d, 1H), 7.55–7.35(m,7H), 7.28(d,2H), 7.22(d, 1H), 7.20(d,1H), 7.10(d,1H), 6.68(d,2H), 5.17(s,2H), 3.76(s, 3H), 3.55(s,2H), 2.51(m, 4H), 1.78(m, 4H), 0.00(s,18H)

Part B. 6-Benzyloxy-3-[3-methoxy-4-[(1-pyrrolidinyl)-methyl]benzyl]-2-(4-aminophenyl)benzo[b]thiophene.

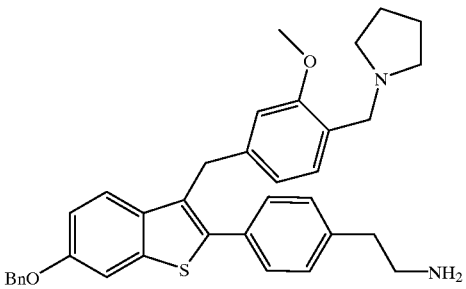

6-Benzyloxy-2-[4-[bis(trimethylsilyl)amino]phenyl] benzo-[b]thiophen-3-yl 3-methoxy-4-[(1-pyrrolidinyl) methyl]phenyl ketone (0.73 g) was dissolved in THF (10 mL), cooled to 0° C. in an ice bath before treated with lithium aluminum hydride (110 mg) at 0° C. for 1 h, then quenched with water(1 mL) and sodium hydroxide (1.0M, 1 mL). Stirring continued for 30 min. The reaction mixture was diluted with brine(30 mL) and extracted with dichloromethane (20 mL×3). The combined organic layers were dried with sodium sulfate and concentrated in vacuo to give the crude alcohol. This material was dissolved in dichloromethane (15 mL), treated with triethylsilane (1.5 mL) and trifluroacetic acid (1.5 mL) sequentially, allowed to stir at ambient temperature for 1.5 h, and concentrated under reduced pressure. The residue was extracted with dichloromethane (20 mL×3) from saturated aqueous sodium bicarbonate (30 mL). The combined organic layers were dried with sodium sulfate and concentrated. Chromatography with ET$_3$N:MeOH:EtOAc (5:5:90) afforded the title compound as a yellow foam (0.53 g).

FDMS m/e: found 535(M+H$^+$); $^1$H NMR(CDCl$_3$): δ 7.60–7.45(m,7H), 7.30(d,2H), 6.98(d, 1H), 6.70(m,4H), 5.13(s,2H), 4.21(s, 2H), 3.78(s,2H), 3.70(s,3H), 3.62(s,2H), 2.56(m, 4H), 1.78(m, 4H).

Part C. 6-Hydroxy-3-[3-methoxy-4-(1-pyrrolidinylmethyl) benzyl]-2-[4-[(2-dimethylamino-1-oxoethyl)-amino] phenyl]benzo[b]thiophene.

6-Benzyloxy-3-[3-methoxy-4-(1-pyrrolidinylmethyl)-benzyl]-2-(4-aminophenyl)benzo[b]thiophene (110 mg) and N,N-dimethylglycine were dissolved in DMF (5.0 mL), treated with DCC (60 mg) and HOAt (40 mg) sequentially, and allowed to stir at ambient temperature under argon for 23 h. The reaction mixture was diluted with saturated sodium bicarbonate solution (30 mL) and extracted with ethyl acetate (20 mL×3). The combined organic layers were dried with sodium sulfate and concentrated. Chromatography with ET$_3$N:MeOH:EtOAc (5:5:90) afforded the benzyl protected product (80 mg). This product was dissolved in THF (3.0 mL) and treated with a solution of ammonium formate (25% in H$_{20, 2.0}$ mL) and 10% palladium on carbon (50 mg) sequentially at ambient temperature. The resulting mixture was stirred at ambient temperature under argon for 7 h before it was filtered through diatomaceous earth followed by rinsing with dichloromethane and methanol. The filtrate was extracted with dichloromethane (20 mL×3) from water (30 mL). The combined organic layers were dried with sodium sulfate and concentrated under reduced pressure. Chromatography with ET$_3$N:MeOH:EtOAc (5:10:85) afforded the title compound (49 mg).

FDMS m/e: found 530(M+H$^+$); $^1$H NMR(CDCl$_3$): δ 9.18 (bs,lH), 7.60(d,2H), 7.42(d, 2H), 7.20(m, 2H), 7.13(s, 1H), 6.69(d,1H), 6.61(s,lH), 6.53(d,1H), 4.19(s, 2H), 3.76(s, 2H), 3.52(s,3H), 3.09(s,2H), 2.76(m, 4H), 2.39(s,6H), 1.85(m, 4H).

EXAMPLE 211

Preparation of 6-Hydroxy-3-[3-methoxy-4-(1-pyrrolidin-ylmethyl)benzyl]-2-[4-[1-oxo-2-(1,1-dioxothiomorpholin-4-yl)ethyl]aminophenyl]benzo b]thiophene.

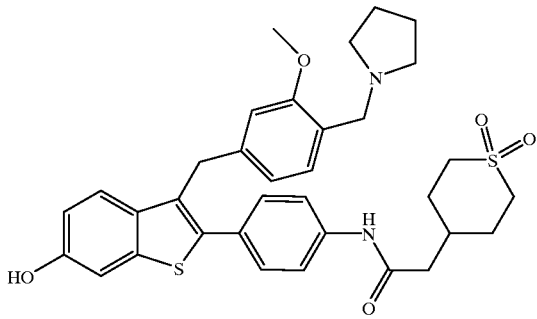

6-Benzyloxy-3-[3-methoxy-4-(1-pyrrolidinylmethyl)-benzyl]-2-(4-aminophenyl)benzo[b]thiophene (140 mg) and 1,1-dioxothiomorphlin-4-yl acetic acid (60 mg) were dissolved in DMF (3.0 mL), treated with DCC (60 mg) and HOAt (40 mg) sequentially, and allowed to stir at ambient temperature under argon for 23 h. The reaction mixture was diluted with brine (30 mL) and extracted with ethyl acetate (20 mL×3). The combined organic layers were dried with sodium sulfate and concentrated. Chromatography with ET₃N:MeOH:EtOAc (5:5:90) afforded the benzyl protected product (110 mg). This product was dissolved in THF (3.0 mL), treated with a solution of ammonium formate (25% in H₂O, 1.0 mL) and 10% palladium on carbon (50 mg) sequentially at ambient temperature. The resulting mixture was stirred at ambient temperature under argon for 16 h before it was filtered through diatomaceous earth followed by rinsing with dichloromethane and methanol. The filtrate was extracted with dichloromethane (20 mL×3) from water (30 mL). The combined organic layers were dried with sodium sulfate and concentrated under reduced pressure. Chromatography with ET₃N:MeOH:EtOAc (5:10:85) afforded the title compound (80 mg).

$^1$H NMR(CDCl₃): δ 8.85(s,1H), 7.56(d,2H), 7.40(d, 2H), 7.22(d, 1H), 7.18(d,1H), 7.03(s, 1H), 6.62(d,1H), 6.60(s,₁H), 6.51(d,1H), 4.15(s, 2H), 3.75(s, 2H), 3.49(s,3H), 3.35 (s,2H), 3.19(m,8H), 2.75(m,4H), 1.85(m, 4H).

EXAMPLE 212

Preparation of 6-Hydroxy-3-[3-methoxy-4-(1-pyrrolidinylmethyl)benzyl]-2-[4-[(2-amino-1-oxoethyl)amino]-phenyl]benzo[b]thiophene.

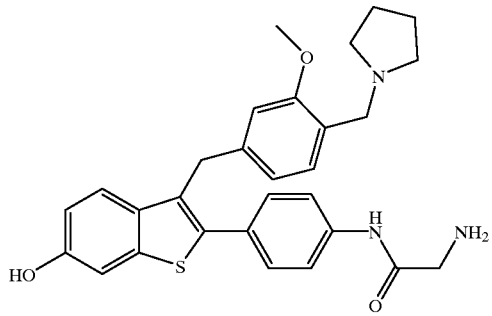

6-Benzyloxy-3-[3-methoxy-4-(1-pyrrolidinylmethyl)-benzyl]-2-(4-aminophenyl)benzo[b]thiophene (210 mg) and N-benzyloxycarbonylglycine (85 mg) were dissolved in DMF (5.0 mL), treated with DCC (85 mg) and HOAt (55 mg) sequentially, and allowed to stir at ambient temperature under argon for 24 h. The reaction mixture was diluted with brine (30 mL) and extracted with ethyl acetate (20 mL×3). The combined organic layers were dried with sodium sulfate and concentrated. Chromatography with ET₃N:MeOH:EtOAc (5:5:90) afforded the dibenzyl protected product (220 mg). This product was dissolved in THF (10.0 mL), treated with a solution of ammonium formate (25% in H₂O, 3.0 mL) and 10% palladium on carbon (100 mg) sequentially at ambient temperature. The resulting mixture was stirred at ambient temperature under argon for 21 h before it was filtered through diatomaceous earth followed by rinsing with dichloromethane and methanol. The filtrate was extracted with dichloromethane (20 mL×3) from water (30 mL). The combined organic layers were dried with sodium sulfate and concentrated under reduced pressure. Chromatography with ET₃N:MeOH:EtOAc (5:5:90) afforded the title compound (70 mg).

FDMS m/e: found 502(M+H⁺); $^1$H NMR(CDCl₃): 69.44(s, 1H), 7.60(d,2H), 7.41(d, 2H), 7.20(d, 1H), 7.18(d,1H), 7.02 (s, 1H), 6.62(d,1H), 6.60(s,1H), 6.38(d,1H), 4.19(s, 2H), 3.66(s, 2H), 3.45(s,3H), 3.42(s,2H), 2.62(m,4H), 1.78(m, 4H).

EXAMPLE 213

Preparation of 3-[4-[2-(1-Pyrrolidinyl)ethoxy]benzyl]-2-[4-[1-oxo-2-(1,1-dioxothiomorpholin-4-yl)ethyl-amino]phenyl]benzo[b]thiophene.

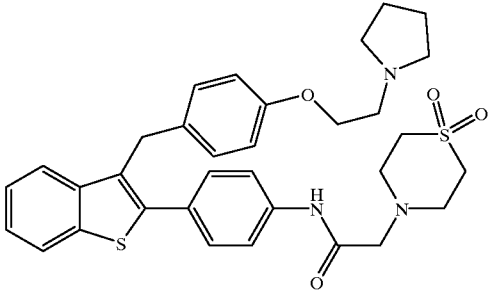

Part A. 2-Dimethylaminobenzo[b]thiophene-3-yl 4-Nitrophenyl Ketone.

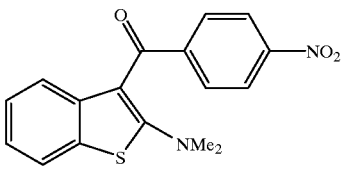

A mixture of 5.00 g (28.2 mmol) of 2-dimethylaminobenzo[b]thiophene (Vesterager et al., Tetrahedron, 1973, 29, 321–329) and 6.3 g (33.9 mmol) of 4-nitrobenzoyl chloride in 100 mL of chlorobenzene was heated at 105° C. for 6 h. The reaction was cooled and concentrated in vacuo. Purification of the residue by flash chromatography (SiO₂; 5% then 10% then 25% EtOAc in hexanes) afforded 7.51 g (23.0 mmol; 82%) of the title compound as burgundy flakes.

FDMS 326 (M+); Anal. calcd for C₁₇H14N₂O₃S: C, 62.56; H, 4.32; N, 8.58. Found: C, 62.71; H, 4.04; N, 8.37.

Part B. 2-Dimethylaminobenzo[b]thiophene-3-yl 4-[2-(1-Pyrrolidinyl)ethoxy3phenyl ]Ketone.

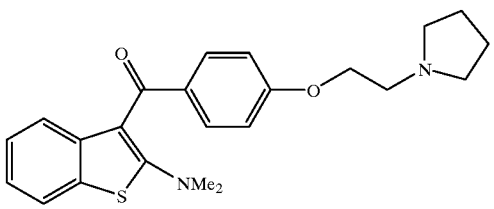

A mixture of 7.00 g (21.4 mmol) of 2-dimethylaminobenzo[b]thiophene-3-yl 4-nitrophenyl ketone (Part A) and sodium hydride (2.0 g, 50 mmol; 60% dispersion in mineral oil) in 150 mL of DMF was treated slowly with a solution of 5.30 mL (45.3 mmole) of 1-(2-hydroxyethyl)pyrrolidine in 25 mL of DMF. The reaction was stirred at ambient temperature for 4 hrs, cooled to 0 oC and quenched by the careful addition of 10 mL of $H_2O$. The solution was poured into 500 mL of $H_2O$ and the mixture extracted with EtOAc (5×100 mL). The combined organic layers were washed with $H_2O$ (3×100 mL), dried over $K_2CO_3$, filtered, and concentrated in vacuo to give 12.41 g of an oil. Purification by MPLC (0.5% then 1% then 2% MeOH in $CHCl_3$ sat'd with $NH_4OH$) afforded a quantitative yield of the title compound as an oil.

FDMS 394 (M+); Anal. calcd for $C_{23}H_{26}N_2O_2S$-0.3MeOH: C, 69.25; H, 6.78 N, 6.93 Found: C, 69.15; H, 6.76; N, 6.98.

Part C. 2-(4-Aminophenyl)benzolblthiophene-3-yl 4-[2-(1-Pyrrolidinyl)ethoxy]phenyl Ketone.

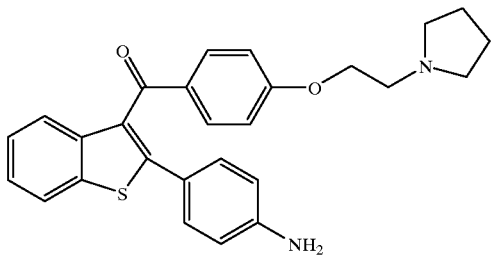

A 3-neck flask containing 580 mg of Mg ribbon was flame-dried under a stream on N2. A solution of 6.7 mL (23.7 mmol) of 4-bromo-N,N-bis(trimethylsilyl)aniline in 15 mL of THF was introduced via cannula and the mixture heated to 60° C. until all the Mg had been consumed. The warm mixture was added via cannula to a 0° C. solution of 8.40 g (21.3 mmol) of 2-dimethylaminobenzo[b]thiophene-3-yl 4-[2-(1-pyrrolidinyl)-ethoxy]phenyl ketone (Part B) in 80 mL of THF. The reaction was stirred for 3 h and was quenched by the addition of 150 mL of sat'd aq. $NH_4Cl$. The two layers were separated and the aqueous layer was extracted with EtOAc (3×300 mL). The combined organic layers were dried over $K_2CO_3$, filtered and concentrated in vacuo to give 11.91 g of an oil.

The crude product was taken up in 250 mL of THF and was treated with 30 mL of a 1M solution of tetrabutylammonium fluoride in THF. The reaction was stirred for 1 hr and was poured into 300 mL of sat'd aq $NaHCO_3$. The two layers were separated and the aqueous layer extracted with EtOAc (4×150 mL). The combined organic layers were dried over $K_2CO_3$, filtered and concentrated in vacuo to give an oil. Purification by MPLC ($SiO_2$; 30% then 40% then 50% THF in hexanes containing 5% triethylamine) afforded 8.31 g (18.8 mmol; 88% over two steps) of the title compound as a yellow foam.

FDMS 442 (M+); Anal. calcd for $C_{27}H_{26}N_2O_2S \cdot C_2H_2O_4 \cdot 1.2 H_2O$: C, 62.85 H, 5.53; N, 5.05. Found: C, 62.52; H, 5.14; N, 4.77.

Part D. 2-(4-Aminophenyl)-3-[4-[2-(I-pyrrolidinyl)-ethoxy]benzyl]benzo[b]thiophene.

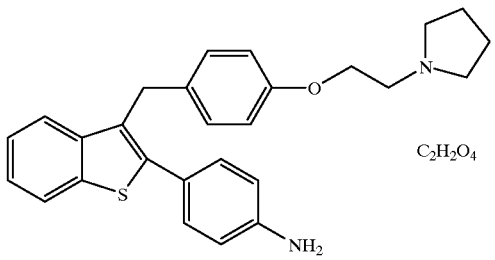

By essentially following the conditions described in Example 179, Part A, the free base of the title compound was prepared as an oil from 2-(4-aminophenyl)benzo[b]thiophene-3-yl 4-[2-(1-pyrrolidinyl)ethoxy]phenyl ketone (Part C) in 85% yield following MPLC ($SiO_2$; 30% then 40% THF with 5% TEA in hexanes). The product was converted to the oxalate salt according to the conditions described in Example 1, Part G.

FDMS 442 (M+); Anal. calcd for $C_{27}H_{28}N_2OS \cdot 2C_2H_2O_4$: C, 61.17; H, 5.30; N, 4.60. Found: C, 61.38; H, 5.57; N, 4.43.

Part E. 3-[4-[2-(1-Pyrrolidinyl)ethoxy]benzyl]-2-[4-[1-oxo-2-(1,1-dioxothiomorpholin-4-yl)ethylamino]phenyl]benzo[b]thiophene.

3-[4-[2-(1-Pyrrolidinyl)ethoxy]benzyl]-2-(4-aminophenyl)benzo[b]thiophene (50 mg) and (1,1-dioxothiomorpholin-4-yl)acetic acid (30 mg) were dissolved in DMF (2.0 mL), treated with DCC (30 mg) and HOAt (28 mg) sequentially, and allowed to stir at ambient temperature under argon for 19 h. The reaction mixture was diluted with brine (30 mL), extracted with ethyl acetate (20 mL×3). The combined organic layers were dried with sodium sulfate and concentrated. Chromatography with $ET_3N$:MeOH:EtOAc (5:5:90) afforded the title compound (65 mg).

$^1H$ NMR($CDCl_3$): 68.82(s,lH), 7.88(d,1H), 7.64(d, 2H), 7.58(d, 1H), 7.53(d,2H), 7.35(m, 2H), 7.07(d,2H), 6.85(d, 2H), 4.25 (s,2H), 4.11(t, 2H), 3.39(s, 2H), 3.24(m,4H), 3.21(m,4H), 2.94(t,2H), 2.68(m,4H), 1.85(m, 4H).

EXAMPLE 214

Preparation of 0-[4-[3-[4-[2-(1-Pyrrolidinyl)ethoxy]-benzyl]benzo[b]thiophene-2-yl]phenyl]-L-serine Methyl Ester.

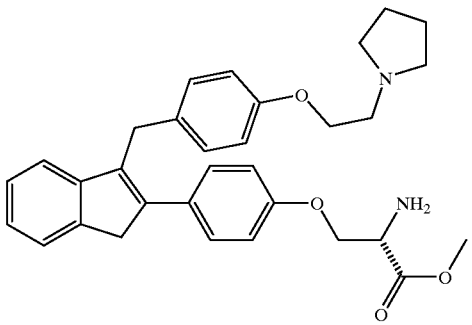

To a stirring solution of 2-(4-hydroxyphenyl)-3-[4-[2-(1-pyrrolidinyl)ethoxy]benzyl]benzo[b]thiophene (200 mg), triphenylphosphine (200 mg) and N-trityl-L-serine methyl ester (290 mg) in THF (7 mL) at 0° C. was added diethyl azodicarboxylate (0.15 mL) over 5 min. The mixture was stirred at ambient temperature under argon for 17 h before it was concentrated under reduced pressure. Chromatography with ET$_3$N:EtOAc (0–5%) afforded the trityl protected product (104 mg). This product was dissolved in dichloromethane (5 mL), treated with triethylsilane (0.2 mL) and trifluoroacetic acid (0.2 mL) at ambient temperature for 2 h. The solvent and excess reagents were removed under reduced pressure. The residue was extracted with dichloromethane(20 mL×3) from saturated sodium bicarbonate (30 mL). The combined organic layers were dried with sodium sulfate and concentrated under reduced pressure. Chromatography with NH$_4$OH:MeOH:EtOAc (5:10:85) afforded the title compound (53 mg).

$^1$H NMR(CDCl$_3$): 87.84(m,lH), 7.50(m,$_1$lH), 7.42(d,2H), 7.30(m, 2H), 7.06(d,2H), 6.95(d, 2H), 6.80(d,2H), 4.26 (m,4H), 4.20(s, 2H), 3.88(t,1H), 3.78(s,3H), 3.14(m,2H), 2.97(m,4H), 1.96(m,4H).

EXAMPLE 215

Preparation of (S)-2-Amino-3-[4-[3-[4-[2-(1-pyrrolidinyl)ethoxy]benzyl]benzo[b]thiophen-2-yl]phenoxy]-propanol.

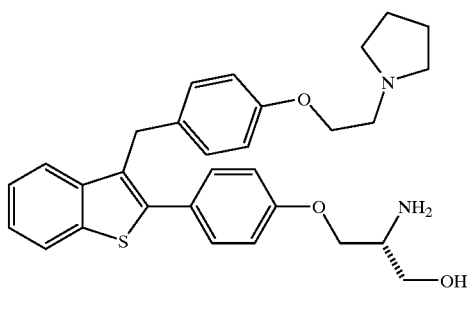

0-[4-[3-[4-[2-(1-Pyrrolidinyl)ethoxy]benzyl]benzo[b]-thiophen-2-yl]phenyl]-L-serine methyl ester in THF (4 mL) was treated with lithium aluminum hydride (22 mg) at ambient temperature under argon for 5 h. The reaction was quenched with water (0.5 mL) and sodium hydroxide solution (1.0M, 1 mL) and stirred for 10 more min. before it was concentrated under reduced pressure. The residue was extracted with dichloromethane (20 mL×3) from brine (30 mL). The combined organic layers were dried with sodium sulfate and concentrated under reduced pressure. Chromatography with ET$_3$N:MeOH:EtOAc (5:10:85) followed by NH$_4$OH:MeOH:EtOAc (5:10:85) afforded the product (27 mg).

$^1$H NMR(CDCl$_3$): δ 7.84(d,1H), 7.52(d,1H), 7.42(d,2H), 7.30(m, 2H), 7.05(d,2H), 6.94(d, 2H), 6.82(d,2H), 4.20(s, 2H), 4.09(t, 2H), 4.10–4.00(m,2H), 3.80–3.70(m,2H), 3.63 (m,1H), 2.92(t, 2H), 2.67(m,4H), 1.83(m,4H).

EXAMPLE 216

Preparation of 0-[4-[3-[4-[2-(1-Pyrrolidinyl)ethoxy]-benzyl]benzo[b]thiophen-2-yl]phenyl]-L-serine.

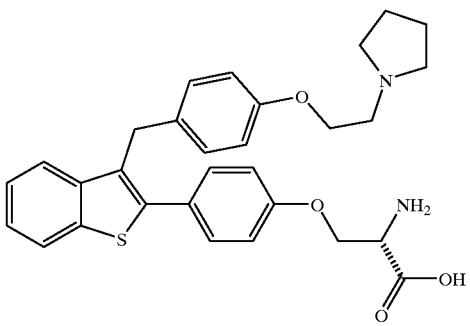

0-[4-[3-[4-[2-(1-Pyrrolidinyl)ethoxy]benzyl]benzo[b]-thiophen-2-yl]phenyl]-L-serine methyl ester (21 mg) was dissolved in THF:MeOH:H$_2$O (3:1:1, 3 mL), treated with LiOH-H$_2$O (5 mg) in one portion and allowed to stir at ambient temperature for 3 h. The reaction mixture was concentrated under reduced pressure. Chromatography with NH$_4$OH:MeOH:EtOAc (10:20:70) afforded the title compound (15 mg).
FDMS m/e: found 517(M+H$^+$); $^1$H NMR(CD$_3$OD): δ 7.83 (d,1H), 7.50(d,1H), 7.43(d,2H), 7.28(m, 2H), 7.05(d,2H), 7.03(d, 2H), 6.85(d,2H), 4.40(m,2H), 4.19(m, 4H), 4.03(m, 1H), 3.44(m,2H), 3.30(m,2H), 3.26(m, 4H), 2.03(m, 4H).

EXAMPLE 217

Preparation of 3-[4-[2-(1-Pyrrolidinyl)ethoxy]benzyl]-2-[4-(2-aminoethyl)phenyl]benzoEb]thiophene.

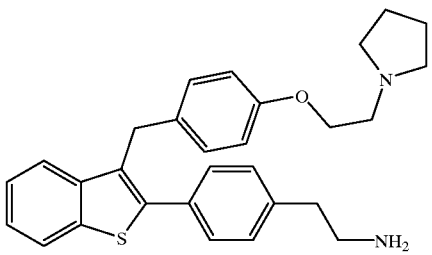

Part A. 2-[4-(Cyanomethyl)phenyl]benzo b]thiophene.

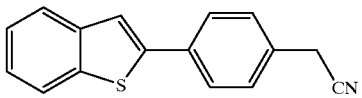

Benzo[b]thiophen-2-yl boronic acid (1.25 g) and 4-bromobenzyl nitrile (1.51 g) were dissolved in THF (25 mL), treated with a solution of sodium carbonate in water (2.0M, 7.0 mL) and tetrakis(triphenylphosphine)palladium (0.25 g) and allowed to stir at reflux in the dark for 15 h. The cooled reaction mixture was diluted with water (100 mL) and extracted with dichloromethane (100 mL×3). The combined organic layers were dried with sodium sulfate and concentrated. The off-white solid was triturated with ethyl acetate and the product was collected as a white precipitate by centrifugation (1.5 g).

¹H NMR(CDCl₃): δ 7.77(d,1H), 7.68(d,1H), 7.31(d,2H), 7.30(d, 2H), 7.28(m,2H), 7.20(s, 1H), 3.75(s,2H).

Part B. 2-[4-(Cyanomethyl)phenyl]benzo b]thiophen-3-yl 4-[2-(1-Pyrrolidin-1-yl)ethoxy]phenyl Ketone.

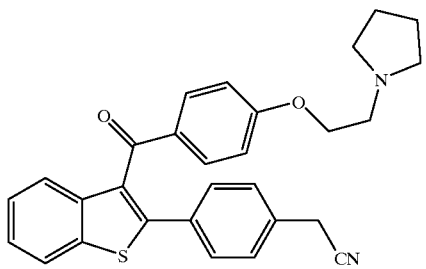

To a solution of 2-[4-(cyanomethyl)phenyl]benzo[b]thiophene (265 mg) and 4-[2-(1-pyrrolidinyl)ethoxy]benzoyl chloride (385 mg) in dichloromethane (20 mL) at 0° C. in the dark was added TiCl₄ (1.3 mL, neat) slowly under argon. The resulting mixture was stirred at 0° C. to ambient temperature for 5.5 h before it was transferred carefully to a stirring solution of saturated aqueous NaHCO₃ (100 mL). After stirring for 30 min, the mixture was extracted with CH₂Cl₂ (3×100 mL). The combined organic layers were dried (Na₂SO₄) and concentrated under reduced pressure. Chromatography with ET₃N:EtOAc (5%) afforded the product (230 mg).

¹H NMR(CDCl₃): δ 7.97(d,1H), 7.86(d,2H), 7.75(d,1H), 7.56(d, 2H), 7.47(m,2H), 7.33(d,2H), 6.87(d,2H), 4.21(t, 2H), 3.80(s, 2H), 3.00(t,2H), 2.72(m,4H), 1.91(m,4H).

Part C. 2-[4-(Cyanomethyl)phenyl]-3-[4-[2-(1-pyrrolidinyl) ethoxy]benzyl]benzo[b]thiophene.

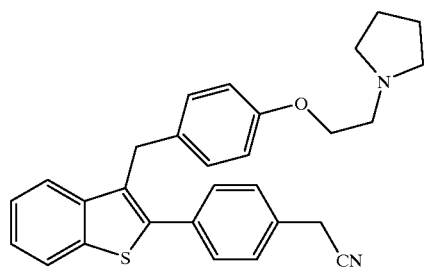

2-[4-(Cyanomethyl)phenyl]benzo[b]thiophen-3-yl 4-[2-(1-pyrrolidinyl)ethoxy]phenyl ketone (158 mg) in THF (5.0 mL) was treated with lithium aluminum hydride (13 mg) at 0° C. for 2 h, and then quenched with water (0.5 mL) and sodium hydroxide (5.0M, 0.5 mL). Stirring was continued for 10 min. The reaction mixture was diluted with brine (50 mL) and extracted with dichloromethane (3×50 mL). The combined organic layers were dried with sodium sulfate and concentrated in vacuo to give a yellow foam-like material. This material was dissolved in dichloromethane (5 mL), treated with triethylsilane (0.3 mL) and trifluroacetic acid (0.2 mL) at 0° C. for 1.5 h, and concentrated under reduced pressure. The residue was extracted with dichloromethane (50 mL×3) from saturated aqueous sodium bicarbonate (50 mL).

The combined organic layers were dried with sodium sulfate and concentrated. Chromatography with ET₃N:EtOAc (0–5%) afforded the product (106 mg).

¹H NMR(CDCl₃): 87.93(d,1H), 7.60(d,1H), 7.58(d,2H), 7.42(d, 2H), 7.34(m,2H), 7.09(d,2H), 6.86(d,2H), 4.24(s, 2H), 4.15(t, 2H), 3.83(s, 2H), 2.97(t,2H), 2.67(m,4H), 1.85 (m,4H).

Part D. 2-[4-(2-Aminoethyl)phenyl]-3-[4-[2-(1-pyrrolidinyl)ethoxy]benzyl]benzo[b]thiophene.

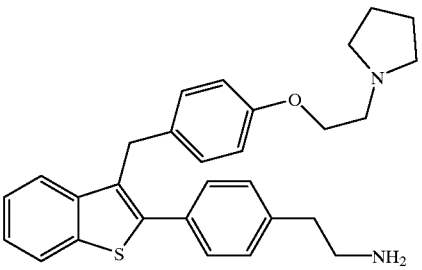

2-[4-(Cyanomethyl)phenyl]-3-[4-[2-(1-pyrrolidinyl)-ethoxy]benzyl]benzo[b]thiophene (1.39 g) was dissolved in ethanol and warmed to 55 oC before it was treated with Raney nickel (1 mL slurry in water) followed by addition of hydrazine monohydrate (1.5 mL). The resulting mixture was allowed to stir at 55° C. for 30 min or until the evolution of gas had stopped. The cooled reaction mixture was filtered through diatomaceous earth, rinsed with methanol and dichloromethane. The filtrate was diluted with saturated sodium bicarbonate (50 mL) and extracted with dichloromethane (50 mL×3). The combined organic layers were dried with sodium sulfate and concentrated. Chromatography with NH₄OH:MeOH:EtOAc (5:10:85) afforded the product (1.30 g).

¹H NMR(CDCl₃): δ 7.89(d,1H), 7.54(d,1H), 7.49(d,2H), 7.30(m, 4H), 7.09(d,2H), 6.86(d,2H), 4.27(s,2H), 4.11(t, 2H), 3.04(t, 2H), 2.92(t,2H), 2.82(m,2H), 2.65(m,4H), 1.84 (m,4H).

EXAMPLE 218

Preparation of 3-[4-[2-(1-Pyrrolidinyl)ethoxy] benzyl]-2-[4-[2-(3,3-dimethylpropylamino)ethyl] phenyl]-benzo[b]thiophene.

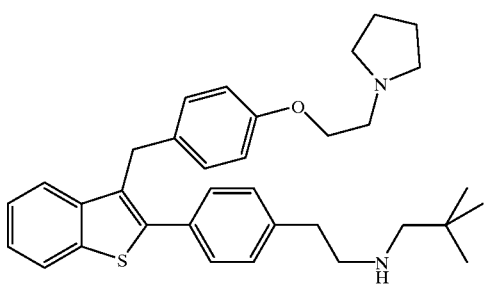

3-[4-[2-(1-Pyrrolidinyl)ethoxy]benzyl]-2-[4-(2-aminoethyl)phenyl]benzo[b]thiophene (75 mg) was dissolved in dichloromethane (3.0 mL), treated with trimethylacetaldehyde (30 μL) and sodium triacetoxyborohydride (56 mg) sequentially and allowed to stir at ambient temperature for 3 h. The reaction mixture was concentrated, and column chromatography with ET₃N:EtOAc (0–5%) afforded the product (55 mg).

FDMS m/e: found 527 (M+H⁺); ¹H NMR(CDCl₃) : 7.86(d, 1H), 7.54(d,1H), 7.46(d,2H), 7.28(m, 4H), 7.07(d,2H), 6.83 (d,2H), 4.24(s,2H), 4.10(t, 2H), 2.91(m, 6H), 2.65(m,4H), 2.42(s,2H), 1.83(m,4H), 0.93(s,9H).

EXAMPLE 219

Preparation of 3-[4-[2-(1-Pyrrolidinyl)ethoxy] benzyl]-2-[4-[2-(cyclohexylmethylamino)ethyl] phenyl]-benzo[b]thiophene.

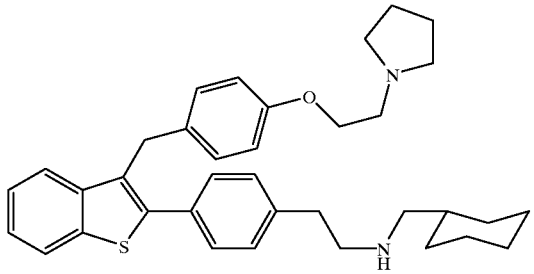

3-[4-[2-(1-Pyrrolidinyl)ethoxy]benzyl]-2-[4-(2-aminoethyl)phenyl]benzo[b]thiophene (73 mg) was dissolved in dichloromethane (3.0 mL), treated with cyclohexanecarboxaldehyde (32 µL) and sodium triacetoxyborohydride (56 mg) sequentially and allowed to stir at ambient temperature for 4 h. The reaction mixture was concentrated, and column chromatography with ET$_3$N:EtOAc (0–5%) afforded the product (8 mg) along with a dicyclohexylmethyl side product (62 mg).

FDMS m/e: found 553 (M+H$^+$); $^1$H NMR(CDCl$_3$): δ 7.93 (d,1H), 7.61(d,1H), 7.54(d,2H), 7.28(m, 4H), 7.14(d,2H), 6.87(d,2H), 4.30(s,2H), 4.24(t, 2H), 3.10(m, 4H), 2.93(m, 4H), 2.68(d,$_1$1H), 2.03(m,4H), 1.78(m,5H), 1.26(m, 4H), 1.02(m,2H).

EXAMPLE 220

Preparation of 3-[4-[2-(1-Pyrrolidinyl)ethoxy] benzyl]-2-[4-[2-(benzylamino)ethyl]phenyl]benzo[b] thiophene.

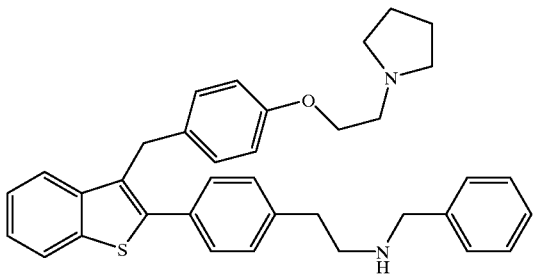

3-[4-[2-(1-Pyrrolidinyl)ethoxy]benzyl]-2-[4-(2-aminoethyl)phenyl]benzo[b]thiophene (116 mg) was dissolved in dichloromethane (5.0 mL), treated with benzaldehyde (40 µL) and sodium triacetoxyborohydride (80 mg) sequentially and allowed to stir at ambient temperature for 18 h. The reaction mixture was concentrated, and column chromatography with ET$_3$N:EtOAc (0–5%) afforded the product (18 mg) along with a dibenzyl side product (52 mg).

FDMS m/e: found 547 (M+H$^+$); $^1$H NMR(CDCl$_3$): δ 7.86 (d,1H), 7.51(d,1H), 7.45(d,2H), 7.32(m, 9H), 7.07(d,2H), 6.81(d,2H), 4.24(s,2H), 4.14(t, 2H), 3.85(s, 2H), 3.02(t,2H), 2.97(m,2H), 2.89(m,2H), 2.80(m,4H), 1.88(m, 4H).

EXAMPLE 221

Preparation of 3-[4-[2-(1-Pyrrolidinyl)ethoxy] benzyl]-2-[4-[2-(3-pyridylmethylamino)ethyl] phenyl]-benzo[b]thiophene.

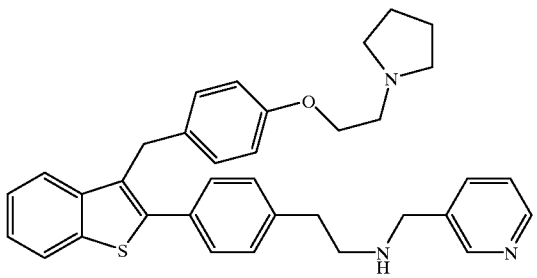

3-[4-[2-(1-Pyrrolidinyl)ethoxy]benzyl]-2-[4-(2-aminoethyl)phenyl]benzo[b]thiophene (39 mg) was dissolved in dichloromethane (3.0 mL), treated with 3-pyridinecarboxaldehyde (8 µL) and sodium triacetoxyborohydride (18 mg) sequentially and allowed to stir at ambient temperature for 18 h. The reaction mixture was concentrated, and column chromatography with ET$_3$N:MeOH:EtOAc (5:10:85) afforded the product (3 mg) along with a bis pyridylmethyl side product (14 mg).

$^1$H NMR(CDCl$_3$): δ 8.70(s,1H), 8.63(m,1H), 7.92(m,2H), 7.58(m, 2H), 7.47(d,2H), 7.38(m,5H), 7.15(d,2H), 6.83(d, 2H), 4.50(m, 2H), 4.30(s, 2H), 4.01(s, 2H), 3.53(m,2H), 3.41(m,4H), 3.02 (m,4H), 2.20(m, 4H).

EXAMPLE 222

Preparation of 3-[4-[2-(1-Pyrrolidinyl)ethoxy] benzyl]-2-[4-[2-(2,3-dihydroxypropylamino)ethyl] phenyl]-benzo[b]thiophene.

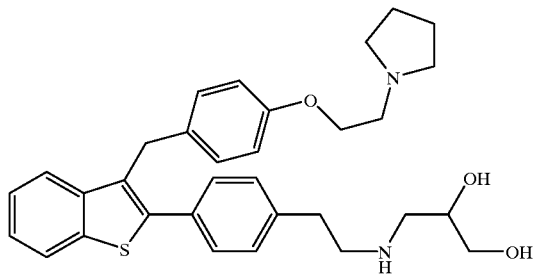

3-[4-[2-(1-Pyrrolidinyl)ethoxy]benzyl]-2-[4-(2-aminoethyl)phenyl]benzo[b]thiophene (113 mg) was dissolved in dichloromethane:methanol (2:1, 6.0 mL), treated with glyceraldehyde (25 mg) and sodium triacetoxyborohydride (60 mg) sequentially and allowed to stir at ambient temperature for 4 h. The reaction mixture was concentrated, and column chromatography with NH$_4$OH:MeOH:EtOAc (3:7:90) afforded the product (56 mg).

FDMS m/e: found 531 (M+H$^+$); $^1$H NMR(CDCl$_3$): δ 7.95 (d,1H), 7.62(d,1H), 7.54(d,2H), 7.40(m, 4H), 7.16(d,2H), 6.92(d,2H), 4.33(s, 2H), 4.21(t,2H), 3.80 (m,2H), 3.22(m, 3H), 2.98(m,6H), 2.76(m,4H), 1.95(m, 4H).

EXAMPLE 223

Preparation of 1-[2-[4-[[2-[4-(4-Aminobutoxy)phenyl]-benzo[b]thiophen-3-yl]methyl]phenoxy]ethyl]-pyrrolidine.

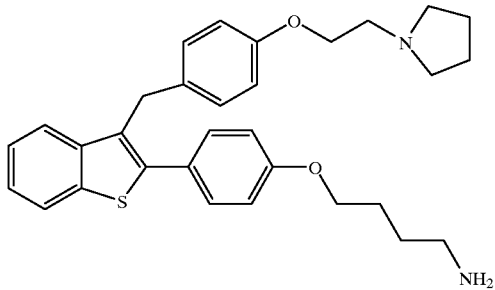

Part A. 1-[2-[4-[[2-[4-[4-(1-Phthalimidyl)butoxy]-phenyl]benzo[b]thiophen-3-yl]methyl]phenoxy]ethyl]-pyrrolidine.

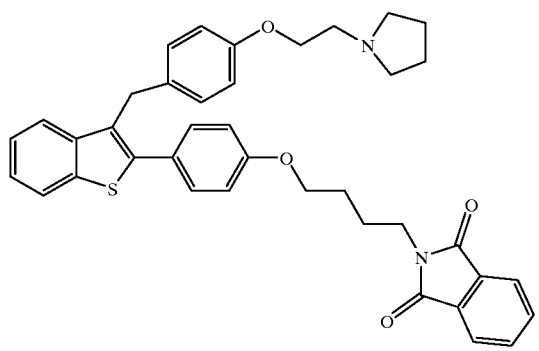

To a solution of 1-[2-[4-[[2-(4-hydroxyphenyl)-benzo[b]thiophen-3-yl]methyl]phenoxy]ethyl]pyrrolidine (53 mg, 0.123 mmol) in THF (1 mL) was added a solution of potassium bis(trimethylsilyl)amide (0.271 mL of 0.5M, 1.36 mmol, 1.1 eq.) in toluene at ambient temperature. After 80 min, N-(4-bromobutyl)phthalimide (75 mg, 0.265 mmol, 2.2 eq) was added and the reaction heated at reflux for 18 h. The reaction was cooled to ambient temperature, diluted with ethyl acetate (50 mL) then washed with 10% aqueous sodium bicarbonate (20 mL). The solvent was removed under reduced pressure then the residue purified by flash chromatography (20:1 $CHCl_3$: MeOH then 5:1 $CHCl_3$: MeOH) to give the protected amine as a tan solid (54 mg, 70%) and recovered starting material (8 mg).
$^1$HNMR (300 MHz, $CDCl_3$) δ 7.83 (dd, J=8.6, 5.6 Hz, 1H), 7.69 (dd, J=5.1, 2.9 Hz, 1H), 7.48 (d, J=8.4 Hz, 1H), 7.38 (d, J=8.3 Hz, 2H),7.28 (m, 3H), 7.03 (d, J=8.3 Hz, 2H), 6.89 (d, J=8.5 Hz, 2H), 6.80 (d, J=8.3 Hz, 2H), 4.18 (s, 2H), 4.07 (t, J=5.9 Hz, 2H), 4.00 (t, J=5.7 Hz, 2H), 3.77 (t J=6.2 Hz, 2H), 2.89 (t, J=5.9 Hz, 2H), 2.63 (bm, 4H), 1.82 (bm, 4H), 1.80 (bm, 4H); FDMS m/e=630 (M+); IR ($CDCl_3$) 1773, 1712, 1656, 1510, 1504, 1399, 1243 $cm^{-1}$; Anal. Cal'c for $C_{39}H_{34}N_2O_{10}S$ $H_2O$: C, 66.65 H, 5.46 N, 3.97 found: C, 67.17 H 5.47 N, 4.04.

Part B. 1-[2-[4-[[2-[4-(4-Aminobutoxy)phenyl]-benzo[b]thiophen-3-yl]methyl]phenoxy]ethyl]-pyrrolidine.

To a solution of 1-[2-[4-[[2-[4-[4-(1-phthalimidyl)-butoxy]phenyl]benzo[b]thiophen-3-yl]methyl]phenoxy]ethyl]-pyrrolidine (389 mg, 0.617 mmol) in 95% ethanol (1.5 mL) and dichloromethane (1.5 mL) was added hydrazine hydrate (85% w/w, 0.228 mL, 6.17 mmol, 10 eq.). The reaction mixture was heated at reflux for 2 h. The reaction mixture was cooled to ambient temperature; then the solvent removed under reduced pressure. The residue was taken up in ethyl acetate (50 mL) and water (50 mL); then the organic layer was separated and washed with brine (20 mL). The solvent was removed under reduced pressure; then the residue purified by flash chromatography (9:1 $CHCl_3$: MeOH, 1% TEA) to give the amine as a soft tan solid (269 mg, 87%).
$^1$HNMR (300 MHz, $CDCl_3$) δ 7.87 (dd, J=8.2, 2.0 Hz, 1H), 7.55 (dd, J=8.8, 2.1 Hz, 1H), 7.45 (d, J=8.6 Hz, 2H), 7.27 (m, 2H), 7.09 (d, J=8.4 Hz, 2H), 6.96 (d, J=8.7 Hz, 2H), 6.85 (d, J=8.5 Hz, 2H), 4.24 (s, 2H), 4.13 (t, J=6.9 Hz, 2H), 4.05 (t, J=6.3 Hz, 2H), 2.96 (t, J=5.9 Hz, 2H), 2.82 (m, 2H), 2.70 (bm, 4H), 2.09 (m, 2H), 1.86 (bm, 4H), 1.67 (bm, 2H); FDMS m/e=501 (M+H); IR ($CDCl_3$) 2939, 1609, 1510, 1246, 1176 $cm^{-1}$; Anal. Cal'c for $C_{31}H_{36}N_2O_2S \cdot 0.5$ $H_{20}$ : C, 72.99 H, 7.32N, 5.49 found: C, 72.99 H 7.36N, 5.18.

EXAMPLE 224

Preparation of 6-Hydroxy-2-[4-[2-(1-imidazolyl)-ethoxy]phenyl]benzo[b]thiophen-3-yl 3-Methoxy-4-[(1-imidazolyl)methyl]phenyl Ketone Dioxalate.

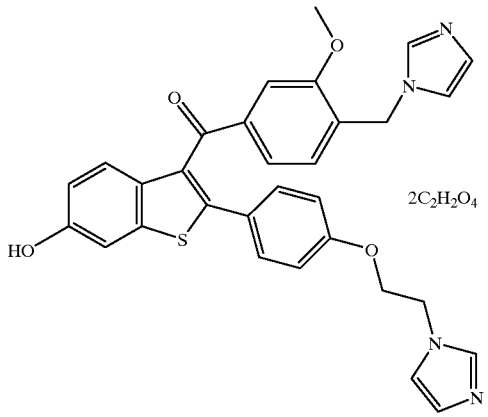

A. 1-Bromo-4-[2-(t-butyldimethylsilyloxy)ethoxy]-benzene.

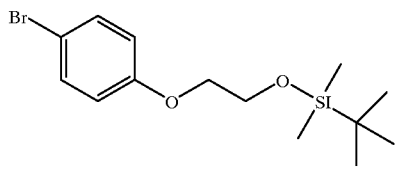

To a solution of 2-(4-bromophenoxy)ethanol (10.94 g, 50.4 mmol), in dry DMF (50 mL), was added t-butyldimethylsilyl chloride (7.6g , 50.4 mmol) and imidazole (3.77g , 55.5 mmol). The reaction was stirred at ambient temperature for 18 h, then partitioned with hexane (300 mL) and water (300 mL). The aqueous layer was extracted with hexane (3×100 mL). The combined organic extracts were dried ($MgSO_4$) and the solvent removed under reduced pressure to give the desired product as an oil (16.6 g, 99%).
$^1$H NMR ($CDCl_3$) δ 7.37 (d, J=8.6 Hz, 2H), 6.80 (d, J=8.6 Hz, 2H), 4.00 (t, J=6.0 Hz, 2H), 3.98 (t, J=6.0 Hz, 2H), 0.91 (s, 6H), 0.10 (s, 9H).

B. 6-Benzyloxy-2-[4-[2-(t-butyldimethylsilyloxy)-ethoxy]phenyl]benzo[b]thiophen-3-yl 3-Methoxy-4-[(1-pyrrolidinyl)methyl]phenyl Ketone.

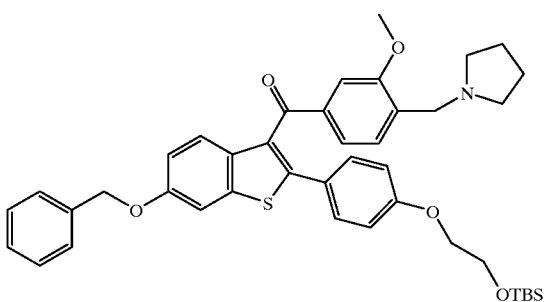

The above bromide (1.25 g, 3.39 mmol), in THF (1.5 mL), was added to a mixture of THF (1.5 mL) and Mg°. The material was stirred at 60° C. for 1 h, during which time the Mg° dissolved. This solution was then added, via syringe, to a THF (5 mL) solution of 6-benzyloxy-2-(dimethylamino)-benzo[b]thiophen-3-yl 3-methoxy-4-[(1-pyrrolidinyl)-methyl]phenyl ketone (Example 163, Part B, 1.1 g, 2.26 mmol). After 1 h, the solution was diluted 25 fold with EtOAc, the organics washed with saturated $NH_4Cl$ solution and concentrated under reduced pressure. Material was purified by flash chromatography ($SiO_2$, 10% MeOH in $CHCl_3$); yielding 827 mg (50%).
$^1$H NMR ($CDCl_3$) δ 7.63 (d, J=8.7 Hz, 1H), 7.49 (d, J=4.3 Hz, 2H), 7.21–7.43 (m, 8H), 7.15 (dd, J=2.1, 8.7 Hz, 1H), 6.95 (d, J=6.4 Hz, 1H), 6.75 (d, J=8.7 Hz, 2H), 5.17 (s, 2H), 3.90–4.0 (m, 4H), 3.80 (s, 3H), 3.65 (s, 2H), 2.55 (s, 4H), 1.90 (s, 4H), 0.95 (s, 9H), 0.15 (s, 6H).

C. 6-Benzyloxy-2-[4-[2-(t-butyldimethylsilyloxy)-ethoxy]phenyl]benzo[b]thiophen-3-yl 3-Methoxy-4-[(1-imidazolyl)methyl]phenyl Ketone.

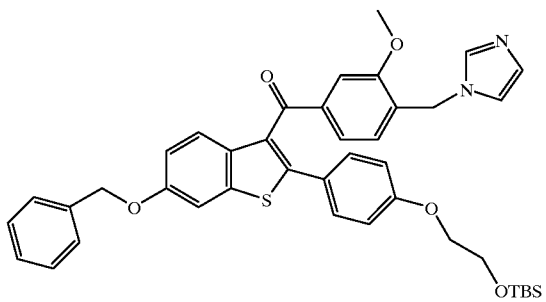

A solution of the above amine (103 mg, 0.146 mmol) in $CHCl_3$ (1 mL) was added to a solution of cyanogen bromide (17 mg, 0.161 mmol) in $CHCl_3$ (1 mL). After completion of the reaction, as indicated by TLC, the mixture was diluted 25 fold with EtOAc, the organics washed with saturated $NaHCO_3$ solution and $H_2O$, and concentrated under reduced pressure. To this crude residue was added the sodium salt of imidazole (50 mg, 0.732 mmol, pre-formed from an equimolar amount of NaH in 1 mL of THF) and the mixture stirred at 60° C. for 35 min. After diluting 25 fold with EtOAc, the organics were washed with saturated $NaHCO_3$ solution, $H_2O$, and concentrated under reduced pressure. Material was purified by flash chromatography ($SiO_2$, 20% Hexane in EtOAc); yielding the title compound in 83% yield from the amine.
$^1$H NMR ($CDCl_3$) δ 7.62 (d, J=8.9 Hz, 2H), 7.35–7.49 (m, 6H), 7.23–7.29 (m, 4H), 7.05–7.10 (m, 2H), 6.78 (d, J=10.5 Hz, 2H), 6.72 (d, J=8.2 Hz, 2H), 5.16 (s, 2H), 5.06 (s, 2H), 3.97 (s, 4H), 3.82 (s, 3H), 0.91 (s, 9H), 0.01 (s, 6H); FDMS 704.1.

D. 6-Benzyloxy-2-[4-[2-(1-imidazolyl)ethoxy]phenyl]-benzo[b]thiophen-3-yl 3-Methoxy-4-[(1-imidazolyl)-methyl]phenyl Ketone.

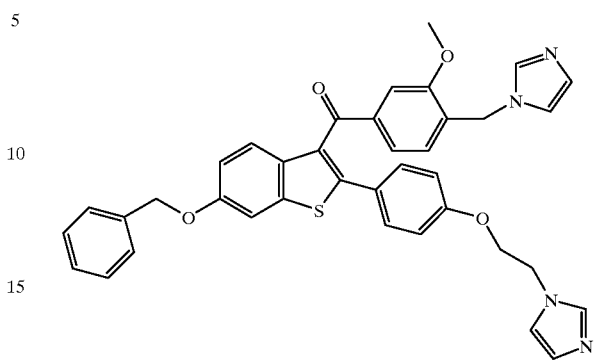

To the above silyl ether (75 mg, 0.106 mmol) in THF (1 mL) was added 1.0M TBAF (0.12 mL, 0.117 mmol) and the mixture stirred at room temperature for 45 min. After diluting 50 fold with EtOAc, the organics were washed with $H_2O$ and concentrated under reduced pressure. The resulting residue was purified by flash chromatography ($SiO_2$, 5% MeOH in EtOAc). This compound was then taken up in pyridine (0.25 mL) and methanesulfonyl chloride (18 mg, 0.159 mmol) added. The mixture was stirred under $N_2$ for 35 min and then the sodium salt of imidazole (72 mg, 1.06 mmol) added and the solution heated at 60° C. for 45 min. After cooling, the mixture was diluted 50 fold with EtOAc and the organics washed with saturated $NaHCO_3$ and $H_2O$ and concentrated under reduced pressure. Material was purified by flash chromatography ($SiO_2$, 15% MeOH in EtOAc, 1% $ET_3N$ v/v added); yielding the title compound in 41% yield from the silyl ether.

$^1$H NMR ($CDCl_3$) δ 7.61 (d, J=8.9 Hz, 1H), 7.58 (s, 1H), 7.37–7.48 (m, 8H), 7.27 (d, J=8.5 Hz, 2H), 7.20 (d, J=7.6 Hz, 1H), 7.07 (dd, J=2.2, 8.7 Hz, 2H), 7.02 (s, 2H), 6.83 (s, 1H), 6.75 (d, J=7.8 Hz, 1H), 6.69 (d, J=8.6 Hz, 2H), 5.15 (s, 2H), 5.04 (s, 2H), 4.31 (t, J=5.0 Hz, 2H), 4.13 (t, J=5.1 Hz, 2H), 3.82 (s, 3H); FDMS 640.

E. 6-Hydroxy-2-[4-[2-(1-imidazolyl)ethoxy]phenyl]-benzo[b]thiophen-3-yl 3-Methoxy-4-[(1-imidazolyl)-methyl]phenyl Ketone Dioxalate.

To the above benzyl ether (27 mg, 0.042 mmol) was added aqueous ammonium formate (1 mL of 25% w/v), THF (1 mL), and Pd/C (10%, 27 mg). The mixture was rapidly stirred at room temperature for 2 h and then diluted 25 fold with THF and passed through a pad of diatomaceous earth. The filtrate was concentrated under reduced pressure and the resulting residue purified by flash chromatography ($SiO_2$, 10% MeOH in $CHCl_3$). The oxalate salt was prepared according to the procedure described in Example 16, affording the title compound in 23% yield from the benzyl ether.

$^1$H NMR ($CDCl_3$) δ 7.66 (s, 1H), 7.56 (d, J=8.7 Hz, 1H), 7.39 (d, J=12 Hz, 2H), 7.16–7.21 (m, 4H), 6.95–7.08 (m, 4H), 6.89 (s, 1H), 6.69 (d, J=7.8 Hz, 1H), 6.59 (d, J=8.3 Hz, 2H), 5.04 (s, 2H), 4.32 (s, 2H), 4.09 (s, 2H), 3.82 (s, 3H); FAB MS 551.2 (M+1).

EXAMPLE 225

Preparation of 6-Hydroxy-2-[4-[2-(1-pyrazolyl)ethoxy]-phenyl]benzo[b]thiophen-3-yl 3-Methoxy-4-[(1-pyrrolidinyl)methyl]phenyl Ketone Dioxalate.

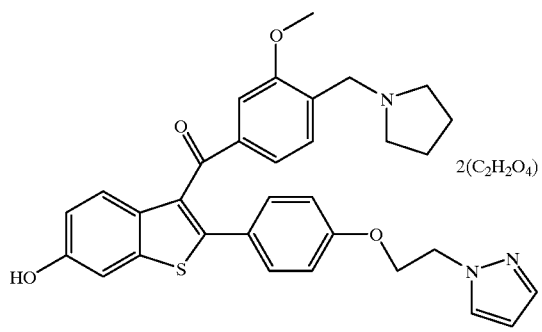

A. 6-Benzyloxy-2-[4-[2-(1-pyrazolyl)ethoxy]phenyl]benzo[b]thiophen-3-yl 3-Methoxy-4-[(1-pyrrolidinyl)methyl]phenyl Ketone.

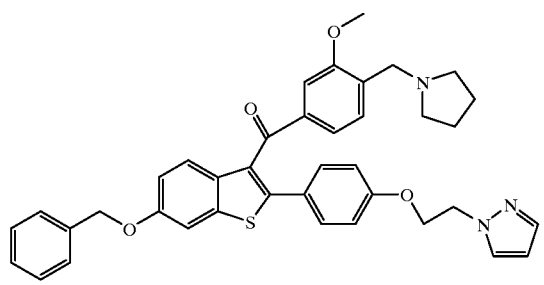

The desired product was formed in 35% yield by following essentially the same procedure as that for Example 224, Part D.

$^1$HNMR (300 MHz, CDCl$_3$) δ 7.61 (d, J=8.9 Hz, 2H), 7.60–7.21 (m, 12H), 7.07 (dd, J=8.9, 2.3 Hz, 1H), 6.71 (d, J=8.7 Hz, 2H), 6.25 (d, J=1.7 Hz, 1H), 5.16 (s, 2H), 4.48 (t, J=5.2 Hz, 2H), 4.27 (t, J=5.2 Hz, 2H), 3.80 (s, 3H), 3.67 (s, 2H), 2.56 (bm, 4H) 1.79 (bm, 4H).

Part B. 6-Hydroxy-2-[4-[2-(1-pyrazolyl)ethoxy]-phenyl] benzo[b]thiophen-3-yl 3-Methoxy-4-[(1-pyrrolidinyl)methyl]phenyl Ketone Dioxalate.

The title compound was formed in the following manner: To the protected phenol (18 mg, 0.028 mmol) in THF (1.5 mL) was added an aqueous solution of ammonium formate (0.150 mL of 25% w/v) and 5% palladium on carbon (18 mg, 1 wt eq.). The reaction was stirred vigorously until all of the protected phenol had been consumed by tlc (9:1 CHCl$_3$:MeOH). The reaction mixture was filtered through a pad of diatomaceous earth with THF (15 mL), then concentrated under reduced pressure. The desired phenol was obtained as a tan foam after flash chromatography (5–30% MeOH in CHCl$_3$) (8 mg, 50%). The oxalate salt was formed by dissolution in ethyl acetate followed by the addition of an oxalic acid solution in ethyl acetate (0.288 mL of 0.1M). The solid was separated by centrifugation. The supernatant was removed then the pellet was suspended in ethyl acetate (1 mL) then subjected to centrifugation once more. The supernatant was removed then the pellet dried under vacuum to give the title salt as a tan solid (10 mg, 97%).

$^1$HNMR (300 MHz, CD$_3$OD) δ 7.70 (m, 3H), 7.54 (d, J=1.5 Hz, 1H), 7.40 (s, 1H), 7.38–7.20 (m, 6H), 6.97 (dd, J=6.9, 3.1 Hz, 1H), 6.76 (d, J=8.4 Hz, 2H), 6.32 (t, J=1.8 Hz, 1H), 4.51 (t, J=4.8 Hz, 2H), 4.28 (m, 4H), 3.87 (s, 3H), 3.16 (bm, 4H), 2.02 (bm, 4H); FABHRMS cal'c for C$_{32}$H$_{32}$N$_3$O$_4$S 554.2114; found 544.2120.

EXAMPLE 226

Preparation of 6-Hydroxy-2-[4-[2-(1-pyrazolyl)ethoxy]phenyl]-3-[3-methoxy-4-[(1-pyrrolidinyl)methyl]benzylbenzo[b]thiophene Dioxalate.

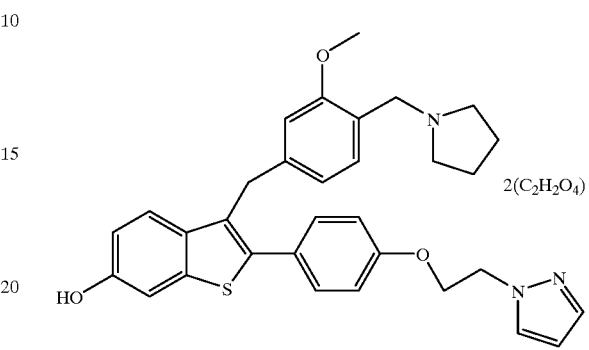

Part A. 6-Benzyloxy-2-[4-[2-(1-pyrazolyl)ethoxy]-phenyl]-3-[3-methoxy-4-[(1-pyrrolidinyl)methyl]benzyl-benzo[b]thiophene.

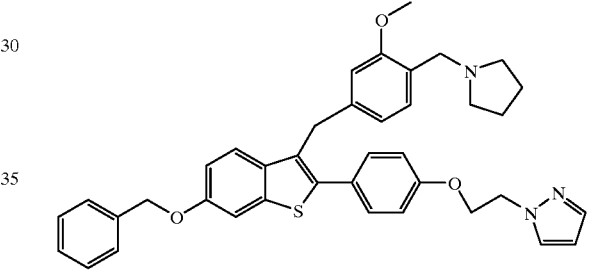

To the ketone (Example 225, Part A, 40 mg, 0.06 mmol) in CH$_2$Cl$_2$ (1 mL), at 0° C. and under N$_2$, was added a solution of DIBAL-H (1.0M, 0.18 mL, 0.18 mmol) in toluene. The mixture was stirred for 55 min and then quenched with MeOH (0.5 mL). Saturated Rochelle's salt (6 mL) and EtOAc (25 mL) were then added. The bi-layer solution was stirred at room temperature for 1 h and then the organic layer concentrated under reduced pressure. After taking the resulting residue up in CH$_2$Cl$_2$ (1 mL), the material was treated sequentially with ET$_3$SiH (0.069 mL, 0.4 mmol) and TFA (0.048 mL, 0.6 mmol) at 0° C. and under N$_2$. The solution was stirred for 1 h and then diluted 25 fold with EtOAc and the organics washed with saturated NaHCO$_3$ solution and H$_2$O. The organics were then concentrated under reduced pressure and purified by flash chromatography (SiO$_2$, 10% MeOH in CHCl$_3$); affording the benzyl compound in 68% yield.

$^1$HNMR (300 MHz, CDCl$_3$) δ 7.61–7.21 (m, 12H), 7.01 (dd, J=8.9, 2.4 Hz, 1H), 6.90 (d, J=8.7 Hz, 2H), 6.74 (d, J=8.1 Hz, 1H), 6.66 (s, 2H), 6.28 (s, 1H), 5.13 (s, 2H), 4.55 (t, J=5.2 Hz, 2H), 4.36 (t, J=5.2 Hz, 2H), 4.20 (s, 2H), 3.92 (s, 2H), 3.70 (s, 3H), 2.92 (bm, 4H) 1.94 (bm, 4H).

Part B. 6-Hydroxy-2-[4-[2-(1-pyrazolyl)ethoxy]-phenyl]-3-[3-methoxy-4-[(1-pyrrolidinyl)methyl]benzy]-benzo[b]thiophene Dioxalate.

The title compound was formed in 50% yield by following essentially the same procedure as that for Example 224, Part E.

¹HNMR (300 MHz, CD₃OD) δ 7.70 (d, J=2.1 Hz, 1H), 7.49 (d, J=1.5 Hz, 1H), 7.35 (d, J=8.7 Hz, 2H), 7.20 (d, J=7.8 Hz, 1H), 7.18 (d, J=2.1 Hz, 1H), 6.92 (d, J=8.7 Hz, 2H), 6.83 (s, 1H), 6.75 (d, J=7.8 Hz, 2H), 6.73 (d, J=8.7 Hz, 2H), 66.28 (d, J=2.1 Hz, 1H), 4.53 (t, J=5.1 Hz, 2H), 4.34 (t, J=5.1 Hz, 2H), 4.26 (s, 2H) 4.22 (s, 2H), 3.75 (s, 3H), 3.40 (bm, 2H), 3.10 (bm, 2H), 2.11 (bm, 2H) 1.98 (bm, 2H); FABHRMS cal'c for C₃₂H₃₄N₃O₃S 540.2321, found 540.2316.

EXAMPLE 227

Preparation of 6-Hydroxy-2-[4-[2-(1,2,4-triazol-[1 or 4]-yl)ethoxy]phenyl]benzo[b]thiophen-3-yl 3-Methoxy-4-[(1-pyrrolidinyl)methyl]phenyl Ketone Dihydrochloride.

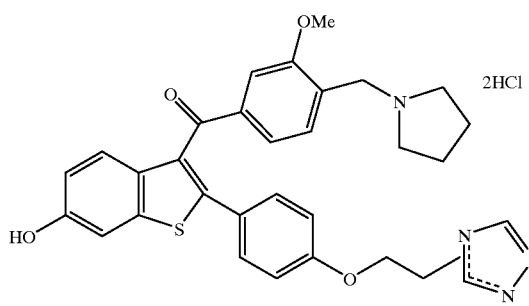

Part A. 6-Benzyloxy-2-[4-[2-(1,2,4-triazol-[1 or 4]-yl)ethoxy]phenyl]benzo[b]thiophen-3-yl 3-Methoxy-4-[(1-pyrrolidinyl)methyl]phenyl Ketone.

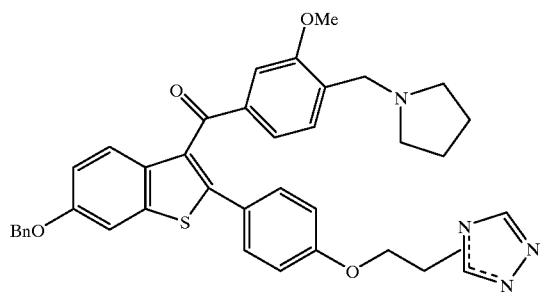

The desired product was formed in 53% yield by following essentially the same procedure as that for Example 224, Part D, but using the sodium salt of 1,2,4-triazole. Two isomeric products were formed, and one of them was isolated by chromatography in this and the following steps.
¹HNMR (300 MHz, CDCl₃) δ 7.61 (d, J=8.9 Hz, 1H), 7.50–7.25 (m, 13H), 7.08 (dd, J=8.9, 2.3 Hz, 1H), 6.72 (d, J=8.7 Hz, 2H), 5.17 (s, 2H), 4.55 (t, J=4.8 Hz, 2H), 4.28 (t, J=4.8 Hz, 2H), 3.75 (s, 3H), 3.71 (s, 2H), 2.61 (bm, 4H) 1.80 (bm, 4H).

Part B. 6-Hydroxy-2-[4-[2-(1,2,4-triazol-l or 4]-yl)ethoxy]phenyl]benzo[b]thiophen-3-yl 3-Methoxy-4-[(1-pyrrolidinyl)methyl]phenyl Ketone Dihydrochloride.

The title compound was formed by following essentially the same procedure as that for Example 224, Part E with additional purification by reversed-phase HPLC: Following chromatography and after concentrating under reduced pressure, the residue was taken up in H₂O (5 mL) and the pH lowered to 3 by addition of 6N HCl and reconcentrated. The material was then purified by semi-preparative HPLC, using a Vyadac™ C18 column (25×250 mm), and following a gradient elution 98:2 (H₂O with 0.1% HCl added/CH₃CN) to 50:50, to provide the dihydrochloride salt.

¹HNMR (300 MHz, CD₃OD) δ 9.10 (s, 1H), 8.38 (s, 1H), 7.60 (d, J=8.7 Hz, 2H), 7.40 (s, 1H), 7.39–7.20 (m, 5H), 6.91 (dd, J=8.7, 1.8 Hz, 1H), 6.77 (d, J=8.7 Hz, 2H), 4.69 (t, J=4.5 Hz, 2H), 4.34 (t, J=4.5 Hz, 2H), 4.29 (s, 2H), 3.85 (s, 3H), 3.30 (bm, 2H), 3.10 (bm, 2H), 2.11 (bm, 2H) 1.98 (bm, 2H); HPLC R_f=32.9 min.

EXAMPLE 228

Preparation of 2-[4-(6-Aminohexyloxy)phenyl]-3-[4-[2-(1-pyrrolidinyl)ethoxy]benzylbenzo[b]thiophene.

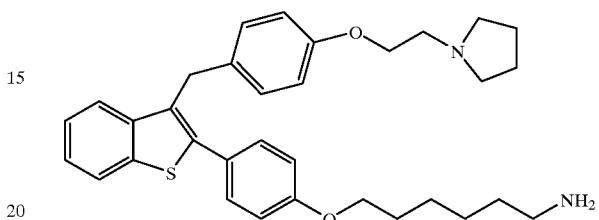

Part A. 2-[4-[6-(N-Phthalimidyl)hexyloxy]phenyl]-3-[4-[2-(1-pyrrolidinyl)ethoxy]benzylbenzo[b]thiophene.

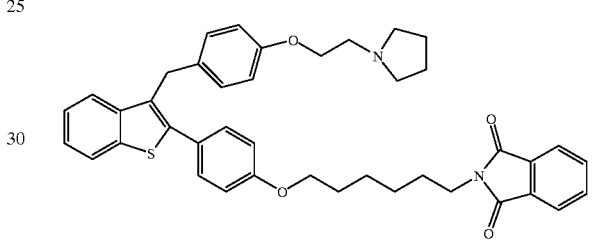

To 2-(4-hydroxyphenyl)-3-[4-[2-(1-pyrrolidinyl)-ethoxy]benzyl]benzo[b]thiophene (Example 196; Part A; 324 mg, 0.754 mmol) in THF (1 mL) was added potassium hexamethyldisilazane (KHMDS) (0.5M in toluene, 1.96 mL, 0.981 mmol) and the mixture stirred under N2 for 30 min. N-(6-bromo-hexyl)phthalimide (257 mg, 0.829 mmol) in THF (1 mL) and a catalytic amount of Bu₄NI was added to the phenoxide solution and heated at reflux for 5 h. After cooling to room temperature, the mixture was diluted 25 fold with EtOAc, the organics washed with saturated NaHCO₃ (aq) and H₂O and concentrated under reduced pressure. Material was purified by flash chromatography (SiO₂, 10% MeOH in CHCl₃); yielding 240 mg (48%) of the desired product.
¹H NMR (CDCl₃) δ 7.85–7.89 (m, 3H), 7.74 (dd, J=3.0, 5.3 Hz, 2H), 7.53 (d, J=8.7 Hz, 1H), 7.44 (d, J=8.6 Hz, 2H), 7.32 (dd, J=2.1, 5.5 Hz, 2H), 7.09 (d, J=8.5 Hz, 2H), 6.94 (d, J=8.6 Hz, 2H), 6.85 (d, J=8.5 Hz, 2H), 4.24 (s, 2H), 4.19 (t, J=5.7 Hz, 2H), 4.01 (t, J=6.3 Hz, 2H), 3.75 (t, J=7.2 Hz, 2H), 3.04 (t, J=5.6 Hz, 2H), 2.82 (s, 4H), 1.91 (s, 4H), 1.74–1.90 (m, 4H), 1.47–1.57 (m, 4H); FDMS 658.2.

Part B. 2-[4-(6-Aminohexyloxy)phenyl]-3-[4-[2-(1-pyrrolidinyl)ethoxy]benzylbenzo[b]thiophene.

To the above phthalimide (221 mg, 0.336 mmol), in EtOH (3 mL), was added H₂NNH₂·H₂O (85%, 0.11 mL, 3.36 mmol) and the mixture heated at 65° C. for 1 h. After cooling to room temperature, the mixture was concentrated under reduced pressure and the resulting residue taken up in EtOAc. The organics were washed with saturated NaHCO₃ (aq) and H₂O and reconcentrated. Material was purified by flash chromatography (SiO₂, 10% MeOH in CHCl₃ with 1% ET₃N v/v added); yielding 119 mg (67%) of the title compound.

¹H NMR (CDCl₃) δ 7.80 (d, J=5.5 Hz, 1H), 7.48 (d, J=6.5 Hz, 1H), 7.38 (d, J=8.7 Hz, 2H), 7.24–7.28 (m, 2H), 7.02 (d, J=8.5 Hz, 2H), 6.88 (d, J=8.6 Hz, 2H), 6.78 (d, 8.5 Hz, 2H), 4.52 (s, 2H), 4.18 (s, 2H), 4.06 (t, J=5.9 Hz, 2H), 3.95 (t, J=6.3 Hz, 2H), 2.88 (t, J=6.0 Hz, 2H), 2.81 (t, J=6.5 Hz, 2H), 2.62 (s, 4H), 1.78–1.81 (m, 6H), 1.41–1.76 (m, 6H); FDMS 529.1 (M+1).

EXAMPLE 229

Preparation of 2-[4-(3-Aminopropoxy)phenyl)-3-[⁴-[2-(1-pyrrolidinyl)ethoxy]benzylbenzo blthiophene.

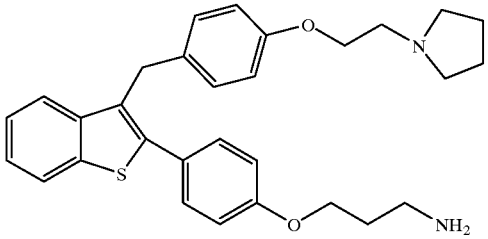

Part A. 2-[4-[3-(N-Phthalimidyl)propoxy]phenyl)-³-[⁴-[2-(1-pyrrolidinyl)ethoxy]benzylbenzo[b]thiophene.

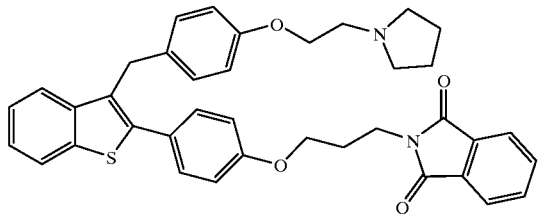

The title compound was formed in 71% yield from the phenol and N-(3 -bromopropyl) phthalimide by essentially following the procedure outlined in Example 228, Part A.

¹H NMR (CDCl₃) δ 7.83–7.88 (m, 3H), 7.71–7.75 (m, 2H), 7.50 (d, J=5.7 Hz, 1H), 7.38 (d, J=8.5 Hz, 2H), 7.29–7.34 (m, 2H), 7.06 (d, J=8.2 Hz, 2H) , 6.79–6.88 (m, 4H) , 4.34 (t, J=4.1 Hz, 2H), 4.21 (s, 2H), 4.08 (t, J=3.7, 2H), 3.94 (t, J=3.0 Hz, 2H), 3.24 (t, J=4.0 Hz, 2H), 3.12 (s, 4H), 2.03–2.24 (m, 2H), 2.02 (s, 4H); FDMS 616.3.

Part B. 2-[4-(3-Aminopropoxy)phenyl)-3-[⁴-[²-(1-pyrrolidinyl)ethoxy]benzylbenzo[b]thiophene.

The title compound was formed in 73% yield from the above phthalimide by following the procedure outlined in Example 228, Part B.

¹H NMR (CDCl₃) δ 7.82 (d, J=8.4 Hz, 1H), 7.51 (d, J=6.3 Hz, 1H), 7.41 (d, J=8.6 Hz, 2H), 7.28 (m, 2H), 7.03 (d, J=8.4 Hz, 2H), 6.91 (d, J=8.6 Hz, 2H), 6.81 (d, J=8.4 Hz, 2H), 4.19 (s, 2H), 4.10 (m, 4H), 3.02 (s, 2H), 2.90 (t, J=5.9 Hz, 2H), 2.65 (s, 4H), 2.04 (m, 2H), 1.82 (s, 4H); FDMS 487 (M+1).

EXAMPLE 230

Preparation of 2-[4-[2-(1-Iminoethylamino)ethyl]-phenyl]-3-[4-[2-(1-pyrrolidinyl)ethoxy]benzyl]-benzo[b]thiophene.

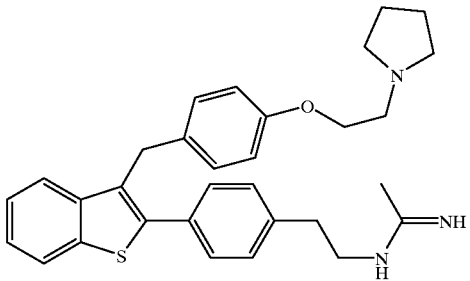

2-[4-(2-Aminoethyl)phenyl]-3-[4-[2-(1-pyrrolidinyl)-ethoxy]benzyl]benzo[b]thiophene (100 mg) was dissolved in dichloromethane:methanol (2:5, 7.0 mL), treated with triethylamine (0.2 mL) and ethyl acetimidate hydrochloride (135 mg) sequentially and allowed to stir at ambient temperature for 4 h. The reaction mixture was concentrated and fractionated by column chromatography with NH₄OH:MeOH:EtOAc (10:20:70) to afford the title compound (51 mg).

FDMS m/e: found 498 (M+H⁺); ¹H NMR(CDCl₃) : δ 7.81(d,1H), 7.51(d,1H), 7.42(d,2H), 7.28(m, 4H), 7.02(d, 2H), 6.79(d,2H), 4.19(s, 2H), 4.03(t,2H), 3.48 (m,2H), 2.93 (m,2H), 2.85(m,2H), 2.59(m,4H), 2.00(s,3H), 1.78 (m, 4H).

EXAMPLE 231

Preparation of 6-Hydroxy-2-[4-[2-(1-imidazolyl)-ethoxy]phenyl]-3-[3-methoxy-4-[(1-pyrrolidinyl)-methyl]benzylbenzo[b]thiophene Dioxalate.

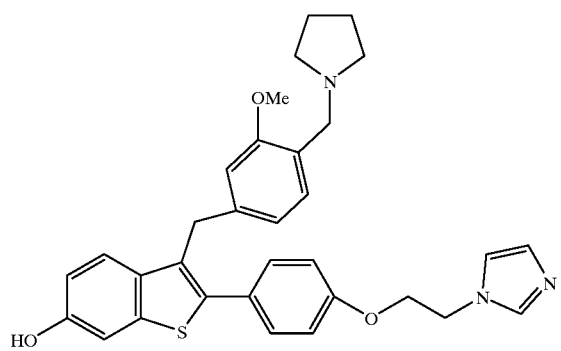

Part A. 6-Benzyloxy-2-[4-[2-(1-imidazolyl)ethoxy]-phenyl]-3-[3-methoxy-4-[(1-pyrrolidinyl)methyl]benzyl-benzo[b]thiophene.

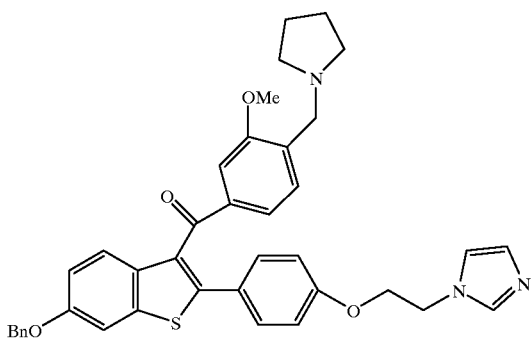

The desired product was formed from the silyl ether of Example 224, Part B, in 86% yield by following essentially the same procedure as that for Example 224, Part D.

¹H NMR (CDCl₃) 7.60 (d, 1H), 7.58 (s, 1H), 7.52–7.20 (m, 7H), 7.18–6.95 (m, 3H), 6.72 (d, 2H), 5.12 (s, 2H), 4.31 (br t, 2H), 4.18 (br t, 2H), 3.80 (s, 3H), 3.63 (s, 2H), 2.58 (m, 4H), 1.80 (m, 4H).

Part B. 6-Hydroxy-2-[4-[2-(1-imidazolyl)ethoxy]-phenyl]-3-[3-methoxy-4-[(1-pyrrolidinyl)methyl]benzyl-benzo[b]thiophene Dioxalate.

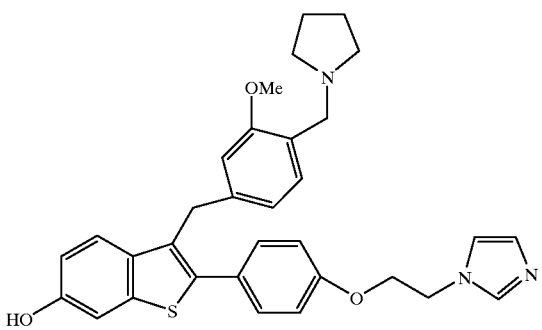

The material from Part A (0.065 g, 0.105 mmol) was dissolved in THF (2 mL), treated with lithium aluminum hydride (0.005 g, 0.105 mmol), and the resulting solution was stirred at room temperature for 1 h. The mixture was then quenched by the addition of H₂O (5 μL), 15% NaOH (5 μL) and H₂O (15 μL). The mixture was then filtered through a plug of cotton and then concentrated. The crude residue was taken up in CH₂Cl₂ (3 mL) and treated with ET₃SiH (0.12 mL) and TFA (0.08 mL) and the resulting solution was stirred at room temperature for 1 h. This solution was then quenched with saturated aqueous NaHCO₃ (5 mL) and the resulting mixture was extracted with EtOAc (3×5 mL). The organic material was then dried (MgSO₄) and concentrated. The resulting crude material was then subjected to debenzylation with Pd/C (5%) and saturated ammonium formate (1 mL) in THF (2 mL). After 2 h at room temperature, this mixture was filtered and the mixture extracted with EtOAc (3×5 mL). The extracts were washed with H₂O (1×5 mL) and then concentrated. The crude material thus obtained was passed through a plug of silica gel, eluting with EtOAc-ET₃N-MeOH (90/5/5), to give the title compound as an oil. Treatment with a solution of oxalic acid in EtOAc provided the title compound as the oxalate salt.

¹HNMR (CD₃OD) δ 9.0 (br s, 1H), 7.75 (br s, 1H), 7.60 (br s, 1H), 7.44 (d, 2H), 7.38 (d, 1H), 7.25 (d, 1H), 7.20 (d, 1H), 7.0 (d, 2H), 6.85 (br s, 1H), 6.75 (m, 2H), 4.75 (m, 2), 4.40 (m, 2H), 4.25 (s, 2H), 4.20 (s, 2H), 3.80 (s, 2H), 3.4–3.0 (br m, 4H), 2.12 (br m, 4H).

EXAMPLE 232

Preparation of 6-Hydroxy-2-[4-[2-(1-pyrrolidinyl)-ethoxy]phenyl]-3-[3-methoxy-4-[(1-imidazolyl)-methyl]benzylbenzo[b]thiophene Dioxalate.

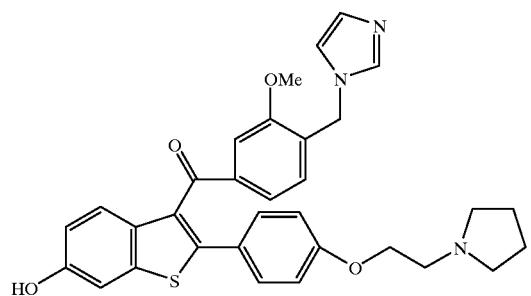

Part A. 6-Benzyloxy-2-[4-[2-(1-pyrrolidinyl)ethoxy]-phenyl]-3-[3-methoxy-4-[(1-imidazolyl)methyl]benzyl-benzo[b]thiophene.

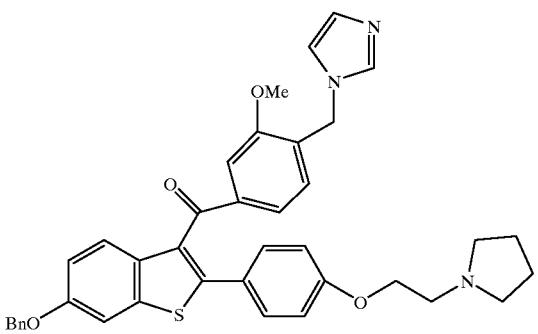

This intermediate was obtained from silyl ether of Example 224, Part C and pyrrolidine by essentially following the procedure outlined in Example 224, Part E.

¹HNMR (CDCl₃) δ 7.65 (d, 1H), 7.5–7.3 (m, 9H), 7.25 (d, 2H), 7.20 (d, 2H), 7.15 (m, 1H), 6.78 (m, 3H), 5.20 (s, 2H), 5.08 (s, 2H), 4.10 (t, 2H), 3.80 (s, 3H), 2.95 (t, 2h), 2.70 (m, 4H), 1.80 (m, 4H)

Part B. 6-Hydroxy-2-[4-[2-(1-pyrrolidinyl)-ethoxy]phenyl]-3-[3-methoxy-4-[(1-imidazolyl)-methyl]benzylbenzo[b]thiophene Dioxalate.

The above benzyl ether was transformed into the title compound using essentially the same conditions as described in Example 224, Part D. Data reported is for the free base.

¹HNMR (CDCl₃) δ 7.62 (d, 1H), 7.45 (s, 1H), 7.41 (s, 1H), 7.25–7.05 (m, 5H), 7.06 (d, 1H), 6.95 (dd, 1H), 6.90 (s, 1H), 6.85 (d, 1H), 6.80 (d, 2H), 5.08 (s, 2H), 4.10 (t, 2H), 3.90 (s, 3H), 3.05 (t, 2H), 2.90 (m, 4H), 1.90 (m, 4H).

EXAMPLE 233

Preparation of 6-Hydroxy-2-[4-[2-(1-pyrrolidinyl)-ethoxy]phenyl]-3-[3-methoxy-4-[(1-pyrazolyl)methyl]-benzylbenzo[b]thiophene Oxalate.

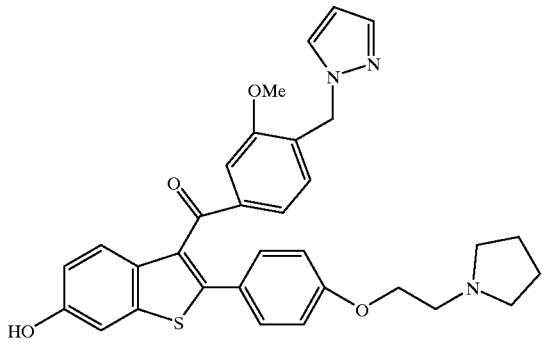

Part A. 6-Benzyloxy-2-[4-[2-(1-pyrrolidinyl)ethoxy]-phenyl]-3-[3-methoxy-4-[(1-pyrazolyl)methyl]benzyl-benzo[b]thiophene.

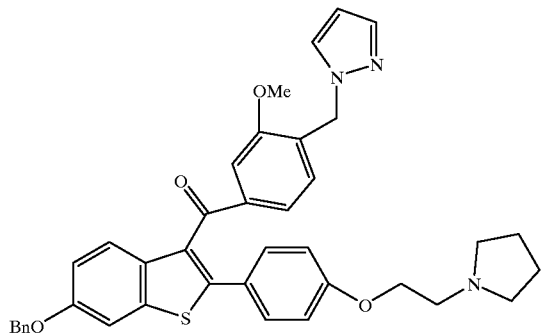

A solution of the amine of Example 224, Part B (0.125 g, 0.186 mmol) in CHCl$_3$ (5 mL) was treated with cyanogen bromide (0.029 g, 0.280 mmol) and the resulting solution was allowed to stir for 5 minutes. The solution was then diluted with EtOAc (25 mL) and washed with saturated NaHCO$_3$. The organic material was dried (MgSO$_4$) and concentrated. The crude residue was taken up in THF (5 mL) and treated with the sodium salt of pyrazole (0.41 mmol). The resulting solution was allowed to stand overnight at room temperature. The mixture was then diluted with EtOAc (15 mL) and washed with H$_2$O (2×5 mL). The organic material was then concentrated and the crude residue was then treated with a 1M solution of tetrabutylammonium fluoride in THF (0.22 mL). After 1 h at room temperature, this solution was diluted with EtOAc (15 mL) and washed with H$_2$O. The organic material was dried (MgSO$_4$) and concentrated. The crude residue was taken up in pyridine (5 mL) and treated with methanesulfonyl chloride (0.015 mL) and the resulting solution was allowed to stir at room temperature for 1 h. This solution was then treated with pyrrolidine (0.5 mL). After 1 h, the solution was diluted with EtOAc (20 mL) and washed with H$_2$O (3×5 mL). The material was dried (MgSO$_4$) and concentrated. The material was purified on silica gel eluting with EtOAc-ET$_3$N-MeOH (90/5/5).
$^1$HNMR (CDCl$_3$) 7.6–7.2 (m, 13H), 7.05 (d, 1H), 7.80 (d, 2H), 7.75 (d, 1H), 6.25 (m, 1H), 5.35 (S, 2H), 5.19 (s, 2H), 4.12 (t, 2H), 3.82 (S, 3H), 2.95 (t, 2H), 2.75 (m, 4H), 1.80 (m, 4H).

Part B. 6-Hydroxy-2-[4-[2-(1-pyrrolidinyl)ethoxy]-phenyl]-3-[3-methoxy-4-[(1-pyrazolyl)methyl]benzyl-benzo[b]thiophene Oxalate.

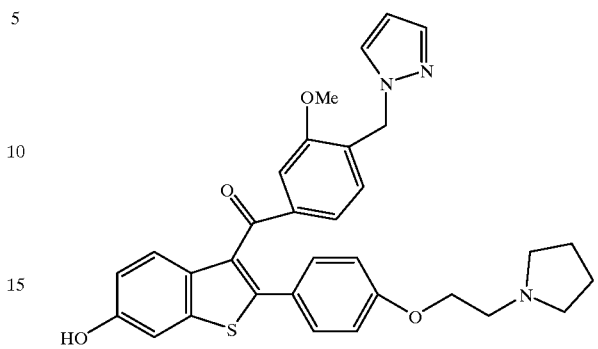

The title compound was prepared using the same procedure outlined in Example 224, Part E.
$^1$HNMR (CD$_3$OD) 7.65 (m, 1H), 7.55 (m, 1H), 7.45 (d, 1H), 7.40 (s, 1H), 7.35 (br d, 2H), 7.30 (m, 1H), 7.22 (d, 1H), 6.95 (m, 3H), 6.70 (d, 2H), 6.35 (m, 1H), 5.35 (S, 2H), 4.30 (m, 2H), 3.92 (s, 3H), 3.65 (m, 2H), 3.45–3.15 (m, 4H), 2.19 (m, 4H).

What is claimed is:

1. A method of inhibiting thrombin in a mammal comprising administering to a mammal in need thereof an effective amount of a thrombin inhibiting compound of formula I (or a pharmaceutically acceptable salt thereof)

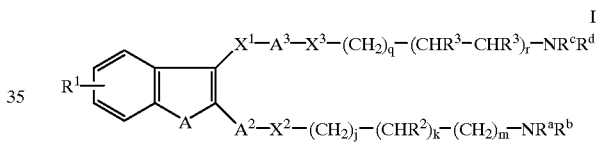

wherein

A is O or S;

A$^2$ is para-phenylene which divalent radical may bear a hydroxymethyl, benzyloxymethyl, (1–3C)alkyl, (1–2C)alkoxy, hydroxy or halo substituent;

A$^3$ is para-phenylene which divalent radical may bear one or two substituents independently selected from dimethylamino, (1–4C)alkyl, halo, trifluoromethyl, (1–2C)alkoxy, hydroxy, cyano, aminomethyl, nitro, —NHCH$_2$R$^f$, —NHC(O)R$^f$ or —NHS(O)$_2$R$^g$ in which R$^f$ is hydrogen or (1–2C)alkyl and R$^g$ is (1–2C)alkyl or phenyl;

R$^1$ denotes 0, 1 or 2 substituents on the benz-ring independently selected from halo, methyl, ethyl, hydroxy, methoxy, carbamoyl, aminomethyl and hydroxymethyl;

X$^1$ is O, S, methylene, carbonyl or ethene-1,1-diyl;

(a) X$^2$ is imino, a direct bond, methylene, O or S; j is 0; k is 0; m is 5, 1, 2, 3 or 4; provided that when m is 1, then X$^2$ is a direct bond; and Ra and Rb are independently hydrogen or (1–3C)alkyl or the group NRaRb is 1-imidazolyl, 1-pyrazolyl, N-(1,2,4-triazolyl), neopentylamino, (cyclohexylmethyl) amino, benzylamino, (3-pyridylmethyl) amino, (2, 3-dihydroxypropyl) amino, (1-iminoethyl) amino, 2-(hydroxymethyl)-1-pyrrolidinyl, 2-(methoxymethyl)-1-pyrrolidinyl, pyrrolidino, piperidino, 2-methyl-1-piperidinyl, morpholino or hexamethyleneimino; or (b) $X^2$ is imino, O or S; j is 1; k is 1; m is 1; $R^2$ is hydroxy; and $R^a$ and $R^b$ are independently hydrogen or (1–3C)alkyl or the group NRaRb is pyrrolidino, piperidino, morpholino or hexamethyleneimino; or (c) $X^2$ is imino, O or S; j is 1; k is 1; m is 0; $R^2$ is methyl, carboxy, hydroxymethyl or methoxycarbonyl; and $R^a$ and $R^b$ are independently hydrogen or (1–3C)alkyl; or (d) $x^2$ is imino, O or S; j is 0, 1, 2 or 3; k is 1; m is 0 or 1; provided that j and m are not both 0; $R^2$ and $R^a$ together form a diradical —$(CH_2)_n$— in which n is 2, 3 or 4 and the sum of m and n is 3 or 4; and $R^b$ is hydrogen or (1–3C)alkyl; or (e) $X^2$ is —NH—C(O)—; j is 0; k is 0; m is 1; and $R^a$ and $R^b$ are independently hydrogen or (1–3C)alkyl or the group $NR^aR^b$ is 1,1-dioxothiomorpholin-4-yl, pyrrolidino, piperidino, morpholino or hexamethyleneimino; and (1) $X^3$ is a direct bond, methylene, imino, O or S; q is 0, 1 or 2; and r is 0 or 1; provided that q and r are not both zero, and provided that when q is 1 and r is 0, then $X^3$ is a direct bond; each $R^3$ is hydrogen or the two $R^3$ groups together form a divalent radical —$(CH_2)_s$— in which s is 3 or 4; or q and r are each 1 and the group —(CHR$^3$—CHR$^3$)— is propane-2,2-diyl; and $R^c$ and $R^d$ are independently hydrogen or (1–4C)alkyl or the group NRCRd is 1-pyrazolyl, 2-(hydroxymethyl)-1-pyrrolidinyl, 2-(methoxymethyl)-1-pyrrolidinyl, pyrrolidino, piperidino, morpholino, hexamethyleneimino, 1-imidazolyl or 4,5-dihydro-1-imidazolyl; or (2) $X^3$ is imino, O or S; q is 0; r is 1; one $R^3$ group is (1–5C)alkyl and the other $R^3$ group is independently hydrogen or (1–5C)alkyl; and $R^c$ and $R^d$ are independently hydrogen or (1–3C)alkyl or the group $NR^cR^d$ is pyrrolidino, piperidino, morpholino or hexamethyleneimino; or (3) $X^3$ is imino, O or S; q is 0, 1 or 2; r is 1; one $R^3$ group is hydrogen and the other $R^3$ group together with the group $R^c$ forms a divalent radical —$(CH_2)_t$— in which t is 2, 3 or 4 such that the resulting ring is a pyrrolidine or piperidine; and $R^d$ is hydrogen or (1–3C)alkyl; or (4) $X^3$ is —N(Rh)—; q is 0; r is 1; the $R^3$ group on the carbon bonded to $X^3$ and the group $R^h$ together form a diradical —$(CH_2)_3$—; the other $R^3$ group is hydrogen; and Rc and $R^d$ are independently (1–3C)alkyl or the group $NR^cR^d$ is pyrrolidino, piperidino, morpholino or hexamethyleneimino; or (5) $X^3$ is ethene-1,2-diyl or ethyne-1,2-diyl; q is 1; r is 0; and Rc and Rd are independently (1–3C)alkyl or the group $NR^cR^d$ is pyrrolidino, piperidino, morpholino or hexamethyleneimino.

2. The method of claim 1 wherein said compound is a compound of formula Ia

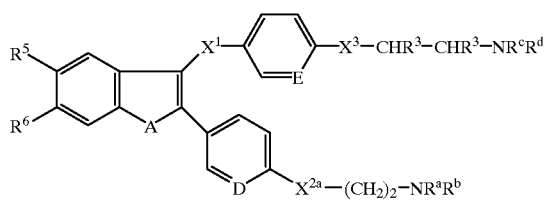

Ia wherein

A is S;

D is CH or $CR^j$ in which $R^j$ is methyl, hydroxy or methoxy;

E is CH or $CR^e$ in which $R^e$ is (1–3C)alkyl, (1–2C)alkoxy or halo;

$R^5$ is hydrogen, halo, methyl, hydroxy or methoxy;

$R^6$ is hydrogen, hydroxy or methoxy;

$X^1$ is O, S, methylene, carbonyl or ethene-1,1-diyl;

$x^{2a}$ is methylene or O; and $R^a$ and $R^b$ are independently hydrogen or (1–3C)alkyl or the group $NR^aR^b$ is pyrrolidino or piperidino;

$x^3a$ is methylene, imino, O, or S; and each $R^3$ is hydrogen or the two $R^3$ groups together form a divalent radical —$(CH_2)_s$— in which s is 3 or 4; and $R^c$ and $R^d$ are independently (1–3C)alkyl or the group $NR^cR^d$ is pyrrolidino, piperidino, morpholino or hexamethyleneimino or 1-imidazolyl.

3. The method of claim 2 wherein D is CH; and E is CH or $CR^e$ in which $R^e$ is (1–3C)alkyl or halo.

4. The method of claim 2 wherein A is S; D is CH; E is CRe in which Re is methoxy; $R^5$ is hydrogen; $R^6$ is hydroxy; $X^1$ is methylene; $X^{2a}$ is O; and the group $NR^aR^b$ is pyrrolidino; $X^{3a}$ is O; and the two $R^3$ groups together form a divalent radical —$(CH_2)_s$— in which s is 4 and which forms a trans-1,2-cyclohexanediyl group; and $R^c$ and $R^d$ are each methyl or the group $NR^cR^d$ is pyrrolidino.

5. The method of claim 1 wherein said compound is a compound of formula Ib

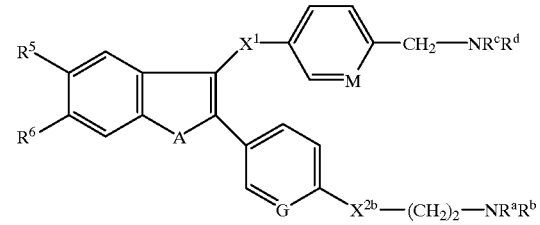

Ib wherein

A is S;

G is CH or $CR^k$ in which $R^k$ is methyl, hydroxy or methoxy;

M is CH or $CR^m$ in which $R^m$ is (1–3C)alkyl, (1–2C) alkoxy or halo;

$R^5$ is hydrogen, halo, methyl, hydroxy or methoxy;

$R^6$ is hydrogen, hydroxy or methoxy;

$X^1$ is O, S, methylene, carbonyl or ethene-1,1-diyl;

$X^{2b}$ is a direct bond or O; $R^a$ and $R^b$ are independently hydrogen or (1–3C)alkyl or the group $NR^aR^b$ is pyrrolidino or piperidino; and $R^c$ and $R^d$ are independently (1–3C)alkyl or the group NRCRd is 2-(hydroxymethyl)-1-pyrrolidinyl, 2-(methoxymethyl)-1-pyrrolidinyl, pyrrolidino, piperidino or morpholino.

6. The method of claim 5 wherein A is S; G is CH; M is CH or $CR^m$ in which $R^m$ is methyl, methoxy, chloro or bromo; $R^5$ is hydrogen; $R^6$ is hydroxy; $X^1$ is methylene; $X^{2b}$ is a direct bond or O; the group $NR^aR^b$ is pyrrolidino; and $R^c$ and $R^d$ are each methyl or the group $NR^cR^d$ is 2-(hydroxymethyl)-1-pyrrolidinyl, 2-(methoxymethyl)-1-pyrrolidinyl, pyrrolidino or morpholino.

7. The method as claimed in claim 1 wherein said compound is one in which $X^1$ is methylene, s (when present) is 4, and A is S.

8. The method as claimed in claim 1 wherein said compound is a compound of formula I in which $R^1$ denotes a hydroxy substituent at the 6-position of the benzo[b]thiophene.

9. A novel compound of formula I (or a pharmaceutically acceptable salt thereof)

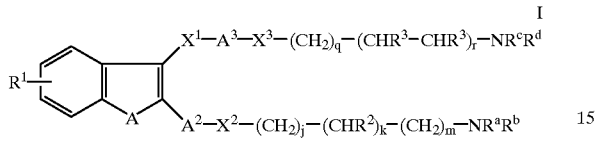

I wherein

A is O or S;

$A^2$ is para-phenylene which divalent radical may bear a hydroxymethyl, benzyloxymethyl, (1–3C)alkyl, (1–2C)alkoxy, hydroxy or halo substituent;

$A^3$ is para-phenylene which divalent radical may bear one or two substituents independently selected from dimethylamino, (1–4C)alkyl, halo, trifluoromethyl, (1–2C)alkoxy, hydroxy, cyano, aminomethyl, nitro, —NHCH$_2$R$^f$, —NHC(O)R$^f$ or —NHS(O)$_2$R$^g$ in which R$^f$ is hydrogen or (1–2C)alkyl and R$^g$ is (1–2C)alkyl or phenyl;

$R^1$ denotes 0, 1 or 2 substituents on the benz-ring independently selected from halo, methyl, ethyl, hydroxy, methoxy, carbamoyl, aminomethyl and hydroxymethyl;

$X^1$ is O, S, methylene, carbonyl or ethene-1,1-diyl;

(a) $X^2$ is imino, a direct bond, methylene, O or S; j is 0; k is 0; m is 5, 1, 2, 3 or 4; provided that when m is 1, then $X^2$ is a direct bond; and R$^a$ and R$^b$ are independently hydrogen or (1–3C)alkyl or the group NR$^a$R$^b$ is 1-imidazolyl, 1-pyrazolyl, N-(1,2,4-triazolyl), neopentylamino, (cyclohexylmethyl) amino, benzylamino, (3-pyridylmethyl) amino, (2,3-dihydroxypropyl) amino, (1-iminoethyl) amino, 2-(hydroxymethyl)-1-pyrrolidinyl, 2-(methoxymethyl)-1-pyrrolidinyl, pyrrolidino, piperidino, 2-methyl-1-piperidinyl, morpholino or hexamethyleneimino; or (b) $X^2$ is imino, O or S; j is 1; k is 1; m is 1; $R^2$ is hydroxy; and R$^a$ and R$^b$ are independently hydrogen or (1–3C) alkyl or the group NR$^a$R$^b$ is pyrrolidino, piperidino, morpholino or hexamethyleneimino; or (c) $X^2$ is imino, O or S; j is 1; k is 1; m is 0; $R^2$ is methyl, carboxy, hydroxymethyl or methoxycarbonyl; and R$^a$ and R$^b$ are independently hydrogen or (1–3C)alkyl; or (d) $X^2$ is imino, O or S; j is 0, 1, 2 or 3; k is 1; m is 0 or 1; provided that j and m are not both 0; $R^2$ and R$^a$ together form a diradical —(CH$_2$)$_n$— in which n is 2, 3 or 4 and the sum of m and n is 3 or 4; and Rb is hydrogen or (1–3C)alkyl; or (e) $X^2$ is —NH—C(O)—; j is 0; k is 0; m is 1; and R$^a$ and R$^b$ are independently hydrogen or (1–3C)alkyl or the group NR$^a$R$^b$ is 1,1-dioxothiomorpholin-4-yl, pyrrolidino, piperidino, morpholino or hexamethyleneimino; and (1) $X^3$ is a direct bond, methylene, imino, O or S; q is 0, 1 or 2; r is 0 or 1; provided that q and r are not both zero, and provided that when q is 1 and r is 0, then $X^3$ is a direct bond; each $R^3$ is hydrogen or the two $R^3$ groups together form a divalent radical —(CH$_2$)$_s$— in which s is 3 or 4; or q and r are each 1 and the group —(CHR$^3$—CHR$^3$)— is propane-2,2-diyl; and R$^c$ and R$^d$ are independently hydrogen or (1–4C)alkyl or the group NR$^c$R$^d$ is 1-pyrazolyl, 2-(hydroxymethyl)-1-pyrrolidinyl, 2-(methoxymethyl)-1-pyrrolidinyl, pyrrolidino, piperidino, morpholino, hexamethyleneimino, 1-imidazolyl or 4,5-dihydro-1-imidazolyl; or (2) $X^3$ is imino, O or S; q is 0; r is 1; one $R^3$ group is (1–5C)alkyl and the other $R^3$ group is independently hydrogen or (1–5C)alkyl; and R$^c$ and R$^d$ are independently hydrogen or (1–3C)alkyl or the group NR$^c$R$^d$ is pyrrolidino, piperidino, morpholino or hexamethyleneimino; or (3) $X^3$ is imino, O or S; q is 0, 1 or 2; r is 1; one $R^3$ group is hydrogen and the other $R^3$ group together with the group RC forms a divalent radical —(CH$_2$)$_t$— in which t is 2, 3 or 4 such that the resulting ring is a pyrrolidine or piperidine; and Rd is hydrogen or (1–3C)alkyl; or (4) $X^3$ is —N(R$^h$)—; q is 0; r is 1; the $R^3$ group on the carbon bonded to $X^3$ and the group R$^h$ together form a diradical —(CH$_2$)$_3$—; the other $R^3$ group is hydrogen; and R$^c$ and R$^d$ are independently (1–3C)alkyl or the group NR$^c$R$^d$ is pyrrolidino, piperidino, morpholino or hexamethyleneimino; or (5) $X^3$ is ethene-1,2-diyl or ethyne-1,2-diyl; q is 1; r is 0; and R$^c$ and R$^d$ are independently (1–3C)alkyl or the group NR$^c$R$^d$ is pyrrolidino, piperidino, morpholino or hexamethyleneimino;

provided that the compound is not one in which A is S; $A^2$ is para-phenylene; $A^3$ is para-phenylene; $R^1$ denotes zero substituents on the benz-ring or $R^1$ denotes a hydroxy or methoxy substituent at the 6-position of the benzo[b]thiophene ring; $X^1$ is carbonyl; $X^2$ is O; j and k are both 0, the group —(CH$_2$)$_m$— is ethylene or propylene; R$^a$ and R$^b$ are independently (1–3C)alkyl or the group NR$^a$R$^b$ is pyrrolidino, piperidino, morpholino or hexamethyleneimino; $X^3$ is 0; the group —(CH$_2$)$_q$— (CHR$^3$—CHR$^3$)$_r$— is ethylene or propylene; and R$^c$ and R$^d$ are independently (1–3C)alkyl or the group NR$^c$R$^d$ is pyrrolidino, piperidino, morpholino or hexamethyleneimino.

10. The compound (or pharmaceutically acceptable salt thereof) as claimed in claim 9 which is a compound of formula Ia

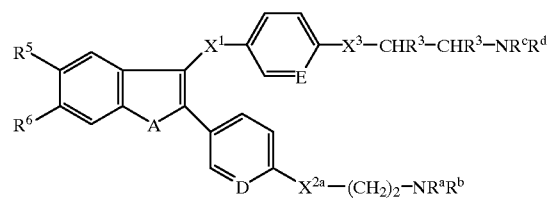

Ia wherein

A is S;

D is CH or CR$^j$ in which R$^j$ is methyl, hydroxy or methoxy;

E is CH or CR$^e$ in which R$^e$ is (1–3C)alkyl, (1–2C)alkoxy or halo;

$R^5$ is hydrogen, halo, methyl, hydroxy or methoxy;

$R^6$ is hydrogen, hydroxy or methoxy;

$X^1$ is O, S, methylene, carbonyl or ethene-1,1-diyl;

$X^{2a}$ is methylene or O; and $R^a$ and $R^b$ are independently hydrogen or (1–3C)alkyl or the group $NR^aR^b$ is pyrrolidino or piperidino;

$X^{3a}$ is methylene, imino, O, or S; and each $R^3$ is hydrogen or the two $R^3$ groups together form a divalent radical —(CH$_2$)$_s$— in which s is 3 or 4; and $R^c$ and $R^d$ are independently (1–3C)alkyl or the group $NR^cR^d$ is pyrrolidino, piperidino, morpholino or hexamethyleneimino or 1-imidazolyl;

provided that the compound is not one in which A is S; D is CH; E is CH; $R^5$ is hydrogen, $R^6$ is hydrogen, hydroxy or methoxy; $X^1$ is carbonyl; x$^2$a is O; Ra and Rb are independently (1–3C)alkyl or the group $NR^aR^b$ is pyrrolidino or piperidino; $X^{3a}$ is O; each $R^3$ is hydrogen; and $R^c$ and $R^d$ are independently (1–3C) alkyl or the group $NR^cR^d$ is pyrrolidino, piperidino, morpholino or hexamethylenemino.

11. The compound (or pharmaceutically acceptable salt thereof) of claim 10 wherein D is CH; and E is CH or CR$^e$ in which R$^e$ is (1–3C)alkyl or halo.

12. The compound (or pharmaceutically acceptable salt thereof) of claim 10 wherein A is S; D is CH; E is CR$^e$ in which R$^e$ is methoxy; $R^5$ is hydrogen; $R^6$ is hydroxy; $X^1$ is methylene; $X^{2a}$ is O; and the group $NR^aR^b$ is pyrrolidino; $X^{3a}$ is O; and the two $R^3$ groups together form a divalent radical —(CH$_2$)$_s$— in which s is 4 and which forms a trans-1,2-cyclohexanediyl group; and $R^c$ and $R^d$ are each methyl or the group $NR^cR^d$ is pyrrolidino.

13. The compound (or pharmaceutically acceptable salt thereof) as claimed in claim 9 which is a compound of formula Ib

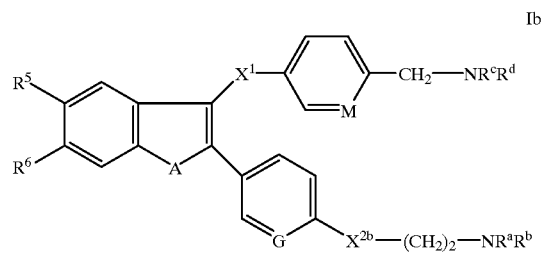

wherein

A is S;

G is CH or CR$^k$ in which R$^k$ is methyl, hydroxy or methoxy;

M is CH or CR$^m$ in which R$^m$ is (1–3C)alkyl, (1–2C) alkoxy or halo;

$R^5$ is hydrogen, halo, methyl, hydroxy or methoxy;

$R^6$ is hydrogen, hydroxy or methoxy;

$X^1$ is O, S, methylene, carbonyl or ethene-1,1-diyl;

$X^{2b}$ is a direct bond or O; $R^a$ and $R^b$ are independently hydrogen or (1–3C)alkyl or the group $NR^aR^b$ is pyrrolidino or piperidino; and $R^c$ and $R^d$ are independently (1–3C)alkyl or the group $NR^cR^d$ is 2-(hydroxymethyl)-1-pyrrolidinyl, 2-(methoxymethyl)-1-pyrrolidinyl, pyrrolidino, piperidino or morpholino.

14. The compound (or pharmaceutically acceptable salt thereof) of claim 13 wherein A is S; G is CH; M is CH or CR$^m$ in which R$^m$ is methyl, methoxy, chloro or bromo; $R^5$ is hydrogen; $R^6$ is hydroxy; $X^1$ is methylene; $X^{2b}$ is a direct bond or O; the group $NR^aR^b$ is pyrrolidino; and $R^c$ and $R^d$ are each methyl or the group $NR^cR^d$ is 2-(hydroxymethyl)-1-pyrrolidinyl, 2-(methoxymethyl)-1-pyrrolidinyl, pyrrolidino or morpholino.

15. The compound (or pharmaceutically acceptable salt thereof) as claimed in claim 9 wherein $X^1$ is methylene, s (when present) is 4, and A is S.

16. The compound (or pharmaceutically acceptable salt thereof) as claimed in claim 15 wherein said compound is a compound of formula I in which $R^1$ denotes a hydroxy substituent at the 6-position of the benzo[b]thiophene.

17. An acid addition salt of a novel compound of formula I as claimed in claim 9 made with an acid which affords a pharmaceutically acceptable anion.

18. A pharmaceutical formulation comprising in association with a pharmaceutically acceptable carrier, diluent or excipient, a novel compound of formula I (or a pharmaceutically acceptable salt thereof) as claimed in claim 9.

19. An alcohol of formula II

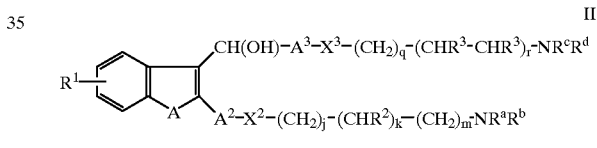

wherein the values of A, $A^2$, $A^3$, $R^1$, $R^2$, $R^3$, $R^a$, $R^b$, $R^c$, $R^d$, $X^1$, $X^2$, $X^3$, j, k, m, q, and r are as defined in claim 1.

20. The method of claim 1 wherein said compound is 6-hydroxy-3-[3-methoxy-4-[(1-pyrrolidinyl)methyl]benzyl]-2-[4-[2-(1-pyrrolidinyl)ethoxy]phenyl]benzo[b]thiophene.

21. The novel compound (or pharmaceutically acceptable salt thereof) of claim 9 wherein said compound is 6-hydroxy-3-[3-methoxy-4-[(1-pyrrolidinyl)methyl]benzyl]-2-[4-[2-(1-pyrrolidinyl)ethoxy]phenyl]benzo[b]thiophene.

* * * * *

UNITED STATES PATENT AND TRADEMARK OFFICE
CERTIFICATE OF CORRECTION

PATENT NO.     : 6,025,382

DATED          : February 15, 2000

INVENTOR(S)    : Bastian, et al.

It is certified that an error appears in the above-identified patent and that said Letters Patent is hereby corrected as shown below:

Column 355, line 27, delete "NRCRd" and insert --$NR^CR^d$--.

Column 356, line 58, delete "NRCRd" and insert --$NR^CR^d$--.

Column 358, line 20, delete "RC" and insert --$R^C$--.

Signed and Sealed this

Third Day of April, 2001

Attest:

NICHOLAS P. GODICI

*Attesting Officer*     Acting Director of the United States Patent and Trademark Office